(12) United States Patent
Görgens et al.

(10) Patent No.: US 9,271,499 B2
(45) Date of Patent: Mar. 1, 2016

(54) PESTICIDAL ARYLPYRROLIDINES

(71) Applicant: Bayer Intellectual Property GmbH, D 40789 Monheim (DE)

(72) Inventors: Ulrich Görgens, Ratingen (DE); Jun Mihara, Tochigi (JP); Tetsuya Murata, Tochigi (JP); Daiei Yamazaki, Tochigi (JP); Yasushi Yoneta, Saitama (JP); Koichi Araki, Ibaraki (JP); Norio Sasaki, Ibaraki (JP); Kei Domon, Tochigi (JP); Mamoru Hatazawa, Ibaraki (JP); Eiichi Shimojo, Tochigi (JP); Teruyuki Ichihara, Tochigi (JP); Masashi Ataka, Ibaraki (JP); Katsuhiko Shibuya, Tochigi (JP)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/323,755

(22) Filed: Jul. 3, 2014

(65) Prior Publication Data

US 2015/0011553 A1    Jan. 8, 2015

Related U.S. Application Data

(60) Division of application No. 13/829,353, filed on Mar. 14, 2013, now Pat. No. 8,785,647, which is a continuation of application No. 12/588,411, filed on Oct. 14, 2009, now Pat. No. 8,450,483.

(30) Foreign Application Priority Data

Oct. 17, 2008 (JP) ................. 2008-268729
Apr. 30, 2009 (JP) ................. 2009-111390

(51) Int. Cl.
| | |
|---|---|
| C07D 207/09 | (2006.01) |
| A01N 43/36 | (2006.01) |
| A01N 43/84 | (2006.01) |
| A01N 43/40 | (2006.01) |
| A01N 43/54 | (2006.01) |
| A01N 43/78 | (2006.01) |
| C07D 207/08 | (2006.01) |
| C07D 401/04 | (2006.01) |
| C07D 401/12 | (2006.01) |
| C07D 401/14 | (2006.01) |
| C07D 403/04 | (2006.01) |
| C07D 403/12 | (2006.01) |
| C07D 403/14 | (2006.01) |
| C07D 405/12 | (2006.01) |
| C07D 405/14 | (2006.01) |
| C07D 409/12 | (2006.01) |
| C07D 409/14 | (2006.01) |
| C07D 413/12 | (2006.01) |
| C07D 417/04 | (2006.01) |
| C07D 417/14 | (2006.01) |

(Continued)

(52) U.S. Cl.
CPC ................ *A01N 43/84* (2013.01); *A01N 43/36* (2013.01); *A01N 43/40* (2013.01); *A01N 43/54* (2013.01); *A01N 43/56* (2013.01); *A01N 43/653* (2013.01); *A01N 43/713* (2013.01); *A01N 43/76* (2013.01); *A01N 43/78* (2013.01); *C07D 207/08* (2013.01); *C07D 207/09* (2013.01); *C07D 401/04* (2013.01); *C07D 401/12* (2013.01); *C07D 401/14* (2013.01); *C07D 403/04* (2013.01); *C07D 403/12* (2013.01); *C07D 403/14* (2013.01); *C07D 405/12* (2013.01); *C07D 405/14* (2013.01); *C07D 409/12* (2013.01); *C07D 409/14* (2013.01); *C07D 413/12* (2013.01); *C07D 417/04* (2013.01); *C07D 417/14* (2013.01)

(58) Field of Classification Search
CPC .............................. C07D 207/09; A01N 43/36
See application file for complete search history.

(56) References Cited

U.S. PATENT DOCUMENTS

| | | | |
|---|---|---|---|
| 8,188,122 B2 | 5/2012 | Mihara et al. | |
| 8,450,483 B2 | 5/2013 | Görgens et al. | |

(Continued)

FOREIGN PATENT DOCUMENTS

| | | |
|---|---|---|
| JP | 2008-110971 | 5/2008 |
| WO | WO 2008/128711 A1 | 10/2008 |

OTHER PUBLICATIONS

Bégué, J., et al., "Enhancement of Alkene Reactivity by a Trifluoromethyl group: Synthesis of Pyrrolidines via 1,3-Dipolar Cycloaddition," *Tetrahedron Letters* 34:3279-3282, Elsevier, United Kingdom (1993).

(Continued)

*Primary Examiner* — Robert Havlin
(74) *Attorney, Agent, or Firm* — Sterne, Kessler, Goldstein & Fox P.L.L.C.

(57) ABSTRACT

The invention is directed to arylpyrrolidines compounds which exhibit excellent insecticidal efficacy and which may be used as in the agrochemical field or in the field of veterinary medicine. The compounds are represented by formula (I):

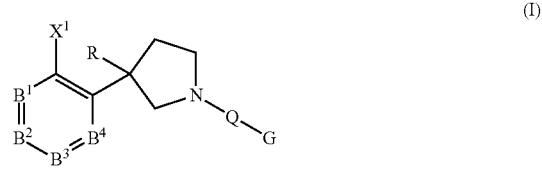

wherein the respective substituents are defined in the specification.

20 Claims, No Drawings

(51) Int. Cl.
*A01N 43/56* (2006.01)
*A01N 43/653* (2006.01)
*A01N 43/713* (2006.01)
*A01N 43/76* (2006.01)

(56) References Cited

U.S. PATENT DOCUMENTS

| | | |
|---|---|---|
| 8,785,647 B2 | 7/2014 | Görgens et al. |
| 2007/0066617 A1 | 3/2007 | Mita et al. |
| 2012/0232278 A1 | 9/2012 | Mihara et al. |

OTHER PUBLICATIONS

Hosomi, A., et al., "N-(Trimethylsilylmethyl) Aminomethyl Ethers as Azomethine Ylide Synthons. A New and Convenient Access to Pyrolidine Derivatives," *Chemistry Letters* 13:1117-1120, The Chemical Society of Japan, Japan (1984).

Iwata, A., et al., "Preparation of nitrogen-containing heterocyclic compounds and their use as pesticides," Accession No. 2008:582853 CAPLUS, JP 2008-110971.

Jiang, B. and Xu, Y., "Trifluoroisopropenylzinc Reagent as a Useful α-(Trifluoromethyl)ethenyl Carbanion Synthetic Equivalent. Preparation and Palladium-Catalyzed Coupling with Aryl Halides," *J. Org. Chem.* 56:7336-7340, American Chemical Society, United States (1991).

Nader, B., et al., "A Novel Fluoride Ion Mediated Olefination of Electron-Deficient Aryl Ketones by Alkanesulfonyl Halides," *J. Org. Chem.* 59:2898-2901, American Chemical Society, United States (1994).

Olofson, R., et al., "A New Reagent for the Selective, High-Yield N-Dealkylation of Tertiary Amines: Improved Syntheses of Naltrexone and Nalbuphine," *J. Org. Chem.* 49:2081-2082, American Chemical Society, United States (1984).

Pan, R., et al., "A novel and convenient synthetic method for producing α-(trifluoromethyl)styrenes (3)," *J. Fluor. Chem.* 95:167-170, Elsevier Science S.A, United States (1999).

Sun, R., et al., "Synthesis, larvicidal activity, and SAR studies of new benzoylphenylureas containing oxime ether and oxime ester group," *Bioorganic & Medicinal Chemistry Letters* 20:4693-4699, Elsevier Ltd., United Kingdom (2010).

Terfloth, L. and Gasteiger, J., "Electronic Screening: Lead Finding from Database Mining," in The Practice of Medicinal Chemistry, 2d ed., Wermuth, C., ed., pp. 131-157, Academic Press, United States (2003).

Patent Abstracts of Japan (PAJ), Unverified English language abstract of JP 2008-110971, Japan Patent Office.

International Search Report and Written Opinion of PCT Application No. PCT/EP2009/007095, (2009).

Wermuth, The Practice of Medicinal Chemistry, 2d ed. (2003), 768 pages. Chapters 9-10 provided.

PESTICIDAL ARYLPYRROLIDINES

The present invention relates to novel arylpyrrolidines and their use as pesticides in the agricultural field or as pharmaceutical for treating parasites in or on animals.

It is known that certain compounds containing a 5-membered heterocyclic ring can be used as pesticides. Substituted benzamide compounds containing a 5-membered ring which is isoxazoline, and which compounds are supposed to be useful for controlling noxious animal pests are described in WO2005/085216. Compounds, wherein the 5-membered ring is a pyrrolidine ring and which may be used as an agent for controlling noxious bioorganisms are described in JP2008-110971A and WO2008/128711.

Modern crop protection compositions have to satisfy many demands, for example in relation to efficacy, persistence and spectrum of their action, and possible use. Important questions relate to toxicity, combinability with other active ingredients or formulating assistants, and another is that of the effort and expense of synthesizing an active ingredient. Moreover, resistances can occur. For all these reasons, the search for novel crop protection compositions cannot be considered to be complete, and there is a constant need for novel compounds with improved properties over the known compounds, at least in relation to individual aspects. Thus, the inventors of the present invention intensively studied to develop novel compounds which exhibit a high pesticidal efficacy and have a broad spectrum of use.

As a result, the inventors have found that novel arylpyrrolidines represented by the following formula (I) have high pesticidal activity, a broad spectrum of use, safety, and also have an efficacy against noxious insects that are resistant to an organophosphorus agent or a carbamate agent.

Thus, this invention is directed to arylpyrrolidine compounds of formula (I)

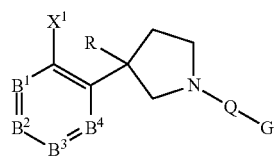

(I)

wherein
R represents alkyl or haloalkyl;
Q represents one of the chemical groups represented by the formula (II) or (III)

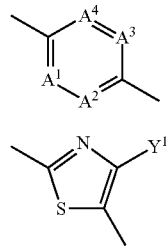

(II)

(III)

wherein in formula (II) the carbon atom between $A^1$ and $A^4$ is bound to the nitrogen atom in formula (I) and wherein in formula (III) the carbon atom between the S atom and the N atom is bound to the nitrogen atom in formula (I);

$A^1$, $A^2$, $A^3$ and $A^4$ each independently represents C—$Y^2$ or nitrogen, and if $A^1$ and $A^2$ (or $A^3$ and $A^4$) stand for C—$Y^2$, then the substituents $Y^2$ may together with the carbon atoms to which they are bound form a 5- or 6-membered saturated or unsaturated hydrocarbon ring or heterocyclic ring;

$B^1$, $B^2$, $B^3$ and $B^4$ each independently represents C—$X^2$ or nitrogen, and if either $B^1$ and $B^2$, or $B^2$ and $B^3$, or $B^3$ and $B^4$ stand for C—$X^2$, then the substituents $X^2$ may together with the carbon atoms to which they are bound form a 5- or 6-membered saturated or unsaturated hydrocarbon ring or heterocyclic ring;

$X^1$, $X^2$ each independently represents hydrogen, halogen, nitro, cyano, hydroxy, mercapto, amino, alkyl, haloalkyl, alkoxy, haloalkoxy, alkylsulfanyl, alkylsulfinyl, alkylsulfonyl, haloalkylsulfanyl, haloalkylsulfinyl, haloalkylsulfonyl, acylamino, alkoxycarbonylamino, haloalkoxycarbonylamino, alkoxyimino, haloalkoxyimino, alkylsulfonylamino, or pentafluorosulfur;

$Y^1$, $Y^2$ each independently represents hydrogen, halogen, nitro, cyano, hydroxy, mercapto, amino, alkyl, haloalkyl, cycloalkyl, cyclohaloalkyl, alkenyl, alkynyl, alkoxy, haloalkoxy, alkylsulfanyl, alkylsulfinyl, alkylsulfonyl, haloalkylsulfanyl, haloalkylsulfinyl, haloalkylsulfonyl, alkylsulfonyloxy, haloalkylsulfonyloxy, alkylaminosulfonyl, haloalkylaminosulfonyl, dialkylaminosulfonyl, di(haloalkyl)aminosulfonyl, alkylamino, dialkylamino, acylamino, alkoxycarbonylamino, haloalkoxycarbonylamino, alkylsulfonylamino, haloalkylsulfonylamino, trialkylsilyl, alkoxyimino, haloalkoxyimino, alkoxyiminoalkyl, haloalkoxyiminoalkyl, alkylsulfinylimino, alkylsulfinyliminoalkyl, alkylsulfinyliminoalkylcarbonyl, alkylsulfoxyimino, alkylsulfoxyiminoalkyl, alkoxycarbonyl, alkylcarbonyl, aminocarbonyl, alkylaminocarbonyl, aminothiocarbonyl, alkylaminothiocarbonyl, dialkylaminocarbonyl, or dialkylaminothiocarbonyl;

G represents

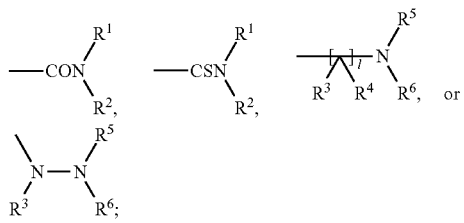

l represents an integer of 1 to 3;
$R^1$ and $R^2$ each independently represents hydrogen, cyano, alkyl, haloalkyl, cycloalkyl, cyclohaloalkyl, alkenyl, alkynyl, haloalkenyl, haloalkynyl, alkoxycarbonyl, alkoxythiocarbonyl, alkylsulfonyl, haloalkylsulfonyl, aryl, aralkyl, a heterocyclic group, heterocyclic substituted alkyl, alkoxyalkyl, alkylsulfanylalkyl, alkylsulfinylalkyl, alkylsulfonylalkyl, alkyl-O—N=CH—, alkylaminocarbonylalkyl, haloalkylaminocarbonylalkyl or cycloalkylaminocarbonylalkyl, or $R^1$ and $R^2$ may together with the nitrogen to which they are attached form a 3- to 7-membered heterocycle;

$R^3$ and $R^4$ each independently represents hydrogen, cyano, alkyl, alkenyl, alkynyl, cycloalkyl or alkoxycarbonyl, or when $A^2$ or $A^3$ is C—$Y^2$, then said $Y^2$ and $R^3$, said $Y^2$ and $R^4$ or said $Y^2$, $R^3$ and $R^4$ together may form a 5- to 7-membered saturated or unsaturated hydrocarbon ring or heterocyclic ring together with the carbon atoms to which said $Y^2$ and $R^3$, said $Y^2$ and $R^4$ or said $Y^2$, $R^3$ and $R^4$ are bound and further with the carbon atom between the carbon atom to which $Y^2$ is bound and the carbon atom to which $R^3$ and $R^4$ are bound, or when $A^2$ or $A^3$ is C—$Y^2$ and 1 is 2, then the carbon atom bound to $R^6$—N($R^5$)— may form carbonyl together with $R^3$ and $R^4$, and the carbon atom bound to Q may form a 5- to 7-membered saturated or unsaturated hydrocarbon ring or heterocyclic ring together with any one or both of $R^3$ and $R^4$ bound thereto and further with $Y^2$, wherein the ring may be substituted with alkyl, haloalkyl, alkoxy, haloalkoxy, alkylcarbonyl, alkoxycarbonyl or carbonyl substituted with a 5- or 6-membered heterocyclic ring, and when one or more of the carbon atoms of the ring are substituted with two or more alkyls, any two of the alkyls may form cycloalkyl together with the carbon atoms to which they are bound, or $Y^1$ may form a 5- to 7-membered saturated or unsaturated hydrocarbon ring or heterocyclic ring together with any one or both of $R^3$ and $R^4$, with the carbon atoms to which said $Y^1$ and said $R^3$ and $R^4$ are bound and further with the carbon atom between the carbon atom to which $Y^1$ is bound and the carbon atom to which $R^3$ and $R^4$ are bound, and when 1 is 2, then the carbon atom bound to $R^6$—N($R^5$)— may form carbonyl together with $R^3$ and $R^4$, and the carbon atom bound to Q may form a 5- to 7-membered saturated or unsaturated hydrocarbon ring or heterocyclic ring together with any one or both of $R^3$ and $R^4$ bound thereto and further with $Y^1$, wherein the ring may be substituted with alkyl, haloalkyl, alkoxy, haloalkoxy, alkylcarbonyl, alkoxycarbonyl or carbonyl substituted with a 5- or 6-membered heterocyclic ring, and when one or more of the carbon atoms of the ring are substituted with two or more alkyls, and any two of said alkyls may form cycloalkyl together with the carbon atoms to which they are bound;

$R^5$ represents hydrogen, amino, hydroxy, cyano, alkyl, haloalkyl, cycloalkyl, alkenyl, alkynyl, alkoxy, aminocarbonylalkyl, iminoalkyl, alkylcarbonyl, alkylcarbonylamino, alkylimino, aryl, aralkyl, a heterocycle, a heterocyclic ring substituted alkyl, $R^7$—C(=O)— or $R^7$—C(=S)—;

$R^6$ represents hydrogen, cyano, carbonyl, thiocarbonyl, alkylcarbonyl, alkylthiocarbonyl, haloalkylcarbonyl, haloalkylthiocarbonyl, alkylaminocarbonyl, alkylaminothiocarbonyl, dialkylaminocarbonyl, dialkylaminothiocarbonyl, alkoxyaminocarbonyl, alkoxyaminothiocarbonyl, alkoxycarbonyl, alkoxythiocarbonyl, alkylsulfanylcarbonyl, alkylsulfanylthiocarbonyl, alkylsulfonyl, haloalkylsulfonyl, cycloalkylcarbonyl, alkenylcarbonyl, alkynylcarbonyl, cycloalkylalkylcarbonyl, alkylsulfanylalkylcarbonyl, alkylsulfinylalkylcarbonyl, alkylsulfonylalkylcarbonyl, alkylcarbonylalkylcarbonyl, cycloalkylaminocarbonyl, alkenylaminocarbonyl, alkynylaminocarbonyl, alkylaminosulfonyl, dialkylaminosulfonyl, alkoxyalkylcarbonyl, alkylcarbonylaminoalkylcarbonyl, haloalkylcarbonylaminoalkylcarbonyl, alkylsulfanylalkylcarbonylaminoalkylcarbonyl, alkylsulfinylalkylcarbonylaminoalkylcarbonyl, alkylsulfonylalkylcarbonylaminoalkylcarbonyl, aralkylcarbonyl, heterocyclic substituted alkylcarbonyl, $R^7$—C(=O)— or $R^7$—C(=S)—, or $R^5$ and $R^6$ may form a 3- to 6-membered heterocyclic ring, together with the nitrogen atom to which they are bound, and said ring may be substituted with keto, thioketo or a nitroimino group; and $R^7$ represents an optionally substituted phenyl or an optionally substituted heterocycle.

Compounds of Formula (I) are Preferred Wherein

R represents $C_{1-6}$ alkyl, or $C_{1-6}$ haloalkyl; preferably represents $C_{1-4}$ alkyl or $C_{1-4}$ haloalkyl, more preferably represents trifluoromethyl;

Q stands for one of the chemical groups represented by formula (II) or (III) in which $A^1$, $A^2$, $A^3$ and $A^4$ each independently represents C—$Y^2$ or nitrogen, and if $A^1$ and $A^2$ (or $A^3$ and $A^4$) stand for C—$Y^2$, then the substituents $Y^2$ may together with the carbon atoms to which they are bound form a 5- or 6-membered saturated or unsaturated hydrocarbon ring or heterocyclic ring;

$B^1$, $B^2$, $B^3$ and $B^4$ each independently represents C—$X^2$ or nitrogen, and if either $B^1$ and $B^2$, or $B^2$ and $B^3$, or $B^3$ and $B^4$ stand for C—$X^2$, then the substituents $X^2$ may together with the carbon atoms to which they are bound form a 5- or 6-membered saturated or unsaturated hydrocarbon ring or heterocyclic ring;

$X^1$, $X^2$ each independently represents hydrogen, halogen, nitro, cyano, hydroxy, mercapto, amino, $C_{1-6}$alkyl, $C_{1-6}$haloalkyl, $C_{1-6}$alkoxy, $C_{1-6}$haloalkoxy, $C_{1-6}$alkylsulfanyl, $C_{1-6}$alkylsulfinyl, $C_{1-6}$alkylsulfonyl, $C_{1-6}$haloalkylsulfanyl, $C_{1-6}$haloalkylsulfinyl, $C_{1-6}$haloalkylsulfonyl, (total carbon atom number) $C_{2-7}$acylamino, (total carbon atom number) $C_{2-7}$alkoxycarbonylamino, (total carbon atom number) $C_{2-7}$haloalkoxycarbonylamino, $C_{1-6}$alkoxyimino, $C_{1-6}$haloalkoxyimino, $C_{1-6}$alkylsulfonylamino or pentafluorosulfur; preferably represents hydrogen, halogen, nitro, cyano, hydroxy, mercapto, amino, $C_{1-4}$alkyl, $C_{1-4}$haloalkyl, $C_{1-4}$alkoxy, $C_{1-4}$haloalkoxy, $C_{1-4}$alkylsulfanyl, $C_{1-4}$alkylsulfinyl, $C_{1-4}$alkylsulfonyl, $C_{1-4}$haloalkylsulfanyl, $C_{1-4}$haloalkylsulfinyl, $C_{1-4}$haloalkylsulfonyl, (total carbon atom number) $C_{2-5}$acylamino, (total carbon atom number) $C_{2-5}$alkoxycarbonylamino, (total carbon atom number) $C_{2-5}$haloalkoxycarbonylamino, $C_{1-4}$alkoxyimino, $C_{1-4}$haloalkoxyimino, $C_{1-4}$alkylsulfonylamino or pentafluorosulfur, more preferably represents hydrogen, fluoro, chloro, bromo, trifluoromethyl;

$Y^1$, $Y^2$ each independently represents hydrogen, halogen, nitro, cyano, hydroxy, mercapto, amino, $C_{1-6}$alkyl, $C_{1-6}$haloalkyl, $C_{3-7}$cycloalkyl, $C_{3-7}$cyclohaloalkyl, $C_{2-6}$alkenyl, $C_{2-6}$alkynyl, $C_{1-6}$alkoxy, $C_{1-6}$haloalkoxy, $C_{1-6}$alkylsulfanyl, $C_{1-6}$alkylsulfinyl, $C_{1-6}$alkylsulfonyl, $C_{1-6}$haloalkylsulfanyl, $C_{1-6}$haloalkylsulfinyl, $C_{1-6}$haloalkylsulfonyl, $C_{1-6}$alkylsulfonyloxy, $C_{1-6}$haloalkylsulfonyloxy, $C_{1-6}$alkylaminosulfonyl, $C_{1-6}$haloalkylaminosulfonyl, (total carbon atom number) $C_{2-12}$dialkylaminosulfonyl, (total carbon atom number) $C_{2-12}$di(haloalkyl)aminosulfonyl, $C_{1-6}$alkylamino, (total carbon atom number) $C_{2-12}$dialkylamino, (total carbon atom number) $C_{2-7}$acylamino, (total carbon atom number) $C_{2-7}$alkoxycarbonylamino, (total carbon atom number) $C_{2-7}$haloalkoxycarbonylamino, $C_{1-6}$alkylsulfonylamino, $C_{1-6}$haloalkylsulfonylamino, (total carbon atom number) $C_{3-18}$trialkylsilyl, $C_{1-6}$alkoxyimino, $C_{1-6}$haloalkoxyimino, (total carbon atom number) $C_{2-12}$alkoxyiminoalkyl, (total carbon atom number) $C_{2-12}$haloalkoxyiminoalkyl, $C_{1-6}$alkylsulfinylimino, (total carbon atom number) $C_{2-12}$alkylsulfinyliminoalkyl, (total carbon atom number) $C_{3-13}$alkylsulfinyliminoalkylcarbonyl, $C_{1-6}$alkylsulfoxyimino, (total carbon atom number) $C_{2-12}$alkylsulfoxyiminoalkyl, (total carbon atom number) $C_{2-7}$alkoxycarbonyl, (total carbon atom number) $C_{2-7}$alkylcarbonyl, aminocarbonyl, (total carbon atom number) $C_{2-7}$alkylaminocarbonyl, aminothiocarbonyl, (total carbon atom number) $C_{2-7}$alkylaminothiocarbonyl, (total carbon atom number) $C_{3-13}$dialkylaminocarbonyl or (total carbon atom number) $C_{3-13}$dialkylaminothiocarbonyl, preferably represents hydrogen, halogen, nitro, cyano, hydroxy, mercapto, amino, $C_{1-4}$alkyl, $C_{1-4}$haloalkyl, $C_{3-6}$cycloalkyl, $C_{3-6}$cyclohaloalkyl, $C_{2-4}$alkenyl, $C_{2-4}$alkynyl, $C_{1-4}$alkoxy, $C_{1-4}$haloalkoxy, $C_{1-4}$alkylsulfanyl, $C_{1-4}$alkylsulfinyl, $C_{1-4}$alkylsulfonyl, $C_{1-4}$haloalkylsulfanyl, $C_{1-4}$haloalkylsulfinyl, $C_{1-4}$haloalkylsulfonyl, $C_{1-4}$alkylsulfonyloxy, $C_{1-4}$haloalkylsulfonyloxy, $C_{1-4}$alkylaminosulfonyl, $C_{1-4}$haloalkylaminosulfonyl, (total carbon atom number) $C_{2-8}$dialkylaminosulfonyl, (total carbon atom number) $C_{2-8}$di(haloalkyl)aminosulfonyl, $C_{1-4}$alkylamino, (total carbon atom number) $C_{2-8}$dialkylamino, (total carbon atom number) $C_{2-5}$acylamino, (total carbon atom number) $C_{2-5}$alkoxycarbonylamino, (total carbon atom number) $C_{2-5}$haloalkoxycarbonylamino, $C_{1-4}$alkylsulfonylamino, $C_{1-4}$haloalkylsulfonylamino, (total carbon atom number) $C_{3-12}$-trialkylsilyl, $C_{1-4}$alkoxyimino, $C_{1-4}$haloalkoxyimino, (total carbon atom number) $C_{2-5}$alkoxyiminoalkyl, (total carbon atom number) $C_{2-5}$haloalkoxyiminoalkyl, (total carbon atom number) $C_{1-4}$alkylsulfinylimino, (total carbon atom number) $C_{2-5}$alkylsulfinyliminoalkyl, (total carbon atom number) $C_{3-9}$alkylsulfinyliminoalkylcarbonyl, $C_{1-4}$alkylsulfoxyimino, (total carbon atom number) $C_{2-5}$alkylsulfoxyiminoalkyl, (total carbon atom number) $C_{2-5}$alkoxycarbonyl, (total carbon atom number) $C_{2-5}$alkylcarbonyl, aminocarbonyl, (total carbon atom number) $C_{2-5}$alkylaminocarbonyl, aminothiocarbonyl, (total carbon atom number) $C_{2-5}$alkylaminothiocarbonyl, (total carbon atom number) $C_{3-11}$dialkylaminocarbonyl or (total carbon atom number) $C_{3-9}$dialkylaminothiocarbonyl, more preferably represents hydrogen, halogen, methyl, or trifluoromethyl;

G represents

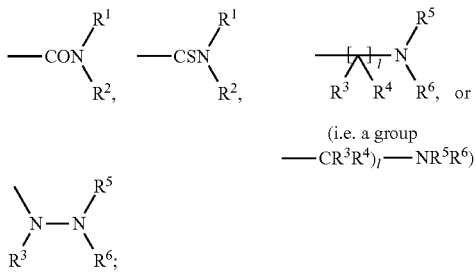

(i.e. a group —$CR^3R^4)_l$—$NR^5R^6$)

l represents 1 or 2, preferably 1;

$R^1$ and $R^2$ each independently represents hydrogen, cyano, $C_{1-6}$alkyl, $C_{1-6}$haloalkyl, $C_{3-7}$cycloalkyl, $C_{3-7}$cyclohaloalkyl, $C_{2-6}$alkenyl, $C_{2-6}$alkynyl, $C_{2-6}$haloalkenyl, $C_{2-6}$haloalkynyl, (total carbon atom number) $C_{2-7}$alkoxycarbonyl, (total carbon atom number) $C_{2-7}$alkoxythiocarbonyl, $C_{1-6}$alkylsulfonyl, $C_{1-6}$haloalkylsulfonyl, phenyl, 4-chlorophenyl, 4-bromophenyl, 4-cyanophenyl, 1-naphthyl, 2-naphthyl, benzyl, 2-fluorobenzyl, 4-fluorobenzyl, 4-chlorobenzyl, 4-bromobenzyl, 1-naphthylmethyl, 2-naphthylmethyl, 1,3-thiazol-2-yl, pyridin-2-yl, pyridin-3-yl, pyridin-4-yl, 2-chloropyridin-3-yl, 2-chloropyridin-5-yl, pyrimidin-2-yl, pyrimidin-4-yl, 5-chloropyrimidin-2-yl, 5-bromopyrimidin-2-yl, 5-cyanopyrimidin-2-yl, quinolin-3-yl, quinolin-6-yl, (1-methyl-1H-pyrazol-4-yl)methyl, (1,3-thiazol-4-yl)methyl, (2-chloro-1,3-thiazol-4-yl)methyl, pyridin-2-ylmethyl, pyridin-3-ylmethyl, pyridin-4-ylmethyl, (6-chloropyridin-3-yl)methyl, pyrimidin-2-ylmethyl, pyridine-2-ylethyl, 1-(pyridin-2-yl)ethyl], (total carbon atom number) $C_{2-12}$alkoxyalkyl, (total carbon atom number) $C_{2-12}$alkylsulfanylalkyl, (total carbon atom number) $C_{2-12}$ alkylsulfinylalkyl, (total carbon atom number) $C_{2-12}$alkylsulfonylalkyl, (total carbon atom number) $C_{2-7}$alkyl-O—N=CH—, (total carbon atom number) $C_{3-13}$alkylaminocarbonylalkyl, (total carbon atom number) $C_{3-13}$haloalkylaminocarbonylalkyl or (total carbon atom number) $C_{5-14}$ cycloalkylaminocarbonylalkyl, preferably represents hydrogen, cyano, $C_{1-4}$ alkyl, $C_{1-4}$haloalkyl, $C_{3-6}$cycloalkyl, $C_{3-6}$cyclohaloalkyl, $C_{2-4}$alkenyl, $C_{2-4}$alkynyl, $C_{2-4}$ haloalkenyl, $C_{2-4}$haloalkynyl, (total carbon atom number) $C_{2-5}$alkoxycarbonyl, (total carbon atom number) $C_{2-5}$ alkoxythiocarbonyl, $C_{1-4}$alkylsulfonyl, $C_{1-4}$haloalkylsulfonyl, $C_{6-12}$ aryl, (total carbon atom number) benzyl, 2-fluorobenzyl, 4-fluorobenzyl, 4-chlorobenzyl, 4-bromobenzyl, 2-chloropyridin-5-yl, pyrimidin-2-yl, 5-chloropyrimidin-2-yl, 5-bromopyrimidin-2-yl, 5-cyanopyrimidin-2-yl, (1-methyl-1H-pyrazol-4-yl)methyl, (1,3-thiazol-4-yl)methyl, pyridin-2-ylmethyl, pyrimidin-2-ylmethyl, 1-(pyridin-2-yl)ethyl, (total carbon atom number) $C_{2-8}$ alkoxyalkyl, (total carbon atom number) $C_{2-8}$alkylsulfanylalkyl, (total carbon atom number) $C_{2-8}$ alkylsulfinylalkyl, (total carbon atom number) $C_{2-8}$alkylsulfonylalkyl, (total carbon atom number) $C_{2-5}$ alkyl-O—N=CH—, (total carbon atom number) $C_{3-9}$alkylaminocarbonylalkyl, (total carbon atom number) $C_{3-9}$haloalkylaminocarbonylalkyl or (total carbon atom number) $C_{5-11}$ cycloalkylaminocarbonylalk, more preferably represents $C_{1-2}$haloalkyl particularly 2,2,2-trifluoroethyl, heterocyclic substituted alkyl, particularly pyridin-2-ylmethyl and pyrimidin-2-ylmethyl), $C_{1-2}$ haloalkylaminocarbonylmethyl, particularly 2-oxo-2-[(2,2,2-trifluoroethyl)amino]ethyl and 2-oxo-2-[(2-chloroethyl)amino]ethyl;

$R^1$ and $R^2$ may together with the nitrogen to which they are attached form a 3- to 7-membered heterocycle;

$R^3$ and $R^4$ each independently represents hydrogen, cyano, $C_{1-6}$alkyl, $C_{2-6}$alkenyl, $C_{2-6}$alkynyl, $C_{3-7}$cycloalkyl or (total carbon atom number) $C_{2-7}$alkoxycarbonyl, preferably represents hydrogen, cyano, $C_{1-4}$ alkyl, $C_{2-4}$alkenyl, $C_{2-4}$alkynyl, $C_{3-6}$cycloalkyl or (total carbon atom number) $C_{2-5}$ alkoxycarbonyl, more preferably represents hydrogen;

when $A^2$ or $A^3$ is C—$Y^2$, then said $Y^2$ and $R^3$, said $Y^2$ and $R^4$, or said $Y^2$, $R^3$ and $R^4$ together may form a 5- to 7-membered saturated or unsaturated hydrocarbon ring or heterocyclic ring together with the carbon atoms to which said $Y^2$ and $R^3$, said $Y^2$ and $R^4$, or said $Y^2$, $R^3$ and $R^4$ are bound and further with the carbon atom between the carbon atom to which $Y^2$ is bound and the carbon atom to which $R^3$ and $R^4$ are bound, or when $A^2$ or $A^3$ is C—$Y^2$ and l is 2, then the carbon atom bound to $R^6$—N($R^5$)— may form carbonyl together with $R^3$ and $R^4$, and the carbon atom bound to Q may form a 5- to 7-membered saturated or unsaturated hydrocarbon ring or heterocyclic ring together with any one or both of $R^3$ and $R^4$ bound thereto and further with $Y^2$, wherein the ring may be substituted with $C_{1-6}$ alkyl, $C_{1-6}$ haloalkyl, $C_{1-6}$ alkoxy, $C_{1-6}$ haloalkoxy, (total carbon atom number) $C_{2-7}$alkylcarbonyl, (total carbon atom number) $C_{2-7}$alkoxycarbonyl, preferably with $C_{1-4}$ alkyl, $C_{1-4}$ haloalkyl, $C_{1-4}$ alkoxy, $C_{1-4}$ haloalkoxy, (total carbon atom number) $C_{2-5}$alkylcarbonyl, (total carbon atom number) $C_{2-5}$alkoxycarbonyl, or carbonyl substituted with a 5- or 6-membered heterocyclic ring, and when one or more of the carbon atoms of the ring are substituted with two or more alkyls, any two of the alkyls may form $C_{3-7}$cycloalkyl, preferably $C_{3-6}$cycloalkyl together with the carbon atoms to which they are bound, or $Y^1$ may form a 5- to 7-membered saturated or unsaturated hydrocarbon ring or heterocyclic ring together with any one or both of $R^3$ and $R^4$, with the carbon atoms to which said $Y^1$ and said $R^3$ and R⁴ are bound and further with the carbon atom between the carbon atom to which Y¹ is bound and the carbon atom to which R³ and R⁴ are bound, and when 1 is 2, then the carbon atom bound to R⁶—N(R⁵)— may form carbonyl together with R³ and R⁴, and the carbon atom bound to Q may form a 5- to 7-membered saturated or unsaturated hydrocarbon ring or heterocyclic ring together with any one or both of R³ and R⁴ bound thereto and further with Y¹, wherein the ring may be substituted with $C_{1-6}$ alkyl, $C_{1-6}$ haloalkyl, $C_{1-6}$ alkoxy, $C_{1-6}$ haloalkoxy, (total carbon atom number) $C_{2-7}$ alkylcarbonyl, (total carbon atom number) $C_{2-7}$ alkoxycarbonyl, preferably with $C_{1-4}$ alkyl, $C_{1-4}$ haloalkyl, $C_{1-4}$ alkoxy, $C_{1-4}$ haloalkoxy, (total carbon atom number) $C_{2-5}$alkylcarbonyl, (total carbon atom number) $C_{2-5}$alkoxycarbonyl or carbonyl substituted with a 5- or 6-membered heterocyclic ring, and when one or more of the carbon atoms of the ring are substituted with two or more alkyls, and any two of said alkyls may form $C_{3-7}$ cycloalkyl, preferably $C_{3-6}$cycloalkyl together with the carbon atoms to which they are bound;

R⁵ represents hydrogen, amino, hydroxy, cyano, $C_{1-6}$alkyl, $C_{1-6}$haloalkyl, $C_{3-7}$cycloalkyl, $C_{2-6}$alkenyl, $C_{2-6}$alkynyl, $C_{1-6}$alkoxy, (total carbon atom number) $C_{2-7}$-aminocarbonylalkyl, $C_{1-6}$iminoalkyl, (total carbon atom number) $C_{2-7}$alkylcarbonyl, (total carbon atom number) $C_{2-7}$alkylcarbonylamino, (total carbon atom number) $C_{2-7}$alkylimino, (total carbon atom number) $C_{6-12}$aryl, (total carbon atom number) $C_{7-16}$aralkyl, a heterocyclic group, heterocyclic ring substituted alkyl, R⁷—C(=O)— or R⁷—C(=S)—, preferably represents hydrogen, amino, hydroxy, cyano, $C_{1-4}$alkyl, $C_{1-4}$haloalkyl, $C_{3-6}$cycloalkyl, $C_{2-4}$alkenyl, $C_{2-4}$alkynyl, $C_{1-4}$alkoxy, (total carbon atom number) $C_{2-5}$aminocarbonylalkyl, $C_{1-4}$iminoalkyl, (total carbon atom number) $C_{2-5}$alkylcarbonyl, (total carbon atom number) $C_{2-5}$alkylcarbonylamino, (total carbon atom number) $C_{2-5}$alkylimino, (total carbon atom number) $C_{6-12}$aryl, (total carbon atom number) $C_{7-10}$aralkyl, a heterocyclic group, heterocyclic ring substituted alkyl, R⁷—C(=O)— or R⁷—C(=S)—, more preferably represents hydrogen or methyl;

R⁶ represents hydrogen, cyano, carbonyl, thiocarbonyl, (total carbon atom number) $C_{2-7}$alkylcarbonyl, (total carbon atom number) $C_{2-7}$alkylthiocarbonyl, (total carbon atom number) $C_{2-7}$haloalkylcarbonyl, (total carbon atom number) $C_{2-7}$haloalkylthiocarbonyl, (total carbon atom number) $C_{2-7}$alkylaminocarbonyl, (total carbon atom number) $C_{2-7}$alkylaminothiocarbonyl, (total carbon atom number) $C_{3-13}$dialkylaminocarbonyl, (total carbon atom number) $C_{3-13}$dialkylaminothiocarbonyl, (total carbon atom number) $C_{2-7}$alkoxyaminocarbonyl, (total carbon atom number) $C_{2-7}$alkoxyaminothiocarbonyl, (total carbon atom number) $C_{2-7}$alkoxycarbonyl, (total carbon atom number) $C_{2-7}$alkoxythiocarbonyl, (total carbon atom number) $C_{2-7}$alkylsulfanylcarbonyl, (total carbon atom number) $C_{2-7}$alkylsulfanylthiocarbonyl, $C_{1-6}$alkylsulfonyl, $C_{1-6}$haloalkylsulfonyl, (total carbon atom number) $C_{4-8}$cycloalkylcarbonyl, (total carbon atom number) $C_{3-7}$alkenylcarbonyl, (total carbon atom number) $C_{3-7}$alkynylcarbonyl, (total carbon atom number) $C_{5-14}$cycloalkylalkylcarbonyl, (total carbon atom number) $C_{3-13}$alkylsulfanylalkylcarbonyl, (total carbon atom number) $C_{3-13}$alkylsulfinylalkylcarbonyl, (total carbon atom number) $C_{3-13}$alkylsulfonylalkylcarbonyl, (total carbon atom number) $C_{4-14}$alkylcarbonylalkylcarbonyl, (total carbon atom number) $C_{4-8}$cycloalkylaminocarbonyl, (total carbon atom number) $C_{3-7}$alkenylaminocarbonyl, (total carbon atom number) $C_{3-7}$alkynylaminocarbonyl, $C_{1-6}$alkylaminosulfonyl, (total carbon atom number) $C_{2-12}$dialkylaminosulfonyl, (total carbon atom number) $C_{3-13}$alkoxyalkylcarbonyl, (total carbon atom number) $C_{4-14}$alkylcarbonylaminoalkylcarbonyl, (total carbon atom number) $C_{4-14}$haloalkylcarbonylaminoalkylcarbonyl, (total carbon atom number) $C_{5-20}$alkylsulfanylalkylcarbonylaminoalkylcarbonyl, (total carbon atom number) $C_{5-20}$alkylsulfinylalkylcarbonylaminoalkylcarbonyl, (total carbon atom number) $C_{5-20}$alkylsulfonylalkylcarbonylaminoalkylcarbonyl, (total carbon atom number) $C_{8-17}$aralkylcarbonyl, heterocyclic substituted (total carbon atom number) $C_{2-7}$alkylcarbonyl, R⁷—C(=O)— or R⁷—C(=S)—, preferably represents hydrogen, cyano, carbonyl, thiocarbonyl, (total carbon atom number) $C_{2-5}$alkylcarbonyl, (total carbon atom number) $C_{2-5}$alkylthiocarbonyl, (total carbon atom number) $C_{2-5}$haloalkylcarbonyl, (total carbon atom number) $C_{2-5}$haloalkylthiocarbonyl, (total carbon atom number) $C_{2-5}$alkylaminocarbonyl, (total carbon atom number) $C_{2-5}$alkylaminothiocarbonyl, (total carbon atom number) $C_{3-9}$dialkylaminocarbonyl, (total carbon atom number) $C_{3-9}$dialkylaminothiocarbonyl, (total carbon atom number) $C_{2-5}$alkoxyaminocarbonyl, (total carbon atom number) $C_{2-5}$alkoxyaminothiocarbonyl, (total carbon atom number) $C_{2-5}$alkoxycarbonyl, (total carbon atom number) $C_{2-5}$alkoxythiocarbonyl, (total carbon atom number) $C_{2-5}$alkylsulfanylcarbonyl, (total carbon atom number) $C_{2-5}$alkylsulfanylthiocarbonyl, $C_{1-4}$alkylsulfonyl, $C_{1-4}$haloalkylsulfonyl, (total carbon atom number) $C_{4-7}$cycloalkylcarbonyl, (total carbon atom number) $C_{3-5}$alkenylcarbonyl, (total carbon atom number) $C_{3-5}$alkynylcarbonyl, (total carbon atom number) $C_{5-11}$cycloalkylalkylcarbonyl, (total carbon atom number) $C_{3-9}$alkylsulfanylalkylcarbonyl, (total carbon atom number) $C_{3-9}$alkylsulfinylalkylcarbonyl, (total carbon atom number) $C_{3-9}$alkylsulfonylalkylcarbonyl, (total carbon atom number) $C_{4-10}$alkylcarbonylalkylcarbonyl, (total carbon atom number) $C_{4-7}$cycloalkylaminocarbonyl, (total carbon atom number) $C_{3-5}$alkenylaminocarbonyl, (total carbon atom number) $C_{3-5}$alkynylaminocarbonyl, $C_{1-4}$alkylaminosulfonyl, (total carbon atom number) $C_{2-8}$dialkylaminosulfonyl, (total carbon atom number) $C_{3-9}$alkoxyalkylcarbonyl, (total carbon atom number) $C_{4-10}$alkylcarbonylaminoalkylcarbonyl, (total carbon atom number) $C_{4-10}$haloalkylcarbonylaminoalkylcarbonyl, (total carbon atom number) $C_{5-14}$alkylsulfanylalkylcarbonylaminoalkylcarbonyl, (total carbon atom number) $C_{5-14}$alkylsulfinylalkylcarbonylaminoalkylcarbonyl, (total carbon atom number) $C_{5-14}$alkylsulfonylalkylcarbonylaminoalkylcarbonyl, (total carbon atom number) $C_{8-11}$aralkylcarbonyl, heterocyclic substituted (total carbon atom number) $C_{2-5}$alkylcarbonyl, R⁷—C(=O)— or R⁷—C(=S)—, more preferably represents $C_{2-5}$alkylcarbonyl particularly acetyl, propionyl, n-propylcarbonyl, iso-propylcarbonyl, n-butylcarbonyl, (total carbon atom number) $C_{2-3}$haloalkylcarbonyl particularly difluoroacetyl, 3,3,3-trifluoropropanoyl, (total carbon atom number) $C_{2-3}$alkylaminocarbonyl particularly ethylcarbamoyl and propylcarbamoyl, (total carbon atom number) $C_{4-5}$cycloalkylcarbonyl particularly cyclopropylcarbonyl and cyclobutylcarbonyl, $C_{3-6}$cycloalkyl($C_{1-4}$)alkylcarbonyl particularly cyclopropylacetyl, (total carbon atom number) $C_{4-7}$ cycloalkylaminocarbonyl particularly cyclopropylcarbamoyl, cyclobutylcarbamoyl and $C_{1-4}$alkoxy($C_{1-4}$)alkylcarbonyl(3-methoxypropanoyl, $C_{1-2}$alkyl-S($C_{1-2}$)alkylcarbonyl, $C_{1-2}$alkyl-SO($C_{1-2}$)alkylcarbonyl, $C_{1-2}$alkyl-SO₂($C_{1-2}$)alkylcarbonyl;

$R^5$ and $R^6$ may form a 3- to 6-membered heterocyclic ring, together with the nitrogen atom to which they are bound, and said ring may be substituted with keto, thioketo or a nitroimino group; and $R^7$ represents phenyl, or a saturated or unsaturated heterocyclic ring;

Moreover, the invention is directed to a pesticide comprising as an active ingredient a compound according to the invention.

Additionally, the invention is directed to an animal parasite-controlling agent comprising as an active ingredient a compound according to the invention.

In another aspect, the invention is directed to compounds which are useful intermediates in the preparation of compounds according to the invention and which are represented by the following formula (XXIV)

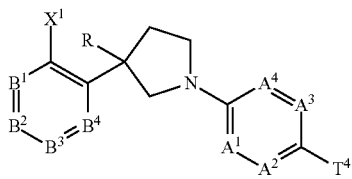

(XXIV)

wherein
$X^1$, R, $A^1$ to $A^4$ and $B^1$ to $B^4$ have the same meaning as defined herein, and wherein $T^4$ is selected among cyano, amino or nitro, and the following chemical groups —C(O)OR$^8$, —C(O)L$^2$, —(CR$^3$R$^4$)$_l$-L$^3$, —(CR$^3$R$^4$)$_l$—NHR$^5$). Wherein 1, $R^3$, $R^4$ and $R^5$ have the same meaning as defined herein;

$R^8$ stands for hydrogen or $C_{1-4}$ alkyl;

$L^2$ represents chloro, bromo, (total carbon number) $C_{2-5}$ alkylcarbonyloxy, (total carbon number) $C_{2-5}$alkoxycarbonyloxy or azolyl; and $L^3$ represents chloro, bromo, iodo, $C_{1-4}$ alkylsulfonyloxy, $C_{1-4}$ haloalkylsulfonyloxy, arylsulfonyloxy or azolyl.

Additionally, the invention is directed to a preparation method (a) for the preparation of compounds of formula (I) which comprises reacting a compound represented by formula (IV):

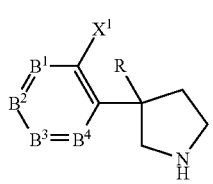

(IV)

wherein $X^1$, R and $B^1$ to $B^4$ have the same meaning as defined herein, with a compound represented by formula (V-I)

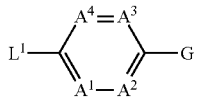

(V-I)

wherein $A^1$ to $A^4$, G and Y have the same meaning as defined above, and $L^1$ stands for halogen or a $C_1$-$C_4$ haloalkylsulfonyloxy group, or with a compound represented by formula (V-II):

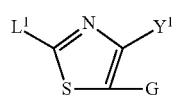

(V-II)

wherein G, $Y^1$ and $L^1$ have the same meaning as defined herein, preferably in the presence of a base and, if necessary, in the presence of a metal catalyst.

And to a preparation method (b) for the preparation of compounds of formula (I) wherein G stands for —CONR$^1$R$^2$ which method comprises reacting an amin represented by formula (VIII):

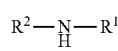

(VIII)

wherein $R^1$ and $R^2$ are as defined herein,
with a compound represented by formula (VI-I), (VI-II), (VII-I), or (VII-II)

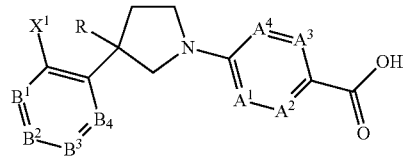

(VI-I)

wherein $X^1$, R, $A^1$ to $A^4$ and $B^1$ to $B^4$ have the same meaning as defined herein,

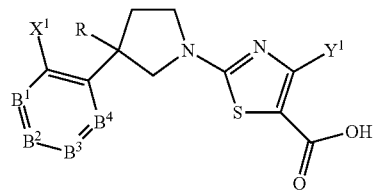

(VI-II)

wherein $X^1$, $Y^1$, R and $B^1$ to $B^4$ have the same meaning as defined herein,

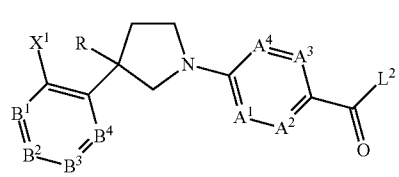

(VII-I)

wherein $X^1$, R, $A^1$ to $A^4$ and $B^1$ to $B^4$ have the same meaning as defined herein, and $L^2$ represents chloro, bromo, (total carbon number) $C_{2-5}$alkylcarbonyloxy, (total carbon number) $C_{2-5}$aloxycarbonyloxy or azolyl,

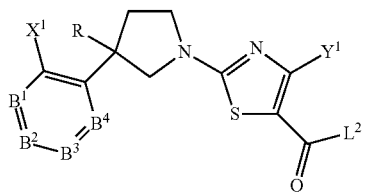
(VII-II)

wherein $X^1$, $Y^1$, R, $B^1$ to $B^4$ and $L^2$ have the same meaning as defined above, in the presence of a condensation agent, and preferably in the presence of a suitable base.

And to a preparation method (c) for the preparation of compounds of formula (I) wherein G stands for —$CONR^1R^2$ and which method comprises reacting a compound represented by formula (Ib-I) or (Ib-II):

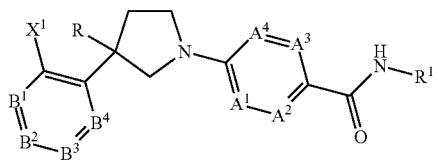
(Ib-I)

wherein $X^1$, R, $R^1$, $A^1$ to $A^4$ and $B^1$ to $B^4$ have the same meaning as defined above,

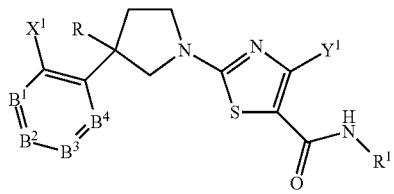
(Ib-II)

wherein $X^1$, $Y^1$, R, $R^1$ and $B^1$ to $B^4$ have the same meaning as defined herein, with a compound $R^2$-$L^3$ (IX) wherein $R^2$ has the same meaning as defined herein, and $L^3$ represents chloro, bromo, iodo, $C_{1-4}$alkylsulfonyloxy, $C_{1-4}$ haloalkylsulfonyloxy, arylsulfonyloxy or azolyl, preferably, in the presence of a base.

And to a preparation method (d) for the preparation of compounds of formula (I) wherein G stands for —$CSNR^1R^2$, which method comprises reacting a compound represented by formula (Ia-I), or (Ia-II)

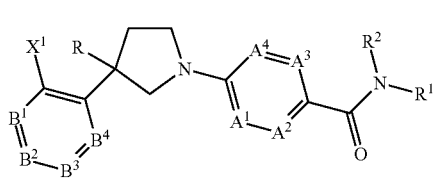
(Ia-I)

wherein $X^1$, R, $R^1$, $R^2$, $A^1$ to $A^4$ and $B^1$ to $B^4$ have the same meaning as defined herein,

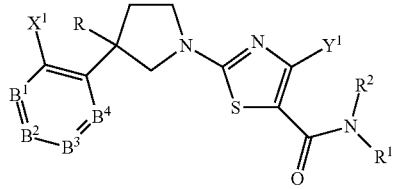
(Ia-II)

wherein $X^1$, $Y^1$, R, $R^1$, $R^2$ and $B^1$ to $B^4$ have the same meaning as defined herein, with a sulfurizing agent.

And to a preparation method (e) for the preparation of compounds of formula (I) wherein G stands for

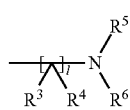

which method comprises reacting a compound represented by formula (X-I), or (X-II)

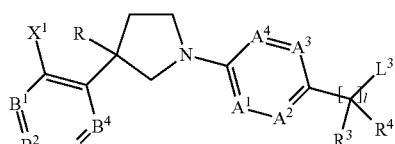
(X-I)

wherein $X^1$, R, $R^3$, $R^4$, $A^1$ to $A^4$, $B^1$ to $B^4$, l and $L^3$ have the same meaning as defined herein,

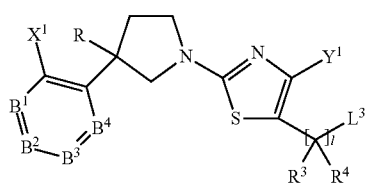
(X-II)

wherein $X^1$, $Y^1$, R, $R^3$, $R^4$, $B^1$ to $B^4$, l and $L^3$ have the same meaning as defined herein, with a compound represented by formula (XI)

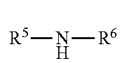
(XI)

wherein $R^5$ and $R^6$ have the same meaning as defined herein, preferably in the presence of a base.

And to a preparation method (f) for the preparation of compounds of formula (I) wherein G stands for

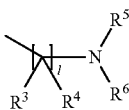

which method comprises reacting a compound represented by formula (XII-I), or (XII-II):

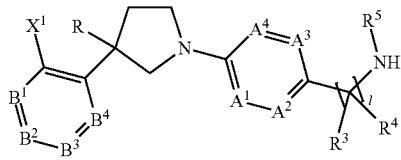
(XII-I)

wherein $X^1$, R, $R^3$, $R^4$, $R^5$, $A^1$ to $A^4$, l and $B^1$ to $B^4$ have the same meaning as defined herein,

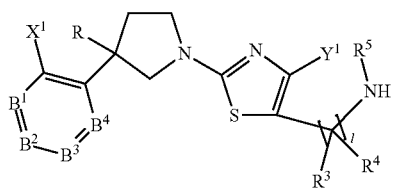
(XII-II)

wherein $X^1$, $Y^1$, R, $R^3$, $R^4$, $R^5$, l and $B^1$ to $B^4$ have the same meaning as defined herein, with a compound $R^6$-$L^4$ (XIII)

wherein $R^6$ has the same meaning as defined above, and wherein $L^4$ represents fluoro, chloro, bromo, a $C_{1-4}$alkylcarbonyloxy group, a $C_{1-4}$alkoxy-carbonyloxy group, an azolyl group, a $C_{1-4}$ alkylsulfonyloxy group, a $C_{1-4}$ haloalkylsulfonyloxy group, or an arylsulfonyloxy group), preferably in the presence of a base.

And to a preparation method (g) for the preparation of compounds of formula (I) wherein G stands for

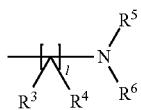

which method comprises reacting a compound represented by formula (Ic-I) or (Ic-II):

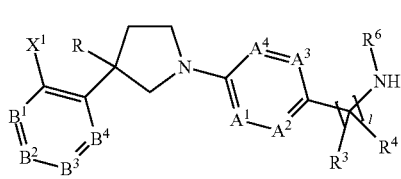
(Ic-1)

wherein $X^1$, R, $R^3$, $R^4$, $R^6$, $A^1$ to $A^4$, l and $B^1$ to $B^4$ have the same meaning as defined herein,

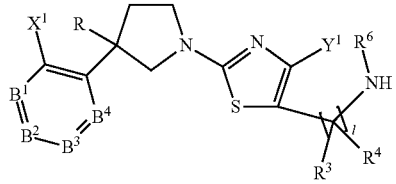
(Ic-II)

wherein $X^1$, $Y^1$, R, $R^3$, $R^4$, $R^6$, l and $B^1$ to $B^4$ have the same meaning as defined herein, with a compound $R^5$-$L^4$ (XIV), wherein $R^5$ and $L^4$ have the same meaning as defined herein, preferably in the presence of a base.

According to the present invention, the arylpyrrolidines represented by formula (I) of the present invention have a very strong pesticidal efficacy.

In the present specification, the term "alkyl" indicates linear or branched $C_{1-12}$ alkyl, for example, methyl, ethyl, n- or iso-propyl, n-, iso-, sec- or tert-butyl, n-pentyl, n-hexyl, n-heptyl, n-octyl, n-nonyl, n-decyl, n-undecyl, n-dodecyl and the like, preferably $C_{1-6}$ alkyl, and more preferably $C_{1-4}$ alkyl.

In addition, for an alkyl moiety that is comprised in other groups as a part of their constitution, those described in the above for the "alkyl" can be exemplified.

The term "haloalkyl" indicates a carbon chain in which at least one hydrogen on linear or branched $C_{1-12}$ alkyl, preferably $C_{1-6}$alkyl, and more preferably $C_{1-4}$alkyl is substituted with a halogen(s), for example, $CH_2F$, $CHF_2$, $CF_3$, $CF_2Cl$, $CFCl_2$, $CF_2Br$, $CF_2CF_3$, $CFHCF_3$, $CH_2CF_3$, $CFClCF_3$, $CCl_2CF_3$, $CF_2CH_3$, $CF_2CH_2F$, $CF_2CHF_2$, $CF_2CF_2Cl$, $CF_2CF_2Br$, $CFHCH_3$, $CFHCHF_2$, $CFHCHF_2$, $CHFCF_3$, $CHFCF_2Cl$, $CHFCF_2Br$, $CFClCF_3$, $CCl_2CF_3$, $CF_2CF_2CF_3$, $CH_2CF_2CF_3$, $CF_2CH_2CF_3$, $CF_2CF_2CH_3$, $CHFCF_2CF_3$, $CF_2CHFCF_3$, $CF_2CF_2CHF_2$, $CF_2CF_2CH_2F$, $CF_2CF_2CF_2Cl$, and $CF_2CF_2CF_2Br$. The haloalkyl may be further substituted.

The term "alkoxy" indicates linear or branched $C_{1-12}$, preferably $C_{1-6}$, and more preferably $C_{1-4}$ alkoxy, for example, methoxy, ethoxy, n-propoxy, i-propoxy, n-, iso-, sec- or tert-butoxy, pentyloxy, or hexyloxy. The alkoxy may be further substituted.

The term "acylamino" for example indicates alkylcarbonylamino, cyclopropylcarbonylamino and benzoylamino. In addition, for an alkyl moiety that is comprised in these groups as a part of their constitution, those described in the above for the "alkyl" can be exemplified.

The term "halogen" and the halogen moiety that is comprised in halogen-substituted groups represent fluoro, chloro, bromo, or iodo, and preferably fluoro, chloro, or bromo.

The term "cycloalkyl" indicates $C_{3-8}$ cycloalkyl of cyclopropyl, cyclobutyl, cyclopentyl, cyclohexyl, cycloheptyl, and cyclooctyl, preferably $C_{3-7}$cycloalkyl, and more preferably $C_{3-6}$ cycloalkyl.

The term "alkenyl" indicates $C_{2-6}$alkenyl, preferably $C_{2-5}$alkenyl, such as vinyl, allyl, 1-propenyl, 1-(or 2-, or 3-)butenyl, 1-pentenyl, and the like, and more preferably $C_{2-4}$alkenyl.

The term "alkynyl" indicates $C_{2-6}$alkynyl, preferably $C_{2-5}$alkynyl such as ethynyl, propargyl, 1-propynyl, butan-3-ynyl, pentan-4-ynyl, and the like, and more preferably $C_{2-4}$alkynyl.

The term "aryl" indicates a $C_6$-$C_{12}$ aromatic hydrocarbon group, for example, phenyl, naphthyl, and biphenyl, and preferably a $C_{6-10}$ aromatic hydrocarbon group, and more preferably phenyl.

The term "aralkyl" indicates arylalkyl, for example, benzyl and phenethyl.

The term "heterocyclic ring" represents a 5- or 6-membered heterocyclic ring wherein at least one heteroatom selected from the group consisting of N, O and S is comprised and also the ring represents a fused heterocyclic ring that can be benzo-fused.

Specific examples of the heterocyclic ring may include furyl, thienyl, pyrrolyl, isoxazolyl, pyrazolyl, oxazolyl, thiazolyl, imidazolyl, triazolyl, oxadiazolyl, thiadiazolyl, tetrazolyl, pyridyl, pyrimidinyl, pyridazinyl, pyrazinyl, triazinyl, indolyl, benzoxazolyl, quinolyl and the like.

All chemical groups, particularly the groups amino, alkyl, haloalkyl, cycloalkyl, cyclohaloalkyl, alkenyl, alkynyl, alkoxy, haloalkoxy, alkylsulfanyl, alkylsulfinyl, alkylsulfonyl, haloalkylsulfanyl, haloalkylsulfinyl, haloalkylsulfonyl, alkylsulfonyloxy, haloalkylsulfonyloxy, alkylaminosulfonyl, haloalkylaminosulfonyl, dialkylaminosulfonyl, di(haloalkyl)aminosulfonyl, alkylamino, dialkylamino, acylamino, alkoxycarbonylamino, haloalkoxycarbonylamino, alkylsulfonylamino, haloalkylsulfonylamino, trialkylsilyl, alkoxyimino, haloalkoxyimino, alkoxyiminoalkyl, haloalkoxyiminoalkyl, alkylsulfinylimino, alkylsulfinyliminoalkyl, alkylsulfinyliminoalkylcarbonyl, alkylsulfoxyimino, alkylsulfoxyiminoalkyl, alkoxycarbonyl, alkylcarbonyl, aminocarbonyl, alkylaminocarbonyl, aminothiocarbonyl, alkylaminothiocarbonyl, dialkylaminocarbonyl, or dialkylaminothiocarbonyl, may be substituted by at least one substitutent which may be selected among amino, hydroxy, halogen, nitro, cyano, isocyano, mercapto, isothiocyanate, carboxy, carboamide, $SF_5$, aminosulfonyl, alkyl, cycloalkyl, alkenyl, cycloalkenyl, alkynyl, monoalkylamino, dialkylamino, N-alkylcarbonyl-amino, alkoxy, alkenyloxy, alkynyloxy, cycloalkyloxy, cycloalkenyloxy, alkoxycarbonyl, alkenyloxycarbonyl, alkynyloxycarbonyl, aryloxycarbonyl, alkylcarbonyl, alkenylcarbonyl, alkynylcarbonyl, arylcarbonyl, alkylthio, cycloalkylthio, alkenylthio, cycloalkenylthio, alkynylthio, alkylsulfanyl, alkylsulfinyl, alkylsulfinyl including their isomers, alkylsulfonyl, monoalkylaminosulfonyl, dialkylaminosulfonyl, alkylphosphinyl, alkylphosphonyl, alkylphosphinyl including their isomers, alkylphosphonyl including their isomers, N-alkyl-aminocarbonyl, N,N-dialkyl-aminocarbonyl, N-alkylcarbonyl-aminocarbonyl, N-alkylcarbonyl-N-alkylaminocarbonyl, aryl, aryloxy, benzyl, benzyloxy, benzylthio, arylthio, arylamino, benzylamino, heterocyclic ring, trialkylsilyl, alkoxyalkyl, alkylthioalkyl, alkylthioalkoxy, alkoxyalkoxy, phenethyl, benzyloxy, haloalkyl, haloalkoxy, haloalkylthio, haloalkylcarbonyl, haloalkoxycarbonyl, haloalkoxyalkoxy, haloalkoxyalkylthio, haloalkoxyalkylcarbonyl and haloalkoxyalkyl, preferably, chloro, fluoro, bromo, iodo, amino, nitro, cyano, hydroxy, thio and carboxy.

The expression, "$Y^2$, $R^3$ and $R^4$ together" in the expression, "said $Y^2$ and $R^3$, said $Y^2$ and $R^4$ or said $Y^2$, $R^3$ and $R^4$ together may form a 5- to 7-membered saturated or unsaturated hydrocarbon ring or heterocyclic ring together with the carbon atoms to which said $Y^2$ and $R^3$, said $Y^2$ and $R^4$ or said $Y^2$, $R^3$ and $R^4$ are bound and further with the carbon atom between the carbon atom to which $Y^2$ is bound and the carbon atom to which $R^3$ and $R^4$ are bound" which is specified when $A^2$ or $A^3$ is C—$Y^2$ indicates that, for example, $R^3$ and $R^4$ together form an alkenylene group, and further form an unsaturated hydrocarbon ring (e.g., phenyl, cyclopentenyl or cyclohexenyl) together with $Y^2$. In addition, the expression, "both of $R^3$ and $R^4$" in the expression, "the carbon atom bound to $R^6$—N ($R^5$)— may form carbonyl together with $R^3$ and $R^4$, and the carbon atom bound to Q may form a 5- to 7-membered saturated or unsaturated hydrocarbon ring or heterocyclic ring together with any one or both of $R^3$ and $R^4$ bound thereto and further with $Y^2$" which is specified when 1 is 2 also indicates that, for example, $R^3$ and $R^4$ together form an alkenylene group, and further form an unsaturated hydrocarbon ring (e.g., phenyl, cyclopentenyl, cyclohexenyl) together with the carbon atom bound to Q and $Y^2$.

The same is applied to the case where $Y^1$ forms a ring together with both of $R^3$ and $R^4$.

The phrase "(total carbon atom number)", which is used in relation to a group with any substituent, indicates the number of carbon atom included in the whole group without such substituent.

In an aspect of the invention compounds of formula (A) or (B) are preferred

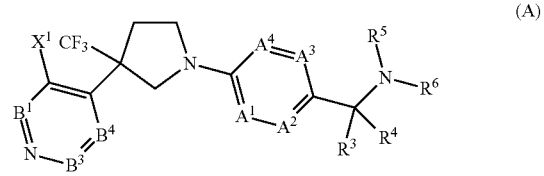

(A)

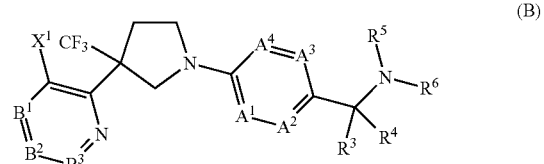

(B)

wherein $B^1$, $B^3$, $B^4$, $X^1$, $A^1$ to $A^4$ and $R^2$ to $R^6$ are as defined herein.

Among the compounds of formula (A), compounds having the following structures (A-I) to (A-III) are particularly preferred

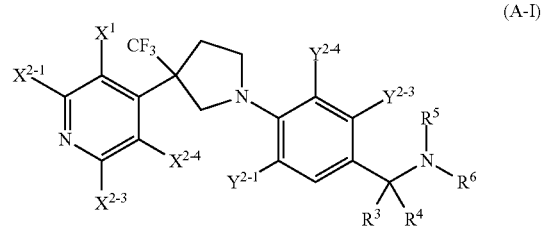

(A-I)

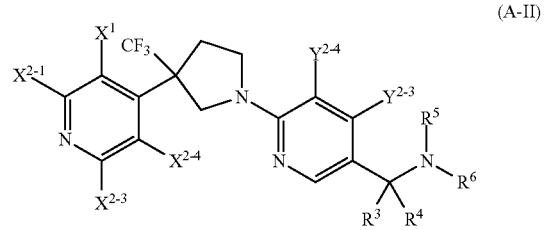

(A-II)

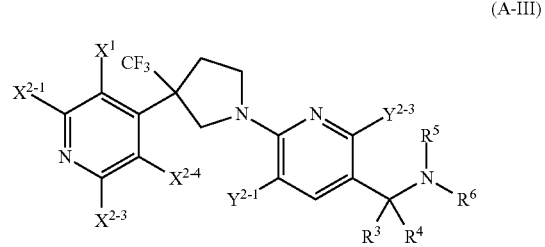

(A-III)

and wherein $X^1$, $R^3$, $R^4$, $R^5$ and $R^6$ are as defined herein, each $X^{2-1}$, $X^{2-2}$, $X^{2-3}$ and $X^{2-4}$ are as defined herein for $X^2$, and wherein each $Y^{2-1}$, $Y^{2-3}$ and $Y^{2-4}$ are as defined herein for $Y^2$.

Among the compounds of formula (B), compounds having the following structures (B-I) to (B-III) are particularly preferred

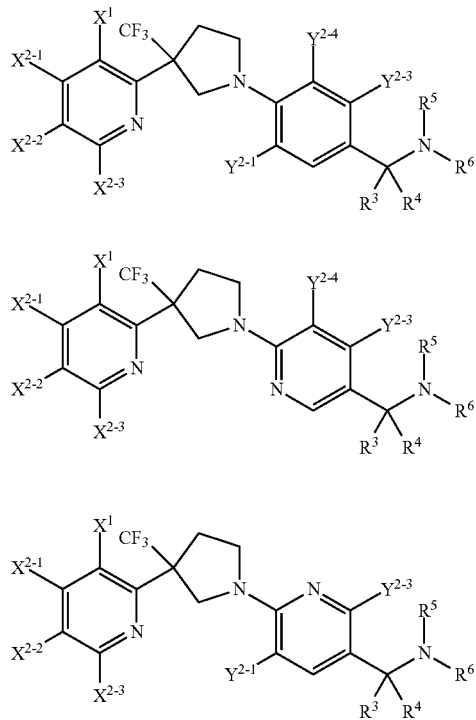

and wherein $X^1$, $R^3$, $R^4$, $R^5$ and $R^6$ are as defined herein, each $X^{2-1}$, $X^{2-2}$, $X^{2-3}$ and $X^{2-4}$ are as defined herein for $X^2$, and wherein each $Y^{2-1}$, $Y^{2-3}$ and $Y^{2-4}$ are as defined herein for $Y^2$.

In another aspect of the invention compounds of formula (C-I) to (C-IV) are preferred having the following formula

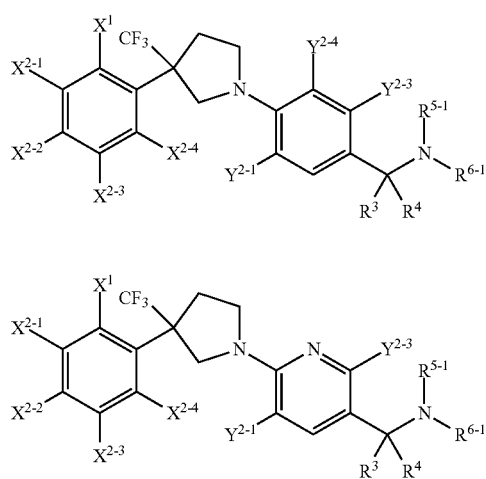

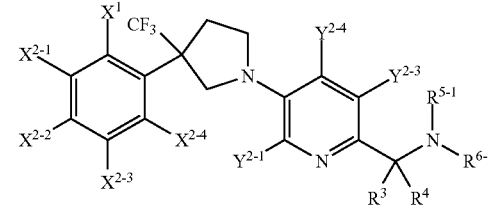

and wherein the chemical groups $X^1$ is defined as for $X^1$, $X^{2-1}$, $X^{2-2}$, $X^{2-3}$, $X^{2-4}$ are as defined for $X^2$ and $Y^{2-1}$, $Y^{2-3}$ and $Y^{2-4}$ are as defined for $Y^2$, and $R^3$, $R^4$ are as defined herein, whereas $R^{5-1}$ is defined as for $R^5$ and $R^{6-1}$ is as defined for $R^6$.

In the formula (C-I) to (C-IV), the chemical groups $X^1$, $X^{2-1}$, $X^{2-2}$, $X^{2-3}$ and $X^{2-4}$ independently of each other preferably represents hydrogen, halogen (i.e. F, Cl, Br, I) or $C_{1-4}$-haloalkyl (e.g. $CF_3$, $CF_2H$, $CFH_2$, $CH_2CF_3$, $CF_2$—$CF_3$), whereas it is preferred that at least one of the groups $X^1$, $X^{2-1}$, $X^{2-2}$, $X^{2-3}$, $X^{2-4}$ stands for hydrogen, preferably one of $X^1$ and/or $X^{2-4}$ and/or $X^{2-2}$ stands for hydrogen, it is most preferred that $X^1$ and $X^{2-4}$ both are standing for hydrogen while the other groups are standing independently of each other for $CF_3$, F, Cl, Br, and/or the chemical groups $Y^{2-1}$, $Y^{2-3}$ and $Y^{2-4}$ independently of each other preferably represents hydrogen, halogen (e.g. F, Cl, Br, I), $C_{1-4}$-alkyl, $C_{1-4}$-alkoxy, $C_{1-4}$-haloalkoxy, $C_{3-6}$-cycloalkyl, $C_{1-4}$-haloalkyl (e.g. $CF_3$, $CF_2H$, $CFH_2$, $CH_2CF_3$, $CF_2$—$CF_3$), $C_{1-4}$-alkylsulfanyl, or $C_{1-4}$-haloalkylsulfanyl, and/or wherein $R^3$ or $R^4$ independently of each other preferably stands for hydrogen, and wherein $R^{5-1}$ independently of each other preferably stands for hydrogen, $C_{1-4}$alkyl or $C_{1-4}$haloalkyl, preferably hydrogen;

and/or wherein $R^{6-1}$ preferably represents $C_{3-6}$cycloalkyl $(C_{1-4})$alkylcarbonyl, $C_{1-4}$alkoxy$(C_{1-4})$alkylcarbonyl, $C_{1-4}$alkyl-S$(C_{1-4})$alkylcarbonyl, $C_{1-4}$alkyl-SO$(C_{1-4})$alkylcarbonyl, $C_{1-4}$alkyl-SO$_2(C_{1-14})$alkylcarbonyl, more preferably represents one of the following groups

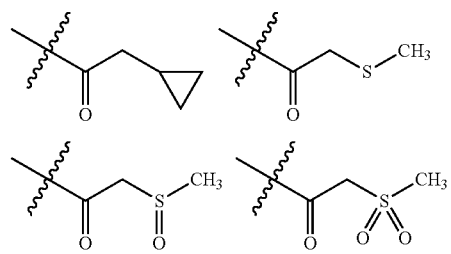

-continued

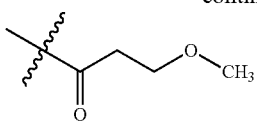

In another aspect of the invention compounds of formula (D-I) to (D-III) are preferred having the following formula

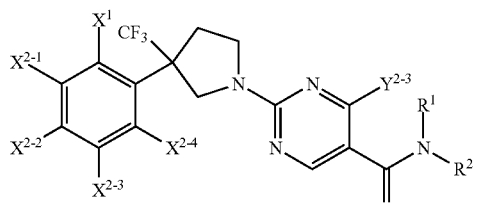
(D-I)

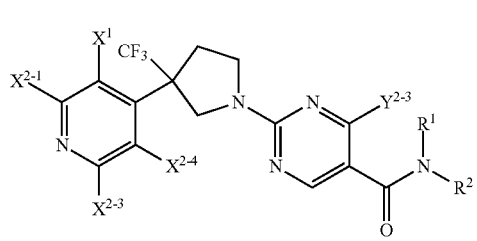
(D-II)

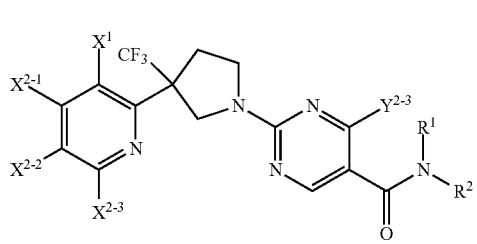
(D-III)

and wherein each $X^1$, $R^1$ and $R^2$ are as defined herein, and each $X^{2-1}$, $X^{2-2}$, $X^{2-3}$ and $X^{2-4}$ are as defined herein for $X^2$, and wherein $Y^{2-3}$ is as defined herein for $Y^2$.

In another aspect of the invention compounds of formula (E-I) to (E-III) are preferred having the following formula

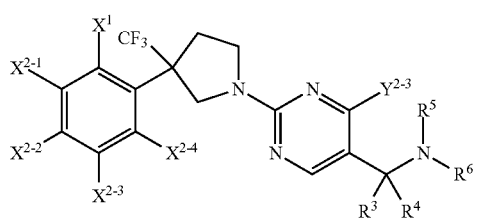
(E-I)

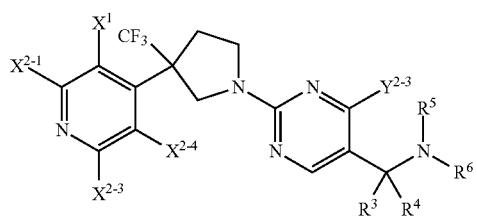
(E-II)

-continued

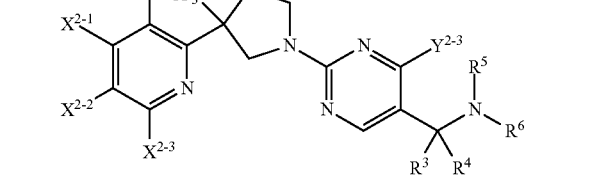
(E-III)

and wherein each $X^1$, $R^3$, $R^4$, $R^5$ and $R^6$ are as defined herein, and each $X^{2-1}$, $X^{2-2}$, $X^{2-3}$ and $X^{24}$ are as defined herein for $X^2$, and wherein $Y^{2-3}$ is as defined herein for $Y^2$.

In another aspect of the invention compounds of formula (F-I) to (F-III) are preferred having the following formula

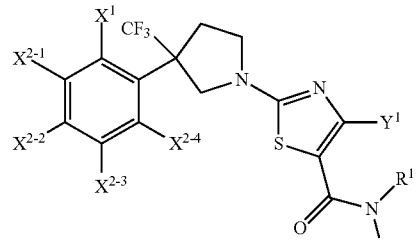
(F-I)

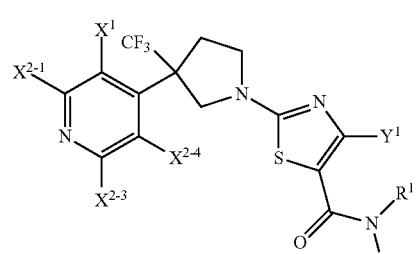
(F-II)

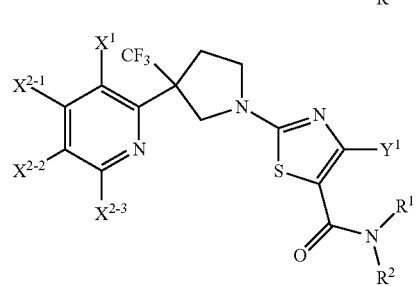
(F-III)

and wherein each $X^1$, $Y^1$, $R^1$ and $R^2$ are as defined herein, and wherein each $X^{2-1}$, $X^{2-2}$, $X^{2-3}$ and $X^{2-4}$ are as defined herein for $X^2$.

In another aspect of the invention compounds of formula (G-I) to (G-III) are preferred having the following formula

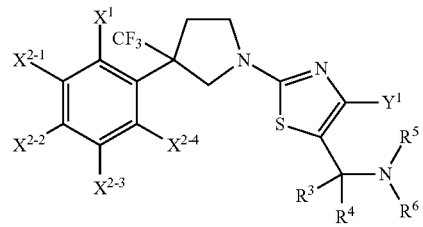
(G-I)

-continued (G-II)

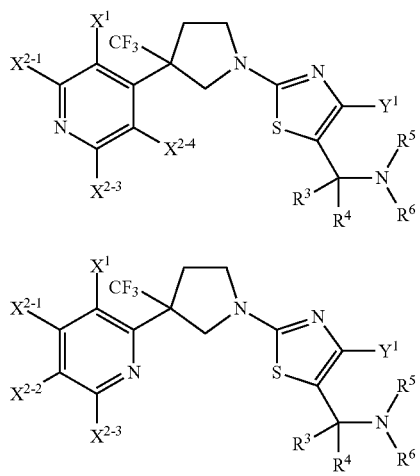

(G-III)

and wherein each $X^1$, $Y^1$, $R^3$, $R^4$, $R^5$ and $R^6$ are as defined herein, and wherein each $X^{2-1}$, $X^{2-2}$, $X^{2-3}$ and $X^{2-4}$ are as defined herein for $X^2$ In another aspect of the invention compounds of formula (H-I) to (H-III) are preferred having the following formula (H-I)

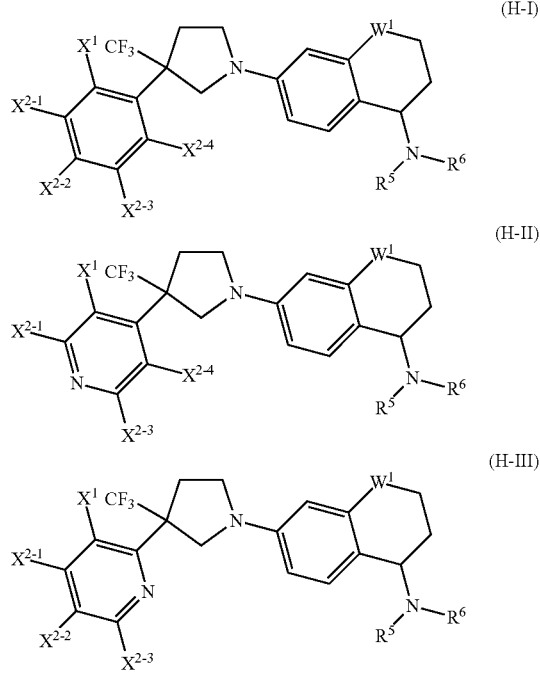

(H-II)

(H-III)

and wherein each $X^1$, $Y^1$, $R^5$ and $R^6$ are as defined herein, each $X^{2-1}$, $X^{2-2}$, $X^{2-3}$ and $X^{2-4}$ are as defined herein for $X^2$, and wherein $W^1$ represents single bond or —CH$_2$—;

The compounds of formula (I) of the present invention have asymmetric carbons, and thus the compounds encompass optical isomers.

The nitrogen atom on the pyrrolidine backbone of the compounds of formula (I) of the present invention may be substituted with oxygen, alkyl or haloalkyl or may form a salt.

Preparation method (a) is exemplified by the reaction given below in which 3-(3,4,5-trichlorophenyl)-3-(trifluorom-ethyl)pyrrolidine and N-{[2-bromo-4-(trifluoromethyl)pyrimidin-5-yl]methyl}acetamide are used as starting materials:

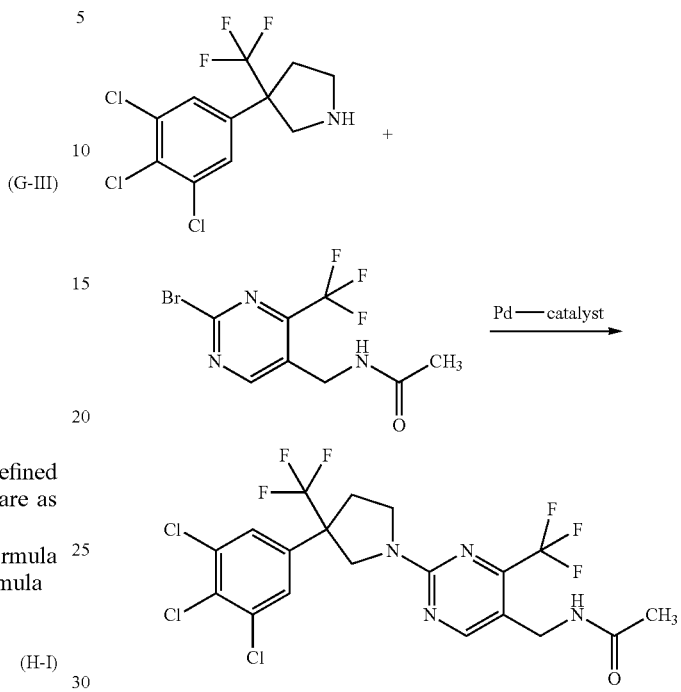

Preparation method (b) is exemplified by the reaction given below in which 2-[3-(3,4,5-trichlorophenyl)-3-(trifluoromethyl)pyrrolidin-1-yl]-4-(trifluoromethyl)-pyrimidine-5-carboxylic acid and 2-picolylamine are used as starting materials:

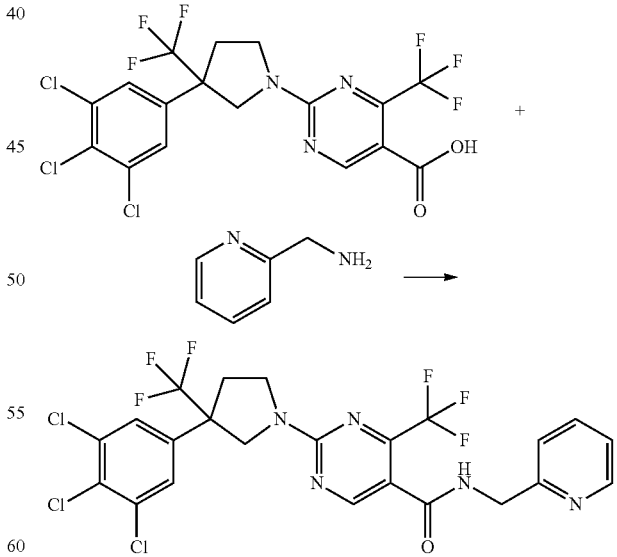

Preparation method (c) is exemplified by the reaction given below in which N-(pyridin-2-ylmethyl)-2-[3-(3,4,5-trichlorophenyl)-3-(trifluoromethyl)pyrrolidin-1-yl]-4-(trifluoromethyl)pyrimidine-5-carboxamide and iodomethane are used as starting materials:

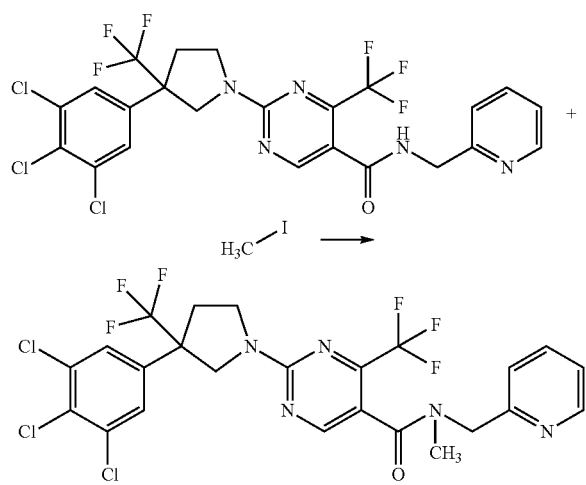

Preparation method (d) is exemplified by the reaction given below in which N-(pyridin-2-ylmethyl)-2-[3-(3,4,5-trichlorophenyl)-3-(trifluoromethyl)pyrrolidin-1-yl]-4-(trifluoromethyl)pyrimidine-5-carboxamide and Lawesson reagent are used as starting materials:

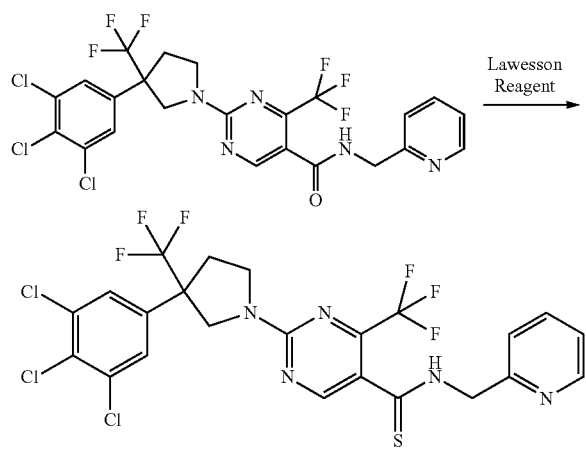

Preparation method (e) is exemplified by the reaction given below in which 5-(bromomethyl)-2-[3-(3,4,5-trichlorophenyl)-3-(trifluoromethyl)pyrrolidin-1-yl]-4-(trifluoromethyl)pyrimidine and benzamide are used as starting materials:

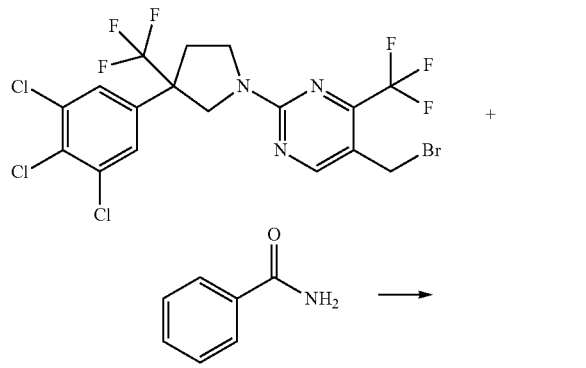

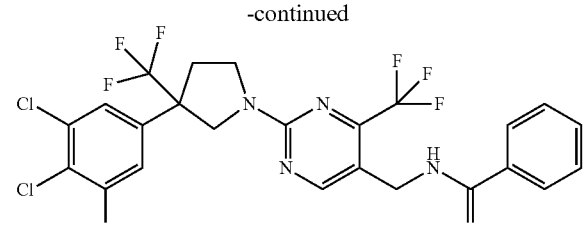

Preparation method (f) is exemplified by the reaction given below in which 1-{2-[3-(3,4,5-trichlorophenyl)-3-(trifluoromethyl)pyrrolidin-1-yl]-4-(trifluoromethyl)-pyrimidin-5-yl}methanamine and acetyl chloride are used as starting materials:

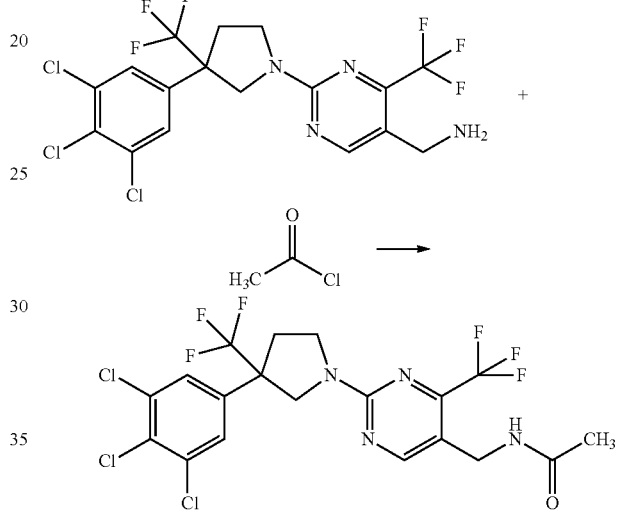

Preparation method (g) is exemplified by the reaction given below in which N-({2-[3-(3,4,5-trichlorophenyl)-3-(trifluoromethyl)pyrrolidin-1-yl]-4-(trifluoro-methyl)pyrimidin-5-yl}methyl)acetamide and iodomethane are used as starting materials:

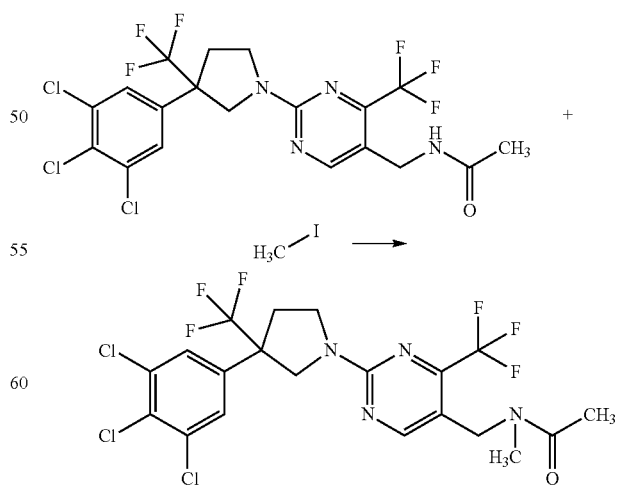

The compounds of formula (IV), which are the starting materials in the Preparation method (a), can be synthesized by the method described below. Specifically, the compounds represented by the following formula (XV):

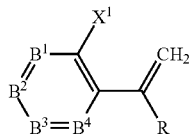

(XV)

wherein $X^1$, $B^1$ to $B^4$ and R have the same meaning as defined herein can be reacted with N-benzyl-1-methoxy-N-[(trimethylsilyl)-methyl]methanamine in the presence of a catalyst (e.g. trifluoroacetic acid, trimethylsilyl trifluoromethane sulfonate, iodotrimethylsilane, cesium fluoride) to give the compounds represented by formula (XVI):

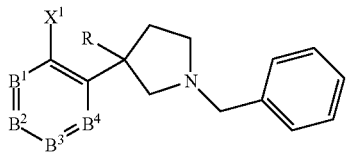

(XVI)

wherein $X^1$, $B^1$ to $B^4$ and R have the same meaning as defined herein, followed by debenzylation to obtain the compounds represented by the above formula (IV).

The reaction which yields compounds of formula (XVI) may be carried out according to the methods described in "Chemistry Letters, 1984, 1117-1120" and "Tetrahedron Letters, 1993, 34, 3279-3282". The deprotection reaction such as the debenzylation of compounds of formula (XVI) may be carried out according to the methods described in "Journal of the Organic Chemistry, 1984, 49, 2081" and "PROTECTIVE GROUPS in ORGANIC CHEMISTRY THIRD EDITION, JOHN WILEY & SONS, INC".

The compounds of the above formula (XV) encompass the compounds that are known and described, for example in "The Journal of Organic Chemistry, 1991, vol. 56, pp. 7336-7340"; "The Journal of Organic Chemistry, 1994, vol. 59, pp. 2898-2901"; "Journal of Fluorine Chemistry, 1999, vol. 95, pp. 167-170"; "WO2005/05085216A". Such compounds may be synthesized by the methods described therein.

Representative examples of the compounds of formula (XV) include [1-(trifluoromethyl)vinyl]benzene, 1-chloro-3-[1-(trifluoromethyl)vinyl]benzene, 1-bromo-3-[1-(trifluoromethyl)vinyl]benzene, 1-nitro-3-[1-(trifluoromethyl)vinyl]benzene, 1-trifluoromethyl-3-[1-(trifluoromethyl)vinyl]benzene, 1,3-difluoro-5-[1-(trifluoromethyl)vinyl]benzene, 1,3-dichloro-5-[1-(trifluoromethyl)vinyl]benzene, 1,3-difluoro-5-[1-(trifluoromethyl)vinyl]benzene, 1-fluoro-2-(trifluoromethyl)-4-[1-(trifluoromethyl)vinyl]benzene, 1,2,3-trichloro-5-[1-(trifluoromethyl)vinyl]benzene, 1,3-dimethyl-2-nitro-5-[1-(trifluoromethyl)vinyl]benzene.

Instead of N-benzyl-1-methoxy-N-[(trimethylsilyl)methyl]methanamine in the above reaction, N-benzyl-1-butoxy-N-[(trimethylsilyl)methyl]methanamine or N-(butoxymethyl)-N-[(trimethylsilyl)methyl]cyclohexylamine may be used.

Representative examples of the compounds of formula (IV) in the Preparation method (a) include 3-(3,5-dichlorophenyl)-3-(trifluoromethyl)pyrrolidine, 3-[3,5-bis(trifluoromethyl)phenyl]-3-(trifluoromethyl)pyrrolidine, 3-(3,4,5-trichlorophenyl)-3-(trifluoromethyl)pyrrolidine, and 3-(3,5-dimethyl-4-nitrophenyl)-3-(trifluoromethyl)pyrrolidine.

Many of the compounds of formula (V-I) or (V-II), which are starting materials in the Preparation method (a), are known compounds, and they may be readily synthesized by the methods widely known in organic chemistry.

The specific examples of formula (V-I) include for example 2-chloro-N-ethyl-4-(trifluoromethyl)pyrimidine-5-carboxamide, tert-butyl (5-bromo-2,3-dihydro-1H-inden-1-yl)carbamate that is described in US Pat. No. 2008/0021024.

Further, the specific examples of formula (V-II) may include: 2-chloro-N-ethyl-4-(trifluoromethyl)-1,3-thiazole-5-carboxamide and the like.

The reaction of the Preparation method (a) can be carried out in a suitable diluent, and examples thereof include aliphatic hydrocarbons (e.g. hexane, cyclohexane, heptane etc.), aliphatic halogenated hydrocarbons (e.g. dichloromethane, chloroform, carbon tetrachloride, dichloroethane, etc.), aromatic hydrocarbons (e.g. benzene, toluene, xylene, chlorobenzene etc.), ethers (e.g. diethyl ether, dibutyl ether, dimethoxyethane (DME), tetrohydrofuran, dioxane etc.), esters (e.g. ethyl acetate, ethyl propionate etc.), acid amides (e.g. dimethylformamide (DMF), dimethylacetamide (DMA), N-methylpyrrolidone etc.), nitriles (e.g. acetonitrile, propionitrile etc.), dimethylsulfoxide (DMSO), water or mixed solvents thereof and the like.

The reaction of the Preparation method (a) can be carried out in the presence of a base, such as alkali metal bases (e.g. lithium hydride, sodium hydride, potassium hydride, butyl lithium, tert-butyl lithium, trimethylsilyl lithium, lithium hexamethyldisilazide, sodium carbonate, potassium carbonate, cesium carbonate, tripotassium phosphate, sodium acetate, potassium acetate, sodium methoxide, sodium ethoxide, sodium-tert-butoxide and potassium-tert-butoxide etc.), organic bases (e.g. triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane, imidazole etc.) and optionally in the presence of a metal catalyst such as transition metal catalysts (eg. $Pd_2(dba)_3$, $Pd_2(dba)_3CHCl_3$ (dba=dibenzylideneacetone), $Pd(OAc)_2$, CuI, $Cu_2O$). The transition metal catalyst can be used in the presence of phosphine ligands such as 2,2'-bis(diphenylphosphino)-1,1'-binaphtalene (BINAP), 4,5-bis(diphenylphosphino)-9,9-dimethylxanthene (Xantphos), tributylphosphine, triphenylphosphine, or amine ligands such as 8-quinolinol, proline, N,N-dimethylglycine.

The preparation method (a) can be carried out within a substantially wide temperature range. It may be generally carried out at the temperature between about −78° C. and about 200° C., preferably between −10° C. and about 150° C. Said reaction is desirably carried out at normal pressure although it may be carried out under elevated or reduced pressure. The reaction time is 0.1 to 72 hours, preferably 0.1 to 24 hours.

For carrying out the Preparation method (a), for example, 1 mole of the compound of formula (IV) can be reacted with 1 to 3 moles of the compound of formula (V-I) or (V-II) in the presence of 1 to 3 moles of a base (e.g. sodium-tert-butoxide and a catalytic amount (e.g. in the range of about 1 to 10 mol-%) of the transitional metal catalyst (e.g. $Pd_2(dba)_3$ or $Pd_2(dba)_3CHCl_3$) and a suitable amount (e.g. in the range of about 3 to 30 mol-%) of phosphine ligand compound (e.g. 4,5-bis(diphenylphosphino)-9,9-dimethylxanthen) in a diluent (e.g. toluene) to obtain the compound of formula (I) of the present invention.

Some of the compounds of formula (VI-I) and (VI-II), which are the starting materials in the Preparation method (b), are novel compounds and they can be synthesized by the methods below. Specifically, the compounds of the above formula (IV) can be reacted with a compound represented by the following formula (XVII-I):

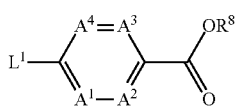

(XVII-I)

wherein $A^1$ to $A^4$ and $L^1$ have the same meaning as defined above, and $R^8$ represents hydrogen or $C_{1-4}$ alkyl, or with a compound represented by the following formula (XVII-II):

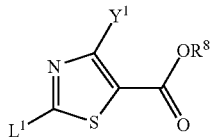

(XVII-II)

wherein $Y^1$, $R^8$, $A^1$ to $A^4$ and $L^1$ have the same meaning as defined herein to obtain the compounds represented by formula (XVIII-I):

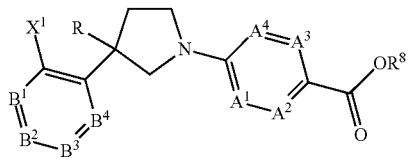

(XVIII-I)

wherein $X^1$, $B^1$ to $B^4$, R, $A^1$ to $A^4$ and $R^8$ have the same meaning as defined herein, or the compounds represented by formula (XVIII-II):

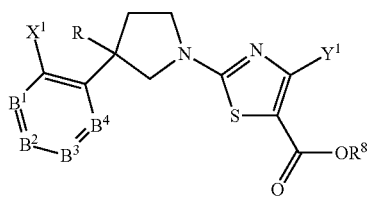

(XVIII-II)

wherein $X^1$, $B^1$ to $B^4$, R, $Y^1$ and $R^8$ have the same meaning as defined herein. In addition, when $R^8$ represents $C_{1-4}$alkyl, by subjecting the compounds represented by the above formula (XVIII-I) or (XVIII-II) to a hydrolysis reaction, the compounds represented by formula (VI-I) or (VI-II) can be obtained.

The compounds represented by the above formula (XVII-I) and (XVII-II) in above Preparation method, which are well known compounds in the field of organic chemistry, may include the following compounds, for example: ethyl 2-chloro-4-(trifluoromethyl)pyrimidine-5-carboxylate, and ethyl 2-chloro-4-(trifluoromethyl)-1,3-thiazole-5-carboxylate.

Furthermore, the compounds represented by formula (VII-I) or (VII-II), which are the starting materials in the Preparation method (b), can be synthesized according to well known methods in the field of organic chemistry.

For example, they can be readily obtained by the method comprising a reaction of the compounds represented by the above formula (VI-I) or (VI-II) with a chlorinating agent such as thionyl chloride, oxalyl chloride, phosphorus pentachloride and the like, or by the method comprising a reaction with an organic acid halide such as pivaloyl chloride and the like, or the method comprising a reaction with carbonyl diimidazole or sulfonyl imidazole and the like.

Representative compounds of formula (VI-I) or (VI-II) in the Preparation method (b) may include: 2-chloro-4-(trifluoromethyl)pyrimidine-5-carboxylic acid, 2-chloro-4-(trifluoromethyl)-1,3-thiazole-5-carboxylic acid, and the like.

Representative compounds of formula (VII-I) or (VII-II) may include: 2-chloro-4-(trifluoromethyl)pyrimidine-5-carbonyl chloride, 2-chloro-4-(trifluoromethyl)-1,3-thiazole-5-carbonyl chloride, and the like.

The compounds of formula (VIII), which are the starting materials in the Preparation method (b), are well known compounds and their specific examples may include: methylamine, ethylamine, cyclopropylamine, propargylamine, 2,2,2-trifluoroethylamine, 2-picolylamine, 3-aminomethyl-6-chloropyridine, and the like.

The reaction of the Preparation method (b) can be carried out in a suitable diluent, and examples thereof include aliphatic hydrocarbons (e.g. hexane, cyclohexane, heptane etc.), aliphatic halogenated hydrocarbons (e.g. dichloromethane, chloroform, carbon tetrachloride, dichloroethane etc.), aromatic hydrocarbons (e.g. benzene, toluene, xylene, chlorobenzene etc.), ethers (e.g. diethyl ether, dibutyl ether, dimethoxyethane (DME), tetrohydrofuran, dioxane etc.), esters (e.g. ethyl acetate, ethyl propionate etc.), acid amides (e.g. dimethylformamide (DMF), dimethylacetamide (DMA), N-methylpyrrolidone etc.), nitriles (e.g. acetonitrile, propionitrile etc.), dimethylsulfoxide (DMSO), water or mixed solvents thereof and the like.

The reaction can be carried out using the following bases such as alkali metal bases including sodium hydroxide, potassium hydroxide, sodium carbonate, potassium carbonate, cesium carbonate, tripotassium phosphate, sodium acetate, potassium acetate and the like and organic bases inclusing triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane, imidazole and the like.

The reaction can be carried out using the following condensation agents: 1,3-dicyclohexylcarbodiimide (DCC), 1-ethyl-3-(3'-dimethylaminopropyl)-carbodiimide hydrochloride (WSCI), carbonyldiimidazole (CDI), diethyl cyanophosphate (DEPC), 2-chloro-1-methylpyridinium iodide (Mukaiyama's reagent) and the like.

The Preparation method (b) can be carried out within a substantially wide temperature range. It may be generally carried out between about −78° C. and about 200° C., preferably between −10° C. and about 150° C. Said reaction is desirably carried out at normal pressure although it may be carried out under elevated or reduced pressure. The reaction time is 0.1 to 72 hours, preferably 0.1 to 24 hours.

For carrying out the Preparation method (b), for example, 1 mole of the compound of formula (VI-I) or (VI-II) can be reacted with 1 to 3 moles of the compound of formula (VIII) using 1 mole to 3 moles of a condensation agent and, if desired, with a catalytic amount of an additive such as 1-hydroxybenzotriazole in a diluent (e.g. DMF) to obtain the corresponding compound of formula (I).

The compounds of formula (Ib-I) or (Ib-II), which are the starting materials in the Preparation method (c), are encompassed by formula (I) of the present invention obtained by above Preparation method (b).

The compounds of formula (IX), which are the starting materials, are well known compounds and their specific examples may include iodomethane, iodoethane and the like. In addition, with respect to formula (IX), when $L^3$ represents arylsulfonyloxy, the aryl includes phenyl, 4-methylphenyl, 4-chlorophenyl and the like.

The reaction of the Preparation method (c) can be carried out in a suitable diluent, and examples thereof include aliphatic hydrocarbons (e.g. hexane, cyclohexane, heptane etc.), aliphatic halogenated hydrocarbons (e.g. dichloromethane, chloroform, carbon tetrachloride, dichloroethane etc.), aromatic hydrocarbons (e.g. benzene, toluene, xylene, chlorobenzene etc.), ethers (e.g. diethyl ether, dibutyl ether, dimethoxyethane (DME), tetrahydrofuran, dioxane etc.), esters (e.g. ethyl acetate, ethyl propionate etc.), acid amides (e.g. dimethylformamide (DMF), dimethylacetamide (DMA), N-methylpyrrolidone etc.), nitriles (e.g. acetonitrile, propionitrile etc.), dimethylsulfoxide (DMSO), water or mixed solvents thereof and the like.

The reaction can be carried out using the following bases such as alkali metal bases including lithium hydride, sodium hydride, potassium hydride, sodium hydroxide, potassium hydroxide, sodium carbonate, potassium carbonate, cesium carbonate, tripotassium phosphate, sodium acetate, potassium acetate and the like, organic bases such as triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane, imidazole and the like.

The Preparation method (c) can be carried out within a substantially wide temperature range. It may be generally carried out between about −78° C. and about 200° C., preferably between −10° C. and about 150° C. Said reaction is preferably carried out at normal pressure although it may be carried out under elevated or reduced pressure. The reaction time is 0.1 to 72 hours, preferably 0.1 to 24 hours.

For carrying out the Preparation method (c), for example, 1 mole of the compound of formula (Ib-I) or (Ib-II) can be reacted with 1 to 5 moles of the compound of formula (IX) in a diluent (e.g. THF) in the presence of a base to obtain the corresponding compound of formula (I).

The compounds of formula (Ia-I) or (Ia-II), which are the starting materials in the Preparation method (d), are encompassed by formula (I) of the present invention obtained by the above Preparation method (b) or Preparation method (c).

As a sulfurizing agent used in the Preparation method (d), phosphorus pentasulfide, Lawesson reagent and the like can be mentioned.

The reaction of the Preparation method (d) can be carried out in a suitable diluent, and examples thereof include aliphatic hydrocarbons (e.g. hexane, cyclohexane, heptane etc.), aliphatic halogenated hydrocarbons (e.g. dichloromethane, chloroform, carbon tetrachloride, dichloroethane etc.), aromatic hydrocarbons (e.g. benzene, toluene, xylene, chlorobenzene etc.), ethers (e.g. diethyl ether, dibutyl ether, dimethoxyethane (DME), tetrahydrofuran, dioxane etc.) or mixed solvents thereof and the like.

The Preparation method (d) can be carried out within a substantially wide temperature range. It may be generally carried out between about −78° C. and about 200° C., preferably between room temperature and about 150° C. Said reaction is desirably carried out at normal pressure although it may be carried out under elevated or reduced pressure. The reaction time is 0.1 to 72 hours, preferably 0.1 to 24 hours.

For carrying out the Preparation method (d), for example, 1 mole of the compound of formula (Ia-I) or (Ia-II) can be reacted with 0.5 mole to 3 moles of a Lawesson reagent in a diluent (e.g. toluene) to obtain the corresponding compound of formula (I).

The compounds of formula (X-I) or (X-II), which are the starting materials in the Preparation method (e), are novel compounds and may be synthesized by the method below, for example. Specifically, the compounds of the above formula (VII-I) or (VII-II) can be reduced to obtain the compounds represented by the following formula (XIX-Ia):

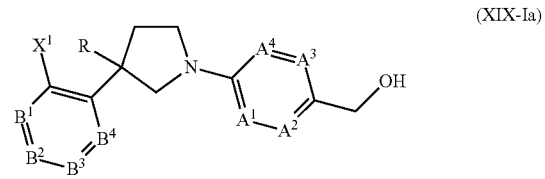

(XIX-Ia)

wherein $X^1$, $B^1$ to $B^4$, R and $A^1$ to $A^4$ have the same meaning as defined herein, or the compounds represented by the following formula (XIX-IIa):

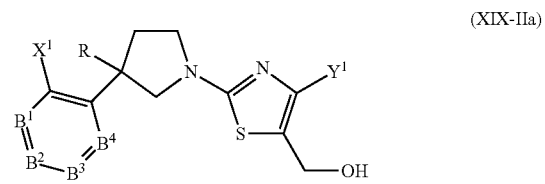

(XIX-IIa)

wherein $X^1$, $B^1$ to $B^4$, R and $Y^1$ have the same meaning as defined herein, which are then subjected to the reaction such as halogenation or alkylsulfonylation in a typical manner to obtain the compounds represented by the following formula (X-Ia):

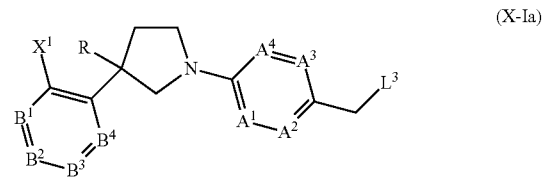

(X-Ia)

wherein $X^1$, $B^1$ to $B^4$, R, $A^1$ to $A^4$ and $L^3$ have the same meaning as defined herein, or the compounds represented by the following formula (X-IIa):

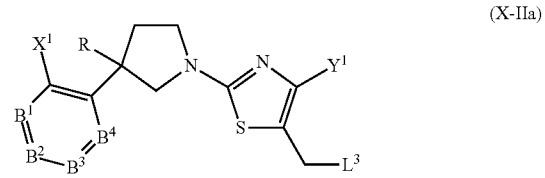

(X-IIa)

wherein $X^1$, $B^1$ to $B^4$, R, $Y^1$ and $L^3$ have the same meaning as defined herein.

Representative examples of the compounds of formula (X-I) or (X-II) in the Preparation method (e) may include: 5-(chloromethyl)-2-[3-(3,4,5-trichlorophenyl)-3-(trifluoromethyl)pyrrolidin-1-yl]-4-(trifluoromethyl)pyrimidine, 5-(chloromethyl)-2-[3-(3,4,5-trichlorophenyl)-3-(trifluoromethyl)pyrrolidin-1-yl]-4-(trifluoromethyl)-1,3-thiazole, and the like.

The compounds of formula (XI), which are the starting materials in the Preparation method (e), are well known compounds and the representative examples may include: ammonia, acetamide, propionamide, benzamide, 2-chlorobenzamide, 3-chlorobenzamide, 4-chlorobenzamide and the like.

The reaction of the Preparation method (e) can be carried out in a suitable diluent, and examples thereof include aliphatic hydrocarbons (e.g. hexane, cyclohexane, heptane etc.), aliphatic halogenated hydrocarbons (e.g. dichloromethane, chloroform, carbon tetrachloride, dichloroethane etc.), aromatic hydrocarbons (e.g. benzene, toluene, xylene, chlorobenzene etc.), ethers (e.g. diethyl ether, dibutyl ether, dimethoxyethane (DME), tetrohydrofuran, dioxane etc.), esters (e.g. ethyl acetate, ethyl propionate etc.), acid amides (e.g. dimethylformamide (DMF), dimethylacetamide (DMA), N-methylpyrrolidone etc.), nitriles (e.g. acetonitrile, propionitrile etc.), dimethylsulfoxide (DMSO), water or mixed solvents thereof and the like.

The reaction can be carried out using the following bases such as alkali metal bases including lithium hydride, sodium hydride, potassium hydride, sodium hydroxide, potassium hydroxide, sodium carbonate, potassium carbonate, cesium carbonate, tripotassium phosphate, sodium acetate, potassium acetate and the like and organic bases such as triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane, imidazole and the like.

The Preparation method (e) can be carried out within a substantially wide temperature range. It may be generally carried out between about −78° C. and about 200° C., preferably between −10° C. and about 150° C. Said reaction is desirably carried out at normal pressure although it may be carried out under elevated or reduced pressure. The reaction time is 0.1 to 72 hours, preferably 0.1 to 24 hours.

For carrying out the Preparation method (e), for example, 1 mole of the compound of formula (X-I) or (X-II) can be reacted with 1 to 3 moles of the compound of formula (XI) in the presence of a base in a diluent (e.g. THF) to obtain the corresponding compound of formula (I).

The compounds of formula (XII-I) or (XII-II), which are the starting materials in the Preparation method (f), are novel compounds and may be obtained by reacting a compound of the above formula (X-I) or (X-II) with a compound represented by the following formula (XX):

$$R^5-NH_2 \qquad (XX)$$

wherein $R^5$ has the same meaning as described in the above).

Furthermore, regarding the compounds represented by formula (XII-I) or (XII-II) wherein l=1, they can be also synthesized by an alternative method comprising reacting a compound of the above formula (IV) with a compound represented by the following formula (XXI-I):

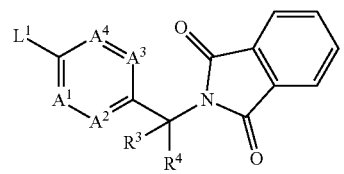

(XXI-I)

wherein $A^1$ to $A^4$, $R^3$, $R^4$ and $L^1$ have the same meaning as defined herein or with a compound represented by the following formula (XXI-II):

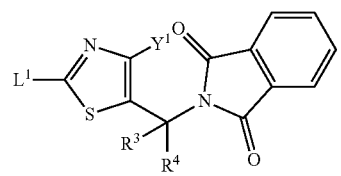

(XXI-II)

wherein $Y^1$, $R^3$, $R^4$ and $L^1$ have the same meaning as defined herein to obtain the compounds represented by the following formula (XXII-I):

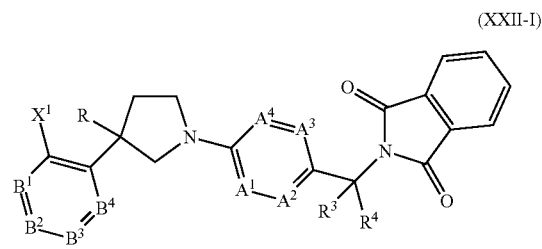

(XXII-I)

wherein $X^1$, $B^1$ to $B^4$, $A^1$ to $A^4$, $R^3$, $R^4$ and R have the same meaning as defined herein, or the compounds represented by the following formula (XXII-II):

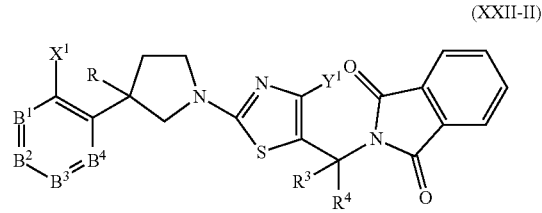

(XXII-II)

wherein $X^1$, $B^1$ to $B^4$, $Y^1$, $R^3$, $R^4$ and R have the same meaning as defined herein, followed by carrying out an amino Gabriel amine synthesis reaction.

The compounds of above formula (XXI-I) or (XXI-II) are known compounds and may include the followings:

2-{[2-chloro-4-(trifluoromethyl)pyrimidin-5-yl]methyl}-1H-isoindol-1,3(2H)-dione, 2-{[2-chloro-4-(trifluoromethyl)-1,3-thiazol-5-yl]methyl}-1H-isoindol-1,3(2H)-dione, 2-(4-bromobenzyl)-1H-isoindol-1,3(2H)-dione, 2-(4- bromo-2-nitrobenzyl)-1H-isoindol-1,3(2H)-dione, 2-(4-io-dobenzyl)-1H-isoindol-1,3(2H)-dione, 2-(4-iodo-2-nitrobenzyl)-1H-isoindol-1,3(2H)-dione, 2-(2-chloro-4-iodobenzyl)-1H-isoindol-1,3(2H)-dione and the like.

Furthermore, the compounds of formula (XII-I) or (XII-II) wherein $R^3$, $R^4$ and $R^5$ represent hydrogen may be also readily synthesized by an alternative method which includes a usual reduction reaction of the nitrile compounds represented by formula (XXIII-I):

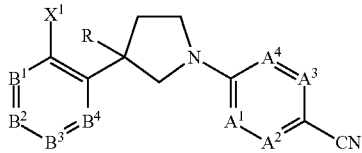

(XXIII-I)

wherein $X^1$, $B^1$ to $B^4$, $A^1$ to $A^4$ and R have the same meaning as defined herein, or the nitrile compounds represented by formula (XXIII-II):

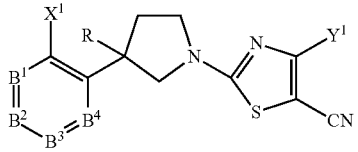

(XXIII-II)

wherein $X^1$, $B^1$ to $B^4$, $Y^1$ and R have the same meaning as defined herein, followed by a subsequent hydrolysis reaction.

Representative examples of the compounds of formula (XII-I) or (XII-II) in the Preparation method (f) may include:
1-{2-[3-(3,4,5-trichlorophenyl)-3-(trifluoromethyl)pyrrolidin-1-yl]-4-(trifluoromethyl)pyrimidin-5-yl}methanamine,
1-{2-[3-(3,4,5-trichlorophenyl)-3-(trifluoromethyl)pyrrolidin-1-yl]-4-(trifluoromethyl)-1,3-thiazol-5-yl}methanamine, 1-{2-chloro-4-[3-(3,5-dichlorophenyl)-3-(trifluoromethyl)pyrrolidin-1-yl]-phenyl}methanamine,
1-{2-bromo-4-[3-(3,5-dichlorophenyl)-3-(trifluoromethyl)pyrrolidin-1-yl]-phenyl}methanamine and the like.

The compounds of formula (XIII), which are the starting materials in the Preparation method (f), are well known compounds, and the specific examples may include: acetyl chloride; propionyl chloride; benzoyl chloride; 2-chlorobenzoyl chloride;
3-chlorobenzoyl chloride; 4-chlorobenzoyl chloride; nicotinoylchloride hydrochloride salt and the like.

The reaction of the Preparation method (f) can be carried out in a suitable diluent, and examples thereof include aliphatic hydrocarbons (e.g. hexane, cyclohexane, heptane etc.), aliphatic halogenated hydrocarbons (e.g. dichloromethane, chloroform, carbon tetrachloride, dichloroethane etc.), aromatic hydrocarbons (e.g. benzene, toluene, xylene, chlorobenzene etc.), ethers (e.g. diethyl ether, dibutyl ether, dimethoxyethane (DME), tetrohydrofuran, dioxane etc.), esters (e.g. ethyl acetate, ethyl propionate etc.), acid amides (e.g. dimethylformamide (DMF), dimethylacetamide (DMA), N-methylpyrrolidone etc.), nitriles (e.g. acetonitrile, propionitrile etc.), dimethylsulfoxide (DMSO), water or mixed solvents thereof and the like.

The reaction can be carried out using the following bases such as alkali metal bases including lithium hydride, sodium hydride, potassium hydride, sodium hydroxide, potassium hydroxide, sodium carbonate, potassium carbonate, cesium carbonate, tripotassium phosphate, sodium acetate, potassium acetate and the like and organic bases such as triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane, imidazole and the like.

The Preparation method (f) can be carried out within a substantially wide temperature range. It may be generally carried out between about −78° C. and about 200° C., preferably between −10° C. and about 150° C. Said reaction is desirably carried out at normal pressure although it may be carried out under elevated or reduced pressure. The reaction time is 0.1 to 72 hours, preferably 0.1 to 24 hours.

For carrying out the Preparation method (f), for example, 1 mole of the compound of formula (XII-I) or (XII-II) can be reacted with 1 to 3 moles of the compound of formula (XIII) in the presence of a base in a diluent (e.g. THF) to obtain the corresponding compound of formula (I).

The compounds of formula (Ic-I) or (Ic-II), which are the starting materials in the Preparation method (g), are encompassed by formula (I) of the present invention obtained by the above Preparation method (e) or Preparation method (f).

The compounds of formula (XIV) as the starting materials are well known and the specific examples may include iodomethane, iodoethane, acetyl chloride and the like.

The reaction of the Preparation method (g) can be carried out in a suitable diluent, and examples thereof include aliphatic hydrocarbons (e.g. hexane, cyclohexane, heptane etc.), aliphatic halogenated hydrocarbons (e.g. dichloromethane, chloroform, carbon tetrachloride, dichloroethane etc.), aromatic hydrocarbons (e.g. benzene, toluene, xylene, chlorobenzene etc.), ethers (e.g. diethyl ether, dibutyl ether, dimethoxyethane (DME), tetrohydrofuran, dioxane etc.), esters (e.g. ethyl acetate, ethyl propionate etc.), acid amides (e.g. dimethylformamide (DMF), dimethylacetamide (DMA), N-methylpyrrolidone etc.), nitriles (e.g. acetonitrile, propionitrile etc.), dimethylsulfoxide (DMSO), water or mixed solvents thereof and the like.

The reaction can be carried out using the following bases such as alkali metal bases including lithium hydride, sodium hydride, potassium hydride, sodium hydroxide, potassium hydroxide, sodium carbonate, potassium carbonate, cesium carbonate, tripotassium phosphate, sodium acetate, potassium acetate and the like and organic bases such as triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane, imidazole and the like.

The Preparation method (g) can be carried out within a substantially wide temperature range. It may be generally carried out between about −78° C. and about 200° C., preferably between −10° C. and about 150° C. Said reaction is desirably carried out at normal pressure although it may be carried out under elevated or reduced pressure. The reaction time is 0.1 to 72 hours, preferably 0.1 to 24 hours.

For carrying out the Preparation method (g), for example, 1 mole of the compound of formula (Ic-1) or (Ic-II) can be reacted with 1 to 3 moles of the compound of formula (XIV) in the presence of a base in a diluent (e.g. THF) to obtain the corresponding compound of formula (I).

With respect to the above Preparation methods for the compounds of formula (I) of the present invention, novel raw materials thereof (i.e., starting materials and intermediates) can be collectively represented by formula (XXIV) described below:

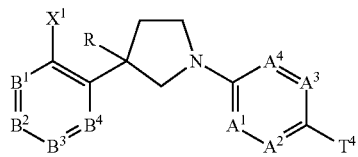

(XXIV)

wherein $X^1$, R, $A^1$ to $A^4$ and $B^1$ to $B^4$ have the same meaning as defined above, and $T^4$ represents,

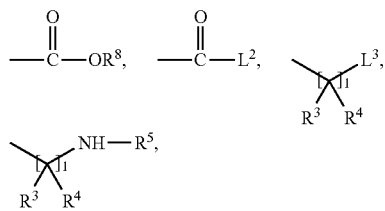

cyano, amino, or nitro, and 1, $L^2$, $L^3$, $R^3$, $R^4$, $R^5$ and $R^8$ have the same meaning as defined above.

The active compounds of the invention, in combination with good plant tolerance and favourable toxicity to warm-blooded animals and being tolerated well by the environment, are suitable for protecting plants and plant organs, for increasing harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can be preferably employed as plant protection agents. They are active against normally sensitive and resistant species and against all or some stages of development.

Such unwanted insects which may damage plants and/or technical materials include e.g. beetles (Coleopteran), such as adzuki bean beetle (*Callosobruchus Chinensis*), maize weevil (*Sitophilus zeamais*), red flour beetle (*Tribolium Castaneum*), large twenty-wight-spotted lady beetle (*Epilachna vigintioctomaculata*), barley wireworm (*Agriotes ogurae fuscicollis*), soy bean beetle (*Anomala rufocuprea*), Colorado potato beetle (*Leptinotarsa decemlineata*), corn root worm (*Diabrotica* spp.), Matsunomadra long-horned beetle (*Monochamus alternatus endai*), rice water weevil (*Lissorhoptrus oryzophilus*), powder-post beetle (*Lyctus brunneus*); lepidopteran pests, such as gypsy moth (*Lymantria dispar*), Lackey moth (*Malacosoma neustria*), small white (*Pieris rapae crucivora*), cotton leafworm (*Spodoptera litura*), cabbage moth (*Mamestra brassicae*), rice stem borer (*Chilo suppressalis*), European corn borer (*Ostrinia nubilalis*), dried currant moth (*Cadra cautella*), chyanokokakumonhamaki (*Adoxophyes honmai*), codling moth (*Cydia pomonella*), Turnip Moth (*Agrotis segetum*), Wax Moth (*Galleria mellonella*), Diamondback moth (*Plutella xylostella*), tobacco budworm moth (*Heliothis virescens*), citrus leaf miner (*Phyllocnistis citrella*); hemipterous pests, such as green rice leafhopper (*Nephotettix cincticeps*), brown planthopper (*Nilaparvata lugens*), comstock mealybug (*Pseudococcus comstocki*), arrowheat scale (*Unaspis yanonensis*), Momoaka-aburamusi (*Myzus persicas*), green apple aphid (*Aphis pomi*), cotton aphid (*Aphis gossypii*), turnip aphid (*Lipaphis erysimi*), Nashi-gunbai (*Stephanitis nashi*), Nezara (*Nezara* spp.), greenhouse whitefly (*Trialeurodes vaporariorm*), Pshylla (*Pshylla* spp.); thysanoptera pests, such as palm thrips (*Thrips palmi*), western flower thrips (*Franklinella occidentalis*); orthopteran pests, such as mole cricket (*Gryllotalpa Africana*), migratory locust (*Locusta migratoria*); blattarian pests, such as German cockroach (*Blatella germanica*), American cockroach (*Periplaneta americana*), yamato white ant (*Reticulitermes speratus*), Formosan subterranean termite (*Coptotermes formosanus*); dipterous pests, such as housefly (*Musca domestica*), yellow fever mosquito (*Aedes aegypti*), Seedcorn maggot (*Delia platura*), Aka-ie-ka (*Culex pipiens pallens*), Sina-hamadara-ka (*Anopheles sinensis*), kodaka-aka-ie-ka (*Culex tritaeniorhynchus*), serpentine leafminer (*Liriomyza trifolii*) and the like.

Further, as mites, Carmine spider mite (*Tetranychus cinnabarinus*), two-spotted spider mite (*Tetrahychus urticae*), Citrus red mite (*Panonychus citri*), Pink citrus rust mite (*Aculops pelekassi*), Tarsonemus (*Tarsonemus* spp.) and the like can be mentioned.

In addition, as nematodes, sweet potato root-knot nematode (*Meloidogyne incognita*), pine wood nematode (*Bursaphelenchus xylophilus*), rice white-tip nematode (*Aphelenchoides besseyi*), soybean cyst nematode (*Heterodera glycines*), meadow nematode (*Pratylenchus* spp.) and the like can be mentioned.

The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus mactans*, *Metatetranychus* spp., *Nuphersa* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acalymma vittatum*, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnosterna consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Nip-* tus hololeucus, Oryctes rhinoceros, Oryzaephilus surinamensis, Oryzaphagus oryzae, Otiorrhynchus spp., Oxycetonia jucunda, Phaedon cochleariae, Phyllophaga spp., Phyllotreta spp., Popillia japonica, Premnotrypes spp., Psylliodes spp., Ptinus spp., Rhizobius ventralis, Rhizopertha dominica, Sitophilus spp., Sphenophorus spp., Sternechus spp., Symphyletes spp., Tanymecus spp., Tenebrio molitor, Tribolium spp., Trogoderma spp., Tychius spp., Xylotrechus spp., Zabrus spp.

From the order of the Collembola, for example, Onychiurus armatus.

From the order of the Diplopoda, for example, Blaniulus guttulatus.

From the order of the Diptera, for example, Aedes spp., Agromyza spp., Anastrepha spp., Anopheles spp., Asphondylia spp., Bactrocera spp., Bibio hortulanus, Calliphora erythrocephala, Ceratitis capitata, Chironomus spp., Chrysomyia spp., Cochliomyia spp., Contarinia spp., Cordylobia anthropophaga, Culex spp., Cuterebra spp., Dacus oleae, Dasyneura spp., Delia spp., Dermatobia hominis, Drosophila spp., Echinocnemus spp., Fannia spp., Gastrophilus spp., Hydrellia spp., Hylemyia spp., Hyppobosca spp., Hypoderma spp., Liriomyza spp. Lucilia spp., Musca spp., Nezara spp., Oestrus spp., Oscinella frit, Pegomyia spp., Phorbia spp., Prodiplosis spp., Psila rosae, Rhagoletis spp., Stomoxys spp., Tabanus spp., Tannia spp., Tetanops spp., Tipula spp.

From the class of the Gastropoda, for example, Arion spp., Biomphalaria spp., Bulinus spp., Deroceras spp., Galba spp., Lymnaea spp., Oncomelania spp., Pomacea spp., Succinea spp.

From the class of the Helminthen, for example, Ancylostoma duodenale, Ancylostoma ceylanicum, Acylostoma braziliensis, Ancylostoma spp., Ascaris lubricoides, Ascaris spp., Brugia malayi, Brugia timori, Bunostomum spp., Chabertia spp., Clonorchis spp., Cooperia spp., Dicrocoelium spp., Dictyocaulus filaria, Diphyllobothrium latum, Dracunculus medinensis, Echinococcus granulosus, Echinococcus multilocularis, Enterobius vermicularis, Faciola spp., Haemonchus spp., Heterakis spp., Hymenolepis nana, Hyostrongulus spp., Loa Loa, Nematodirus spp., Oesophagostomum spp., Opisthorchis spp., Onchocerca volvulus, Ostertagia spp., Paragonimus spp., Schistosomen spp., Strongyloides fuelleborni, Strongyloides stercoralis, Stronyloides spp., Taenia saginata, Taenia solium, Trichinella spiralis, Trichinella nativa, Trichinella britovi, Trichinella nelsoni, Trichinella pseudopsiralis, Trichostrongulus spp., Trichuris trichuria, Wuchereria bancrofti.

It is furthermore possible to control protozoa, such as Eimeria.

From the order of the Heteroptera, for example, Anasa tristis, Antestiopsis spp., Blissus spp., Calocoris spp., Campylomma livida, Cavelerius spp., Cimex spp., Collaria spp., Creontiades dilutus, Dasynus piperis, Dichelops furcatus, Diconocoris hewetti, Dysdercus spp., Euschistus spp., Eurygaster spp., Heliopeltis spp., Horcias nobilellus, Leptocorisa spp., Leptoglossus phyllopus, Lygus spp., Macropes excavatus, Miridae, Monalonion atratum, Nezara spp., Oebalus spp., Pentomidae, Piesma quadrata, Piezodorus spp., Psallus spp., Pseudacysta persea, Rhodnius spp., Sahlbergella singularis, Scaptocoris castanea, Scotinophora spp., Stephanitis nashi, Tibraca spp., Triatoma spp.

From the order of the Homoptera, for example, Acyrthosipon spp., Acrogonia spp., Aeneolamia spp., Agonoscena spp., Aleurodes spp., Aleurolobus barodensis, Aleurothrixus spp., Amrasca spp., Anuraphis cardui, Aonidiella spp., Aphanostigma piri, Aphis spp., Arboridia apicalis, Aspidiella spp., Aspidiotus spp., Atanus spp., Aulacorthum solani, Bemisia spp., Brachycaudus helichrysii, Brachycolus spp., Brevicoryne brassicae, Calligypona marginata, Carneocephala fulgida, Ceratovacuna lanigera, Cercopidae, Ceroplastes spp., Chaetosiphon fragaefolii, Chionaspis tegalensis, Chlorita onukii, Chromaphis juglandicola, Chrysomphalus ficus, Clcadulina mbila, Coccomytilus halli, Coccus spp., Cryptomyzus ribis, Dalbulus spp., Dialeurodes spp., Diaphorina spp., Diaspis spp., Drosicha spp., Dysaphis spp., Dysmicoccus spp., Empoasca spp., Eriosoma spp., Erythroneura spp., Euscelis bilobatus, Ferrisia spp., Geococcus coffeae, Hieroglyphus spp., Homalodisca coagulata, Hyalopterus arundinis, Icerya spp., Idiocerus spp., Idioscopus spp., Laodelphax striatellus, Lecanium spp., Lepidosaphes spp., Lipaphis erysimi, Macrosiphum spp., Mahanarva spp., Melanaphis sacchari, Metcalfiella spp., Metopolophium dirhodum, Monellia costalis, Monelliopsis pecanis, Myzus spp., Nasonovia ribisnigri, Nephotettix spp., Nilaparvata lugens, Oncometopia spp., Orthezia praelonga, Parabemisia myricae, Paratrioza spp., Parlatoria spp., Pemphigus spp., Peregrinus maidis, Phenacoccus spp., Phloeomyzus passerinii, Phorodon humuli, Phylloxera spp., Pinnaspis aspidistrae, Planococcus spp., Protopulvinaria pyriformis, Pseudaulacaspis pentagona, Pseudococcus spp., Psylla spp., Pteromalus spp., Pyrilla spp., Quadraspidiotus spp., Quesada gigas, Rastrococcus spp., Rhopalosiphum spp., Saissetia spp., Scaphoides titanus, Schizaphis graminum, Selenaspidus articulatus, Sogata spp., Sogatella furcifera, Sogatodes spp., Stictocephala festina, Tenalaphara malayensis, Tinocallis caryaefoliae, Tomaspis spp., Toxoptera spp., Trialeurodes spp., Trioza spp., Typhlocyba spp., Unaspis spp., Viteus vitifolii, Zygina spp.

From the order of the Hymenoptera, for example, Athalia spp., Diprion spp., Hoplocampa spp., Lasius spp., Monomorium pharaonis, Vespa spp.

From the order of the Isopoda, for example, Armadillidium vulgare, Oniscus asellus, Porcellio scaber.

From the order of the Isoptera, for example, Acromyrmex spp., Atta spp., Cornitermes cumulans, Microtermes obesi, Odontotermes spp., Reticulitermes spp.

From the order of the Lepidoptera, for example, Acronicta major, Adoxophyes spp., Aedia leucomelas, Agrotis spp., Alabama spp., Amyelois transitella, Anarsia spp., Anticarsia spp., Argyroploce spp., Barathra brassicae, Borbo cinnara, Bucculatrix thurberiella, Bupalus piniarius, Busseola spp., Cacoecia spp., Caloptilia theivora, Capua reticulana, Carpocapsa pomonella, Carposina niponensis, Chematobia brumata, Chilo spp., Choristoneura spp., Clysia ambiguella, Cnaphalocerus spp., Cnephasia spp., Conopomorpha spp., Conotrachelus spp., Copitarsia spp., Cydia spp., Dalaca noctuides, Diaphania spp., Diatraea saccharalis, Earias spp., Ecdytolopha aurantium, Elasmopalpus lignosellus, Eldana saccharina, Ephestia kuehniella, Epinotia spp., Epiphyas postvittana, Etiella spp., Eulia spp., Eupoecilia ambiguella, Euproctis spp., Euxoa spp., Feltia spp., Galleria mellonella, Gracillaria spp., Grapholitha spp., Hedylepta spp., Helicoverpa spp., Heliothis spp., Hofmannophila pseudopretella, Homoeosoma spp., Homona spp., Hyponomeuta padella, Kakivoria flavofasciata, Laphygma spp., Laspeyresia molesta, Leucinodes orbonalis, Leucoptera spp., Lithocolletis spp., Lithophane antennata, Lobesia spp., Loxagrotis albicosta, Lymantria spp., Lyonetia spp., Malacosoma neustria, Maruca testulalis, Mamestra brassicae, Mocis spp., Mythimna separata, Nymphula spp., Oiketicus spp., Oria spp., Orthaga spp., Ostrinia spp., Oulema oryzae, Panolis flammea, Parnara spp., Pectinophora spp., Perileucoptera spp., Phthorimaea spp., Phyllocnistis citrella, Phyllono-

*rycter* spp., *Pieris* spp., *Platynota stultana, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichoplusia* spp., *Tuta absoluta, Virachola* spp.

From the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, Lepisma saccharina.

The phytoparasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof, are treated. The terms "parts", "parts of plants" and "plant parts" have been explained above.

Particularly preferably, plants of the plant cultivars which are in each case commercially available or in use are treated according to the invention. Plant cultivars are understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are the increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD gARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds according to the invention at a suitable concentration.

In the veterinary sector, that is, in veterinary medicine, the active compounds according to the present invention are effective in controlling animal parasites, specifically endoparasites or ectoparasites. The term "endoparasite" includes, specifically, helminths (tapeworms, nematodes, trematodes, and the like) and protozoa (coccidium and the like).

Ectoparasites include, typically and preferably, arthropods, specifically, insects (flies (stinging and licking), parasitic fly larvae, sucking lice, crab lice, biting lice, fleas, and the like), acaridae (ticks and the like, for example, hard ticks or soft ticks), or acarina (itchmites, trombiculid mites, bird mites, and the like).

These parasites are as follows: from Anoplurida, for example, *Haematopinus* spp., *Linognathus* spp., *Pediculus* spp., *Phtirus* spp., *Solenopotes* spp.; particularly, for representative examples, *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus*; from Mallophagida, Amblycerina, and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particularly, for representative examples, *Bovicola bovis, Bovicola ovis, Bovicola limbata, Damalina bovis, Trichodectes canis, Felicola subrostratus, Bovicola caprae, Lepikentron ovis, Werneckiella equi*; from Diptera, Nematocerina, and Brachycerina, for example, *Aedes* spp., *Anopheles* ssp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particularly, for representative examples, *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus interrnis, Gasterophilus nasalis, Gasterophilus nigricornis, Gasterophilus pecorum, Braula coeca*;

from Siphonapterida, for example, *Pulex* spp., *Ctenocephalides* spp., *Tunga* spp., *Xenopsylla* spp., *Ceratophyllus* spp.; particularly, for representative examples, *Ctenocephalides canis, Ctenocephalides felis, Pulex irritans, Tunga penetrans, Xenopsylla cheopis*;

from Heteropterida, for example, *Cimex* spp., *Triatoma* spp., *Rhodnius* spp., *Panstrongylus* spp.;

from Blattarida, for example, *Blatta orientalis, Periplaneta americana, Blattela germanica, Supella* spp. (for example, *Suppella longipalpa*);

from Acari(*Acarina*), Metastigmata, and Mesostigmata, for example, *Argas* spp., *Ornithodorus* spp., *Otobius* spp., *Ixodes* spp., *Amblyomma* spp., *Rhipicephalus*(*Boophilus*) spp., *Dermacentor* spp., *Haemophysalis* spp., *Hyalomma* spp., *Dermanyssus* spp., *Rhipicephalus* spp. (original genus of heteroxenous mites), *Ornithonyssus* spp., *Pneumonyssus* spp., *Raillietia* spp., *Pneumonyssus* spp., *Sternostoma* spp., *Varroa* spp., *Acarapis* spp.); particularly, for representative examples, *Argas persicus, Argas reflexus, Ornithodorus moubata, Otobius megnini, Rhipicephalus*(*Boophilus*) *microplus, Rhipicephalus*(*Boophilus*) *decoloratus, Rhipicephalus*(*Boophilus*) *annulatus, Rhipicephalus*(*Boophilus*) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsconi*;

from Actinedida (Prostigmata), and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particularly, for example, *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleli, Neoschonegastia xerothermobia, Trombicula akamushi, Otodectes cynotis*,

*Notoedres cati, Sarcoptis canis, Sarcoptes bovis, Sarcoptes ovis, Sarcoptes rupicaprae*(=*S. caprae*), *Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

In addition, the compounds according to the invention can be used for controlling pathogenic endoparasites which occur in humans and in animal breeding and animal husbandry in livestock, breeding, zoo, laboratory, experimental and domestic animals. In this case they are effective against all or specific stages of development of the endoparasites and also against resistant and normally sensitive species. By controlling the pathogenic endoparasites, it is intended to reduce illness, deaths and performance reductions (e.g. in the production of meat, milk, wool, hides, eggs, honey and the like), so that more economical and simpler animal keeping is made possible by the use of the active compounds. Pathogenic endoparasites include cestodes, trematodes, nematodes, acanthocephales.

The active compounds according to the present invention are suitable for the control of arthropods, helminths, and protozoa that attack animals. The animals include, for example, agricultural animals such as cattle, sheep, goats, horses, pigs, donkeys, camels, buffalo, rabbits, chickens, turkeys, ducks, geese, hatchery fish, and bees. In addition, the animals include pet animals (also known as companion animals), such as dogs, cats, cage birds, and aquarium fish, and experimental animals (for example, hamsters, guinea pigs, rats and mice).

Death rates of host animals will be reduced and productivity (in the cases of meat, milk, wool, hides, eggs, honey, and the like) and animal health will be improved by the control of these arthropods, helminths, and/or protozoa using the active compounds according to the present invention, and as a result, a more economic and simpler animal husbandry can be achieved.

For example, it is preferable that the acceptance of blood from a host by parasites should be prevented or inhibited (where applicable). The control of parasites can be helpful for prevention of infections by infectious organisms.

The term "control" used herein in the veterinary field means that the active compounds are effective in reducing each parasite incidence in animals infected by these parasites to harmless levels. More specifically, "controlling" used herein means that the active compounds are effective in killing, inhibiting the growth of, or inhibiting the proliferation of each parasite.

In the present invention, substances having insecticidal efficacies against noxious insects encompassing all of such pests are referred to as insecticides.

In the case of the active compounds of the present invention used as insecticides, they may be formed in general formulation forms. Such formulation forms may include, for example, solutions, emulsions, wettable powders, wettable granules, suspensions, powders, foams, pastes, tablets, granules, aerosols, natural products and synthetic products impregnated with the active compounds, microcapsules, coating agents for seeds, formulations with combustion device (e.g. the combustion devices include fumigation or fume cartridges, cans, coils and the like), UVL (cold mist, warm mist) and the like.

These formulations may be prepared by a method known per se. For example, they can be prepared by mixing the active compounds together with spreading agents, i.e. liquid diluents or carriers; liquefied gas diluents or carriers; solid diluents or carriers, and, optionally, with surfactants i.e. emulsifiers and/or dispersants and/or foam-forming agents.

When water is used as a spreading agent, for example, organic solvents may be used as an auxiliary solvent.

Liquid diluents or carriers may include, for example, aromatic hydrocarbons (e.g. xylene, toluene, alkylnaphthalene etc.), chlorinated aromatic or chlorinated aliphatic hydrocarbons (e.g. chlorobenzenes, ethylene chlorides, methylene chlorides etc.), aliphatic hydrocarbons (e.g. cyclohexanes or paraffins (e.g. mineral oil fractions)), alcohols (e.g. butanol, glycol and ethers or esters thereof, etc.), ketones (e.g. acetone, methyl ethyl ketone, methyl isobutyl ketone, cyclohexanone etc.), strong polar solvents (e.g. dimethylformamide, dimethylsulfoxide etc.), water and the like.

Liquefied gas diluents or carriers may include substances which exist as gas at ambient temperature and normal pressure, for example aerosol propellants such as bulan, propane, nitrogen gas, carbon dioxide and halogenated hydrocarbons.

Solid diluents may include, for example, crushed natural minerals (e.g. kaolin, clay, talc, chalk, quartz, attapulgite, montmorillonite or diatomaceous earth etc.), crushed synthetic minerals (e.g. highly-dispersive silic acid, alumina, silicate etc.) and the like.

Solid carriers for granules may include, for example, crushed and fractionated rocks (e.g. calcite, marble, pumice stone, sepiolite, dolomite etc.), synthetic granules of inorganic or organic powders, fine particles of organic materials (e.g. sawdust, coconut shells, maize cobs, tobacco stalks, etc.).

Emulsifiers and/or foam-forming agents may include, for example, nonionic or anionic emulsifiers (e.g. polyoxyethylene fatty acid esters, polyoxyethylene fatty alcohol ethers (e.g. alkylarylpolyglycol ether), alkyl sulfonates, alkyl sulfates, aryl sulfonates etc.), albumin hydrolysates and the like.

Examples of dispersants include, for example, lignin sulfite waste liquor, methylcellulose and the like.

Adhesive agents may also be used for the formulations (powders, granules, emulsions), such as carboxymethylcellulose, natural or synthetic polymers (e.g. gum Arabic, polyvinyl alcohols, polyvinyl acetates etc.) and the like.

Colorants may be used, such as inorganic pigments (e.g. iron oxide, titanium oxide, Prussian blue etc.), organic pigments (e.g. alizarin dyes, azo dyes or metallophthalocyanine dyes etc.) as well as trace elements (e.g. salts of iron, manganese, boron, copper, cobalt, molybdenum or zinc etc.).

Generally such formulations may contain the active compounds described above in a range from 0.1 to 95% by weight, preferably 0.5 to 90% by weight.

The active compounds of formula (I) of the present invention may be present in the commercially useful formulations and usage forms prepared from their formulations, as mixed formulation forms with other active compounds such as insecticides, poison baits, bactericides, acaricides, nematocides, fungicides, growth regulating agents, herbicides and the like. Above mentioned insecticides may include, for example, organophosphorus agents, carbamate agents, carboxylate chemical agents, chlorohydrocarbon type chemical agents, neonicotinoid type insecticides, insecticidal substances produced by microorganisms and the like.

In addition, the active compounds of formula (I) of the present invention may be present as mixed formulations with synergists and such formulations and usage forms may include commercially useful formulations and forms. Such synergists, which are not necessarily active per se, are the compounds that are capable of enhancing the activity of the active compounds.

The content of the active compounds of formula (I) of the present invention in a commercially useful usage form may vary over a wide range.

The practical usage concentration of the active compounds of formula (I) of the present invention may be within a range of 0.0000001 to 100% by weight, preferably 0.00001 to 1% by weight.

The compounds of formula (I) of the present invention may be used in general manners suitable for their usage forms.

The active compounds of the present invention, when used against hygienic insects and stored grain pests, have effective stability against alkaline substances present in lime materials. In addition, they have excellent residual efficacies in woods and soils.

In general, for the treatment of animals, the active compounds of the present invention may be directly applied to animals. Preferably, they are applied as pharmaceutical compositions which may contain either one or both of pharmaceutically acceptable excipients and adjuvants widely known in the art.

The active compounds in the veterinary field and animal husbandry are applied (administered) by known means, such as by enteral administration in the form of, for example, tablets, capsules, drinks, orally-taken medicines, granulates, pastes, boluses, the feed-through process, and suppositories; by parenteral administration, for example, by injection (intramuscular, subcutaneous, intravenous, intraperitoneal, and the like), by implants, by intranasal application, by dermal use in the form of, for example, dipping or immersing, spraying, pour-on and spot-on, washing, and powdering, and with the help of appliances containing the active compound, such as collars, ear markers, tail markers, limb bands, halters, marking devices, and the like. The active compounds may be formulated in a suitable form such as shampoo, aerosol, or non-pressurized spray, for example, pump spray and nebulizer.

When used in live stock, poultry, and pet animals, the active compounds according to the present invention may be applied in any formulation (for example, powder, wettable powder (WP), emulsion, emulsion concentrate (EC), flowable agent, homogenous solution, and suspension concentrate (SC)) containing the active compounds in an amount of 1 to 80% by weight, either directly or after dilution (for example, 10- to 10000-fold dilution), or by other methods such as chemical baths.

When used in the veterinary field, the active compounds according to the present invention may be used in combination with a suitable synergist or another active compound, such as a tickicide, insecticide, anthelmintic, and antiprotozoal agent.

Furthermore, the active compounds of the present invention have low toxicity and can be safely used for warm-blooded animals.

For the use in the animal health field, in particular for controlling ectoparasitic arthropods, the following compounds may be mentioned as preferred examples:

1-174, 1-967, 1-729, 1-968, 1-1471, 1-1472, 1-1998, 1-945, 1-308, 1-143, 1-317, 1-307, 1-301, 1-305, 6-267, 6-4, 6-273, 1-675, 1-404, 1-313, 1-1488, 1-1490, 1-494, 1-495, 1-730, 1-491, 1-146, 1-319, 1-357, 1-304, 1-338, 1-1991, 1-345, 1-1291, 1-1292, 1-19, 1-36, 1-150, 1-258, 1-173, 1-180, 1-186, 1-231, 1-224, 1-966, 1-963, 1-500, 1-1467, 1-925, 1-926, 1-314, 1-312, 1-296, 1-297, 1-327, 1-302, 1-309, 1-220, 1-330, 1-341, 1-339, 6-268, 1-866, 1-856, 5-144, 1-346, 1-347, 1-285, 1-398, 1-1289, 1-1290, 1-1489, 1-1427, 1-1434, 1-155, 1-329, 1-340,

As more preferred examples for the abovementioned use in the animal health field the following compounds may be mentioned:

1-174, 1-967, 1-729, 1-968, 1-1471, 1-1472, 1-1998, 1-945, 1-308, 1-143, 1-317, 1-307, 1-301, 1-305, 6-267, 6-4, 6-273, 1-675, 1-404, 1-313, 1-1488, 1-1490, 1-494, 1-495, 1-730, 1-491, 1-146, 1-319, 1-357, 1-304, 1-338, 1-1991, 1-345, 1-1291, 1-1292, 1-1471,

Of these compounds the following are particularly preferred:

1-967, 1-729, 1-968, 1-1998, 1-945, 1-308, 1-143, 1-307, 1-301, 1-305, 6-267, 6-4, 6-273, 1-675, 1-404, 1-313, 1-1488, 1-1490,

In the field of animal health the compound I-967 may be mentioned as an especially preferred example.

Further, in the field of animal health the compound I-729 may be mentioned as an especially preferred example.

Further, in the field of animal health the compound I-143 may be mentioned as an especially preferred example.

Further, in the field of animal health the compound I-307 may be mentioned as an especially preferred example.

Further, in the field of animal health the compound 6-4 may be mentioned as an especially preferred example.

Further, in the field of animal health the compound 6-273 may be mentioned as an especially preferred example.

When used in the animal health field the active compounds according to the invention may be used in combination with suitable synergists or other active compounds, such as for example, acaricides, insecticides, anthelmintics, growth regulators (e.g. juvenile hormone analogues, chitin synthesis inhibitors) and anti-protozoal drugs.

An active compound of the present invention can be prepared in conventional formulation forms, when used as an insecticide. Examples of the formulation forms include solutions, emulsions, wettable powders, water dispersible granules, suspensions, powders, foams, pastes, tablets, granules, aerosols, active compound-infiltrated natural and synthetic materials, microcapsules, seed coating agents, formulations used with a combustion apparatus (for example, fumigation and smoking cartridges, cans, coils or the like as the combustion apparatus), ULV (cold mist, warm mist), and the like.

These formulations can be produced by methods that are known per se. For example, a formulation can be produced by mixing the active compound with a developer, that is, a liquid diluent or carrier; a liquefied gas diluent or carrier; a solid diluent or carrier, and optionally with a surfactant, that is, an emulsifier and/or dispersant and/or foaming agent.

In the case where water is used as the developer, for example, an organic solvent can also be used as an auxiliary solvent.

Examples of the liquid diluent or carrier include aromatic hydrocarbons (for example, xylene, toluene, alkylnaphthalene and the like), chlorinated aromatic or chlorinated aliphatic hydrocarbons (for example, chlorobenzenes, ethylene chlorides, methylene chlorides), aliphatic hydrocarbons (for example, cyclohexanes), paraffins (for example, mineral oil fractions), alcohols (for example, butanol, glycols and their ethers, esters and the like), ketones (for example, acetone, methyl ethyl ketone, methyl isobutyl ketone, cyclohexanone and the like), strongly polar solvents (for example, dimethylformamide, dimethylsulfoxide and the like), water and the like.

The liquefied gas diluent or carrier may be those which are gaseous at normal temperature and normal pressure, for example, aerosol propellants such as butane, propane, nitrogen gas, carbon dioxide and halogenated hydrocarbons.

Examples of the solid diluent include pulverized natural minerals (for example, kaolin, clay, talc, chalk, quartz, attapulgite, montmorillonite, diatomaceous earth, and the like), pulverized synthetic minerals (for example, highly dispersed silicic acid, alumina, silicates and the like), and the like.

Examples of the solid carrier for granules include pulverized and screened rocks (for example, calcite, marble, pumice, sepiolite, dolomite and the like), synthetic granules of inorganic and organic powder, fine particles of organic materials (for example, sawdust, coconut shells, maize cobs, tobacco stalk and the like), and the like.

Examples of the emulsifier and/or foaming agent include nonionic and anionic emulsifiers [for example, polyoxyethylene fatty acid esters, polyoxyethylene fatty acid alcohol ethers (for example, alkylaryl polyglycol ether), alkylsulfonates, alkylsulfates, arylsulfonates and the like], albumin hydrolyzate, and the like.

Examples of the dispersant include lignin sulfite waste liquor and methylcellulose.

Fixing agents can also be used in the formulations (powders, granules, emulsions), and examples of the fixing agent include carboxymethylcellulose, natural and synthetic polymers (for example, gum arabic, polyvinyl alcohol, polyvinyl acetate, and the like) and the like.

Colorants can also be used, and examples of the colorants include inorganic pigments (for example, iron oxide, titanium oxide, Prussian Blue and the like), organic dyes such as alizarin dyes, azo dyes or metal phthalocyanine dyes, and in addition, trace elements such as the salts of iron, manganese, boron, copper, cobalt, molybdenum and zinc.

The formulations in general can contain the active ingredient in an amount ranging from 0.1 to 95% by weight, and preferably 0.5 to 90% by weight.

The compound according to the present invention can also exist as an admixture with other active compounds, for example, insecticides, poisonous baits, bactericides, miticides, nematicides, fungicides, growth regulators, herbicides and the like, in the form of their commercially useful formulation forms and in the application forms prepared from those formulations.

The content of the compound according to the present invention in a commercially useful application form can be varied within a wide range.

The concentration of the active compound according to the present invention in actual usage can be, for example, in the range of 0.0000001 to 100% by weight, and preferably 0.00001 to 1% by weight.

The compounds according to the present invention can be used through conventional methods that are appropriate for the usage form.

The active compound of the present invention have, when used against hygiene pests and pests associated with stored products, stability effective against alkali on lime materials, and also shows excellent residual effectiveness on wood and soil.

Next, the present invention is exemplified by way of the following examples, but the invention is not intended to be limited thereto.

SYNTHESIS EXAMPLE 1

Synthesis of 6-chloro-N-{4-[3-(3,5-dichlorophenyl)-3-(trifluoromethyl)pyrrolidin-1-yl]-2-(trifluoromethyl)benzyl}pyridine-3-carboxyamide (No. 1-198)

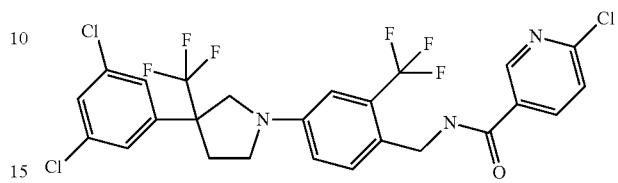

Step 1-1. Synthesis of 4-[3-(3,5-dichlorophenyl)-3-(trifluoromethyl)pyrrolidin-1-yl]-2-(trifluoromethyl)-benzonitrile

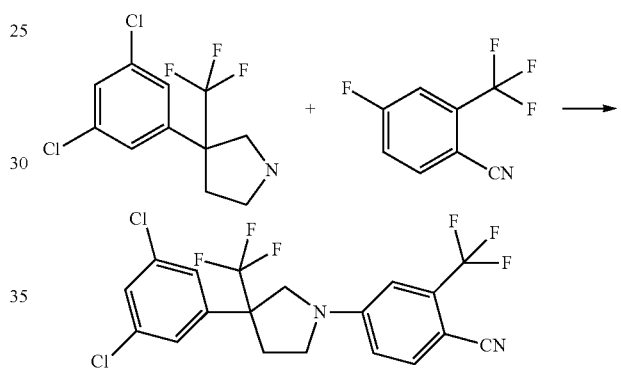

3-(3,5-Dichlorophenyl)-3-(trifluoromethyl)pyrrolidine (5.6 g), 4-fluoro-2-trifluoromethylbenzonitrile (4.5 g) and potassium carbonate (5.4 g) were added to N,N-dimethylformamide (50 mL), and the mixture was stirred at 110° C. for 4 hours. After cooling the mixture to room temperature, the solution was diluted with ethyl acetate and washed with water three times. The organic layer was dried over anhydrous magnesium sulfate. The solvent was evaporated off under reduced pressure, and the residue was then purified by a column chromatography to obtain the title compound (3.8 g).

$^1$H-NMR (CDCl$_3$) δ: 2.56-2.66 (1H, m), 2.91-2.99 (1H, m), 3.55-3.71 (2H, m), 3.84 (1H, d), 4.16 (1H, d), 6.72 (1H, dd), 6.86 (1H, d), 7.27 (2H, d), 7.42 (1H, t), 7.65 (1H, d).

Step 1-2. Synthesis of t-butyl {4-[3-(3,5-dichlorophenyl)-3-(trifluoromethyl)-pyrrolidin-1-yl]-2-(trifluoromethyl)-benzyl}carbamate

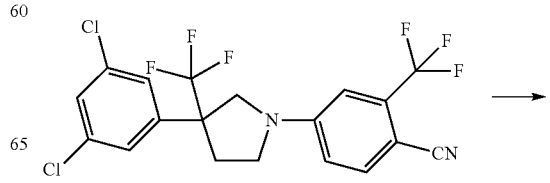

-continued

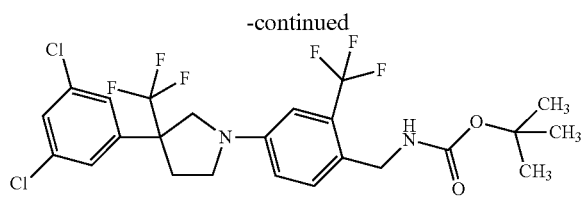

To the mixture comprising 4-[3-(3,5-dichlorophenyl)-3-(trifluoromethyl)-pyrrolidin-1-yl]-2-(trifluoro-methyl)benzonitrile (3.2 g), di-t-butyl bicarbonate (3.1 g), nickel chloride dihydrate (1.7 g), methanol (50 mL) and dioxane (100 mL), sodium borohydrate (1.3 g) was added under ice cooling, followed by stirring for 30 minutes. After the dilution with ethyl acetate, the solution was washed with water, saturated sodium bicarbonate solution, and saturated brine. The organic layer was dried over anhydrous magnesium sulfate. The solvent was evaporated off under reduced pressure, and the residue was then purified by a column chromatography to obtain the title compound (2.5 g).

$^1$H-NMR (CDCl$_3$) δ: 1.45 (9H, s), 2.50-2.60 (1H, m), 2.83-2.91 (1H, m), 3.45-3.61 (2H, m), 3.78 (1H, d), 4.06 (1H, d), 4.38 (2H, d), 4.83 (1H, br s), 6.71 (1H, dd), 6.79 (1H, d), 7.29 (2H, d), 7.39 (1H, t), 7.44 (1H, d).

Step 1-3. Synthesis of 1-{4-[3-(3,5-dichlorophenyl)-3-(trifluoromethyl)-pyrrolidin-1-yl]-2-(trifluoromethyl)phenyl}methanamine

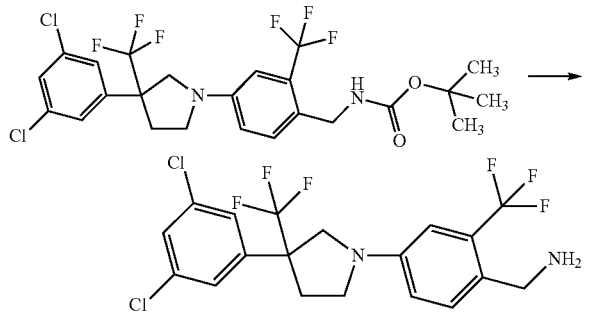

A mixture comprising t-butyl {4-[3-(3,5-dichlorophenyl)-3-(trifluoromethyl)-pyrrolidin-1-yl]-2-(trifluoromethyl)benzyl}carbamate (6.0 g), concentrated hydrochloric acid (20 mL) and ethanol (100 mL) was stirred at 50° C. for three hours. After cooling the mixture to room temperature, the reaction solution was diluted by adding water (150 mL) and ethyl acetate (150 mL). By adding sodium carbonate in small portions, the solution was neutralized. After the extraction using ethyl acetate, the organic layer was washed with saturated brine, and dried over anhydrous magnesium sulfate. The solvent was evaporated off under reduced pressure to obtain the title compound (5.2 g).

$^1$H-NMR (CDCl$_3$) δ: 2.50-2.60 (1H, m), 2.83-2.91 (1H, m), 3.48-3.61 (2H, m), 3.79 (1H, d), 3.91 (2H, s), 4.06 (1H, d), 6.74 (1H, d), 6.80 (1H, d), 7.30 (2H, d), 7.40 (2H, dd).

Step 1-4. Synthesis of 6-chloro-N-{4-[3-(3,5-dichlorophenyl)-3-(trifluoro-methyl)-pyrrolidin-1-yl]-2-(trifluoromethyl)benzyl}pyridine-3-carboxyamide

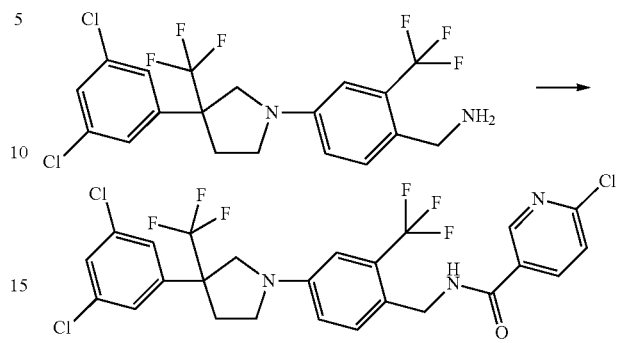

1-{4-[3-(3,5-Dichlorophenyl)-3-(trifluoromethyl)pyrrolidin-1-yl]-2-(trifluoro-methyl)phenyl}methanamine (0.1 g) and 6-chloronicotinic acid chloride (0.04 g) were dissolved in methylene chloride (5 mL), and then pyridine (0.03 g) was added thereto. The resulting mixture was stirred at room temperature for one hour. The solvent was evaporated off under reduced pressure, and the residue was then purified by a column chromatography to obtain the title compound (0.1 g).

$^1$H-NMR (CDCl$_3$) δ: 2.50-2.64 (1H, m), 2.83-2.88 (1H, m), 3.36 (2H, s), 3.49-3.60 (2H, m), 3.79 (1H, d), 4.08 (1H, d), 4.70 (2H, d), 6.30 (1H, bt), 6.70-6.83 (2H, m), 7.26-7.51 (5H, m), 8.01-8.71 (2H, m).

SYNTHESIS EXAMPLE 2

Synthesis of N-({2-[3-(3,4,5-trichlorophenyl)-3-(trifluoromethyl)-pyrrolidin-1-yl]-4-(tri-fluoromethyl)pyrimidin-5-yl}methyl)propanamide (No. 3-168)

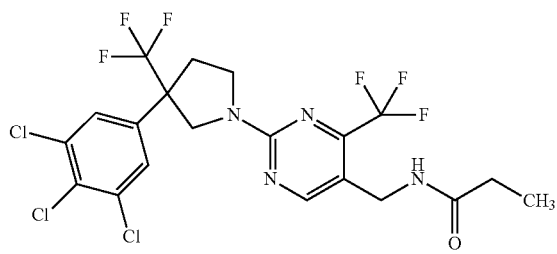 [SMILES: CCC(=O)NCc1cnc(N2CCC(c3cc(Cl)c(Cl)c(Cl)c3)(C(F)(F)F)C2)nc1C(F)(F)F]

Step 2-1. Synthesis of ethyl 2-[3-(3,4,5-trichlorophenyl)-3-(trifluoromethyl)-pyrrolidin-1-yl]-4-(trifluoromethyl)pyrimidine-5-carboxylate

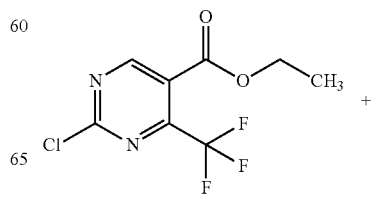

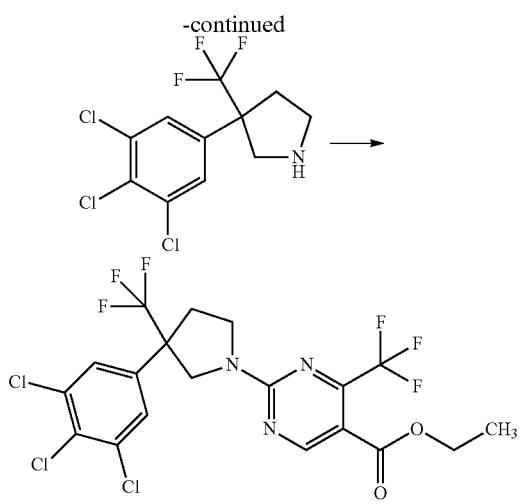

Ethyl 2-chloro-4-(trifluoromethyl)pyrimidine-5-carboxylate (1.2 g) [see J. Med. Chem., 43, 3995 (2000)], 3-(3,4,5-trichlorophenyl)-3-(trifluoromethyl)pyrrolidine (1.5 g), and potassium carbonate (0.7 g) were added to N,N-dimethylformamide (50 mL) and the mixture was heated at 100° C. for 5 hours. After cooling, the reaction solution was poured over ice water, and then extracted with ethyl acetate. The organic layer was dried over magnesium sulfate. The solvent was evaporated off under reduced pressure, and the residue was then purified by a silica gel chromatography to obtain the title compound (2.4 g, 95%).

¹H-NMR (CDCl₃) δ: 1.39 (3H, t), 2.50-2.60 (1H, m), 2.89-2.93 (1H, m), 3.87-3.89 (2H, m), 4.08-4.16 (1H, m), 4.37 (2H, q,), 4.52-4.56 (1H, m), 7.45 (2H, s), 8.95 (1H, s).

Step 2-2. Synthesis of 2-[3-(3,4,5-trichlorophenyl)-3-(trifluoromethyl)-pyrrolidin-1-yl]-4-(trifluoromethyl)pyrimidine-5-carboxylic acid

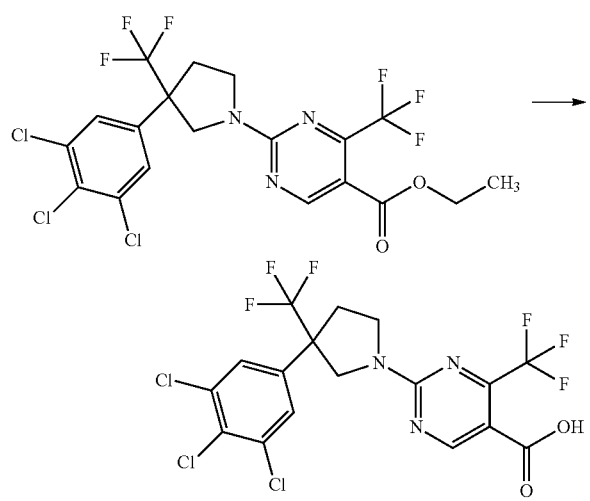

Ethyl 2-[3-(3,4,5-trichlorophenyl)-3-(trifluoromethyl)pyrrolidin-1-yl]-4-(trifluoromethyl)pyrimidine-5-carboxylate (2.4 g) was added to a mixture solution comprising 1,4-dioxane (40 mL) and an aqueous solution (40 mL) of sodium hydroxide (2.0 g), and then heated at 80° C. for 10 hours. After cooling, the reaction solution was poured over ice water, acidified by adding concentrated hydrochloric acid, and then extracted with ethyl acetate. The organic layer was dried over magnesium sulfate. The solvent was evaporated off under reduced pressure to obtain the title compound (2.1 g, 92%).

Step 2-3. Synthesis of {2-[3-(3,4,5-trichlorophenyl)-3-(trifluoromethyl)-pyrrolidin-1-yl]-4-(trifluoromethyl)-pyrimidin-5-yl}methanol

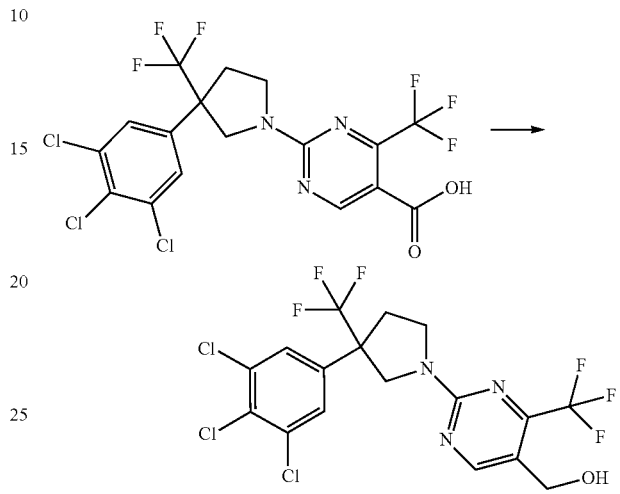

2-[3-(3,4,5-Trichlorophenyl)-3-(trifluoromethyl)pyrrolidin-1-yl]-4-(trifluoro-methyl)pyrimidine-5-carboxylic acid (2.0 g) was added to 1,2-dichloroethane (50 mL). To the resulting mixture, thionyl chloride (1.0 g), and one drop of N,N-dimethylformamide was added and the mixture was refluxed under heating for 5 hours. After removing the solvent by evaporation, the residues were dissolved in 1,4-dioxane (20 mL), and the resulting solution was added dropwise to the mixture solution comprising water (30 mL), 1,4-dioxane (30 mL), and sodium borohydride (0.4 g) under ice cooling. After the dropwise addition was completed, the solution was refluxed under heating for one hour. After cooling, the reaction solution was poured over ice water and then extracted with ethyl acetate. After cooling, the extraction was carried out by adding water and ethyl acetate to the solution. The organic layer was dried over magnesium sulfate. The solvent was evaporated off under reduced pressure, and the residue was then purified by a silica gel chromatography to obtain the title compound (1.65 g, 86%).

¹H-NMR (CDCl₃) δ: 1.81 (1H, t), 2.35-2.58 (1H, m), 2.83-2.92 (1H, m), 3.82-3.88 (2H, m), 4.02-4.06 (1H, m), 4.47-4.51 (1H, m), 4.73 (2H, d), 7.44 (2H, s), 8.63 (1H, s).

Step 2-4. Synthesis of 1-{2-[3-(3,4,5-trichlorophenyl)-3-(tri-fluoromethyl)-pyrrolidin-1-yl]-4-(trifluoromethyl)pyrimidin-5-yl}methanamine

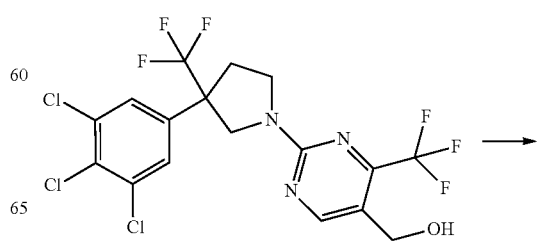

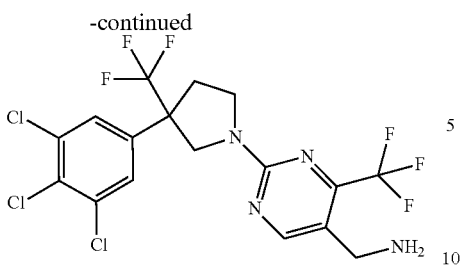

{2-[3-(3,4,5-Trichlorophenyl)-3-(trifluoromethyl)pyrrolidin-1-yl]-4-(tri-fluoromethyl)pyrimidin-5-yl}methanol (1.0 g) was added to tetrahydrofuran (30 mL), and then, under ice cooling, tetrahydrofuran solution (10 mL) comprising methanesulfonyl chloride (0.3 g) was added dropwise thereto. After the dropwise addition was completed, the solution was stirred at room temperature for one hour. The resulting solution was added dropwise to a mixture solution, which was separately prepared to comprise 28% ammonia water (50 mL), tetrahydrofuran (100 mL), and methanol (100 mL), under ice cooling. After the stirring for 12 hours at room temperature, the reaction solution was poured over ice water, and then extracted with ethyl acetate. The organic layer was dried over magnesium sulfate. The solvent was evaporated off under reduced pressure, and the residue was then purified by a silica gel chromatography to obtain the title compound (0.4 g, 45%).

$^1$H-NMR (CDCl$_3$) δ: 1.65 (2H, br s), 2.49-2.54 (1H, m), 2.82-2.91 (1H, m), 3.68-4.16 (6H, m), 4.46-4.50 (1H, m), 7.44 (2H, s), 8.58 (1H, s).

Step 2-5. Synthesis of N-{2-[3-(3,4,5-trichlorophenyl)-3-(trifluoromethyl)-pyrrolidin-1-yl]-4-(trifluoromethyl)pyrimidin-5-yl}methyl)propanamide

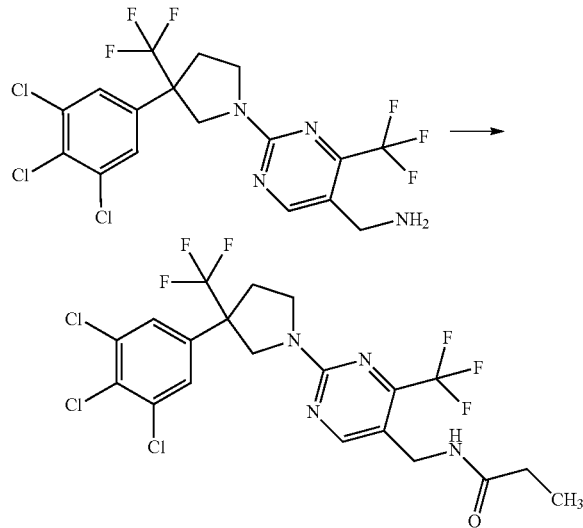

1-{2-[3-(3,4,5-Trichlorophenyl)-3-(trifluoromethyl)pyrrolidin-1-yl]-4-(trifluoromethyl)pyrimidin-5-yl}methanamine (0.1 g) and triethylamine (0.05 g) were added to dichloromethane (20 mL), and then dichloromethane solution (10 mL) comprising anhydrous propionic acid (0.05 g) was added dropwise thereto under ice cooling. After the dropwise addition was completed, the reaction solution was stirred at room temperature for one hour. The solvent was evaporated off under reduced pressure, and the residue was then purified by a silica gel chromatography to obtain the title compound (0.1 g, 90%).

$^1$H-NMR (CDCl$_3$) δ: 1.16 (3H, t), 2.21 (2H, q), 2.46-2.56 (1H, m), 2.82-2.90 (1H, m), 3.80-3.83 (2H, m), 3.98-4.02 (1H, m), 4.42-4.47 (3H, m), 5.75-5.78 (1H, m), 7.43 (2H, s), 8.63 (1H, s).

SYNTHESIS EXAMPLE 3

Synthesis of N-(2-[3-(3,4,5-trichlorophenyl)-3-(trifluoromethyl)pyrrolidin-1-yl]-4-(trifluoromethyl)-1,3-thiazol-5-yvl methyl)propanamide (No. 5-142)

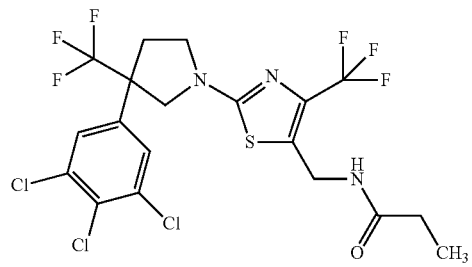 [SMILES: CCC(=O)NCc1sc(N2CCC(c3cc(Cl)c(Cl)c(Cl)c3)(C(F)(F)F)C2)nc1C(F)(F)F]

Step 3-1. Synthesis of ethyl 2-[3-(3,4,5-trichlorophenyl)-3-(trifluoro-methyl)pyrrolidin-1-yl]-4-(trifluoromethyl)-1,3-thiazole-5-carboxylate

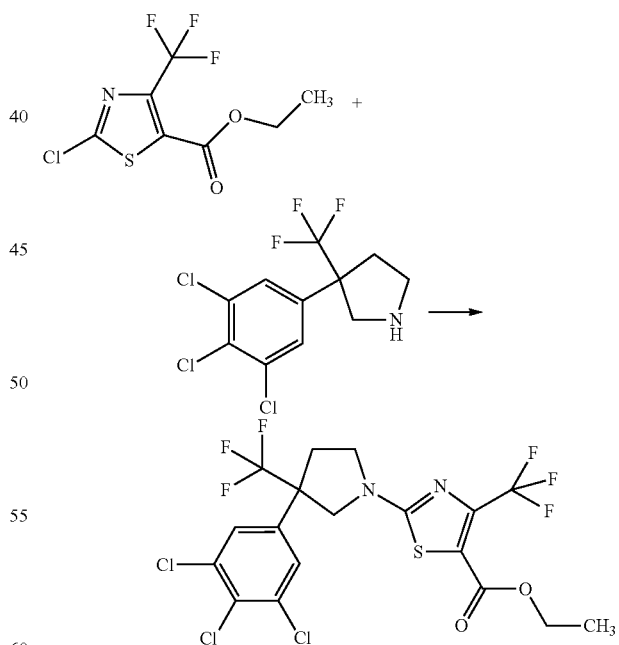

Ethyl 2-chloro-4-(trifluoromethyl)-1,3-thiazole-5-carboxylate (1.4 g) [see J. Het. Chem., 22, 1621 (1985)], 3-(3,4,5-trichlorophenyl)-3-(trifluoromethyl)pyrrolidine (1.7 g), and potassium carbonate (0.8 g) were added to N,N-dimethylformamide (50 mL), followed by heating at 100° C. for five hours. After cooling, the reaction solution was poured over ice water, and then extracted with ethyl acetate. The organic layer was dried over magnesium sulfate. The solvent was evaporated off under reduced pressure, and the residue was then purified by a silica gel chromatography to obtain the title compound (2.5 g, 86%).

¹H-NMR (CDCl₃) δ: 1.35 (3H, t), 2.59-2.64 (1H, m), 2.93-2.97 (1H, m), 3.61-3.73 (2H, m), 3.96-4.00 (1H, m), 4.32 (2H, q), 4.42-4.46 (1H, m), 7.41 (2H, s).

Step 3-2. Synthesis of 2-[3-(3,4,5-trichlorophenyl)-3-(trifluoromethyl)-pyrrolidin-1-yl]-4-(trifluoromethyl)-1,3-thiazole-5-carboxylic acid

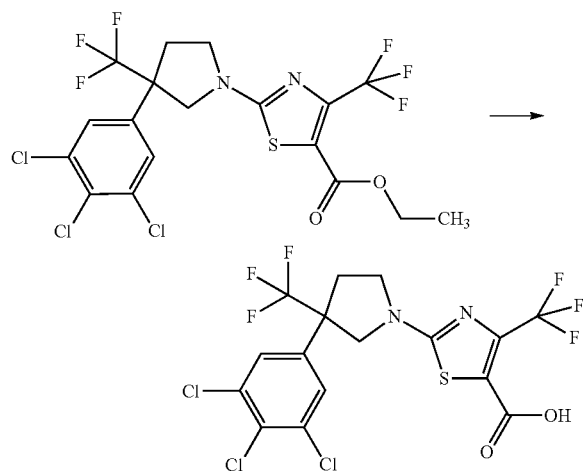

Ethyl 2-[3-(3,4,5-trichlorophenyl)-3-(trifluoromethyl)pyrrolidin-1-yl]-4-(tri-fluoromethyl)-1,3-thiazole-5-carboxylate (2.4 g) was added to a mixture solution comprising 1,4-dioxane (40 mL) and an aqueous solution (40 mL) of sodium hydroxide (2.0 g), followed by heating at 80° C. for ten hours. After cooling, the reaction solution was poured over ice water, acidified by adding concentrated hydrochloric acid, and then extracted with ethyl acetate. The organic layer was dried over magnesium sulfate. The solvent was evaporated off under reduced pressure to obtain the title compound (2.25 g, 99%).

Step 3-3. Synthesis of {2-[3-(3,4,5-trichlorophenyl)-3-(trifluoromethyl)-pyrrolidin-1-yl]-4-(trifluoromethyl)-1,3-thiazol-5-yl}methanol

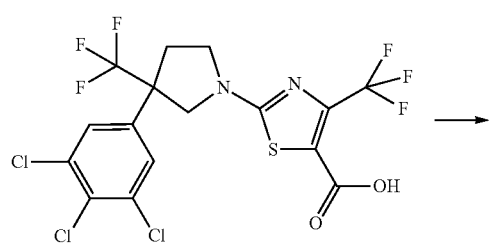

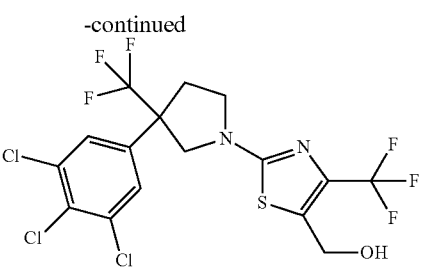

2-[3-(3,4,5-Trichlorophenyl)-3-(trifluoromethyl)pyrrolidin-1-yl]-4-(trifluoro-methyl)-1,3-thiazole-5-carboxylic acid (2.2 g) was added to 1,2-dichloroethane (50 mL). Thionyl chloride (1.0 g) and one drop of N,N-dimethylformamide were added to the mixture, which was then refluxed under heating for 5 hours. After removing the solvent by evaporation, the residues were dissolved in 1,4-dioxane (20 mL), and then added dropwise to the mixture solution comprising water (30 mL), 1,4-dioxane (30 mL), and sodium borohydride (0.5 g) under ice cooling. After the dropwise addition was completed, the reaction solution was refluxed under heating for one hour. After cooling, the reaction solution was poured over ice water, and then extracted with ethyl acetate. After cooling, the extraction was again carried out by adding water and ethyl acetate. The organic layer was dried over magnesium sulfate. The solvent was evaporated off under reduced pressure, and the residue was then purified by a silica gel chromatography to obtain the title compound (1.1 g, 65%).

¹H-NMR (CDCl₃) δ: 1.94 (1H, t), 2.57-2.61 (1H, m), 2.87-2.95 (1H, m), 3.56-3.70 (2H, m), 3.93-3.97 (1H, m), 4.36-4.40 (1H, m), 4.86 (2H, d), 7.40 (2H, s).

Step 3-4. Synthesis of 1-{2-[3-(3,4,5-trichlorophenyl)-3-(trifluoromethyl)-pyrrolidin-1-yl]-4-(trifluoromethyl)-1,3-thiazol-5-yl}methanamine

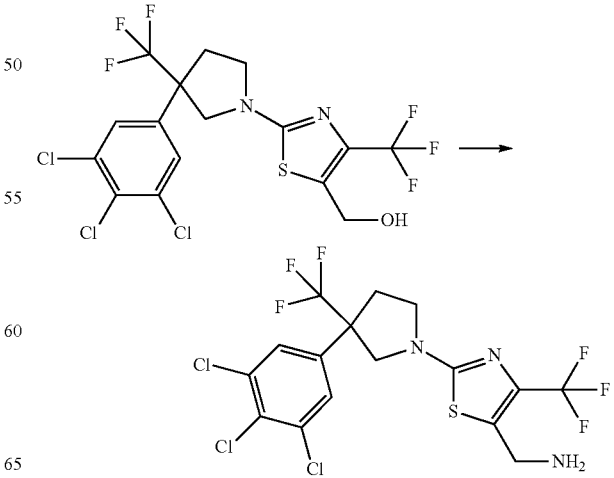

{2-[3-(3,4,5-trichlorophenyl)-3-(trifluoromethyl)pyrrolidin-1-yl]-4-(trifluoro-methyl)-1,3-thiazol-5-yl}methanol (1.05 g) was added to tetrahydrofuran (30 mL). Then, tetrahydrofuran solution (10 mL) comprising methanesulfonyl chloride (0.3 g) was added dropwise thereto under ice cooling. After the dropwise addition was completed, the reaction solution was stirred at room temperature for one hour. The resulting solution was added dropwise to a mixture solution, which was separately prepared to contain 28% ammonia water (50 mL), tetrahydrofuran (100 mL), and methanol (100 mL), under ice cooling. After stirring the mixture at room temperature for 12 hours, the reaction solution was poured over ice water, and then extracted with ethyl acetate. The organic layer was dried over magnesium sulfate. The solvent was evaporated off under reduced pressure, and the residue was then purified by a silica gel chromatography to obtain the title compound (0.4 g, 45%).

$^1$H-NMR (CDCl$_3$) δ: 1.64 (2H, br s), 2.51-2.61 (1H, m), 2.88-2.92 (1H, m), 3.56-3.65 (2H, m), 3.92-3.96 (1H, m), 4.02-4.16 (2H, m), 4.16-4.38 (1H, m), 7.41 (2H, s).

Step 3-5. Synthesis of N-({2-[3-(3,4,5-trichlorophenyl)-3-(trifluoromethyl)-pyrrolidin-1-yl]-4-(trifluoromethyl)-1,3-thiazol-5-yl}methyl)propanamide

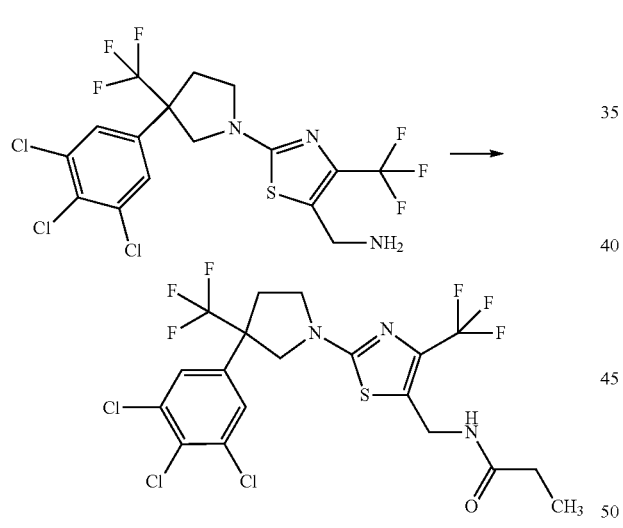

1-{2-[3-(3,4,5-Trichlorophenyl)-3-(trifluoromethyl)pyrrolidin-1-yl]-4-(trifluoro-methyl)-1,3-thiazol-5-yl}methanamine (0.1 g) and triethylamine (0.05 g) were added to dichloromethane (20 mL), followed by the dropwise addition of dichloromethane solution (10 mL) comprising anhydrous propionic acid (0.05 g) under ice cooling. After the dropwise addition was completed, the reaction solution was stirred at room temperature for one hour. The solvent was evaporated off under reduced pressure, and the residue was then purified by a silica gel chromatography to obtain the title compound (0.1 g, 90%).

$^1$H-NMR (CDCl$_3$) δ: 1.14 (3H, t), 2.25 (2H, q), 2.52-2.58 (1H, m), 2.87-2.91 (1H, m), 3.55-3.64 (2H, m), 3.91 (1H, m), 4.34 (1H, m), 4.55-4.57 (2H, m), 5.91-5.93 (1H, m), 7.39 (2H, s).

SYNTHESIS EXAMPLE 4

Synthesis of N-(5-{3-[3,5-bis(trifluoromethyl)phenyl]-3-(trifluoromethyl)-pyrrolidin-1-yl}-2,3-dihydro-1H-inden-1-yl)propanamide (No. 6-273)

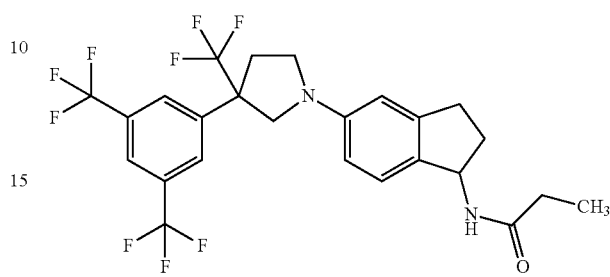

Step 4-1. Synthesis of 5-bromo-N-hydroxyindan-1-imine

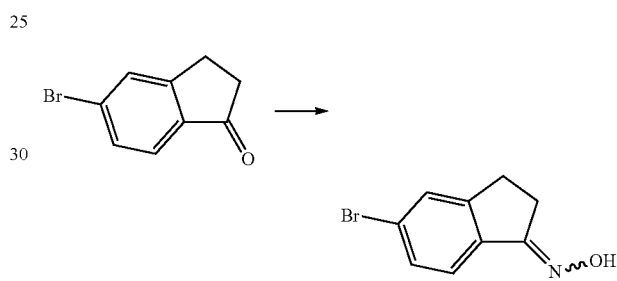

5-Bromoindan-1-one (5.0 g) was dissolved in methanol. Hydroxylammonium chloride (2.5 g) and sodium acetate (2.9 g) were added to the solution at room temperature, and then stirred overnight. The reaction solution was diluted with water and extracted twice with ethyl acetate. The organic layers were combined, washed with water, and dried over anhydrous magnesium sulfate. The desiccant was filtered and separated, and then the solvent was evaporated off under reduced pressure to obtain 5-bromo-N-hydroxyindan-1-imine (5.1 g).

$^1$H-NMR (DMSO-d$_6$) δ: 2.76-2.81 (2H, m), 2.98-3.03 (2H, m), 7.41-7.49 (2H, m), 7.59 (1H, s), 10.98 (1H, s).

Step 4-2. Synthesis of N-(5-bromo-2,3-dihydro-1H-inden-1-yl)propanamide

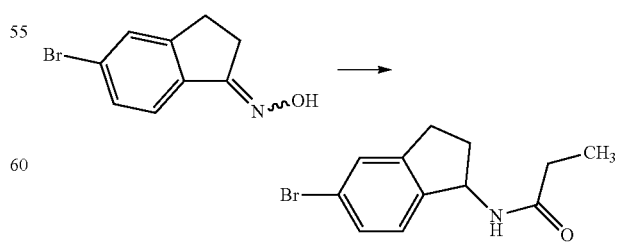

5-Bromo-N-hydroxyindan-1-imine (2.0 g), propionic acid anhydride (2.3 g) and nickel chloride dihydrate (1.1 g) were dissolved in methanol. Sodium borohydride (1.3 g) was slowly added to the solution under ice cooling, and the mixture was stirred for 30 minutes. Diethylenetriamine (2.9 ml) was added to the reaction solution, which was heated back to room temperature, and stirred for 30 minutes. The mixture was diluted with ethyl acetate and water, and stirred for 5 minutes. The organic layer was separated and the aqueous layer was extracted with ethyl acetate. The organic layers were combined, washed with saturated sodium bicarbonate aqueous solution, and dried over magnesium sulfate. The desiccant was filtered and separated, and the solvent was evaporated off under reduced pressure. The Residue was separated and purified by a column chromatography to obtain N-(5-bromo-2,3-dihydro-1H-inden-1-yl)propanamide (1.1 g).

$^1$H-NMR (acetone-$d_6$) δ: 1.19 (3H, t), 1.84-1.96 (1H, m), 2.26 (2H, q), 2.49-2.60 (1H, m), 2.88-3.10 (2H, m), 5.36-5.46 (1H, m), 6.65 (1H, s), 7.24 (1H, d), 7.44 (1H, d), 7.51 (1H, s).

Step 4-3. Synthesis of N-(5-{3-[3,5-bis(trifluoromethyl)phenyl]-3-(trifluoro-methyl)pyrrolidin-1-yl}-2,3-dihydro-1H-inden-1-yl)propanamide

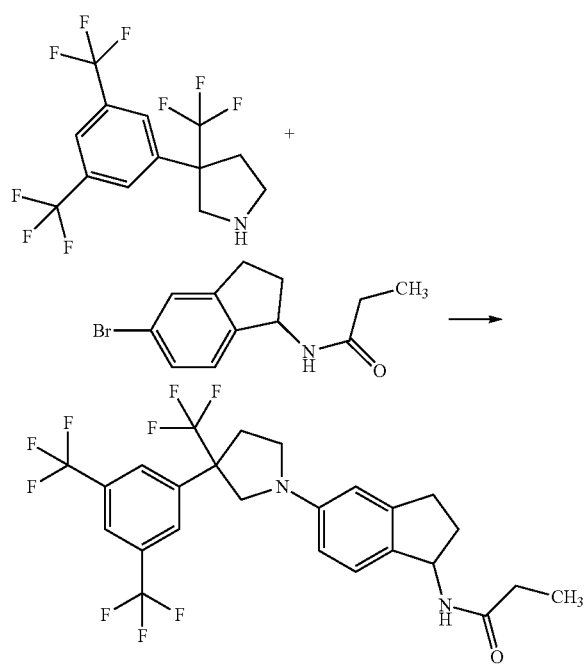

3-[3,5-bis(trifluoromethyl)phenyl]-3-(trifluoromethyl)pyrrolidine (0.46 g) and N-(5-bromo-2,3-dihydro-1H-inden-1-yl)propanamide (0.35 g) were dissolved in toluene and deaeration procedure was performed three times under argon atmosphere. Sodium tert-butoxide (0.25 g), Xantphos (0.05 g) and tris(dibenzylideneacetone)dipalladium (0) (chloroform adduct)(0.03 g) were added to the mixture and heated and stirred at 100° C. under argon atmosphere for 2 hours. The solution was cooled to room temperature and the reaction liquid was diluted with ethyl acetate followed by washing with water and brine. The organic layer was dried over anhydrous magnesium sulfate. The desiccant was filtered and separated, the solvent was evaporated off under reduced pressure, and the residue was purified by a silica gel chromatography to obtain N-(5-{3-[3,5-bis(trifluoromethyl)phenyl]-3-(trifluoromethyl)pyrrolidin-1-yl}-2,3-dihydro-1H-1-inden-1-yl)propanamide (0.51 g).

$^1$H-NMR (CDCl$_3$) δ: 1.18 (3H, t), 1.75-1.86 (1H, m), 2.23 (2H, q), 2.54-2.64 (2H, m), 2.79-3.02 (3H, m), 3.47-3.64 (2H, m), 3.84 (1H, d), 4.15 (1H, d), 5.38-5.57 (2H, m), 6.52-6.49 (2H, m), 7.20 (1H, d), 7.85 (2H, s), 7.91 (1H, s).

The compounds according to the present invention as well as useful intermediates for the manufacturing of the compounds are described in the following tables.

In tables, abbreviations are as follows: Me: methyl, Et: ethyl, Pr: propyl, Bu: butyl, Allyl: allyl, Pen: pentyl, Hex: hexyl, Ph: phenyl, cyclo-: cyclic, py: pyridyl, pyrro or pyrrolidine: pyrrolidinyl, pipe or piperidine: piperidinyl, morph or morpholine: morpholinyl, thiomorph or thiomorpholine: thiomorpholinyl. In the tables, cyclic groups to which a carbonyl group is attached to,

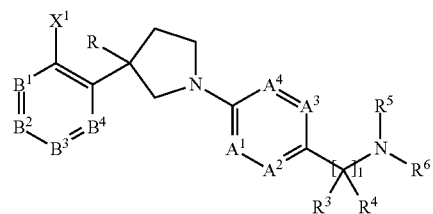

are bound to the appropriate position in the general formula through the carbonyl carbon atom as follows:

TABLE 1

| Ex.-No. | B$^1$ | B$^2$ | B$^3$ | B$^4$ | X$^1$ | R | A$^1$ | A$^2$ | A$^3$ | A$^4$ | R$^3$ | R$^4$ | R$^5$ | R$^6$ | |
|---|---|---|---|---|---|---|---|---|---|---|---|---|---|---|---|
| 1-1 | C—Cl | C—H | C—Cl | C—H | H | CF3 | CH | CH | C—Cl | CH | H | H | H | H | 1 |
| 1-2 | C—Cl | C—H | C—Cl | C—H | H | CF3 | CH | CH | C—Cl | CH | H | H | H | n-PrCO | 1 |

TABLE 1-continued

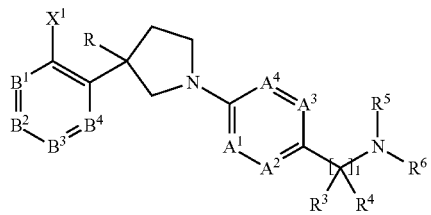

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-3 | C—Cl | C—H | C—Cl | C—H | H | CF3 | CH | CH | C—Cl | CH | H | H | H | iso-PrCO | 1 |
| 1-4 | C—Cl | C—H | C—Cl | C—H | H | CF3 | CH | CH | C—Cl | CH | H | H | H | cyclo-PrCO | 1 |
| 1-5 | C—Cl | C—H | C—Cl | C—H | H | CF3 | CH | CH | C—Cl | CH | H | H | H | n-BuCO | 1 |
| 1-6 | C—Cl | C—H | C—Cl | C—H | H | CF3 | CH | CH | C—Cl | CH | H | H | H | tert-BuCO | 1 |
| 1-7 | C—Cl | C—H | C—Cl | C—H | H | CF3 | CH | CH | C—Cl | CH | H | H | H | iso-BuCO | 1 |
| 1-8 | C—Cl | C—H | C—Cl | C—H | H | CF3 | CH | CH | C—Cl | CH | H | H | H | cyclo-BuCO | 1 |
| 1-9 | C—Cl | C—H | C—Cl | C—H | H | CF3 | CH | CH | C—Cl | CH | H | H | H | (CH3)3CCH2CO | 1 |
| 1-10 | C—Cl | C—H | C—Cl | C—H | H | CF3 | CH | CH | C—Cl | CH | H | H | H | cyclo-PenCO | 1 |
| 1-11 | C—Cl | C—H | C—Cl | C—H | H | CF3 | CH | CH | C—Cl | CH | H | H | H | cyclo-HexCO | 1 |
| 1-12 | C—Cl | C—H | C—Cl | C—H | H | CF3 | CH | CH | C—Cl | CH | H | H | H | cyclo-PrCH2CO | 1 |
| 1-13 | C—Cl | C—H | C—Cl | C—H | H | CF3 | CH | CH | C—Cl | CH | H | H | H | CF3CO | 1 |
| 1-14 | C—Cl | C—H | C—Cl | C—H | H | CF3 | CH | CH | C—Cl | CH | H | H | H | CCl3CO | 1 |
| 1-15 | C—Cl | C—H | C—Cl | C—H | H | CF3 | CH | CH | C—Cl | CH | H | H | H | ClCH2CO | 1 |
| 1-16 | C—Cl | C—H | C—Cl | C—H | H | CF3 | CH | CH | C—Cl | CH | H | H | H | CF2ClCO | 1 |
| 1-17 | C—Cl | C—H | C—Cl | C—H | H | CF3 | CH | CH | C—Cl | CH | H | H | H | ClCH2CH2CO | 1 |
| 1-18 | C—Cl | C—H | C—Cl | C—H | H | CF3 | CH | CH | C—Cl | CH | H | H | H | HCF2CF2CO | 1 |
| 1-19 | C—Cl | C—H | C—Cl | C—H | H | CF3 | CH | CH | C—Cl | CH | H | H | H | CF3CH2CO | 1 |
| 1-20 | C—Cl | C—H | C—Cl | C—H | H | CF3 | CH | CH | C—Cl | CH | H | H | H | (CF3)2CHCO | 1 |
| 1-21 | C—Cl | C—H | C—Cl | C—H | H | CF3 | CH | CH | C—Cl | CH | H | H | H | HCF2CO | 1 |
| 1-22 | C—Cl | C—H | C—Cl | C—H | H | CF3 | CH | CH | C—Cl | CH | H | H | H | ClCH2CO | 1 |
| 1-23 | C—Cl | C—H | C—Cl | C—H | H | CF3 | CH | CH | C—Cl | CH | H | H | H | 1-methylcyclopropyl-CO | 1 |
| 1-24 | C—Cl | C—H | C—Cl | C—H | H | CF3 | CH | CH | C—Cl | CH | H | H | H | 2,2-dichlorocyclopropyl-CO | 1 |
| 1-25 | C—Cl | C—H | C—Cl | C—H | H | CF3 | CH | CH | C—Cl | CH | H | H | H | 2,2-difluorocyclopropyl-CO | 1 |
| 1-26 | C—Cl | C—H | C—Cl | C—H | H | CF3 | CH | CH | C—Cl | CH | H | H | H | 2-fluorocyclopropyl-CO | 1 |
| 1-27 | C—Cl | C—H | C—Cl | C—H | H | CF3 | CH | CH | C—Cl | CH | H | H | H | 2-methylcyclopropyl-CO | 1 |
| 1-28 | C—Cl | C—H | C—Cl | C—H | H | CF3 | CH | CH | C—Cl | CH | H | H | H | 1-isocyanocyclopropyl-CO | 1 |
| 1-29 | C—Cl | C—H | C—Cl | C—H | H | CF3 | CH | CH | C—Cl | CH | H | H | H | CH2=CH—CO | 1 |
| 1-30 | C—Cl | C—H | C—Cl | C—H | H | CF3 | CH | CH | C—Cl | CH | H | H | H | CH3CH=CH—CO | 1 |
| 1-31 | C—Cl | C—H | C—Cl | C—H | H | CF3 | CH | CH | C—Cl | CH | H | H | H | CH2=C(CH3)—CO | 1 |
| 1-32 | C—Cl | C—H | C—Cl | C—H | H | CF3 | CH | CH | C—Cl | CH | H | H | H | CH3CH=C(CH3)—CO | 1 |
| 1-33 | C—Cl | C—H | C—Cl | C—H | H | CF3 | CH | CH | C—Cl | CH | H | H | H | (CH3)2C=CH—CO | 1 |
| 1-34 | C—Cl | C—H | C—Cl | C—H | H | CF3 | CH | CH | C—Cl | CH | H | H | H | CH2=C(Cl)—CO | 1 |
| 1-35 | C—Cl | C—H | C—Cl | C—H | H | CF3 | CH | CH | C—Cl | CH | H | H | H | ClCH=C(CH3)—CO | 1 |
| 1-36 | C—Cl | C—H | C—Cl | C—H | H | CF3 | CH | CH | C—Cl | CH | H | H | H | CH2=CHCH2—CO | 1 |
| 1-37 | C—Cl | C—H | C—Cl | C—H | H | CF3 | CH | CH | C—Cl | CH | H | H | H | HCC—CO | 1 |
| 1-38 | C—Cl | C—H | C—Cl | C—H | H | CF3 | CH | CH | C—Cl | CH | H | H | H | CH3CC—CO | 1 |
| 1-39 | C—Cl | C—H | C—Cl | C—H | H | CF3 | CH | CH | C—Cl | CH | H | H | H | NCCH2—CO | 1 |
| 1-40 | C—Cl | C—H | C—Cl | C—H | H | CF3 | CH | CH | C—Cl | CH | H | H | H | CH3OCH2CO | 1 |
| 1-41 | C—Cl | C—H | C—Cl | C—H | H | CF3 | CH | CH | C—Cl | CH | H | H | H | C2H5OCH2—CO | 1 |
| 1-42 | C—Cl | C—H | C—Cl | C—H | H | CF3 | CH | CH | C—Cl | CH | H | H | H | CH3SCH2CO | 1 |
| 1-43 | C—Cl | C—H | C—Cl | C—H | H | CF3 | CH | CH | C—Cl | CH | H | H | H | CH3O(CO)CH2—CO | 1 |
| 1-44 | C—Cl | C—H | C—Cl | C—H | H | CF3 | CH | CH | C—Cl | CH | H | H | H | CH3(CO)OCH2—CO | 1 |
| 1-45 | C—Cl | C—H | C—Cl | C—H | H | CF3 | CH | CH | C—Cl | CH | H | H | H | CH3O(CO)—CO | 1 |
| 1-46 | C—Cl | C—H | C—Cl | C—H | H | CF3 | CH | CH | C—Cl | CH | H | H | H | CF3O(CO)—CO | 1 |

TABLE 1-continued

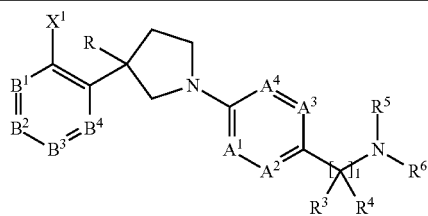

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-47 | C—Cl | C—H | C—Cl | C—H | H | CF3 | CH | CH | C—Cl | CH | H | H | H | CH3(CO)CH2—CO | 1 |
| 1-48 | C—Cl | C—H | C—Cl | C—H | H | CF3 | CH | CH | C—Cl | CH | H | H | H | (CH3)2NCH2—CO | 1 |
| 1-49 | C—Cl | C—H | C—Cl | C—H | H | CF3 | CH | CH | C—Cl | CH | H | H | H | PhCO | 1 |
| 1-50 | C—Cl | C—H | C—Cl | C—H | H | CF3 | CH | CH | C—Cl | CH | H | H | H | PhCH2CO | 1 |
| 1-51 | C—Cl | C—H | C—Cl | C—H | H | CF3 | CH | CH | C—Cl | CH | H | H | H | 2-py—CO | 1 |
| 1-52 | C—Cl | C—H | C—Cl | C—H | H | CF3 | CH | CH | C—Cl | CH | H | H | H | 3-py—CO | 1 |
| 1-53 | C—Cl | C—H | C—Cl | C—H | H | CF3 | CH | CH | C—Cl | CH | H | H | H | 4-py—CO | 1 |
| 1-54 | C—Cl | C—H | C—Cl | C—H | H | CF3 | CH | CH | C—Cl | CH | H | H | H | 6-chloropyridin-3-yl—CO | 1 |
| 1-55 | C—Cl | C—H | C—Cl | C—H | H | CF3 | CH | CH | C—Cl | CH | H | H | H | 2-F—PhCO | 1 |
| 1-56 | C—Cl | C—H | C—Cl | C—H | H | CF3 | CH | CH | C—Cl | CH | H | H | H | 3-F—PhCO | 1 |
| 1-57 | C—Cl | C—H | C—Cl | C—H | H | CF3 | CH | CH | C—Cl | CH | H | H | H | 4-F—PhCO | 1 |
| 1-58 | C—Cl | C—H | C—Cl | C—H | H | CF3 | CH | CH | C—Cl | CH | H | H | H | 2-Cl—PhCO | 1 |
| 1-59 | C—Cl | C—H | C—Cl | C—H | H | CF3 | CH | CH | C—Cl | CH | H | H | H | 3-Cl—PhCO | 1 |
| 1-60 | C—Cl | C—H | C—Cl | C—H | H | CF3 | CH | CH | C—Cl | CH | H | H | H | 4-Cl—PhCO | 1 |
| 1-61 | C—Cl | C—H | C—Cl | C—H | H | CF3 | CH | CH | C—Cl | CH | H | H | H | 2-Br—PhCO | 1 |
| 1-62 | C—Cl | C—H | C—Cl | C—H | H | CF3 | CH | CH | C—Cl | CH | H | H | H | 2-CF3—PhCO | 1 |
| 1-63 | C—Cl | C—H | C—Cl | C—H | H | CF3 | CH | CH | C—Cl | CH | H | H | H | 2-CH3—PhCO | 1 |
| 1-64 | C—Cl | C—H | C—Cl | C—H | H | CF3 | CH | CH | C—Cl | CH | H | H | H | furan-2-yl—CO | 1 |
| 1-65 | C—Cl | C—H | C—Cl | C—H | H | CF3 | CH | CH | C—Cl | CH | H | H | H | furan-3-yl—CO | 1 |
| 1-66 | C—Cl | C—H | C—Cl | C—H | H | CF3 | CH | CH | C—Cl | CH | H | H | H | thiophen-2-yl—CO | 1 |
| 1-67 | C—Cl | C—H | C—Cl | C—H | H | CF3 | CH | CH | C—Cl | CH | H | H | H | pyrrol-2-yl—CO | 1 |
| 1-68 | C—Cl | C—H | C—Cl | C—H | H | CF3 | CH | CH | C—Cl | CH | H | H | H | 3-CF3-pyrazol-4-yl—CO | 1 |
| 1-69 | C—Cl | C—H | C—Cl | C—H | H | CF3 | CH | CH | C—Cl | CH | H | H | H | 3-CF3-pyridin-2-yl—CO | 1 |
| 1-70 | C—Cl | C—H | C—Cl | C—H | H | CF3 | CH | CH | C—Cl | CH | H | H | H | pyridin-3-yl-CH2—CO | 1 |
| 1-72 | C—Cl | C—H | C—Cl | C—H | H | CF3 | CH | CH | C—Cl | CH | H | H | CH3 | CH3CO | 1 |
| 1-73 | C—Cl | C—H | C—Cl | C—H | H | CF3 | CH | CH | C—Cl | CH | H | H | CH3 | CH3CH2CO | 1 |
| 1-74 | C—Cl | C—H | C—Cl | C—H | H | CF3 | CH | CH | C—Cl | CH | H | H | CH3 | cyclo-PrCO | 1 |
| 1-75 | C—Cl | C—H | C—Cl | C—H | H | CF3 | CH | CH | C—Cl | CH | H | H | CH3 | CF3CH2CO | 1 |

TABLE 1-continued

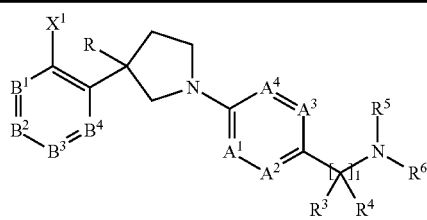

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-76 | C—Cl | C—H | C—Cl | C—H | H | CF3 | CH | CH | C—Cl | CH | H | H | H | CH3NHCO | 1 |
| 1-77 | C—Cl | C—H | C—Cl | C—H | H | CF3 | CH | CH | C—Cl | CH | H | H | H | CH3CH2NHCO | 1 |
| 1-78 | C—Cl | C—H | C—Cl | C—H | H | CF3 | CH | CH | C—Cl | CH | H | H | H | CF3CH2NHCO | 1 |
| 1-79 | C—Cl | C—H | C—Cl | C—H | H | CF3 | CH | CH | C—Cl | CH | H | H | H | n-PrNHCO | 1 |
| 1-80 | C—Cl | C—H | C—Cl | C—H | H | CF3 | CH | CH | C—Cl | CH | H | H | H | iso-PrNHCO | 1 |
| 1-81 | C—Cl | C—H | C—Cl | C—H | H | CF3 | CH | CH | C—Cl | CH | H | H | H | cyclo-PrNHCO | 1 |
| 1-82 | C—Cl | C—H | C—Cl | C—H | H | CF3 | CH | CH | C—Cl | CH | H | H | H | n-BuNHCO | 1 |
| 1-83 | C—Cl | C—H | C—Cl | C—H | H | CF3 | CH | CH | C—Cl | CH | H | H | H | tert-BuNHCO | 1 |
| 1-84 | C—Cl | C—H | C—Cl | C—H | H | CF3 | CH | CH | C—Cl | CH | H | H | H | cyclo-BuNHCO | 1 |
| 1-85 | C—Cl | C—H | C—Cl | C—H | H | CF3 | CH | CH | C—Cl | CH | H | H | H | cyclo-PenNHCO | 1 |
| 1-86 | C—Cl | C—H | C—Cl | C—H | H | CF3 | CH | CH | C—Cl | CH | H | H | H | cyclo-HexNHCO | 1 |
| 1-87 | C—Cl | C—H | C—Cl | C—H | H | CF3 | CH | CH | C—Cl | CH | H | H | H | CH2=CHCH2NHCO | 1 |
| 1-88 | C—Cl | C—H | C—Cl | C—H | H | CF3 | CH | CH | C—Cl | CH | H | H | H | HCCCH2NHCO | 1 |
| 1-89 | C—Cl | C—H | C—Cl | C—H | H | CF3 | CH | CH | C—Cl | CH | H | H | H | cyclo-PrCH2NHCO | 1 |
| 1-90 | C—Cl | C—H | C—Cl | C—H | H | CF3 | CH | CH | C—Cl | CH | H | H | H | NCCH2NHCO | 1 |
| 1-91 | C—Cl | C—H | C—Cl | C—H | H | CF3 | CH | CH | C—Cl | CH | H | H | H | CF3(CH3)CHNHCO | 1 |
| 1-92 | C—Cl | C—H | C—Cl | C—H | H | CF3 | CH | CH | C—Cl | CH | H | H | H | CF3(CH3)2CNCO | 1 |
| 1-94 | C—Cl | C—H | C—Cl | C—H | H | CF3 | CH | CH | C—Cl | CH | H | H | H | FCH2CH2NHCO | 1 |
| 1-95 | C—Cl | C—H | C—Cl | C—H | H | CF3 | CH | CH | C—Cl | CH | H | H | H | CF3CH2CH2NHCO | 1 |
| 1-96 | C—Cl | C—H | C—Cl | C—H | H | CF3 | CH | CH | C—Cl | CH | H | H | H | HCF2CF2CH2NHCO | 1 |
| 1-97 | C—Cl | C—H | C—Cl | C—H | H | CF3 | CH | CH | C—Cl | CH | H | H | H | CH3OCH2CH2NHCO | 1 |
| 1-98 | C—Cl | C—H | C—Cl | C—H | H | CF3 | CH | CH | C—Cl | CH | H | H | H | CH3SCH2CH2NHCO | 1 |
| 1-99 | C—Cl | C—H | C—Cl | C—H | H | CF3 | CH | CH | C—Cl | CH | H | H | H | F-cyclopropyl-NHCO | 1 |
| 1-100 | C—Cl | C—H | C—Cl | C—H | H | CF3 | CH | CH | C—Cl | CH | H | H | H | CF3-cyclohexyl-NHCO | 1 |
| 1-101 | C—Cl | C—H | C—Cl | C—H | H | CF3 | CH | CH | C—Cl | CH | H | H | H | EtO2CCH2NHCO | 1 |
| 1-102 | C—Cl | C—H | C—Cl | C—H | H | CF3 | CH | CH | C—Cl | CH | H | H | H | 2-CF3—PhNHCO | 1 |
| 1-103 | C—Cl | C—H | C—Cl | C—H | H | CF3 | CH | CH | C—Cl | CH | H | H | H | 3-CF3—PhNHCO | 1 |
| 1-104 | C—Cl | C—H | C—Cl | C—H | H | CF3 | CH | CH | C—Cl | CH | H | H | H | 4-CF3—PhNHCO | 1 |
| 1-105 | C—Cl | C—H | C—Cl | C—H | H | CF3 | CH | CH | C—Cl | CH | H | H | H | 2-py—NHCO | 1 |
| 1-106 | C—Cl | C—H | C—Cl | C—H | H | CF3 | CH | CH | C—Cl | CH | H | H | H | 3-py—NHCO | 1 |
| 1-107 | C—Cl | C—H | C—Cl | C—H | H | CF3 | CH | CH | C—Cl | CH | H | H | H | 4-py—NHCO | 1 |
| 1-108 | C—Cl | C—H | C—Cl | C—H | H | CF3 | CH | CH | C—Cl | CH | H | H | H | 5-CF3-2-pyridyl-NHCO | 1 |
| 1-109 | C—Cl | C—H | C—Cl | C—H | H | CF3 | CH | CH | C—Cl | CH | H | H | H | 6-CF3-3-pyridyl-NHCO | 1 |
| 1-110 | C—Cl | C—H | C—Cl | C—H | H | CF3 | CH | CH | C—Cl | CH | H | H | H | PhCH2HNCO | 1 |
| 1-111 | C—Cl | C—H | C—Cl | C—H | H | CF3 | CH | CH | C—Cl | CH | H | H | H | (2-pyridyl)CH2NHCO | 1 |
| 1-112 | C—Cl | C—H | C—Cl | C—H | H | CF3 | CH | CH | C—Cl | CH | H | H | CH3 | CH3NHCO | 1 |

TABLE 1-continued

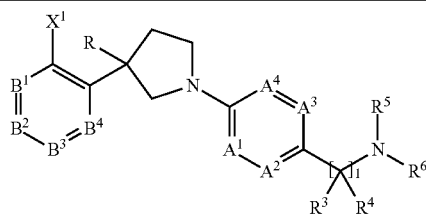

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-113 | C—Cl | C—H | C—Cl | C—H | H | CF3 | CH | CH | C—Cl | CH | H | H | CH3 | CH3CH2NHCO | 1 |
| 1-114 | C—Cl | C—H | C—Cl | C—H | H | CF3 | CH | CH | C—Cl | CH | H | H | CH3 | cyclo-PrNHCO | 1 |
| 1-115 | C—Cl | C—H | C—Cl | C—H | H | CF3 | CH | CH | C—Cl | CH | H | H | H | pyrrolidineCO | 1 |
| 1-116 | C—Cl | C—H | C—Cl | C—H | H | CF3 | CH | CH | C—Cl | CH | H | H | H | piperidineCO | 1 |
| 1-117 | C—Cl | C—H | C—Cl | C—H | H | CF3 | CH | CH | C—Cl | CH | H | H | H | morpholineCO | 1 |
| 1-118 | C—Cl | C—H | C—Cl | C—H | H | CF3 | CH | CH | C—Cl | CH | H | H | H | (CH3)2NCO | 1 |
| 1-119 | C—Cl | C—H | C—Cl | C—H | H | CF3 | CH | CH | C—Cl | CH | H | H | H | CH3OCO | 1 |
| 1-120 | C—Cl | C—H | C—Cl | C—H | H | CF3 | CH | CH | C—Cl | CH | H | H | H | CH3CH2OCO | 1 |
| 1-121 | C—Cl | C—H | C—Cl | C—H | H | CF3 | CH | CH | C—Cl | CH | H | H | H | c-PrOCO | 1 |
| 1-122 | C—Cl | C—H | C—Cl | C—H | H | CF3 | CH | CH | C—Cl | CH | H | H | H | c-PrCH2OCO | 1 |
| 1-123 | C—Cl | C—H | C—Cl | C—H | H | CF3 | CH | CH | C—Cl | CH | H | H | H | CF3CH2OCO | 1 |
| 1-124 | C—Cl | C—H | C—Cl | C—H | H | CF3 | CH | CH | C—Cl | CH | H | H | H | CH2=CHCH2OCO | 1 |
| 1-125 | C—Cl | C—H | C—Cl | C—H | H | CF3 | CH | CH | C—Cl | CH | H | H | H | HCCCH2OCO | 1 |
| 1-126 | C—Cl | C—H | C—Cl | C—H | H | CF3 | CH | CH | C—Cl | CH | H | H | H | PhOCO | 1 |
| 1-127 | C—Cl | C—H | C—Cl | C—H | H | CF3 | CH | CH | C—Cl | CH | H | H | H | PhCH2OCO | 1 |
| 1-128 | C—Cl | C—H | C—Cl | C—H | H | CF3 | CH | CH | C—Cl | CH | H | H | H | tert-BuOCO | 1 |
| 1-129 | C—Cl | C—H | C—Cl | C—H | H | CF3 | CH | CH | C—Cl | CH | H | H | CH3 | tert-BuOCO | 1 |
| 1-130 | C—Cl | C—H | C—Cl | C—H | H | CF3 | CH | CH | C—Cl | CH | H | H | H | CH3SO2 | 1 |
| 1-131 | C—Cl | C—H | C—Cl | C—H | H | CF3 | CH | CH | C—Cl | CH | H | H | H | CH3CH2SO2 | 1 |
| 1-132 | C—Cl | C—H | C—Cl | C—H | H | CF3 | CH | CH | C—Cl | CH | H | H | H | CF3SO2 | 1 |
| 1-133 | C—Cl | C—H | C—Cl | C—H | H | CF3 | CH | CH | C—Cl | CH | H | H | H | CF3CH2SO2 | 1 |
| 1-134 | C—Cl | C—H | C—Cl | C—H | H | CF3 | CH | CH | C—Cl | CH | H | H | H | PhSO2 | 1 |
| 1-135 | C—Cl | C—H | C—Cl | C—H | H | CF3 | CH | CH | C—Cl | CH | H | H | H | CH3NHCONHSO2 | 1 |
| 1-136 | C—Cl | C—H | C—Cl | C—H | H | CF3 | CH | CH | C—Cl | CH | H | H | H | (CH3)2NCONHSO2 | 1 |
| 1-137 | C—Cl | C—H | C—Cl | C—H | H | CF3 | CH | CH | C—Cl | CH | H | H | H | CH3CS | 1 |
| 1-138 | C—Cl | C—H | C—Cl | C—H | H | CF3 | CH | CH | C—Cl | CH | H | H | H | CH3CH2CS | 1 |
| 1-139 | C—Cl | C—H | C—Cl | C—H | H | CF3 | CH | CH | C—Cl | CH | H | H | H | cyclo-PrCS | 1 |
| 1-140 | C—Cl | C—H | C—Cl | C—H | H | CF3 | CH | CH | C—Cl | CH | H | H | H | CF3CH2CS | 1 |
| 1-141 | C—Cl | C—H | C—Cl | C—H | H | CF3 | CH | CH | C—CF3 | CH | H | H | H | H | 1 |
| 1-143 | C—Cl | C—H | C—Cl | C—H | H | CF3 | CH | CH | C—CF3 | CH | H | H | H | CH3CH2CO | 1 |
| 1-144 | C—Cl | C—H | C—Cl | C—H | H | CF3 | CH | CH | C—CF3 | CH | H | H | H | n-PrCO | 1 |
| 1-145 | C—Cl | C—H | C—Cl | C—H | H | CF3 | CH | CH | C—CF3 | CH | H | H | H | iso-PrCO | 1 |
| 1-146 | C—Cl | C—H | C—Cl | C—H | H | CF3 | CH | CH | C—CF3 | CH | H | H | H | cyclo-PrCO | 1 |
| 1-147 | C—Cl | C—H | C—Cl | C—H | H | CF3 | CH | CH | C—CF3 | CH | H | H | H | n-BuCO | 1 |
| 1-148 | C—Cl | C—H | C—Cl | C—H | H | CF3 | CH | CH | C—CF3 | CH | H | H | H | tert-BuCO | 1 |

TABLE 1-continued

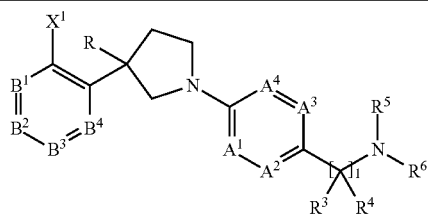

| Ex.-No. | B$^1$ | B$^2$ | B$^3$ | B$^4$ | X$^1$ | R | A$^1$ | A$^2$ | A$^3$ | A$^4$ | R$^3$ | R$^4$ | R$^5$ | R$^6$ | 1 |
|---|---|---|---|---|---|---|---|---|---|---|---|---|---|---|---|
| 1-149 | C—Cl | C—H | C—Cl | C—H | H | CF3 | CH | CH | C—CF3 | CH | H | H | H | iso-BuCO | 1 |
| 1-150 | C—Cl | C—H | C—Cl | C—H | H | CF3 | CH | CH | C—CF3 | CH | H | H | H | cyclo-BuCO | 1 |
| 1-151 | C—Cl | C—H | C—Cl | C—H | H | CF3 | CH | CH | C—CF3 | CH | H | H | H | (CH3)3CCH2CO | 1 |
| 1-152 | C—Cl | C—H | C—Cl | C—H | H | CF3 | CH | CH | C—CF3 | CH | H | H | H | cyclo-PenCO | 1 |
| 1-153 | C—Cl | C—H | C—Cl | C—H | H | CF3 | CH | CH | C—CF3 | CH | H | H | H | cyclo-HexCO | 1 |
| 1-154 | C—Cl | C—H | C—Cl | C—H | H | CF3 | CH | CH | C—CF3 | CH | H | H | H | cyclopentenyl-CO | 1 |
| 1-155 | C—Cl | C—H | C—Cl | C—H | H | CF3 | CH | CH | C—CF3 | CH | H | H | H | cyclo-PrCH2CO | 1 |
| 1-156 | C—Cl | C—H | C—Cl | C—H | H | CF3 | CH | CH | C—CF3 | CH | H | H | H | CF3CO | 1 |
| 1-157 | C—Cl | C—H | C—Cl | C—H | H | CF3 | CH | CH | C—CF3 | CH | H | H | H | CCl3CO | 1 |
| 1-158 | C—Cl | C—H | C—Cl | C—H | H | CF3 | CH | CH | C—CF3 | CH | H | H | H | ClCH2CO | 1 |
| 1-159 | C—Cl | C—H | C—Cl | C—H | H | CF3 | CH | CH | C—CF3 | CH | H | H | H | CF2ClCO | 1 |
| 1-160 | C—Cl | C—H | C—Cl | C—H | H | CF3 | CH | CH | C—CF3 | CH | H | H | H | ClCH2CH2CO | 1 |
| 1-161 | C—Cl | C—H | C—Cl | C—H | H | CF3 | CH | CH | C—CF3 | CH | H | H | H | HCF2CF2CO | 1 |
| 1-162 | C—Cl | C—H | C—Cl | C—H | H | CF3 | CH | CH | C—CF3 | CH | H | H | H | CF3CH2CO | 1 |
| 1-163 | C—Cl | C—H | C—Cl | C—H | H | CF3 | CH | CH | C—CF3 | CH | H | H | H | (CF3)2CHCO | 1 |
| 1-164 | C—Cl | C—H | C—Cl | C—H | H | CF3 | CH | CH | C—CF3 | CH | H | H | H | HCF2CO | 1 |
| 1-165 | C—Cl | C—H | C—Cl | C—H | H | CF3 | CH | CH | C—CF3 | CH | H | H | H | ClCH2CO | 1 |
| 1-166 | C—Cl | C—H | C—Cl | C—H | H | CF3 | CH | CH | C—CF3 | CH | H | H | H | 4-(CF3)-cyclohexyl-CO | 1 |
| 1-167 | C—Cl | C—H | C—Cl | C—H | H | CF3 | CH | CH | C—CF3 | CH | H | H | H | 1-methyl-cyclopropyl-CO | 1 |
| 1-168 | C—Cl | C—H | C—Cl | C—H | H | CF3 | CH | CH | C—CF3 | CH | H | H | H | 2,2-dichloro-cyclopropyl-CO | 1 |
| 1-169 | C—Cl | C—H | C—Cl | C—H | H | CF3 | CH | CH | C—CF3 | CH | H | H | H | 2,2-difluoro-cyclopropyl-CO | 1 |
| 1-170 | C—Cl | C—H | C—Cl | C—H | H | CF3 | CH | CH | C—CF3 | CH | H | H | H | 2-fluoro-cyclopropyl-CO | 1 |
| 1-171 | C—Cl | C—H | C—Cl | C—H | H | CF3 | CH | CH | C—CF3 | CH | H | H | H | 2-methyl-cyclopropyl-CO | 1 |
| 1-172 | C—Cl | C—H | C—Cl | C—H | H | CF3 | CH | CH | C—CF3 | CH | H | H | H | 1-isocyano-cyclopropyl-CO | 1 |

TABLE 1-continued

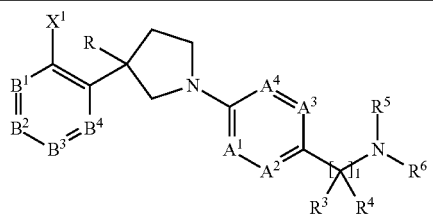

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-173 | C—Cl | C—H | C—Cl | C—H | H | CF3 | CH | CH | C—CF3 | CH | H | H | H | CH2=CH—CO | 1 |
| 1-174 | C—Cl | C—H | C—Cl | C—H | H | CF3 | CH | CH | C—CF3 | CH | H | H | H | CH3CH=CH—CO | 1 |
| 1-175 | C—Cl | C—H | C—Cl | C—H | H | CF3 | CH | CH | C—CF3 | CH | H | H | H | CH2=C(CH3)—CO | 1 |
| 1-176 | C—Cl | C—H | C—Cl | C—H | H | CF3 | CH | CH | C—CF3 | CH | H | H | H | CH3CH=C(CH3)—CO | 1 |
| 1-177 | C—Cl | C—H | C—Cl | C—H | H | CF3 | CH | CH | C—CF3 | CH | H | H | H | (CH3)2C=CH—CO | 1 |
| 1-178 | C—Cl | C—H | C—Cl | C—H | H | CF3 | CH | CH | C—CF3 | CH | H | H | H | CH2=C(Cl)—CO | 1 |
| 1-179 | C—Cl | C—H | C—Cl | C—H | H | CF3 | CH | CH | C—CF3 | CH | H | H | H | ClCH=C(CH3)—CO | 1 |
| 1-180 | C—Cl | C—H | C—Cl | C—H | H | CF3 | CH | CH | C—CF3 | CH | H | H | H | CH2=CHCH2—CO | 1 |
| 1-181 | C—Cl | C—H | C—Cl | C—H | H | CF3 | CH | CH | C—CF3 | CH | H | H | H | HCC—CO | 1 |
| 1-182 | C—Cl | C—H | C—Cl | C—H | H | CF3 | CH | CH | C—CF3 | CH | H | H | H | CH3CC—CO | 1 |
| 1-183 | C—Cl | C—H | C—Cl | C—H | H | CF3 | CH | CH | C—CF3 | CH | H | H | H | NCCH2—CO | 1 |
| 1-184 | C—Cl | C—H | C—Cl | C—H | H | CF3 | CH | CH | C—CF3 | CH | H | H | H | CH3OCH2CO | 1 |
| 1-185 | C—Cl | C—H | C—Cl | C—H | H | CF3 | CH | CH | C—CF3 | CH | H | H | H | C2H5OCH2—CO | 1 |
| 1-186 | C—Cl | C—H | C—Cl | C—H | H | CF3 | CH | CH | C—CF3 | CH | H | H | H | CH3SCH2CO | 1 |
| 1-187 | C—Cl | C—H | C—Cl | C—H | H | CF3 | CH | CH | C—CF3 | CH | H | H | H | CH3O(CO)CH2—CO | 1 |
| 1-188 | C—Cl | C—H | C—Cl | C—H | H | CF3 | CH | CH | C—CF3 | CH | H | H | H | CH3(CO)OCH2—CO | 1 |
| 1-189 | C—Cl | C—H | C—Cl | C—H | H | CF3 | CH | CH | C—CF3 | CH | H | H | H | CH3O(CO)—CO | 1 |
| 1-190 | C—Cl | C—H | C—Cl | C—H | H | CF3 | CH | CH | C—CF3 | CH | H | H | H | CF3O(CO)—CO | 1 |
| 1-191 | C—Cl | C—H | C—Cl | C—H | H | CF3 | CH | CH | C—CF3 | CH | H | H | H | CH3(CO)CH2—CO | 1 |
| 1-192 | C—Cl | C—H | C—Cl | C—H | H | CF3 | CH | CH | C—CF3 | CH | H | H | H | (CH3)2NCH2—CO | 1 |
| 1-193 | C—Cl | C—H | C—Cl | C—H | H | CF3 | CH | CH | C—CF3 | CH | H | H | H | PhCO | 1 |
| 1-194 | C—Cl | C—H | C—Cl | C—H | H | CF3 | CH | CH | C—CF3 | CH | H | H | H | PhCH2CO | 1 |
| 1-195 | C—Cl | C—H | C—Cl | C—H | H | CF3 | CH | CH | C—CF3 | CH | H | H | H | 2-py—CO | 1 |
| 1-196 | C—Cl | C—H | C—Cl | C—H | H | CF3 | CH | CH | C—CF3 | CH | H | H | H | 3-py—CO | 1 |
| 1-197 | C—Cl | C—H | C—Cl | C—H | H | CF3 | CH | CH | C—CF3 | CH | H | H | H | 4-py—CO | 1 |
| 1-198 | C—Cl | C—H | C—Cl | C—H | H | CF3 | CH | CH | C—CF3 | CH | H | H | H | | 1 |
| 1-199 | C—Cl | C—H | C—Cl | C—H | H | CF3 | CH | CH | C—CF3 | CH | H | H | H | 2-F—PhCO | 1 |
| 1-200 | C—Cl | C—H | C—Cl | C—H | H | CF3 | CH | CH | C—CF3 | CH | H | H | H | 3-F—PhCO | 1 |
| 1-201 | C—Cl | C—H | C—Cl | C—H | H | CF3 | CH | CH | C—CF3 | CH | H | H | H | 4-F—PhCO | 1 |
| 1-202 | C—Cl | C—H | C—Cl | C—H | H | CF3 | CH | CH | C—CF3 | CH | H | H | H | 2-Cl—PhCO | 1 |
| 1-203 | C—Cl | C—H | C—Cl | C—H | H | CF3 | CH | CH | C—CF3 | CH | H | H | H | 3-Cl—PhCO | 1 |
| 1-204 | C—Cl | C—H | C—Cl | C—H | H | CF3 | CH | CH | C—CF3 | CH | H | H | H | 4-Cl—PhCO | 1 |
| 1-205 | C—Cl | C—H | C—Cl | C—H | H | CF3 | CH | CH | C—CF3 | CH | H | H | H | 2-Br—PhCO | 1 |

TABLE 1-continued

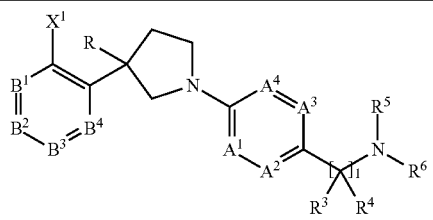

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-206 | C—Cl | C—H | C—Cl | C—H | H | CF3 | CH | CH | C—CF3 | CH | H | H | H | 2-CF3—PhCO | 1 |
| 1-207 | C—Cl | C—H | C—Cl | C—H | H | CF3 | CH | CH | C—CF3 | CH | H | H | H | 2-CH3—PhCO | 1 |
| 1-208 | C—Cl | C—H | C—Cl | C—H | H | CF3 | CH | CH | C—CF3 | CH | H | H | H | furan-2-CO | 1 |
| 1-209 | C—Cl | C—H | C—Cl | C—H | H | CF3 | CH | CH | C—CF3 | CH | H | H | H | furan-3-CO | 1 |
| 1-210 | C—Cl | C—H | C—Cl | C—H | H | CF3 | CH | CH | C—CF3 | CH | H | H | H | thiophene-2-CO | 1 |
| 1-211 | C—Cl | C—H | C—Cl | C—H | H | CF3 | CH | CH | C—CF3 | CH | H | H | H | pyrrole-2-CO | 1 |
| 1-212 | C—Cl | C—H | C—Cl | C—H | H | CF3 | CH | CH | C—CF3 | CH | H | H | H | 3-CF3-pyrazole-4-CO | 1 |
| 1-213 | C—Cl | C—H | C—Cl | C—H | H | CF3 | CH | CH | C—CF3 | CH | H | H | H | 3-CF3-pyridine-2-CO | 1 |
| 1-214 | C—Cl | C—H | C—Cl | C—H | H | CF3 | CH | CH | C—CF3 | CH | H | H | H | pyridin-3-yl-CH2CO | 1 |
| 1-215 | C—Cl | C—H | C—Cl | C—H | H | CF3 | CH | CH | C—CF3 | CH | H | H | H | PhCH2CO | 1 |
| 1-216 | C—Cl | C—H | C—Cl | C—H | H | CF3 | CH | CH | C—CF3 | CH | H | H | H | PhCH=CHCO | 1 |
| 1-217 | C—Cl | C—H | C—Cl | C—H | H | CF3 | CH | CH | C—CF3 | CH | H | H | CH3 | CH3CO | 1 |
| 1-218 | C—Cl | C—H | C—Cl | C—H | H | CF3 | CH | CH | C—CF3 | CH | H | H | CH3 | cyclo-PrCO | 1 |
| 1-219 | C—Cl | C—H | C—Cl | C—H | H | CF3 | CH | CH | C—CF3 | CH | H | H | H | CH3NHCO | 1 |
| 1-220 | C—Cl | C—H | C—Cl | C—H | H | CF3 | CH | CH | C—CF3 | CH | H | H | H | CH3CH2NHCO | 1 |
| 1-221 | C—Cl | C—H | C—Cl | C—H | H | CF3 | CH | CH | C—CF3 | CH | H | H | H | CF3CH2NHCO | 1 |
| 1-222 | C—Cl | C—H | C—Cl | C—H | H | CF3 | CH | CH | C—CF3 | CH | H | H | H | n-PrNHCO | 1 |

TABLE 1-continued

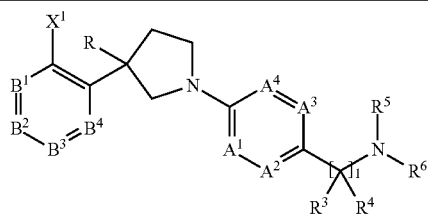

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-223 | C—Cl | C—H | C—Cl | C—H | H | CF3 | CH | CH | C—CF3 | CH | H | H | H | iso-PrNHCO | 1 |
| 1-224 | C—Cl | C—H | C—Cl | C—H | H | CF3 | CH | CH | C—CF3 | CH | H | H | H | cyclo-PrNHCO | 1 |
| 1-225 | C—Cl | C—H | C—Cl | C—H | H | CF3 | CH | CH | C—CF3 | CH | H | H | H | n-BuNHCO | 1 |
| 1-226 | C—Cl | C—H | C—Cl | C—H | H | CF3 | CH | CH | C—CF3 | CH | H | H | H | tert-BuNHCO | 1 |
| 1-227 | C—Cl | C—H | C—Cl | C—H | H | CF3 | CH | CH | C—CF3 | CH | H | H | H | cyclo-BuNHCO | 1 |
| 1-228 | C—Cl | C—H | C—Cl | C—H | H | CF3 | CH | CH | C—CF3 | CH | H | H | H | cyclo-PenNHCO | 1 |
| 1-229 | C—Cl | C—H | C—Cl | C—H | H | CF3 | CH | CH | C—CF3 | CH | H | H | H | cyclo-HexNHCO | 1 |
| 1-230 | C—Cl | C—H | C—Cl | C—H | H | CF3 | CH | CH | C—CF3 | CH | H | H | H | CH2=CHCH2NHCO | 1 |
| 1-231 | C—Cl | C—H | C—Cl | C—H | H | CF3 | CH | CH | C—CF3 | CH | H | H | H | HCCCH2NHCO | 1 |
| 1-232 | C—Cl | C—H | C—Cl | C—H | H | CF3 | CH | CH | C—CF3 | CH | H | H | H | cyclo-PrCH2NHCO | 1 |
| 1-233 | C—Cl | C—H | C—Cl | C—H | H | CF3 | CH | CH | C—CF3 | CH | H | H | H | NCCH2NHCO | 1 |
| 1-234 | C—Cl | C—H | C—Cl | C—H | H | CF3 | CH | CH | C—CF3 | CH | H | H | H | CF3(CH3)CHNHCO | 1 |
| 1-235 | C—Cl | C—H | C—Cl | C—H | H | CF3 | CH | CH | C—CF3 | CH | H | H | H | CF3(CH3)2CNCO | 1 |
| 1-237 | C—Cl | C—H | C—Cl | C—H | H | CF3 | CH | CH | C—CF3 | CH | H | H | H | FCH2CH2NHCO | 1 |
| 1-238 | C—Cl | C—H | C—Cl | C—H | H | CF3 | CH | CH | C—CF3 | CH | H | H | H | CF3CH2CH2NHCO | 1 |
| 1-239 | C—Cl | C—H | C—Cl | C—H | H | CF3 | CH | CH | C—CF3 | CH | H | H | H | HCF2CF2CH2NHCO | 1 |
| 1-240 | C—Cl | C—H | C—Cl | C—H | H | CF3 | CH | CH | C—CF3 | CH | H | H | H | F-cyclopropyl-NHCO | 1 |
| 1-241 | C—Cl | C—H | C—Cl | C—H | H | CF3 | CH | CH | C—CF3 | CH | H | H | H | CF3-cyclohexyl-NHCO | 1 |
| 1-242 | C—Cl | C—H | C—Cl | C—H | H | CF3 | CH | CH | C—CF3 | CH | H | H | H | EtO2CCH2NHCO | 1 |
| 1-243 | C—Cl | C—H | C—Cl | C—H | H | CF3 | CH | CH | C—CF3 | CH | H | H | H | CH3OCH2CH2NHCO | 1 |
| 1-244 | C—Cl | C—H | C—Cl | C—H | H | CF3 | CH | CH | C—CF3 | CH | H | H | H | CH3SCH2CH2NHCO | 1 |
| 1-245 | C—Cl | C—H | C—Cl | C—H | H | CF3 | CH | CH | C—CF3 | CH | H | H | H | 2-CF3—PhNHCO | 1 |
| 1-246 | C—Cl | C—H | C—Cl | C—H | H | CF3 | CH | CH | C—CF3 | CH | H | H | H | 3-CF3—PhNHCO | 1 |
| 1-247 | C—Cl | C—H | C—Cl | C—H | H | CF3 | CH | CH | C—CF3 | CH | H | H | H | 4-CF3—PhNHCO | 1 |
| 1-248 | C—Cl | C—H | C—Cl | C—H | H | CF3 | CH | CH | C—CF3 | CH | H | H | H | 2-py—NHCO | 1 |
| 1-249 | C—Cl | C—H | C—Cl | C—H | H | CF3 | CH | CH | C—CF3 | CH | H | H | H | 3-py—NHCO | 1 |
| 1-250 | C—Cl | C—H | C—Cl | C—H | H | CF3 | CH | CH | C—CF3 | CH | H | H | H | 4-py—NHCO | 1 |
| 1-251 | C—Cl | C—H | C—Cl | C—H | H | CF3 | CH | CH | C—CF3 | CH | H | H | H | 5-CF3-2-pyridyl-NHCO | 1 |
| 1-252 | C—Cl | C—H | C—Cl | C—H | H | CF3 | CH | CH | C—CF3 | CH | H | H | H | 6-CF3-3-pyridyl-NHCO | 1 |

TABLE 1-continued

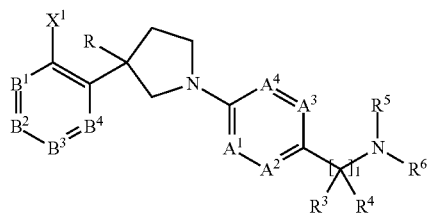

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-253 | C—Cl | C—H | C—Cl | C—H | H | CF3 | CH | CH | C—CF3 | CH | H | H | H | PhCH2HNCO | 1 |
| 1-254 | C—Cl | C—H | C—Cl | C—H | H | CF3 | CH | CH | C—CF3 | CH | H | H | H | 2-pyridyl-CH2NHCO | 1 |
| 1-255 | C—Cl | C—H | C—Cl | C—H | H | CF3 | CH | CH | C—CF3 | CH | H | H | H | pyrrolidineCO | 1 |
| 1-256 | C—Cl | C—H | C—Cl | C—H | H | CF3 | CH | CH | C—CF3 | CH | H | H | H | piperidineCO | 1 |
| 1-257 | C—Cl | C—H | C—Cl | C—H | H | CF3 | CH | CH | C—CF3 | CH | H | H | H | morpholineCO | 1 |
| 1-258 | C—Cl | C—H | C—Cl | C—H | H | CF3 | CH | CH | C—CF3 | CH | H | H | CH3 | CH3NHCO | 1 |
| 1-259 | C—Cl | C—H | C—Cl | C—H | H | CF3 | CH | CH | C—CF3 | CH | H | H | CH3 | CH3CH2NHCO | 1 |
| 1-260 | C—Cl | C—H | C—Cl | C—H | H | CF3 | CH | CH | C—CF3 | CH | H | H | CH3 | cyclo-PrNHCO | 1 |
| 1-261 | C—Cl | C—H | C—Cl | C—H | H | CF3 | CH | CH | C—CF3 | CH | H | H | H | CH3OCO | 1 |
| 1-262 | C—Cl | C—H | C—Cl | C—H | H | CF3 | CH | CH | C—CF3 | CH | H | H | H | CH3CH2OCO | 1 |
| 1-263 | C—Cl | C—H | C—Cl | C—H | H | CF3 | CH | CH | C—CF3 | CH | H | H | H | c-PrOCO | 1 |
| 1-264 | C—Cl | C—H | C—Cl | C—H | H | CF3 | CH | CH | C—CF3 | CH | H | H | H | c-PrCH2OCO | 1 |
| 1-265 | C—Cl | C—H | C—Cl | C—H | H | CF3 | CH | CH | C—CF3 | CH | H | H | H | CF3CH2OCO | 1 |
| 1-266 | C—Cl | C—H | C—Cl | C—H | H | CF3 | CH | CH | C—CF3 | CH | H | H | H | CH2=CHCH2OCO | 1 |
| 1-267 | C—Cl | C—H | C—Cl | C—H | H | CF3 | CH | CH | C—CF3 | CH | H | H | H | HCCCH2OCO | 1 |
| 1-268 | C—Cl | C—H | C—Cl | C—H | H | CF3 | CH | CH | C—CF3 | CH | H | H | H | PhOCO | 1 |
| 1-269 | C—Cl | C—H | C—Cl | C—H | H | CF3 | CH | CH | C—CF3 | CH | H | H | H | PhCH2OCO | 1 |
| 1-270 | C—Cl | C—H | C—Cl | C—H | H | CF3 | CH | CH | C—CF3 | CH | H | H | H | tert-BuOCO | 1 |
| 1-271 | C—Cl | C—H | C—Cl | C—H | H | CF3 | CH | CH | C—CF3 | CH | H | H | CH3 | tert-BuOCO | 1 |
| 1-272 | C—Cl | C—H | C—Cl | C—H | H | CF3 | CH | CH | C—CF3 | CH | H | H | H | CH3SO2 | 1 |
| 1-273 | C—Cl | C—H | C—Cl | C—H | H | CF3 | CH | CH | C—CF3 | CH | H | H | H | CH3CH2SO2 | 1 |
| 1-274 | C—Cl | C—H | C—Cl | C—H | H | CF3 | CH | CH | C—CF3 | CH | H | H | H | CF3SO2 | 1 |
| 1-275 | C—Cl | C—H | C—Cl | C—H | H | CF3 | CH | CH | C—CF3 | CH | H | H | H | CF3CH2SO2 | 1 |
| 1-276 | C—Cl | C—H | C—Cl | C—H | H | CF3 | CH | CH | C—CF3 | CH | H | H | H | PhSO2 | 1 |
| 1-277 | C—Cl | C—H | C—Cl | C—H | H | CF3 | CH | CH | C—CF3 | CH | H | H | H | CH3NHCONHSO2 | 1 |
| 1-278 | C—Cl | C—H | C—Cl | C—H | H | CF3 | CH | CH | C—CF3 | CH | H | H | H | (CH3)2NCONHSO2 | 1 |
| 1-279 | C—Cl | C—H | C—Cl | C—H | H | CF3 | CH | CH | C—CF3 | CH | H | H | H | CH3CS | 1 |
| 1-280 | C—Cl | C—H | C—Cl | C—H | H | CF3 | CH | CH | C—CF3 | CH | H | H | H | CH3CH2CS | 1 |
| 1-281 | C—Cl | C—H | C—Cl | C—H | H | CF3 | CH | CH | C—CF3 | CH | H | H | H | cyclo-PrCS | 1 |
| 1-282 | C—Cl | C—H | C—Cl | C—H | H | CF3 | CH | CH | C—CF3 | CH | H | H | H | CF3CH2CS | 1 |

TABLE 1-continued

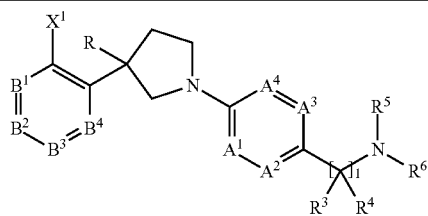

| Ex.-No. | $B^1$ | $B^2$ | $B^3$ | $B^4$ | $X^1$ | R | $A^1$ | $A^2$ | $A^3$ | $A^4$ | $R^3$ | $R^4$ | $R^5$ | $R^6$ | 1 |
|---|---|---|---|---|---|---|---|---|---|---|---|---|---|---|---|
| 1-283 | C—Cl | C—H | C—Cl | C—H | H | CF3 | CH | CH | C—Br | CH | H | H | H | H | 1 |
| 1-284 | C—Cl | C—H | C—Cl | C—H | H | CF3 | CH | CH | C—Br | CH | H | H | H | n-PrCO | 1 |
| 1-285 | C—Cl | C—H | C—Cl | C—H | H | CF3 | CH | CH | C—Br | CH | H | H | H | CH3CH2CO | 1 |
| 1-286 | C—Cl | C—H | C—Cl | C—H | H | CF3 | CH | CH | C—Br | CH | H | H | H | cyclo-PrCO | 1 |
| 1-287 | C—Cl | C—H | C—Cl | C—H | H | CF3 | CH | CH | C—Br | CH | H | H | H | CF3CH2CO | 1 |
| 1-288 | C—Cl | C—H | C—Cl | C—H | H | CF3 | CH | CH | C—Br | CH | H | H | H | CH3CH2NHCO | 1 |
| 1-289 | C—Cl | C—H | C—Cl | C—H | H | CF3 | CH | CH | C—CH3 | CH | H | H | H | H | 1 |
| 1-290 | C—Cl | C—H | C—Cl | C—H | H | CF3 | CH | CH | C—CH3 | CH | H | H | H | CH3CO | 1 |
| 1-291 | C—Cl | C—H | C—Cl | C—H | H | CF3 | CH | CH | C—CH3 | CH | H | H | H | CH3CH2CO | 1 |
| 1-292 | C—Cl | C—H | C—Cl | C—H | H | CF3 | CH | CH | C—CH3 | CH | H | H | H | cyclo-PrCO | 1 |
| 1-293 | C—Cl | C—H | C—Cl | C—H | H | CF3 | CH | CH | C—CH3 | CH | H | H | H | CF3CH2CO | 1 |
| 1-294 | C—Cl | C—H | C—Cl | C—H | H | CF3 | CH | CH | C—CH3 | CH | H | H | H | CH3CH2NHCO | 1 |
| 1-295 | C—CF3 | C—H | C—CF3 | C—H | H | CF3 | CH | CH | C—CF3 | CH | H | H | H | H | 1 |
| 1-296 | C—CF3 | C—H | C—CF3 | C—H | H | CF3 | CH | CH | C—CF3 | CH | H | H | H | CF3CH2CO | 1 |
| 1-297 | C—CF3 | C—H | C—CF3 | C—H | H | CF3 | CH | CH | C—CF3 | CH | H | H | H | ClCH2CH2CO | 1 |
| 1-298 | C—CF3 | C—H | C—CF3 | C—H | H | CF3 | CH | CH | C—CF3 | CH | H | H | H | CH3OCO | 1 |
| 1-299 | C—CF3 | C—H | C—CF3 | C—H | H | CF3 | CH | CH | C—CF3 | CH | H | H | H | CH3CH2OCO | 1 |
| 1-300 | C—CF3 | C—H | C—CF3 | C—H | H | CF3 | CH | CH | C—CF3 | CH | H | H | H | tert-BuOCO | 1 |
| 1-301 | C—CF3 | C—H | C—CF3 | C—H | H | CF3 | CH | CH | C—CF3 | CH | H | H | H | CH3NHCO | 1 |
| 1-302 | C—CF3 | C—H | C—CF3 | C—H | H | CF3 | CH | CH | C—CF3 | CH | H | H | H | CH3CH2NHCO | 1 |
| 1-303 | C—CF3 | C—H | C—CF3 | C—H | H | CF3 | CH | CH | C—CF3 | CH | H | H | H | n-PrNHCO | 1 |
| 1-304 | C—CF3 | C—H | C—CF3 | C—H | H | CF3 | CH | CH | C—CF3 | CH | H | H | H | iso-PrNHCO | 1 |
| 1-305 | C—CF3 | C—H | C—CF3 | C—H | H | CF3 | CH | CH | C—CF3 | CH | H | H | H | cyclo-PrNHCO | 1 |
| 1-306 | C—CF3 | C—H | C—CF3 | C—H | H | CF3 | CH | CH | C—Cl | CH | H | H | H | H | 1 |
| 1-307 | C—CF3 | C—H | C—CF3 | C—H | H | CF3 | CH | CH | C—Cl | CH | H | H | H | CH3CH2CO | 1 |
| 1-308 | C—CF3 | C—H | C—CF3 | C—H | H | CF3 | CH | CH | C—Cl | CH | H | H | H | cyclo-PrCO | 1 |
| 1-309 | C—CF3 | C—H | C—CF3 | C—H | H | CF3 | CH | CH | C—Cl | CH | H | H | H | CF3CH2CO | 1 |
| 1-310 | C—CF3 | C—H | C—CF3 | C—H | H | CF3 | CH | CH | C—Cl | CH | H | H | H | tert-BuOCO | 1 |
| 1-311 | C—CF3 | C—H | C—CF3 | C—H | H | CF3 | CH | CH | C—Br | CH | H | H | H | H | 1 |
| 1-312 | C—CF3 | C—H | C—CF3 | C—H | H | CF3 | CH | CH | C—Br | CH | H | H | H | CH3CH2CO | 1 |
| 1-313 | C—CF3 | C—H | C—CF3 | C—H | H | CF3 | CH | CH | C—Br | CH | H | H | H | cyclo-PrCO | 1 |
| 1-314 | C—CF3 | C—H | C—CF3 | C—H | H | CF3 | CH | CH | C—Br | CH | H | H | H | CF3CH2CO | 1 |
| 1-315 | C—CF3 | C—H | C—CF3 | C—H | H | CF3 | CH | CH | C—Br | CH | H | H | H | tert-BuOCO | 1 |
| 1-316 | C—CF3 | C—H | C—CF3 | C—H | H | CF3 | CH | CH | C—NO2 | CH | H | H | H | H | 1 |
| 1-317 | C—CF3 | C—H | C—CF3 | C—H | H | CF3 | CH | CH | C—NO2 | CH | H | H | H | CH3CO | 1 |

TABLE 1-continued

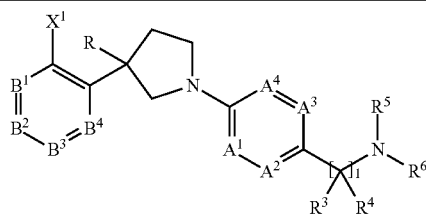

| Ex.-No. | $B^1$ | $B^2$ | $B^3$ | $B^4$ | $X^1$ | R | $A^1$ | $A^2$ | $A^3$ | $A^4$ | $R^3$ | $R^4$ | $R^5$ | $R^6$ | 1 |
|---|---|---|---|---|---|---|---|---|---|---|---|---|---|---|---|
| 1-318 | C—CF3 | C—H | C—CF3 | C—H | H | CF3 | CH | CH | C—NO2 | CH | H | H | H | CH3CH2CO | 1 |
| 1-319 | C—CF3 | C—H | C—CF3 | C—H | H | CF3 | CH | CH | C—NO2 | CH | H | H | H | cyclo-PrCO | 1 |
| 1-320 | C—CF3 | C—H | C—CF3 | C—H | H | CF3 | CH | CH | C—NO2 | CH | H | H | H | CF3CH2CO | 1 |
| 1-321 | C—CF3 | C—H | C—CF3 | C—H | H | CF3 | CH | CH | C—CF3 | CH | H | H | H | CH3SO2 | 1 |
| 1-322 | C—CF3 | C—H | C—CF3 | C—H | H | CF3 | CH | CH | C—CF3 | CH | H | H | H | CH3CH2SO2 | 1 |
| 1-323 | C—CF3 | C—H | C—CF3 | C—H | H | CF3 | CH | CH | C—CF3 | CH | H | H | H | CF3SO2 | 1 |
| 1-324 | C—CF3 | C—H | C—CF3 | C—H | H | CF3 | CH | CH | C—CF3 | CH | H | H | H | CF3CH2SO2 | 1 |
| 1-325 | C—CF3 | C—H | C—CF3 | C—H | H | CF3 | CH | CH | C—CF3 | CH | H | H | H | PhSO2 | 1 |
| 1-326 | C—Cl | C—Cl | C—Cl | C—H | H | CF3 | CH | CH | C—CF3 | CH | H | H | H | H | 1 |
| 1-327 | C—Cl | C—Cl | C—Cl | C—H | H | CF3 | CH | CH | C—CF3 | CH | H | H | H | CF3CH2CO | 1 |
| 1-328 | C—Cl | C—Cl | C—Cl | C—H | H | CF3 | CH | CH | C—CF3 | CH | H | H | H | n-PrCO | 1 |
| 1-329 | C—Cl | C—Cl | C—Cl | C—H | H | CF3 | CH | CH | C—CF3 | CH | H | H | H | iso-PrCO | 1 |
| 1-330 | C—Cl | C—Cl | C—Cl | C—H | H | CF3 | CH | CH | C—CF3 | CH | H | H | H | CH3CH2NHCO | 1 |
| 1-331 | C—Cl | C—Cl | C—Cl | C—H | H | CF3 | CH | CH | C—CF3 | CH | H | H | H | CH3SO2 | 1 |
| 1-332 | C—Cl | C—Cl | C—Cl | C—H | H | CF3 | CH | CH | C—CF3 | CH | H | H | H | CH3CH2SO2 | 1 |
| 1-333 | C—Cl | C—Cl | C—Cl | C—H | H | CF3 | CH | CH | C—CF3 | CH | H | H | H | CF3SO2 | 1 |
| 1-334 | C—Cl | C—Cl | C—Cl | C—H | H | CF3 | CH | CH | C—CF3 | CH | H | H | H | CF3CH2SO2 | 1 |
| 1-335 | C—Cl | C—Cl | C—Cl | C—H | H | CF3 | CH | CH | C—CF3 | CH | H | H | H | PhSO2 | 1 |
| 1-336 | C—Cl | C—Cl | C—Cl | C—H | H | CF3 | CH | CH | C—Cl | CH | H | H | H | H | 1 |
| 1-337 | C—Cl | C—Cl | C—Cl | C—H | H | CF3 | CH | CH | C—Cl | CH | H | H | H | CH3CO | 1 |
| 1-338 | C—Cl | C—Cl | C—Cl | C—H | H | CF3 | CH | CH | C—Cl | CH | H | H | H | CH3CH2CO | 1 |
| 1-339 | C—Cl | C—Cl | C—Cl | C—H | H | CF3 | CH | CH | C—Cl | CH | H | H | H | cyclo-PrCO | 1 |
| 1-340 | C—Cl | C—Cl | C—Cl | C—H | H | CF3 | CH | CH | C—Cl | CH | H | H | H | CF3CH2CO | 1 |
| 1-341 | C—Cl | C—Cl | C—Cl | C—H | H | CF3 | CH | CH | C—Cl | CH | H | H | H | CH3CH2NHCO | 1 |
| 1-342 | C—Cl | C—Cl | C—Cl | C—H | H | CF3 | CH | CH | C—Cl | CH | H | H | H | CH3SO2 | 1 |
| 1-343 | C—Cl | C—Cl | C—Cl | C—H | H | CF3 | CH | CH | C—Br | CH | H | H | H | H | 1 |
| 1-344 | C—Cl | C—Cl | C—Cl | C—H | H | CF3 | CH | CH | C—Br | CH | H | H | H | CH3CO | 1 |
| 1-345 | C—Cl | C—Cl | C—Cl | C—H | H | CF3 | CH | CH | C—Br | CH | H | H | H | CH3CH2CO | 1 |
| 1-346 | C—Cl | C—Cl | C—Cl | C—H | H | CF3 | CH | CH | C—Br | CH | H | H | H | cyclo-PrCO | 1 |
| 1-347 | C—Cl | C—Cl | C—Cl | C—H | H | CF3 | CH | CH | C—Br | CH | H | H | H | CF3CH2CO | 1 |
| 1-348 | C—Cl | C—Cl | C—Cl | C—H | H | CF3 | CH | CH | C—Br | CH | H | H | H | CH3CH2NHCO | 1 |
| 1-349 | C—Cl | C—Cl | C—Cl | C—H | H | CF3 | CH | CH | C—Br | CH | H | H | H | CH3SO2 | 1 |
| 1-350 | C—Cl | C—H | C—CF3 | C—H | H | CF3 | CH | CH | C—Cl | CH | H | H | H | CH3CO | 1 |
| 1-351 | C—Cl | C—H | C—CF3 | C—H | H | CF3 | CH | CH | C—Cl | CH | H | H | H | CH3CH2CO | 1 |
| 1-352 | C—Cl | C—H | C—CF3 | C—H | H | CF3 | CH | CH | C—Cl | CH | H | H | H | cyclo-PrCO | 1 |

TABLE 1-continued

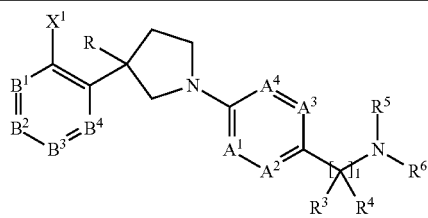

| Ex.-No. | $B^1$ | $B^2$ | $B^3$ | $B^4$ | $X^1$ | R | $A^1$ | $A^2$ | $A^3$ | $A^4$ | $R^3$ | $R^4$ | $R^5$ | $R^6$ | 1 |
|---|---|---|---|---|---|---|---|---|---|---|---|---|---|---|---|
| 1-353 | C—Cl | C—H | C—CF3 | C—H | H | CF3 | CH | CH | C—Cl | CH | H | H | H | CF3CH2CO | 1 |
| 1-354 | C—Cl | C—H | C—CF3 | C—H | H | CF3 | CH | CH | C—Cl | CH | H | H | H | CH3CH2NHCO | 1 |
| 1-355 | C—Cl | C—H | C—CF3 | C—H | H | CF3 | CH | CH | C—CF3 | CH | H | H | H | CH3CO | 1 |
| 1-356 | C—Cl | C—H | C—CF3 | C—H | H | CF3 | CH | CH | C—CF3 | CH | H | H | H | CH3CH2CO | 1 |
| 1-357 | C—Cl | C—H | C—CF3 | C—H | H | CF3 | CH | CH | C—CF3 | CH | H | H | H | cyclo-PrCO | 1 |
| 1-358 | C—Cl | C—H | C—CF3 | C—H | H | CF3 | CH | CH | C—CF3 | CH | H | H | H | CF3CH2CO | 1 |
| 1-359 | C—Cl | C—H | C—CF3 | C—H | H | CF3 | CH | CH | C—CF3 | CH | H | H | H | CH3CH2NHCO | 1 |
| 1-360 | C—Cl | C—Cl | C—CF3 | C—H | H | CF3 | CH | CH | C—Cl | CH | H | H | H | CH3CO | 1 |
| 1-361 | C—Cl | C—Cl | C—CF3 | C—H | H | CF3 | CH | CH | C—Cl | CH | H | H | H | CH3CH2CO | 1 |
| 1-362 | C—Cl | C—Cl | C—CF3 | C—H | H | CF3 | CH | CH | C—Cl | CH | H | H | H | cyclo-PrCO | 1 |
| 1-363 | C—Cl | C—Cl | C—CF3 | C—H | H | CF3 | CH | CH | C—Cl | CH | H | H | H | CF3CH2CO | 1 |
| 1-364 | C—Cl | C—Cl | C—CF3 | C—H | H | CF3 | CH | CH | C—Cl | CH | H | H | H | CH3CH2NHCO | 1 |
| 1-365 | C—Cl | C—Cl | C—CF3 | C—H | H | CF3 | CH | CH | C—CF3 | CH | H | H | H | CH3CO | 1 |
| 1-366 | C—Cl | C—Cl | C—CF3 | C—H | H | CF3 | CH | CH | C—CF3 | CH | H | H | H | CH3CH2CO | 1 |
| 1-367 | C—Cl | C—Cl | C—CF3 | C—H | H | CF3 | CH | CH | C—CF3 | CH | H | H | H | cyclo-PrCO | 1 |
| 1-368 | C—Cl | C—Cl | C—CF3 | C—H | H | CF3 | CH | CH | C—CF3 | CH | H | H | H | CF3CH2CO | 1 |
| 1-369 | C—Cl | C—Cl | C—CF3 | C—H | H | CF3 | CH | CH | C—CF3 | CH | H | H | H | CH3CH2NHCO | 1 |
| 1-370 | C—Cl | C—H | C—Cl | C—H | H | CF3 | N | CH | C—CF3 | CH | H | H | H | H | 1 |
| 1-372 | C—Cl | C—H | C—Cl | C—H | H | CF3 | N | CH | C—CF3 | CH | H | H | H | CH3CH2CO | 1 |
| 1-373 | C—Cl | C—H | C—Cl | C—H | H | CF3 | N | CH | C—CF3 | CH | H | H | H | cyclo-PrCO | 1 |
| 1-374 | C—Cl | C—H | C—Cl | C—H | H | CF3 | N | CH | C—CF3 | CH | H | H | H | CF3CH2CO | 1 |
| 1-375 | C—Cl | C—H | C—Cl | C—H | H | CF3 | N | CH | C—CF3 | CH | H | H | H | CH3CH2NHCO | 1 |
| 1-376 | C—Cl | C—Cl | C—Cl | C—H | H | CF3 | N | CH | C—CF3 | CH | H | H | H | H | 1 |
| 1-377 | C—Cl | C—Cl | C—Cl | C—H | H | CF3 | N | CH | C—CF3 | CH | H | H | H | CH3CO | 1 |
| 1-378 | C—Cl | C—Cl | C—Cl | C—H | H | CF3 | N | CH | C—CF3 | CH | H | H | H | CH3CH2CO | 1 |
| 1-379 | C—Cl | C—Cl | C—Cl | C—H | H | CF3 | N | CH | C—CF3 | CH | H | H | H | cyclo-PrCO | 1 |
| 1-380 | C—Cl | C—Cl | C—Cl | C—H | H | CF3 | N | CH | C—CF3 | CH | H | H | H | CF3CH2CO | 1 |
| 1-381 | C—Cl | C—Cl | C—Cl | C—H | H | CF3 | N | CH | C—CF3 | CH | H | H | H | CH3CH2NHCO | 1 |
| 1-382 | C—CF3 | C—H | C—CF3 | C—H | H | CF3 | N | CH | C—CF3 | CH | H | H | H | H | 1 |
| 1-386 | C—CF3 | C—H | C—CF3 | C—H | H | CF3 | N | CH | C—CF3 | CH | H | H | H | CF3CH2CO | 1 |
| 1-387 | C—CF3 | C—H | C—CF3 | C—H | H | CF3 | N | CH | C—CF3 | CH | H | H | H | CH3CH2NHCO | 1 |
| 1-388 | C—Cl | C—H | C—Cl | C—H | H | CF3 | CH | CH | C—CF3 | N | H | H | H | H | 1 |
| 1-390 | C—Cl | C—H | C—Cl | C—H | H | CF3 | CH | CH | C—CF3 | N | H | H | H | CH3CH2CO | 1 |
| 1-391 | C—Cl | C—H | C—Cl | C—H | H | CF3 | CH | CH | C—CF3 | N | H | H | H | cyclo-PrCO | 1 |
| 1-392 | C—Cl | C—H | C—Cl | C—H | H | CF3 | CH | CH | C—CF3 | N | H | H | H | CF3CH2CO | 1 |

TABLE 1-continued

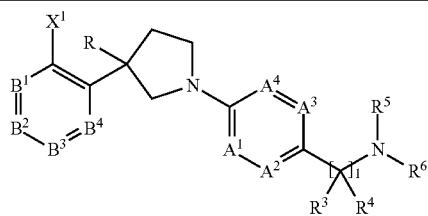

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-393 | C—Cl | C—H | C—Cl | C—H | H | CF3 | CH | CH | C—CF3 | N | H | H | H | CH3CH2NHCO | 1 |
| 1-394 | C—Cl | C—Cl | C—Cl | C—H | H | CF3 | CH | CH | C—CF3 | N | H | H | H | H | 1 |
| 1-398 | C—Cl | C—Cl | C—Cl | C—H | H | CF3 | CH | CH | C—CF3 | N | H | H | H | CF3CH2CO | 1 |
| 1-399 | C—Cl | C—Cl | C—Cl | C—H | H | CF3 | CH | CH | C—CF3 | N | H | H | H | CH3CH2NHCO | 1 |
| 1-400 | C—CF3 | C—H | C—CF3 | C—H | H | CF3 | CH | CH | C—CF3 | N | H | H | H | H | 1 |
| 1-404 | C—CF3 | C—H | C—CF3 | C—H | H | CF3 | CH | CH | C—CF3 | N | H | H | H | CF3CH2CO | 1 |
| 1-405 | C—CF3 | C—H | C—CF3 | C—H | H | CF3 | CH | CH | C—CF3 | N | H | H | H | CH3CH2NHCO | 1 |
| 1-406 | C—Cl | C—Cl | C—Cl | C—H | H | CF3 | CH | CH | C—SCF3 | CH | H | H | H | H | 1 |
| 1-407 | C—Cl | C—Cl | C—Cl | C—H | H | CF3 | CH | CH | C—SCF3 | CH | H | H | H | CH3CO | 1 |
| 1-408 | C—Cl | C—Cl | C—Cl | C—H | H | CF3 | CH | CH | C—SCF3 | CH | H | H | H | CH3CH2CO | 1 |
| 1-409 | C—Cl | C—Cl | C—Cl | C—H | H | CF3 | CH | CH | C—SCF3 | CH | H | H | H | cyclo-PrCO | 1 |
| 1-410 | C—Cl | C—Cl | C—Cl | C—H | H | CF3 | CH | CH | C—SCF3 | CH | H | H | H | CF3CH2CO | 1 |
| 1-411 | C—Cl | C—Cl | C—Cl | C—H | H | CF3 | CH | CH | C—S(O)CF3 | CH | H | H | H | H | 1 |
| 1-412 | C—Cl | C—Cl | C—Cl | C—H | H | CF3 | CH | CH | C—S(O)CF3 | CH | H | H | H | CH3CO | 1 |
| 1-413 | C—Cl | C—Cl | C—Cl | C—H | H | CF3 | CH | CH | C—S(O)CF3 | CH | H | H | H | CH3CH2CO | 1 |
| 1-414 | C—Cl | C—Cl | C—Cl | C—H | H | CF3 | CH | CH | C—S(O)CF3 | CH | H | H | H | cyclo-PrCO | 1 |
| 1-415 | C—Cl | C—Cl | C—Cl | C—H | H | CF3 | CH | CH | C—S(O)CF3 | CH | H | H | H | CF3CH2CO | 1 |
| 1-416 | C—Cl | C—Cl | C—Cl | C—H | H | CF3 | CH | CH | C—S(O)CF3 | CH | H | H | H | CH3CH2NHCO | 1 |
| 1-417 | C—Cl | C—Cl | C—Cl | C—H | H | CF3 | CH | CH | C—SO2CF3 | CH | H | H | H | H | 1 |
| 1-418 | C—Cl | C—Cl | C—Cl | C—H | H | CF3 | CH | CH | C—SO2CF3 | CH | H | H | H | CH3CO | 1 |
| 1-419 | C—Cl | C—Cl | C—Cl | C—H | H | CF3 | CH | CH | C—SO2CF3 | CH | H | H | H | CH3CH2CO | 1 |
| 1-420 | C—Cl | C—Cl | C—Cl | C—H | H | CF3 | CH | CH | C—SO2CF3 | CH | H | H | H | cyclo-PrCO | 1 |
| 1-421 | C—Cl | C—Cl | C—Cl | C—H | H | CF3 | CH | CH | C—SO2CF3 | CH | H | H | H | CF3CH2CO | 1 |
| 1-422 | C—Cl | C—Cl | C—Cl | C—H | H | CF3 | CH | CH | C—SO2CF3 | CH | H | H | H | CH3CH2NHCO | 1 |
| 1-423 | C—CF3 | C—Cl | C—CF3 | C—H | H | CF3 | CH | CH | C—SCH2CF3 | CH | H | H | H | H | 1 |
| 1-424 | C—CF3 | C—Cl | C—CF3 | C—H | H | CF3 | CH | CH | C—SCH2CF3 | CH | H | H | H | CH3CO | 1 |
| 1-425 | C—CF3 | C—Cl | C—CF3 | C—H | H | CF3 | CH | CH | C—SCH2CF3 | CH | H | H | H | CH3CH2CO | 1 |
| 1-426 | C—CF3 | C—Cl | C—CF3 | C—H | H | CF3 | CH | CH | C—SCH2CF3 | CH | H | H | H | cyclo-PrCO | 1 |
| 1-427 | C—CF3 | C—Cl | C—CF3 | C—H | H | CF3 | CH | CH | C—SCH2CF3 | CH | H | H | H | CF3CH2CO | 1 |
| 1-428 | C—CF3 | C—Cl | C—CF3 | C—H | H | CF3 | CH | CH | C—S(O)CH2CF3 | CH | H | H | H | H | 1 |
| 1-429 | C—CF3 | C—Cl | C—CF3 | C—H | H | CF3 | CH | CH | C—S(O)CH2CF3 | CH | H | H | H | CH3CO | 1 |
| 1-430 | C—CF3 | C—Cl | C—CF3 | C—H | H | CF3 | CH | CH | C—S(O)CH2CF3 | CH | H | H | H | CH3CH2CO | 1 |
| 1-431 | C—CF3 | C—Cl | C—CF3 | C—H | H | CF3 | CH | CH | C—S(O)CH2CF3 | CH | H | H | H | cyclo-PrCO | 1 |
| 1-432 | C—CF3 | C—Cl | C—CF3 | C—H | H | CF3 | CH | CH | C—S(O)CH2CF3 | CH | H | H | H | CF3CH2CO | 1 |
| 1-433 | C—CF3 | C—Cl | C—CF3 | C—H | H | CF3 | CH | CH | C—S(O)CH2CF3 | CH | H | H | H | CH3CH2NHCO | 1 |

TABLE 1-continued

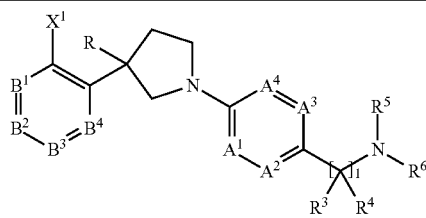

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-434 | C—CF3 | C—Cl | C—CF3 | C—H | H | CF3 | CH | CH | C—SO2CH2CF3 | CH | H | H | H | H | 1 |
| 1-435 | C—CF3 | C—Cl | C—CF3 | C—H | H | CF3 | CH | CH | C—SO2CH2CF3 | CH | H | H | H | CH3CO | 1 |
| 1-436 | C—CF3 | C—Cl | C—CF3 | C—H | H | CF3 | CH | CH | C—SO2CH2CF3 | CH | H | H | H | CH3CH2CO | 1 |
| 1-437 | C—CF3 | C—Cl | C—CF3 | C—H | H | CF3 | CH | CH | C—SO2CH2CF3 | CH | H | H | H | cyclo-PrCO | 1 |
| 1-438 | C—CF3 | C—Cl | C—CF3 | C—H | H | CF3 | CH | CH | C—SO2CH2CF3 | CH | H | H | H | CF3CH2CO | 1 |
| 1-439 | C—CF3 | C—Cl | C—CF3 | C—H | H | CF3 | CH | CH | C—SO2CH2CF3 | CH | H | H | H | CH3CH2NHCO | 1 |
| 1-440 | C—CF3 | C—H | C—CF3 | C—H | H | CF3 | CH | CH | C—CF3 | CH | H | H | H | CH3(CO)CO | 1 |
| 1-441 | C—Cl | C—H | C—Cl | C—H | H | CF3 | CH | CH | C—Cl | CH | H | H | H | NCCO | 1 |
| 1-442 | C—Cl | C—H | C—Cl | C—H | H | CF3 | CH | CH | C—Cl | CH | H | H | H | CF3CH(CH3)NHCO | 1 |
| 1-443 | C—Cl | C—H | C—Cl | C—H | H | CF3 | CH | CH | C—Cl | CH | H | H | H | thiomorpholineCO | 1 |
| 1-444 | C—Cl | C—H | C—Cl | C—H | H | CF3 | CH | CH | C—Cl | CH | H | H | H | (CH3O)2CHCH2NHCO | 1 |
| 1-445 | C—Cl | C—H | C—Cl | C—H | H | CF3 | CH | CH | C—Cl | CH | H | H | H | tetrahydrofurufuryl aminoCO | 1 |
| 1-446 | C—Cl | C—H | C—Cl | C—H | H | CF3 | CH | CH | C—Cl | CH | H | H | H | 1-(2-thiazolyl)ethyl aminoCO | 1 |
| 1-447 | C—Cl | C—H | C—Cl | C—H | H | CF3 | CH | CH | C—F | CH | H | H | H | CH3CO | 1 |
| 1-448 | C—Cl | C—H | C—Cl | C—H | H | CF3 | CH | CH | C—F | CH | H | H | H | CH3CH2CO | 1 |
| 1-449 | C—Cl | C—H | C—Cl | C—H | H | CF3 | CH | CH | C—F | CH | H | H | H | nPrCO | 1 |
| 1-450 | C—Cl | C—H | C—Cl | C—H | H | CF3 | CH | CH | C—F | CH | H | H | H | cyclo-PrCO | 1 |
| 1-451 | C—Cl | C—H | C—Cl | C—H | H | CF3 | CH | CH | C—F | CH | H | H | H | cyclo-PrCH2CO | 1 |
| 1-452 | C—Cl | C—H | C—Cl | C—H | H | CF3 | CH | CH | C—F | CH | H | H | H | CF3CH2CO | 1 |
| 1-453 | C—Cl | C—H | C—Cl | C—H | H | CF3 | CH | CH | C—F | CH | H | H | H | CH3SCH2CO | 1 |
| 1-454 | C—Cl | C—H | C—Cl | C—H | H | CF3 | CH | CH | C—F | CH | H | H | H | CH3S(O)CH2CO | 1 |
| 1-455 | C—Cl | C—H | C—Cl | C—H | H | CF3 | CH | CH | C—F | CH | H | H | H | CH3SO2CH2CO | 1 |
| 1-456 | C—Cl | C—H | C—Cl | C—H | H | CF3 | CH | CH | C—F | CH | H | H | H | CH3CH2NHCO | 1 |
| 1-457 | C—Cl | C—H | C—Cl | C—H | H | CF3 | CH | CH | C—Cl | CH | H | H | H | CH3 | 1 |
| 1-458 | C—Cl | C—H | C—Cl | C—H | H | CF3 | CH | CH | C—Cl | CH | H | H | H | CH3CH(Br)CO | 1 |
| 1-459 | C—Cl | C—H | C—Cl | C—H | H | CF3 | CH | CH | C—Cl | CH | H | H | H | CH3S(O)CH2CO | 1 |
| 1-460 | C—Cl | C—H | C—Cl | C—H | H | CF3 | CH | CH | C—Cl | CH | H | H | H | CH3SO2CH2CO | 1 |
| 1-461 | C—Cl | C—H | C—Cl | C—H | H | CF3 | CH | CH | C—Cl | CH | H | H | H | CH3CH2SCH2CO | 1 |
| 1-462 | C—Cl | C—H | C—Cl | C—H | H | CF3 | CH | CH | C—Cl | CH | H | H | H | CH3CH2S(O)CH2CO | 1 |
| 1-463 | C—Cl | C—H | C—Cl | C—H | H | CF3 | CH | CH | C—Cl | CH | H | H | H | CH3CH2SO2CH2CO | 1 |
| 1-464 | C—Cl | C—H | C—Cl | C—H | H | CF3 | CH | CH | C—Cl | CH | H | H | H | iso-PrSCH2CO | 1 |
| 1-465 | C—Cl | C—H | C—Cl | C—H | H | CF3 | CH | CH | C—Cl | CH | H | H | H | iso-PrS(O)CH2CO | 1 |
| 1-466 | C—Cl | C—H | C—Cl | C—H | H | CF3 | CH | CH | C—Cl | CH | H | H | H | iso-PrSO2CH2CO | 1 |
| 1-467 | C—Cl | C—H | C—Cl | C—H | H | CF3 | CH | CH | C—Cl | CH | H | H | H | CH3SCH2CH2CO | 1 |
| 1-468 | C—Cl | C—H | C—Cl | C—H | H | CF3 | CH | CH | C—Cl | CH | H | H | H | cyclo-PrNHCS | 1 |

TABLE 1-continued

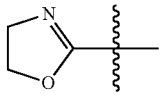

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-469 | C—Cl | C—H | C—Cl | C—H | H | CF3 | CH | CH | C—Cl | CH | H | H | H | 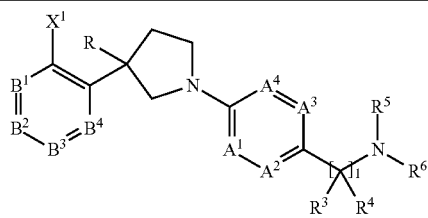 | 1 |
| 1-470 | C—Cl | C—H | C—Cl | C—H | H | CF3 | CH | CH | C—Br | CH | H | H | H | cyclo-PrCH2CO | 1 |
| 1-471 | C—Cl | C—H | C—Cl | C—H | H | CF3 | CH | CH | C—Br | CH | H | H | H | CH3SCH2CO | 1 |
| 1-472 | C—Cl | C—H | C—Cl | C—H | H | CF3 | CH | CH | C—Br | CH | H | H | H | CH3S(O)CH2CO | 1 |
| 1-473 | C—Cl | C—H | C—Cl | C—H | H | CF3 | CH | CH | C—Br | CH | H | H | H | CH3SO2CH2CO | 1 |
| 1-474 | C—Cl | C—H | C—Cl | C—H | H | CF3 | CH | CH | C—I | CH | H | H | H | CH3CH2CO | 1 |
| 1-475 | C—Cl | C—H | C—Cl | C—H | H | CF3 | CH | CH | C—I | CH | H | H | H | n-PrCO | 1 |
| 1-476 | C—Cl | C—H | C—Cl | C—H | H | CF3 | CH | CH | C—I | CH | H | H | H | cyclo-PrCO | 1 |
| 1-477 | C—Cl | C—H | C—Cl | C—H | H | CF3 | CH | CH | C—I | CH | H | H | H | cyclo-PrCH2CO | 1 |
| 1-478 | C—Cl | C—H | C—Cl | C—H | H | CF3 | CH | CH | C—I | CH | H | H | H | CF3CH2CO | 1 |
| 1-479 | C—Cl | C—H | C—Cl | C—H | H | CF3 | CH | CH | C—I | CH | H | H | H | CH3SCH2CO | 1 |
| 1-480 | C—Cl | C—H | C—Cl | C—H | H | CF3 | CH | CH | C—I | CH | H | H | H | CH3S(O)CH2CO | 1 |
| 1-481 | C—Cl | C—H | C—Cl | C—H | H | CF3 | CH | CH | C—I | CH | H | H | H | CH3SO2CH2CO | 1 |
| 1-482 | C—Cl | C—H | C—Cl | C—H | H | CF3 | CH | CH | C—I | CH | H | H | H | CH3CH2NHCO | 1 |
| 1-483 | C—Cl | C—H | C—Cl | C—H | H | CF3 | CH | CH | C—CH3 | CH | H | H | H | n-PrCO | 1 |
| 1-484 | C—Cl | C—H | C—Cl | C—H | H | CF3 | CH | CH | C—CH3 | CH | H | H | H | cyclo-PrCH2CO | 1 |
| 1-485 | C—Cl | C—H | C—Cl | C—H | H | CF3 | CH | CH | C—CH3 | CH | H | H | H | CH3SCH2CO | 1 |
| 1-486 | C—Cl | C—H | C—Cl | C—H | H | CF3 | CH | CH | C—CH3 | CH | H | H | H | CH3S(O)CH2CO | 1 |
| 1-487 | C—Cl | C—H | C—Cl | C—H | H | CF3 | CH | CH | C—CH3 | CH | H | H | H | CH3SO2CH2CO | 1 |
| 1-488 | C—Cl | C—H | C—Cl | C—H | H | CF3 | CH | CH | C-cyclo-Pr | CH | H | H | H | CH3CH2CO | 1 |
| 1-489 | C—Cl | C—H | C—Cl | C—H | H | CF3 | CH | CH | C-cyclo-Pr | CH | H | H | H | CF3CH2CO | 1 |
| 1-490 | C—Cl | C—H | C—Cl | C—H | H | CF3 | CH | CH | C—CF3 | CH | H | H | H | CH3(CO)CO | 1 |
| 1-491 | C—Cl | C—H | C—Cl | C—H | H | CF3 | CH | CH | C—CF3 | CH | H | H | H | CH3OCH2CH2CO | 1 |
| 1-492 | C—Cl | C—H | C—Cl | C—H | H | CF3 | CH | CH | C—CF3 | CH | H | H | H | CH3CH2OCH2CH2CO | 1 |
| 1-493 | C—Cl | C—H | C—Cl | C—H | H | CF3 | CH | CH | C—CF3 | CH | H | H | H | HSCH2CO | 1 |
| 1-494 | C—Cl | C—H | C—Cl | C—H | H | CF3 | CH | CH | C—CF3 | CH | H | H | H | CH3S(O)CH2CO | 1 |
| 1-495 | C—Cl | C—H | C—Cl | C—H | H | CF3 | CH | CH | C—CF3 | CH | H | H | H | CH3SO2CH2CO | 1 |
| 1-496 | C—Cl | C—H | C—Cl | C—H | H | CF3 | CH | CH | C—CF3 | CH | H | H | H | CF3SCH2CO | 1 |
| 1-497 | C—Cl | C—H | C—Cl | C—H | H | CF3 | CH | CH | C—CF3 | CH | H | H | H | CF3S(O)CH2CO | 1 |
| 1-498 | C—Cl | C—H | C—Cl | C—H | H | CF3 | CH | CH | C—CF3 | CH | H | H | H | CF3SO2CH2CO | 1 |
| 1-499 | C—Cl | C—H | C—Cl | C—H | H | CF3 | CH | CH | C—CF3 | CH | H | H | H | CH3CH2SCH2CO | 1 |
| 1-500 | C—Cl | C—H | C—Cl | C—H | H | CF3 | CH | CH | C—CF3 | CH | H | H | H | CH3CH2S(O)CH2CO | 1 |
| 1-501 | C—Cl | C—H | C—Cl | C—H | H | CF3 | CH | CH | C—CF3 | CH | H | H | H | CH3CH2SO2CH2CO | 1 |

TABLE 1-continued

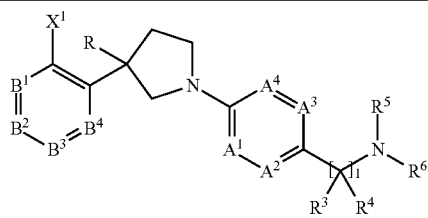

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-502 | C—Cl | C—H | C—Cl | C—H | H | CF3 | CH | CH | C—CF3 | CH | H | H | H | CH3COSCH2CO | 1 |
| 1-503 | C—Cl | C—H | C—Cl | C—H | H | CF3 | CH | CH | C—CF3 | CH | H | H | H | (Allyl)SCH2CO | 1 |
| 1-504 | C—Cl | C—H | C—Cl | C—H | H | CF3 | CH | CH | C—CF3 | CH | H | H | H | (Allyl)S(O)CH2CO | 1 |
| 1-505 | C—Cl | C—H | C—Cl | C—H | H | CF3 | CH | CH | C—CF3 | CH | H | H | H | (Allyl)SO2CH2CO | 1 |
| 1-506 | C—Cl | C—H | C—Cl | C—H | H | CF3 | CH | CH | C—CF3 | CH | H | H | H | CH3SCH(CH3)CO | 1 |
| 1-507 | C—Cl | C—H | C—Cl | C—H | H | CF3 | CH | CH | C—CF3 | CH | H | H | H | CH3S(O)CH(CH3)CO | 1 |
| 1-508 | C—Cl | C—H | C—Cl | C—H | H | CF3 | CH | CH | C—CF3 | CH | H | H | H | CH3SO2CH(CH3)CO | 1 |
| 1-509 | C—Cl | C—H | C—Cl | C—H | H | CF3 | CH | CH | C—CF3 | CH | H | H | H | CH3SCH2CH2CO | 1 |
| 1-510 | C—Cl | C—H | C—Cl | C—H | H | CF3 | CH | CH | C—CF3 | CH | H | H | H | CH3SC(CH3)2CO | 1 |
| 1-511 | C—Cl | C—H | C—Cl | C—H | H | CF3 | CH | CH | C—CF3 | CH | H | H | H | CH3S(O)C(CH3)2CO | 1 |
| 1-512 | C—Cl | C—H | C—Cl | C—H | H | CF3 | CH | CH | C—CF3 | CH | H | H | H | CH3SO2C(CH3)2CO | 1 |
| 1-513 | C—Cl | C—H | C—Cl | C—H | H | CF3 | CH | CH | C—CF3 | CH | H | H | H | CH3CONHCH2CO | 1 |
| 1-514 | C—Cl | C—H | C—Cl | C—H | H | CF3 | CH | CH | C—CF3 | CH | H | H | H | CH3CH2CONHCH2CO | 1 |
| 1-515 | C—Cl | C—H | C—Cl | C—H | H | CF3 | CH | CH | C—CF3 | CH | H | H | H | cyclo-PrCONHCH2CO | 1 |
| 1-516 | C—Cl | C—H | C—Cl | C—H | H | CF3 | CH | CH | C—CF3 | CH | H | H | H | CF3CH2CONHCH2CO | 1 |
| 1-517 | C—Cl | C—H | C—Cl | C—H | H | CF3 | CH | CH | C—CF3 | CH | H | H | H | CH3SCH2CONHCH2CO | 1 |
| 1-518 | C—Cl | C—H | C—Cl | C—H | H | CF3 | CH | CH | C—CF3 | CH | H | H | H | CH3S(O)CH2CONHCH2CO | 1 |
| 1-519 | C—Cl | C—H | C—Cl | C—H | H | CF3 | CH | CH | C—CF3 | CH | H | H | H | CH3SO2CH2CONHCH2CO | 1 |
| 1-520 | C—Cl | C—H | C—Cl | C—H | H | CF3 | CH | CH | C—CF3 | CH | H | H | H | tert-BuOCONHCH2CO | 1 |
| 1-521 | C—Cl | C—H | C—Cl | C—H | H | CF3 | CH | CH | C—CF3 | CH | H | H | H | CH3CONHCH(CH3)CO | 1 |
| 1-522 | C—Cl | C—H | C—Cl | C—H | H | CF3 | CH | CH | C—CF3 | CH | H | H | H | CH3CH2CONHCH(CH3)CO | 1 |
| 1-523 | C—Cl | C—H | C—Cl | C—H | H | CF3 | CH | CH | C—CF3 | CH | H | H | H | cyclo-PrCONHCH(CH3)CO | 1 |
| 1-524 | C—Cl | C—H | C—Cl | C—H | H | CF3 | CH | CH | C—CF3 | CH | H | H | H | CF3CH2CONHCH(CH3)CO | 1 |
| 1-525 | C—Cl | C—H | C—Cl | C—H | H | CF3 | CH | CH | C—CF3 | CH | H | H | H | CH3SCH2CONHCH(CH3)CO | 1 |
| 1-526 | C—Cl | C—H | C—Cl | C—H | H | CF3 | CH | CH | C—CF3 | CH | H | H | H | CH3S(O)CH2CONHCH(CH3)CO | 1 |
| 1-527 | C—Cl | C—H | C—Cl | C—H | H | CF3 | CH | CH | C—CF3 | CH | H | H | H | CH3SO2CH2CONHCH(CH3)CO | 1 |
| 1-528 | C—Cl | C—H | C—Cl | C—H | H | CF3 | CH | CH | C—CF3 | CH | H | H | H | CH3CONHC(CH3)2CO | 1 |
| 1-529 | C—Cl | C—H | C—Cl | C—H | H | CF3 | CH | CH | C—CF3 | CH | H | H | H | CH3CH2CONHC(CH3)2CO | 1 |
| 1-530 | C—Cl | C—H | C—Cl | C—H | H | CF3 | CH | CH | C—CF3 | CH | H | H | H | cyclo-PrCONHC(CH3)2CO | 1 |
| 1-531 | C—Cl | C—H | C—Cl | C—H | H | CF3 | CH | CH | C—CF3 | CH | H | H | H | CF3CH2CONHC(CH3)2CO | 1 |
| 1-532 | C—Cl | C—H | C—Cl | C—H | H | CF3 | CH | CH | C—CF3 | CH | H | H | H | CH3SCH2CONHC(CH3)2CO | 1 |
| 1-533 | C—Cl | C—H | C—Cl | C—H | H | CF3 | CH | CH | C—CF3 | CH | H | H | H | CH3S(O)CH2CONHC(CH3)2CO | 1 |
| 1-534 | C—Cl | C—H | C—Cl | C—H | H | CF3 | CH | CH | C—CF3 | CH | H | H | H | CH3SO2CH2CONHC(CH3)2CO | 1 |
| 1-535 | C—Cl | C—H | C—Cl | C—H | H | CF3 | CH | CH | C—CF3 | CH | H | H | H | CH3CONHCH2CH2CO | 1 |
| 1-536 | C—Cl | C—H | C—Cl | C—H | H | CF3 | CH | CH | C—CF3 | CH | H | H | H | CH3CH2CONHCH2CH2CO | 1 |

TABLE 1-continued

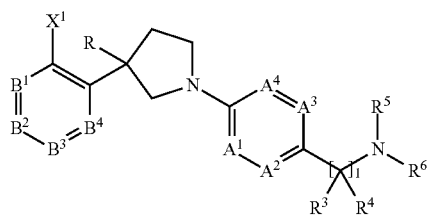

| Ex.-No. | B¹ | B² | B³ | B⁴ | X¹ | R | A¹ | A² | A³ | A⁴ | R³ | R⁴ | R⁵ | R⁶ | l |
|---|---|---|---|---|---|---|---|---|---|---|---|---|---|---|---|
| 1-537 | C—Cl | C—H | C—Cl | C—H | H | CF3 | CH | CH | C—CF3 | CH | H | H | H | cyclo-PrCONHCH2CH2CO | 1 |
| 1-538 | C—Cl | C—H | C—Cl | C—H | H | CF3 | CH | CH | C—CF3 | CH | H | H | H | CF3CH2CONHCH2CH2CO | 1 |
| 1-539 | C—Cl | C—H | C—Cl | C—H | H | CF3 | CH | CH | C—CF3 | CH | H | H | H | CH3SCH2CONHCH2CH2CO | 1 |
| 1-540 | C—Cl | C—H | C—Cl | C—H | H | CF3 | CH | CH | C—CF3 | CH | H | H | H | CH3S(O)CH2CONHCH2CH2CO | 1 |
| 1-541 | C—Cl | C—H | C—Cl | C—H | H | CF3 | CH | CH | C—CF3 | CH | H | H | H | CH3SO2CH2CONHCH2CH2CO | 1 |
| 1-542 | C—Cl | C—H | C—Cl | C—H | H | CF3 | CH | CH | C—CF3 | CH | H | H | H | pyrrol-1-yl-CH2CO | 1 |
| 1-543 | C—Cl | C—H | C—Cl | C—H | H | CF3 | CH | CH | C—CF3 | CH | H | H | H | imidazol-1-yl-CH2CO | 1 |
| 1-544 | C—Cl | C—H | C—Cl | C—H | H | CF3 | CH | CH | C—CF3 | CH | H | H | H | pyrazol-1-yl-CH2CO | 1 |
| 1-545 | C—Cl | C—H | C—Cl | C—H | H | CF3 | CH | CH | C—CF3 | CH | H | H | H | 4-F-pyrazol-1-yl-CH2CO | 1 |
| 1-546 | C—Cl | C—H | C—Cl | C—H | H | CF3 | CH | CH | C—CF3 | CH | H | H | H | 3-Cl-pyrazol-1-yl-CH2CO | 1 |
| 1-547 | C—Cl | C—H | C—Cl | C—H | H | CF3 | CH | CH | C—CF3 | CH | H | H | H | 4-Cl-pyrazol-1-yl-CH2CO | 1 |
| 1-548 | C—Cl | C—H | C—Cl | C—H | H | CF3 | CH | CH | C—CF3 | CH | H | H | H | 3-Br-pyrazol-1-yl-CH2CO | 1 |
| 1-549 | C—Cl | C—H | C—Cl | C—H | H | CF3 | CH | CH | C—CF3 | CH | H | H | H | 4-Br-pyrazol-1-yl-CH2CO | 1 |
| 1-550 | C—Cl | C—H | C—Cl | C—H | H | CF3 | CH | CH | C—CF3 | CH | H | H | H | 3-I-pyrazol-1-yl-CH2CO | 1 |
| 1-551 | C—Cl | C—H | C—Cl | C—H | H | CF3 | CH | CH | C—CF3 | CH | H | H | H | 4-I-pyrazol-1-yl-CH2CO | 1 |
| 1-552 | C—Cl | C—H | C—Cl | C—H | H | CF3 | CH | CH | C—CF3 | CH | H | H | H | 4-O2N-pyrazol-1-yl-CH2CO | 1 |

TABLE 1-continued

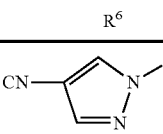

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-553 | C—Cl | C—H | C—Cl | C—H | H | CF3 | CH | CH | C—CF3 | CH | H | H | H | 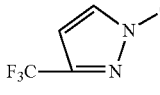 | 1 |
| 1-554 | C—Cl | C—H | C—Cl | C—H | H | CF3 | CH | CH | C—CF3 | CH | H | H | H | 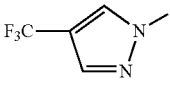 | 1 |
| 1-555 | C—Cl | C—H | C—Cl | C—H | H | CF3 | CH | CH | C—CF3 | CH | H | H | H | 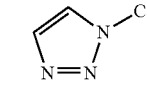 | 1 |
| 1-556 | C—Cl | C—H | C—Cl | C—H | H | CF3 | CH | CH | C—CF3 | CH | H | H | H | 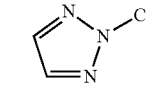 | 1 |
| 1-557 | C—Cl | C—H | C—Cl | C—H | H | CF3 | CH | CH | C—CF3 | CH | H | H | H | 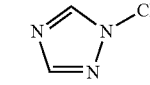 | 1 |
| 1-558 | C—Cl | C—H | C—Cl | C—H | H | CF3 | CH | CH | C—CF3 | CH | H | H | H | 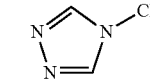 | 1 |
| 1-559 | C—Cl | C—H | C—Cl | C—H | H | CF3 | CH | CH | C—CF3 | CH | H | H | H | 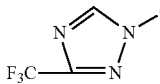 | 1 |
| 1-560 | C—Cl | C—H | C—Cl | C—H | H | CF3 | CH | CH | C—CF3 | CH | H | H | H | 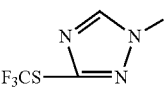 | 1 |
| 1-561 | C—Cl | C—H | C—Cl | C—H | H | CF3 | CH | CH | C—CF3 | CH | H | H | H | 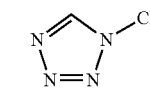 | 1 |
| 1-562 | C—Cl | C—H | C—Cl | C—H | H | CF3 | CH | CH | C—CF3 | CH | H | H | H | 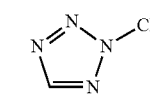 | 1 |
| 1-563 | C—Cl | C—H | C—Cl | C—H | H | CF3 | CH | CH | C—CF3 | CH | H | H | H |  | 1 |
| 1-564 | C—Cl | C—H | C—Cl | C—H | H | CF3 | CH | CH | C—CF3 | CH | H | H | H | 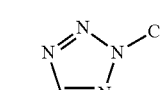 | 1 |
| 1-565 | C—Cl | C—H | C—Cl | C—H | H | CF3 | CH | CH | C—CF3 | CH | H | H | H |  | 1 |

TABLE 1-continued

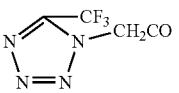

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-566 | C—Cl | C—H | C—Cl | C—H | H | CF3 | CH | CH | C—CF3 | CH | H | H | H | 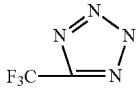 | 1 |
| 1-567 | C—Cl | C—H | C—Cl | C—H | H | CF3 | CH | CH | C—CF3 | CH | H | H | H | 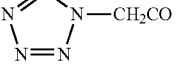 | 1 |
| 1-568 | C—Cl | C—H | C—Cl | C—H | H | CF3 | CH | CH | C—CF3 | CH | H | H | H | 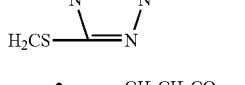 | 1 |
| 1-569 | C—Cl | C—H | C—Cl | C—H | H | CF3 | CH | CH | C—CF3 | CH | H | H | H | 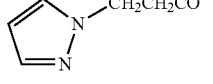 | 1 |
| 1-570 | C—Cl | C—H | C—Cl | C—H | H | CF3 | CH | CH | C—CF3 | CH | H | H | H | 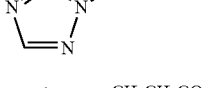 | 1 |
| 1-571 | C—Cl | C—H | C—Cl | C—H | H | CF3 | CH | CH | C—CF3 | CH | H | H | H | 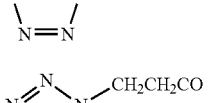 | 1 |
| 1-572 | C—Cl | C—H | C—Cl | C—H | H | CF3 | CH | CH | C—CF3 | CH | H | H | H | 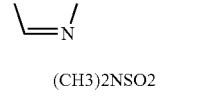 | 1 |
| 1-573 | C—Cl | C—H | C—Cl | C—H | H | CF3 | CH | CH | C—CF3 | CH | H | H | H |  | 1 |
| 1-574 | C—Cl | C—H | C—Cl | C—H | H | CF3 | CH | CH | C—CF3 | CH | H | H | H | (CH3)2NSO2 | 1 |
| 1-575 | C—Cl | C—H | C—Cl | C—H | H | CF3 | CH | CH | C—CN | CH | H | H | H | CH3CO | 1 |
| 1-576 | C—Cl | C—H | C—Cl | C—H | H | CF3 | CH | CH | C—CN | CH | H | H | H | CH3CH2CO | 1 |
| 1-577 | C—Cl | C—H | C—Cl | C—H | H | CF3 | CH | CH | C—CN | CH | H | H | H | nPrCO | 1 |
| 1-578 | C—Cl | C—H | C—Cl | C—H | H | CF3 | CH | CH | C—CN | CH | H | H | H | cyclo-PrCO | 1 |
| 1-579 | C—Cl | C—H | C—Cl | C—H | H | CF3 | CH | CH | C—CN | CH | H | H | H | cyclo-PrCH2CO | 1 |
| 1-580 | C—Cl | C—H | C—Cl | C—H | H | CF3 | CH | CH | C—CN | CH | H | H | H | CF3CH2CO | 1 |
| 1-581 | C—Cl | C—H | C—Cl | C—H | H | CF3 | CH | CH | C—CN | CH | H | H | H | CH3SCH2CO | 1 |
| 1-582 | C—Cl | C—H | C—Cl | C—H | H | CF3 | CH | CH | C—CN | CH | H | H | H | CH3S(O)CH2CO | 1 |
| 1-583 | C—Cl | C—H | C—Cl | C—H | H | CF3 | CH | CH | C—CN | CH | H | H | H | CH3SO2CH2CO | 1 |
| 1-584 | C—Cl | C—H | C—Cl | C—H | H | CF3 | CH | CH | C—CN | CH | H | H | H | CH3CH2NHCO | 1 |
| 1-586 | C—Cl | C—H | C—Cl | C—H | H | CF3 | CH | CH | C—SCH3 | CH | H | H | H | CH3CH2CO | 1 |
| 1-587 | C—Cl | C—H | C—Cl | C—H | H | CF3 | CH | CH | C—SCH3 | CH | H | H | H | cyclo-PrCO | 1 |

TABLE 1-continued

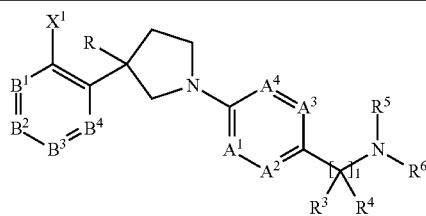

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-588 | C—Cl | C—H | C—Cl | C—H | H | CF3 | CH | CH | C—SCH3 | CH | H | H | H | CF3CH2CO | 1 |
| 1-589 | C—Cl | C—H | C—Cl | C—H | H | CF3 | CH | CH | C—S(O)CH3 | CH | H | H | H | CH3CO | 1 |
| 1-590 | C—Cl | C—H | C—Cl | C—H | H | CF3 | CH | CH | C—S(O)CH3 | CH | H | H | H | CH3CH2CO | 1 |
| 1-591 | C—Cl | C—H | C—Cl | C—H | H | CF3 | CH | CH | C—S(O)CH3 | CH | H | H | H | cyclo-PrCO | 1 |
| 1-592 | C—Cl | C—H | C—Cl | C—H | H | CF3 | CH | CH | C—S(O)CH3 | CH | H | H | H | CF3CH2CO | 1 |
| 1-593 | C—Cl | C—H | C—Cl | C—H | H | CF3 | CH | CH | C—S(O)CH3 | CH | H | H | H | CH3SCH2CO | 1 |
| 1-594 | C—Cl | C—H | C—Cl | C—H | H | CF3 | CH | CH | C—SO2CH3 | CH | H | H | H | CH3CO | 1 |
| 1-595 | C—Cl | C—H | C—Cl | C—H | H | CF3 | CH | CH | C—SO2CH3 | CH | H | H | H | CH3CH2CO | 1 |
| 1-596 | C—Cl | C—H | C—Cl | C—H | H | CF3 | CH | CH | C—SO2CH3 | CH | H | H | H | cyclo-PrCO | 1 |
| 1-597 | C—Cl | C—H | C—Cl | C—H | H | CF3 | CH | CH | C—SO2CH3 | CH | H | H | H | CF3CH2CO | 1 |
| 1-598 | C—Cl | C—H | C—Cl | C—H | H | CF3 | CH | CH | C—SCF3 | CH | H | H | H | CH3CH2CO | 1 |
| 1-599 | C—Cl | C—H | C—Cl | C—H | H | CF3 | CH | CH | C—SCF3 | CH | H | H | H | nPrCO | 1 |
| 1-600 | C—Cl | C—H | C—Cl | C—H | H | CF3 | CH | CH | C—SCF3 | CH | H | H | H | cyclo-PrCO | 1 |
| 1-601 | C—Cl | C—H | C—Cl | C—H | H | CF3 | CH | CH | C—SCF3 | CH | H | H | H | cyclo-PrCH2CO | 1 |
| 1-602 | C—Cl | C—H | C—Cl | C—H | H | CF3 | CH | CH | C—SCF3 | CH | H | H | H | CF3CH2CO | 1 |
| 1-603 | C—Cl | C—H | C—Cl | C—H | H | CF3 | CH | CH | C—SCF3 | CH | H | H | H | CH3SCH2CO | 1 |
| 1-604 | C—Cl | C—H | C—Cl | C—H | H | CF3 | CH | CH | C—SCF3 | CH | H | H | H | CH3S(O)CH2CO | 1 |
| 1-605 | C—Cl | C—H | C—Cl | C—H | H | CF3 | CH | CH | C—SCF3 | CH | H | H | H | CH3SO2CH2CO | 1 |
| 1-606 | C—Cl | C—H | C—Cl | C—H | H | CF3 | CH | CH | C—SCF3 | CH | H | H | H | CH3CH2NHCO | 1 |
| 1-607 | C—Cl | C—H | C—Cl | C—H | H | CF3 | CH | CH | C—S(O)CF3 | CH | H | H | H | CH3CH2CO | 1 |
| 1-608 | C—Cl | C—H | C—Cl | C—H | H | CF3 | CH | CH | C—S(O)CF3 | CH | H | H | H | nPrCO | 1 |
| 1-609 | C—Cl | C—H | C—Cl | C—H | H | CF3 | CH | CH | C—S(O)CF3 | CH | H | H | H | cyclo-PrCO | 1 |
| 1-610 | C—Cl | C—H | C—Cl | C—H | H | CF3 | CH | CH | C—S(O)CF3 | CH | H | H | H | cyclo-PrCH2CO | 1 |
| 1-611 | C—Cl | C—H | C—Cl | C—H | H | CF3 | CH | CH | C—S(O)CF3 | CH | H | H | H | CF3CH2CO | 1 |
| 1-612 | C—Cl | C—H | C—Cl | C—H | H | CF3 | CH | CH | C—S(O)CF3 | CH | H | H | H | CH3SCH2CO | 1 |
| 1-613 | C—Cl | C—H | C—Cl | C—H | H | CF3 | CH | CH | C—S(O)CF3 | CH | H | H | H | CH3S(O)CH2CO | 1 |
| 1-614 | C—Cl | C—H | C—Cl | C—H | H | CF3 | CH | CH | C—S(O)CF3 | CH | H | H | H | CH3SO2CH2CO | 1 |
| 1-615 | C—Cl | C—H | C—Cl | C—H | H | CF3 | CH | CH | C—S(O)CF3 | CH | H | H | H | CH3CH2NHCO | 1 |
| 1-616 | C—Cl | C—H | C—Cl | C—H | H | CF3 | CH | CH | C—SO2CF3 | CH | H | H | H | CH3CH2CO | 1 |
| 1-617 | C—Cl | C—H | C—Cl | C—H | H | CF3 | CH | CH | C—SO2CF3 | CH | H | H | H | nPrCO | 1 |
| 1-618 | C—Cl | C—H | C—Cl | C—H | H | CF3 | CH | CH | C—SO2CF3 | CH | H | H | H | cyclo-PrCO | 1 |
| 1-619 | C—Cl | C—H | C—Cl | C—H | H | CF3 | CH | CH | C—SO2CF3 | CH | H | H | H | cyclo-PrCH2CO | 1 |
| 1-620 | C—Cl | C—H | C—Cl | C—H | H | CF3 | CH | CH | C—SO2CF3 | CH | H | H | H | CF3CH2CO | 1 |
| 1-621 | C—Cl | C—H | C—Cl | C—H | H | CF3 | CH | CH | C—SO2CF3 | CH | H | H | H | CH3SCH2CO | 1 |
| 1-622 | C—Cl | C—H | C—Cl | C—H | H | CF3 | CH | CH | C—SO2CF3 | CH | H | H | H | CH3S(O)CH2CO | 1 |

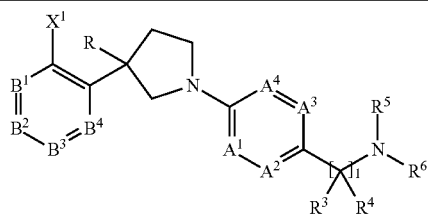

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-623 | C—Cl | C—H | C—Cl | C—H | H | CF3 | CH | CH | C—SO2CF3 | CH | H | H | H | CH3SO2CH2CO | 1 |
| 1-624 | C—Cl | C—H | C—Cl | C—H | H | CF3 | CH | CH | C—SO2CF3 | CH | H | H | H | CH3CH2NHCO | 1 |
| 1-625 | C—Br | C—H | C—Br | C—H | H | CF3 | CH | CH | C—Cl | CH | H | H | H | CH3CH2CO | 1 |
| 1-626 | C—Br | C—H | C—Br | C—H | H | CF3 | CH | CH | C—Cl | CH | H | H | H | n-PrCO | 1 |
| 1-627 | C—Br | C—H | C—Br | C—H | H | CF3 | CH | CH | C—Cl | CH | H | H | H | cyclo-PrCO | 1 |
| 1-628 | C—Br | C—H | C—Br | C—H | H | CF3 | CH | CH | C—Cl | CH | H | H | H | cyclo-PrCH2CO | 1 |
| 1-629 | C—Br | C—H | C—Br | C—H | H | CF3 | CH | CH | C—Cl | CH | H | H | H | CF3CH2CO | 1 |
| 1-630 | C—Br | C—H | C—Br | C—H | H | CF3 | CH | CH | C—Cl | CH | H | H | H | CH3SCH2CO | 1 |
| 1-631 | C—Br | C—H | C—Br | C—H | H | CF3 | CH | CH | C—Cl | CH | H | H | H | CH3S(O)CH2CO | 1 |
| 1-632 | C—Br | C—H | C—Br | C—H | H | CF3 | CH | CH | C—Cl | CH | H | H | H | CH3SO2CH2CO | 1 |
| 1-633 | C—Br | C—H | C—Br | C—H | H | CF3 | CH | CH | C—Cl | CH | H | H | H | CH3CH2NHCO | 1 |
| 1-634 | C—Br | C—H | C—Br | C—H | H | CF3 | CH | CH | C—Br | CH | H | H | H | CH3CO | 1 |
| 1-635 | C—Br | C—H | C—Br | C—H | H | CF3 | CH | CH | C—Br | CH | H | H | H | CH3CH2CO | 1 |
| 1-636 | C—Br | C—H | C—Br | C—H | H | CF3 | CH | CH | C—Br | CH | H | H | H | n-PrCO | 1 |
| 1-637 | C—Br | C—H | C—Br | C—H | H | CF3 | CH | CH | C—Br | CH | H | H | H | cyclo-PrCO | 1 |
| 1-638 | C—Br | C—H | C—Br | C—H | H | CF3 | CH | CH | C—Br | CH | H | H | H | cyclo-PrCH2CO | 1 |
| 1-639 | C—Br | C—H | C—Br | C—H | H | CF3 | CH | CH | C—Br | CH | H | H | H | CF3CH2CO | 1 |
| 1-640 | C—Br | C—H | C—Br | C—H | H | CF3 | CH | CH | C—Br | CH | H | H | H | CH3SCH2CO | 1 |
| 1-641 | C—Br | C—H | C—Br | C—H | H | CF3 | CH | CH | C—Br | CH | H | H | H | CH3S(O)CH2CO | 1 |
| 1-642 | C—Br | C—H | C—Br | C—H | H | CF3 | CH | CH | C—Br | CH | H | H | H | CH3SO2CH2CO | 1 |
| 1-643 | C—Br | C—H | C—Br | C—H | H | CF3 | CH | CH | C—Br | CH | H | H | H | CH3CH2NHCO | 1 |
| 1-644 | C—Br | C—H | C—Br | C—H | H | CF3 | CH | CH | C—CF3 | CH | H | H | H | CH3CO | 1 |
| 1-645 | C—Br | C—H | C—Br | C—H | H | CF3 | CH | CH | C—CF3 | CH | H | H | H | CH3CH2CO | 1 |
| 1-646 | C—Br | C—H | C—Br | C—H | H | CF3 | CH | CH | C—CF3 | CH | H | H | H | n-PrCO | 1 |
| 1-647 | C—Br | C—H | C—Br | C—H | H | CF3 | CH | CH | C—CF3 | CH | H | H | H | cyclo-PrCO | 1 |
| 1-648 | C—Br | C—H | C—Br | C—H | H | CF3 | CH | CH | C—CF3 | CH | H | H | H | cyclo-PrCH2CO | 1 |
| 1-649 | C—Br | C—H | C—Br | C—H | H | CF3 | CH | CH | C—CF3 | CH | H | H | H | CF3CH2CO | 1 |
| 1-650 | C—Br | C—H | C—Br | C—H | H | CF3 | CH | CH | C—CF3 | CH | H | H | H | CH3SCH2CO | 1 |
| 1-651 | C—Br | C—H | C—Br | C—H | H | CF3 | CH | CH | C—CF3 | CH | H | H | H | CH3S(O)CH2CO | 1 |
| 1-652 | C—Br | C—H | C—Br | C—H | H | CF3 | CH | CH | C—CF3 | CH | H | H | H | CH3SO2CH2CO | 1 |
| 1-653 | C—Br | C—H | C—Br | C—H | H | CF3 | CH | CH | C—CF3 | CH | H | H | H | CH3CH2NHCO | 1 |
| 1-654 | C—Cl | C—F | C—Cl | C—H | H | CF3 | CH | CH | C—Cl | CH | H | H | H | CH3CO | 1 |
| 1-655 | C—Cl | C—F | C—Cl | C—H | H | CF3 | CH | CH | C—Cl | CH | H | H | H | CH3CH2CO | 1 |
| 1-656 | C—Cl | C—F | C—Cl | C—H | H | CF3 | CH | CH | C—Cl | CH | H | H | H | nPrCO | 1 |
| 1-657 | C—Cl | C—F | C—Cl | C—H | H | CF3 | CH | CH | C—Cl | CH | H | H | H | cyclo-PrCO | 1 |

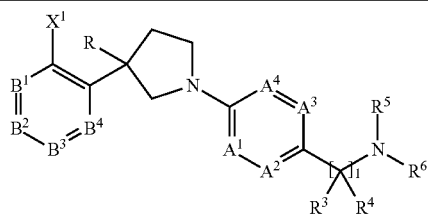

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-658 | C—Cl | C—F | C—Cl | C—H | H | CF3 | CH | CH | C—Cl | CH | H | H | H | cyclo-PrCH2CO | 1 |
| 1-659 | C—Cl | C—F | C—Cl | C—H | H | CF3 | CH | CH | C—Cl | CH | H | H | H | CF3CH2CO | 1 |
| 1-660 | C—Cl | C—F | C—Cl | C—H | H | CF3 | CH | CH | C—Cl | CH | H | H | H | CH3SCH2CO | 1 |
| 1-661 | C—Cl | C—F | C—Cl | C—H | H | CF3 | CH | CH | C—Cl | CH | H | H | H | CH3S(O)CH2CO | 1 |
| 1-662 | C—Cl | C—F | C—Cl | C—H | H | CF3 | CH | CH | C—Cl | CH | H | H | H | CH3SO2CH2CO | 1 |
| 1-663 | C—Cl | C—F | C—Cl | C—H | H | CF3 | CH | CH | C—Cl | CH | H | H | H | CH3CH2NHCO | 1 |
| 1-664 | C—Cl | C—F | C—Cl | C—H | H | CF3 | CH | CH | C—Br | CH | H | H | H | CH3CO | 1 |
| 1-665 | C—Cl | C—F | C—Cl | C—H | H | CF3 | CH | CH | C—Br | CH | H | H | H | CH3CH2CO | 1 |
| 1-666 | C—Cl | C—F | C—Cl | C—H | H | CF3 | CH | CH | C—Br | CH | H | H | H | nPrCO | 1 |
| 1-667 | C—Cl | C—F | C—Cl | C—H | H | CF3 | CH | CH | C—Br | CH | H | H | H | cyclo-PrCO | 1 |
| 1-668 | C—Cl | C—F | C—Cl | C—H | H | CF3 | CH | CH | C—Br | CH | H | H | H | cyclo-PrCH2CO | 1 |
| 1-669 | C—Cl | C—F | C—Cl | C—H | H | CF3 | CH | CH | C—Br | CH | H | H | H | CF3CH2CO | 1 |
| 1-670 | C—Cl | C—F | C—Cl | C—H | H | CF3 | CH | CH | C—Br | CH | H | H | H | CH3SCH2CO | 1 |
| 1-671 | C—Cl | C—F | C—Cl | C—H | H | CF3 | CH | CH | C—Br | CH | H | H | H | CH3S(O)CH2CO | 1 |
| 1-672 | C—Cl | C—F | C—Cl | C—H | H | CF3 | CH | CH | C—Br | CH | H | H | H | CH3SO2CH2CO | 1 |
| 1-673 | C—Cl | C—F | C—Cl | C—H | H | CF3 | CH | CH | C—Br | CH | H | H | H | CH3CH2NHCO | 1 |
| 1-674 | C—Cl | C—F | C—Cl | C—H | H | CF3 | CH | CH | C—CF3 | CH | H | H | H | CH3CO | 1 |
| 1-675 | C—Cl | C—F | C—Cl | C—H | H | CF3 | CH | CH | C—CF3 | CH | H | H | H | CH3CH2CO | 1 |
| 1-676 | C—Cl | C—F | C—Cl | C—H | H | CF3 | CH | CH | C—CF3 | CH | H | H | H | nPrCO | 1 |
| 1-677 | C—Cl | C—F | C—Cl | C—H | H | CF3 | CH | CH | C—CF3 | CH | H | H | H | cyclo-PrCO | 1 |
| 1-678 | C—Cl | C—F | C—Cl | C—H | H | CF3 | CH | CH | C—CF3 | CH | H | H | H | cyclo-PrCH2CO | 1 |
| 1-679 | C—Cl | C—F | C—Cl | C—H | H | CF3 | CH | CH | C—CF3 | CH | H | H | H | CF3CH2CO | 1 |
| 1-680 | C—Cl | C—F | C—Cl | C—H | H | CF3 | CH | CH | C—CF3 | CH | H | H | H | CH3SCH2CO | 1 |
| 1-681 | C—Cl | C—F | C—Cl | C—H | H | CF3 | CH | CH | C—CF3 | CH | H | H | H | CH3S(O)CH2CO | 1 |
| 1-682 | C—Cl | C—F | C—Cl | C—H | H | CF3 | CH | CH | C—CF3 | CH | H | H | H | CH3SO2CH2CO | 1 |
| 1-683 | C—Cl | C—F | C—Cl | C—H | H | CF3 | CH | CH | C—CF3 | CH | H | H | H | CH3CH2NHCO | 1 |
| 1-684 | C—Cl | C—Cl | C—Cl | C—H | H | CF3 | CH | CH | C—F | CH | H | H | H | CH3CO | 1 |
| 1-685 | C—Cl | C—Cl | C—Cl | C—H | H | CF3 | CH | CH | C—F | CH | H | H | H | CH3CH2CO | 1 |
| 1-686 | C—Cl | C—Cl | C—Cl | C—H | H | CF3 | CH | CH | C—F | CH | H | H | H | nPrCO | 1 |
| 1-687 | C—Cl | C—Cl | C—Cl | C—H | H | CF3 | CH | CH | C—F | CH | H | H | H | cyclo-PrCO | 1 |
| 1-688 | C—Cl | C—Cl | C—Cl | C—H | H | CF3 | CH | CH | C—F | CH | H | H | H | cyclo-PrCH2CO | 1 |
| 1-689 | C—Cl | C—Cl | C—Cl | C—H | H | CF3 | CH | CH | C—F | CH | H | H | H | CF3CH2CO | 1 |
| 1-690 | C—Cl | C—Cl | C—Cl | C—H | H | CF3 | CH | CH | C—F | CH | H | H | H | CH3SCH2CO | 1 |
| 1-691 | C—Cl | C—Cl | C—Cl | C—H | H | CF3 | CH | CH | C—F | CH | H | H | H | CH3S(O)CH2CO | 1 |
| 1-692 | C—Cl | C—Cl | C—Cl | C—H | H | CF3 | CH | CH | C—F | CH | H | H | H | CH3SO2CH2CO | 1 |

TABLE 1-continued

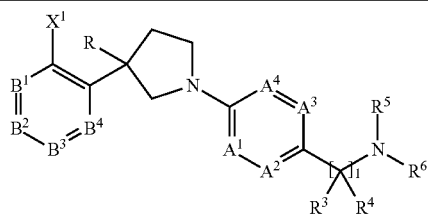

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-693 | C—Cl | C—Cl | C—Cl | C—H | H | CF3 | CH | CH | C—F | CH | H | H | H | CH3CH2NHCO | 1 |
| 1-694 | C—Cl | C—Cl | C—Cl | C—H | H | CF3 | CH | CH | C—Cl | CH | H | H | H | tert-BuOCO | 1 |
| 1-695 | C—Cl | C—Cl | C—Cl | C—H | H | CF3 | CH | CH | C—Cl | CH | H | H | H | n-PrCO | 1 |
| 1-696 | C—Cl | C—Cl | C—Cl | C—H | H | CF3 | CH | CH | C—Cl | CH | H | H | H | cyclo-PrCH2CO | 1 |
| 1-697 | C—Cl | C—Cl | C—Cl | C—H | H | CF3 | CH | CH | C—Cl | CH | H | H | H | HSCH2CO | 1 |
| 1-698 | C—Cl | C—Cl | C—Cl | C—H | H | CF3 | CH | CH | C—Cl | CH | H | H | H | CH3SCH2CO | 1 |
| 1-699 | C—Cl | C—Cl | C—Cl | C—H | H | CF3 | CH | CH | C—Cl | CH | H | H | H | CH3S(O)CH2CO | 1 |
| 1-700 | C—Cl | C—Cl | C—Cl | C—H | H | CF3 | CH | CH | C—Cl | CH | H | H | H | CH3SO2CH2CO | 1 |
| 1-701 | C—Cl | C—Cl | C—Cl | C—H | H | CF3 | CH | CH | C—Cl | CH | H | H | H | CH3COSCH2CO | 1 |
| 1-702 | C—Cl | C—Cl | C—Cl | C—H | H | CF3 | CH | CH | C—Br | CH | H | H | H | n-PrCO | 1 |
| 1-707 | C—Cl | C—Cl | C—Cl | C—H | H | CF3 | CH | CH | C—Br | CH | H | H | H | cyclo-PrCH2CO | 1 |
| 1-708 | C—Cl | C—Cl | C—Cl | C—H | H | CF3 | CH | CH | C—Br | CH | H | H | H | CH3SCH2CO | 1 |
| 1-709 | C—Cl | C—Cl | C—Cl | C—H | H | CF3 | CH | CH | C—Br | CH | H | H | H | CH3S(O)CH2CO | 1 |
| 1-710 | C—Cl | C—Cl | C—Cl | C—H | H | CF3 | CH | CH | C—Br | CH | H | H | H | CH3SO2CH2CO | 1 |
| 1-711 | C—Cl | C—Cl | C—Cl | C—H | H | CF3 | CH | CH | C—CH3 | CH | H | H | H | CH3CO | 1 |
| 1-712 | C—Cl | C—Cl | C—Cl | C—H | H | CF3 | CH | CH | C—CH3 | CH | H | H | H | CH3CH2CO | 1 |
| 1-713 | C—Cl | C—Cl | C—Cl | C—H | H | CF3 | CH | CH | C—CH3 | CH | H | H | H | nPrCO | 1 |
| 1-714 | C—Cl | C—Cl | C—Cl | C—H | H | CF3 | CH | CH | C—CH3 | CH | H | H | H | cyclo-PrCO | 1 |
| 1-715 | C—Cl | C—Cl | C—Cl | C—H | H | CF3 | CH | CH | C—CH3 | CH | H | H | H | cyclo-PrCH2CO | 1 |
| 1-716 | C—Cl | C—Cl | C—Cl | C—H | H | CF3 | CH | CH | C—CH3 | CH | H | H | H | CF3CH2CO | 1 |
| 1-717 | C—Cl | C—Cl | C—Cl | C—H | H | CF3 | CH | CH | C—CH3 | CH | H | H | H | CH3SCH2CO | 1 |
| 1-718 | C—Cl | C—Cl | C—Cl | C—H | H | CF3 | CH | CH | C—CH3 | CH | H | H | H | CH3S(O)CH2CO | 1 |
| 1-719 | C—Cl | C—Cl | C—Cl | C—H | H | CF3 | CH | CH | C—CH3 | CH | H | H | H | CH3SO2CH2CO | 1 |
| 1-720 | C—Cl | C—Cl | C—Cl | C—H | H | CF3 | CH | CH | C—CH3 | CH | H | H | H | CH3CH2NHCO | 1 |
| 1-721 | C—Cl | C—Cl | C—Cl | C—H | H | CF3 | CH | CH | C-cyclo-Pr | CH | H | H | H | CH3CH2CO | 1 |
| 1-722 | C—Cl | C—Cl | C—Cl | C—H | H | CF3 | CH | CH | C-cyclo-Pr | CH | H | H | H | CF3CH2CO | 1 |
| 1-723 | C—Cl | C—Cl | C—Cl | C—H | H | CF3 | CH | CH | C—CF3 | CH | H | H | H | ClCH2CO | 1 |
| 1-724 | C—Cl | C—Cl | C—Cl | C—H | H | CF3 | CH | CH | C—CF3 | CH | H | H | H | cyclo-PrCH2CO | 1 |
| 1-725 | C—Cl | C—Cl | C—Cl | C—H | H | CF3 | CH | CH | C—CF3 | CH | H | H | H | CH3OCH2CO | 1 |
| 1-726 | C—Cl | C—Cl | C—Cl | C—H | H | CF3 | CH | CH | C—CF3 | CH | H | H | H | CH3CH2OCH2CH2CO | 1 |
| 1-727 | C—Cl | C—Cl | C—Cl | C—H | H | CF3 | CH | CH | C—CF3 | CH | H | H | H | HSCH2CO | 1 |
| 1-728 | C—Cl | C—Cl | C—Cl | C—H | H | CF3 | CH | CH | C—CF3 | CH | H | H | H | CH3SCH2CO | 1 |
| 1-729 | C—Cl | C—Cl | C—Cl | C—H | H | CF3 | CH | CH | C—CF3 | CH | H | H | H | CH3S(O)CH2CO | 1 |
| 1-730 | C—Cl | C—Cl | C—Cl | C—H | H | CF3 | CH | CH | C—CF3 | CH | H | H | H | CH3SO2CH2CO | 1 |
| 1-731 | C—Cl | C—Cl | C—Cl | C—H | H | CF3 | CH | CH | C—CF3 | CH | H | H | H | CF3SCH2CO | 1 |

TABLE 1-continued

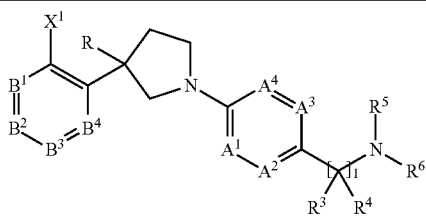

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-732 | C—Cl | C—Cl | C—Cl | C—H | H | CF3 | CH | CH | C—CF3 | CH | H | H | H | (Allyl)SCH2CO | 1 |
| 1-733 | C—Cl | C—Cl | C—Cl | C—H | H | CF3 | CH | CH | C—CF3 | CH | H | H | H | (Allyl)S(O)CH2CO | 1 |
| 1-734 | C—Cl | C—Cl | C—Cl | C—H | H | CF3 | CH | CH | C—CF3 | CH | H | H | H | (Allyl)SO2CH2CO | 1 |
| 1-735 | C—Cl | C—Cl | C—Cl | C—H | H | CF3 | CH | CH | C—CF3 | CH | H | H | H | CH3COSCH2CO | 1 |
| 1-736 | C—Cl | C—Cl | C—Cl | C—H | H | CF3 | CH | CH | C—CN | CH | H | H | H | CH3CO | 1 |
| 1-737 | C—Cl | C—Cl | C—Cl | C—H | H | CF3 | CH | CH | C—CN | CH | H | H | H | CH3CH2CO | 1 |
| 1-738 | C—Cl | C—Cl | C—Cl | C—H | H | CF3 | CH | CH | C—CN | CH | H | H | H | nPrCO | 1 |
| 1-739 | C—Cl | C—Cl | C—Cl | C—H | H | CF3 | CH | CH | C—CN | CH | H | H | H | cyclo-PrCO | 1 |
| 1-740 | C—Cl | C—Cl | C—Cl | C—H | H | CF3 | CH | CH | C—CN | CH | H | H | H | cyclo-PrCH2CO | 1 |
| 1-741 | C—Cl | C—Cl | C—Cl | C—H | H | CF3 | CH | CH | C—CN | CH | H | H | H | CF3CH2CO | 1 |
| 1-742 | C—Cl | C—Cl | C—Cl | C—H | H | CF3 | CH | CH | C—CN | CH | H | H | H | CH3SCH2CO | 1 |
| 1-743 | C—Cl | C—Cl | C—Cl | C—H | H | CF3 | CH | CH | C—CN | CH | H | H | H | CH3S(O)CH2CO | 1 |
| 1-744 | C—Cl | C—Cl | C—Cl | C—H | H | CF3 | CH | CH | C—CN | CH | H | H | H | CH3SO2CH2CO | 1 |
| 1-745 | C—Cl | C—Cl | C—Cl | C—H | H | CF3 | CH | CH | C—CN | CH | H | H | H | CH3CH2NHCO | 1 |
| 1-746 | C—Cl | C—Cl | C—Cl | C—H | H | CF3 | CH | CH | C—SCH3 | CH | H | H | H | CH3CO | 1 |
| 1-747 | C—Cl | C—Cl | C—Cl | C—H | H | CF3 | CH | CH | C—SCH3 | CH | H | H | H | CH3CH2CO | 1 |
| 1-748 | C—Cl | C—Cl | C—Cl | C—H | H | CF3 | CH | CH | C—SCH3 | CH | H | H | H | cyclo-PrCO | 1 |
| 1-749 | C—Cl | C—Cl | C—Cl | C—H | H | CF3 | CH | CH | C—SCH3 | CH | H | H | H | CF3CH2CO | 1 |
| 1-750 | C—Cl | C—Cl | C—Cl | C—H | H | CF3 | CH | CH | C—S(O)CH3 | CH | H | H | H | CH3CO | 1 |
| 1-751 | C—Cl | C—Cl | C—Cl | C—H | H | CF3 | CH | CH | C—S(O)CH3 | CH | H | H | H | CH3CH2CO | 1 |
| 1-752 | C—Cl | C—Cl | C—Cl | C—H | H | CF3 | CH | CH | C—S(O)CH3 | CH | H | H | H | cyclo-PrCO | 1 |
| 1-753 | C—Cl | C—Cl | C—Cl | C—H | H | CF3 | CH | CH | C—S(O)CH3 | CH | H | H | H | CF3CH2CO | 1 |
| 1-754 | C—Cl | C—Cl | C—Cl | C—H | H | CF3 | CH | CH | C—S(O)CH3 | CH | H | H | H | CH3SCH2CO | 1 |
| 1-755 | C—Cl | C—Cl | C—Cl | C—H | H | CF3 | CH | CH | C—SO2CH3 | CH | H | H | H | CH3CO | 1 |
| 1-756 | C—Cl | C—Cl | C—Cl | C—H | H | CF3 | CH | CH | C—SO2CH3 | CH | H | H | H | CH3CH2CO | 1 |
| 1-757 | C—Cl | C—Cl | C—Cl | C—H | H | CF3 | CH | CH | C—SO2CH3 | CH | H | H | H | cyclo-PrCO | 1 |
| 1-758 | C—Cl | C—Cl | C—Cl | C—H | H | CF3 | CH | CH | C—SO2CH3 | CH | H | H | H | CF3CH2CO | 1 |
| 1-759 | C—Cl | C—Cl | C—Cl | C—H | H | CF3 | CH | CH | C—SCF3 | CH | H | H | H | nPrCO | 1 |
| 1-760 | C—Cl | C—Cl | C—Cl | C—H | H | CF3 | CH | CH | C—SCF3 | CH | H | H | H | cyclo-PrCH2CO | 1 |
| 1-761 | C—Cl | C—Cl | C—Cl | C—H | H | CF3 | CH | CH | C—SCF3 | CH | H | H | H | CH3SCH2CO | 1 |
| 1-762 | C—Cl | C—Cl | C—Cl | C—H | H | CF3 | CH | CH | C—SCF3 | CH | H | H | H | CH3S(O)CH2CO | 1 |
| 1-763 | C—Cl | C—Cl | C—Cl | C—H | H | CF3 | CH | CH | C—SCF3 | CH | H | H | H | CH3SO2CH2CO | 1 |
| 1-764 | C—Cl | C—Cl | C—Cl | C—H | H | CF3 | CH | CH | C—SCF3 | CH | H | H | H | CH3CH2NHCO | 1 |
| 1-765 | C—Cl | C—Cl | C—Cl | C—H | H | CF3 | CH | CH | C—S(O)CF3 | CH | H | H | H | nPrCO | 1 |
| 1-766 | C—Cl | C—Cl | C—Cl | C—H | H | CF3 | CH | CH | C—S(O)CF3 | CH | H | H | H | cyclo-PrCH2CO | 1 |

TABLE 1-continued

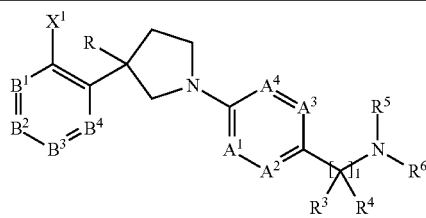

| Ex.-No. | $B^1$ | $B^2$ | $B^3$ | $B^4$ | $X^1$ | R | $A^1$ | $A^2$ | $A^3$ | $A^4$ | $R^3$ | $R^4$ | $R^5$ | $R^6$ | 1 |
|---|---|---|---|---|---|---|---|---|---|---|---|---|---|---|---|
| 1-767 | C—Cl | C—Cl | C—Cl | C—H | H | CF3 | CH | CH | C—S(O)CF3 | CH | H | H | H | CH3SCH2CO | 1 |
| 1-768 | C—Cl | C—Cl | C—Cl | C—H | H | CF3 | CH | CH | C—S(O)CF3 | CH | H | H | H | CH3S(O)CH2CO | 1 |
| 1-769 | C—Cl | C—Cl | C—Cl | C—H | H | CF3 | CH | CH | C—S(O)CF3 | CH | H | H | H | CH3SO2CH2CO | 1 |
| 1-770 | C—Cl | C—Cl | C—Cl | C—H | H | CF3 | CH | CH | C—SO2CF3 | CH | H | H | H | nPrCO | 1 |
| 1-771 | C—Cl | C—Cl | C—Cl | C—H | H | CF3 | CH | CH | C—SO2CF3 | CH | H | H | H | cyclo-PrCH2CO | 1 |
| 1-772 | C—Cl | C—Cl | C—Cl | C—H | H | CF3 | CH | CH | C—SO2CF3 | CH | H | H | H | CH3SCH2CO | 1 |
| 1-773 | C—Cl | C—Cl | C—Cl | C—H | H | CF3 | CH | CH | C—SO2CF3 | CH | H | H | H | CH3S(O)CH2CO | 1 |
| 1-774 | C—Cl | C—Cl | C—Cl | C—H | H | CF3 | CH | CH | C—SO2CF3 | CH | H | H | H | CH3SO2CH2CO | 1 |
| 1-775 | C—Cl | C—Br | C—Cl | C—H | H | CF3 | CH | CH | C—Cl | CH | H | H | H | CH3CO | 1 |
| 1-776 | C—Cl | C—Br | C—Cl | C—H | H | CF3 | CH | CH | C—Cl | CH | H | H | H | CH3CH2CO | 1 |
| 1-777 | C—Cl | C—Br | C—Cl | C—H | H | CF3 | CH | CH | C—Cl | CH | H | H | H | nPrCO | 1 |
| 1-778 | C—Cl | C—Br | C—Cl | C—H | H | CF3 | CH | CH | C—Cl | CH | H | H | H | cyclo-PrCO | 1 |
| 1-779 | C—Cl | C—Br | C—Cl | C—H | H | CF3 | CH | CH | C—Cl | CH | H | H | H | cyclo-PrCH2CO | 1 |
| 1-780 | C—Cl | C—Br | C—Cl | C—H | H | CF3 | CH | CH | C—Cl | CH | H | H | H | CF3CH2CO | 1 |
| 1-781 | C—Cl | C—Br | C—Cl | C—H | H | CF3 | CH | CH | C—Cl | CH | H | H | H | CH3SCH2CO | 1 |
| 1-782 | C—Cl | C—Br | C—Cl | C—H | H | CF3 | CH | CH | C—Cl | CH | H | H | H | CH3S(O)CH2CO | 1 |
| 1-783 | C—Cl | C—Br | C—Cl | C—H | H | CF3 | CH | CH | C—Cl | CH | H | H | H | CH3SO2CH2CO | 1 |
| 1-784 | C—Cl | C—Br | C—Cl | C—H | H | CF3 | CH | CH | C—Cl | CH | H | H | H | CH3CH2NHCO | 1 |
| 1-785 | C—Cl | C—Br | C—Cl | C—H | H | CF3 | CH | CH | C—Br | CH | H | H | H | CH3CO | 1 |
| 1-786 | C—Cl | C—Br | C—Cl | C—H | H | CF3 | CH | CH | C—Br | CH | H | H | H | CH3CH2CO | 1 |
| 1-787 | C—Cl | C—Br | C—Cl | C—H | H | CF3 | CH | CH | C—Br | CH | H | H | H | nPrCO | 1 |
| 1-788 | C—Cl | C—Br | C—Cl | C—H | H | CF3 | CH | CH | C—Br | CH | H | H | H | cyclo-PrCO | 1 |
| 1-789 | C—Cl | C—Br | C—Cl | C—H | H | CF3 | CH | CH | C—Br | CH | H | H | H | cyclo-PrCH2CO | 1 |
| 1-790 | C—Cl | C—Br | C—Cl | C—H | H | CF3 | CH | CH | C—Br | CH | H | H | H | CF3CH2CO | 1 |
| 1-791 | C—Cl | C—Br | C—Cl | C—H | H | CF3 | CH | CH | C—Br | CH | H | H | H | CH3SCH2CO | 1 |
| 1-792 | C—Cl | C—Br | C—Cl | C—H | H | CF3 | CH | CH | C—Br | CH | H | H | H | CH3S(O)CH2CO | 1 |
| 1-793 | C—Cl | C—Br | C—Cl | C—H | H | CF3 | CH | CH | C—Br | CH | H | H | H | CH3SO2CH2CO | 1 |
| 1-794 | C—Cl | C—Br | C—Cl | C—H | H | CF3 | CH | CH | C—Br | CH | H | H | H | CH3CH2NHCO | 1 |
| 1-795 | C—Cl | C—Br | C—Cl | C—H | H | CF3 | CH | CH | C—CF3 | CH | H | H | H | CH3CO | 1 |
| 1-796 | C—Cl | C—Br | C—Cl | C—H | H | CF3 | CH | CH | C—CF3 | CH | H | H | H | CH3CH2CO | 1 |
| 1-797 | C—Cl | C—Br | C—Cl | C—H | H | CF3 | CH | CH | C—CF3 | CH | H | H | H | nPrCO | 1 |
| 1-798 | C—Cl | C—Br | C—Cl | C—H | H | CF3 | CH | CH | C—CF3 | CH | H | H | H | cyclo-PrCO | 1 |
| 1-799 | C—Cl | C—Br | C—Cl | C—H | H | CF3 | CH | CH | C—CF3 | CH | H | H | H | cyclo-PrCH2CO | 1 |
| 1-800 | C—Cl | C—Br | C—Cl | C—H | H | CF3 | CH | CH | C—CF3 | CH | H | H | H | CF3CH2CO | 1 |
| 1-801 | C—Cl | C—Br | C—Cl | C—H | H | CF3 | CH | CH | C—CF3 | CH | H | H | H | CH3SCH2CO | 1 |

TABLE 1-continued

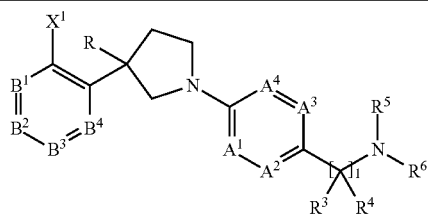

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-802 | C—Cl | C—Br | C—Cl | C—H | H | CF3 | CH | CH | C—CF3 | CH | H | H | H | CH3S(O)CH2CO | 1 |
| 1-803 | C—Cl | C—Br | C—Cl | C—H | H | CF3 | CH | CH | C—CF3 | CH | H | H | H | CH3SO2CH2CO | 1 |
| 1-804 | C—Cl | C—Br | C—Cl | C—H | H | CF3 | CH | CH | C—CF3 | CH | H | H | H | CH3CH2NHCO | 1 |
| 1-805 | C—Cl | C—Cl | C—Br | C—H | H | CF3 | CH | CH | C—Cl | CH | H | H | H | CH3CO | 1 |
| 1-806 | C—Cl | C—Cl | C—Br | C—H | H | CF3 | CH | CH | C—Cl | CH | H | H | H | CH3CH2CO | 1 |
| 1-807 | C—Cl | C—Cl | C—Br | C—H | H | CF3 | CH | CH | C—Cl | CH | H | H | H | nPrCO | 1 |
| 1-808 | C—Cl | C—Cl | C—Br | C—H | H | CF3 | CH | CH | C—Cl | CH | H | H | H | cyclo-PrCO | 1 |
| 1-809 | C—Cl | C—Cl | C—Br | C—H | H | CF3 | CH | CH | C—Cl | CH | H | H | H | cyclo-PrCH2CO | 1 |
| 1-810 | C—Cl | C—Cl | C—Br | C—H | H | CF3 | CH | CH | C—Cl | CH | H | H | H | CF3CH2CO | 1 |
| 1-811 | C—Cl | C—Cl | C—Br | C—H | H | CF3 | CH | CH | C—Cl | CH | H | H | H | CH3SCH2CO | 1 |
| 1-812 | C—Cl | C—Cl | C—Br | C—H | H | CF3 | CH | CH | C—Cl | CH | H | H | H | CH3S(O)CH2CO | 1 |
| 1-813 | C—Cl | C—Cl | C—Br | C—H | H | CF3 | CH | CH | C—Cl | CH | H | H | H | CH3SO2CH2CO | 1 |
| 1-814 | C—Cl | C—Cl | C—Br | C—H | H | CF3 | CH | CH | C—Cl | CH | H | H | H | CH3CH2NHCO | 1 |
| 1-815 | C—Cl | C—Cl | C—Br | C—H | H | CF3 | CH | CH | C—Br | CH | H | H | H | CH3CO | 1 |
| 1-816 | C—Cl | C—Cl | C—Br | C—H | H | CF3 | CH | CH | C—Br | CH | H | H | H | CH3CH2CO | 1 |
| 1-817 | C—Cl | C—Cl | C—Br | C—H | H | CF3 | CH | CH | C—Br | CH | H | H | H | nPrCO | 1 |
| 1-818 | C—Cl | C—Cl | C—Br | C—H | H | CF3 | CH | CH | C—Br | CH | H | H | H | cyclo-PrCO | 1 |
| 1-819 | C—Cl | C—Cl | C—Br | C—H | H | CF3 | CH | CH | C—Br | CH | H | H | H | cyclo-PrCH2CO | 1 |
| 1-820 | C—Cl | C—Cl | C—Br | C—H | H | CF3 | CH | CH | C—Br | CH | H | H | H | CF3CH2CO | 1 |
| 1-821 | C—Cl | C—Cl | C—Br | C—H | H | CF3 | CH | CH | C—Br | CH | H | H | H | CH3SCH2CO | 1 |
| 1-822 | C—Cl | C—Cl | C—Br | C—H | H | CF3 | CH | CH | C—Br | CH | H | H | H | CH3S(O)CH2CO | 1 |
| 1-823 | C—Cl | C—Cl | C—Br | C—H | H | CF3 | CH | CH | C—Br | CH | H | H | H | CH3SO2CH2CO | 1 |
| 1-824 | C—Cl | C—Cl | C—Br | C—H | H | CF3 | CH | CH | C—Br | CH | H | H | H | CH3CH2NHCO | 1 |
| 1-825 | C—Cl | C—Cl | C—Br | C—H | H | CF3 | CH | CH | C—CF3 | CH | H | H | H | CH3CO | 1 |
| 1-826 | C—Cl | C—Cl | C—Br | C—H | H | CF3 | CH | CH | C—CF3 | CH | H | H | H | CH3CH2CO | 1 |
| 1-827 | C—Cl | C—Cl | C—Br | C—H | H | CF3 | CH | CH | C—CF3 | CH | H | H | H | nPrCO | 1 |
| 1-828 | C—Cl | C—Cl | C—Br | C—H | H | CF3 | CH | CH | C—CF3 | CH | H | H | H | cyclo-PrCO | 1 |
| 1-829 | C—Cl | C—Cl | C—Br | C—H | H | CF3 | CH | CH | C—CF3 | CH | H | H | H | cyclo-PrCH2CO | 1 |
| 1-830 | C—Cl | C—Cl | C—Br | C—H | H | CF3 | CH | CH | C—CF3 | CH | H | H | H | CF3CH2CO | 1 |
| 1-831 | C—Cl | C—Cl | C—Br | C—H | H | CF3 | CH | CH | C—CF3 | CH | H | H | H | CH3SCH2CO | 1 |
| 1-832 | C—Cl | C—Cl | C—Br | C—H | H | CF3 | CH | CH | C—CF3 | CH | H | H | H | CH3S(O)CH2CO | 1 |
| 1-833 | C—Cl | C—Cl | C—Br | C—H | H | CF3 | CH | CH | C—CF3 | CH | H | H | H | CH3SO2CH2CO | 1 |
| 1-834 | C—Cl | C—Cl | C—Br | C—H | H | CF3 | CH | CH | C—CF3 | CH | H | H | H | CH3CH2NHCO | 1 |
| 1-835 | C—Cl | C—F | C—Cl | C—H | F | CF3 | CH | CH | C—Cl | CH | H | H | H | CH3CO | 1 |
| 1-836 | C—Cl | C—F | C—Cl | C—H | F | CF3 | CH | CH | C—Cl | CH | H | H | H | CH3CH2CO | 1 |

TABLE 1-continued

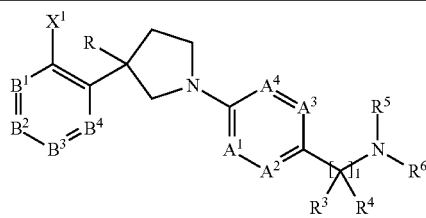

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-837 | C—Cl | C—F | C—Cl | C—H | F | CF3 | CH | CH | C—Cl | CH | H | H | H | nPrCO | 1 |
| 1-838 | C—Cl | C—F | C—Cl | C—H | F | CF3 | CH | CH | C—Cl | CH | H | H | H | cyclo-PrCO | 1 |
| 1-839 | C—Cl | C—F | C—Cl | C—H | F | CF3 | CH | CH | C—Cl | CH | H | H | H | cyclo-PrCH2CO | 1 |
| 1-840 | C—Cl | C—F | C—Cl | C—H | F | CF3 | CH | CH | C—Cl | CH | H | H | H | CF3CH2CO | 1 |
| 1-841 | C—Cl | C—F | C—Cl | C—H | F | CF3 | CH | CH | C—Cl | CH | H | H | H | CH3SCH2CO | 1 |
| 1-842 | C—Cl | C—F | C—Cl | C—H | F | CF3 | CH | CH | C—Cl | CH | H | H | H | CH3S(O)CH2CO | 1 |
| 1-843 | C—Cl | C—F | C—Cl | C—H | F | CF3 | CH | CH | C—Cl | CH | H | H | H | CH3SO2CH2CO | 1 |
| 1-844 | C—Cl | C—F | C—Cl | C—H | F | CF3 | CH | CH | C—Cl | CH | H | H | H | CH3CH2NHCO | 1 |
| 1-845 | C—Cl | C—F | C—Cl | C—H | F | CF3 | CH | CH | C—Br | CH | H | H | H | CH3CO | 1 |
| 1-846 | C—Cl | C—F | C—Cl | C—H | F | CF3 | CH | CH | C—Br | CH | H | H | H | CH3CH2CO | 1 |
| 1-847 | C—Cl | C—F | C—Cl | C—H | F | CF3 | CH | CH | C—Br | CH | H | H | H | nPrCO | 1 |
| 1-848 | C—Cl | C—F | C—Cl | C—H | F | CF3 | CH | CH | C—Br | CH | H | H | H | cyclo-PrCO | 1 |
| 1-849 | C—Cl | C—F | C—Cl | C—H | F | CF3 | CH | CH | C—Br | CH | H | H | H | cyclo-PrCH2CO | 1 |
| 1-850 | C—Cl | C—F | C—Cl | C—H | F | CF3 | CH | CH | C—Br | CH | H | H | H | CF3CH2CO | 1 |
| 1-851 | C—Cl | C—F | C—Cl | C—H | F | CF3 | CH | CH | C—Br | CH | H | H | H | CH3SCH2CO | 1 |
| 1-852 | C—Cl | C—F | C—Cl | C—H | F | CF3 | CH | CH | C—Br | CH | H | H | H | CH3S(O)CH2CO | 1 |
| 1-853 | C—Cl | C—F | C—Cl | C—H | F | CF3 | CH | CH | C—Br | CH | H | H | H | CH3SO2CH2CO | 1 |
| 1-854 | C—Cl | C—F | C—Cl | C—H | F | CF3 | CH | CH | C—Br | CH | H | H | H | CH3CH2NHCO | 1 |
| 1-855 | C—Cl | C—F | C—Cl | C—H | F | CF3 | CH | CH | C—CF3 | CH | H | H | H | CH3CO | 1 |
| 1-856 | C—Cl | C—F | C—Cl | C—H | F | CF3 | CH | CH | C—CF3 | CH | H | H | H | CH3CH2CO | 1 |
| 1-857 | C—Cl | C—F | C—Cl | C—H | F | CF3 | CH | CH | C—CF3 | CH | H | H | H | nPrCO | 1 |
| 1-858 | C—Cl | C—F | C—Cl | C—H | F | CF3 | CH | CH | C—CF3 | CH | H | H | H | cyclo-PrCO | 1 |
| 1-859 | C—Cl | C—F | C—Cl | C—H | F | CF3 | CH | CH | C—CF3 | CH | H | H | H | cyclo-PrCH2CO | 1 |
| 1-860 | C—Cl | C—F | C—Cl | C—H | F | CF3 | CH | CH | C—CF3 | CH | H | H | H | CF3CH2CO | 1 |
| 1-861 | C—Cl | C—F | C—Cl | C—H | F | CF3 | CH | CH | C—CF3 | CH | H | H | H | CH3SCH2CO | 1 |
| 1-862 | C—Cl | C—F | C—Cl | C—H | F | CF3 | CH | CH | C—CF3 | CH | H | H | H | CH3S(O)CH2CO | 1 |
| 1-863 | C—Cl | C—F | C—Cl | C—H | F | CF3 | CH | CH | C—CF3 | CH | H | H | H | CH3SO2CH2CO | 1 |
| 1-864 | C—Cl | C—F | C—Cl | C—H | F | CF3 | CH | CH | C—CF3 | CH | H | H | H | CH3CH2NHCO | 1 |
| 1-865 | C—CF3 | C—H | C—H | C—H | H | CF3 | CH | CH | C—CF3 | CH | H | H | H | CH3CO | 1 |
| 1-866 | C—CF3 | C—H | C—H | C—H | H | CF3 | CH | CH | C—CF3 | CH | H | H | H | CH3CH2CO | 1 |
| 1-867 | C—CF3 | C—H | C—H | C—H | H | CF3 | CH | CH | C—CF3 | CH | H | H | H | nPrCO | 1 |
| 1-868 | C—CF3 | C—H | C—H | C—H | H | CF3 | CH | CH | C—CF3 | CH | H | H | H | cyclo-PrCO | 1 |
| 1-869 | C—CF3 | C—H | C—H | C—H | H | CF3 | CH | CH | C—CF3 | CH | H | H | H | cyclo-PrCH2CO | 1 |
| 1-870 | C—CF3 | C—H | C—H | C—H | H | CF3 | CH | CH | C—CF3 | CH | H | H | H | CF3CH2CO | 1 |
| 1-871 | C—CF3 | C—H | C—H | C—H | H | CF3 | CH | CH | C—CF3 | CH | H | H | H | CH3SOCH2CO | 1 |

TABLE 1-continued

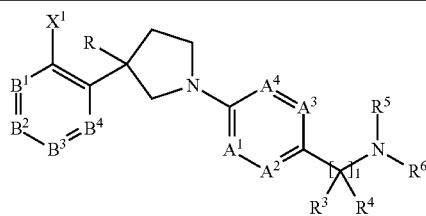

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-872 | C—CF3 | C—H | C—H | C—H | H | CF3 | CH | CH | C—CF3 | CH | H | H | H | CH3S(O)CH2CO | 1 |
| 1-873 | C—CF3 | C—H | C—H | C—H | H | CF3 | CH | CH | C—CF3 | CH | H | H | H | CH3SO2CH2CO | 1 |
| 1-874 | C—CF3 | C—H | C—H | C—H | H | CF3 | CH | CH | C—CF3 | CH | H | H | H | CH3CH2NHCO | 1 |
| 1-875 | C—CF3 | C—F | C—H | C—H | H | CF3 | CH | CH | C—CF3 | CH | H | H | H | CH3CO | 1 |
| 1-876 | C—CF3 | C—F | C—H | C—H | H | CF3 | CH | CH | C—CF3 | CH | H | H | H | CH3CH2CO | 1 |
| 1-877 | C—CF3 | C—F | C—H | C—H | H | CF3 | CH | CH | C—CF3 | CH | H | H | H | nPrCO | 1 |
| 1-878 | C—CF3 | C—F | C—H | C—H | H | CF3 | CH | CH | C—CF3 | CH | H | H | H | cyclo-PrCO | 1 |
| 1-879 | C—CF3 | C—F | C—H | C—H | H | CF3 | CH | CH | C—CF3 | CH | H | H | H | cyclo-PrCH2CO | 1 |
| 1-880 | C—CF3 | C—F | C—H | C—H | H | CF3 | CH | CH | C—CF3 | CH | H | H | H | CF3CH2CO | 1 |
| 1-881 | C—CF3 | C—F | C—H | C—H | H | CF3 | CH | CH | C—CF3 | CH | H | H | H | CH3SOCH2CO | 1 |
| 1-882 | C—CF3 | C—F | C—H | C—H | H | CF3 | CH | CH | C—CF3 | CH | H | H | H | CH3S(O)CH2CO | 1 |
| 1-883 | C—CF3 | C—F | C—H | C—H | H | CF3 | CH | CH | C—CF3 | CH | H | H | H | CH3SO2CH2CO | 1 |
| 1-884 | C—CF3 | C—F | C—H | C—H | H | CF3 | CH | CH | C—CF3 | CH | H | H | H | CH3CH2NHCO | 1 |
| 1-885 | C—CF3 | C—H | C—H | C—H | F | CF3 | CH | CH | C—CF3 | CH | H | H | H | CH3CO | 1 |
| 1-886 | C—CF3 | C—H | C—H | C—H | F | CF3 | CH | CH | C—CF3 | CH | H | H | H | CH3CH2CO | 1 |
| 1-887 | C—CF3 | C—H | C—H | C—H | F | CF3 | CH | CH | C—CF3 | CH | H | H | H | nPrCO | 1 |
| 1-888 | C—CF3 | C—H | C—H | C—H | F | CF3 | CH | CH | C—CF3 | CH | H | H | H | cyclo-PrCO | 1 |
| 1-889 | C—CF3 | C—H | C—H | C—H | F | CF3 | CH | CH | C—CF3 | CH | H | H | H | cyclo-PrCH2CO | 1 |
| 1-890 | C—CF3 | C—H | C—H | C—H | F | CF3 | CH | CH | C—CF3 | CH | H | H | H | CF3CH2CO | 1 |
| 1-891 | C—CF3 | C—H | C—H | C—H | F | CF3 | CH | CH | C—CF3 | CH | H | H | H | CH3SOCH2CO | 1 |
| 1-892 | C—CF3 | C—H | C—H | C—H | F | CF3 | CH | CH | C—CF3 | CH | H | H | H | CH3S(O)CH2CO | 1 |
| 1-893 | C—CF3 | C—H | C—H | C—H | F | CF3 | CH | CH | C—CF3 | CH | H | H | H | CH3SO2CH2CO | 1 |
| 1-894 | C—CF3 | C—H | C—H | C—H | F | CF3 | CH | CH | C—CF3 | CH | H | H | H | CH3CH2NHCO | 1 |
| 1-895 | C—Cl | C—H | C—CF3 | C—H | H | CF3 | CH | CH | C—Cl | CH | H | H | H | nPrCO | 1 |
| 1-896 | C—Cl | C—H | C—CF3 | C—H | H | CF3 | CH | CH | C—Cl | CH | H | H | H | cyclo-PrCO | 1 |
| 1-897 | C—Cl | C—H | C—CF3 | C—H | H | CF3 | CH | CH | C—CH3 | CH | H | H | H | CH3CO | 1 |
| 1-898 | C—Cl | C—H | C—CF3 | C—H | H | CF3 | CH | CH | C—CH3 | CH | H | H | H | CH3CH2CO | 1 |
| 1-899 | C—Cl | C—H | C—CF3 | C—H | H | CF3 | CH | CH | C—CH3 | CH | H | H | H | nPrCO | 1 |
| 1-900 | C—Cl | C—H | C—CF3 | C—H | H | CF3 | CH | CH | C—CH3 | CH | H | H | H | cyclo-PrCO | 1 |
| 1-901 | C—Cl | C—H | C—CF3 | C—H | H | CF3 | CH | CH | C—CH3 | CH | H | H | H | cyclo-PrCH2CO | 1 |
| 1-902 | C—Cl | C—H | C—CF3 | C—H | H | CF3 | CH | CH | C—CH3 | CH | H | H | H | CF3CH2CO | 1 |
| 1-903 | C—Cl | C—H | C—CF3 | C—H | H | CF3 | CH | CH | C—CH3 | CH | H | H | H | CH3SCH2CO | 1 |
| 1-904 | C—Cl | C—H | C—CF3 | C—H | H | CF3 | CH | CH | C—CH3 | CH | H | H | H | CH3S(O)CH2CO | 1 |
| 1-905 | C—Cl | C—H | C—CF3 | C—H | H | CF3 | CH | CH | C—CH3 | CH | H | H | H | CH3SO2CH2CO | 1 |
| 1-906 | C—Cl | C—H | C—CF3 | C—H | H | CF3 | CH | CH | C—CH3 | CH | H | H | H | CH3CH2NHCO | 1 |

TABLE 1-continued

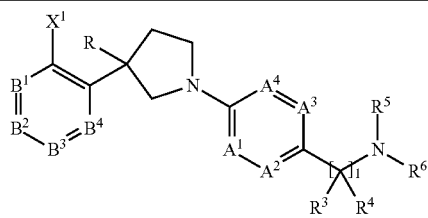

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-907 | C—Cl | C—H | C—CF3 | C—H | H | CF3 | CH | CH | C—CF3 | CH | H | H | H | CH3OCH2CH2CO | 1 |
| 1-908 | C—Cl | C—H | C—CF3 | C—H | H | CF3 | CH | CH | C—CF3 | CH | H | H | H | CH3CH2OCH2CH2CO | 1 |
| 1-909 | C—Cl | C—H | C—CF3 | C—H | H | CF3 | CH | CH | C—Cl | CH | H | H | H | CH3SCH2CO | 1 |
| 1-910 | C—Cl | C—H | C—CF3 | C—H | H | CF3 | CH | CH | C—Cl | CH | H | H | H | CH3S(O)CH2CO | 1 |
| 1-911 | C—Cl | C—H | C—CF3 | C—H | H | CF3 | CH | CH | C—Cl | CH | H | H | H | CH3SO2CH2CO | 1 |
| 1-912 | C—Cl | C—H | C—CF3 | C—H | H | CF3 | CH | CH | C—Br | CH | H | H | H | CH3CO | 1 |
| 1-913 | C—Cl | C—H | C—CF3 | C—H | H | CF3 | CH | CH | C—Br | CH | H | H | H | CH3CH2CO | 1 |
| 1-914 | C—Cl | C—H | C—CF3 | C—H | H | CF3 | CH | CH | C—Br | CH | H | H | H | nPrCO | 1 |
| 1-915 | C—Cl | C—H | C—CF3 | C—H | H | CF3 | CH | CH | C—Br | CH | H | H | H | cyclo-PrCO | 1 |
| 1-916 | C—Cl | C—H | C—CF3 | C—H | H | CF3 | CH | CH | C—Br | CH | H | H | H | cyclo-PrCH2CO | 1 |
| 1-917 | C—Cl | C—H | C—CF3 | C—H | H | CF3 | CH | CH | C—Br | CH | H | H | H | CF3CH2CO | 1 |
| 1-918 | C—Cl | C—H | C—CF3 | C—H | H | CF3 | CH | CH | C—Br | CH | H | H | H | CH3SCH2CO | 1 |
| 1-919 | C—Cl | C—H | C—CF3 | C—H | H | CF3 | CH | CH | C—Br | CH | H | H | H | CH3S(O)CH2CO | 1 |
| 1-920 | C—Cl | C—H | C—CF3 | C—H | H | CF3 | CH | CH | C—Br | CH | H | H | H | CH3SO2CH2CO | 1 |
| 1-921 | C—Cl | C—H | C—CF3 | C—H | H | CF3 | CH | CH | C—Br | CH | H | H | H | CH3CH2NHCO | 1 |
| 1-922 | C—Cl | C—H | C—CF3 | C—H | H | CF3 | CH | CH | C—CF3 | CH | H | H | H | nPrCO | 1 |
| 1-923 | C—Cl | C—H | C—CF3 | C—H | H | CF3 | CH | CH | C—CF3 | CH | H | H | H | cyclo-PrCO | 1 |
| 1-924 | C—Cl | C—H | C—CF3 | C—H | H | CF3 | CH | CH | C—CF3 | CH | H | H | H | CH3SCH2CO | 1 |
| 1-925 | C—Cl | C—H | C—CF3 | C—H | H | CF3 | CH | CH | C—CF3 | CH | H | H | H | CH3S(O)CH2CO | 1 |
| 1-926 | C—Cl | C—H | C—CF3 | C—H | H | CF3 | CH | CH | C—CF3 | CH | H | H | H | CH3SO2CH2CO | 1 |
| 1-927 | C—CF3 | C—H | C—CF3 | C—H | H | CF3 | CH | CH | C—F | CH | H | H | H | CH3CO | 1 |
| 1-928 | C—CF3 | C—H | C—CF3 | C—H | H | CF3 | CH | CH | C—F | CH | H | H | H | CH3CH2CO | 1 |
| 1-929 | C—CF3 | C—H | C—CF3 | C—H | H | CF3 | CH | CH | C—F | CH | H | H | H | nPrCO | 1 |
| 1-930 | C—CF3 | C—H | C—CF3 | C—H | H | CF3 | CH | CH | C—F | CH | H | H | H | cyclo-PrCO | 1 |
| 1-931 | C—CF3 | C—H | C—CF3 | C—H | H | CF3 | CH | CH | C—F | CH | H | H | H | cyclo-PrCH2CO | 1 |
| 1-932 | C—CF3 | C—H | C—CF3 | C—H | H | CF3 | CH | CH | C—F | CH | H | H | H | CF3CH2CO | 1 |
| 1-933 | C—CF3 | C—H | C—CF3 | C—H | H | CF3 | CH | CH | C—F | CH | H | H | H | CH3SCH2CO | 1 |
| 1-934 | C—CF3 | C—H | C—CF3 | C—H | H | CF3 | CH | CH | C—F | CH | H | H | H | CH3S(O)CH2CO | 1 |
| 1-935 | C—CF3 | C—H | C—CF3 | C—H | H | CF3 | CH | CH | C—F | CH | H | H | H | CH3SO2CH2CO | 1 |
| 1-936 | C—CF3 | C—H | C—CF3 | C—H | H | CF3 | CH | CH | C—F | CH | H | H | H | CH3CH2NHCO | 1 |
| 1-937 | C—CF3 | C—H | C—CF3 | C—H | H | CF3 | CH | CH | C—Cl | CH | H | H | H | nPrCO | 1 |
| 1-938 | C—CF3 | C—H | C—CF3 | C—H | H | CF3 | CH | CH | C—Cl | CH | H | H | H | cyclo-PrCH2CO | 1 |
| 1-939 | C—CF3 | C—H | C—CF3 | C—H | H | CF3 | CH | CH | C—Cl | CH | H | H | H | CH3SCH2CO | 1 |
| 1-940 | C—CF3 | C—H | C—CF3 | C—H | H | CF3 | CH | CH | C—Cl | CH | H | H | H | CH3S(O)CH2CO | 1 |
| 1-941 | C—CF3 | C—H | C—CF3 | C—H | H | CF3 | CH | CH | C—Cl | CH | H | H | H | CH3SO2CH2CO | 1 |

TABLE 1-continued

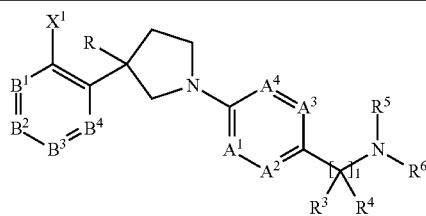

| Ex.-No. | $B^1$ | $B^2$ | $B^3$ | $B^4$ | $X^1$ | R | $A^1$ | $A^2$ | $A^3$ | $A^4$ | $R^3$ | $R^4$ | $R^5$ | $R^6$ | 1 |
|---|---|---|---|---|---|---|---|---|---|---|---|---|---|---|---|
| 1-942 | C—CF3 | C—H | C—CF3 | C—H | H | CF3 | CH | CH | C—Cl | CH | H | H | H | CH3CH2NHCO | 1 |
| 1-943 | C—CF3 | C—H | C—CF3 | C—H | H | CF3 | CH | CH | C—Br | CH | H | H | H | nPrCO | 1 |
| 1-944 | C—CF3 | C—H | C—CF3 | C—H | H | CF3 | CH | CH | C—Br | CH | H | H | H | cyclo-PrCH2CO | 1 |
| 1-945 | C—CF3 | C—H | C—CF3 | C—H | H | CF3 | CH | CH | C—Br | CH | H | H | H | CH3SCH2CO | 1 |
| 1-946 | C—CF3 | C—H | C—CF3 | C—H | H | CF3 | CH | CH | C—Br | CH | H | H | H | CH3S(O)CH2CO | 1 |
| 1-947 | C—CF3 | C—H | C—CF3 | C—H | H | CF3 | CH | CH | C—Br | CH | H | H | H | CH3SO2CH2CO | 1 |
| 1-948 | C—CF3 | C—H | C—CF3 | C—H | H | CF3 | CH | CH | C—Br | CH | H | H | H | CH3CH2NHCO | 1 |
| 1-949 | C—CF3 | C—H | C—CF3 | C—H | H | CF3 | CH | CH | C—CH3 | CH | H | H | H | CH3CO | 1 |
| 1-950 | C—CF3 | C—H | C—CF3 | C—H | H | CF3 | CH | CH | C—CH3 | CH | H | H | H | CH3CH2CO | 1 |
| 1-951 | C—CF3 | C—H | C—CF3 | C—H | H | CF3 | CH | CH | C—CH3 | CH | H | H | H | nPrCO | 1 |
| 1-952 | C—CF3 | C—H | C—CF3 | C—H | H | CF3 | CH | CH | C—CH3 | CH | H | H | H | cyclo-PrCO | 1 |
| 1-953 | C—CF3 | C—H | C—CF3 | C—H | H | CF3 | CH | CH | C—CH3 | CH | H | H | H | cyclo-PrCH2CO | 1 |
| 1-954 | C—CF3 | C—H | C—CF3 | C—H | H | CF3 | CH | CH | C—CH3 | CH | H | H | H | CF3CH2CO | 1 |
| 1-955 | C—CF3 | C—H | C—CF3 | C—H | H | CF3 | CH | CH | C—CH3 | CH | H | H | H | CH3SCH2CO | 1 |
| 1-956 | C—CF3 | C—H | C—CF3 | C—H | H | CF3 | CH | CH | C—CH3 | CH | H | H | H | CH3S(O)CH2CO | 1 |
| 1-957 | C—CF3 | C—H | C—CF3 | C—H | H | CF3 | CH | CH | C—CH3 | CH | H | H | H | CH3SO2CH2CO | 1 |
| 1-958 | C—CF3 | C—H | C—CF3 | C—H | H | CF3 | CH | CH | C—CH3 | CH | H | H | H | CH3CH2NHCO | 1 |
| 1-959 | C—CF3 | C—H | C—CF3 | C—H | H | CF3 | CH | CH | C-cyclo-Pr | CH | H | H | H | CH3CH2CO | 1 |
| 1-960 | C—CF3 | C—H | C—CF3 | C—H | H | CF3 | CH | CH | C-cyclo-Pr | CH | H | H | H | CF3CH2CO | 1 |
| 1-961 | C—CF3 | C—H | C—CF3 | C—H | H | CF3 | CH | CH | C—CF3 | CH | H | H | H | nPrCO | 1 |
| 1-962 | C—CF3 | C—H | C—CF3 | C—H | H | CF3 | CH | CH | C—CF3 | CH | H | H | H | cyclo-PrCH2CO | 1 |
| 1-963 | C—CF3 | C—H | C—CF3 | C—H | H | CF3 | CH | CH | C—CF3 | CH | H | H | H | CH3C(O)CH2CO | 1 |
| 1-964 | C—CF3 | C—H | C—CF3 | C—H | H | CF3 | CH | CH | C—CF3 | CH | H | H | H | CH3OCH2CH2CO | 1 |
| 1-965 | C—CF3 | C—H | C—CF3 | C—H | H | CF3 | CH | CH | C—CF3 | CH | H | H | H | CH3CH2OCH2CH2CO | 1 |
| 1-966 | C—CF3 | C—H | C—CF3 | C—H | H | CF3 | CH | CH | C—CF3 | CH | H | H | H | CH3SCH2CO | 1 |
| 1-967 | C—CF3 | C—H | C—CF3 | C—H | H | CF3 | CH | CH | C—CF3 | CH | H | H | H | CH3S(O)CH2CO | 1 |
| 1-968 | C—CF3 | C—H | C—CF3 | C—H | H | CF3 | CH | CH | C—CF3 | CH | H | H | H | CH3SO2CH2CO | 1 |
| 1-969 | C—CF3 | C—H | C—CF3 | C—H | H | CF3 | CH | CH | C—CF3 | CH | H | H | H | (Allyl)SCH2CO | 1 |
| 1-970 | C—CF3 | C—H | C—CF3 | C—H | H | CF3 | CH | CH | C—CF3 | CH | H | H | H | (Allyl)S(O)CH2CO | 1 |
| 1-971 | C—CF3 | C—H | C—CF3 | C—H | H | CF3 | CH | CH | C—CF3 | CH | H | H | H | (Allyl)SO2CH2CO | 1 |
| 1-972 | C—CF3 | C—H | C—CF3 | C—H | H | CF3 | CH | CH | C—CN | CH | H | H | H | CH3CO | 1 |
| 1-973 | C—CF3 | C—H | C—CF3 | C—H | H | CF3 | CH | CH | C—CN | CH | H | H | H | CH3CH2CO | 1 |
| 1-974 | C—CF3 | C—H | C—CF3 | C—H | H | CF3 | CH | CH | C—CN | CH | H | H | H | nPrCO | 1 |
| 1-975 | C—CF3 | C—H | C—CF3 | C—H | H | CF3 | CH | CH | C—CN | CH | H | H | H | cyclo-PrCO | 1 |
| 1-976 | C—CF3 | C—H | C—CF3 | C—H | H | CF3 | CH | CH | C—CN | CH | H | H | H | cyclo-PrCH2CO | 1 |

TABLE 1-continued

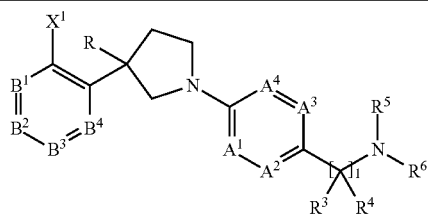

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-977 | C—CF3 | C—H | C—CF3 | C—H | H | CF3 | CH | CH | C—CN | CH | H | H | H | CF3CH2CO | 1 |
| 1-978 | C—CF3 | C—H | C—CF3 | C—H | H | CF3 | CH | CH | C—CN | CH | H | H | H | CH3SCH2CO | 1 |
| 1-979 | C—CF3 | C—H | C—CF3 | C—H | H | CF3 | CH | CH | C—CN | CH | H | H | H | CH3S(O)CH2CO | 1 |
| 1-980 | C—CF3 | C—H | C—CF3 | C—H | H | CF3 | CH | CH | C—CN | CH | H | H | H | CH3SO2CH2CO | 1 |
| 1-981 | C—CF3 | C—H | C—CF3 | C—H | H | CF3 | CH | CH | C—CN | CH | H | H | H | CH3CH2NHCO | 1 |
| 1-982 | C—CF3 | C—H | C—CF3 | C—H | H | CF3 | CH | CH | C—SCH3 | CH | H | H | H | CH3CO | 1 |
| 1-983 | C—CF3 | C—H | C—CF3 | C—H | H | CF3 | CH | CH | C—SCH3 | CH | H | H | H | CH3CH2CO | 1 |
| 1-984 | C—CF3 | C—H | C—CF3 | C—H | H | CF3 | CH | CH | C—SCH3 | CH | H | H | H | cyclo-PrCO | 1 |
| 1-985 | C—CF3 | C—H | C—CF3 | C—H | H | CF3 | CH | CH | C—SCH3 | CH | H | H | H | CF3CH2CO | 1 |
| 1-986 | C—CF3 | C—H | C—CF3 | C—H | H | CF3 | CH | CH | C—S(O)CH3 | CH | H | H | H | CH3CO | 1 |
| 1-987 | C—CF3 | C—H | C—CF3 | C—H | H | CF3 | CH | CH | C—S(O)CH3 | CH | H | H | H | CH3CH2CO | 1 |
| 1-988 | C—CF3 | C—H | C—CF3 | C—H | H | CF3 | CH | CH | C—S(O)CH3 | CH | H | H | H | cyclo-PrCO | 1 |
| 1-989 | C—CF3 | C—H | C—CF3 | C—H | H | CF3 | CH | CH | C—S(O)CH3 | CH | H | H | H | CF3CH2CO | 1 |
| 1-990 | C—CF3 | C—H | C—CF3 | C—H | H | CF3 | CH | CH | C—S(O)CH3 | CH | H | H | H | CH3SCH2CO | 1 |
| 1-991 | C—CF3 | C—H | C—CF3 | C—H | H | CF3 | CH | CH | C—SO2CH3 | CH | H | H | H | CH3CO | 1 |
| 1-992 | C—CF3 | C—H | C—CF3 | C—H | H | CF3 | CH | CH | C—SO2CH3 | CH | H | H | H | CH3CH2CO | 1 |
| 1-993 | C—CF3 | C—H | C—CF3 | C—H | H | CF3 | CH | CH | C—SO2CH3 | CH | H | H | H | cyclo-PrCO | 1 |
| 1-994 | C—CF3 | C—H | C—CF3 | C—H | H | CF3 | CH | CH | C—SO2CH3 | CH | H | H | H | CF3CH2CO | 1 |
| 1-995 | C—CF3 | C—H | C—CF3 | C—H | H | CF3 | CH | CH | C—SCF3 | CH | H | H | H | CH3CO | 1 |
| 1-996 | C—CF3 | C—H | C—CF3 | C—H | H | CF3 | CH | CH | C—SCF3 | CH | H | H | H | CH3CH2CO | 1 |
| 1-997 | C—CF3 | C—H | C—CF3 | C—H | H | CF3 | CH | CH | C—SCF3 | CH | H | H | H | nPrCO | 1 |
| 1-998 | C—CF3 | C—H | C—CF3 | C—H | H | CF3 | CH | CH | C—SCF3 | CH | H | H | H | cyclo-PrCO | 1 |
| 1-999 | C—CF3 | C—H | C—CF3 | C—H | H | CF3 | CH | CH | C—SCF3 | CH | H | H | H | cyclo-PrCH2CO | 1 |
| 1-1000 | C—CF3 | C—H | C—CF3 | C—H | H | CF3 | CH | CH | C—SCF3 | CH | H | H | H | CF3CH2CO | 1 |
| 1-1001 | C—CF3 | C—H | C—CF3 | C—H | H | CF3 | CH | CH | C—SCF3 | CH | H | H | H | CH3SCH2CO | 1 |
| 1-1002 | C—CF3 | C—H | C—CF3 | C—H | H | CF3 | CH | CH | C—SCF3 | CH | H | H | H | CH3S(O)CH2CO | 1 |
| 1-1003 | C—CF3 | C—H | C—CF3 | C—H | H | CF3 | CH | CH | C—SCF3 | CH | H | H | H | CH3SO2CH2CO | 1 |
| 1-1004 | C—CF3 | C—H | C—CF3 | C—H | H | CF3 | CH | CH | C—SCF3 | CH | H | H | H | CH3CH2NHCO | 1 |
| 1-1005 | C—CF3 | C—H | C—CF3 | C—H | H | CF3 | CH | CH | C—S(O)CF3 | CH | H | H | H | CH3CO | 1 |
| 1-1006 | C—CF3 | C—H | C—CF3 | C—H | H | CF3 | CH | CH | C—S(O)CF3 | CH | H | H | H | CH3CH2CO | 1 |
| 1-1007 | C—CF3 | C—H | C—CF3 | C—H | H | CF3 | CH | CH | C—S(O)CF3 | CH | H | H | H | nPrCO | 1 |
| 1-1008 | C—CF3 | C—H | C—CF3 | C—H | H | CF3 | CH | CH | C—S(O)CF3 | CH | H | H | H | cyclo-PrCO | 1 |
| 1-1009 | C—CF3 | C—H | C—CF3 | C—H | H | CF3 | CH | CH | C—S(O)CF3 | CH | H | H | H | cyclo-PrCH2CO | 1 |
| 1-1010 | C—CF3 | C—H | C—CF3 | C—H | H | CF3 | CH | CH | C—S(O)CF3 | CH | H | H | H | CF3CH2CO | 1 |
| 1-1011 | C—CF3 | C—H | C—CF3 | C—H | H | CF3 | CH | CH | C—S(O)CF3 | CH | H | H | H | CH3SCH2CO | 1 |

TABLE 1-continued

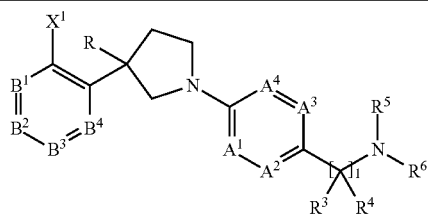

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1012 | C—CF3 | C—H | C—CF3 | C—H | H | CF3 | CH | CH | C—S(O)CF3 | CH | H | H | H | CH3S(O)CH2CO | 1 |
| 1-1013 | C—CF3 | C—H | C—CF3 | C—H | H | CF3 | CH | CH | C—S(O)CF3 | CH | H | H | H | CH3SO2CH2CO | 1 |
| 1-1014 | C—CF3 | C—H | C—CF3 | C—H | H | CF3 | CH | CH | C—S(O)CF3 | CH | H | H | H | CH3CH2NHCO | 1 |
| 1-1015 | C—CF3 | C—H | C—CF3 | C—H | H | CF3 | CH | CH | C—SO2CF3 | CH | H | H | H | CH3CO | 1 |
| 1-1016 | C—CF3 | C—H | C—CF3 | C—H | H | CF3 | CH | CH | C—SO2CF3 | CH | H | H | H | CH3CH2CO | 1 |
| 1-1017 | C—CF3 | C—H | C—CF3 | C—H | H | CF3 | CH | CH | C—SO2CF3 | CH | H | H | H | nPrCO | 1 |
| 1-1018 | C—CF3 | C—H | C—CF3 | C—H | H | CF3 | CH | CH | C—SO2CF3 | CH | H | H | H | cyclo-PrCO | 1 |
| 1-1019 | C—CF3 | C—H | C—CF3 | C—H | H | CF3 | CH | CH | C—SO2CF3 | CH | H | H | H | cyclo-PrCH2CO | 1 |
| 1-1020 | C—CF3 | C—H | C—CF3 | C—H | H | CF3 | CH | CH | C—SO2CF3 | CH | H | H | H | CF3CH2CO | 1 |
| 1-1021 | C—CF3 | C—H | C—CF3 | C—H | H | CF3 | CH | CH | C—SO2CF3 | CH | H | H | H | CH3SCH2CO | 1 |
| 1-1022 | C—CF3 | C—H | C—CF3 | C—H | H | CF3 | CH | CH | C—SO2CF3 | CH | H | H | H | CH3S(O)CH2CO | 1 |
| 1-1023 | C—CF3 | C—H | C—CF3 | C—H | H | CF3 | CH | CH | C—SO2CF3 | CH | H | H | H | CH3SO2CH2CO | 1 |
| 1-1024 | C—CF3 | C—H | C—CF3 | C—H | H | CF3 | CH | CH | C—SO2CF3 | CH | H | H | H | CH3CH2NHCO | 1 |
| 1-1025 | C—Cl | C—Cl | C—CF3 | C—H | H | CF3 | CH | CH | C—Cl | CH | H | H | H | nPrCO | 1 |
| 1-1026 | C—Cl | C—Cl | C—CF3 | C—H | H | CF3 | CH | CH | C—Cl | CH | H | H | H | cyclo-PrCO | 1 |
| 1-1027 | C—Cl | C—Cl | C—CF3 | C—H | H | CF3 | CH | CH | C—Cl | CH | H | H | H | CH3SCH2CO | 1 |
| 1-1028 | C—Cl | C—Cl | C—CF3 | C—H | H | CF3 | CH | CH | C—Cl | CH | H | H | H | CH3S(O)CH2CO | 1 |
| 1-1029 | C—Cl | C—Cl | C—CF3 | C—H | H | CF3 | CH | CH | C—Cl | CH | H | H | H | CH3SO2CH2CO | 1 |
| 1-1030 | C—Cl | C—Cl | C—CF3 | C—H | H | CF3 | CH | CH | C—Br | CH | H | H | H | CH3CO | 1 |
| 1-1031 | C—Cl | C—Cl | C—CF3 | C—H | H | CF3 | CH | CH | C—Br | CH | H | H | H | CH3CH2CO | 1 |
| 1-1032 | C—Cl | C—Cl | C—CF3 | C—H | H | CF3 | CH | CH | C—Br | CH | H | H | H | nPrCO | 1 |
| 1-1033 | C—Cl | C—Cl | C—CF3 | C—H | H | CF3 | CH | CH | C—Br | CH | H | H | H | cyclo-PrCO | 1 |
| 1-1034 | C—Cl | C—Cl | C—CF3 | C—H | H | CF3 | CH | CH | C—Br | CH | H | H | H | cyclo-PrCH2CO | 1 |
| 1-1035 | C—Cl | C—Cl | C—CF3 | C—H | H | CF3 | CH | CH | C—Br | CH | H | H | H | CF3CH2CO | 1 |
| 1-1036 | C—Cl | C—Cl | C—CF3 | C—H | H | CF3 | CH | CH | C—Br | CH | H | H | H | CH3SCH2CO | 1 |
| 1-1037 | C—Cl | C—Cl | C—CF3 | C—H | H | CF3 | CH | CH | C—Br | CH | H | H | H | CH3S(O)CH2CO | 1 |
| 1-1038 | C—Cl | C—Cl | C—CF3 | C—H | H | CF3 | CH | CH | C—Br | CH | H | H | H | CH3SO2CH2CO | 1 |
| 1-1039 | C—Cl | C—Cl | C—CF3 | C—H | H | CF3 | CH | CH | C—Br | CH | H | H | H | CH3CH2NHCO | 1 |
| 1-1040 | C—Cl | C—Cl | C—CF3 | C—H | H | CF3 | CH | CH | C—CF3 | CH | H | H | H | nPrCO | 1 |
| 1-1041 | C—Cl | C—Cl | C—CF3 | C—H | H | CF3 | CH | CH | C—CF3 | CH | H | H | H | cyclo-PrCO | 1 |
| 1-1042 | C—Cl | C—Cl | C—CF3 | C—H | H | CF3 | CH | CH | C—CF3 | CH | H | H | H | CH3SCH2CO | 1 |
| 1-1043 | C—Cl | C—Cl | C—CF3 | C—H | H | CF3 | CH | CH | C—CF3 | CH | H | H | H | CH3S(O)CH2CO | 1 |
| 1-1044 | C—Cl | C—Cl | C—CF3 | C—H | H | CF3 | CH | CH | C—CF3 | CH | H | H | H | CH3SO2CH2CO | 1 |
| 1-1045 | C—Cl | N | C—Cl | C—H | H | CF3 | CH | CH | C—Cl | CH | H | H | H | CH3CO | 1 |
| 1-1046 | C—Cl | N | C—Cl | C—H | H | CF3 | CH | CH | C—Cl | CH | H | H | H | CH3CH2CO | 1 |

TABLE 1-continued

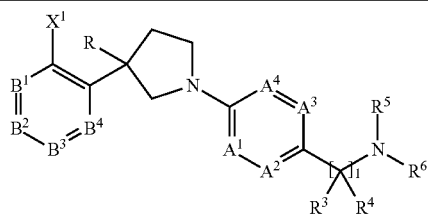

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1047 | C—Cl | N | C—Cl | C—H | H | CF3 | CH | CH | C—Cl | CH | H | H | H | nPrCO | 1 |
| 1-1048 | C—Cl | N | C—Cl | C—H | H | CF3 | CH | CH | C—Cl | CH | H | H | H | cyclo-PrCO | 1 |
| 1-1049 | C—Cl | N | C—Cl | C—H | H | CF3 | CH | CH | C—Cl | CH | H | H | H | cyclo-PrCH2CO | 1 |
| 1-1050 | C—Cl | N | C—Cl | C—H | H | CF3 | CH | CH | C—Cl | CH | H | H | H | CF3CH2CO | 1 |
| 1-1051 | C—Cl | N | C—Cl | C—H | H | CF3 | CH | CH | C—Cl | CH | H | H | H | CH3SCH2CO | 1 |
| 1-1052 | C—Cl | N | C—Cl | C—H | H | CF3 | CH | CH | C—Cl | CH | H | H | H | CH3S(O)CH2CO | 1 |
| 1-1053 | C—Cl | N | C—Cl | C—H | H | CF3 | CH | CH | C—Cl | CH | H | H | H | CH3SO2CH2CO | 1 |
| 1-1054 | C—Cl | N | C—Cl | C—H | H | CF3 | CH | CH | C—Cl | CH | H | H | H | CH3CH2NHCO | 1 |
| 1-1055 | C—Cl | N | C—Cl | C—H | H | CF3 | CH | CH | C—Br | CH | H | H | H | CH3CO | 1 |
| 1-1056 | C—Cl | N | C—Cl | C—H | H | CF3 | CH | CH | C—Br | CH | H | H | H | CH3CH2CO | 1 |
| 1-1057 | C—Cl | N | C—Cl | C—H | H | CF3 | CH | CH | C—Br | CH | H | H | H | nPrCO | 1 |
| 1-1058 | C—Cl | N | C—Cl | C—H | H | CF3 | CH | CH | C—Br | CH | H | H | H | cyclo-PrCO | 1 |
| 1-1059 | C—Cl | N | C—Cl | C—H | H | CF3 | CH | CH | C—Br | CH | H | H | H | cyclo-PrCH2CO | 1 |
| 1-1060 | C—Cl | N | C—Cl | C—H | H | CF3 | CH | CH | C—Br | CH | H | H | H | CF3CH2CO | 1 |
| 1-1061 | C—Cl | N | C—Cl | C—H | H | CF3 | CH | CH | C—Br | CH | H | H | H | CH3SCH2CO | 1 |
| 1-1062 | C—Cl | N | C—Cl | C—H | H | CF3 | CH | CH | C—Br | CH | H | H | H | CH3S(O)CH2CO | 1 |
| 1-1063 | C—Cl | N | C—Cl | C—H | H | CF3 | CH | CH | C—Br | CH | H | H | H | CH3SO2CH2CO | 1 |
| 1-1064 | C—Cl | N | C—Cl | C—H | H | CF3 | CH | CH | C—Br | CH | H | H | H | CH3CH2NHCO | 1 |
| 1-1065 | C—Cl | N | C—Cl | C—H | H | CF3 | CH | CH | C—CF3 | CH | H | H | H | CH3CO | 1 |
| 1-1066 | C—Cl | N | C—Cl | C—H | H | CF3 | CH | CH | C—CF3 | CH | H | H | H | CH3CH2CO | 1 |
| 1-1067 | C—Cl | N | C—Cl | C—H | H | CF3 | CH | CH | C—CF3 | CH | H | H | H | nPrCO | 1 |
| 1-1068 | C—Cl | N | C—Cl | C—H | H | CF3 | CH | CH | C—CF3 | CH | H | H | H | cyclo-PrCO | 1 |
| 1-1069 | C—Cl | N | C—Cl | C—H | H | CF3 | CH | CH | C—CF3 | CH | H | H | H | cyclo-PrCH2CO | 1 |
| 1-1070 | C—Cl | N | C—Cl | C—H | H | CF3 | CH | CH | C—CF3 | CH | H | H | H | CF3CH2CO | 1 |
| 1-1071 | C—Cl | N | C—Cl | C—H | H | CF3 | CH | CH | C—CF3 | CH | H | H | H | CH3SCH2CO | 1 |
| 1-1072 | C—Cl | N | C—Cl | C—H | H | CF3 | CH | CH | C—CF3 | CH | H | H | H | CH3S(O)CH2CO | 1 |
| 1-1073 | C—Cl | N | C—Cl | C—H | H | CF3 | CH | CH | C—CF3 | CH | H | H | H | CH3SO2CH2CO | 1 |
| 1-1074 | C—Cl | N | C—Cl | C—H | H | CF3 | CH | CH | C—CF3 | CH | H | H | H | CH3CH2NHCO | 1 |
| 1-1075 | C—CF3 | N | C—H | C—H | H | CF3 | CH | CH | C—CF3 | CH | H | H | H | CH3CO | 1 |
| 1-1076 | C—CF3 | N | C—H | C—H | H | CF3 | CH | CH | C—CF3 | CH | H | H | H | CH3CH2CO | 1 |
| 1-1077 | C—CF3 | N | C—H | C—H | H | CF3 | CH | CH | C—CF3 | CH | H | H | H | nPrCO | 1 |
| 1-1078 | C—CF3 | N | C—H | C—H | H | CF3 | CH | CH | C—CF3 | CH | H | H | H | cyclo-PrCO | 1 |
| 1-1079 | C—CF3 | N | C—H | C—H | H | CF3 | CH | CH | C—CF3 | CH | H | H | H | cyclo-PrCH2CO | 1 |
| 1-1080 | C—CF3 | N | C—H | C—H | H | CF3 | CH | CH | C—CF3 | CH | H | H | H | CF3CH2CO | 1 |
| 1-1081 | C—CF3 | N | C—H | C—H | H | CF3 | CH | CH | C—CF3 | CH | H | H | H | CH3SCH2CO | 1 |

TABLE 1-continued

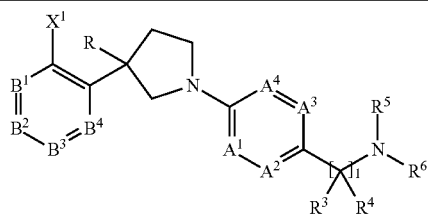

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1082 | C—CF3 | N | C—H | C—H | H | CF3 | CH | CH | C—CF3 | CH | H | H | H | CH3S(O)CH2CO | 1 |
| 1-1083 | C—CF3 | N | C—H | C—H | H | CF3 | CH | CH | C—CF3 | CH | H | H | H | CH3SO2CH2CO | 1 |
| 1-1084 | C—CF3 | N | C—H | C—H | H | CF3 | CH | CH | C—CF3 | CH | H | H | H | CH3CH2NHCO | 1 |
| 1-1085 | C—CF3 | C—H | C—H | N | H | CF3 | CH | CH | C—CF3 | CH | H | H | H | CH3CO | 1 |
| 1-1086 | C—CF3 | C—H | C—H | N | H | CF3 | CH | CH | C—CF3 | CH | H | H | H | CH3CH2CO | 1 |
| 1-1087 | C—CF3 | C—H | C—H | N | H | CF3 | CH | CH | C—CF3 | CH | H | H | H | nPrCO | 1 |
| 1-1088 | C—CF3 | C—H | C—H | N | H | CF3 | CH | CH | C—CF3 | CH | H | H | H | cyclo-PrCO | 1 |
| 1-1089 | C—CF3 | C—H | C—H | N | H | CF3 | CH | CH | C—CF3 | CH | H | H | H | cyclo-PrCH2CO | 1 |
| 1-1090 | C—CF3 | C—H | C—H | N | H | CF3 | CH | CH | C—CF3 | CH | H | H | H | CF3CH2CO | 1 |
| 1-1091 | C—CF3 | C—H | C—H | N | H | CF3 | CH | CH | C—CF3 | CH | H | H | H | CH3SCH2CO | 1 |
| 1-1092 | C—CF3 | C—H | C—H | N | H | CF3 | CH | CH | C—CF3 | CH | H | H | H | CH3S(O)CH2CO | 1 |
| 1-1093 | C—CF3 | C—H | C—H | N | H | CF3 | CH | CH | C—CF3 | CH | H | H | H | CH3SO2CH2CO | 1 |
| 1-1094 | C—CF3 | C—H | C—H | N | H | CF3 | CH | CH | C—CF3 | CH | H | H | H | CH3CH2NHCO | 1 |
| 1-1095 | C—H | C—H | C—CF3 | N | H | CF3 | CH | CH | C—CF3 | CH | H | H | H | CH3CO | 1 |
| 1-1096 | C—H | C—H | C—CF3 | N | H | CF3 | CH | CH | C—CF3 | CH | H | H | H | CH3CH2CO | 1 |
| 1-1097 | C—H | C—H | C—CF3 | N | H | CF3 | CH | CH | C—CF3 | CH | H | H | H | nPrCO | 1 |
| 1-1098 | C—H | C—H | C—CF3 | N | H | CF3 | CH | CH | C—CF3 | CH | H | H | H | cyclo-PrCO | 1 |
| 1-1099 | C—H | C—H | C—CF3 | N | H | CF3 | CH | CH | C—CF3 | CH | H | H | H | cyclo-PrCH2CO | 1 |
| 1-1100 | C—H | C—H | C—CF3 | N | H | CF3 | CH | CH | C—CF3 | CH | H | H | H | CF3CH2CO | 1 |
| 1-1101 | C—H | C—H | C—CF3 | N | H | CF3 | CH | CH | C—CF3 | CH | H | H | H | CH3SCH2CO | 1 |
| 1-1102 | C—H | C—H | C—CF3 | N | H | CF3 | CH | CH | C—CF3 | CH | H | H | H | CH3S(O)CH2CO | 1 |
| 1-1103 | C—H | C—H | C—CF3 | N | H | CF3 | CH | CH | C—CF3 | CH | H | H | H | CH3SO2CH2CO | 1 |
| 1-1104 | C—H | C—H | C—CF3 | N | H | CF3 | CH | CH | C—CF3 | CH | H | H | H | CH3CH2NHCO | 1 |
| 1-1105 | C—CF3 | N | C—CF3 | C—H | H | CF3 | CH | CH | C—Cl | CH | H | H | H | CH3CO | 1 |
| 1-1106 | C—CF3 | N | C—CF3 | C—H | H | CF3 | CH | CH | C—Cl | CH | H | H | H | CH3CH2CO | 1 |
| 1-1107 | C—CF3 | N | C—CF3 | C—H | H | CF3 | CH | CH | C—Cl | CH | H | H | H | nPrCO | 1 |
| 1-1108 | C—CF3 | N | C—CF3 | C—H | H | CF3 | CH | CH | C—Cl | CH | H | H | H | cyclo-PrCO | 1 |
| 1-1109 | C—CF3 | N | C—CF3 | C—H | H | CF3 | CH | CH | C—Cl | CH | H | H | H | cyclo-PrCH2CO | 1 |
| 1-1110 | C—CF3 | N | C—CF3 | C—H | H | CF3 | CH | CH | C—Cl | CH | H | H | H | CF3CH2CO | 1 |
| 1-1111 | C—CF3 | N | C—CF3 | C—H | H | CF3 | CH | CH | C—Cl | CH | H | H | H | CH3SCH2CO | 1 |
| 1-1112 | C—CF3 | N | C—CF3 | C—H | H | CF3 | CH | CH | C—Cl | CH | H | H | H | CH3S(O)CH2CO | 1 |
| 1-1113 | C—CF3 | N | C—CF3 | C—H | H | CF3 | CH | CH | C—Cl | CH | H | H | H | CH3SO2CH2CO | 1 |
| 1-1114 | C—CF3 | N | C—CF3 | C—H | H | CF3 | CH | CH | C—Cl | CH | H | H | H | CH3CH2NHCO | 1 |
| 1-1115 | C—CF3 | N | C—CF3 | C—H | H | CF3 | CH | CH | C—Br | CH | H | H | H | CH3CO | 1 |
| 1-1116 | C—CF3 | N | C—CF3 | C—H | H | CF3 | CH | CH | C—Br | CH | H | H | H | CH3CH2CO | 1 |

TABLE 1-continued

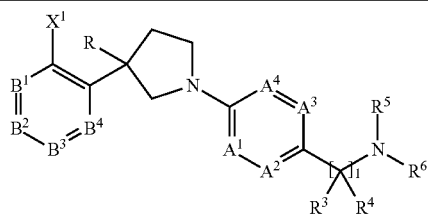

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1117 | C—CF3 | N | C—CF3 | C—H | H | CF3 | CH | CH | C—Br | CH | H | H | H | nPrCO | 1 |
| 1-1118 | C—CF3 | N | C—CF3 | C—H | H | CF3 | CH | CH | C—Br | CH | H | H | H | cyclo-PrCO | 1 |
| 1-1119 | C—CF3 | N | C—CF3 | C—H | H | CF3 | CH | CH | C—Br | CH | H | H | H | cyclo-PrCH2CO | 1 |
| 1-1120 | C—CF3 | N | C—CF3 | C—H | H | CF3 | CH | CH | C—Br | CH | H | H | H | CF3CH2CO | 1 |
| 1-1121 | C—CF3 | N | C—CF3 | C—H | H | CF3 | CH | CH | C—Br | CH | H | H | H | CH3SCH2CO | 1 |
| 1-1122 | C—CF3 | N | C—CF3 | C—H | H | CF3 | CH | CH | C—Br | CH | H | H | H | CH3S(O)CH2CO | 1 |
| 1-1123 | C—CF3 | N | C—CF3 | C—H | H | CF3 | CH | CH | C—Br | CH | H | H | H | CH3SO2CH2CO | 1 |
| 1-1124 | C—CF3 | N | C—CF3 | C—H | H | CF3 | CH | CH | C—Br | CH | H | H | H | CH3CH2NHCO | 1 |
| 1-1125 | C—CF3 | N | C—CF3 | C—H | H | CF3 | CH | CH | C—CF3 | CH | H | H | H | CH3CO | 1 |
| 1-1126 | C—CF3 | N | C—CF3 | C—H | H | CF3 | CH | CH | C—CF3 | CH | H | H | H | CH3CH2CO | 1 |
| 1-1127 | C—CF3 | N | C—CF3 | C—H | H | CF3 | CH | CH | C—CF3 | CH | H | H | H | nPrCO | 1 |
| 1-1128 | C—CF3 | N | C—CF3 | C—H | H | CF3 | CH | CH | C—CF3 | CH | H | H | H | cyclo-PrCO | 1 |
| 1-1129 | C—CF3 | N | C—CF3 | C—H | H | CF3 | CH | CH | C—CF3 | CH | H | H | H | cyclo-PrCH2CO | 1 |
| 1-1130 | C—CF3 | N | C—CF3 | C—H | H | CF3 | CH | CH | C—CF3 | CH | H | H | H | CF3CH2CO | 1 |
| 1-1131 | C—CF3 | N | C—CF3 | C—H | H | CF3 | CH | CH | C—CF3 | CH | H | H | H | CH3SCH2CO | 1 |
| 1-1132 | C—CF3 | N | C—CF3 | C—H | H | CF3 | CH | CH | C—CF3 | CH | H | H | H | CH3S(O)CH2CO | 1 |
| 1-1133 | C—CF3 | N | C—CF3 | C—H | H | CF3 | CH | CH | C—CF3 | CH | H | H | H | CH3SO2CH2CO | 1 |
| 1-1134 | C—CF3 | N | C—CF3 | C—H | H | CF3 | CH | CH | C—CF3 | CH | H | H | H | CH3CH2NHCO | 1 |
| 1-1135 | C—CF3 | C—H | C—CF3 | N | H | CF3 | CH | CH | C—Cl | CH | H | H | H | CH3CO | 1 |
| 1-1136 | C—CF3 | C—H | C—CF3 | N | H | CF3 | CH | CH | C—Cl | CH | H | H | H | CH3CH2CO | 1 |
| 1-1137 | C—CF3 | C—H | C—CF3 | N | H | CF3 | CH | CH | C—Cl | CH | H | H | H | nPrCO | 1 |
| 1-1138 | C—CF3 | C—H | C—CF3 | N | H | CF3 | CH | CH | C—Cl | CH | H | H | H | cyclo-PrCO | 1 |
| 1-1139 | C—CF3 | C—H | C—CF3 | N | H | CF3 | CH | CH | C—Cl | CH | H | H | H | cyclo-PrCH2CO | 1 |
| 1-1140 | C—CF3 | C—H | C—CF3 | N | H | CF3 | CH | CH | C—Cl | CH | H | H | H | CF3CH2CO | 1 |
| 1-1141 | C—CF3 | C—H | C—CF3 | N | H | CF3 | CH | CH | C—Cl | CH | H | H | H | CH3SCH2CO | 1 |
| 1-1142 | C—CF3 | C—H | C—CF3 | N | H | CF3 | CH | CH | C—Cl | CH | H | H | H | CH3S(O)CH2CO | 1 |
| 1-1143 | C—CF3 | C—H | C—CF3 | N | H | CF3 | CH | CH | C—Cl | CH | H | H | H | CH3SO2CH2CO | 1 |
| 1-1144 | C—CF3 | C—H | C—CF3 | N | H | CF3 | CH | CH | C—Cl | CH | H | H | H | CH3CH2NHCO | 1 |
| 1-1145 | C—CF3 | C—H | C—CF3 | N | H | CF3 | CH | CH | C—Br | CH | H | H | H | CH3CO | 1 |
| 1-1146 | C—CF3 | C—H | C—CF3 | N | H | CF3 | CH | CH | C—Br | CH | H | H | H | CH3CH2CO | 1 |
| 1-1147 | C—CF3 | C—H | C—CF3 | N | H | CF3 | CH | CH | C—Br | CH | H | H | H | nPrCO | 1 |
| 1-1148 | C—CF3 | C—H | C—CF3 | N | H | CF3 | CH | CH | C—Br | CH | H | H | H | cyclo-PrCO | 1 |
| 1-1149 | C—CF3 | C—H | C—CF3 | N | H | CF3 | CH | CH | C—Br | CH | H | H | H | cyclo-PrCH2CO | 1 |
| 1-1150 | C—CF3 | C—H | C—CF3 | N | H | CF3 | CH | CH | C—Br | CH | H | H | H | CF3CH2CO | 1 |
| 1-1151 | C—CF3 | C—H | C—CF3 | N | H | CF3 | CH | CH | C—Br | CH | H | H | H | CH3SCH2CO | 1 |

TABLE 1-continued

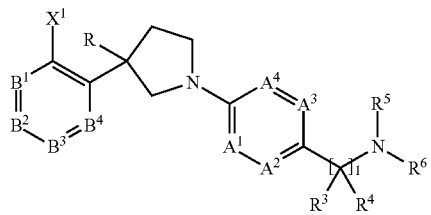

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1152 | C—CF3 | C—H | C—CF3 | N | H | CF3 | CH | CH | C—Br | CH | H | H | H | CH3S(O)CH2CO | 1 |
| 1-1153 | C—CF3 | C—H | C—CF3 | N | H | CF3 | CH | CH | C—Br | CH | H | H | H | CH3SO2CH2CO | 1 |
| 1-1154 | C—CF3 | C—H | C—CF3 | N | H | CF3 | CH | CH | C—Br | CH | H | H | H | CH3CH2NHCO | 1 |
| 1-1155 | C—CF3 | C—H | C—CF3 | N | H | CF3 | CH | CH | C—CF3 | CH | H | H | H | CH3CO | 1 |
| 1-1156 | C—CF3 | C—H | C—CF3 | N | H | CF3 | CH | CH | C—CF3 | CH | H | H | H | CH3CH2CO | 1 |
| 1-1157 | C—CF3 | C—H | C—CF3 | N | H | CF3 | CH | CH | C—CF3 | CH | H | H | H | nPrCO | 1 |
| 1-1158 | C—CF3 | C—H | C—CF3 | N | H | CF3 | CH | CH | C—CF3 | CH | H | H | H | cyclo-PrCO | 1 |
| 1-1159 | C—CF3 | C—H | C—CF3 | N | H | CF3 | CH | CH | C—CF3 | CH | H | H | H | cyclo-PrCH2CO | 1 |
| 1-1160 | C—CF3 | C—H | C—CF3 | N | H | CF3 | CH | CH | C—CF3 | CH | H | H | H | CF3CH2CO | 1 |
| 1-1161 | C—CF3 | C—H | C—CF3 | N | H | CF3 | CH | CH | C—CF3 | CH | H | H | H | CH3SCH2CO | 1 |
| 1-1162 | C—CF3 | C—H | C—CF3 | N | H | CF3 | CH | CH | C—CF3 | CH | H | H | H | CH3S(O)CH2CO | 1 |
| 1-1163 | C—CF3 | C—H | C—CF3 | N | H | CF3 | CH | CH | C—CF3 | CH | H | H | H | CH3SO2CH2CO | 1 |
| 1-1164 | C—CF3 | C—H | C—CF3 | N | H | CF3 | CH | CH | C—CF3 | CH | H | H | H | CH3CH2NHCO | 1 |
| 1-1167 | C—Cl | C—H | C—Cl | C—H | H | CF3 | CH | CH | C—Cl | N | H | H | H | n-PrCO | 1 |
| 1-1168 | C—Cl | C—H | C—Cl | C—H | H | CF3 | CH | CH | C—Cl | N | H | H | H | cyclo-PrCO | 1 |
| 1-1169 | C—Cl | C—H | C—Cl | C—H | H | CF3 | CH | CH | C—Cl | N | H | H | H |  | 1 |
| 1-1170 | C—Cl | C—H | C—Cl | C—H | H | CF3 | CH | CH | C—Cl | N | H | H | H | cyclo-PrCH2CO | 1 |
| 1-1171 | C—Cl | C—H | C—Cl | C—H | H | CF3 | CH | CH | C—Cl | N | H | H | H | CF3CH2CO | 1 |
| 1-1172 | C—Cl | C—H | C—Cl | C—H | H | CF3 | CH | CH | C—Cl | N | H | H | H | CH3SCH2CO | 1 |
| 1-1173 | C—Cl | C—H | C—Cl | C—H | H | CF3 | CH | CH | C—Cl | N | H | H | H | CH3S(O)CH2CO | 1 |
| 1-1174 | C—Cl | C—H | C—Cl | C—H | H | CF3 | CH | CH | C—Cl | N | H | H | H | CH3SO2CH2CO | 1 |
| 1-1175 | C—Cl | C—H | C—Cl | C—H | H | CF3 | CH | CH | C—Cl | N | H | H | H | CH3CH2NHCO | 1 |
| 1-1178 | C—Cl | C—H | C—Cl | C—H | H | CF3 | CH | CH | C—Br | N | H | H | H | nPrCO | 1 |
| 1-1179 | C—Cl | C—H | C—Cl | C—H | H | CF3 | CH | CH | C—Br | N | H | H | H | cyclo-PrCO | 1 |
| 1-1180 | C—Cl | C—H | C—Cl | C—H | H | CF3 | CH | CH | C—Br | N | H | H | H | cyclo-PrCH2CO | 1 |
| 1-1181 | C—Cl | C—H | C—Cl | C—H | H | CF3 | CH | CH | C—Br | N | H | H | H | CF3CH2CO | 1 |
| 1-1182 | C—Cl | C—H | C—Cl | C—H | H | CF3 | CH | CH | C—Br | N | H | H | H | CH3SCH2CO | 1 |
| 1-1183 | C—Cl | C—H | C—Cl | C—H | H | CF3 | CH | CH | C—Br | N | H | H | H | CH3S(O)CH2CO | 1 |
| 1-1184 | C—Cl | C—H | C—Cl | C—H | H | CF3 | CH | CH | C—Br | N | H | H | H | CH3SO2CH2CO | 1 |
| 1-1185 | C—Cl | C—H | C—Cl | C—H | H | CF3 | CH | CH | C—Br | N | H | H | H | CH3CH2NHCO | 1 |
| 1-1186 | C—Cl | C—H | C—Cl | C—H | H | CF3 | CH | CH | C—CF3 | N | H | H | H | n-PrCO | 1 |
| 1-1187 | C—Cl | C—H | C—Cl | C—H | H | CF3 | CH | CH | C—CF3 | N | H | H | H | cyclo-PrCH2CO | 1 |
| 1-1188 | C—Cl | C—H | C—Cl | C—H | H | CF3 | CH | CH | C—CF3 | N | H | H | H | CH3OCH2CO | 1 |
| 1-1189 | C—Cl | C—H | C—Cl | C—H | H | CF3 | CH | CH | C—CF3 | N | H | H | H | CH3CH2OCH2CO | 1 |
| 1-1190 | C—Cl | C—H | C—Cl | C—H | H | CF3 | CH | CH | C—CF3 | N | H | H | H | CH3CH2OCH2CH2CO | 1 |

TABLE 1-continued

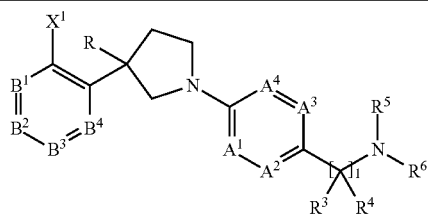

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1192 | C—Cl | C—H | C—Cl | C—H | H | CF3 | CH | CH | C—CF3 | N | H | H | H | CH3SCH2CO | 1 |
| 1-1193 | C—Cl | C—H | C—Cl | C—H | H | CF3 | CH | CH | C—CF3 | N | H | H | H | CH3S(O)CH2CO | 1 |
| 1-1194 | C—Cl | C—H | C—Cl | C—H | H | CF3 | CH | CH | C—CF3 | N | H | H | H | CH3SO2CH2CO | 1 |
| 1-1196 | C—Cl | C—H | C—Cl | C—H | H | CF3 | CH | CH | C—SCH3 | N | H | H | H | CH3CH2CO | 1 |
| 1-1197 | C—Cl | C—H | C—Cl | C—H | H | CF3 | CH | CH | C—SCH3 | N | H | H | H | cyclo-PrCO | 1 |
| 1-1198 | C—Cl | C—H | C—Cl | C—H | H | CF3 | CH | CH | C—SCH3 | N | H | H | H | CF3CH2CO | 1 |
| 1-1200 | C—Cl | C—H | C—Cl | C—H | H | CF3 | CH | CH | C—SOCH3 | N | H | H | H | CH3CH2CO | 1 |
| 1-1201 | C—Cl | C—H | C—Cl | C—H | H | CF3 | CH | CH | C—SOCH3 | N | H | H | H | cyclo-PrCO | 1 |
| 1-1202 | C—Cl | C—H | C—Cl | C—H | H | CF3 | CH | CH | C—SOCH3 | N | H | H | H | CF3CH2CO | 1 |
| 1-1203 | C—Cl | C—H | C—Cl | C—H | H | CF3 | CH | CH | C—SOCH3 | N | H | H | H | CH3SCH2CO | 1 |
| 1-1205 | C—Cl | C—H | C—Cl | C—H | H | CF3 | CH | CH | C—SO2CH3 | N | H | H | H | CH3CH2CO | 1 |
| 1-1206 | C—Cl | C—H | C—Cl | C—H | H | CF3 | CH | CH | C—SO2CH3 | N | H | H | H | cyclo-PrCO | 1 |
| 1-1207 | C—Cl | C—H | C—Cl | C—H | H | CF3 | CH | CH | C—SO2CH3 | N | H | H | H | CF3CH2CO | 1 |
| 1-1209 | C—Cl | C—H | C—Cl | C—H | H | CF3 | CH | CH | C—SCF3 | N | H | H | H | CH3CH2CO | 1 |
| 1-1210 | C—Cl | C—H | C—Cl | C—H | H | CF3 | CH | CH | C—SCF3 | N | H | H | H | nPrCO | 1 |
| 1-1211 | C—Cl | C—H | C—Cl | C—H | H | CF3 | CH | CH | C—SCF3 | N | H | H | H | cyclo-PrCO | 1 |
| 1-1212 | C—Cl | C—H | C—Cl | C—H | H | CF3 | CH | CH | C—SCF3 | N | H | H | H | cyclo-PrCH2CO | 1 |
| 1-1213 | C—Cl | C—H | C—Cl | C—H | H | CF3 | CH | CH | C—SCF3 | N | H | H | H | CF3CH2CO | 1 |
| 1-1214 | C—Cl | C—H | C—Cl | C—H | H | CF3 | CH | CH | C—SCF3 | N | H | H | H | CH3SCH2CO | 1 |
| 1-1215 | C—Cl | C—H | C—Cl | C—H | H | CF3 | CH | CH | C—SCF3 | N | H | H | H | CH3S(O)CH2CO | 1 |
| 1-1216 | C—Cl | C—H | C—Cl | C—H | H | CF3 | CH | CH | C—SCF3 | N | H | H | H | CH3SO2CH2CO | 1 |
| 1-1217 | C—Cl | C—H | C—Cl | C—H | H | CF3 | CH | CH | C—SCF3 | N | H | H | H | CH3CH2NHCO | 1 |
| 1-1219 | C—Cl | C—H | C—Cl | C—H | H | CF3 | CH | CH | C—S(O)CF3 | N | H | H | H | CH3CH2CO | 1 |
| 1-1220 | C—Cl | C—H | C—Cl | C—H | H | CF3 | CH | CH | C—S(O)CF3 | N | H | H | H | nPrCO | 1 |
| 1-1221 | C—Cl | C—H | C—Cl | C—H | H | CF3 | CH | CH | C—S(O)CF3 | N | H | H | H | cyclo-PrCO | 1 |
| 1-1222 | C—Cl | C—H | C—Cl | C—H | H | CF3 | CH | CH | C—S(O)CF3 | N | H | H | H | cyclo-PrCH2CO | 1 |
| 1-1223 | C—Cl | C—H | C—Cl | C—H | H | CF3 | CH | CH | C—S(O)CF3 | N | H | H | H | CF3CH2CO | 1 |
| 1-1224 | C—Cl | C—H | C—Cl | C—H | H | CF3 | CH | CH | C—S(O)CF3 | N | H | H | H | CH3SCH2CO | 1 |
| 1-1225 | C—Cl | C—H | C—Cl | C—H | H | CF3 | CH | CH | C—S(O)CF3 | N | H | H | H | CH3S(O)CH2CO | 1 |
| 1-1226 | C—Cl | C—H | C—Cl | C—H | H | CF3 | CH | CH | C—S(O)CF3 | N | H | H | H | CH3SO2CH2CO | 1 |
| 1-1227 | C—Cl | C—H | C—Cl | C—H | H | CF3 | CH | CH | C—S(O)CF3 | N | H | H | H | CH3CH2NHCO | 1 |
| 1-1229 | C—Cl | C—H | C—Cl | C—H | H | CF3 | CH | CH | C—SO2CF3 | N | H | H | H | CH3CH2CO | 1 |
| 1-1230 | C—Cl | C—H | C—Cl | C—H | H | CF3 | CH | CH | C—SO2CF3 | N | H | H | H | nPrCO | 1 |
| 1-1231 | C—Cl | C—H | C—Cl | C—H | H | CF3 | CH | CH | C—SO2CF3 | N | H | H | H | cyclo-PrCO | 1 |
| 1-1232 | C—Cl | C—H | C—Cl | C—H | H | CF3 | CH | CH | C—SO2CF3 | N | H | H | H | cyclo-PrCH2CO | 1 |

TABLE 1-continued

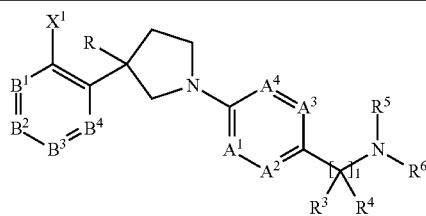

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1233 | C—Cl | C—H | C—Cl | C—H | H | CF3 | CH | CH | C—SO2CF3 | N | H | H | H | CF3CH2CO | 1 |
| 1-1234 | C—Cl | C—H | C—Cl | C—H | H | CF3 | CH | CH | C—SO2CF3 | N | H | H | H | CH3SCH2CO | 1 |
| 1-1235 | C—Cl | C—H | C—Cl | C—H | H | CF3 | CH | CH | C—SO2CF3 | N | H | H | H | CH3S(O)CH2CO | 1 |
| 1-1236 | C—Cl | C—H | C—Cl | C—H | H | CF3 | CH | CH | C—SO2CF3 | N | H | H | H | CH3SO2CH2CO | 1 |
| 1-1237 | C—Cl | C—H | C—Cl | C—H | H | CF3 | CH | CH | C—SO2CF3 | N | H | H | H | CH3CH2NHCO | 1 |
| 1-1238 | C—Cl | C—F | C—Cl | C—H | H | CF3 | CH | CH | C—Cl | N | H | H | H | CH3CO | 1 |
| 1-1239 | C—Cl | C—F | C—Cl | C—H | H | CF3 | CH | CH | C—Cl | N | H | H | H | CH3CH2CO | 1 |
| 1-1240 | C—Cl | C—F | C—Cl | C—H | H | CF3 | CH | CH | C—Cl | N | H | H | H | nPrCO | 1 |
| 1-1241 | C—Cl | C—F | C—Cl | C—H | H | CF3 | CH | CH | C—Cl | N | H | H | H | cyclo-PrCO | 1 |
| 1-1242 | C—Cl | C—F | C—Cl | C—H | H | CF3 | CH | CH | C—Cl | N | H | H | H | cyclo-PrCH2CO | 1 |
| 1-1243 | C—Cl | C—F | C—Cl | C—H | H | CF3 | CH | CH | C—Cl | N | H | H | H | CF3CH2CO | 1 |
| 1-1244 | C—Cl | C—F | C—Cl | C—H | H | CF3 | CH | CH | C—Cl | N | H | H | H | CH3SCH2CO | 1 |
| 1-1245 | C—Cl | C—F | C—Cl | C—H | H | CF3 | CH | CH | C—Cl | N | H | H | H | CH3S(O)CH2CO | 1 |
| 1-1246 | C—Cl | C—F | C—Cl | C—H | H | CF3 | CH | CH | C—Cl | N | H | H | H | CH3SO2CH2CO | 1 |
| 1-1247 | C—Cl | C—F | C—Cl | C—H | H | CF3 | CH | CH | C—Cl | N | H | H | H | CH3CH2NHCO | 1 |
| 1-1248 | C—Cl | C—F | C—Cl | C—H | H | CF3 | CH | CH | C—Br | N | H | H | H | CH3CO | 1 |
| 1-1249 | C—Cl | C—F | C—Cl | C—H | H | CF3 | CH | CH | C—Br | N | H | H | H | CH3CH2CO | 1 |
| 1-1250 | C—Cl | C—F | C—Cl | C—H | H | CF3 | CH | CH | C—Br | N | H | H | H | nPrCO | 1 |
| 1-1251 | C—Cl | C—F | C—Cl | C—H | H | CF3 | CH | CH | C—Br | N | H | H | H | cyclo-PrCO | 1 |
| 1-1252 | C—Cl | C—F | C—Cl | C—H | H | CF3 | CH | CH | C—Br | N | H | H | H | cyclo-PrCH2CO | 1 |
| 1-1253 | C—Cl | C—F | C—Cl | C—H | H | CF3 | CH | CH | C—Br | N | H | H | H | CF3CH2CO | 1 |
| 1-1254 | C—Cl | C—F | C—Cl | C—H | H | CF3 | CH | CH | C—Br | N | H | H | H | CH3SCH2CO | 1 |
| 1-1255 | C—Cl | C—F | C—Cl | C—H | H | CF3 | CH | CH | C—Br | N | H | H | H | CH3S(O)CH2CO | 1 |
| 1-1256 | C—Cl | C—F | C—Cl | C—H | H | CF3 | CH | CH | C—Br | N | H | H | H | CH3SO2CH2CO | 1 |
| 1-1257 | C—Cl | C—F | C—Cl | C—H | H | CF3 | CH | CH | C—Br | N | H | H | H | CH3CH2NHCO | 1 |
| 1-1258 | C—Cl | C—F | C—Cl | C—H | H | CF3 | CH | CH | C—CF3 | N | H | H | H | CH3CO | 1 |
| 1-1259 | C—Cl | C—F | C—Cl | C—H | H | CF3 | CH | CH | C—CF3 | N | H | H | H | CH3CH2CO | 1 |
| 1-1260 | C—Cl | C—F | C—Cl | C—H | H | CF3 | CH | CH | C—CF3 | N | H | H | H | nPrCO | 1 |
| 1-1261 | C—Cl | C—F | C—Cl | C—H | H | CF3 | CH | CH | C—CF3 | N | H | H | H | cyclo-PrCO | 1 |
| 1-1262 | C—Cl | C—F | C—Cl | C—H | H | CF3 | CH | CH | C—CF3 | N | H | H | H | cyclo-PrCH2CO | 1 |
| 1-1263 | C—Cl | C—F | C—Cl | C—H | H | CF3 | CH | CH | C—CF3 | N | H | H | H | CF3CH2CO | 1 |
| 1-1264 | C—Cl | C—F | C—Cl | C—H | H | CF3 | CH | CH | C—CF3 | N | H | H | H | CH3SCH2CO | 1 |
| 1-1265 | C—Cl | C—F | C—Cl | C—H | H | CF3 | CH | CH | C—CF3 | N | H | H | H | CH3S(O)CH2CO | 1 |
| 1-1266 | C—Cl | C—F | C—Cl | C—H | H | CF3 | CH | CH | C—CF3 | N | H | H | H | CH3SO2CH2CO | 1 |
| 1-1267 | C—Cl | C—F | C—Cl | C—H | H | CF3 | CH | CH | C—CF3 | N | H | H | H | CH3CH2NHCO | 1 |

TABLE 1-continued

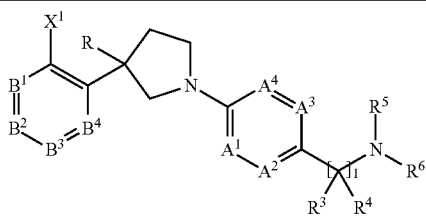

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1269 | C—Cl | C—Cl | C—Cl | C—H | H | CF3 | CH | CH | C—Cl | N | H | H | H | CH3CH2CO | 1 |
| 1-1270 | C—Cl | C—Cl | C—Cl | C—H | H | CF3 | CH | CH | C—Cl | N | H | H | H | nPrCO | 1 |
| 1-1271 | C—Cl | C—Cl | C—Cl | C—H | H | CF3 | CH | CH | C—Cl | N | H | H | H | cyclo-PrCO | 1 |
| 1-1272 | C—Cl | C—Cl | C—Cl | C—H | H | CF3 | CH | CH | C—Cl | N | H | H | H | cyclo-PrCH2CO | 1 |
| 1-1273 | C—Cl | C—Cl | C—Cl | C—H | H | CF3 | CH | CH | C—Cl | N | H | H | H | CF3CH2CO | 1 |
| 1-1274 | C—Cl | C—Cl | C—Cl | C—H | H | CF3 | CH | CH | C—Cl | N | H | H | H | CH3SCH2CO | 1 |
| 1-1275 | C—Cl | C—Cl | C—Cl | C—H | H | CF3 | CH | CH | C—Cl | N | H | H | H | CH3S(O)CH2CO | 1 |
| 1-1276 | C—Cl | C—Cl | C—Cl | C—H | H | CF3 | CH | CH | C—Cl | N | H | H | H | CH3SO2CH2CO | 1 |
| 1-1277 | C—Cl | C—Cl | C—Cl | C—H | H | CF3 | CH | CH | C—Cl | N | H | H | H | CH3CH2NHCO | 1 |
| 1-1278 | C—Cl | C—Cl | C—Cl | C—H | H | CF3 | CH | CH | C—Br | N | H | H | H | CH3CO | 1 |
| 1-1279 | C—Cl | C—Cl | C—Cl | C—H | H | CF3 | CH | CH | C—Br | N | H | H | H | CH3CH2CO | 1 |
| 1-1280 | C—Cl | C—Cl | C—Cl | C—H | H | CF3 | CH | CH | C—Br | N | H | H | H | nPrCO | 1 |
| 1-1281 | C—Cl | C—Cl | C—Cl | C—H | H | CF3 | CH | CH | C—Br | N | H | H | H | cyclo-PrCO | 1 |
| 1-1282 | C—Cl | C—Cl | C—Cl | C—H | H | CF3 | CH | CH | C—Br | N | H | H | H | cyclo-PrCH2CO | 1 |
| 1-1283 | C—Cl | C—Cl | C—Cl | C—H | H | CF3 | CH | CH | C—Br | N | H | H | H | CF3CH2CO | 1 |
| 1-1284 | C—Cl | C—Cl | C—Cl | C—H | H | CF3 | CH | CH | C—Br | N | H | H | H | CH3SCH2CO | 1 |
| 1-1285 | C—Cl | C—Cl | C—Cl | C—H | H | CF3 | CH | CH | C—Br | N | H | H | H | CH3S(O)CH2CO | 1 |
| 1-1286 | C—Cl | C—Cl | C—Cl | C—H | H | CF3 | CH | CH | C—Br | N | H | H | H | CH3SO2CH2CO | 1 |
| 1-1287 | C—Cl | C—Cl | C—Cl | C—H | H | CF3 | CH | CH | C—Br | N | H | H | H | CH3CH2NHCO | 1 |
| 1-1288 | C—Cl | C—Cl | C—Cl | C—H | H | CF3 | CH | CH | C—CF3 | N | H | H | H | nPrCO | 1 |
| 1-1289 | C—Cl | C—Cl | C—Cl | C—H | H | CF3 | CH | CH | C—CF3 | N | H | H | H | cyclo-PrCH2CO | 1 |
| 1-1290 | C—Cl | C—Cl | C—Cl | C—H | H | CF3 | CH | CH | C—CF3 | N | H | H | H | CH3SCH2CO | 1 |
| 1-1291 | C—Cl | C—Cl | C—Cl | C—H | H | CF3 | CH | CH | C—CF3 | N | H | H | H | CH3S(O)CH2CO | 1 |
| 1-1292 | C—Cl | C—Cl | C—Cl | C—H | H | CF3 | CH | CH | C—CF3 | N | H | H | H | CH3SO2CH2CO | 1 |
| 1-1293 | C—Cl | C—Cl | C—Cl | C—H | H | CF3 | CH | CH | C—SCH3 | N | H | H | H | CH3CO | 1 |
| 1-1294 | C—Cl | C—Cl | C—Cl | C—H | H | CF3 | CH | CH | C—SCH3 | N | H | H | H | CH3CH2CO | 1 |
| 1-1295 | C—Cl | C—Cl | C—Cl | C—H | H | CF3 | CH | CH | C—SCH3 | N | H | H | H | cyclo-PrCO | 1 |
| 1-1296 | C—Cl | C—Cl | C—Cl | C—H | H | CF3 | CH | CH | C—SCH3 | N | H | H | H | CF3CH2CO | 1 |
| 1-1297 | C—Cl | C—Cl | C—Cl | C—H | H | CF3 | CH | CH | C—S(O)CH3 | N | H | H | H | CH3CO | 1 |
| 1-1298 | C—Cl | C—Cl | C—Cl | C—H | H | CF3 | CH | CH | C—S(O)CH3 | N | H | H | H | CH3CH2CO | 1 |
| 1-1299 | C—Cl | C—Cl | C—Cl | C—H | H | CF3 | CH | CH | C—S(O)CH3 | N | H | H | H | cyclo-PrCO | 1 |
| 1-1300 | C—Cl | C—Cl | C—Cl | C—H | H | CF3 | CH | CH | C—S(O)CH3 | N | H | H | H | CF3CH2CO | 1 |
| 1-1301 | C—Cl | C—Cl | C—Cl | C—H | H | CF3 | CH | CH | C—S(O)CH3 | N | H | H | H | CH3SCH2CO | 1 |
| 1-1302 | C—Cl | C—Cl | C—Cl | C—H | H | CF3 | CH | CH | C—SO2CH3 | N | H | H | H | CH3CO | 1 |
| 1-1303 | C—Cl | C—Cl | C—Cl | C—H | H | CF3 | CH | CH | C—SO2CH3 | N | H | H | H | CH3CH2CO | 1 |

TABLE 1-continued

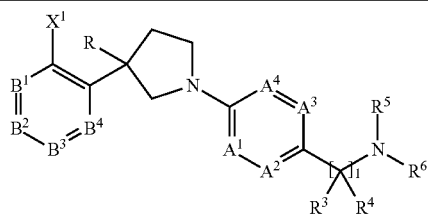

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1304 | C—Cl | C—Cl | C—Cl | C—H | H | CF3 | CH | CH | C—SO2CH3 | N | H | H | H | cyclo-PrCO | 1 |
| 1-1305 | C—Cl | C—Cl | C—Cl | C—H | H | CF3 | CH | CH | C—SO2CH3 | N | H | H | H | CF3CH2CO | 1 |
| 1-1306 | C—Cl | C—Cl | C—Cl | C—H | H | CF3 | CH | CH | C—SCF3 | N | H | H | H | CH3CO | 1 |
| 1-1307 | C—Cl | C—Cl | C—Cl | C—H | H | CF3 | CH | CH | C—SCF3 | N | H | H | H | CH3CH2CO | 1 |
| 1-1308 | C—Cl | C—Cl | C—Cl | C—H | H | CF3 | CH | CH | C—SCF3 | N | H | H | H | nPrCO | 1 |
| 1-1309 | C—Cl | C—Cl | C—Cl | C—H | H | CF3 | CH | CH | C—SCF3 | N | H | H | H | cyclo-PrCO | 1 |
| 1-1310 | C—Cl | C—Cl | C—Cl | C—H | H | CF3 | CH | CH | C—SCF3 | N | H | H | H | cyclo-PrCH2CO | 1 |
| 1-1311 | C—Cl | C—Cl | C—Cl | C—H | H | CF3 | CH | CH | C—SCF3 | N | H | H | H | CF3CH2CO | 1 |
| 1-1312 | C—Cl | C—Cl | C—Cl | C—H | H | CF3 | CH | CH | C—SCF3 | N | H | H | H | CH3SCH2CO | 1 |
| 1-1313 | C—Cl | C—Cl | C—Cl | C—H | H | CF3 | CH | CH | C—SCF3 | N | H | H | H | CH3S(O)CH2CO | 1 |
| 1-1314 | C—Cl | C—Cl | C—Cl | C—H | H | CF3 | CH | CH | C—SCF3 | N | H | H | H | CH3SO2CH2CO | 1 |
| 1-1315 | C—Cl | C—Cl | C—Cl | C—H | H | CF3 | CH | CH | C—SCF3 | N | H | H | H | CH3CH2NHCO | 1 |
| 1-1316 | C—Cl | C—Cl | C—Cl | C—H | H | CF3 | CH | CH | C—S(O)CF3 | N | H | H | H | CH3CO | 1 |
| 1-1317 | C—Cl | C—Cl | C—Cl | C—H | H | CF3 | CH | CH | C—S(O)CF3 | N | H | H | H | CH3CH2CO | 1 |
| 1-1318 | C—Cl | C—Cl | C—Cl | C—H | H | CF3 | CH | CH | C—S(O)CF3 | N | H | H | H | nPrCO | 1 |
| 1-1319 | C—Cl | C—Cl | C—Cl | C—H | H | CF3 | CH | CH | C—S(O)CF3 | N | H | H | H | cyclo-PrCO | 1 |
| 1-1320 | C—Cl | C—Cl | C—Cl | C—H | H | CF3 | CH | CH | C—S(O)CF3 | N | H | H | H | cyclo-PrCH2CO | 1 |
| 1-1321 | C—Cl | C—Cl | C—Cl | C—H | H | CF3 | CH | CH | C—S(O)CF3 | N | H | H | H | CF3CH2CO | 1 |
| 1-1322 | C—Cl | C—Cl | C—Cl | C—H | H | CF3 | CH | CH | C—S(O)CF3 | N | H | H | H | CH3SCH2CO | 1 |
| 1-1323 | C—Cl | C—Cl | C—Cl | C—H | H | CF3 | CH | CH | C—S(O)CF3 | N | H | H | H | CH3S(O)CH2CO | 1 |
| 1-1324 | C—Cl | C—Cl | C—Cl | C—H | H | CF3 | CH | CH | C—S(O)CF3 | N | H | H | H | CH3SO2CH2CO | 1 |
| 1-1325 | C—Cl | C—Cl | C—Cl | C—H | H | CF3 | CH | CH | C—S(O)CF3 | N | H | H | H | CH3CH2NHCO | 1 |
| 1-1326 | C—Cl | C—Cl | C—Cl | C—H | H | CF3 | CH | CH | C—SO2CF3 | N | H | H | H | CH3CO | 1 |
| 1-1327 | C—Cl | C—Cl | C—Cl | C—H | H | CF3 | CH | CH | C—SO2CF3 | N | H | H | H | CH3CH2CO | 1 |
| 1-1328 | C—Cl | C—Cl | C—Cl | C—H | H | CF3 | CH | CH | C—SO2CF3 | N | H | H | H | nPrCO | 1 |
| 1-1329 | C—Cl | C—Cl | C—Cl | C—H | H | CF3 | CH | CH | C—SO2CF3 | N | H | H | H | cyclo-PrCO | 1 |
| 1-1330 | C—Cl | C—Cl | C—Cl | C—H | H | CF3 | CH | CH | C—SO2CF3 | N | H | H | H | cyclo-PrCH2CO | 1 |
| 1-1331 | C—Cl | C—Cl | C—Cl | C—H | H | CF3 | CH | CH | C—SO2CF3 | N | H | H | H | CF3CH2CO | 1 |
| 1-1332 | C—Cl | C—Cl | C—Cl | C—H | H | CF3 | CH | CH | C—SO2CF3 | N | H | H | H | CH3SCH2CO | 1 |
| 1-1333 | C—Cl | C—Cl | C—Cl | C—H | H | CF3 | CH | CH | C—SO2CF3 | N | H | H | H | CH3S(O)CH2CO | 1 |
| 1-1334 | C—Cl | C—Cl | C—Cl | C—H | H | CF3 | CH | CH | C—SO2CF3 | N | H | H | H | CH3SO2CH2CO | 1 |
| 1-1335 | C—Cl | C—Cl | C—Cl | C—H | H | CF3 | CH | CH | C—SO2CF3 | N | H | H | H | CH3CH2NHCO | 1 |
| 1-1336 | C—Cl | C—Br | C—Cl | C—H | H | CF3 | CH | CH | C—Cl | N | H | H | H | CH3CO | 1 |
| 1-1337 | C—Cl | C—Br | C—Cl | C—H | H | CF3 | CH | CH | C—Cl | N | H | H | H | CH3CH2CO | 1 |
| 1-1338 | C—Cl | C—Br | C—Cl | C—H | H | CF3 | CH | CH | C—Cl | N | H | H | H | nPrCO | 1 |

TABLE 1-continued

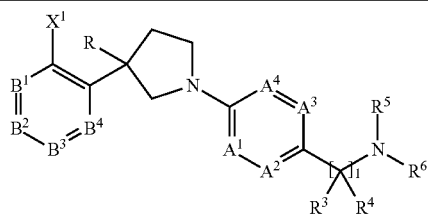

| Ex.-No. | $B^1$ | $B^2$ | $B^3$ | $B^4$ | $X^1$ | R | $A^1$ | $A^2$ | $A^3$ | $A^4$ | $R^3$ | $R^4$ | $R^5$ | $R^6$ | 1 |
|---|---|---|---|---|---|---|---|---|---|---|---|---|---|---|---|
| 1-1339 | C—Cl | C—Br | C—Cl | C—H | H | CF3 | CH | CH | C—Cl | N | H | H | H | cyclo-PrCO | 1 |
| 1-1340 | C—Cl | C—Br | C—Cl | C—H | H | CF3 | CH | CH | C—Cl | N | H | H | H | cyclo-PrCH2CO | 1 |
| 1-1341 | C—Cl | C—Br | C—Cl | C—H | H | CF3 | CH | CH | C—Cl | N | H | H | H | CF3CH2CO | 1 |
| 1-1342 | C—Cl | C—Br | C—Cl | C—H | H | CF3 | CH | CH | C—Cl | N | H | H | H | CH3SCH2CO | 1 |
| 1-1343 | C—Cl | C—Br | C—Cl | C—H | H | CF3 | CH | CH | C—Cl | N | H | H | H | CH3S(O)CH2CO | 1 |
| 1-1344 | C—Cl | C—Br | C—Cl | C—H | H | CF3 | CH | CH | C—Cl | N | H | H | H | CH3SO2CH2CO | 1 |
| 1-1345 | C—Cl | C—Br | C—Cl | C—H | H | CF3 | CH | CH | C—Cl | N | H | H | H | CH3CH2NHCO | 1 |
| 1-1346 | C—Cl | C—Br | C—Cl | C—H | H | CF3 | CH | CH | C—Br | N | H | H | H | CH3CO | 1 |
| 1-1347 | C—Cl | C—Br | C—Cl | C—H | H | CF3 | CH | CH | C—Br | N | H | H | H | CH3CH2CO | 1 |
| 1-1348 | C—Cl | C—Br | C—Cl | C—H | H | CF3 | CH | CH | C—Br | N | H | H | H | nPrCO | 1 |
| 1-1349 | C—Cl | C—Br | C—Cl | C—H | H | CF3 | CH | CH | C—Br | N | H | H | H | cyclo-PrCO | 1 |
| 1-1350 | C—Cl | C—Br | C—Cl | C—H | H | CF3 | CH | CH | C—Br | N | H | H | H | cyclo-PrCH2CO | 1 |
| 1-1351 | C—Cl | C—Br | C—Cl | C—H | H | CF3 | CH | CH | C—Br | N | H | H | H | CF3CH2CO | 1 |
| 1-1352 | C—Cl | C—Br | C—Cl | C—H | H | CF3 | CH | CH | C—Br | N | H | H | H | CH3SCH2CO | 1 |
| 1-1353 | C—Cl | C—Br | C—Cl | C—H | H | CF3 | CH | CH | C—Br | N | H | H | H | CH3S(O)CH2CO | 1 |
| 1-1354 | C—Cl | C—Br | C—Cl | C—H | H | CF3 | CH | CH | C—Br | N | H | H | H | CH3SO2CH2CO | 1 |
| 1-1355 | C—Cl | C—Br | C—Cl | C—H | H | CF3 | CH | CH | C—Br | N | H | H | H | CH3CH2NHCO | 1 |
| 1-1356 | C—Cl | C—Br | C—Cl | C—H | H | CF3 | CH | CH | C—CF3 | N | H | H | H | CH3CO | 1 |
| 1-1357 | C—Cl | C—Br | C—Cl | C—H | H | CF3 | CH | CH | C—CF3 | N | H | H | H | CH3CH2CO | 1 |
| 1-1358 | C—Cl | C—Br | C—Cl | C—H | H | CF3 | CH | CH | C—CF3 | N | H | H | H | nPrCO | 1 |
| 1-1359 | C—Cl | C—Br | C—Cl | C—H | H | CF3 | CH | CH | C—CF3 | N | H | H | H | cyclo-PrCO | 1 |
| 1-1360 | C—Cl | C—Br | C—Cl | C—H | H | CF3 | CH | CH | C—CF3 | N | H | H | H | cyclo-PrCH2CO | 1 |
| 1-1361 | C—Cl | C—Br | C—Cl | C—H | H | CF3 | CH | CH | C—CF3 | N | H | H | H | CF3CH2CO | 1 |
| 1-1362 | C—Cl | C—Br | C—Cl | C—H | H | CF3 | CH | CH | C—CF3 | N | H | H | H | CH3SCH2CO | 1 |
| 1-1363 | C—Cl | C—Br | C—Cl | C—H | H | CF3 | CH | CH | C—CF3 | N | H | H | H | CH3S(O)CH2CO | 1 |
| 1-1364 | C—Cl | C—Br | C—Cl | C—H | H | CF3 | CH | CH | C—CF3 | N | H | H | H | CH3SO2CH2CO | 1 |
| 1-1365 | C—Cl | C—Br | C—Cl | C—H | H | CF3 | CH | CH | C—CF3 | N | H | H | H | CH3CH2NHCO | 1 |
| 1-1366 | C—Cl | C—Cl | C—Br | C—H | H | CF3 | CH | CH | C—Cl | N | H | H | H | CH3CO | 1 |
| 1-1367 | C—Cl | C—Cl | C—Br | C—H | H | CF3 | CH | CH | C—Cl | N | H | H | H | CH3CH2CO | 1 |
| 1-1368 | C—Cl | C—Cl | C—Br | C—H | H | CF3 | CH | CH | C—Cl | N | H | H | H | nPrCO | 1 |
| 1-1369 | C—Cl | C—Cl | C—Br | C—H | H | CF3 | CH | CH | C—Cl | N | H | H | H | cyclo-PrCO | 1 |
| 1-1370 | C—Cl | C—Cl | C—Br | C—H | H | CF3 | CH | CH | C—Cl | N | H | H | H | cyclo-PrCH2CO | 1 |
| 1-1371 | C—Cl | C—Cl | C—Br | C—H | H | CF3 | CH | CH | C—Cl | N | H | H | H | CF3CH2CO | 1 |
| 1-1372 | C—Cl | C—Cl | C—Br | C—H | H | CF3 | CH | CH | C—Cl | N | H | H | H | CH3SCH2CO | 1 |
| 1-1373 | C—Cl | C—Cl | C—Br | C—H | H | CF3 | CH | CH | C—Cl | N | H | H | H | CH3S(O)CH2CO | 1 |

TABLE 1-continued

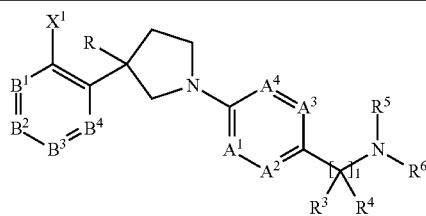

| Ex.-No. | $B^1$ | $B^2$ | $B^3$ | $B^4$ | $X^1$ | R | $A^1$ | $A^2$ | $A^3$ | $A^4$ | $R^3$ | $R^4$ | $R^5$ | $R^6$ | 1 |
|---|---|---|---|---|---|---|---|---|---|---|---|---|---|---|---|
| 1-1374 | C—Cl | C—Cl | C—Br | C—H | H | CF3 | CH | CH | C—Cl | N | H | H | H | CH3SO2CH2CO | 1 |
| 1-1375 | C—Cl | C—Cl | C—Br | C—H | H | CF3 | CH | CH | C—Cl | N | H | H | H | CH3CH2NHCO | 1 |
| 1-1376 | C—Cl | C—Cl | C—Br | C—H | H | CF3 | CH | CH | C—Br | N | H | H | H | CH3CO | 1 |
| 1-1377 | C—Cl | C—Cl | C—Br | C—H | H | CF3 | CH | CH | C—Br | N | H | H | H | CH3CH2CO | 1 |
| 1-1378 | C—Cl | C—Cl | C—Br | C—H | H | CF3 | CH | CH | C—Br | N | H | H | H | nPrCO | 1 |
| 1-1379 | C—Cl | C—Cl | C—Br | C—H | H | CF3 | CH | CH | C—Br | N | H | H | H | cyclo-PrCO | 1 |
| 1-1380 | C—Cl | C—Cl | C—Br | C—H | H | CF3 | CH | CH | C—Br | N | H | H | H | cyclo-PrCH2CO | 1 |
| 1-1381 | C—Cl | C—Cl | C—Br | C—H | H | CF3 | CH | CH | C—Br | N | H | H | H | CF3CH2CO | 1 |
| 1-1382 | C—Cl | C—Cl | C—Br | C—H | H | CF3 | CH | CH | C—Br | N | H | H | H | CH3SCH2CO | 1 |
| 1-1383 | C—Cl | C—Cl | C—Br | C—H | H | CF3 | CH | CH | C—Br | N | H | H | H | CH3S(O)CH2CO | 1 |
| 1-1384 | C—Cl | C—Cl | C—Br | C—H | H | CF3 | CH | CH | C—Br | N | H | H | H | CH3SO2CH2CO | 1 |
| 1-1385 | C—Cl | C—Cl | C—Br | C—H | H | CF3 | CH | CH | C—Br | N | H | H | H | CH3CH2NHCO | 1 |
| 1-1386 | C—Cl | C—Cl | C—Br | C—H | H | CF3 | CH | CH | C—CF3 | N | H | H | H | CH3CO | 1 |
| 1-1387 | C—Cl | C—Cl | C—Br | C—H | H | CF3 | CH | CH | C—CF3 | N | H | H | H | CH3CH2CO | 1 |
| 1-1388 | C—Cl | C—Cl | C—Br | C—H | H | CF3 | CH | CH | C—CF3 | N | H | H | H | nPrCO | 1 |
| 1-1389 | C—Cl | C—Cl | C—Br | C—H | H | CF3 | CH | CH | C—CF3 | N | H | H | H | cyclo-PrCO | 1 |
| 1-1390 | C—Cl | C—Cl | C—Br | C—H | H | CF3 | CH | CH | C—CF3 | N | H | H | H | cyclo-PrCH2CO | 1 |
| 1-1391 | C—Cl | C—Cl | C—Br | C—H | H | CF3 | CH | CH | C—CF3 | N | H | H | H | CF3CH2CO | 1 |
| 1-1392 | C—Cl | C—Cl | C—Br | C—H | H | CF3 | CH | CH | C—CF3 | N | H | H | H | CH3SCH2CO | 1 |
| 1-1393 | C—Cl | C—Cl | C—Br | C—H | H | CF3 | CH | CH | C—CF3 | N | H | H | H | CH3S(O)CH2CO | 1 |
| 1-1394 | C—Cl | C—Cl | C—Br | C—H | H | CF3 | CH | CH | C—CF3 | N | H | H | H | CH3SO2CH2CO | 1 |
| 1-1395 | C—Cl | C—Cl | C—Br | C—H | H | CF3 | CH | CH | C—CF3 | N | H | H | H | CH3CH2NHCO | 1 |
| 1-1396 | C—Cl | C—F | C—Cl | C—H | F | CF3 | CH | CH | C—Cl | N | H | H | H | CH3CO | 1 |
| 1-1397 | C—Cl | C—F | C—Cl | C—H | F | CF3 | CH | CH | C—Cl | N | H | H | H | CH3CH2CO | 1 |
| 1-1398 | C—Cl | C—F | C—Cl | C—H | F | CF3 | CH | CH | C—Cl | N | H | H | H | nPrCO | 1 |
| 1-1399 | C—Cl | C—F | C—Cl | C—H | F | CF3 | CH | CH | C—Cl | N | H | H | H | cyclo-PrCO | 1 |
| 1-1400 | C—Cl | C—F | C—Cl | C—H | F | CF3 | CH | CH | C—Cl | N | H | H | H | cyclo-PrCH2CO | 1 |
| 1-1401 | C—Cl | C—F | C—Cl | C—H | F | CF3 | CH | CH | C—Cl | N | H | H | H | CF3CH2CO | 1 |
| 1-1402 | C—Cl | C—F | C—Cl | C—H | F | CF3 | CH | CH | C—Cl | N | H | H | H | CH3SCH2CO | 1 |
| 1-1403 | C—Cl | C—F | C—Cl | C—H | F | CF3 | CH | CH | C—Cl | N | H | H | H | CH3S(O)CH2CO | 1 |
| 1-1404 | C—Cl | C—F | C—Cl | C—H | F | CF3 | CH | CH | C—Cl | N | H | H | H | CH3SO2CH2CO | 1 |
| 1-1405 | C—Cl | C—F | C—Cl | C—H | F | CF3 | CH | CH | C—Cl | N | H | H | H | CH3CH2NHCO | 1 |
| 1-1406 | C—Cl | C—F | C—Cl | C—H | F | CF3 | CH | CH | C—Br | N | H | H | H | CH3CO | 1 |
| 1-1407 | C—Cl | C—F | C—Cl | C—H | F | CF3 | CH | CH | C—Br | N | H | H | H | CH3CH2CO | 1 |
| 1-1408 | C—Cl | C—F | C—Cl | C—H | F | CF3 | CH | CH | C—Br | N | H | H | H | nPrCO | 1 |

TABLE 1-continued

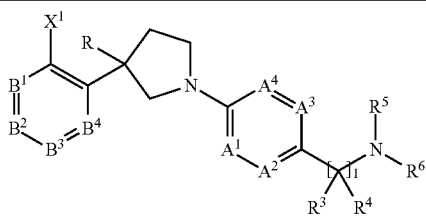

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1409 | C—Cl | C—F | C—Cl | C—H | F | CF3 | CH | CH | C—Br | N | H | H | H | cyclo-PrCO | 1 |
| 1-1410 | C—Cl | C—F | C—Cl | C—H | F | CF3 | CH | CH | C—Br | N | H | H | H | cyclo-PrCH2CO | 1 |
| 1-1411 | C—Cl | C—F | C—Cl | C—H | F | CF3 | CH | CH | C—Br | N | H | H | H | CF3CH2CO | 1 |
| 1-1412 | C—Cl | C—F | C—Cl | C—H | F | CF3 | CH | CH | C—Br | N | H | H | H | CH3SCH2CO | 1 |
| 1-1413 | C—Cl | C—F | C—Cl | C—H | F | CF3 | CH | CH | C—Br | N | H | H | H | CH3S(O)CH2CO | 1 |
| 1-1414 | C—Cl | C—F | C—Cl | C—H | F | CF3 | CH | CH | C—Br | N | H | H | H | CH3SO2CH2CO | 1 |
| 1-1415 | C—Cl | C—F | C—Cl | C—H | F | CF3 | CH | CH | C—Br | N | H | H | H | CH3CH2NHCO | 1 |
| 1-1416 | C—Cl | C—F | C—Cl | C—H | F | CF3 | CH | CH | C—CF3 | N | H | H | H | CH3CO | 1 |
| 1-1417 | C—Cl | C—F | C—Cl | C—H | F | CF3 | CH | CH | C—CF3 | N | H | H | H | CH3CH2CO | 1 |
| 1-1418 | C—Cl | C—F | C—Cl | C—H | F | CF3 | CH | CH | C—CF3 | N | H | H | H | nPrCO | 1 |
| 1-1419 | C—Cl | C—F | C—Cl | C—H | F | CF3 | CH | CH | C—CF3 | N | H | H | H | cyclo-PrCO | 1 |
| 1-1420 | C—Cl | C—F | C—Cl | C—H | F | CF3 | CH | CH | C—CF3 | N | H | H | H | cyclo-PrCH2CO | 1 |
| 1-1421 | C—Cl | C—F | C—Cl | C—H | F | CF3 | CH | CH | C—CF3 | N | H | H | H | CF3CH2CO | 1 |
| 1-1422 | C—Cl | C—F | C—Cl | C—H | F | CF3 | CH | CH | C—CF3 | N | H | H | H | CH3SCH2CO | 1 |
| 1-1423 | C—Cl | C—F | C—Cl | C—H | F | CF3 | CH | CH | C—CF3 | N | H | H | H | CH3S(O)CH2CO | 1 |
| 1-1424 | C—Cl | C—F | C—Cl | C—H | F | CF3 | CH | CH | C—CF3 | N | H | H | H | CH3SO2CH2CO | 1 |
| 1-1425 | C—Cl | C—F | C—Cl | C—H | F | CF3 | CH | CH | C—CF3 | N | H | H | H | CH3CH2NHCO | 1 |
| 1-1426 | C—CF3 | C—H | C—H | C—H | H | CF3 | CH | CH | C—CF3 | N | H | H | H | CH3CO | 1 |
| 1-1427 | C—CF3 | C—H | C—H | C—H | H | CF3 | CH | CH | C—CF3 | N | H | H | H | CH3CH2CO | 1 |
| 1-1428 | C—CF3 | C—H | C—H | C—H | H | CF3 | CH | CH | C—CF3 | N | H | H | H | nPrCO | 1 |
| 1-1429 | C—CF3 | C—H | C—H | C—H | H | CF3 | CH | CH | C—CF3 | N | H | H | H | cyclo-PrCO | 1 |
| 1-1430 | C—CF3 | C—H | C—H | C—H | H | CF3 | CH | CH | C—CF3 | N | H | H | H | cyclo-PrCH2CO | 1 |
| 1-1431 | C—CF3 | C—H | C—H | C—H | H | CF3 | CH | CH | C—CF3 | N | H | H | H | CF3CH2CO | 1 |
| 1-1432 | C—CF3 | C—H | C—H | C—H | H | CF3 | CH | CH | C—CF3 | N | H | H | H | CH3SCH2CO | 1 |
| 1-1433 | C—CF3 | C—H | C—H | C—H | H | CF3 | CH | CH | C—CF3 | N | H | H | H | CH3S(O)CH2CO | 1 |
| 1-1434 | C—CF3 | C—H | C—H | C—H | H | CF3 | CH | CH | C—CF3 | N | H | H | H | CH3SO2CH2CO | 1 |
| 1-1435 | C—CF3 | C—H | C—H | C—H | H | CF3 | CH | CH | C—CF3 | N | H | H | H | CH3CH2NHCO | 1 |
| 1-1436 | C—CF3 | C—F | C—H | C—H | H | CF3 | CH | CH | C—CF3 | N | H | H | H | CH3CO | 1 |
| 1-1437 | C—CF3 | C—F | C—H | C—H | H | CF3 | CH | CH | C—CF3 | N | H | H | H | CH3CH2CO | 1 |
| 1-1438 | C—CF3 | C—F | C—H | C—H | H | CF3 | CH | CH | C—CF3 | N | H | H | H | nPrCO | 1 |
| 1-1439 | C—CF3 | C—F | C—H | C—H | H | CF3 | CH | CH | C—CF3 | N | H | H | H | cyclo-PrCO | 1 |
| 1-1440 | C—CF3 | C—F | C—H | C—H | H | CF3 | CH | CH | C—CF3 | N | H | H | H | cyclo-PrCH2CO | 1 |
| 1-1441 | C—CF3 | C—F | C—H | C—H | H | CF3 | CH | CH | C—CF3 | N | H | H | H | CF3CH2CO | 1 |
| 1-1442 | C—CF3 | C—F | C—H | C—H | H | CF3 | CH | CH | C—CF3 | N | H | H | H | CH3SOCH2CO | 1 |
| 1-1443 | C—CF3 | C—F | C—H | C—H | H | CF3 | CH | CH | C—CF3 | N | H | H | H | CH3S(O)CH2CO | 1 |

TABLE 1-continued

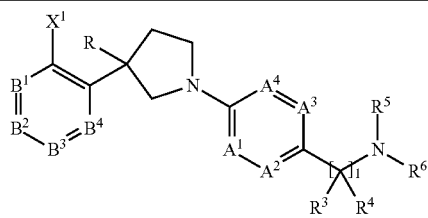

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1444 | C—CF3 | C—F | C—H | C—H | H | CF3 | CH | CH | C—CF3 | N | H | H | H | CH3SO2CH2CO | 1 |
| 1-1445 | C—CF3 | C—F | C—H | C—H | H | CF3 | CH | CH | C—CF3 | N | H | H | H | CH3CH2NHCO | 1 |
| 1-1446 | C—CF3 | C—H | C—H | C—H | F | CF3 | CH | CH | C—CF3 | N | H | H | H | CH3CO | 1 |
| 1-1447 | C—CF3 | C—H | C—H | C—H | F | CF3 | CH | CH | C—CF3 | N | H | H | H | CH3CH2CO | 1 |
| 1-1448 | C—CF3 | C—H | C—H | C—H | F | CF3 | CH | CH | C—CF3 | N | H | H | H | nPrCO | 1 |
| 1-1449 | C—CF3 | C—H | C—H | C—H | F | CF3 | CH | CH | C—CF3 | N | H | H | H | cyclo-PrCO | 1 |
| 1-1450 | C—CF3 | C—H | C—H | C—H | F | CF3 | CH | CH | C—CF3 | N | H | H | H | cyclo-PrCH2CO | 1 |
| 1-1451 | C—CF3 | C—H | C—H | C—H | F | CF3 | CH | CH | C—CF3 | N | H | H | H | CF3CH2CO | 1 |
| 1-1452 | C—CF3 | C—H | C—H | C—H | F | CF3 | CH | CH | C—CF3 | N | H | H | H | CH3SOCH2CO | 1 |
| 1-1453 | C—CF3 | C—H | C—H | C—H | F | CF3 | CH | CH | C—CF3 | N | H | H | H | CH3S(O)CH2CO | 1 |
| 1-1454 | C—CF3 | C—H | C—H | C—H | F | CF3 | CH | CH | C—CF3 | N | H | H | H | CH3SO2CH2CO | 1 |
| 1-1455 | C—CF3 | C—H | C—H | C—H | F | CF3 | CH | CH | C—CF3 | N | H | H | H | CH3CH2NHCO | 1 |
| 1-1456 | C—Cl | C—CF3 | C—H | C—H | H | CF3 | CH | CH | C—CF3 | N | H | H | H | CH3CO | 1 |
| 1-1457 | C—Cl | C—CF3 | C—H | C—H | H | CF3 | CH | CH | C—CF3 | N | H | H | H | CH3CH2CO | 1 |
| 1-1458 | C—Cl | C—CF3 | C—H | C—H | H | CF3 | CH | CH | C—CF3 | N | H | H | H | nPrCO | 1 |
| 1-1459 | C—Cl | C—CF3 | C—H | C—H | H | CF3 | CH | CH | C—CF3 | N | H | H | H | cyclo-PrCO | 1 |
| 1-1460 | C—Cl | C—CF3 | C—H | C—H | H | CF3 | CH | CH | C—CF3 | N | H | H | H | cyclo-PrCH2CO | 1 |
| 1-1461 | C—Cl | C—CF3 | C—H | C—H | H | CF3 | CH | CH | C—CF3 | N | H | H | H | CF3CH2CO | 1 |
| 1-1462 | C—Cl | C—CF3 | C—H | C—H | H | CF3 | CH | CH | C—CF3 | N | H | H | H | CH3SOCH2CO | 1 |
| 1-1463 | C—Cl | C—CF3 | C—H | C—H | H | CF3 | CH | CH | C—CF3 | N | H | H | H | CH3S(O)CH2CO | 1 |
| 1-1464 | C—Cl | C—CF3 | C—H | C—H | H | CF3 | CH | CH | C—CF3 | N | H | H | H | CH3SO2CH2CO | 1 |
| 1-1465 | C—Cl | C—CF3 | C—H | C—H | H | CF3 | CH | CH | C—CF3 | N | H | H | H | CH3CH2NHCO | 1 |
| 1-1467 | C—CF3 | C—H | C—CF3 | C—H | H | CF3 | CH | CH | C—Cl | N | H | H | H | CH3CH2CO | 1 |
| 1-1468 | C—CF3 | C—H | C—CF3 | C—H | H | CF3 | CH | CH | C—Cl | N | H | H | H | nPrCO | 1 |
| 1-1469 | C—CF3 | C—H | C—CF3 | C—H | H | CF3 | CH | CH | C—Cl | N | H | H | H | cyclo-PrCO | 1 |
| 1-1470 | C—CF3 | C—H | C—CF3 | C—H | H | CF3 | CH | CH | C—Cl | N | H | H | H | cyclo-PrCH2CO | 1 |
| 1-1471 | C—CF3 | C—H | C—CF3 | C—H | H | CF3 | CH | CH | C—Cl | N | H | H | H | CF3CH2CO | 1 |
| 1-1472 | C—CF3 | C—H | C—CF3 | C—H | H | CF3 | CH | CH | C—Cl | N | H | H | H | CH3SCH2CO | 1 |
| 1-1473 | C—CF3 | C—H | C—CF3 | C—H | H | CF3 | CH | CH | C—Cl | N | H | H | H | CH3S(O)CH2CO | 1 |
| 1-1474 | C—CF3 | C—H | C—CF3 | C—H | H | CF3 | CH | CH | C—Cl | N | H | H | H | CH3SO2CH2CO | 1 |
| 1-1475 | C—CF3 | C—H | C—CF3 | C—H | H | CF3 | CH | CH | C—Cl | N | H | H | H | CH3CH2NHCO | 1 |
| 1-1476 | C—CF3 | C—H | C—CF3 | C—H | H | CF3 | CH | CH | C—Br | N | H | H | H | CH3CO | 1 |
| 1-1477 | C—CF3 | C—H | C—CF3 | C—H | H | CF3 | CH | CH | C—Br | N | H | H | H | CH3CH2CO | 1 |
| 1-1478 | C—CF3 | C—H | C—CF3 | C—H | H | CF3 | CH | CH | C—Br | N | H | H | H | nPrCO | 1 |
| 1-1479 | C—CF3 | C—H | C—CF3 | C—H | H | CF3 | CH | CH | C—Br | N | H | H | H | cyclo-PrCO | 1 |

TABLE 1-continued

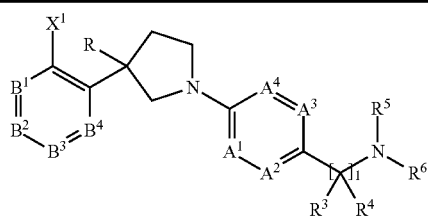

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1480 | C—CF3 | C—H | C—CF3 | C—H | H | CF3 | CH | CH | C—Br | N | H | H | H | cyclo-PrCH2CO | 1 |
| 1-1481 | C—CF3 | C—H | C—CF3 | C—H | H | CF3 | CH | CH | C—Br | N | H | H | H | CF3CH2CO | 1 |
| 1-1482 | C—CF3 | C—H | C—CF3 | C—H | H | CF3 | CH | CH | C—Br | N | H | H | H | CH3SCH2CO | 1 |
| 1-1483 | C—CF3 | C—H | C—CF3 | C—H | H | CF3 | CH | CH | C—Br | N | H | H | H | CH3S(O)CH2CO | 1 |
| 1-1484 | C—CF3 | C—H | C—CF3 | C—H | H | CF3 | CH | CH | C—Br | N | H | H | H | CH3SO2CH2CO | 1 |
| 1-1485 | C—CF3 | C—H | C—CF3 | C—H | H | CF3 | CH | CH | C—Br | N | H | H | H | CH3CH2NHCO | 1 |
| 1-1486 | C—CF3 | C—H | C—CF3 | C—H | H | CF3 | CH | CH | C—CF3 | N | H | H | H | nPrCO | 1 |
| 1-1487 | C—CF3 | C—H | C—CF3 | C—H | H | CF3 | CH | CH | C—CF3 | N | H | H | H | cyclo-PrCH2CO | 1 |
| 1-1488 | C—CF3 | C—H | C—CF3 | C—H | H | CF3 | CH | CH | C—CF3 | N | H | H | H | CH3SCH2CO | 1 |
| 1-1489 | C—CF3 | C—H | C—CF3 | C—H | H | CF3 | CH | CH | C—CF3 | N | H | H | H | CH3S(O)CH2CO | 1 |
| 1-1490 | C—CF3 | C—H | C—CF3 | C—H | H | CF3 | CH | CH | C—CF3 | N | H | H | H | CH3SO2CH2CO | 1 |
| 1-1491 | C—CF3 | C—H | C—CF3 | C—H | H | CF3 | CH | CH | C—SCH3 | N | H | H | H | CH3CO | 1 |
| 1-1492 | C—CF3 | C—H | C—CF3 | C—H | H | CF3 | CH | CH | C—SCH3 | N | H | H | H | CH3CH2CO | 1 |
| 1-1493 | C—CF3 | C—H | C—CF3 | C—H | H | CF3 | CH | CH | C—SCH3 | N | H | H | H | cyclo-PrCO | 1 |
| 1-1494 | C—CF3 | C—H | C—CF3 | C—H | H | CF3 | CH | CH | C—SCH3 | N | H | H | H | CF3CH2CO | 1 |
| 1-1495 | C—CF3 | C—H | C—CF3 | C—H | H | CF3 | CH | CH | C—SOCH3 | N | H | H | H | CH3CO | 1 |
| 1-1496 | C—CF3 | C—H | C—CF3 | C—H | H | CF3 | CH | CH | C—SOCH3 | N | H | H | H | CH3CH2CO | 1 |
| 1-1497 | C—CF3 | C—H | C—CF3 | C—H | H | CF3 | CH | CH | C—SOCH3 | N | H | H | H | cyclo-PrCO | 1 |
| 1-1498 | C—CF3 | C—H | C—CF3 | C—H | H | CF3 | CH | CH | C—SOCH3 | N | H | H | H | CF3CH2CO | 1 |
| 1-1499 | C—CF3 | C—H | C—CF3 | C—H | H | CF3 | CH | CH | C—SOCH3 | N | H | H | H | CH3SCH2CO | 1 |
| 1-1500 | C—CF3 | C—H | C—CF3 | C—H | H | CF3 | CH | CH | C—SO2CH3 | N | H | H | H | CH3CO | 1 |
| 1-1501 | C—CF3 | C—H | C—CF3 | C—H | H | CF3 | CH | CH | C—SO2CH3 | N | H | H | H | CH3CH2CO | 1 |
| 1-1502 | C—CF3 | C—H | C—CF3 | C—H | H | CF3 | CH | CH | C—SO2CH3 | N | H | H | H | cyclo-PrCO | 1 |
| 1-1503 | C—CF3 | C—H | C—CF3 | C—H | H | CF3 | CH | CH | C—SO2CH3 | N | H | H | H | CF3CH2CO | 1 |
| 1-1504 | C—CF3 | C—H | C—CF3 | C—H | H | CF3 | CH | CH | C—SCF3 | N | H | H | H | CH3CO | 1 |
| 1-1505 | C—CF3 | C—H | C—CF3 | C—H | H | CF3 | CH | CH | C—SCF3 | N | H | H | H | CH3CH2CO | 1 |
| 1-1506 | C—CF3 | C—H | C—CF3 | C—H | H | CF3 | CH | CH | C—SCF3 | N | H | H | H | nPrCO | 1 |
| 1-1507 | C—CF3 | C—H | C—CF3 | C—H | H | CF3 | CH | CH | C—SCF3 | N | H | H | H | cyclo-PrCO | 1 |
| 1-1508 | C—CF3 | C—H | C—CF3 | C—H | H | CF3 | CH | CH | C—SCF3 | N | H | H | H | cyclo-PrCH2CO | 1 |
| 1-1509 | C—CF3 | C—H | C—CF3 | C—H | H | CF3 | CH | CH | C—SCF3 | N | H | H | H | CF3CH2CO | 1 |
| 1-1510 | C—CF3 | C—H | C—CF3 | C—H | H | CF3 | CH | CH | C—SCF3 | N | H | H | H | CH3SCH2CO | 1 |
| 1-1511 | C—CF3 | C—H | C—CF3 | C—H | H | CF3 | CH | CH | C—SCF3 | N | H | H | H | CH3S(O)CH2CO | 1 |
| 1-1512 | C—CF3 | C—H | C—CF3 | C—H | H | CF3 | CH | CH | C—SCF3 | N | H | H | H | CH3SO2CH2CO | 1 |
| 1-1513 | C—CF3 | C—H | C—CF3 | C—H | H | CF3 | CH | CH | C—SCF3 | N | H | H | H | CH3CH2NHCO | 1 |
| 1-1514 | C—CF3 | C—H | C—CF3 | C—H | H | CF3 | CH | CH | C—S(O)CF3 | N | H | H | H | CH3CO | 1 |

TABLE 1-continued

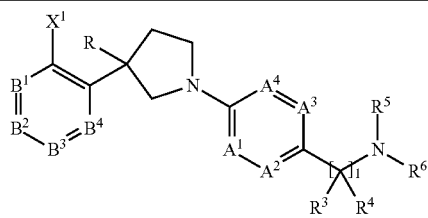

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1515 | C—CF3 | C—H | C—CF3 | C—H | H | CF3 | CH | CH | C—S(O)CF3 | N | H | H | H | CH3CH2CO | 1 |
| 1-1516 | C—CF3 | C—H | C—CF3 | C—H | H | CF3 | CH | CH | C—S(O)CF3 | N | H | H | H | nPrCO | 1 |
| 1-1517 | C—CF3 | C—H | C—CF3 | C—H | H | CF3 | CH | CH | C—S(O)CF3 | N | H | H | H | cyclo-PrCO | 1 |
| 1-1518 | C—CF3 | C—H | C—CF3 | C—H | H | CF3 | CH | CH | C—S(O)CF3 | N | H | H | H | cyclo-PrCH2CO | 1 |
| 1-1519 | C—CF3 | C—H | C—CF3 | C—H | H | CF3 | CH | CH | C—S(O)CF3 | N | H | H | H | CF3CH2CO | 1 |
| 1-1520 | C—CF3 | C—H | C—CF3 | C—H | H | CF3 | CH | CH | C—S(O)CF3 | N | H | H | H | CH3SCH2CO | 1 |
| 1-1521 | C—CF3 | C—H | C—CF3 | C—H | H | CF3 | CH | CH | C—S(O)CF3 | N | H | H | H | CH3S(O)CH2CO | 1 |
| 1-1522 | C—CF3 | C—H | C—CF3 | C—H | H | CF3 | CH | CH | C—S(O)CF3 | N | H | H | H | CH3SO2CH2CO | 1 |
| 1-1523 | C—CF3 | C—H | C—CF3 | C—H | H | CF3 | CH | CH | C—S(O)CF3 | N | H | H | H | CH3CH2NHCO | 1 |
| 1-1524 | C—CF3 | C—H | C—CF3 | C—H | H | CF3 | CH | CH | C—SO2CF3 | N | H | H | H | CH3CO | 1 |
| 1-1525 | C—CF3 | C—H | C—CF3 | C—H | H | CF3 | CH | CH | C—SO2CF3 | N | H | H | H | CH3CH2CO | 1 |
| 1-1526 | C—CF3 | C—H | C—CF3 | C—H | H | CF3 | CH | CH | C—SO2CF3 | N | H | H | H | nPrCO | 1 |
| 1-1527 | C—CF3 | C—H | C—CF3 | C—H | H | CF3 | CH | CH | C—SO2CF3 | N | H | H | H | cyclo-PrCO | 1 |
| 1-1528 | C—CF3 | C—H | C—CF3 | C—H | H | CF3 | CH | CH | C—SO2CF3 | N | H | H | H | cyclo-PrCH2CO | 1 |
| 1-1529 | C—CF3 | C—H | C—CF3 | C—H | H | CF3 | CH | CH | C—SO2CF3 | N | H | H | H | CF3CH2CO | 1 |
| 1-1530 | C—CF3 | C—H | C—CF3 | C—H | H | CF3 | CH | CH | C—SO2CF3 | N | H | H | H | CH3SCH2CO | 1 |
| 1-1531 | C—CF3 | C—H | C—CF3 | C—H | H | CF3 | CH | CH | C—SO2CF3 | N | H | H | H | CH3S(O)CH2CO | 1 |
| 1-1532 | C—CF3 | C—H | C—CF3 | C—H | H | CF3 | CH | CH | C—SO2CF3 | N | H | H | H | CH3SO2CH2CO | 1 |
| 1-1533 | C—CF3 | C—H | C—CF3 | C—H | H | CF3 | CH | CH | C—SO2CF3 | N | H | H | H | CH3CH2NHCO | 1 |
| 1-1534 | C—Cl | C—CF3 | C—Cl | C—H | H | CF3 | CH | CH | C—CF3 | N | H | H | H | CH3CO | 1 |
| 1-1535 | C—Cl | C—CF3 | C—Cl | C—H | H | CF3 | CH | CH | C—CF3 | N | H | H | H | CH3CH2CO | 1 |
| 1-1536 | C—Cl | C—CF3 | C—Cl | C—H | H | CF3 | CH | CH | C—CF3 | N | H | H | H | nPrCO | 1 |
| 1-1537 | C—Cl | C—CF3 | C—Cl | C—H | H | CF3 | CH | CH | C—CF3 | N | H | H | H | cyclo-PrCO | 1 |
| 1-1538 | C—Cl | C—CF3 | C—Cl | C—H | H | CF3 | CH | CH | C—CF3 | N | H | H | H | cyclo-PrCH2CO | 1 |
| 1-1539 | C—Cl | C—CF3 | C—Cl | C—H | H | CF3 | CH | CH | C—CF3 | N | H | H | H | CF3CH2CO | 1 |
| 1-1540 | C—Cl | C—CF3 | C—Cl | C—H | H | CF3 | CH | CH | C—CF3 | N | H | H | H | CH3SOCH2CO | 1 |
| 1-1541 | C—Cl | C—CF3 | C—Cl | C—H | H | CF3 | CH | CH | C—CF3 | N | H | H | H | CH3S(O)CH2CO | 1 |
| 1-1542 | C—Cl | C—CF3 | C—Cl | C—H | H | CF3 | CH | CH | C—CF3 | N | H | H | H | CH3SO2CH2CO | 1 |
| 1-1543 | C—Cl | C—CF3 | C—Cl | C—H | H | CF3 | CH | CH | C—CF3 | N | H | H | H | CH3CH2NHCO | 1 |
| 1-1544 | C—CF3 | C—Cl | C—Cl | C—H | H | CF3 | CH | CH | C—Cl | N | H | H | H | CH3CO | 1 |
| 1-1545 | C—CF3 | C—Cl | C—Cl | C—H | H | CF3 | CH | CH | C—Cl | N | H | H | H | CH3CH2CO | 1 |
| 1-1546 | C—CF3 | C—Cl | C—Cl | C—H | H | CF3 | CH | CH | C—Cl | N | H | H | H | nPrCO | 1 |
| 1-1547 | C—CF3 | C—Cl | C—Cl | C—H | H | CF3 | CH | CH | C—Cl | N | H | H | H | cyclo-PrCO | 1 |
| 1-1548 | C—CF3 | C—Cl | C—Cl | C—H | H | CF3 | CH | CH | C—Cl | N | H | H | H | cyclo-PrCH2CO | 1 |
| 1-1549 | C—CF3 | C—Cl | C—Cl | C—H | H | CF3 | CH | CH | C—Cl | N | H | H | H | CF3CH2CO | 1 |

TABLE 1-continued

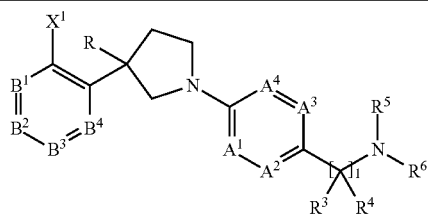

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1550 | C—CF3 | C—Cl | C—Cl | C—H | H | CF3 | CH | CH | C—Cl | N | H | H | H | CH3SCH2CO | 1 |
| 1-1551 | C—CF3 | C—Cl | C—Cl | C—H | H | CF3 | CH | CH | C—Cl | N | H | H | H | CH3S(O)CH2CO | 1 |
| 1-1552 | C—CF3 | C—Cl | C—Cl | C—H | H | CF3 | CH | CH | C—Cl | N | H | H | H | CH3SO2CH2CO | 1 |
| 1-1553 | C—CF3 | C—Cl | C—Cl | C—H | H | CF3 | CH | CH | C—Cl | N | H | H | H | CH3CH2NHCO | 1 |
| 1-1554 | C—CF3 | C—Cl | C—Cl | C—H | H | CF3 | CH | CH | C—Br | N | H | H | H | CH3CO | 1 |
| 1-1555 | C—CF3 | C—Cl | C—Cl | C—H | H | CF3 | CH | CH | C—Br | N | H | H | H | CH3CH2CO | 1 |
| 1-1556 | C—CF3 | C—Cl | C—Cl | C—H | H | CF3 | CH | CH | C—Br | N | H | H | H | nPrCO | 1 |
| 1-1557 | C—CF3 | C—Cl | C—Cl | C—H | H | CF3 | CH | CH | C—Br | N | H | H | H | cyclo-PrCO | 1 |
| 1-1558 | C—CF3 | C—Cl | C—Cl | C—H | H | CF3 | CH | CH | C—Br | N | H | H | H | cyclo-PrCH2CO | 1 |
| 1-1559 | C—CF3 | C—Cl | C—Cl | C—H | H | CF3 | CH | CH | C—Br | N | H | H | H | CF3CH2CO | 1 |
| 1-1560 | C—CF3 | C—Cl | C—Cl | C—H | H | CF3 | CH | CH | C—Br | N | H | H | H | CH3SCH2CO | 1 |
| 1-1561 | C—CF3 | C—Cl | C—Cl | C—H | H | CF3 | CH | CH | C—Br | N | H | H | H | CH3S(O)CH2CO | 1 |
| 1-1562 | C—CF3 | C—Cl | C—Cl | C—H | H | CF3 | CH | CH | C—Br | N | H | H | H | CH3SO2CH2CO | 1 |
| 1-1563 | C—CF3 | C—Cl | C—Cl | C—H | H | CF3 | CH | CH | C—Br | N | H | H | H | CH3CH2NHCO | 1 |
| 1-1564 | C—CF3 | C—Cl | C—Cl | C—H | H | CF3 | CH | CH | C—CF3 | N | H | H | H | CH3CO | 1 |
| 1-1565 | C—CF3 | C—Cl | C—Cl | C—H | H | CF3 | CH | CH | C—CF3 | N | H | H | H | CH3CH2CO | 1 |
| 1-1566 | C—CF3 | C—Cl | C—Cl | C—H | H | CF3 | CH | CH | C—CF3 | N | H | H | H | nPrCO | 1 |
| 1-1567 | C—CF3 | C—Cl | C—Cl | C—H | H | CF3 | CH | CH | C—CF3 | N | H | H | H | cyclo-PrCO | 1 |
| 1-1568 | C—CF3 | C—Cl | C—Cl | C—H | H | CF3 | CH | CH | C—CF3 | N | H | H | H | cyclo-PrCH2CO | 1 |
| 1-1569 | C—CF3 | C—Cl | C—Cl | C—H | H | CF3 | CH | CH | C—CF3 | N | H | H | H | CF3CH2CO | 1 |
| 1-1570 | C—CF3 | C—Cl | C—Cl | C—H | H | CF3 | CH | CH | C—CF3 | N | H | H | H | CH3SCH2CO | 1 |
| 1-1571 | C—CF3 | C—Cl | C—Cl | C—H | H | CF3 | CH | CH | C—CF3 | N | H | H | H | CH3S(O)CH2CO | 1 |
| 1-1572 | C—CF3 | C—Cl | C—Cl | C—H | H | CF3 | CH | CH | C—CF3 | N | H | H | H | CH3SO2CH2CO | 1 |
| 1-1573 | C—CF3 | C—Cl | C—Cl | C—H | H | CF3 | CH | CH | C—CF3 | N | H | H | H | CH3CH2NHCO | 1 |
| 1-1574 | C—Cl | N | C—Cl | C—H | H | CF3 | CH | CH | C—Cl | N | H | H | H | CH3CO | 1 |
| 1-1575 | C—Cl | N | C—Cl | C—H | H | CF3 | CH | CH | C—Cl | N | H | H | H | CH3CH2CO | 1 |
| 1-1576 | C—Cl | N | C—Cl | C—H | H | CF3 | CH | CH | C—Cl | N | H | H | H | nPrCO | 1 |
| 1-1577 | C—Cl | N | C—Cl | C—H | H | CF3 | CH | CH | C—Cl | N | H | H | H | cyclo-PrCO | 1 |
| 1-1578 | C—Cl | N | C—Cl | C—H | H | CF3 | CH | CH | C—Cl | N | H | H | H | cyclo-PrCH2CO | 1 |
| 1-1579 | C—Cl | N | C—Cl | C—H | H | CF3 | CH | CH | C—Cl | N | H | H | H | CF3CH2CO | 1 |
| 1-1580 | C—Cl | N | C—Cl | C—H | H | CF3 | CH | CH | C—Cl | N | H | H | H | CH3SCH2CO | 1 |
| 1-1581 | C—Cl | N | C—Cl | C—H | H | CF3 | CH | CH | C—Cl | N | H | H | H | CH3S(O)CH2CO | 1 |
| 1-1582 | C—Cl | N | C—Cl | C—H | H | CF3 | CH | CH | C—Cl | N | H | H | H | CH3SO2CH2CO | 1 |
| 1-1583 | C—Cl | N | C—Cl | C—H | H | CF3 | CH | CH | C—Cl | N | H | H | H | CH3CH2NHCO | 1 |
| 1-1584 | C—Cl | N | C—Cl | C—H | H | CF3 | CH | CH | C—Br | N | H | H | H | CH3CO | 1 |

TABLE 1-continued

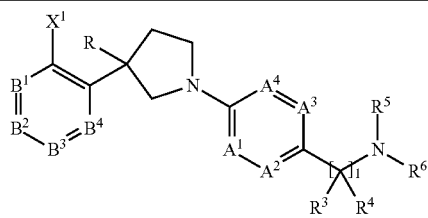

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1585 | C—Cl | N | C—Cl | C—H | H | CF3 | CH | CH | C—Br | N | H | H | H | CH3CH2CO | 1 |
| 1-1586 | C—Cl | N | C—Cl | C—H | H | CF3 | CH | CH | C—Br | N | H | H | H | nPrCO | 1 |
| 1-1587 | C—Cl | N | C—Cl | C—H | H | CF3 | CH | CH | C—Br | N | H | H | H | cyclo-PrCO | 1 |
| 1-1588 | C—Cl | N | C—Cl | C—H | H | CF3 | CH | CH | C—Br | N | H | H | H | cyclo-PrCH2CO | 1 |
| 1-1589 | C—Cl | N | C—Cl | C—H | H | CF3 | CH | CH | C—Br | N | H | H | H | CF3CH2CO | 1 |
| 1-1590 | C—Cl | N | C—Cl | C—H | H | CF3 | CH | CH | C—Br | N | H | H | H | CH3SCH2CO | 1 |
| 1-1591 | C—Cl | N | C—Cl | C—H | H | CF3 | CH | CH | C—Br | N | H | H | H | CH3S(O)CH2CO | 1 |
| 1-1592 | C—Cl | N | C—Cl | C—H | H | CF3 | CH | CH | C—Br | N | H | H | H | CH3SO2CH2CO | 1 |
| 1-1593 | C—Cl | N | C—Cl | C—H | H | CF3 | CH | CH | C—Br | N | H | H | H | CH3CH2NHCO | 1 |
| 1-1594 | C—Cl | N | C—Cl | C—H | H | CF3 | CH | CH | C—CF3 | N | H | H | H | CH3CO | 1 |
| 1-1595 | C—Cl | N | C—Cl | C—H | H | CF3 | CH | CH | C—CF3 | N | H | H | H | CH3CH2CO | 1 |
| 1-1596 | C—Cl | N | C—Cl | C—H | H | CF3 | CH | CH | C—CF3 | N | H | H | H | nPrCO | 1 |
| 1-1597 | C—Cl | N | C—Cl | C—H | H | CF3 | CH | CH | C—CF3 | N | H | H | H | cyclo-PrCO | 1 |
| 1-1598 | C—Cl | N | C—Cl | C—H | H | CF3 | CH | CH | C—CF3 | N | H | H | H | cyclo-PrCH2CO | 1 |
| 1-1599 | C—Cl | N | C—Cl | C—H | H | CF3 | CH | CH | C—CF3 | N | H | H | H | CF3CH2CO | 1 |
| 1-1600 | C—Cl | N | C—Cl | C—H | H | CF3 | CH | CH | C—CF3 | N | H | H | H | CH3SCH2CO | 1 |
| 1-1601 | C—Cl | N | C—Cl | C—H | H | CF3 | CH | CH | C—CF3 | N | H | H | H | CH3S(O)CH2CO | 1 |
| 1-1602 | C—Cl | N | C—Cl | C—H | H | CF3 | CH | CH | C—CF3 | N | H | H | H | CH3SO2CH2CO | 1 |
| 1-1603 | C—Cl | N | C—Cl | C—H | H | CF3 | CH | CH | C—CF3 | N | H | H | H | CH3CH2NHCO | 1 |
| 1-1604 | C—CF3 | C—H | C—H | N | H | CF3 | CH | CH | C—CF3 | N | H | H | H | CH3CO | 1 |
| 1-1605 | C—CF3 | C—H | C—H | N | H | CF3 | CH | CH | C—CF3 | N | H | H | H | CH3CH2CO | 1 |
| 1-1606 | C—CF3 | C—H | C—H | N | H | CF3 | CH | CH | C—CF3 | N | H | H | H | nPrCO | 1 |
| 1-1607 | C—CF3 | C—H | C—H | N | H | CF3 | CH | CH | C—CF3 | N | H | H | H | cyclo-PrCO | 1 |
| 1-1608 | C—CF3 | C—H | C—H | N | H | CF3 | CH | CH | C—CF3 | N | H | H | H | cyclo-PrCH2CO | 1 |
| 1-1609 | C—CF3 | C—H | C—H | N | H | CF3 | CH | CH | C—CF3 | N | H | H | H | CF3CH2CO | 1 |
| 1-1610 | C—CF3 | C—H | C—H | N | H | CF3 | CH | CH | C—CF3 | N | H | H | H | CH3SCH2CO | 1 |
| 1-1611 | C—CF3 | C—H | C—H | N | H | CF3 | CH | CH | C—CF3 | N | H | H | H | CH3S(O)CH2CO | 1 |
| 1-1612 | C—CF3 | C—H | C—H | N | H | CF3 | CH | CH | C—CF3 | N | H | H | H | CH3SO2CH2CO | 1 |
| 1-1613 | C—CF3 | C—H | C—H | N | H | CF3 | CH | CH | C—CF3 | N | H | H | H | CH3CH2NHCO | 1 |
| 1-1614 | C—H | C—H | C—CF3 | N | H | CF3 | CH | CH | C—CF3 | N | H | H | H | CH3CO | 1 |
| 1-1615 | C—H | C—H | C—CF3 | N | H | CF3 | CH | CH | C—CF3 | N | H | H | H | CH3CH2CO | 1 |
| 1-1616 | C—H | C—H | C—CF3 | N | H | CF3 | CH | CH | C—CF3 | N | H | H | H | nPrCO | 1 |
| 1-1617 | C—H | C—H | C—CF3 | N | H | CF3 | CH | CH | C—CF3 | N | H | H | H | cyclo-PrCO | 1 |
| 1-1618 | C—H | C—H | C—CF3 | N | H | CF3 | CH | CH | C—CF3 | N | H | H | H | cyclo-PrCH2CO | 1 |
| 1-1619 | C—H | C—H | C—CF3 | N | H | CF3 | CH | CH | C—CF3 | N | H | H | H | CF3CH2CO | 1 |

TABLE 1-continued

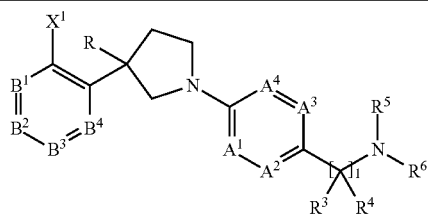

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1620 | C—H | C—H | C—CF3 | N | H | CF3 | CH | CH | C—CF3 | N | H | H | H | CH3SCH2CO | 1 |
| 1-1621 | C—H | C—H | C—CF3 | N | H | CF3 | CH | CH | C—CF3 | N | H | H | H | CH3S(O)CH2CO | 1 |
| 1-1622 | C—H | C—H | C—CF3 | N | H | CF3 | CH | CH | C—CF3 | N | H | H | H | CH3SO2CH2CO | 1 |
| 1-1623 | C—H | C—H | C—CF3 | N | H | CF3 | CH | CH | C—CF3 | N | H | H | H | CH3CH2NHCO | 1 |
| 1-1624 | C—CF3 | N | C—H | C—H | H | CF3 | CH | CH | C—CF3 | N | H | H | H | CH3CO | 1 |
| 1-1625 | C—CF3 | N | C—H | C—H | H | CF3 | CH | CH | C—CF3 | N | H | H | H | CH3CH2CO | 1 |
| 1-1626 | C—CF3 | N | C—H | C—H | H | CF3 | CH | CH | C—CF3 | N | H | H | H | nPrCO | 1 |
| 1-1627 | C—CF3 | N | C—H | C—H | H | CF3 | CH | CH | C—CF3 | N | H | H | H | cyclo-PrCO | 1 |
| 1-1628 | C—CF3 | N | C—H | C—H | H | CF3 | CH | CH | C—CF3 | N | H | H | H | cyclo-PrCH2CO | 1 |
| 1-1629 | C—CF3 | N | C—H | C—H | H | CF3 | CH | CH | C—CF3 | N | H | H | H | CF3CH2CO | 1 |
| 1-1630 | C—CF3 | N | C—H | C—H | H | CF3 | CH | CH | C—CF3 | N | H | H | H | CH3SCH2CO | 1 |
| 1-1631 | C—CF3 | N | C—H | C—H | H | CF3 | CH | CH | C—CF3 | N | H | H | H | CH3S(O)CH2CO | 1 |
| 1-1632 | C—CF3 | N | C—H | C—H | H | CF3 | CH | CH | C—CF3 | N | H | H | H | CH3SO2CH2CO | 1 |
| 1-1633 | C—CF3 | N | C—H | C—H | H | CF3 | CH | CH | C—CF3 | N | H | H | H | CH3CH2NHCO | 1 |
| 1-1634 | C—CF3 | N | C—CF3 | C—H | H | CF3 | CH | CH | C—Cl | N | H | H | H | CH3CO | 1 |
| 1-1635 | C—CF3 | N | C—CF3 | C—H | H | CF3 | CH | CH | C—Cl | N | H | H | H | CH3CH2CO | 1 |
| 1-1636 | C—CF3 | N | C—CF3 | C—H | H | CF3 | CH | CH | C—Cl | N | H | H | H | nPrCO | 1 |
| 1-1637 | C—CF3 | N | C—CF3 | C—H | H | CF3 | CH | CH | C—Cl | N | H | H | H | cyclo-PrCO | 1 |
| 1-1638 | C—CF3 | N | C—CF3 | C—H | H | CF3 | CH | CH | C—Cl | N | H | H | H | cyclo-PrCH2CO | 1 |
| 1-1639 | C—CF3 | N | C—CF3 | C—H | H | CF3 | CH | CH | C—Cl | N | H | H | H | CF3CH2CO | 1 |
| 1-1640 | C—CF3 | N | C—CF3 | C—H | H | CF3 | CH | CH | C—Cl | N | H | H | H | CH3SCH2CO | 1 |
| 1-1641 | C—CF3 | N | C—CF3 | C—H | H | CF3 | CH | CH | C—Cl | N | H | H | H | CH3S(O)CH2CO | 1 |
| 1-1642 | C—CF3 | N | C—CF3 | C—H | H | CF3 | CH | CH | C—Cl | N | H | H | H | CH3SO2CH2CO | 1 |
| 1-1643 | C—CF3 | N | C—CF3 | C—H | H | CF3 | CH | CH | C—Cl | N | H | H | H | CH3CH2NHCO | 1 |
| 1-1644 | C—CF3 | N | C—CF3 | C—H | H | CF3 | CH | CH | C—Br | N | H | H | H | CH3CO | 1 |
| 1-1645 | C—CF3 | N | C—CF3 | C—H | H | CF3 | CH | CH | C—Br | N | H | H | H | CH3CH2CO | 1 |
| 1-1646 | C—CF3 | N | C—CF3 | C—H | H | CF3 | CH | CH | C—Br | N | H | H | H | nPrCO | 1 |
| 1-1647 | C—CF3 | N | C—CF3 | C—H | H | CF3 | CH | CH | C—Br | N | H | H | H | cyclo-PrCO | 1 |
| 1-1648 | C—CF3 | N | C—CF3 | C—H | H | CF3 | CH | CH | C—Br | N | H | H | H | cyclo-PrCH2CO | 1 |
| 1-1649 | C—CF3 | N | C—CF3 | C—H | H | CF3 | CH | CH | C—Br | N | H | H | H | CF3CH2CO | 1 |
| 1-1650 | C—CF3 | N | C—CF3 | C—H | H | CF3 | CH | CH | C—Br | N | H | H | H | CH3SCH2CO | 1 |
| 1-1651 | C—CF3 | N | C—CF3 | C—H | H | CF3 | CH | CH | C—Br | N | H | H | H | CH3S(O)CH2CO | 1 |
| 1-1652 | C—CF3 | N | C—CF3 | C—H | H | CF3 | CH | CH | C—Br | N | H | H | H | CH3SO2CH2CO | 1 |
| 1-1653 | C—CF3 | N | C—CF3 | C—H | H | CF3 | CH | CH | C—Br | N | H | H | H | CH3CH2NHCO | 1 |
| 1-1654 | C—CF3 | N | C—CF3 | C—H | H | CF3 | CH | CH | C—CF3 | N | H | H | H | CH3CO | 1 |

TABLE 1-continued

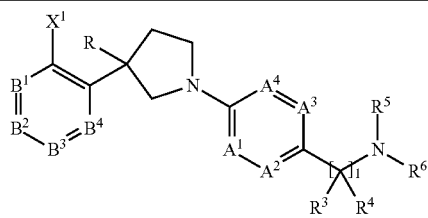

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1655 | C—CF3 | N | C—CF3 | C—H | H | CF3 | CH | CH | C—CF3 | N | H | H | H | CH3CH2CO | 1 |
| 1-1656 | C—CF3 | N | C—CF3 | C—H | H | CF3 | CH | CH | C—CF3 | N | H | H | H | nPrCO | 1 |
| 1-1657 | C—CF3 | N | C—CF3 | C—H | H | CF3 | CH | CH | C—CF3 | N | H | H | H | cyclo-PrCO | 1 |
| 1-1658 | C—CF3 | N | C—CF3 | C—H | H | CF3 | CH | CH | C—CF3 | N | H | H | H | cyclo-PrCH2CO | 1 |
| 1-1659 | C—CF3 | N | C—CF3 | C—H | H | CF3 | CH | CH | C—CF3 | N | H | H | H | CF3CH2CO | 1 |
| 1-1660 | C—CF3 | N | C—CF3 | C—H | H | CF3 | CH | CH | C—CF3 | N | H | H | H | CH3SCH2CO | 1 |
| 1-1661 | C—CF3 | N | C—CF3 | C—H | H | CF3 | CH | CH | C—CF3 | N | H | H | H | CH3S(O)CH2CO | 1 |
| 1-1662 | C—CF3 | N | C—CF3 | C—H | H | CF3 | CH | CH | C—CF3 | N | H | H | H | CH3SO2CH2CO | 1 |
| 1-1663 | C—CF3 | N | C—CF3 | C—H | H | CF3 | CH | CH | C—CF3 | N | H | H | H | CH3CH2NHCO | 1 |
| 1-1664 | C—CF3 | C—H | C—CF3 | N | H | CF3 | CH | CH | C—Cl | N | H | H | H | CH3CO | 1 |
| 1-1665 | C—CF3 | C—H | C—CF3 | N | H | CF3 | CH | CH | C—Cl | N | H | H | H | CH3CH2CO | 1 |
| 1-1666 | C—CF3 | C—H | C—CF3 | N | H | CF3 | CH | CH | C—Cl | N | H | H | H | nPrCO | 1 |
| 1-1667 | C—CF3 | C—H | C—CF3 | N | H | CF3 | CH | CH | C—Cl | N | H | H | H | cyclo-PrCO | 1 |
| 1-1668 | C—CF3 | C—H | C—CF3 | N | H | CF3 | CH | CH | C—Cl | N | H | H | H | cyclo-PrCH2CO | 1 |
| 1-1669 | C—CF3 | C—H | C—CF3 | N | H | CF3 | CH | CH | C—Cl | N | H | H | H | CF3CH2CO | 1 |
| 1-1670 | C—CF3 | C—H | C—CF3 | N | H | CF3 | CH | CH | C—Cl | N | H | H | H | CH3SCH2CO | 1 |
| 1-1671 | C—CF3 | C—H | C—CF3 | N | H | CF3 | CH | CH | C—Cl | N | H | H | H | CH3S(O)CH2CO | 1 |
| 1-1672 | C—CF3 | C—H | C—CF3 | N | H | CF3 | CH | CH | C—Cl | N | H | H | H | CH3SO2CH2CO | 1 |
| 1-1673 | C—CF3 | C—H | C—CF3 | N | H | CF3 | CH | CH | C—Cl | N | H | H | H | CH3CH2NHCO | 1 |
| 1-1674 | C—CF3 | C—H | C—CF3 | N | H | CF3 | CH | CH | C—Br | N | H | H | H | CH3CO | 1 |
| 1-1675 | C—CF3 | C—H | C—CF3 | N | H | CF3 | CH | CH | C—Br | N | H | H | H | CH3CH2CO | 1 |
| 1-1676 | C—CF3 | C—H | C—CF3 | N | H | CF3 | CH | CH | C—Br | N | H | H | H | nPrCO | 1 |
| 1-1677 | C—CF3 | C—H | C—CF3 | N | H | CF3 | CH | CH | C—Br | N | H | H | H | cyclo-PrCO | 1 |
| 1-1678 | C—CF3 | C—H | C—CF3 | N | H | CF3 | CH | CH | C—Br | N | H | H | H | cyclo-PrCH2CO | 1 |
| 1-1679 | C—CF3 | C—H | C—CF3 | N | H | CF3 | CH | CH | C—Br | N | H | H | H | CF3CH2CO | 1 |
| 1-1680 | C—CF3 | C—H | C—CF3 | N | H | CF3 | CH | CH | C—Br | N | H | H | H | CH3SCH2CO | 1 |
| 1-1681 | C—CF3 | C—H | C—CF3 | N | H | CF3 | CH | CH | C—Br | N | H | H | H | CH3S(O)CH2CO | 1 |
| 1-1682 | C—CF3 | C—H | C—CF3 | N | H | CF3 | CH | CH | C—Br | N | H | H | H | CH3SO2CH2CO | 1 |
| 1-1683 | C—CF3 | C—H | C—CF3 | N | H | CF3 | CH | CH | C—Br | N | H | H | H | CH3CH2NHCO | 1 |
| 1-1684 | C—CF3 | C—H | C—CF3 | N | H | CF3 | CH | CH | C—CF3 | N | H | H | H | CH3CO | 1 |
| 1-1685 | C—CF3 | C—H | C—CF3 | N | H | CF3 | CH | CH | C—CF3 | N | H | H | H | CH3CH2CO | 1 |
| 1-1686 | C—CF3 | C—H | C—CF3 | N | H | CF3 | CH | CH | C—CF3 | N | H | H | H | nPrCO | 1 |
| 1-1687 | C—CF3 | C—H | C—CF3 | N | H | CF3 | CH | CH | C—CF3 | N | H | H | H | cyclo-PrCO | 1 |
| 1-1688 | C—CF3 | C—H | C—CF3 | N | H | CF3 | CH | CH | C—CF3 | N | H | H | H | cyclo-PrCH2CO | 1 |
| 1-1689 | C—CF3 | C—H | C—CF3 | N | H | CF3 | CH | CH | C—CF3 | N | H | H | H | CF3CH2CO | 1 |

TABLE 1-continued

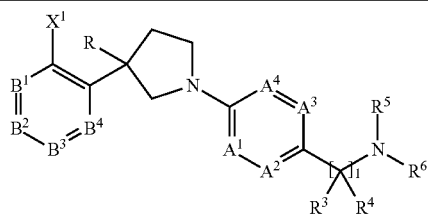

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1690 | C—CF3 | C—H | C—CF3 | N | H | CF3 | CH | CH | C—CF3 | N | H | H | H | CH3SCH2CO | 1 |
| 1-1691 | C—CF3 | C—H | C—CF3 | N | H | CF3 | CH | CH | C—CF3 | N | H | H | H | CH3S(O)CH2CO | 1 |
| 1-1692 | C—CF3 | C—H | C—CF3 | N | H | CF3 | CH | CH | C—CF3 | N | H | H | H | CH3SO2CH2CO | 1 |
| 1-1693 | C—CF3 | C—H | C—CF3 | N | H | CF3 | CH | CH | C—CF3 | N | H | H | H | CH3CH2NHCO | 1 |
| 1-1694 | C—Cl | C—Cl | C—Cl | C—H | H | CF3 | CH | CH | C—SCH3 | N | H | H | H | CF3CH2CO | 1 |
| 1-1695 | C—CF3 | C—H | C—CF3 | C—H | H | CF3 | CH | CH | C—SCH3 | N | H | H | H | CF3CH2CO | 1 |
| 1-1696 | C—Cl | C—H | C—Cl | C—H | H | CF3 | CH | CH | C—SCH3 | N | H | H | H | CH3SCH2CO | 1 |
| 1-1697 | C—Cl | C—H | C—Cl | C—H | H | CF3 | CH | CH | C—SCH3 | N | H | H | H | CH3S(O)CH2CO | 1 |
| 1-1698 | C—Cl | C—H | C—Cl | C—H | H | CF3 | CH | CH | C—SCH3 | N | H | H | H | CH3SO2CH2CO | 1 |
| 1-1699 | C—Cl | C—Cl | C—Cl | C—H | H | CF3 | CH | CH | C—SCH3 | N | H | H | H | CH3SCH2CO | 1 |
| 1-1700 | C—Cl | C—Cl | C—Cl | C—H | H | CF3 | CH | CH | C—SCH3 | N | H | H | H | CH3S(O)CH2CO | 1 |
| 1-1701 | C—Cl | C—Cl | C—Cl | C—H | H | CF3 | CH | CH | C—SCH3 | N | H | H | H | CH3SO2CH2CO | 1 |
| 1-1702 | C—CF3 | C—H | C—CF3 | C—H | H | CF3 | CH | CH | C—SCH3 | N | H | H | H | CH3SCH2CO | 1 |
| 1-1703 | C—CF3 | C—H | C—CF3 | C—H | H | CF3 | CH | CH | C—SCH3 | N | H | H | H | CH3S(O)CH2CO | 1 |
| 1-1704 | C—CF3 | C—H | C—CF3 | C—H | H | CF3 | CH | CH | C—SCH3 | N | H | H | H | CH3SO2CH2CO | 1 |
| 1-1705 | C—Cl | C—H | C—Cl | C—H | H | CF3 | CH | CH | C-cyclo-Pr | CH | H | H | H | CH3CO | 1 |
| 1-1706 | C—Cl | C—H | C—Cl | C—H | H | CF3 | CH | CH | C-cyclo-Pr | CH | H | H | H | n-PrCO | 1 |
| 1-1707 | C—Cl | C—H | C—Cl | C—H | H | CF3 | CH | CH | C-cyclo-Pr | CH | H | H | H | cyclo-PrCO | 1 |
| 1-1708 | C—Cl | C—H | C—Cl | C—H | H | CF3 | CH | CH | C-cyclo-Pr | CH | H | H | H | cyclo-PrCH2CO | 1 |
| 1-1709 | C—Cl | C—H | C—Cl | C—H | H | CF3 | CH | CH | C-cyclo-Pr | CH | H | H | H | CH3SCH2CO | 1 |
| 1-1710 | C—Cl | C—H | C—Cl | C—H | H | CF3 | CH | CH | C-cyclo-Pr | CH | H | H | H | CH3S(O)CH2CO | 1 |
| 1-1711 | C—Cl | C—H | C—Cl | C—H | H | CF3 | CH | CH | C-cyclo-Pr | CH | H | H | H | CH3SO2CH2CO | 1 |
| 1-1712 | C—Cl | C—H | C—Cl | C—H | H | CF3 | CH | CH | C-cyclo-Pr | CH | H | H | H | CH3CH2NHCO | 1 |
| 1-1713 | C—Cl | C—Cl | C—Cl | C—H | H | CF3 | CH | CH | C-cyclo-Pr | CH | H | H | H | CH3CO | 1 |
| 1-1714 | C—Cl | C—Cl | C—Cl | C—H | H | CF3 | CH | CH | C-cyclo-Pr | CH | H | H | H | n-PrCO | 1 |
| 1-1715 | C—Cl | C—Cl | C—Cl | C—H | H | CF3 | CH | CH | C-cyclo-Pr | CH | H | H | H | cyclo-PrCO | 1 |
| 1-1716 | C—Cl | C—Cl | C—Cl | C—H | H | CF3 | CH | CH | C-cyclo-Pr | CH | H | H | H | cyclo-PrCH2CO | 1 |
| 1-1717 | C—Cl | C—Cl | C—Cl | C—H | H | CF3 | CH | CH | C-cyclo-Pr | CH | H | H | H | CH3SCH2CO | 1 |
| 1-1718 | C—Cl | C—Cl | C—Cl | C—H | H | CF3 | CH | CH | C-cyclo-Pr | CH | H | H | H | CH3S(O)CH2CO | 1 |
| 1-1719 | C—Cl | C—Cl | C—Cl | C—H | H | CF3 | CH | CH | C-cyclo-Pr | CH | H | H | H | CH3SO2CH2CO | 1 |
| 1-1720 | C—Cl | C—Cl | C—Cl | C—H | H | CF3 | CH | CH | C-cyclo-Pr | CH | H | H | H | CH3CH2NHCO | 1 |
| 1-1721 | C—CF3 | C—H | C—CF3 | C—H | H | CF3 | CH | CH | C-cyclo-Pr | CH | H | H | H | CH3CO | 1 |
| 1-1722 | C—CF3 | C—H | C—CF3 | C—H | H | CF3 | CH | CH | C-cyclo-Pr | CH | H | H | H | n-PrCO | 1 |
| 1-1723 | C—CF3 | C—H | C—CF3 | C—H | H | CF3 | CH | CH | C-cyclo-Pr | CH | H | H | H | cyclo-PrCO | 1 |
| 1-1724 | C—CF3 | C—H | C—CF3 | C—H | H | CF3 | CH | CH | C-cyclo-Pr | CH | H | H | H | cyclo-PrCH2CO | 1 |

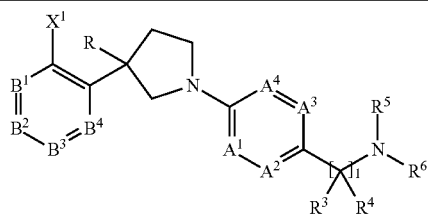

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1725 | C—CF3 | C—H | C—CF3 | C—H | H | CF3 | CH | CH | C-cyclo-Pr | CH | H | H | H | CH3SCH2CO | 1 |
| 1-1726 | C—CF3 | C—H | C—CF3 | C—H | H | CF3 | CH | CH | C-cyclo-Pr | CH | H | H | H | CH3S(O)CH2CO | 1 |
| 1-1727 | C—CF3 | C—H | C—CF3 | C—H | H | CF3 | CH | CH | C-cyclo-Pr | CH | H | H | H | CH3SO2CH2CO | 1 |
| 1-1728 | C—CF3 | C—H | C—CF3 | C—H | H | CF3 | CH | CH | C-cyclo-Pr | CH | H | H | H | CH3CH2NHCO | 1 |
| 1-1730 | C—Cl | C—H | C—Cl | C—H | H | CF3 | CH | CH | C—CH3 | N | H | H | H | CH3CH2CO | 1 |
| 1-1731 | C—Cl | C—H | C—Cl | C—H | H | CF3 | CH | CH | C—CH3 | N | H | H | H | n-PrCO | 1 |
| 1-1732 | C—Cl | C—H | C—Cl | C—H | H | CF3 | CH | CH | C—CH3 | N | H | H | H | cyclo-PrCO | 1 |
| 1-1733 | C—Cl | C—H | C—Cl | C—H | H | CF3 | CH | CH | C—CH3 | N | H | H | H | cyclo-PrCH2CO | 1 |
| 1-1734 | C—Cl | C—H | C—Cl | C—H | H | CF3 | CH | CH | C—CH3 | N | H | H | H | CF3CH2CO | 1 |
| 1-1735 | C—Cl | C—H | C—Cl | C—H | H | CF3 | CH | CH | C—CH3 | N | H | H | H | CH3SCH2CO | 1 |
| 1-1736 | C—Cl | C—H | C—Cl | C—H | H | CF3 | CH | CH | C—CH3 | N | H | H | H | CH3S(O)CH2CO | 1 |
| 1-1737 | C—Cl | C—H | C—Cl | C—H | H | CF3 | CH | CH | C—CH3 | N | H | H | H | CH3SO2CH2CO | 1 |
| 1-1738 | C—Cl | C—H | C—Cl | C—H | H | CF3 | CH | CH | C—CH3 | N | H | H | H | CH3CH2NHCO | 1 |
| 1-1739 | C—Cl | C—Cl | C—Cl | C—H | H | CF3 | CH | CH | C—CH3 | N | H | H | H | CH3CO | 1 |
| 1-1740 | C—Cl | C—Cl | C—Cl | C—H | H | CF3 | CH | CH | C—CH3 | N | H | H | H | CH3CH2CO | 1 |
| 1-1741 | C—Cl | C—Cl | C—Cl | C—H | H | CF3 | CH | CH | C—CH3 | N | H | H | H | nPrCO | 1 |
| 1-1742 | C—Cl | C—Cl | C—Cl | C—H | H | CF3 | CH | CH | C—CH3 | N | H | H | H | cyclo-PrCO | 1 |
| 1-1743 | C—Cl | C—Cl | C—Cl | C—H | H | CF3 | CH | CH | C—CH3 | N | H | H | H | cyclo-PrCH2CO | 1 |
| 1-1744 | C—Cl | C—Cl | C—Cl | C—H | H | CF3 | CH | CH | C—CH3 | N | H | H | H | CF3CH2CO | 1 |
| 1-1745 | C—Cl | C—Cl | C—Cl | C—H | H | CF3 | CH | CH | C—CH3 | N | H | H | H | CH3SCH2CO | 1 |
| 1-1746 | C—Cl | C—Cl | C—Cl | C—H | H | CF3 | CH | CH | C—CH3 | N | H | H | H | CH3S(O)CH2CO | 1 |
| 1-1747 | C—Cl | C—Cl | C—Cl | C—H | H | CF3 | CH | CH | C—CH3 | N | H | H | H | CH3SO2CH2CO | 1 |
| 1-1748 | C—Cl | C—Cl | C—Cl | C—H | H | CF3 | CH | CH | C—CH3 | N | H | H | H | CH3CH2NHCO | 1 |
| 1-1749 | C—CF3 | C—H | C—H | C—H | H | CF3 | CH | CH | C—CH3 | N | H | H | H | CH3CO | 1 |
| 1-1750 | C—CF3 | C—H | C—H | C—H | H | CF3 | CH | CH | C—CH3 | N | H | H | H | CH3CH2CO | 1 |
| 1-1751 | C—CF3 | C—H | C—H | C—H | H | CF3 | CH | CH | C—CH3 | N | H | H | H | nPrCO | 1 |
| 1-1752 | C—CF3 | C—H | C—H | C—H | H | CF3 | CH | CH | C—CH3 | N | H | H | H | cyclo-PrCO | 1 |
| 1-1753 | C—CF3 | C—H | C—H | C—H | H | CF3 | CH | CH | C—CH3 | N | H | H | H | cyclo-PrCH2CO | 1 |
| 1-1754 | C—CF3 | C—H | C—H | C—H | H | CF3 | CH | CH | C—CH3 | N | H | H | H | CF3CH2CO | 1 |
| 1-1755 | C—CF3 | C—H | C—H | C—H | H | CF3 | CH | CH | C—CH3 | N | H | H | H | CH3SCH2CO | 1 |
| 1-1756 | C—CF3 | C—H | C—H | C—H | H | CF3 | CH | CH | C—CH3 | N | H | H | H | CH3S(O)CH2CO | 1 |
| 1-1757 | C—CF3 | C—H | C—H | C—H | H | CF3 | CH | CH | C—CH3 | N | H | H | H | CH3SO2CH2CO | 1 |
| 1-1758 | C—CF3 | C—H | C—H | C—H | H | CF3 | CH | CH | C—CH3 | N | H | H | H | CH3CH2NHCO | 1 |
| 1-1759 | C—CF3 | C—H | C—CF3 | C—H | H | CF3 | CH | CH | C—CH3 | N | H | H | H | CH3CO | 1 |
| 1-1760 | C—CF3 | C—H | C—CF3 | C—H | H | CF3 | CH | CH | C—CH3 | N | H | H | H | CH3CH2CO | 1 |

TABLE 1-continued

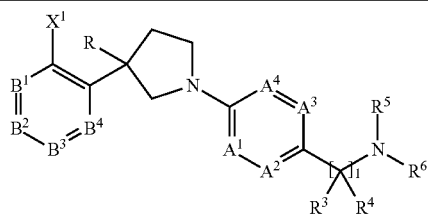

| Ex.-No. | $B^1$ | $B^2$ | $B^3$ | $B^4$ | $X^1$ | R | $A^1$ | $A^2$ | $A^3$ | $A^4$ | $R^3$ | $R^4$ | $R^5$ | $R^6$ | 1 |
|---|---|---|---|---|---|---|---|---|---|---|---|---|---|---|---|
| 1-1761 | C—CF3 | C—H | C—CF3 | C—H | H | CF3 | CH | CH | C—CH3 | N | H | H | H | nPrCO | 1 |
| 1-1762 | C—CF3 | C—H | C—CF3 | C—H | H | CF3 | CH | CH | C—CH3 | N | H | H | H | cyclo-PrCO | 1 |
| 1-1763 | C—CF3 | C—H | C—CF3 | C—H | H | CF3 | CH | CH | C—CH3 | N | H | H | H | cyclo-PrCH2CO | 1 |
| 1-1764 | C—CF3 | C—H | C—CF3 | C—H | H | CF3 | CH | CH | C—CH3 | N | H | H | H | CF3CH2CO | 1 |
| 1-1765 | C—CF3 | C—H | C—CF3 | C—H | H | CF3 | CH | CH | C—CH3 | N | H | H | H | CH3SCH2CO | 1 |
| 1-1766 | C—CF3 | C—H | C—CF3 | C—H | H | CF3 | CH | CH | C—CH3 | N | H | H | H | CH3S(O)CH2CO | 1 |
| 1-1767 | C—CF3 | C—H | C—CF3 | C—H | H | CF3 | CH | CH | C—CH3 | N | H | H | H | CH3SO2CH2CO | 1 |
| 1-1768 | C—CF3 | C—H | C—CF3 | C—H | H | CF3 | CH | CH | C—CH3 | N | H | H | H | CH3CH2NHCO | 1 |
| 1-1769 | C—Cl | C—H | C—Cl | C—H | H | CF3 | CH | CH | C-cyclo-Pr | N | H | H | H | CH3CO | 1 |
| 1-1770 | C—Cl | C—H | C—Cl | C—H | H | CF3 | CH | CH | C-cyclo-Pr | N | H | H | H | CH3CH2CO | 1 |
| 1-1771 | C—Cl | C—H | C—Cl | C—H | H | CF3 | CH | CH | C-cyclo-Pr | N | H | H | H | nPrCO | 1 |
| 1-1772 | C—Cl | C—H | C—Cl | C—H | H | CF3 | CH | CH | C-cyclo-Pr | N | H | H | H | cyclo-PrCO | 1 |
| 1-1773 | C—Cl | C—H | C—Cl | C—H | H | CF3 | CH | CH | C-cyclo-Pr | N | H | H | H | cyclo-PrCH2CO | 1 |
| 1-1774 | C—Cl | C—H | C—Cl | C—H | H | CF3 | CH | CH | C-cyclo-Pr | N | H | H | H | CF3CH2CO | 1 |
| 1-1775 | C—Cl | C—H | C—Cl | C—H | H | CF3 | CH | CH | C-cyclo-Pr | N | H | H | H | CH3SCH2CO | 1 |
| 1-1776 | C—Cl | C—H | C—Cl | C—H | H | CF3 | CH | CH | C-cyclo-Pr | N | H | H | H | CH3S(O)CH2CO | 1 |
| 1-1777 | C—Cl | C—H | C—Cl | C—H | H | CF3 | CH | CH | C-cyclo-Pr | N | H | H | H | CH3SO2CH2CO | 1 |
| 1-1778 | C—Cl | C—H | C—Cl | C—H | H | CF3 | CH | CH | C-cyclo-Pr | N | H | H | H | CH3CH2NHCO | 1 |
| 1-1779 | C—Cl | C—Cl | C—Cl | C—H | H | CF3 | CH | CH | C-cyclo-Pr | N | H | H | H | CH3CO | 1 |
| 1-1780 | C—Cl | C—Cl | C—Cl | C—H | H | CF3 | CH | CH | C-cyclo-Pr | N | H | H | H | CH3CH2CO | 1 |
| 1-1781 | C—Cl | C—Cl | C—Cl | C—H | H | CF3 | CH | CH | C-cyclo-Pr | N | H | H | H | nPrCO | 1 |
| 1-1782 | C—Cl | C—Cl | C—Cl | C—H | H | CF3 | CH | CH | C-cyclo-Pr | N | H | H | H | cyclo-PrCO | 1 |
| 1-1783 | C—Cl | C—Cl | C—Cl | C—H | H | CF3 | CH | CH | C-cyclo-Pr | N | H | H | H | cyclo-PrCH2CO | 1 |
| 1-1784 | C—Cl | C—Cl | C—Cl | C—H | H | CF3 | CH | CH | C-cyclo-Pr | N | H | H | H | CF3CH2CO | 1 |
| 1-1785 | C—Cl | C—Cl | C—Cl | C—H | H | CF3 | CH | CH | C-cyclo-Pr | N | H | H | H | CH3SCH2CO | 1 |
| 1-1786 | C—Cl | C—Cl | C—Cl | C—H | H | CF3 | CH | CH | C-cyclo-Pr | N | H | H | H | CH3S(O)CH2CO | 1 |
| 1-1787 | C—Cl | C—Cl | C—Cl | C—H | H | CF3 | CH | CH | C-cyclo-Pr | N | H | H | H | CH3SO2CH2CO | 1 |
| 1-1788 | C—Cl | C—Cl | C—Cl | C—H | H | CF3 | CH | CH | C-cyclo-Pr | N | H | H | H | CH3CH2NHCO | 1 |
| 1-1789 | C—CF3 | C—H | C—H | C—H | H | CF3 | CH | CH | C-cyclo-Pr | N | H | H | H | CH3CO | 1 |
| 1-1790 | C—CF3 | C—H | C—H | C—H | H | CF3 | CH | CH | C-cyclo-Pr | N | H | H | H | CH3CH2CO | 1 |
| 1-1791 | C—CF3 | C—H | C—H | C—H | H | CF3 | CH | CH | C-cyclo-Pr | N | H | H | H | nPrCO | 1 |
| 1-1792 | C—CF3 | C—H | C—H | C—H | H | CF3 | CH | CH | C-cyclo-Pr | N | H | H | H | cyclo-PrCO | 1 |
| 1-1793 | C—CF3 | C—H | C—H | C—H | H | CF3 | CH | CH | C-cyclo-Pr | N | H | H | H | cyclo-PrCH2CO | 1 |
| 1-1794 | C—CF3 | C—H | C—H | C—H | H | CF3 | CH | CH | C-cyclo-Pr | N | H | H | H | CF3CH2CO | 1 |
| 1-1795 | C—CF3 | C—H | C—H | C—H | H | CF3 | CH | CH | C-cyclo-Pr | N | H | H | H | CH3SCH2CO | 1 |

TABLE 1-continued

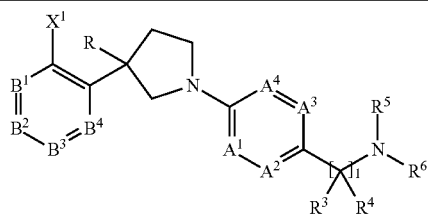

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1796 | C—CF3 | C—H | C—H | C—H | H | CF3 | CH | CH | C-cyclo-Pr | N | H | H | H | CH3S(O)CH2CO | 1 |
| 1-1797 | C—CF3 | C—H | C—H | C—H | H | CF3 | CH | CH | C-cyclo-Pr | N | H | H | H | CH3SO2CH2CO | 1 |
| 1-1798 | C—CF3 | C—H | C—H | C—H | H | CF3 | CH | CH | C-cyclo-Pr | N | H | H | H | CH3CH2NHCO | 1 |
| 1-1799 | C—CF3 | C—H | C—CF3 | C—H | H | CF3 | CH | CH | C-cyclo-Pr | N | H | H | H | CH3CO | 1 |
| 1-1800 | C—CF3 | C—H | C—CF3 | C—H | H | CF3 | CH | CH | C-cyclo-Pr | N | H | H | H | CH3CH2CO | 1 |
| 1-1801 | C—CF3 | C—H | C—CF3 | C—H | H | CF3 | CH | CH | C-cyclo-Pr | N | H | H | H | nPrCO | 1 |
| 1-1802 | C—CF3 | C—H | C—CF3 | C—H | H | CF3 | CH | CH | C-cyclo-Pr | N | H | H | H | cyclo-PrCO | 1 |
| 1-1803 | C—CF3 | C—H | C—CF3 | C—H | H | CF3 | CH | CH | C-cyclo-Pr | N | H | H | H | cyclo-PrCH2CO | 1 |
| 1-1804 | C—CF3 | C—H | C—CF3 | C—H | H | CF3 | CH | CH | C-cyclo-Pr | N | H | H | H | CF3CH2CO | 1 |
| 1-1805 | C—CF3 | C—H | C—CF3 | C—H | H | CF3 | CH | CH | C-cyclo-Pr | N | H | H | H | CH3SCH2CO | 1 |
| 1-1806 | C—CF3 | C—H | C—CF3 | C—H | H | CF3 | CH | CH | C-cyclo-Pr | N | H | H | H | CH3S(O)CH2CO | 1 |
| 1-1807 | C—CF3 | C—H | C—CF3 | C—H | H | CF3 | CH | CH | C-cyclo-Pr | N | H | H | H | CH3SO2CH2CO | 1 |
| 1-1808 | C—CF3 | C—H | C—CF3 | C—H | H | CF3 | CH | CH | C-cyclo-Pr | N | H | H | H | CH3CH2NHCO | 1 |
| 1-1809 | C—Cl | C—H | C—Cl | C—H | H | CF3 | CH | CH | C—CH2CF3 | N | H | H | H | CH3CO | 1 |
| 1-1810 | C—Cl | C—H | C—Cl | C—H | H | CF3 | CH | CH | C—CH2CF3 | N | H | H | H | CH3CH2CO | 1 |
| 1-1811 | C—Cl | C—H | C—Cl | C—H | H | CF3 | CH | CH | C—CH2CF3 | N | H | H | H | nPrCO | 1 |
| 1-1812 | C—Cl | C—H | C—Cl | C—H | H | CF3 | CH | CH | C—CH2CF3 | N | H | H | H | cyclo-PrCO | 1 |
| 1-1813 | C—Cl | C—H | C—Cl | C—H | H | CF3 | CH | CH | C—CH2CF3 | N | H | H | H | cyclo-PrCH2CO | 1 |
| 1-1814 | C—Cl | C—H | C—Cl | C—H | H | CF3 | CH | CH | C—CH2CF3 | N | H | H | H | CF3CH2CO | 1 |
| 1-1815 | C—Cl | C—H | C—Cl | C—H | H | CF3 | CH | CH | C—CH2CF3 | N | H | H | H | CH3SCH2CO | 1 |
| 1-1816 | C—Cl | C—H | C—Cl | C—H | H | CF3 | CH | CH | C—CH2CF3 | N | H | H | H | CH3S(O)CH2CO | 1 |
| 1-1817 | C—Cl | C—H | C—Cl | C—H | H | CF3 | CH | CH | C—CH2CF3 | N | H | H | H | CH3SO2CH2CO | 1 |
| 1-1818 | C—Cl | C—H | C—Cl | C—H | H | CF3 | CH | CH | C—CH2CF3 | N | H | H | H | CH3CH2NHCO | 1 |
| 1-1819 | C—Cl | C—Cl | C—Cl | C—H | H | CF3 | CH | CH | C—CH2CF3 | N | H | H | H | CH3CO | 1 |
| 1-1820 | C—Cl | C—Cl | C—Cl | C—H | H | CF3 | CH | CH | C—CH2CF3 | N | H | H | H | CH3CH2CO | 1 |
| 1-1821 | C—Cl | C—Cl | C—Cl | C—H | H | CF3 | CH | CH | C—CH2CF3 | N | H | H | H | nPrCO | 1 |
| 1-1822 | C—Cl | C—Cl | C—Cl | C—H | H | CF3 | CH | CH | C—CH2CF3 | N | H | H | H | cyclo-PrCO | 1 |
| 1-1823 | C—Cl | C—Cl | C—Cl | C—H | H | CF3 | CH | CH | C—CH2CF3 | N | H | H | H | cyclo-PrCH2CO | 1 |
| 1-1824 | C—Cl | C—Cl | C—Cl | C—H | H | CF3 | CH | CH | C—CH2CF3 | N | H | H | H | CF3CH2CO | 1 |
| 1-1825 | C—Cl | C—Cl | C—Cl | C—H | H | CF3 | CH | CH | C—CH2CF3 | N | H | H | H | CH3SCH2CO | 1 |
| 1-1826 | C—Cl | C—Cl | C—Cl | C—H | H | CF3 | CH | CH | C—CH2CF3 | N | H | H | H | CH3S(O)CH2CO | 1 |
| 1-1827 | C—Cl | C—Cl | C—Cl | C—H | H | CF3 | CH | CH | C—CH2CF3 | N | H | H | H | CH3SO2CH2CO | 1 |
| 1-1828 | C—Cl | C—Cl | C—Cl | C—H | H | CF3 | CH | CH | C—CH2CF3 | N | H | H | H | CH3CH2NHCO | 1 |
| 1-1829 | C—CF3 | C—H | C—H | C—H | H | CF3 | CH | CH | C—CH2CF3 | N | H | H | H | CH3CO | 1 |
| 1-1830 | C—CF3 | C—H | C—H | C—H | H | CF3 | CH | CH | C—CH2CF3 | N | H | H | H | CH3CH2CO | 1 |

TABLE 1-continued

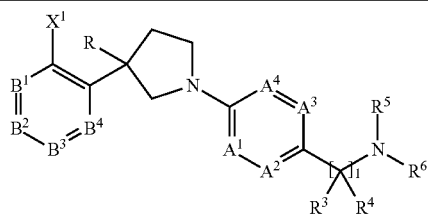

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1831 | C—CF3 | C—H | C—H | C—H | H | CF3 | CH | CH | C—CH2CF3 | N | H | H | H | nPrCO | 1 |
| 1-1832 | C—CF3 | C—H | C—H | C—H | H | CF3 | CH | CH | C—CH2CF3 | N | H | H | H | cyclo-PrCO | 1 |
| 1-1833 | C—CF3 | C—H | C—H | C—H | H | CF3 | CH | CH | C—CH2CF3 | N | H | H | H | cyclo-PrCH2CO | 1 |
| 1-1834 | C—CF3 | C—H | C—H | C—H | H | CF3 | CH | CH | C—CH2CF3 | N | H | H | H | CF3CH2CO | 1 |
| 1-1835 | C—CF3 | C—H | C—H | C—H | H | CF3 | CH | CH | C—CH2CF3 | N | H | H | H | CH3SCH2CO | 1 |
| 1-1836 | C—CF3 | C—H | C—H | C—H | H | CF3 | CH | CH | C—CH2CF3 | N | H | H | H | CH3S(O)CH2CO | 1 |
| 1-1837 | C—CF3 | C—H | C—H | C—H | H | CF3 | CH | CH | C—CH2CF3 | N | H | H | H | CH3SO2CH2CO | 1 |
| 1-1838 | C—CF3 | C—H | C—H | C—H | H | CF3 | CH | CH | C—CH2CF3 | N | H | H | H | CH3CH2NHCO | 1 |
| 1-1839 | C—CF3 | C—H | C—CF3 | C—H | H | CF3 | CH | CH | C—CH2CF3 | N | H | H | H | CH3CO | 1 |
| 1-1840 | C—CF3 | C—H | C—CF3 | C—H | H | CF3 | CH | CH | C—CH2CF3 | N | H | H | H | CH3CH2CO | 1 |
| 1-1841 | C—CF3 | C—H | C—CF3 | C—H | H | CF3 | CH | CH | C—CH2CF3 | N | H | H | H | nPrCO | 1 |
| 1-1842 | C—CF3 | C—H | C—CF3 | C—H | H | CF3 | CH | CH | C—CH2CF3 | N | H | H | H | cyclo-PrCO | 1 |
| 1-1843 | C—CF3 | C—H | C—CF3 | C—H | H | CF3 | CH | CH | C—CH2CF3 | N | H | H | H | cyclo-PrCH2CO | 1 |
| 1-1844 | C—CF3 | C—H | C—CF3 | C—H | H | CF3 | CH | CH | C—CH2CF3 | N | H | H | H | CF3CH2CO | 1 |
| 1-1845 | C—CF3 | C—H | C—CF3 | C—H | H | CF3 | CH | CH | C—CH2CF3 | N | H | H | H | CH3SCH2CO | 1 |
| 1-1846 | C—CF3 | C—H | C—CF3 | C—H | H | CF3 | CH | CH | C—CH2CF3 | N | H | H | H | CH3S(O)CH2CO | 1 |
| 1-1847 | C—CF3 | C—H | C—CF3 | C—H | H | CF3 | CH | CH | C—CH2CF3 | N | H | H | H | CH3SO2CH2CO | 1 |
| 1-1848 | C—CF3 | C—H | C—CF3 | C—H | H | CF3 | CH | CH | C—CH2CF3 | N | H | H | H | CH3CH2NHCO | 1 |
| 1-1849 | C—Cl | C—H | C—Cl | C—H | H | CF3 | CH | CH | C—CF3 | N | H | H | H | CH3OCH2CH2CO | 1 |
| 1-1850 | C—Cl | C—Cl | C—Cl | C—H | H | CF3 | CH | CH | C—CF3 | N | H | H | H | CH3OCH2CH2CO | 1 |
| 1-1851 | C—Cl | C—H | C—CF3 | C—H | H | CF3 | CH | CH | C—CF3 | N | H | H | H | CH3OCH2CH2CO | 1 |
| 1-1852 | C—CF3 | C—H | C—H | C—H | H | CF3 | CH | CH | C—CF3 | N | H | H | H | CH3OCH2CH2CO | 1 |
| 1-1853 | C—CF3 | C—H | C—CF3 | C—H | H | CF3 | CH | CH | C—CF3 | N | H | H | H | CH3OCH2CH2CO | 1 |
| 1-1854 | C—Cl | C—OCH2O—C | | C—H | H | CF3 | CH | CH | C—CF3 | CH | H | H | H | CH3CO | 1 |
| 1-1855 | C—Cl | C—OCH2O—C | | C—H | H | CF3 | CH | CH | C—CF3 | CH | H | H | H | CH3CH2CO | 1 |
| 1-1856 | C—Cl | C—OCH2O—C | | C—H | H | CF3 | CH | CH | C—CF3 | CH | H | H | H | nPrCO | 1 |
| 1-1857 | C—Cl | C—OCH2O—C | | C—H | H | CF3 | CH | CH | C—CF3 | CH | H | H | H | cyclo-PrCO | 1 |
| 1-1858 | C—Cl | C—OCH2O—C | | C—H | H | CF3 | CH | CH | C—CF3 | CH | H | H | H | cyclo-PrCH2CO | 1 |
| 1-1859 | C—Cl | C—OCH2O—C | | C—H | H | CF3 | CH | CH | C—CF3 | CH | H | H | H | CF3CH2CO | 1 |
| 1-1860 | C—Cl | C—OCH2O—C | | C—H | H | CF3 | CH | CH | C—CF3 | CH | H | H | H | CH3OCH2CH2CO | 1 |
| 1-1861 | C—Cl | C—OCH2O—C | | C—H | H | CF3 | CH | CH | C—CF3 | CH | H | H | H | CH3SCH2CO | 1 |
| 1-1862 | C—Cl | C—OCH2O—C | | C—H | H | CF3 | CH | CH | C—CF3 | CH | H | H | H | CH3S(O)CH2CO | 1 |
| 1-1863 | C—Cl | C—OCH2O—C | | C—H | H | CF3 | CH | CH | C—CF3 | CH | H | H | H | CH3SO2CH2CO | 1 |
| 1-1864 | C—Cl | C—OCH2O—C | | C—H | H | CF3 | CH | CH | C—CF3 | CH | H | H | H | CH3CH2NHCO | 1 |
| 1-1865 | C—Cl | C—OCH2O—C | | C—H | H | CF3 | CH | CH | C—CF3 | CH | H | H | H | CH3CO | 1 |

TABLE 1-continued

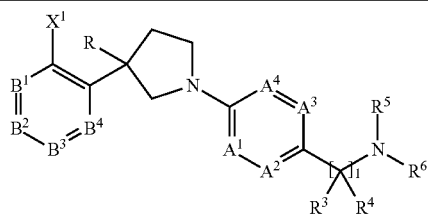

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1866 | C—Cl | C—OCH2O—C | | C—H | H | CF3 | CH | CH | C—CF3 | CH | H | H | H | CH3CH2CO | 1 |
| 1-1867 | C—Cl | C—OCH2O—C | | C—H | H | CF3 | CH | CH | C—CF3 | CH | H | H | H | nPrCO | 1 |
| 1-1868 | C—Cl | C—OCH2O—C | | C—H | H | CF3 | CH | CH | C—CF3 | CH | H | H | H | cyclo-PrCO | 1 |
| 1-1869 | C—Cl | C—OCH2O—C | | C—H | H | CF3 | CH | CH | C—CF3 | CH | H | H | H | cyclo-PrCH2CO | 1 |
| 1-1870 | C—Cl | C—OCH2O—C | | C—H | H | CF3 | CH | CH | C—CF3 | CH | H | H | H | CF3CH2CO | 1 |
| 1-1871 | C—Cl | C—OCH2O—C | | C—H | H | CF3 | CH | CH | C—CF3 | CH | H | H | H | CH3OCH2CH2CO | 1 |
| 1-1872 | C—Cl | C—OCH2O—C | | C—H | H | CF3 | CH | CH | C—CF3 | CH | H | H | H | CH3SCH2CO | 1 |
| 1-1873 | C—Cl | C—OCH2O—C | | C—H | H | CF3 | CH | CH | C—CF3 | CH | H | H | H | CH3S(O)CH2CO | 1 |
| 1-1874 | C—Cl | C—OCH2O—C | | C—H | H | CF3 | CH | CH | C—CF3 | CH | H | H | H | CH3SO2CH2CO | 1 |
| 1-1875 | C—Cl | C—OCH2O—C | | C—H | H | CF3 | CH | CH | C—CF3 | CH | H | H | H | CH3CH2NHCO | 1 |
| 1-1876 | C—Cl | C—OC(CH3)2O—C | | C—H | H | CF3 | CH | CH | C—CF3 | CH | H | H | H | CH3CO | 1 |
| 1-1877 | C—Cl | C—OC(CH3)2O—C | | C—H | H | CF3 | CH | CH | C—CF3 | CH | H | H | H | CH3CH2CO | 1 |
| 1-1878 | C—Cl | C—OC(CH3)2O—C | | C—H | H | CF3 | CH | CH | C—CF3 | CH | H | H | H | nPrCO | 1 |
| 1-1879 | C—Cl | C—OC(CH3)2O—C | | C—H | H | CF3 | CH | CH | C—CF3 | CH | H | H | H | cyclo-PrCO | 1 |
| 1-1880 | C—Cl | C—OC(CH3)2O—C | | C—H | H | CF3 | CH | CH | C—CF3 | CH | H | H | H | cyclo-PrCH2CO | 1 |
| 1-1881 | C—Cl | C—OC(CH3)2O—C | | C—H | H | CF3 | CH | CH | C—CF3 | CH | H | H | H | CF3CH2CO | 1 |
| 1-1882 | C—Cl | C—OC(CH3)2O—C | | C—H | H | CF3 | CH | CH | C—CF3 | CH | H | H | H | CH3OCH2CH2CO | 1 |
| 1-1883 | C—Cl | C—OC(CH3)2O—C | | C—H | H | CF3 | CH | CH | C—CF3 | CH | H | H | H | CH3SCH2CO | 1 |
| 1-1884 | C—Cl | C—OC(CH3)2O—C | | C—H | H | CF3 | CH | CH | C—CF3 | CH | H | H | H | CH3S(O)CH2CO | 1 |
| 1-1885 | C—Cl | C—OC(CH3)2O—C | | C—H | H | CF3 | CH | CH | C—CF3 | CH | H | H | H | CH3SO2CH2CO | 1 |
| 1-1886 | C—Cl | C—OC(CH3)2O—C | | C—H | H | CF3 | CH | CH | C—CF3 | CH | H | H | H | CH3CH2NHCO | 1 |
| 1-1887 | C—Cl | C—OCF2O—C | | C—H | H | CF3 | CH | CH | C—CF3 | CH | H | H | H | CH3CO | 1 |
| 1-1888 | C—Cl | C—OCF2O—C | | C—H | H | CF3 | CH | CH | C—CF3 | CH | H | H | H | CH3CH2CO | 1 |
| 1-1889 | C—Cl | C—OCF2O—C | | C—H | H | CF3 | CH | CH | C—CF3 | CH | H | H | H | nPrCO | 1 |
| 1-1890 | C—Cl | C—OCF2O—C | | C—H | H | CF3 | CH | CH | C—CF3 | CH | H | H | H | cyclo-PrCO | 1 |
| 1-1891 | C—Cl | C—OCF2O—C | | C—H | H | CF3 | CH | CH | C—CF3 | CH | H | H | H | cyclo-PrCH2CO | 1 |
| 1-1892 | C—Cl | C—OCF2O—C | | C—H | H | CF3 | CH | CH | C—CF3 | CH | H | H | H | CF3CH2CO | 1 |
| 1-1893 | C—Cl | C—OCF2O—C | | C—H | H | CF3 | CH | CH | C—CF3 | CH | H | H | H | CH3OCH2CH2CO | 1 |
| 1-1894 | C—Cl | C—OCF2O—C | | C—H | H | CF3 | CH | CH | C—CF3 | CH | H | H | H | CH3SCH2CO | 1 |
| 1-1895 | C—Cl | C—OCF2O—C | | C—H | H | CF3 | CH | CH | C—CF3 | CH | H | H | H | CH3S(O)CH2CO | 1 |
| 1-1896 | C—Cl | C—OCF2O—C | | C—H | H | CF3 | CH | CH | C—CF3 | CH | H | H | H | CH3SO2CH2CO | 1 |
| 1-1897 | C—Cl | C—OCF2O—C | | C—H | H | CF3 | CH | CH | C—CF3 | CH | H | H | H | CH3CH2NHCO | 1 |
| 1-1898 | C—F | C—H | C—CF3 | C—H | H | CF3 | CH | CH | C—Cl | CH | H | H | H | CH3CO | 1 |
| 1-1899 | C—F | C—H | C—CF3 | C—H | H | CF3 | CH | CH | C—Cl | CH | H | H | H | CH3CH2CO | 1 |
| 1-1900 | C—F | C—H | C—CF3 | C—H | H | CF3 | CH | CH | C—Cl | CH | H | H | H | nPrCO | 1 |

TABLE 1-continued

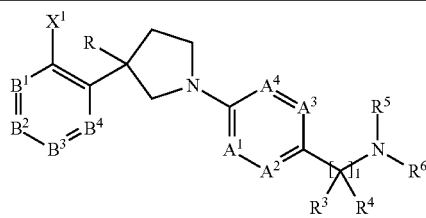

| Ex.-No. | $B^1$ | $B^2$ | $B^3$ | $B^4$ | $X^1$ | R | $A^1$ | $A^2$ | $A^3$ | $A^4$ | $R^3$ | $R^4$ | $R^5$ | $R^6$ | 1 |
|---|---|---|---|---|---|---|---|---|---|---|---|---|---|---|---|
| 1-1901 | C—F | C—H | C—CF3 | C—H | H | CF3 | CH | CH | C—Cl | CH | H | H | H | cyclo-PrCO | 1 |
| 1-1902 | C—F | C—H | C—CF3 | C—H | H | CF3 | CH | CH | C—Cl | CH | H | H | H | cyclo-PrCH2CO | 1 |
| 1-1903 | C—F | C—H | C—CF3 | C—H | H | CF3 | CH | CH | C—Cl | CH | H | H | H | CF3CH2CO | 1 |
| 1-1904 | C—F | C—H | C—CF3 | C—H | H | CF3 | CH | CH | C—Cl | CH | H | H | H | CH3SCH2CO | 1 |
| 1-1905 | C—F | C—H | C—CF3 | C—H | H | CF3 | CH | CH | C—Cl | CH | H | H | H | CH3S(O)CH2CO | 1 |
| 1-1906 | C—F | C—H | C—CF3 | C—H | H | CF3 | CH | CH | C—Cl | CH | H | H | H | CH3SO2CH2CO | 1 |
| 1-1907 | C—F | C—H | C—CF3 | C—H | H | CF3 | CH | CH | C—Cl | CH | H | H | H | CH3CH2NHCO | 1 |
| 1-1908 | C—F | C—H | C—CF3 | C—H | H | CF3 | CH | CH | C—Br | CH | H | H | H | CH3CO | 1 |
| 1-1909 | C—F | C—H | C—CF3 | C—H | H | CF3 | CH | CH | C—Br | CH | H | H | H | CH3CH2CO | 1 |
| 1-1910 | C—F | C—H | C—CF3 | C—H | H | CF3 | CH | CH | C—Br | CH | H | H | H | nPrCO | 1 |
| 1-1911 | C—F | C—H | C—CF3 | C—H | H | CF3 | CH | CH | C—Br | CH | H | H | H | cyclo-PrCO | 1 |
| 1-1912 | C—F | C—H | C—CF3 | C—H | H | CF3 | CH | CH | C—Br | CH | H | H | H | cyclo-PrCH2CO | 1 |
| 1-1913 | C—F | C—H | C—CF3 | C—H | H | CF3 | CH | CH | C—Br | CH | H | H | H | CF3CH2CO | 1 |
| 1-1914 | C—F | C—H | C—CF3 | C—H | H | CF3 | CH | CH | C—Br | CH | H | H | H | CH3SCH2CO | 1 |
| 1-1915 | C—F | C—H | C—CF3 | C—H | H | CF3 | CH | CH | C—Br | CH | H | H | H | CH3S(O)CH2CO | 1 |
| 1-1916 | C—F | C—H | C—CF3 | C—H | H | CF3 | CH | CH | C—Br | CH | H | H | H | CH3SO2CH2CO | 1 |
| 1-1917 | C—F | C—H | C—CF3 | C—H | H | CF3 | CH | CH | C—Br | CH | H | H | H | CH3CH2NHCO | 1 |
| 1-1918 | C—F | C—H | C—CF3 | C—H | H | CF3 | CH | CH | C—CF3 | CH | H | H | H | CH3CO | 1 |
| 1-1919 | C—F | C—H | C—CF3 | C—H | H | CF3 | CH | CH | C—CF3 | CH | H | H | H | CH3CH2CO | 1 |
| 1-1920 | C—F | C—H | C—CF3 | C—H | H | CF3 | CH | CH | C—CF3 | CH | H | H | H | nPrCO | 1 |
| 1-1921 | C—F | C—H | C—CF3 | C—H | H | CF3 | CH | CH | C—CF3 | CH | H | H | H | cyclo-PrCO | 1 |
| 1-1922 | C—F | C—H | C—CF3 | C—H | H | CF3 | CH | CH | C—CF3 | CH | H | H | H | cyclo-PrCH2CO | 1 |
| 1-1923 | C—F | C—H | C—CF3 | C—H | H | CF3 | CH | CH | C—CF3 | CH | H | H | H | CF3CH2CO | 1 |
| 1-1924 | C—F | C—H | C—CF3 | C—H | H | CF3 | CH | CH | C—CF3 | CH | H | H | H | CH3SCH2CO | 1 |
| 1-1925 | C—F | C—H | C—CF3 | C—H | H | CF3 | CH | CH | C—CF3 | CH | H | H | H | CH3S(O)CH2CO | 1 |
| 1-1926 | C—F | C—H | C—CF3 | C—H | H | CF3 | CH | CH | C—CF3 | CH | H | H | H | CH3SO2CH2CO | 1 |
| 1-1927 | C—F | C—H | C—CF3 | C—H | H | CF3 | CH | CH | C—CF3 | CH | H | H | H | CH3CH2NHCO | 1 |
| 1-1928 | C—CF3 | C—H | C—Cl | N | H | CF3 | CH | CH | C—CF3 | CH | H | H | H | CH3CO | 1 |
| 1-1929 | C—CF3 | C—H | C—Cl | N | H | CF3 | CH | CH | C—CF3 | CH | H | H | H | CH3CH2CO | 1 |
| 1-1930 | C—CF3 | C—H | C—Cl | N | H | CF3 | CH | CH | C—CF3 | CH | H | H | H | nPrCO | 1 |
| 1-1931 | C—CF3 | C—H | C—Cl | N | H | CF3 | CH | CH | C—CF3 | CH | H | H | H | cyclo-PrCO | 1 |
| 1-1932 | C—CF3 | C—H | C—Cl | N | H | CF3 | CH | CH | C—CF3 | CH | H | H | H | cyclo-PrCH2CO | 1 |
| 1-1933 | C—CF3 | C—H | C—Cl | N | H | CF3 | CH | CH | C—CF3 | CH | H | H | H | CF3CH2CO | 1 |
| 1-1934 | C—CF3 | C—H | C—Cl | N | H | CF3 | CH | CH | C—CF3 | CH | H | H | H | CH3SCH2CO | 1 |
| 1-1935 | C—CF3 | C—H | C—Cl | N | H | CF3 | CH | CH | C—CF3 | CH | H | H | H | CH3S(O)CH2CO | 1 |

TABLE 1-continued

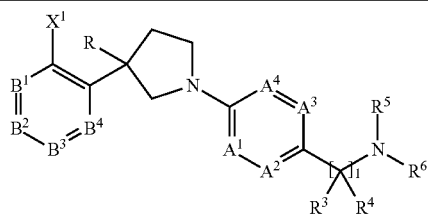

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1936 | C—CF3 | C—H | C—Cl | N | H | CF3 | CH | CH | C—CF3 | CH | H | H | H | CH3SO2CH2CO | 1 |
| 1-1937 | C—CF3 | C—H | C—Cl | N | H | CF3 | CH | CH | C—CF3 | CH | H | H | H | CH3CH2NHCO | 1 |
| 1-1938 | C—CF3 | C—H | C—Br | N | H | CF3 | CH | CH | C—CF3 | CH | H | H | H | CH3CO | 1 |
| 1-1939 | C—CF3 | C—H | C—Br | N | H | CF3 | CH | CH | C—CF3 | CH | H | H | H | CH3CH2CO | 1 |
| 1-1940 | C—CF3 | C—H | C—Br | N | H | CF3 | CH | CH | C—CF3 | CH | H | H | H | nPrCO | 1 |
| 1-1941 | C—CF3 | C—H | C—Br | N | H | CF3 | CH | CH | C—CF3 | CH | H | H | H | cyclo-PrCO | 1 |
| 1-1942 | C—CF3 | C—H | C—Br | N | H | CF3 | CH | CH | C—CF3 | CH | H | H | H | cyclo-PrCH2CO | 1 |
| 1-1943 | C—CF3 | C—H | C—Br | N | H | CF3 | CH | CH | C—CF3 | CH | H | H | H | CF3CH2CO | 1 |
| 1-1944 | C—CF3 | C—H | C—Br | N | H | CF3 | CH | CH | C—CF3 | CH | H | H | H | CH3SCH2CO | 1 |
| 1-1945 | C—CF3 | C—H | C—Br | N | H | CF3 | CH | CH | C—CF3 | CH | H | H | H | CH3S(O)CH2CO | 1 |
| 1-1946 | C—CF3 | C—H | C—Br | N | H | CF3 | CH | CH | C—CF3 | CH | H | H | H | CH3SO2CH2CO | 1 |
| 1-1947 | C—CF3 | C—H | C—Br | N | H | CF3 | CH | CH | C—CF3 | CH | H | H | H | CH3CH2NHCO | 1 |
| 1-1948 | C—CF3 | C—H | C—CH3 | N | H | CF3 | CH | CH | C—CF3 | CH | H | H | H | CH3CO | 1 |
| 1-1949 | C—CF3 | C—H | C—CH3 | N | H | CF3 | CH | CH | C—CF3 | CH | H | H | H | CH3CH2CO | 1 |
| 1-1950 | C—CF3 | C—H | C—CH3 | N | H | CF3 | CH | CH | C—CF3 | CH | H | H | H | nPrCO | 1 |
| 1-1951 | C—CF3 | C—H | C—CH3 | N | H | CF3 | CH | CH | C—CF3 | CH | H | H | H | cyclo-PrCO | 1 |
| 1-1952 | C—CF3 | C—H | C—CH3 | N | H | CF3 | CH | CH | C—CF3 | CH | H | H | H | cyclo-PrCH2CO | 1 |
| 1-1953 | C—CF3 | C—H | C—CH3 | N | H | CF3 | CH | CH | C—CF3 | CH | H | H | H | CF3CH2CO | 1 |
| 1-1954 | C—CF3 | C—H | C—CH3 | N | H | CF3 | CH | CH | C—CF3 | CH | H | H | H | CH3SCH2CO | 1 |
| 1-1955 | C—CF3 | C—H | C—CH3 | N | H | CF3 | CH | CH | C—CF3 | CH | H | H | H | CH3S(O)CH2CO | 1 |
| 1-1956 | C—CF3 | C—H | C—CH3 | N | H | CF3 | CH | CH | C—CF3 | CH | H | H | H | CH3SO2CH2CO | 1 |
| 1-1957 | C—CF3 | C—H | C—CH3 | N | H | CF3 | CH | CH | C—CF3 | CH | H | H | H | CH3CH2NHCO | 1 |
| 1-1958 | C—CF3 | C—H | C—OCH3 | N | H | CF3 | CH | CH | C—CF3 | CH | H | H | H | CH3CO | 1 |
| 1-1959 | C—CF3 | C—H | C—OCH3 | N | H | CF3 | CH | CH | C—CF3 | CH | H | H | H | CH3CH2CO | 1 |
| 1-1960 | C—CF3 | C—H | C—OCH3 | N | H | CF3 | CH | CH | C—CF3 | CH | H | H | H | nPrCO | 1 |
| 1-1961 | C—CF3 | C—H | C—OCH3 | N | H | CF3 | CH | CH | C—CF3 | CH | H | H | H | cyclo-PrCO | 1 |
| 1-1962 | C—CF3 | C—H | C—OCH3 | N | H | CF3 | CH | CH | C—CF3 | CH | H | H | H | cyclo-PrCH2CO | 1 |
| 1-1963 | C—CF3 | C—H | C—OCH3 | N | H | CF3 | CH | CH | C—CF3 | CH | H | H | H | CF3CH2CO | 1 |
| 1-1964 | C—CF3 | C—H | C—OCH3 | N | H | CF3 | CH | CH | C—CF3 | CH | H | H | H | CH3SCH2CO | 1 |
| 1-1965 | C—CF3 | C—H | C—OCH3 | N | H | CF3 | CH | CH | C—CF3 | CH | H | H | H | CH3S(O)CH2CO | 1 |
| 1-1966 | C—CF3 | C—H | C—OCH3 | N | H | CF3 | CH | CH | C—CF3 | CH | H | H | H | CH3SO2CH2CO | 1 |
| 1-1967 | C—CF3 | C—H | C—OCH3 | N | H | CF3 | CH | CH | C—CF3 | CH | H | H | H | CH3CH2NHCO | 1 |
| 1-1968 | C—Cl | C—H | C—Cl | C—H | H | CF3 | C—F | CH | C—Cl | CH | H | H | H | CH3CO | 1 |
| 1-1969 | C—Cl | C—H | C—Cl | C—H | H | CF3 | C—F | CH | C—Cl | CH | H | H | H | CH3CH2CO | 1 |
| 1-1970 | C—Cl | C—H | C—Cl | C—H | H | CF3 | C—F | CH | C—Cl | CH | H | H | H | cyclo-PrCO | 1 |

TABLE 1-continued

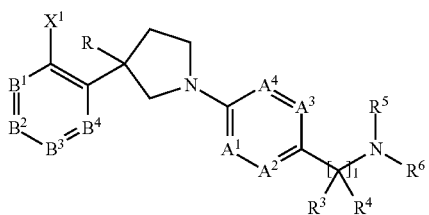

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1971 | C—Cl | C—H | C—Cl | C—H | H | CF3 | C—F | CH | C—Cl | CH | H | H | H | CF3CH2CO | 1 |
| 1-1972 | C—Cl | C—Cl | C—Cl | C—H | H | CF3 | C—F | CH | C—Cl | CH | H | H | H | CH3CO | 1 |
| 1-1973 | C—Cl | C—Cl | C—Cl | C—H | H | CF3 | C—F | CH | C—Cl | CH | H | H | H | CH3CH2CO | 1 |
| 1-1974 | C—Cl | C—Cl | C—Cl | C—H | H | CF3 | C—F | CH | C—Cl | CH | H | H | H | cyclo-PrCO | 1 |
| 1-1975 | C—Cl | C—Cl | C—Cl | C—H | H | CF3 | C—F | CH | C—Cl | CH | H | H | H | CF3CH2CO | 1 |
| 1-1976 | C—CF3 | C—H | C—CF3 | C—H | H | CF3 | C—F | CH | C—Cl | CH | H | H | H | CH3CO | 1 |
| 1-1977 | C—CF3 | C—H | C—CF3 | C—H | H | CF3 | C—F | CH | C—Cl | CH | H | H | H | CH3CH2CO | 1 |
| 1-1978 | C—CF3 | C—H | C—CF3 | C—H | H | CF3 | C—F | CH | C—Cl | CH | H | H | H | cyclo-PrCO | 1 |
| 1-1979 | C—CF3 | C—H | C—CF3 | C—H | H | CF3 | C—F | CH | C—Cl | CH | H | H | H | CF3CH2CO | 1 |
| 1-1980 | C—Cl | C—H | C—Cl | C—H | H | CF3 | CH | CH | C—Cl | C—F | H | H | H | CH3CO | 1 |
| 1-1981 | C—Cl | C—H | C—Cl | C—H | H | CF3 | CH | CH | C—Cl | C—F | H | H | H | CH3CH2CO | 1 |
| 1-1982 | C—Cl | C—H | C—Cl | C—H | H | CF3 | CH | CH | C—Cl | C—F | H | H | H | cyclo-PrCO | 1 |
| 1-1983 | C—Cl | C—H | C—Cl | C—H | H | CF3 | CH | CH | C—Cl | C—F | H | H | H | CF3CH2CO | 1 |
| 1-1984 | C—Cl | C—Cl | C—Cl | C—H | H | CF3 | CH | CH | C—Cl | C—F | H | H | H | CH3CO | 1 |
| 1-1985 | C—Cl | C—Cl | C—Cl | C—H | H | CF3 | CH | CH | C—Cl | C—F | H | H | H | CH3CH2CO | 1 |
| 1-1986 | C—Cl | C—Cl | C—Cl | C—H | H | CF3 | CH | CH | C—Cl | C—F | H | H | H | cyclo-PrCO | 1 |
| 1-1987 | C—Cl | C—Cl | C—Cl | C—H | H | CF3 | CH | CH | C—Cl | C—F | H | H | H | CF3CH2CO | 1 |
| 1-1988 | C—CF3 | C—H | C—CF3 | C—H | H | CF3 | CH | CH | C—Cl | C—F | H | H | H | CH3CO | 1 |
| 1-1989 | C—CF3 | C—H | C—CF3 | C—H | H | CF3 | CH | CH | C—Cl | C—F | H | H | H | CH3CH2CO | 1 |
| 1-1990 | C—CF3 | C—H | C—CF3 | C—H | H | CF3 | CH | CH | C—Cl | C—F | H | H | H | cyclo-PrCO | 1 |
| 1-1991 | C—CF3 | C—H | C—CF3 | C—H | H | CF3 | CH | CH | C—Cl | C—F | H | H | H | CF3CH2CO | 1 |
| 1-1992 | C—Cl | C—H | C—Cl | C—H | H | CF3 | CH | CH | C—SCH3 | CH | H | H | H | CH3SCH2CO | 1 |
| 1-1993 | C—Cl | C—H | C—Cl | C—H | H | CF3 | CH | CH | C—SCH3 | CH | H | H | H | CH3S(O)CH2CO | 1 |
| 1-1994 | C—Cl | C—H | C—Cl | C—H | H | CF3 | CH | CH | C—SCH3 | CH | H | H | H | CH3SO2CH2CO | 1 |
| 1-1995 | C—Cl | C—H | C—Cl | C—H | H | CF3 | CH | CH | C—CF3 | CH | H | H | H | ![O2N-imidazole-CH2CO] | 1 |
| 1-1996 | C—Cl | C—Cl | C—Cl | C—H | H | CF3 | CH | CH | C—CF3 | CH | H | H | H | ![imidazole-CH2CO] | 1 |
| 1-1997 | C—Cl | C—H | C—CF3 | C—H | H | CF3 | CH | CH | C—CF3 | CH | H | H | H | ![pyrazole-CH2CO] | 1 |
| 1-1998 | C—CF3 | C—H | C—CF3 | C—H | H | CF3 | CH | CH | C—Br | CH | H | H | H | CH3CO | 1 |

TABLE 1-continued

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-1999 | C—CF3 | C—H | C—CF3 | C—H | H | CF3 | CH | CH | C—Br | CH | H | H | H | 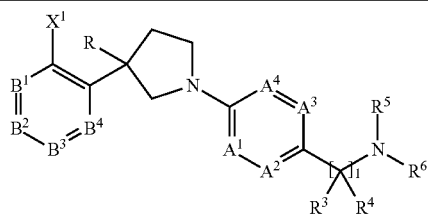 | 1 |
| 1-2000 | C—CF3 | C—H | C—CF3 | C—H | H | CF3 | CH | CH | C—Br | CH | H | H | H | CH3OCH2CH2CO | 1 |
| 1-2001 | C—Cl | C—H | C—Cl | C—H | H | CF3 | CH | CH | C—Br | N | H | H | H | CH3OCH2CH2CO | 1 |
| 1-2002 | C—Cl | C—H | C—Cl | C—H | H | CF3 | CH | CH | C—Br | CH | H | H | H | CH3OCH2CH2CO | 1 |
| 1-2003 | C—Cl | C—Cl | C—Cl | C—H | H | CF3 | CH | CH | C—CF3 | N | H | H | H | CH3SO2 | 1 |
| 1-2004 | C—CF3 | C—H | C—CF3 | C—H | H | CF3 | CH | CH | C—CF3 | N | H | H | H | CH3SO2 | 1 |
| 1-2005 | C—CF3 | C—H | C—CF3 | C—H | H | CF3 | CH | CH | C—CF3 | N | H | H | H | 2-py—CO | 1 |
| 1-2006 | C—CF3 | C—H | C—CF3 | C—H | H | CF3 | CH | CH | C—I | CH | H | H | H | H | 1 |
| 1-2007 | C—CF3 | C—H | C—CF3 | C—H | H | CF3 | CH | CH | C—I | CH | H | H | H | CH3CO | 1 |
| 1-2008 | C—CF3 | C—H | C—CF3 | C—H | H | CF3 | CH | CH | C—I | CH | H | H | H | CH3CH2CO | 1 |
| 1-2009 | C—CF3 | C—H | C—CF3 | C—H | H | CF3 | CH | CH | C—I | CH | H | H | H | cyclo-PrCO | 1 |
| 1-2010 | C—CF3 | C—H | C—CF3 | C—H | H | CF3 | CH | CH | C—I | CH | H | H | H | CF3CH2CO | 1 |
| 1-2011 | C—CF3 | C—H | C—CF3 | C—H | H | CF3 | CH | CH | C—I | CH | H | H | H | CH3SCH2CO | 1 |
| 1-2012 | C—CF3 | C—H | C—CF3 | C—H | H | CF3 | CH | CH | C—I | CH | H | H | H | CH3S(O)CH2CO | 1 |
| 1-2013 | C—CF3 | C—H | C—CF3 | C—H | H | CF3 | CH | CH | C—I | CH | H | H | H | CH3SO2CH2CO | 1 |
| 1-2014 | C—CF3 | C—H | C—CF3 | C—H | H | CF3 | CH | CH | C—F | C—F | H | H | H | H | 1 |
| 1-2015 | C—CF3 | C—H | C—CF3 | C—H | H | CF3 | CH | CH | C—F | C—F | H | H | H | CH3CO | 1 |
| 1-2016 | C—CF3 | C—H | C—CF3 | C—H | H | CF3 | CH | CH | C—F | C—F | H | H | H | CH3CH2CO | 1 |
| 1-2017 | C—CF3 | C—H | C—CF3 | C—H | H | CF3 | CH | CH | C—F | C—F | H | H | H | cyclo-PrCO | 1 |
| 1-2018 | C—CF3 | C—H | C—CF3 | C—H | H | CF3 | CH | CH | C—F | C—F | H | H | H | CF3CH2CO | 1 |
| 1-2019 | C—CF3 | C—H | C—CF3 | C—H | H | CF3 | CH | CH | C—F | C—F | H | H | H | CH3SCH2CO | 1 |
| 1-2020 | C—CF3 | C—H | C—CF3 | C—H | H | CF3 | CH | CH | C—F | C—F | H | H | H | CH3S(O)CH2CO | 1 |
| 1-2021 | C—CF3 | C—H | C—CF3 | C—H | H | CF3 | CH | CH | C—F | C—F | H | H | H | CH3SO2CH2CO | 1 |
| 1-2022 | C—CF3 | C—H | C—CF3 | C—H | H | CF3 | CH | CH | C—F | C—F | H | H | H | tert-BuOCO | 1 |
| 1-2023 | C—CF3 | C—H | C—CF3 | C—H | H | CF3 | CH | CH | C—Cl | C—F | H | H | H | CH3SCH2CO | 1 |
| 1-2024 | C—CF3 | C—H | C—CF3 | C—H | H | CF3 | CH | CH | C—Cl | C—F | H | H | H | CH3S(O)CH2CO | 1 |
| 1-2025 | C—CF3 | C—H | C—CF3 | C—H | H | CF3 | CH | CH | C—Cl | C—F | H | H | H | CH3SO2CH2CO | 1 |
| 1-2026 | C—Cl | C—Cl | C—Cl | C—H | H | CF3 | CH | CH | C—Cl | C—F | H | H | H | CH3SCH2CO | 1 |
| 1-2027 | C—Cl | C—Cl | C—Cl | C—H | H | CF3 | CH | CH | C—Cl | C—F | H | H | H | CH3S(O)CH2CO | 1 |
| 1-2028 | C—Cl | C—Cl | C—Cl | C—H | H | CF3 | CH | CH | C—Cl | C—F | H | H | H | CH3SO2CH2CO | 1 |
| 1-2029 | C—CF3 | C—H | C—CF3 | C—H | H | CF3 | CH | CH | C—CH3 | C—F | H | H | H | H | 1 |
| 1-2030 | C—CF3 | C—H | C—CF3 | C—H | H | CF3 | CH | CH | C—CH3 | C—F | H | H | H | CH3CO | 1 |
| 1-2031 | C—CF3 | C—H | C—CF3 | C—H | H | CF3 | CH | CH | C—CH3 | C—F | H | H | H | CH3CH2CO | 1 |
| 1-2032 | C—CF3 | C—H | C—CF3 | C—H | H | CF3 | CH | CH | C—CH3 | C—F | H | H | H | cyclo-PrCO | 1 |

TABLE 1-continued

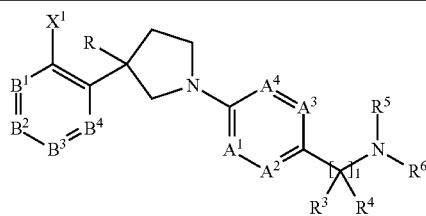

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-2033 | C—CF3 | C—H | C—CF3 | C—H | H | CF3 | CH | CH | C—CH3 | C—F | H | H | H | CF3CH2CO | 1 |
| 1-2034 | C—CF3 | C—H | C—CF3 | C—H | H | CF3 | CH | CH | C—CH3 | C—F | H | H | H | CH3SCH2CO | 1 |
| 1-2035 | C—CF3 | C—H | C—CF3 | C—H | H | CF3 | CH | CH | C—CH3 | C—F | H | H | H | CH3S(O)CH2CO | 1 |
| 1-2036 | C—CF3 | C—H | C—CF3 | C—H | H | CF3 | CH | CH | C—CH3 | C—F | H | H | H | CH3SO2CH2CO | 1 |
| 1-2037 | C—Cl | C—Cl | C—Cl | C—H | H | CF3 | CH | CH | C—CH3 | C—F | H | H | H | H | 1 |
| 1-2038 | C—Cl | C—Cl | C—Cl | C—H | H | CF3 | CH | CH | C—CH3 | C—F | H | H | H | CH3CO | 1 |
| 1-2039 | C—Cl | C—Cl | C—Cl | C—H | H | CF3 | CH | CH | C—CH3 | C—F | H | H | H | CH3CH2CO | 1 |
| 1-2040 | C—Cl | C—Cl | C—Cl | C—H | H | CF3 | CH | CH | C—CH3 | C—F | H | H | H | cyclo-PrCO | 1 |
| 1-2041 | C—Cl | C—Cl | C—Cl | C—H | H | CF3 | CH | CH | C—CH3 | C—F | H | H | H | CF3CH2CO | 1 |
| 1-2042 | C—Cl | C—Cl | C—Cl | C—H | H | CF3 | CH | CH | C—CH3 | C—F | H | H | H | CH3SCH2CO | 1 |
| 1-2043 | C—Cl | C—Cl | C—Cl | C—H | H | CF3 | CH | CH | C—CH3 | C—F | H | H | H | CH3S(O)CH2CO | 1 |
| 1-2044 | C—Cl | C—Cl | C—Cl | C—H | H | CF3 | CH | CH | C—CH3 | C—F | H | H | H | CH3SO2CH2CO | 1 |
| 1-2045 | C—Cl | C—H | C—Cl | C—H | H | CF3 | CH | CH | CH | CH | H | H | CH3 | CH3CH2CO | 1 |
| 1-2046 | C—Cl | C—Cl | C—Cl | C—H | H | CF3 | CH | CH | CH | CH | H | H | H | CH3CH2CO | 1 |
| 1-2047 | C—CF3 | C—H | C—CF3 | C—H | H | CF3 | CH | CH | CH | CH | H | H | H | CH3CH2CO | 1 |
| 1-2048 | C—Cl | C—H | C—Cl | C—H | H | CF3 | CH | CH | CH | CH | H | H | H | CH3CH2CO | 2 |
| 1-2049 | C—Cl | C—Cl | C—Cl | C—H | H | CF3 | CH | CH | CH | CH | H | H | H | CH3CH2CO | 2 |
| 1-2050 | C—CF3 | C—H | C—CF3 | C—H | H | CF3 | CH | CH | CH | CH | H | H | H | CH3CH2CO | 2 |
| 1-2051 | C—Cl | C—H | C—Cl | C—H | H | CF3 | CH | CH | C—OCH3 | CH | H | H | H | CH3CH2CO | 1 |
| 1-2052 | C—Cl | C—H | C—Cl | C—H | H | CF3 | CH | CH | C—OCH3 | CH | H | H | H | CH3SCH2CO | 1 |
| 1-2053 | C—Cl | C—H | C—Cl | C—H | H | CF3 | CH | CH | C—OCH3 | CH | H | H | H | CH3S(O)CH2CO | 1 |
| 1-2054 | C—Cl | C—H | C—Cl | C—H | H | CF3 | CH | CH | C—OCH3 | CH | H | H | H | CH3SO2CH2CO | 1 |
| 1-2055 | C—Cl | C—H | C—Cl | C—H | H | CF3 | CH | CH | C—Cl | CH | H | H | H | CH3OCH2CH2CO | 1 |
| 1-2056 | C—Cl | C—Cl | C—Cl | C—H | H | CF3 | CH | CH | C—Cl | CH | H | H | H | CH3OCH2CH2CO | 1 |
| 1-2057 | C—Cl | C—H | C—CF3 | C—H | H | CF3 | CH | CH | C—Cl | CH | H | H | H | CH3OCH2CH2CO | 1 |
| 1-2058 | C—CF3 | C—H | C—CF3 | C—H | H | CF3 | CH | CH | C—Cl | CH | H | H | H | CH3OCH2CH2CO | 1 |
| 1-2059 | C—Cl | C—H | C—Cl | C—H | H | CF3 | CH | CH | C—Cl | N | H | H | H | CH3OCH2CH2CO | 1 |
| 1-2060 | C—Cl | C—Cl | C—Cl | C—H | H | CF3 | CH | CH | C—Cl | N | H | H | H | CH3OCH2CH2CO | 1 |
| 1-2061 | C—Cl | C—H | C—CF3 | C—H | H | CF3 | CH | CH | C—Cl | N | H | H | H | CH3OCH2CH2CO | 1 |
| 1-2062 | C—CF3 | C—H | C—CF3 | C—H | H | CF3 | CH | CH | C—Cl | N | H | H | H | CH3OCH2CH2CO | 1 |
| 1-2063 | C—Cl | C—Cl | C—Cl | C—H | H | CF3 | CH | CH | C—Br | CH | H | H | H | CH3OCH2CH2CO | 1 |
| 1-2064 | C—Cl | C—H | C—CF3 | C—H | H | CF3 | CH | CH | C—Br | CH | H | H | H | CH3OCH2CH2CO | 1 |
| 1-2065 | C—Cl | C—Cl | C—Cl | C—H | H | CF3 | CH | CH | C—Br | N | H | H | H | CH3OCH2CH2CO | 1 |
| 1-2066 | C—Cl | C—H | C—CF3 | C—H | H | CF3 | CH | CH | C—Br | N | H | H | H | CH3OCH2CH2CO | 1 |
| 1-2067 | C—CF3 | C—H | C—CF3 | C—H | H | CF3 | CH | CH | C—Br | N | H | H | H | CH3OCH2CH2CO | 1 |

TABLE 1-continued

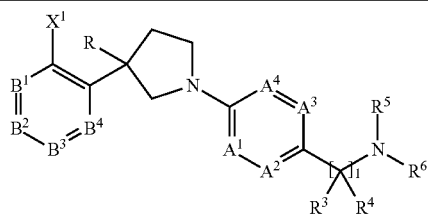

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-2068 | C—Cl | C—H | C—CF3 | C—H | H | CF3 | CH | CH | C—CF3 | N | H | H | H | CH3CH2CO | 1 |
| 1-2069 | C—Cl | C—H | C—CF3 | C—H | H | CF3 | CH | CH | C—CF3 | N | H | H | H | cyclo-PrCO | 1 |
| 1-2070 | C—Cl | C—H | C—CF3 | C—H | H | CF3 | CH | CH | C—CF3 | N | H | H | H | cyclo-PrCH2CO | 1 |
| 1-2071 | C—Cl | C—H | C—CF3 | C—H | H | CF3 | CH | CH | C—CF3 | N | H | H | H | CH3SCH2CO | 1 |
| 1-2072 | C—Cl | C—H | C—CF3 | C—H | H | CF3 | CH | CH | C—CF3 | N | H | H | H | CH3S(O)CH2CO | 1 |
| 1-2073 | C—Cl | C—H | C—CF3 | C—H | H | CF3 | CH | CH | C—CF3 | N | H | H | H | CH3SO2CH2CO | 1 |
| 1-2074 | C—Br | C—H | C—Br | C—H | H | CF3 | CH | CH | C—CF3 | N | H | H | H | CH3CH2CO | 1 |
| 1-2075 | C—Br | C—H | C—Br | C—H | H | CF3 | CH | CH | C—CF3 | N | H | H | H | cyclo-PrCO | 1 |
| 1-2076 | C—Br | C—H | C—Br | C—H | H | CF3 | CH | CH | C—CF3 | N | H | H | H | cyclo-PrCH2CO | 1 |
| 1-2077 | C—Br | C—H | C—Br | C—H | H | CF3 | CH | CH | C—CF3 | N | H | H | H | CH3SCH2CO | 1 |
| 1-2078 | C—Br | C—H | C—Br | C—H | H | CF3 | CH | CH | C—CF3 | N | H | H | H | CH3S(O)CH2CO | 1 |
| 1-2079 | C—Br | C—H | C—Br | C—H | H | CF3 | CH | CH | C—CF3 | N | H | H | H | CH3SO2CH2CO | 1 |
| 1-2080 | C—Br | C—H | C—Br | C—H | H | CF3 | CH | CH | C—CF3 | N | H | H | H | CH3OCH2CH2CO | 1 |
| 1-2081 | C—Cl | C—H | C—Cl | C—H | H | CF3 | CH | CH | CH | N | H | H | H | H | 1 |
| 1-2082 | C—Cl | C—H | C—Cl | C—H | H | CF3 | CH | CH | CH | N | H | H | H | cyclo-PrCO | 1 |
| 1-2083 | C—Cl | C—H | C—Cl | C—H | H | CF3 | CH | CH | CH | N | H | H | H | cyclo-PrCH2CO | 1 |
| 1-2084 | C—Cl | C—H | C—Cl | C—H | H | CF3 | CH | CH | CH | N | H | H | H | CF3CH2CO | 1 |
| 1-2085 | C—Cl | C—H | C—Cl | C—H | H | CF3 | CH | CH | CH | N | H | H | H | CH3SCH2CO | 1 |
| 1-2086 | C—Cl | C—H | C—Cl | C—H | H | CF3 | CH | CH | CH | N | H | H | H | CH3S(O)CH2CO | 1 |
| 1-2087 | C—Cl | C—H | C—Cl | C—H | H | CF3 | CH | CH | CH | N | H | H | H | CH3SO2CH2CO | 1 |
| 1-2088 | C—Cl | C—H | C—Cl | C—H | H | CF3 | CH | CH | CH | N | H | H | H | CH3OCH2CH2CO | 1 |
| 1-2089 | C—Cl | C—H | C—Cl | C—H | H | CF3 | C—F | CH | CH | N | H | H | H | H | 1 |
| 1-2090 | C—Cl | C—H | C—Cl | C—H | H | CF3 | C—F | CH | CH | N | H | H | H | CH3CO | 1 |
| 1-2091 | C—Cl | C—H | C—Cl | C—H | H | CF3 | C—F | CH | CH | N | H | H | H | CH3CH2CO | 1 |
| 1-2092 | C—Cl | C—H | C—Cl | C—H | H | CF3 | C—F | CH | CH | N | H | H | H | cyclo-PrCO | 1 |
| 1-2093 | C—Cl | C—H | C—Cl | C—H | H | CF3 | C—F | CH | CH | N | H | H | H | CF3CH2CO | 1 |
| 1-2094 | C—Cl | C—H | C—Cl | C—H | H | CF3 | C—F | CH | CH | N | H | H | H | CH3SCH2CO | 1 |
| 1-2095 | C—Cl | C—H | C—Cl | C—H | H | CF3 | C—F | CH | CH | N | H | H | H | CH3S(O)CH2CO | 1 |
| 1-2096 | C—Cl | C—H | C—Cl | C—H | H | CF3 | C—F | CH | CH | N | H | H | H | CH3SO2CH2CO | 1 |
| 1-2097 | C—Cl | C—H | C—Cl | C—H | H | CF3 | C—F | CH | CH | N | H | H | H | CH3OCH2CH2CO | 1 |
| 1-2098 | C—Cl | C—Cl | C—Cl | C—H | H | CF3 | C—F | CH | CH | N | H | H | H | H | 1 |
| 1-2099 | C—Cl | C—Cl | C—Cl | C—H | H | CF3 | C—F | CH | CH | N | H | H | H | CH3CO | 1 |
| 1-2100 | C—Cl | C—Cl | C—Cl | C—H | H | CF3 | C—F | CH | CH | N | H | H | H | CH3CH2CO | 1 |
| 1-2101 | C—Cl | C—Cl | C—Cl | C—H | H | CF3 | C—F | CH | CH | N | H | H | H | cyclo-PrCO | 1 |
| 1-2102 | C—Cl | C—Cl | C—Cl | C—H | H | CF3 | C—F | CH | CH | N | H | H | H | CF3CH2CO | 1 |

TABLE 1-continued

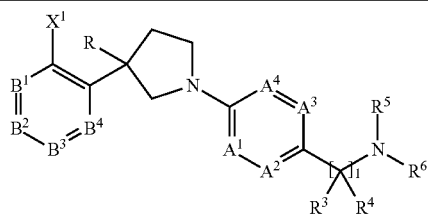

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-2103 | C—Cl | C—Cl | C—Cl | C—H | H | CF3 | C—F | CH | CH | N | H | H | H | CH3SCH2CO | 1 |
| 1-2104 | C—Cl | C—Cl | C—Cl | C—H | H | CF3 | C—F | CH | CH | N | H | H | H | CH3S(O)CH2CO | 1 |
| 1-2105 | C—Cl | C—Cl | C—Cl | C—H | H | CF3 | C—F | CH | CH | N | H | H | H | CH3SO2CH2CO | 1 |
| 1-2106 | C—Cl | C—Cl | C—Cl | C—H | H | CF3 | C—F | CH | CH | N | H | H | H | CH3OCH2CH2CO | 1 |
| 1-2107 | C—CF3 | C—H | C—CF3 | C—H | H | CF3 | C—F | CH | CH | N | H | H | H | H | 1 |
| 1-2108 | C—CF3 | C—H | C—CF3 | C—H | H | CF3 | C—F | CH | CH | N | H | H | H | CH3CO | 1 |
| 1-2109 | C—CF3 | C—H | C—CF3 | C—H | H | CF3 | C—F | CH | CH | N | H | H | H | CH3CH2CO | 1 |
| 1-2110 | C—CF3 | C—H | C—CF3 | C—H | H | CF3 | C—F | CH | CH | N | H | H | H | cyclo-PrCO | 1 |
| 1-2111 | C—CF3 | C—H | C—CF3 | C—H | H | CF3 | C—F | CH | CH | N | H | H | H | CF3CH2CO | 1 |
| 1-2112 | C—CF3 | C—H | C—CF3 | C—H | H | CF3 | C—F | CH | CH | N | H | H | H | CH3SCH2CO | 1 |
| 1-2113 | C—CF3 | C—H | C—CF3 | C—H | H | CF3 | C—F | CH | CH | N | H | H | H | CH3S(O)CH2CO | 1 |
| 1-2114 | C—CF3 | C—H | C—CF3 | C—H | H | CF3 | C—F | CH | CH | N | H | H | H | CH3SO2CH2CO | 1 |
| 1-2115 | C—CF3 | C—H | C—CF3 | C—H | H | CF3 | C—F | CH | CH | N | H | H | H | CH3OCH2CH2CO | 1 |
| 1-2116 | C—Cl | C—H | C—Cl | C—H | H | CF3 | C—F | CH | C—Cl | N | H | H | H | H | 1 |
| 1-2117 | C—Cl | C—H | C—Cl | C—H | H | CF3 | C—F | CH | C—Cl | N | H | H | H | CH3CO | 1 |
| 1-2118 | C—Cl | C—H | C—Cl | C—H | H | CF3 | C—F | CH | C—Cl | N | H | H | H | CH3CH2CO | 1 |
| 1-2119 | C—Cl | C—H | C—Cl | C—H | H | CF3 | C—F | CH | C—Cl | N | H | H | H | cyclo-PrCO | 1 |
| 1-2120 | C—Cl | C—H | C—Cl | C—H | H | CF3 | C—F | CH | C—Cl | N | H | H | H | CF3CH2CO | 1 |
| 1-2121 | C—Cl | C—H | C—Cl | C—H | H | CF3 | C—F | CH | C—Cl | N | H | H | H | CH3SCH2CO | 1 |
| 1-2122 | C—Cl | C—H | C—Cl | C—H | H | CF3 | C—F | CH | C—Cl | N | H | H | H | CH3S(O)CH2CO | 1 |
| 1-2123 | C—Cl | C—H | C—Cl | C—H | H | CF3 | C—F | CH | C—Cl | N | H | H | H | CH3SO2CH2CO | 1 |
| 1-2124 | C—Cl | C—H | C—Cl | C—H | H | CF3 | C—F | CH | C—Cl | N | H | H | H | CH3OCH2CH2CO | 1 |
| 1-2125 | C—Cl | C—Cl | C—Cl | C—H | H | CF3 | C—F | CH | C—Cl | N | H | H | H | H | 1 |
| 1-2126 | C—Cl | C—Cl | C—Cl | C—H | H | CF3 | C—F | CH | C—Cl | N | H | H | H | CH3CO | 1 |
| 1-2127 | C—Cl | C—Cl | C—Cl | C—H | H | CF3 | C—F | CH | C—Cl | N | H | H | H | CH3CH2CO | 1 |
| 1-2128 | C—Cl | C—Cl | C—Cl | C—H | H | CF3 | C—F | CH | C—Cl | N | H | H | H | cyclo-PrCO | 1 |
| 1-2129 | C—Cl | C—Cl | C—Cl | C—H | H | CF3 | C—F | CH | C—Cl | N | H | H | H | CF3CH2CO | 1 |
| 1-2130 | C—Cl | C—Cl | C—Cl | C—H | H | CF3 | C—F | CH | C—Cl | N | H | H | H | CH3SCH2CO | 1 |
| 1-2131 | C—Cl | C—Cl | C—Cl | C—H | H | CF3 | C—F | CH | C—Cl | N | H | H | H | CH3S(O)CH2CO | 1 |
| 1-2132 | C—Cl | C—Cl | C—Cl | C—H | H | CF3 | C—F | CH | C—Cl | N | H | H | H | CH3SO2CH2CO | 1 |
| 1-2133 | C—Cl | C—Cl | C—Cl | C—H | H | CF3 | C—F | CH | C—Cl | N | H | H | H | CH3OCH2CH2CO | 1 |
| 1-2134 | C—CF3 | C—H | C—CF3 | C—H | H | CF3 | C—F | CH | C—Cl | N | H | H | H | H | 1 |
| 1-2135 | C—CF3 | C—H | C—CF3 | C—H | H | CF3 | C—F | CH | C—Cl | N | H | H | H | CH3CO | 1 |
| 1-2136 | C—CF3 | C—H | C—CF3 | C—H | H | CF3 | C—F | CH | C—Cl | N | H | H | H | CH3CH2CO | 1 |
| 1-2137 | C—CF3 | C—H | C—CF3 | C—H | H | CF3 | C—F | CH | C—Cl | N | H | H | H | cyclo-PrCO | 1 |

TABLE 1-continued

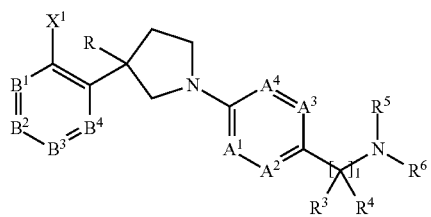

| Ex.-No. | B¹ | B² | B³ | B⁴ | X¹ | R | A¹ | A² | A³ | A⁴ | R³ | R⁴ | R⁵ | R⁶ | 1 |
|---|---|---|---|---|---|---|---|---|---|---|---|---|---|---|---|
| 1-2138 | C—CF3 | C—H | C—CF3 | C—H | H | CF3 | C—F | CH | C—Cl | N | H | H | H | CF3CH2CO | 1 |
| 1-2139 | C—CF3 | C—H | C—CF3 | C—H | H | CF3 | C—F | CH | C—Cl | N | H | H | H | CH3SCH2CO | 1 |
| 1-2140 | C—CF3 | C—H | C—CF3 | C—H | H | CF3 | C—F | CH | C—Cl | N | H | H | H | CH3S(O)CH2CO | 1 |
| 1-2141 | C—CF3 | C—H | C—CF3 | C—H | H | CF3 | C—F | CH | C—Cl | N | H | H | H | CH3SO2CH2CO | 1 |
| 1-2142 | C—CF3 | C—H | C—CF3 | C—H | H | CF3 | C—F | CH | C—Cl | N | H | H | H | CH3OCH2CH2CO | 1 |
| 1-2143 | C—Cl | C—H | C—Cl | C—H | H | CF3 | CH | CH | C—Cl | N | H | H | H | H | 1 |
| 1-2144 | C—Cl | C—Cl | C—Cl | C—H | H | CF3 | CH | CH | C—Cl | N | H | H | H | H | 1 |
| 1-2145 | C—CF3 | C—H | C—CF3 | C—H | H | CF3 | CH | CH | C—Cl | N | H | H | H | H | 1 |
| 1-2146 | C—Cl | C—H | C—Cl | C—H | H | CF3 | CH | CH | C—SCH3 | CH | H | H | H | H | 1 |
| 1-2147 | C—Cl | C—H | C—Cl | C—H | H | CF3 | CH | CH | C—Br | N | H | H | H | H | 1 |
| 1-2148 | C—Cl | C—H | C—CF3 | C—H | H | CF3 | CH | CH | C—Br | N | H | H | H | H | 1 |
| 1-2149 | C—Cl | C—Cl | C—Cl | C—H | H | CF3 | CH | CH | C—Br | N | H | H | H | H | 1 |
| 1-2150 | C—CF3 | C—H | C—CF3 | C—H | H | CF3 | CH | CH | C—Br | N | H | H | H | H | 1 |
| 1-2151 | C—Cl | C—H | C—Cl | C—H | H | CF3 | C—F | CH | C—Cl | N | H | H | H | tert-BuOCO | 1 |
| 1-2152 | C—Cl | C—Cl | C—Cl | C—H | H | CF3 | C—F | CH | C—Cl | N | H | H | H | tert-BuOCO | 1 |
| 1-2153 | C—CF3 | C—H | C—CF3 | C—H | H | CF3 | C—F | CH | C—Cl | N | H | H | H | tert-BuOCO | 1 |
| 1-2154 | C—Cl | C—H | C—Cl | C—H | H | CF3 | C—F | CH | CH | N | H | H | H | tert-BuOCO | 1 |
| 1-2155 | C—Cl | C—Cl | C—Cl | C—H | H | CF3 | C—F | CH | CH | N | H | H | H | tert-BuOCO | 1 |
| 1-2156 | C—CF3 | C—H | C—CF3 | C—H | H | CF3 | C—F | CH | CH | N | H | H | H | tert-BuOCO | 1 |
| 1-2157 | C—CF3 | C—H | C—CF3 | C—H | H | CF3 | CH | CH | C—OCF3 | CH | H | H | H | H | 1 |
| 1-2158 | C—CF3 | C—H | C—CF3 | C—H | H | CF3 | CH | CH | C—OCF3 | CH | H | H | H | CH3CO | 1 |
| 1-2159 | C—CF3 | C—H | C—CF3 | C—H | H | CF3 | CH | CH | C—OCF3 | CH | H | H | H | CH3CH2CO | 1 |
| 1-2160 | C—CF3 | C—H | C—CF3 | C—H | H | CF3 | CH | CH | C—OCF3 | CH | H | H | H | cyclo-PrCO | 1 |
| 1-2161 | C—CF3 | C—H | C—CF3 | C—H | H | CF3 | CH | CH | C—OCF3 | CH | H | H | H | CF3CH2CO | 1 |
| 1-2162 | C—CF3 | C—H | C—CF3 | C—H | H | CF3 | CH | CH | C—OCF3 | CH | H | H | H | CH3SCH2CO | 1 |
| 1-2163 | C—CF3 | C—H | C—CF3 | C—H | H | CF3 | CH | CH | C—OCF3 | CH | H | H | H | CH3S(O)CH2CO | 1 |
| 1-2164 | C—CF3 | C—H | C—CF3 | C—H | H | CF3 | CH | CH | C—OCF3 | CH | H | H | H | CH3SO2CH2CO | 1 |
| 1-2165 | C—CF3 | C—H | C—CF3 | C—H | H | CF3 | CH | CH | C—OCF3 | CH | H | H | H | CH3OCH2CH2CO | 1 |
| 1-2166 | C—CF3 | C—H | C—CF3 | C—H | H | CF3 | CH | CH | C—OCF3 | CH | H | H | H | tert-BuOCO | 1 |
| 1-2167 | C—Cl | C—H | C—Cl | C—H | H | CF3 | CH | CH | C—Cl | C—F | H | H | H | H | 1 |
| 1-2168 | C—Cl | C—Cl | C—Cl | C—H | H | CF3 | CH | CH | C—Cl | C—F | H | H | H | H | 1 |
| 1-2169 | C—CF3 | C—H | C—CF3 | C—H | H | CF3 | CH | CH | C—Cl | C—F | H | H | H | H | 1 |
| 1-2170 | C—Cl | C—Cl | C—Cl | C—H | H | CF3 | CH | CH | CH | N | H | H | H | CH3CH2CO | 1 |
| 1-2171 | C—CF3 | C—H | C—CF3 | C—H | H | CF3 | CH | CH | CH | N | H | H | H | CH3CH2CO | 1 |

TABLE 2

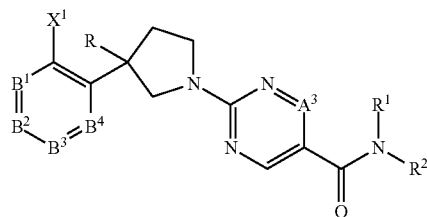

| Table 2-Ex.-No. | B¹ | B² | B³ | B⁴ | X¹ | R | A³ | R¹ | R² |
|---|---|---|---|---|---|---|---|---|---|
| 2-1 | C—Cl | C—H | C—Cl | C—H | H | CF3 | C—CF3 | H | H |
| 2-2 | C—Cl | C—H | C—Cl | C—H | H | CF3 | C—CF3 | H | CH3 |
| 2-3 | C—Cl | C—H | C—Cl | C—H | H | CF3 | C—CF3 | H | CH3CH2 |
| 2-4 | C—Cl | C—H | C—Cl | C—H | H | CF3 | C—CF3 | H | n-Pr |
| 2-5 | C—Cl | C—H | C—Cl | C—H | H | CF3 | C—CF3 | H | cyclo-Pr |
| 2-6 | C—Cl | C—H | C—Cl | C—H | H | CF3 | C—CF3 | H | n-Bu |
| 2-7 | C—Cl | C—H | C—Cl | C—H | H | CF3 | C—CF3 | H | tert-Bu |
| 2-8 | C—Cl | C—H | C—Cl | C—H | H | CF3 | C—CF3 | H | CF3CH2 |
| 2-9 | C—Cl | C—H | C—Cl | C—H | H | CF3 | C—CF3 | H | 2-PyridylCH2 |
| 2-10 | C—Cl | C—H | C—Cl | C—H | H | CF3 | C—CF3 | H | Ph |
| 2-11 | C—Cl | C—H | C—Cl | C—H | H | CF3 | C—CF3 | H | PhCH2 |
| 2-12 | C—Cl | C—H | C—Cl | C—H | H | CF3 | C—CF3 | H | MeO2CCH2 |
| 2-13 | C—Cl | C—H | C—Cl | C—H | H | CF3 | C—CF3 | H | cyclo-PrCH2 |
| 2-14 | C—Cl | C—Cl | C—Cl | C—H | H | CF3 | C—CF3 | H | H |
| 2-15 | C—Cl | C—Cl | C—Cl | C—H | H | CF3 | C—CF3 | H | CH3 |
| 2-16 | C—Cl | C—Cl | C—Cl | C—H | H | CF3 | C—CF3 | H | CH3CH2 |
| 2-17 | C—Cl | C—Cl | C—Cl | C—H | H | CF3 | C—CF3 | H | n-Pr |
| 2-18 | C—Cl | C—Cl | C—Cl | C—H | H | CF3 | C—CF3 | H | cyclo-Pr |
| 2-19 | C—Cl | C—Cl | C—Cl | C—H | H | CF3 | C—CF3 | H | n-Bu |
| 2-20 | C—Cl | C—Cl | C—Cl | C—H | H | CF3 | C—CF3 | H | tert-Bu |
| 2-21 | C—Cl | C—Cl | C—Cl | C—H | H | CF3 | C—CF3 | H | CF3CH2 |
| 2-22 | C—Cl | C—Cl | C—Cl | C—H | H | CF3 | C—CF3 | H | 2-PyridylCH2 |
| 2-23 | C—Cl | C—Cl | C—Cl | C—H | H | CF3 | C—CF3 | H | Ph |
| 2-24 | C—Cl | C—Cl | C—Cl | C—H | H | CF3 | C—CF3 | H | PhCH2 |
| 2-25 | C—Cl | C—Cl | C—Cl | C—H | H | CF3 | C—CF3 | H | MeO2CCH2 |
| 2-26 | C—Cl | C—Cl | C—Cl | C—H | H | CF3 | C—CF3 | H | cyclo-PrCH2 |
| 2-27 | C—CF3 | C—H | C—CF3 | C—H | H | CF3 | C—CF3 | H | H |
| 2-28 | C—CF3 | C—H | C—CF3 | C—H | H | CF3 | C—CF3 | H | CH3 |
| 2-29 | C—CF3 | C—H | C—CF3 | C—H | H | CF3 | C—CF3 | H | CH3CH2 |
| 2-30 | C—CF3 | C—H | C—CF3 | C—H | H | CF3 | C—CF3 | H | n-Pr |
| 2-31 | C—CF3 | C—H | C—CF3 | C—H | H | CF3 | C—CF3 | H | cyclo-Pr |
| 2-32 | C—CF3 | C—H | C—CF3 | C—H | H | CF3 | C—CF3 | H | n-Bu |
| 2-33 | C—CF3 | C—H | C—CF3 | C—H | H | CF3 | C—CF3 | H | tert-Bu |
| 2-34 | C—CF3 | C—H | C—CF3 | C—H | H | CF3 | C—CF3 | H | CF3CH2 |
| 2-35 | C—CF3 | C—H | C—CF3 | C—H | H | CF3 | C—CF3 | H | 2-PyridylCH2 |
| 2-36 | C—CF3 | C—H | C—CF3 | C—H | H | CF3 | C—CF3 | H | Ph |
| 2-37 | C—CF3 | C—H | C—CF3 | C—H | H | CF3 | C—CF3 | H | PhCH2 |
| 2-38 | C—CF3 | C—H | C—CF3 | C—H | H | CF3 | C—CF3 | H | MeO2CCH2 |
| 2-39 | C—CF3 | C—H | C—CF3 | C—H | H | CF3 | C—CF3 | H | cyclo-PrCH2 |
| 2-40 | C—Cl | C—Cl | C—CF3 | C—H | H | CF3 | C—CF3 | H | H |
| 2-41 | C—Cl | C—Cl | C—CF3 | C—H | H | CF3 | C—CF3 | H | CH3 |
| 2-42 | C—Cl | C—Cl | C—CF3 | C—H | H | CF3 | C—CF3 | H | CH3CH2 |
| 2-43 | C—Cl | C—Cl | C—CF3 | C—H | H | CF3 | C—CF3 | H | n-Pr |
| 2-44 | C—Cl | C—Cl | C—CF3 | C—H | H | CF3 | C—CF3 | H | cyclo-Pr |
| 2-45 | C—Cl | C—Cl | C—CF3 | C—H | H | CF3 | C—CF3 | H | n-Bu |
| 2-46 | C—Cl | C—Cl | C—CF3 | C—H | H | CF3 | C—CF3 | H | tert-Bu |
| 2-47 | C—Cl | C—Cl | C—CF3 | C—H | H | CF3 | C—CF3 | H | CF3CH2 |
| 2-48 | C—Cl | C—Cl | C—CF3 | C—H | H | CF3 | C—CF3 | H | 2-PyridylCH2 |
| 2-49 | C—Cl | C—Cl | C—CF3 | C—H | H | CF3 | C—CF3 | H | Ph |
| 2-50 | C—Cl | C—Cl | C—CF3 | C—H | H | CF3 | C—CF3 | H | PhCH2 |
| 2-51 | C—Cl | C—Cl | C—CF3 | C—H | H | CF3 | C—CF3 | H | MeO2CCH2 |
| 2-52 | C—Cl | C—Cl | C—CF3 | C—H | H | CF3 | C—CF3 | H | cyclo-PrCH2 |
| 2-53 | C—Cl | C—H | C—Cl | C—H | H | CF3 | C—H | H | CH3 |
| 2-54 | C—Cl | C—H | C—Cl | C—H | H | CF3 | C—H | H | CF3CH2 |
| 2-55 | C—Cl | C—H | C—Cl | C—H | H | CF3 | C—H | H | 2-PyridylCH2 |
| 2-56 | C—Cl | C—H | C—Cl | C—H | H | CF3 | C—H | H | PhCH2 |
| 2-57 | C—Cl | C—H | C—Cl | C—H | H | CF3 | C—H | H | MeO2CCH2 |
| 2-58 | C—Cl | C—Cl | C—Cl | C—H | H | CF3 | C—H | H | CH3 |
| 2-59 | C—Cl | C—Cl | C—Cl | C—H | H | CF3 | C—H | H | CF3CH2 |
| 2-60 | C—Cl | C—Cl | C—Cl | C—H | H | CF3 | C—H | H | 2-PyridylCH2 |
| 2-61 | C—Cl | C—Cl | C—Cl | C—H | H | CF3 | C—H | H | PhCH2 |
| 2-62 | C—Cl | C—Cl | C—Cl | C—H | H | CF3 | C—H | H | MeO2CCH2 |
| 2-63 | C—CF3 | C—Cl | C—CF3 | C—H | H | CF3 | C—H | H | CH3 |
| 2-64 | C—CF3 | C—Cl | C—CF3 | C—H | H | CF3 | C—H | H | CF3CH2 |
| 2-65 | C—CF3 | C—Cl | C—CF3 | C—H | H | CF3 | C—H | H | 2-PyridylCH2 |
| 2-66 | C—CF3 | C—Cl | C—CF3 | C—H | H | CF3 | C—H | H | PhCH2 |
| 2-67 | C—CF3 | C—Cl | C—CF3 | C—H | H | CF3 | C—H | H | MeO2CCH2 |

TABLE 2-continued

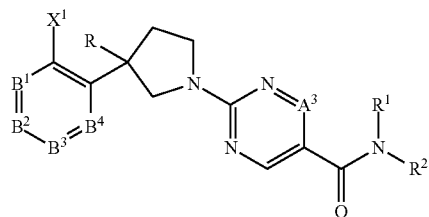

| Table 2-Ex.-No. | $B^1$ | $B^2$ | $B^3$ | $B^4$ | $X^1$ | R | $A^3$ | $R^1$ | $R^2$ |
|---|---|---|---|---|---|---|---|---|---|
| 2-68 | C—Cl | C—H | C—Cl | C—H | H | CF3 | C—CH3 | H | CH3 |
| 2-69 | C—Cl | C—H | C—Cl | C—H | H | CF3 | C—CH3 | H | CF3CH2 |
| 2-70 | C—Cl | C—H | C—Cl | C—H | H | CF3 | C—CH3 | H | 2-PyridylCH2 |
| 2-71 | C—Cl | C—H | C—Cl | C—H | H | CF3 | C—CH3 | H | PhCH2 |
| 2-72 | C—Cl | C—H | C—Cl | C—H | H | CF3 | C—CH3 | H | MeO2CCH2 |
| 2-73 | C—Cl | C—Cl | C—Cl | C—H | H | CF3 | C—CH3 | H | CH3 |
| 2-74 | C—Cl | C—Cl | C—Cl | C—H | H | CF3 | C—CH3 | H | CF3CH2 |
| 2-75 | C—Cl | C—Cl | C—Cl | C—H | H | CF3 | C—CH3 | H | 2-PyridylCH2 |
| 2-76 | C—Cl | C—Cl | C—Cl | C—H | H | CF3 | C—CH3 | H | PhCH2 |
| 2-77 | C—Cl | C—Cl | C—Cl | C—H | H | CF3 | C—CH3 | H | MeO2CCH2 |
| 2-78 | C—CF3 | C—Cl | C—CF3 | C—H | H | CF3 | C—CH3 | H | CH3 |
| 2-79 | C—CF3 | C—Cl | C—CF3 | C—H | H | CF3 | C—CH3 | H | CF3CH2 |
| 2-80 | C—CF3 | C—Cl | C—CF3 | C—H | H | CF3 | C—CH3 | H | 2-PyridylCH2 |
| 2-81 | C—CF3 | C—Cl | C—CF3 | C—H | H | CF3 | C—CH3 | H | PhCH2 |
| 2-82 | C—CF3 | C—Cl | C—CF3 | C—H | H | CF3 | C—CH3 | H | MeO2CCH2 |
| 2-83 | C—Cl | C—H | C—Cl | C—H | H | CF3 | C—Cl | H | CH3 |
| 2-84 | C—Cl | C—H | C—Cl | C—H | H | CF3 | C—Cl | H | CF3CH2 |
| 2-85 | C—Cl | C—H | C—Cl | C—H | H | CF3 | C—Cl | H | 2-PyridylCH2 |
| 2-86 | C—Cl | C—H | C—Cl | C—H | H | CF3 | C—Cl | H | PhCH2 |
| 2-87 | C—Cl | C—H | C—Cl | C—H | H | CF3 | C—Cl | H | MeO2CCH2 |
| 2-88 | C—Cl | C—Cl | C—Cl | C—H | H | CF3 | C—Cl | H | CH3 |
| 2-89 | C—Cl | C—Cl | C—Cl | C—H | H | CF3 | C—Cl | H | CF3CH2 |
| 2-90 | C—Cl | C—Cl | C—Cl | C—H | H | CF3 | C—Cl | H | 2-PyridylCH2 |
| 2-91 | C—Cl | C—Cl | C—Cl | C—H | H | CF3 | C—Cl | H | PhCH2 |
| 2-92 | C—Cl | C—Cl | C—Cl | C—H | H | CF3 | C—Cl | H | MeO2CCH2 |
| 2-93 | C—CF3 | C—Cl | C—CF3 | C—H | H | CF3 | C—Cl | H | CH3 |
| 2-94 | C—CF3 | C—Cl | C—CF3 | C—H | H | CF3 | C—Cl | H | CF3CH2 |
| 2-95 | C—CF3 | C—Cl | C—CF3 | C—H | H | CF3 | C—Cl | H | 2-PyridylCH2 |
| 2-96 | C—CF3 | C—Cl | C—CF3 | C—H | H | CF3 | C—Cl | H | PhCH2 |
| 2-97 | C—CF3 | C—Cl | C—CF3 | C—H | H | CF3 | C—Cl | H | MeO2CCH2 |
| 2-98 | C—CF3 | C—H | C—CF3 | C—H | H | CF3 | C—H | H | CF3CH2 |
| 2-99 | C—CF3 | C—H | C—CF3 | C—H | H | CF3 | C—H | H | 2-PyridylCH2 |
| 2-100 | C—CF3 | C—H | C—CF3 | C—H | H | CF3 | C—CH3 | H | CF3CH2 |
| 2-101 | C—CF3 | C—H | C—CF3 | C—H | H | CF3 | C—CH3 | H | 2-PyridylCH2 |
| 2-102 | C—Cl | C—H | C—Cl | C—H | H | CF3 | C—Cl | H | CH3OCH2 |
| 2-103 | C—Cl | C—H | C—Cl | C—H | H | CF3 | C—Cl | CH3CO | CH3OCH2 |
| 2-104 | C—Cl | C—H | C—Cl | C—H | H | CF3 | C—Cl | H | CH3CH2OCH2 |
| 2-105 | C—Cl | C—H | C—Cl | C—H | H | CF3 | C—Cl | H | CH3OCH2CH2 |
| 2-106 | C—Cl | C—H | C—Cl | C—H | H | CF3 | C—Cl | H | CH3CH2OCH2CH2 |
| 2-107 | C—Cl | C—H | C—Cl | C—H | H | CF3 | C—Cl | H | tetrahydrofuran-2-yl |
| 2-108 | C—Cl | C—H | C—Cl | C—H | H | CF3 | C—Cl | H | CH3SCH2CH2 |
| 2-109 | C—Cl | C—H | C—Cl | C—H | H | CF3 | C—Cl | H | CH3S(O)CH2CH2 |
| 2-110 | C—Cl | C—H | C—Cl | C—H | H | CF3 | C—Cl | H | CH3SO2CH2CH2 |
| 2-111 | C—Cl | C—H | C—Cl | C—H | H | CF3 | C—Cl | H | CH3SCH2CH(CH3) |
| 2-112 | C—Cl | C—H | C—Cl | C—H | H | CF3 | C—Cl | H | CH3S(O)CH2CH(CH3) |
| 2-113 | C—Cl | C—H | C—Cl | C—H | H | CF3 | C—Cl | H | CH3SO2CH2CH(CH3) |
| 2-114 | C—Cl | C—H | C—Cl | C—H | H | CF3 | C—Cl | H | CH3SCH2C(CH3)2 |
| 2-115 | C—Cl | C—H | C—Cl | C—H | H | CF3 | C—Cl | H | CH3S(O)CH2C(CH3)2 |
| 2-116 | C—Cl | C—H | C—Cl | C—H | H | CF3 | C—Cl | H | CH3SO2CH2C(CH3)2 |
| 2-117 | C—Cl | C—H | C—Cl | C—H | H | CF3 | C—Cl | H | (Methoxyimino)methyl |
| 2-118 | C—Cl | C—H | C—Cl | C—H | H | CF3 | C—Cl | H | (Ethoxyimino)methyl |
| 2-119 | C—Cl | C—H | C—Cl | C—H | H | CF3 | C—Cl | H | [1-(1,3-thiazol-4-yl)]CH2 |
| 2-120 | C—Cl | C—H | C—Cl | C—H | H | CF3 | C—Cl | H | [1-(1-methyl-1H-pyrazol-5-yl]CH2 |
| 2-121 | C—Cl | C—H | C—Cl | C—H | H | CF3 | C—Cl | H | 5-chloropyrimidin-2-yl |
| 2-122 | C—Cl | C—H | C—Cl | C—H | H | CF3 | C—Cl | H | 5-bromopyrimidin-2-yl |
| 2-123 | C—Cl | C—H | C—Cl | C—H | H | CF3 | C—Cl | H | 5-cyanopyrimidin-2-yl |
| 2-124 | C—Cl | C—H | C—Cl | C—H | H | CF3 | C—Cl | H | CH3NHC(O)CH2 |
| 2-125 | C—Cl | C—H | C—Cl | C—H | H | CF3 | C—Cl | H | CH3CH2NHC(O)CH2 |
| 2-126 | C—Cl | C—H | C—Cl | C—H | H | CF3 | C—Cl | H | iso-PrNHC(O)CH2 |
| 2-127 | C—Cl | C—H | C—Cl | C—H | H | CF3 | C—Cl | H | cyclo-PrNHC(O)CH2 |
| 2-128 | C—Cl | C—H | C—Cl | C—H | H | CF3 | C—Cl | H | CF3CH2NHC(O)CH2 |
| 2-129 | C—Cl | C—H | C—Cl | C—H | H | CF3 | C—Cl | H | CH3NHC(O)CH(CH3) |
| 2-130 | C—Cl | C—H | C—Cl | C—H | H | CF3 | C—Cl | H | CH3CH2NHC(O)CH(CH3) |
| 2-131 | C—Cl | C—H | C—Cl | C—H | H | CF3 | C—Cl | H | iso-PrNHC(O)CH(CH3) |
| 2-132 | C—Cl | C—H | C—Cl | C—H | H | CF3 | C—Cl | H | cyclo-PrNHC(O)CH(CH3) |
| 2-133 | C—Cl | C—H | C—Cl | C—H | H | CF3 | C—Cl | H | CF3CH2NHC(O)CH(CH3) |
| 2-134 | C—Cl | C—H | C—Cl | C—H | H | CF3 | C—Cl | H | CH3NHC(O)C(CH3)2 |

TABLE 2-continued

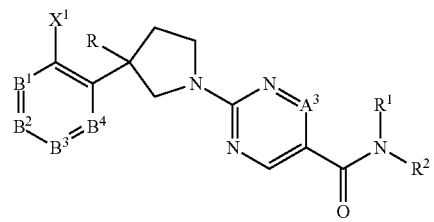

| Table 2-Ex.-No. | B¹ | B² | B³ | B⁴ | X¹ | R | A³ | R¹ | R² |
|---|---|---|---|---|---|---|---|---|---|
| 2-135 | C—Cl | C—H | C—Cl | C—H | H | CF3 | C—Cl | H | CH3CH2NHC(O)C(CH3)2 |
| 2-136 | C—Cl | C—H | C—Cl | C—H | H | CF3 | C—Cl | H | iso-PrNHC(O)C(CH3)2 |
| 2-137 | C—Cl | C—H | C—Cl | C—H | H | CF3 | C—Cl | H | cyclo-PrNHC(O)C(CH3)2 |
| 2-138 | C—Cl | C—H | C—Cl | C—H | H | CF3 | C—Cl | H | CF3CH2NHC(O)C(CH3)2 |
| 2-139 | C—Cl | C—Cl | C—Cl | C—H | H | CF3 | C—Cl | H | CH3OCH2 |
| 2-140 | C—Cl | C—Cl | C—Cl | C—H | H | CF3 | C—Cl | CH3CO | CH3OCH2 |
| 2-141 | C—Cl | C—Cl | C—Cl | C—H | H | CF3 | C—Cl | H | CH3CH2OCH2 |
| 2-142 | C—Cl | C—Cl | C—Cl | C—H | H | CF3 | C—Cl | H | CH3OCH2CH2 |
| 2-143 | C—Cl | C—Cl | C—Cl | C—H | H | CF3 | C—Cl | H | CH3CH2OCH2CH2 |
| 2-144 | C—Cl | C—Cl | C—Cl | C—H | H | CF3 | C—Cl | H | tetrahydrofuran-2-yl |
| 2-145 | C—Cl | C—Cl | C—Cl | C—H | H | CF3 | C—Cl | H | CH3SCH2CH2 |
| 2-146 | C—Cl | C—Cl | C—Cl | C—H | H | CF3 | C—Cl | H | CH3S(O)CH2CH2 |
| 2-147 | C—Cl | C—Cl | C—Cl | C—H | H | CF3 | C—Cl | H | CH3SO2CH2CH2 |
| 2-148 | C—Cl | C—Cl | C—Cl | C—H | H | CF3 | C—Cl | H | CH3SCH2CH(CH3) |
| 2-149 | C—Cl | C—Cl | C—Cl | C—H | H | CF3 | C—Cl | H | CH3S(O)CH2CH(CH3) |
| 2-150 | C—Cl | C—Cl | C—Cl | C—H | H | CF3 | C—Cl | H | CH3SO2CH2CH(CH3) |
| 2-151 | C—Cl | C—Cl | C—Cl | C—H | H | CF3 | C—Cl | H | CH3SCH2C(CH3)2 |
| 2-152 | C—Cl | C—Cl | C—Cl | C—H | H | CF3 | C—Cl | H | CH3S(O)CH2C(CH3)2 |
| 2-153 | C—Cl | C—Cl | C—Cl | C—H | H | CF3 | C—Cl | H | CH3SO2CH2C(CH3)2 |
| 2-154 | C—Cl | C—Cl | C—Cl | C—H | H | CF3 | C—Cl | H | (Methoxyimino)methyl |
| 2-155 | C—Cl | C—Cl | C—Cl | C—H | H | CF3 | C—Cl | H | (Ethoxyimino)methyl |
| 2-156 | C—Cl | C—Cl | C—Cl | C—H | H | CF3 | C—Cl | H | [1-(1,3-thiazol-4-yl)]CH2 |
| 2-157 | C—Cl | C—Cl | C—Cl | C—H | H | CF3 | C—Cl | H | [1-(1-methyl-1H-pyrazol-5-yl]CH2 |
| 2-158 | C—Cl | C—Cl | C—Cl | C—H | H | CF3 | C—Cl | H | 5-chloropyrimidin-2-yl |
| 2-159 | C—Cl | C—Cl | C—Cl | C—H | H | CF3 | C—Cl | H | 5-bromopyrimidin-2-yl |
| 2-160 | C—Cl | C—Cl | C—Cl | C—H | H | CF3 | C—Cl | H | 5-cyanopyrimidin-2-yl |
| 2-161 | C—Cl | C—Cl | C—Cl | C—H | H | CF3 | C—Cl | H | CH3NHC(O)CH2 |
| 2-162 | C—Cl | C—Cl | C—Cl | C—H | H | CF3 | C—Cl | H | CH3CH2NHC(O)CH2 |
| 2-163 | C—Cl | C—Cl | C—Cl | C—H | H | CF3 | C—Cl | H | iso-PrNHC(O)CH2 |
| 2-164 | C—Cl | C—Cl | C—Cl | C—H | H | CF3 | C—Cl | H | cyclo-PrNHC(O)CH2 |
| 2-165 | C—Cl | C—Cl | C—Cl | C—H | H | CF3 | C—Cl | H | CF3CH2NHC(O)CH2 |
| 2-166 | C—Cl | C—Cl | C—Cl | C—H | H | CF3 | C—Cl | H | CH3NHC(O)CH(CH3) |
| 2-167 | C—Cl | C—Cl | C—Cl | C—H | H | CF3 | C—Cl | H | CH3CH2NHC(O)CH(CH3) |
| 2-168 | C—Cl | C—Cl | C—Cl | C—H | H | CF3 | C—Cl | H | iso-PrNHC(O)CH(CH3) |
| 2-169 | C—Cl | C—Cl | C—Cl | C—H | H | CF3 | C—Cl | H | cyclo-PrNHC(O)CH(CH3) |
| 2-170 | C—Cl | C—Cl | C—Cl | C—H | H | CF3 | C—Cl | H | CF3CH2NHC(O)CH(CH3) |
| 2-171 | C—Cl | C—Cl | C—Cl | C—H | H | CF3 | C—Cl | H | CH3NHC(O)C(CH3)2 |
| 2-172 | C—Cl | C—Cl | C—Cl | C—H | H | CF3 | C—Cl | H | CH3CH2NHC(O)C(CH3)2 |
| 2-173 | C—Cl | C—Cl | C—Cl | C—H | H | CF3 | C—Cl | H | iso-PrNHC(O)C(CH3)2 |
| 2-174 | C—Cl | C—Cl | C—Cl | C—H | H | CF3 | C—Cl | H | cyclo-PrNHC(O)C(CH3)2 |
| 2-175 | C—Cl | C—Cl | C—Cl | C—H | H | CF3 | C—Cl | H | CF3CH2NHC(O)C(CH3)2 |
| 2-176 | C—Cl | C—H | C—CF3 | C—H | H | CF3 | C—Cl | H | CF3CH2 |
| 2-177 | C—Cl | C—H | C—CF3 | C—H | H | CF3 | C—Cl | H | CH3OCH2 |
| 2-178 | C—Cl | C—H | C—CF3 | C—H | H | CF3 | C—Cl | CH3CO | CH3OCH2 |
| 2-179 | C—Cl | C—H | C—CF3 | C—H | H | CF3 | C—Cl | H | CH3CH2OCH2 |
| 2-180 | C—Cl | C—H | C—CF3 | C—H | H | CF3 | C—Cl | H | CH3OCH2CH2 |
| 2-181 | C—Cl | C—H | C—CF3 | C—H | H | CF3 | C—Cl | H | CH3CH2OCH2CH2 |
| 2-182 | C—Cl | C—H | C—CF3 | C—H | H | CF3 | C—Cl | H | tetrahydrofuran-2-yl |
| 2-183 | C—Cl | C—H | C—CF3 | C—H | H | CF3 | C—Cl | H | CH3SCH2CH2 |
| 2-184 | C—Cl | C—H | C—CF3 | C—H | H | CF3 | C—Cl | H | CH3S(O)CH2CH2 |
| 2-185 | C—Cl | C—H | C—CF3 | C—H | H | CF3 | C—Cl | H | CH3SO2CH2CH2 |
| 2-186 | C—Cl | C—H | C—CF3 | C—H | H | CF3 | C—Cl | H | CH3SCH2CH(CH3) |
| 2-187 | C—Cl | C—H | C—CF3 | C—H | H | CF3 | C—Cl | H | CH3S(O)CH2CH(CH3) |
| 2-188 | C—Cl | C—H | C—CF3 | C—H | H | CF3 | C—Cl | H | CH3SO2CH2CH(CH3) |
| 2-189 | C—Cl | C—H | C—CF3 | C—H | H | CF3 | C—Cl | H | CH3SCH2C(CH3)2 |
| 2-190 | C—Cl | C—H | C—CF3 | C—H | H | CF3 | C—Cl | H | CH3S(O)CH2C(CH3)2 |
| 2-191 | C—Cl | C—H | C—CF3 | C—H | H | CF3 | C—Cl | H | CH3SO2CH2C(CH3)2 |
| 2-192 | C—Cl | C—H | C—CF3 | C—H | H | CF3 | C—Cl | H | (Methoxyimino)methyl |
| 2-193 | C—Cl | C—H | C—CF3 | C—H | H | CF3 | C—Cl | H | (Ethoxyimino)methyl |
| 2-194 | C—Cl | C—H | C—CF3 | C—H | H | CF3 | C—Cl | H | 2-PyridylCH2 |
| 2-195 | C—Cl | C—H | C—CF3 | C—H | H | CF3 | C—Cl | H | [1-(1,3-thiazol-4-yl)]CH2 |
| 2-196 | C—Cl | C—H | C—CF3 | C—H | H | CF3 | C—Cl | H | [1-(1-methyl-1H-pyrazol-5-yl]CH2 |
| 2-197 | C—Cl | C—H | C—CF3 | C—H | H | CF3 | C—Cl | H | 5-chloropyrimidin-2-yl |
| 2-198 | C—Cl | C—H | C—CF3 | C—H | H | CF3 | C—Cl | H | 5-bromopyrimidin-2-yl |
| 2-199 | C—Cl | C—H | C—CF3 | C—H | H | CF3 | C—Cl | H | 5-cyanopyrimidin-2-yl |
| 2-200 | C—Cl | C—H | C—CF3 | C—H | H | CF3 | C—Cl | H | CH3NHC(O)CH2 |
| 2-201 | C—Cl | C—H | C—CF3 | C—H | H | CF3 | C—Cl | H | CH3CH2NHC(O)CH2 |

TABLE 2-continued

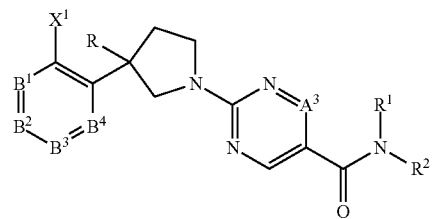

| Table 2-Ex.-No. | B¹ | B² | B³ | B⁴ | X¹ | R | A³ | R¹ | R² |
|---|---|---|---|---|---|---|---|---|---|
| 2-202 | C—Cl | C—H | C—CF3 | C—H | H | CF3 | C—Cl | H | iso-PrNHC(O)CH2 |
| 2-203 | C—Cl | C—H | C—CF3 | C—H | H | CF3 | C—Cl | H | cyclo-PrNHC(O)CH2 |
| 2-204 | C—Cl | C—H | C—CF3 | C—H | H | CF3 | C—Cl | H | CF3CH2NHC(O)CH2 |
| 2-205 | C—Cl | C—H | C—CF3 | C—H | H | CF3 | C—Cl | H | CH3NHC(O)CH(CH3) |
| 2-206 | C—Cl | C—H | C—CF3 | C—H | H | CF3 | C—Cl | H | CH3CH2NHC(O)CH(CH3) |
| 2-207 | C—Cl | C—H | C—CF3 | C—H | H | CF3 | C—Cl | H | iso-PrNHC(O)CH(CH3) |
| 2-208 | C—Cl | C—H | C—CF3 | C—H | H | CF3 | C—Cl | H | cyclo-PrNHC(O)CH(CH3) |
| 2-209 | C—Cl | C—H | C—CF3 | C—H | H | CF3 | C—Cl | H | CF3CH2NHC(O)CH(CH3) |
| 2-210 | C—Cl | C—H | C—CF3 | C—H | H | CF3 | C—Cl | H | CH3NHC(O)C(CH3)2 |
| 2-211 | C—Cl | C—H | C—CF3 | C—H | H | CF3 | C—Cl | H | CH3CH2NHC(O)C(CH3)2 |
| 2-212 | C—Cl | C—H | C—CF3 | C—H | H | CF3 | C—Cl | H | iso-PrNHC(O)C(CH3)2 |
| 2-213 | C—Cl | C—H | C—CF3 | C—H | H | CF3 | C—Cl | H | cyclo-PrNHC(O)C(CH3)2 |
| 2-214 | C—Cl | C—H | C—CF3 | C—H | H | CF3 | C—Cl | H | CF3CH2NHC(O)C(CH3)2 |
| 2-215 | C—CF3 | C—H | C—CF3 | C—H | H | CF3 | C—Cl | H | CF3CH2 |
| 2-216 | C—CF3 | C—H | C—CF3 | C—H | H | CF3 | C—Cl | H | CH3OCH2 |
| 2-217 | C—CF3 | C—H | C—CF3 | C—H | H | CF3 | C—Cl | CH3CO | CH3OCH2 |
| 2-218 | C—CF3 | C—H | C—CF3 | C—H | H | CF3 | C—Cl | H | CH3CH2OCH2 |
| 2-219 | C—CF3 | C—H | C—CF3 | C—H | H | CF3 | C—Cl | H | CH3OCH2CH2 |
| 2-220 | C—CF3 | C—H | C—CF3 | C—H | H | CF3 | C—Cl | H | CH3CH2OCH2CH2 |
| 2-221 | C—CF3 | C—H | C—CF3 | C—H | H | CF3 | C—Cl | H | tetrahydrofuran-2-yl |
| 2-222 | C—CF3 | C—H | C—CF3 | C—H | H | CF3 | C—Cl | H | CH3SCH2CH2 |
| 2-223 | C—CF3 | C—H | C—CF3 | C—H | H | CF3 | C—Cl | H | CH3S(O)CH2CH2 |
| 2-224 | C—CF3 | C—H | C—CF3 | C—H | H | CF3 | C—Cl | H | CH3SO2CH2CH2 |
| 2-225 | C—CF3 | C—H | C—CF3 | C—H | H | CF3 | C—Cl | H | CH3SCH2CH(CH3) |
| 2-226 | C—CF3 | C—H | C—CF3 | C—H | H | CF3 | C—Cl | H | CH3S(O)CH2CH(CH3) |
| 2-227 | C—CF3 | C—H | C—CF3 | C—H | H | CF3 | C—Cl | H | CH3SO2CH2CH(CH3) |
| 2-228 | C—CF3 | C—H | C—CF3 | C—H | H | CF3 | C—Cl | H | CH3SCH2C(CH3)2 |
| 2-229 | C—CF3 | C—H | C—CF3 | C—H | H | CF3 | C—Cl | H | CH3S(O)CH2C(CH3)2 |
| 2-230 | C—CF3 | C—H | C—CF3 | C—H | H | CF3 | C—Cl | H | CH3SO2CH2C(CH3)2 |
| 2-231 | C—CF3 | C—H | C—CF3 | C—H | H | CF3 | C—Cl | H | (Methoxyimino)methyl |
| 2-232 | C—CF3 | C—H | C—CF3 | C—H | H | CF3 | C—Cl | H | (Ethoxyimino)methyl |
| 2-233 | C—CF3 | C—H | C—CF3 | C—H | H | CF3 | C—Cl | H | 2-PyridylCH2 |
| 2-234 | C—CF3 | C—H | C—CF3 | C—H | H | CF3 | C—Cl | H | [1-(1,3-thiazol-4-yl)]CH2 |
| 2-235 | C—CF3 | C—H | C—CF3 | C—H | H | CF3 | C—Cl | H | [1-(1-methyl-1H-pyrazol-5-yl]CH2 |
| 2-236 | C—CF3 | C—H | C—CF3 | C—H | H | CF3 | C—Cl | H | 5-chloropyrimidin-2-yl |
| 2-237 | C—CF3 | C—H | C—CF3 | C—H | H | CF3 | C—Cl | H | 5-bromopyrimidin-2-yl |
| 2-238 | C—CF3 | C—H | C—CF3 | C—H | H | CF3 | C—Cl | H | 5-cyanopyrimidin-2-yl |
| 2-239 | C—CF3 | C—H | C—CF3 | C—H | H | CF3 | C—Cl | H | CH3NHC(O)CH2 |
| 2-240 | C—CF3 | C—H | C—CF3 | C—H | H | CF3 | C—Cl | H | CH3CH2NHC(O)CH2 |
| 2-241 | C—CF3 | C—H | C—CF3 | C—H | H | CF3 | C—Cl | H | iso-PrNHC(O)CH2 |
| 2-242 | C—CF3 | C—H | C—CF3 | C—H | H | CF3 | C—Cl | H | cyclo-PrNHC(O)CH2 |
| 2-243 | C—CF3 | C—H | C—CF3 | C—H | H | CF3 | C—Cl | H | CF3CH2NHC(O)CH2 |
| 2-244 | C—CF3 | C—H | C—CF3 | C—H | H | CF3 | C—Cl | H | CH3NHC(O)CH(CH3) |
| 2-245 | C—CF3 | C—H | C—CF3 | C—H | H | CF3 | C—Cl | H | CH3CH2NHC(O)CH(CH3) |
| 2-246 | C—CF3 | C—H | C—CF3 | C—H | H | CF3 | C—Cl | H | iso-PrNHC(O)CH(CH3) |
| 2-247 | C—CF3 | C—H | C—CF3 | C—H | H | CF3 | C—Cl | H | cyclo-PrNHC(O)CH(CH3) |
| 2-248 | C—CF3 | C—H | C—CF3 | C—H | H | CF3 | C—Cl | H | CF3CH2NHC(O)CH(CH3) |
| 2-249 | C—CF3 | C—H | C—CF3 | C—H | H | CF3 | C—Cl | H | CH3NHC(O)C(CH3)2 |
| 2-250 | C—CF3 | C—H | C—CF3 | C—H | H | CF3 | C—Cl | H | CH3CH2NHC(O)C(CH3)2 |
| 2-251 | C—CF3 | C—H | C—CF3 | C—H | H | CF3 | C—Cl | H | iso-PrNHC(O)C(CH3)2 |
| 2-252 | C—CF3 | C—H | C—CF3 | C—H | H | CF3 | C—Cl | H | cyclo-PrNHC(O)C(CH3)2 |
| 2-253 | C—CF3 | C—H | C—CF3 | C—H | H | CF3 | C—Cl | H | CF3CH2NHC(O)C(CH3)2 |
| 2-254 | C—Cl | C—H | C—Cl | C—H | H | CF3 | C—Br | H | CF3CH2 |
| 2-255 | C—Cl | C—H | C—Cl | C—H | H | CF3 | C—Br | H | 2-PyridylCH2 |
| 2-256 | C—Cl | C—Cl | C—Cl | C—H | H | CF3 | C—Br | H | CF3CH2 |
| 2-257 | C—Cl | C—Cl | C—Cl | C—H | H | CF3 | C—Br | H | 2-PyridylCH2 |
| 2-258 | C—Cl | C—H | C—CF3 | C—H | H | CF3 | C—Br | H | CF3CH2 |
| 2-259 | C—Cl | C—H | C—CF3 | C—H | H | CF3 | C—Br | H | 2-PyridylCH2 |
| 2-260 | C—CF3 | C—H | C—CF3 | C—H | H | CF3 | C—Br | H | CF3CH2 |
| 2-261 | C—CF3 | C—H | C—CF3 | C—H | H | CF3 | C—Br | H | 2-PyridylCH2 |
| 2-262 | C—Cl | C—H | C—Cl | C—H | H | CF3 | C—I | H | CF3CH2 |
| 2-263 | C—Cl | C—H | C—Cl | C—H | H | CF3 | C—I | H | 2-PyridylCH2 |
| 2-264 | C—Cl | C—Cl | C—Cl | C—H | H | CF3 | C—I | H | CF3CH2 |
| 2-265 | C—Cl | C—Cl | C—Cl | C—H | H | CF3 | C—I | H | 2-PyridylCH2 |
| 2-266 | C—Cl | C—H | C—CF3 | C—H | H | CF3 | C—I | H | CF3CH2 |
| 2-267 | C—Cl | C—H | C—CF3 | C—H | H | CF3 | C—I | H | 2-PyridylCH2 |
| 2-268 | C—CF3 | C—H | C—CF3 | C—H | H | CF3 | C—I | H | CF3CH2 |

TABLE 2-continued

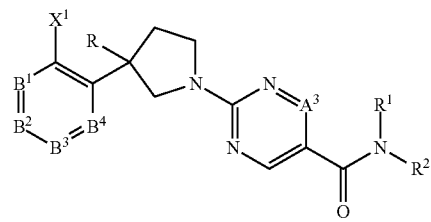

| Table 2-Ex.-No. | B¹ | B² | B³ | B⁴ | X¹ | R | A³ | R¹ | R² |
|---|---|---|---|---|---|---|---|---|---|
| 2-269 | C—CF3 | C—H | C—CF3 | C—H | H | CF3 | C—I | H | 2-PyridylCH2 |
| 2-270 | C—Cl | C—H | C—Cl | C—H | H | CF3 | C—CF3 | H | CH3OCH2 |
| 2-271 | C—Cl | C—H | C—Cl | C—H | H | CF3 | C—CF3 | CH3CO | CH3OCH2 |
| 2-272 | C—Cl | C—H | C—Cl | C—H | H | CF3 | C—CF3 | H | CH3CH2OCH2 |
| 2-273 | C—Cl | C—H | C—Cl | C—H | H | CF3 | C—CF3 | H | CH3OCH2CH2 |
| 2-274 | C—Cl | C—H | C—Cl | C—H | H | CF3 | C—CF3 | H | CH3CH2OCH2CH2 |
| 2-275 | C—Cl | C—H | C—Cl | C—H | H | CF3 | C—CF3 | H | tetrahydrofuran-2-yl |
| 2-276 | C—Cl | C—H | C—Cl | C—H | H | CF3 | C—CF3 | H | CH3SCH2CH2 |
| 2-277 | C—Cl | C—H | C—Cl | C—H | H | CF3 | C—CF3 | H | CH3S(O)CH2CH2 |
| 2-278 | C—Cl | C—H | C—Cl | C—H | H | CF3 | C—CF3 | H | CH3SO2CH2CH2 |
| 2-279 | C—Cl | C—H | C—Cl | C—H | H | CF3 | C—CF3 | H | CH3SCH2CH(CH3) |
| 2-280 | C—Cl | C—H | C—Cl | C—H | H | CF3 | C—CF3 | H | CH3S(O)CH2CH(CH3) |
| 2-281 | C—Cl | C—H | C—Cl | C—H | H | CF3 | C—CF3 | H | CH3SO2CH2CH(CH3) |
| 2-282 | C—Cl | C—H | C—Cl | C—H | H | CF3 | C—CF3 | H | CH3SCH2C(CH3)2 |
| 2-283 | C—Cl | C—H | C—Cl | C—H | H | CF3 | C—CF3 | H | CH3S(O)CH2C(CH3)2 |
| 2-284 | C—Cl | C—H | C—Cl | C—H | H | CF3 | C—CF3 | H | CH3SO2CH2C(CH3)2 |
| 2-285 | C—Cl | C—H | C—Cl | C—H | H | CF3 | C—CF3 | H | (Methoxyimino)methyl |
| 2-286 | C—Cl | C—H | C—Cl | C—H | H | CF3 | C—CF3 | H | (Ethoxyimino)methyl |
| 2-287 | C—Cl | C—H | C—Cl | C—H | H | CF3 | C—CF3 | H | [1-(1,3-thiazol-4-yl)]CH2 |
| 2-288 | C—Cl | C—H | C—Cl | C—H | H | CF3 | C—CF3 | H | [1-(1-methyl-1H-pyrazol-5-yl]CH2 |
| 2-289 | C—Cl | C—H | C—Cl | C—H | H | CF3 | C—CF3 | H | 5-chloropyrimidin-2-yl |
| 2-290 | C—Cl | C—H | C—Cl | C—H | H | CF3 | C—CF3 | H | 5-bromopyrimidin-2-yl |
| 2-291 | C—Cl | C—H | C—Cl | C—H | H | CF3 | C—CF3 | H | 5-cyanopyrimidin-2-yl |
| 2-292 | C—Cl | C—H | C—Cl | C—H | H | CF3 | C—CF3 | H | CH3NHC(O)CH2 |
| 2-293 | C—Cl | C—H | C—Cl | C—H | H | CF3 | C—CF3 | H | CH3CH2NHC(O)CH2 |
| 2-294 | C—Cl | C—H | C—Cl | C—H | H | CF3 | C—CF3 | H | iso-PrNHC(O)CH2 |
| 2-295 | C—Cl | C—H | C—Cl | C—H | H | CF3 | C—CF3 | H | cyclo-PrNHC(O)CH2 |
| 2-296 | C—Cl | C—H | C—Cl | C—H | H | CF3 | C—CF3 | H | CF3CH2NHC(O)CH2 |
| 2-297 | C—Cl | C—H | C—Cl | C—H | H | CF3 | C—CF3 | H | CH3NHC(O)CH(CH3) |
| 2-298 | C—Cl | C—H | C—Cl | C—H | H | CF3 | C—CF3 | H | CH3CH2NHC(O)CH(CH3) |
| 2-299 | C—Cl | C—H | C—Cl | C—H | H | CF3 | C—CF3 | H | iso-PrNHC(O)CH(CH3) |
| 2-300 | C—Cl | C—H | C—Cl | C—H | H | CF3 | C—CF3 | H | cyclo-PrNHC(O)CH(CH3) |
| 2-301 | C—Cl | C—H | C—Cl | C—H | H | CF3 | C—CF3 | H | CF3CH2NHC(O)CH(CH3) |
| 2-302 | C—Cl | C—H | C—Cl | C—H | H | CF3 | C—CF3 | H | CH3NHC(O)C(CH3)2 |
| 2-303 | C—Cl | C—H | C—Cl | C—H | H | CF3 | C—CF3 | H | CH3CH2NHC(O)C(CH3)2 |
| 2-304 | C—Cl | C—H | C—Cl | C—H | H | CF3 | C—CF3 | H | iso-PrNHC(O)C(CH3)2 |
| 2-305 | C—Cl | C—H | C—Cl | C—H | H | CF3 | C—CF3 | H | cyclo-PrNHC(O)C(CH3)2 |
| 2-306 | C—Cl | C—H | C—Cl | C—H | H | CF3 | C—CF3 | H | CF3CH2NHC(O)C(CH3)2 |
| 2-307 | C—Cl | C—Cl | C—Cl | C—H | H | CF3 | C—CF3 | H | CH3OCH2 |
| 2-308 | C—Cl | C—Cl | C—Cl | C—H | H | CF3 | C—CF3 | CH3CO | CH3OCH2 |
| 2-309 | C—Cl | C—Cl | C—Cl | C—H | H | CF3 | C—CF3 | H | CH3CH2OCH2 |
| 2-310 | C—Cl | C—Cl | C—Cl | C—H | H | CF3 | C—CF3 | H | CH3OCH2CH2 |
| 2-311 | C—Cl | C—Cl | C—Cl | C—H | H | CF3 | C—CF3 | H | CH3CH2OCH2CH2 |
| 2-312 | C—Cl | C—Cl | C—Cl | C—H | H | CF3 | C—CF3 | H | tetrahydrofuran-2-yl |
| 2-313 | C—Cl | C—Cl | C—Cl | C—H | H | CF3 | C—CF3 | H | CH3SCH2CH2 |
| 2-314 | C—Cl | C—Cl | C—Cl | C—H | H | CF3 | C—CF3 | H | CH3S(O)CH2CH2 |
| 2-315 | C—Cl | C—Cl | C—Cl | C—H | H | CF3 | C—CF3 | H | CH3SO2CH2CH2 |
| 2-316 | C—Cl | C—Cl | C—Cl | C—H | H | CF3 | C—CF3 | H | CH3SCH2CH(CH3) |
| 2-317 | C—Cl | C—Cl | C—Cl | C—H | H | CF3 | C—CF3 | H | CH3S(O)CH2CH(CH3) |
| 2-318 | C—Cl | C—Cl | C—Cl | C—H | H | CF3 | C—CF3 | H | CH3SO2CH2CH(CH3) |
| 2-319 | C—Cl | C—Cl | C—Cl | C—H | H | CF3 | C—CF3 | H | CH3SCH2C(CH3)2 |
| 2-320 | C—Cl | C—Cl | C—Cl | C—H | H | CF3 | C—CF3 | H | CH3S(O)CH2C(CH3)2 |
| 2-321 | C—Cl | C—Cl | C—Cl | C—H | H | CF3 | C—CF3 | H | CH3SO2CH2C(CH3)2 |
| 2-322 | C—Cl | C—Cl | C—Cl | C—H | H | CF3 | C—CF3 | H | (Methoxyimino)methyl |
| 2-323 | C—Cl | C—Cl | C—Cl | C—H | H | CF3 | C—CF3 | H | (Ethoxyimino)methyl |
| 2-324 | C—Cl | C—Cl | C—Cl | C—H | H | CF3 | C—CF3 | H | [1-(1,3-thiazol-4-yl)]CH2 |
| 2-325 | C—Cl | C—Cl | C—Cl | C—H | H | CF3 | C—CF3 | H | [1-(1-methyl-1H-pyrazol-5-yl]CH2 |
| 2-326 | C—Cl | C—Cl | C—Cl | C—H | H | CF3 | C—CF3 | H | 5-chloropyrimidin-2-yl |
| 2-327 | C—Cl | C—Cl | C—Cl | C—H | H | CF3 | C—CF3 | H | 5-bromopyrimidin-2-yl |
| 2-328 | C—Cl | C—Cl | C—Cl | C—H | H | CF3 | C—CF3 | H | 5-cyanopyrimidin-2-yl |
| 2-329 | C—Cl | C—Cl | C—Cl | C—H | H | CF3 | C—CF3 | H | CH3NHC(O)CH2 |
| 2-330 | C—Cl | C—Cl | C—Cl | C—H | H | CF3 | C—CF3 | H | CH3CH2NHC(O)CH2 |
| 2-331 | C—Cl | C—Cl | C—Cl | C—H | H | CF3 | C—CF3 | H | iso-PrNHC(O)CH2 |
| 2-332 | C—Cl | C—Cl | C—Cl | C—H | H | CF3 | C—CF3 | H | cyclo-PrNHC(O)CH2 |
| 2-333 | C—Cl | C—Cl | C—Cl | C—H | H | CF3 | C—CF3 | H | CF3CH2NHC(O)CH2 |
| 2-334 | C—Cl | C—Cl | C—Cl | C—H | H | CF3 | C—CF3 | H | CH3NHC(O)CH(CH3) |
| 2-335 | C—Cl | C—Cl | C—Cl | C—H | H | CF3 | C—CF3 | H | CH3CH2NHC(O)CH(CH3) |

TABLE 2-continued

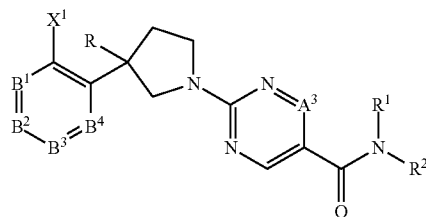

| Table 2-Ex.-No. | B¹ | B² | B³ | B⁴ | X¹ | R | A³ | R¹ | R² |
|---|---|---|---|---|---|---|---|---|---|
| 2-336 | C—Cl | C—Cl | C—Cl | C—H | H | CF3 | C—CF3 | H | iso-PrNHC(O)CH(CH3) |
| 2-337 | C—Cl | C—Cl | C—Cl | C—H | H | CF3 | C—CF3 | H | cyclo-PrNHC(O)CH(CH3) |
| 2-338 | C—Cl | C—Cl | C—Cl | C—H | H | CF3 | C—CF3 | H | CF3CH2NHC(O)CH(CH3) |
| 2-339 | C—Cl | C—Cl | C—Cl | C—H | H | CF3 | C—CF3 | H | CH3NHC(O)C(CH3)2 |
| 2-340 | C—Cl | C—Cl | C—Cl | C—H | H | CF3 | C—CF3 | H | CH3CH2NHC(O)C(CH3)2 |
| 2-341 | C—Cl | C—Cl | C—Cl | C—H | H | CF3 | C—CF3 | H | iso-PrNHC(O)C(CH3)2 |
| 2-342 | C—Cl | C—Cl | C—Cl | C—H | H | CF3 | C—CF3 | H | cyclo-PrNHC(O)C(CH3)2 |
| 2-343 | C—Cl | C—Cl | C—Cl | C—H | H | CF3 | C—CF3 | H | CF3CH2NHC(O)C(CH3)2 |
| 2-344 | C—Cl | C—H | C—CF3 | C—H | H | CF3 | C—CF3 | H | CF3CH2 |
| 2-345 | C—Cl | C—H | C—CF3 | C—H | H | CF3 | C—CF3 | H | CH3OCH2 |
| 2-346 | C—Cl | C—H | C—CF3 | C—H | H | CF3 | C—CF3 | CH3CO | CH3OCH2 |
| 2-347 | C—Cl | C—H | C—CF3 | C—H | H | CF3 | C—CF3 | H | CH3CH2OCH2 |
| 2-348 | C—Cl | C—H | C—CF3 | C—H | H | CF3 | C—CF3 | H | CH3OCH2CH2 |
| 2-349 | C—Cl | C—H | C—CF3 | C—H | H | CF3 | C—CF3 | H | CH3CH2OCH2CH2 |
| 2-350 | C—Cl | C—H | C—CF3 | C—H | H | CF3 | C—CF3 | H | tetrahydrofuran-2-yl |
| 2-351 | C—Cl | C—H | C—CF3 | C—H | H | CF3 | C—CF3 | H | CH3SCH2CH2 |
| 2-352 | C—Cl | C—H | C—CF3 | C—H | H | CF3 | C—CF3 | H | CH3S(O)CH2CH2 |
| 2-353 | C—Cl | C—H | C—CF3 | C—H | H | CF3 | C—CF3 | H | CH3SO2CH2CH2 |
| 2-354 | C—Cl | C—H | C—CF3 | C—H | H | CF3 | C—CF3 | H | CH3SCH2CH(CH3) |
| 2-355 | C—Cl | C—H | C—CF3 | C—H | H | CF3 | C—CF3 | H | CH3S(O)CH2CH(CH3) |
| 2-356 | C—Cl | C—H | C—CF3 | C—H | H | CF3 | C—CF3 | H | CH3SO2CH2CH(CH3) |
| 2-357 | C—Cl | C—H | C—CF3 | C—H | H | CF3 | C—CF3 | H | CH3SCH2C(CH3)2 |
| 2-358 | C—Cl | C—H | C—CF3 | C—H | H | CF3 | C—CF3 | H | CH3S(O)CH2C(CH3)2 |
| 2-359 | C—Cl | C—H | C—CF3 | C—H | H | CF3 | C—CF3 | H | CH3SO2CH2C(CH3)2 |
| 2-360 | C—Cl | C—H | C—CF3 | C—H | H | CF3 | C—CF3 | H | (Methoxyimino)methyl |
| 2-361 | C—Cl | C—H | C—CF3 | C—H | H | CF3 | C—CF3 | H | (Ethoxyimino)methyl |
| 2-362 | C—Cl | C—H | C—CF3 | C—H | H | CF3 | C—CF3 | H | 2-PyridylCH2 |
| 2-363 | C—Cl | C—H | C—CF3 | C—H | H | CF3 | C—CF3 | H | [1-(1,3-thiazol-4-yl)]CH2 |
| 2-364 | C—Cl | C—H | C—CF3 | C—H | H | CF3 | C—CF3 | H | [1-(1-methyl-1H-pyrazol-5-yl]CH2 |
| 2-365 | C—Cl | C—H | C—CF3 | C—H | H | CF3 | C—CF3 | H | 5-chloropyrimidin-2-yl |
| 2-366 | C—Cl | C—H | C—CF3 | C—H | H | CF3 | C—CF3 | H | 5-bromopyrimidin-2-yl |
| 2-367 | C—Cl | C—H | C—CF3 | C—H | H | CF3 | C—CF3 | H | 5-cyanopyrimidin-2-yl |
| 2-368 | C—Cl | C—H | C—CF3 | C—H | H | CF3 | C—CF3 | H | CH3NHC(O)CH2 |
| 2-369 | C—Cl | C—H | C—CF3 | C—H | H | CF3 | C—CF3 | H | CH3CH2NHC(O)CH2 |
| 2-370 | C—Cl | C—H | C—CF3 | C—H | H | CF3 | C—CF3 | H | iso-PrNHC(O)CH2 |
| 2-371 | C—Cl | C—H | C—CF3 | C—H | H | CF3 | C—CF3 | H | cyclo-PrNHC(O)CH2 |
| 2-372 | C—Cl | C—H | C—CF3 | C—H | H | CF3 | C—CF3 | H | CF3CH2NHC(O)CH2 |
| 2-373 | C—Cl | C—H | C—CF3 | C—H | H | CF3 | C—CF3 | H | CH3NHC(O)CH(CH3) |
| 2-374 | C—Cl | C—H | C—CF3 | C—H | H | CF3 | C—CF3 | H | CH3CH2NHC(O)CH(CH3) |
| 2-375 | C—Cl | C—H | C—CF3 | C—H | H | CF3 | C—CF3 | H | iso-PrNHC(O)CH(CH3) |
| 2-376 | C—Cl | C—H | C—CF3 | C—H | H | CF3 | C—CF3 | H | cyclo-PrNHC(O)CH(CH3) |
| 2-377 | C—Cl | C—H | C—CF3 | C—H | H | CF3 | C—CF3 | H | CF3CH2NHC(O)CH(CH3) |
| 2-378 | C—Cl | C—H | C—CF3 | C—H | H | CF3 | C—CF3 | H | CH3NHC(O)C(CH3)2 |
| 2-379 | C—Cl | C—H | C—CF3 | C—H | H | CF3 | C—CF3 | H | CH3CH2NHC(O)C(CH3)2 |
| 2-380 | C—Cl | C—H | C—CF3 | C—H | H | CF3 | C—CF3 | H | iso-PrNHC(O)C(CH3)2 |
| 2-381 | C—Cl | C—H | C—CF3 | C—H | H | CF3 | C—CF3 | H | cyclo-PrNHC(O)C(CH3)2 |
| 2-382 | C—Cl | C—H | C—CF3 | C—H | H | CF3 | C—CF3 | H | CF3CH2NHC(O)C(CH3)2 |
| 2-383 | C—CF3 | C—H | C—CF3 | C—H | H | CF3 | C—CF3 | H | CH3OCH2 |
| 2-384 | C—CF3 | C—H | C—CF3 | C—H | H | CF3 | C—CF3 | CH3CO | CH3OCH2 |
| 2-385 | C—CF3 | C—H | C—CF3 | C—H | H | CF3 | C—CF3 | H | CH3CH2OCH2 |
| 2-386 | C—CF3 | C—H | C—CF3 | C—H | H | CF3 | C—CF3 | H | CH3OCH2CH2 |
| 2-387 | C—CF3 | C—H | C—CF3 | C—H | H | CF3 | C—CF3 | H | CH3CH2OCH2CH2 |
| 2-388 | C—CF3 | C—H | C—CF3 | C—H | H | CF3 | C—CF3 | H | tetrahydrofuran-2-yl |
| 2-389 | C—CF3 | C—H | C—CF3 | C—H | H | CF3 | C—CF3 | H | CH3SCH2CH2 |
| 2-390 | C—CF3 | C—H | C—CF3 | C—H | H | CF3 | C—CF3 | H | CH3S(O)CH2CH2 |
| 2-391 | C—CF3 | C—H | C—CF3 | C—H | H | CF3 | C—CF3 | H | CH3SO2CH2CH2 |
| 2-392 | C—CF3 | C—H | C—CF3 | C—H | H | CF3 | C—CF3 | H | CH3SCH2CH(CH3) |
| 2-393 | C—CF3 | C—H | C—CF3 | C—H | H | CF3 | C—CF3 | H | CH3S(O)CH2CH(CH3) |
| 2-394 | C—CF3 | C—H | C—CF3 | C—H | H | CF3 | C—CF3 | H | CH3SO2CH2CH(CH3) |
| 2-395 | C—CF3 | C—H | C—CF3 | C—H | H | CF3 | C—CF3 | H | CH3SCH2C(CH3)2 |
| 2-396 | C—CF3 | C—H | C—CF3 | C—H | H | CF3 | C—CF3 | H | CH3S(O)CH2C(CH3)2 |
| 2-397 | C—CF3 | C—H | C—CF3 | C—H | H | CF3 | C—CF3 | H | CH3SO2CH2C(CH3)2 |
| 2-398 | C—CF3 | C—H | C—CF3 | C—H | H | CF3 | C—CF3 | H | (Methoxyimino)methyl |
| 2-399 | C—CF3 | C—H | C—CF3 | C—H | H | CF3 | C—CF3 | H | (Ethoxyimino)methyl |
| 2-400 | C—CF3 | C—H | C—CF3 | C—H | H | CF3 | C—CF3 | H | [1-(1,3-thiazol-4-yl)]CH2 |
| 2-401 | C—CF3 | C—H | C—CF3 | C—H | H | CF3 | C—CF3 | H | [1-(1-methyl-1H-pyrazol-5-yl]CH2 |
| 2-402 | C—CF3 | C—H | C—CF3 | C—H | H | CF3 | C—CF3 | H | 5-chloropyrimidin-2-yl |

TABLE 2-continued

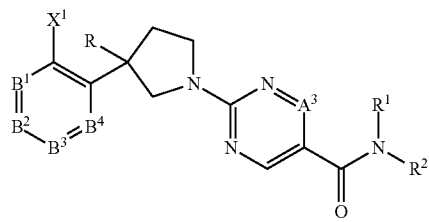

| Table 2-Ex.-No. | B¹ | B² | B³ | B⁴ | X¹ | R | A³ | R¹ | R² |
|---|---|---|---|---|---|---|---|---|---|
| 2-403 | C—CF3 | C—H | C—CF3 | C—H | H | CF3 | C—CF3 | H | 5-bromopyrimidin-2-yl |
| 2-404 | C—CF3 | C—H | C—CF3 | C—H | H | CF3 | C—CF3 | H | 5-cyanopyrimidin-2-yl |
| 2-405 | C—CF3 | C—H | C—CF3 | C—H | H | CF3 | C—CF3 | H | CH3NHC(O)CH2 |
| 2-406 | C—CF3 | C—H | C—CF3 | C—H | H | CF3 | C—CF3 | H | CH3CH2NHC(O)CH2 |
| 2-407 | C—CF3 | C—H | C—CF3 | C—H | H | CF3 | C—CF3 | H | iso-PrNHC(O)CH2 |
| 2-408 | C—CF3 | C—H | C—CF3 | C—H | H | CF3 | C—CF3 | H | cyclo-PrNHC(O)CH2 |
| 2-409 | C—CF3 | C—H | C—CF3 | C—H | H | CF3 | C—CF3 | H | CF3CH2NHC(O)CH2 |
| 2-410 | C—CF3 | C—H | C—CF3 | C—H | H | CF3 | C—CF3 | H | CH3NHC(O)CH(CH3) |
| 2-411 | C—CF3 | C—H | C—CF3 | C—H | H | CF3 | C—CF3 | H | CH3CH2NHC(O)CH(CH3) |
| 2-412 | C—CF3 | C—H | C—CF3 | C—H | H | CF3 | C—CF3 | H | iso-PrNHC(O)CH(CH3) |
| 2-413 | C—CF3 | C—H | C—CF3 | C—H | H | CF3 | C—CF3 | H | cyclo-PrNHC(O)CH(CH3) |
| 2-414 | C—CF3 | C—H | C—CF3 | C—H | H | CF3 | C—CF3 | H | CF3CH2NHC(O)CH(CH3) |
| 2-415 | C—CF3 | C—H | C—CF3 | C—H | H | CF3 | C—CF3 | H | CH3NHC(O)C(CH3)2 |
| 2-416 | C—CF3 | C—H | C—CF3 | C—H | H | CF3 | C—CF3 | H | CH3CH2NHC(O)C(CH3)2 |
| 2-417 | C—CF3 | C—H | C—CF3 | C—H | H | CF3 | C—CF3 | H | iso-PrNHC(O)C(CH3)2 |
| 2-418 | C—CF3 | C—H | C—CF3 | C—H | H | CF3 | C—CF3 | H | cyclo-PrNHC(O)C(CH3)2 |
| 2-419 | C—CF3 | C—H | C—CF3 | C—H | H | CF3 | C—CF3 | H | CF3CH2NHC(O)C(CH3)2 |
| 2-420 | C—Cl | C—Cl | C—CF3 | C—H | H | CF3 | C—CF3 | H | CH3OCH2 |
| 2-421 | C—Cl | C—Cl | C—CF3 | C—H | H | CF3 | C—CF3 | CH3CO | CH3OCH2 |
| 2-422 | C—Cl | C—Cl | C—CF3 | C—H | H | CF3 | C—CF3 | H | CH3CH2OCH2 |
| 2-423 | C—Cl | C—Cl | C—CF3 | C—H | H | CF3 | C—CF3 | H | CH3OCH2CH2 |
| 2-424 | C—Cl | C—Cl | C—CF3 | C—H | H | CF3 | C—CF3 | H | CH3CH2OCH2CH2 |
| 2-425 | C—Cl | C—Cl | C—CF3 | C—H | H | CF3 | C—CF3 | H | tetrahydrofuran-2-yl |
| 2-426 | C—Cl | C—Cl | C—CF3 | C—H | H | CF3 | C—CF3 | H | CH3SCH2CH2 |
| 2-427 | C—Cl | C—Cl | C—CF3 | C—H | H | CF3 | C—CF3 | H | CH3S(O)CH2CH2 |
| 2-428 | C—Cl | C—Cl | C—CF3 | C—H | H | CF3 | C—CF3 | H | CH3SO2CH2CH2 |
| 2-429 | C—Cl | C—Cl | C—CF3 | C—H | H | CF3 | C—CF3 | H | CH3SCH2CH(CH3) |
| 2-430 | C—Cl | C—Cl | C—CF3 | C—H | H | CF3 | C—CF3 | H | CH3S(O)CH2CH(CH3) |
| 2-431 | C—Cl | C—Cl | C—CF3 | C—H | H | CF3 | C—CF3 | H | CH3SO2CH2CH(CH3) |
| 2-432 | C—Cl | C—Cl | C—CF3 | C—H | H | CF3 | C—CF3 | H | CH3SCH2C(CH3)2 |
| 2-433 | C—Cl | C—Cl | C—CF3 | C—H | H | CF3 | C—CF3 | H | CH3S(O)CH2C(CH3)2 |
| 2-434 | C—Cl | C—Cl | C—CF3 | C—H | H | CF3 | C—CF3 | H | CH3SO2CH2C(CH3)2 |
| 2-435 | C—Cl | C—Cl | C—CF3 | C—H | H | CF3 | C—CF3 | H | (Methoxyimino)methyl |
| 2-436 | C—Cl | C—Cl | C—CF3 | C—H | H | CF3 | C—CF3 | H | (Ethoxyimino)methyl |
| 2-437 | C—Cl | C—Cl | C—CF3 | C—H | H | CF3 | C—CF3 | H | [1-(1,3-thiazol-4-yl)]CH2 |
| 2-438 | C—Cl | C—Cl | C—CF3 | C—H | H | CF3 | C—CF3 | H | [1-(1-methyl-1H-pyrazol-5-yl]CH2 |
| 2-439 | C—Cl | C—Cl | C—CF3 | C—H | H | CF3 | C—CF3 | H | 5-chloropyrimidin-2-yl |
| 2-440 | C—Cl | C—Cl | C—CF3 | C—H | H | CF3 | C—CF3 | H | 5-bromopyrimidin-2-yl |
| 2-441 | C—Cl | C—Cl | C—CF3 | C—H | H | CF3 | C—CF3 | H | 5-cyanopyrimidin-2-yl |
| 2-442 | C—Cl | C—Cl | C—CF3 | C—H | H | CF3 | C—CF3 | H | CH3NHC(O)CH2 |
| 2-443 | C—Cl | C—Cl | C—CF3 | C—H | H | CF3 | C—CF3 | H | CH3CH2NHC(O)CH2 |
| 2-444 | C—Cl | C—Cl | C—CF3 | C—H | H | CF3 | C—CF3 | H | iso-PrNHC(O)CH2 |
| 2-445 | C—Cl | C—Cl | C—CF3 | C—H | H | CF3 | C—CF3 | H | cyclo-PrNHC(O)CH2 |
| 2-446 | C—Cl | C—Cl | C—CF3 | C—H | H | CF3 | C—CF3 | H | CF3CH2NHC(O)CH2 |
| 2-447 | C—Cl | C—Cl | C—CF3 | C—H | H | CF3 | C—CF3 | H | CH3NHC(O)CH(CH3) |
| 2-448 | C—Cl | C—Cl | C—CF3 | C—H | H | CF3 | C—CF3 | H | CH3CH2NHC(O)CH(CH3) |
| 2-449 | C—Cl | C—Cl | C—CF3 | C—H | H | CF3 | C—CF3 | H | iso-PrNHC(O)CH(CH3) |
| 2-450 | C—Cl | C—Cl | C—CF3 | C—H | H | CF3 | C—CF3 | H | cyclo-PrNHC(O)CH(CH3) |
| 2-451 | C—Cl | C—Cl | C—CF3 | C—H | H | CF3 | C—CF3 | H | CF3CH2NHC(O)CH(CH3) |
| 2-452 | C—Cl | C—Cl | C—CF3 | C—H | H | CF3 | C—CF3 | H | CH3NHC(O)C(CH3)2 |
| 2-453 | C—Cl | C—Cl | C—CF3 | C—H | H | CF3 | C—CF3 | H | CH3CH2NHC(O)C(CH3)2 |
| 2-454 | C—Cl | C—Cl | C—CF3 | C—H | H | CF3 | C—CF3 | H | iso-PrNHC(O)C(CH3)2 |
| 2-455 | C—Cl | C—Cl | C—CF3 | C—H | H | CF3 | C—CF3 | H | cyclo-PrNHC(O)C(CH3)2 |
| 2-456 | C—Cl | C—Cl | C—CF3 | C—H | H | CF3 | C—CF3 | H | CF3CH2NHC(O)C(CH3)2 |
| 2-457 | C—Cl | N | C—Cl | C—H | H | CF3 | C—CF3 | H | CF3CH2 |
| 2-458 | C—Cl | N | C—Cl | C—H | H | CF3 | C—CF3 | H | CH3OCH2 |
| 2-459 | C—Cl | N | C—Cl | C—H | H | CF3 | C—CF3 | CH3CO | CH3OCH2 |
| 2-460 | C—Cl | N | C—Cl | C—H | H | CF3 | C—CF3 | H | CH3CH2OCH2 |
| 2-461 | C—Cl | N | C—Cl | C—H | H | CF3 | C—CF3 | H | CH3OCH2CH2 |
| 2-462 | C—Cl | N | C—Cl | C—H | H | CF3 | C—CF3 | H | CH3CH2OCH2CH2 |
| 2-463 | C—Cl | N | C—Cl | C—H | H | CF3 | C—CF3 | H | tetrahydrofuran-2-yl |
| 2-464 | C—Cl | N | C—Cl | C—H | H | CF3 | C—CF3 | H | CH3SCH2CH2 |
| 2-465 | C—Cl | N | C—Cl | C—H | H | CF3 | C—CF3 | H | CH3S(O)CH2CH2 |
| 2-466 | C—Cl | N | C—Cl | C—H | H | CF3 | C—CF3 | H | CH3SO2CH2CH2 |
| 2-467 | C—Cl | N | C—Cl | C—H | H | CF3 | C—CF3 | H | CH3SCH2CH(CH3) |
| 2-468 | C—Cl | N | C—Cl | C—H | H | CF3 | C—CF3 | H | CH3S(O)CH2CH(CH3) |
| 2-469 | C—Cl | N | C—Cl | C—H | H | CF3 | C—CF3 | H | CH3SO2CH2CH(CH3) |

TABLE 2-continued

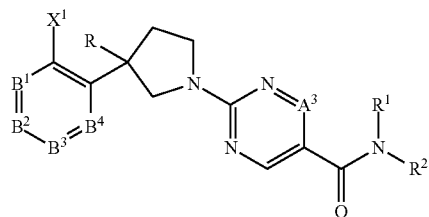

| Table 2-Ex.-No. | B¹ | B² | B³ | B⁴ | X¹ | R | A³ | R¹ | R² |
|---|---|---|---|---|---|---|---|---|---|
| 2-470 | C—Cl | N | C—Cl | C—H | H | CF3 | C—CF3 | H | CH3SCH2C(CH3)2 |
| 2-471 | C—Cl | N | C—Cl | C—H | H | CF3 | C—CF3 | H | CH3S(O)CH2C(CH3)2 |
| 2-472 | C—Cl | N | C—Cl | C—H | H | CF3 | C—CF3 | H | CH3SO2CH2C(CH3)2 |
| 2-473 | C—Cl | N | C—Cl | C—H | H | CF3 | C—CF3 | H | (Methoxyimino)methyl |
| 2-474 | C—Cl | N | C—Cl | C—H | H | CF3 | C—CF3 | H | (Ethoxyimino)methyl |
| 2-475 | C—Cl | N | C—Cl | C—H | H | CF3 | C—CF3 | H | 2-PyridylCH2 |
| 2-476 | C—Cl | N | C—Cl | C—H | H | CF3 | C—CF3 | H | [1-(1,3-thiazol-4-yl)]CH2 |
| 2-477 | C—Cl | N | C—Cl | C—H | H | CF3 | C—CF3 | H | [1-(1-methyl-1H-pyrazol-5-yl]CH2 |
| 2-478 | C—Cl | N | C—Cl | C—H | H | CF3 | C—CF3 | H | 5-chloropyrimidin-2-yl |
| 2-479 | C—Cl | N | C—Cl | C—H | H | CF3 | C—CF3 | H | 5-bromopyrimidin-2-yl |
| 2-480 | C—Cl | N | C—Cl | C—H | H | CF3 | C—CF3 | H | 5-cyanopyrimidin-2-yl |
| 2-481 | C—Cl | N | C—Cl | C—H | H | CF3 | C—CF3 | H | CH3NHC(O)CH2 |
| 2-482 | C—Cl | N | C—Cl | C—H | H | CF3 | C—CF3 | H | CH3CH2NHC(O)CH2 |
| 2-483 | C—Cl | N | C—Cl | C—H | H | CF3 | C—CF3 | H | iso-PrNHC(O)CH2 |
| 2-484 | C—Cl | N | C—Cl | C—H | H | CF3 | C—CF3 | H | cyclo-PrNHC(O)CH2 |
| 2-485 | C—Cl | N | C—Cl | C—H | H | CF3 | C—CF3 | H | CF3CH2NHC(O)CH2 |
| 2-486 | C—Cl | N | C—Cl | C—H | H | CF3 | C—CF3 | H | CH3NHC(O)CH(CH3) |
| 2-487 | C—Cl | N | C—Cl | C—H | H | CF3 | C—CF3 | H | CH3CH2NHC(O)CH(CH3) |
| 2-488 | C—Cl | N | C—Cl | C—H | H | CF3 | C—CF3 | H | iso-PrNHC(O)CH(CH3) |
| 2-489 | C—Cl | N | C—Cl | C—H | H | CF3 | C—CF3 | H | cyclo-PrNHC(O)CH(CH3) |
| 2-490 | C—Cl | N | C—Cl | C—H | H | CF3 | C—CF3 | H | CF3CH2NHC(O)CH(CH3) |
| 2-491 | C—Cl | N | C—Cl | C—H | H | CF3 | C—CF3 | H | CH3NHC(O)C(CH3)2 |
| 2-492 | C—Cl | N | C—Cl | C—H | H | CF3 | C—CF3 | H | CH3CH2NHC(O)C(CH3)2 |
| 2-493 | C—Cl | N | C—Cl | C—H | H | CF3 | C—CF3 | H | iso-PrNHC(O)C(CH3)2 |
| 2-494 | C—Cl | N | C—Cl | C—H | H | CF3 | C—CF3 | H | cyclo-PrNHC(O)C(CH3)2 |
| 2-495 | C—Cl | N | C—Cl | C—H | H | CF3 | C—CF3 | H | CF3CH2NHC(O)C(CH3)2 |
| 2-496 | C—CF3 | N | C—H | C—H | H | CF3 | C—CF3 | H | CF3CH2 |
| 2-497 | C—CF3 | N | C—H | C—H | H | CF3 | C—CF3 | H | CH3OCH2 |
| 2-498 | C—CF3 | N | C—H | C—H | H | CF3 | C—CF3 | CH3CO | CH3OCH2 |
| 2-499 | C—CF3 | N | C—H | C—H | H | CF3 | C—CF3 | H | CH3CH2OCH2 |
| 2-500 | C—CF3 | N | C—H | C—H | H | CF3 | C—CF3 | H | CH3OCH2CH2 |
| 2-501 | C—CF3 | N | C—H | C—H | H | CF3 | C—CF3 | H | CH3CH2OCH2CH2 |
| 2-502 | C—CF3 | N | C—H | C—H | H | CF3 | C—CF3 | H | tetrahydrofuran-2-yl |
| 2-503 | C—CF3 | N | C—H | C—H | H | CF3 | C—CF3 | H | CH3SCH2CH2 |
| 2-504 | C—CF3 | N | C—H | C—H | H | CF3 | C—CF3 | H | CH3S(O)CH2CH2 |
| 2-505 | C—CF3 | N | C—H | C—H | H | CF3 | C—CF3 | H | CH3SO2CH2CH2 |
| 2-506 | C—CF3 | N | C—H | C—H | H | CF3 | C—CF3 | H | CH3SCH2CH(CH3) |
| 2-507 | C—CF3 | N | C—H | C—H | H | CF3 | C—CF3 | H | CH3S(O)CH2CH(CH3) |
| 2-508 | C—CF3 | N | C—H | C—H | H | CF3 | C—CF3 | H | CH3SO2CH2CH(CH3) |
| 2-509 | C—CF3 | N | C—H | C—H | H | CF3 | C—CF3 | H | CH3SCH2C(CH3)2 |
| 2-510 | C—CF3 | N | C—H | C—H | H | CF3 | C—CF3 | H | CH3S(O)CH2C(CH3)2 |
| 2-511 | C—CF3 | N | C—H | C—H | H | CF3 | C—CF3 | H | CH3SO2CH2C(CH3)2 |
| 2-512 | C—CF3 | N | C—H | C—H | H | CF3 | C—CF3 | H | (Methoxyimino)methyl |
| 2-513 | C—CF3 | N | C—H | C—H | H | CF3 | C—CF3 | H | (Ethoxyimino)methyl |
| 2-514 | C—CF3 | N | C—H | C—H | H | CF3 | C—CF3 | H | 2-PyridylCH2 |
| 2-515 | C—CF3 | N | C—H | C—H | H | CF3 | C—CF3 | H | [1-(1,3-thiazol-4-yl)]CH2 |
| 2-516 | C—CF3 | N | C—H | C—H | H | CF3 | C—CF3 | H | [1-(1-methyl-1H-pyrazol-5-yl]CH2 |
| 2-517 | C—CF3 | N | C—H | C—H | H | CF3 | C—CF3 | H | 5-chloropyrimidin-2-yl |
| 2-518 | C—CF3 | N | C—H | C—H | H | CF3 | C—CF3 | H | 5-bromopyrimidin-2-yl |
| 2-519 | C—CF3 | N | C—H | C—H | H | CF3 | C—CF3 | H | 5-cyanopyrimidin-2-yl |
| 2-520 | C—CF3 | N | C—H | C—H | H | CF3 | C—CF3 | H | CH3NHC(O)CH2 |
| 2-521 | C—CF3 | N | C—H | C—H | H | CF3 | C—CF3 | H | CH3CH2NHC(O)CH2 |
| 2-522 | C—CF3 | N | C—H | C—H | H | CF3 | C—CF3 | H | iso-PrNHC(O)CH2 |
| 2-523 | C—CF3 | N | C—H | C—H | H | CF3 | C—CF3 | H | cyclo-PrNHC(O)CH2 |
| 2-524 | C—CF3 | N | C—H | C—H | H | CF3 | C—CF3 | H | CF3CH2NHC(O)CH2 |
| 2-525 | C—CF3 | N | C—H | C—H | H | CF3 | C—CF3 | H | CH3NHC(O)CH(CH3) |
| 2-526 | C—CF3 | N | C—H | C—H | H | CF3 | C—CF3 | H | CH3CH2NHC(O)CH(CH3) |
| 2-527 | C—CF3 | N | C—H | C—H | H | CF3 | C—CF3 | H | iso-PrNHC(O)CH(CH3) |
| 2-528 | C—CF3 | N | C—H | C—H | H | CF3 | C—CF3 | H | cyclo-PrNHC(O)CH(CH3) |
| 2-529 | C—CF3 | N | C—H | C—H | H | CF3 | C—CF3 | H | CF3CH2NHC(O)CH(CH3) |
| 2-530 | C—CF3 | N | C—H | C—H | H | CF3 | C—CF3 | H | CH3NHC(O)C(CH3)2 |
| 2-531 | C—CF3 | N | C—H | C—H | H | CF3 | C—CF3 | H | CH3CH2NHC(O)C(CH3)2 |
| 2-532 | C—CF3 | N | C—H | C—H | H | CF3 | C—CF3 | H | iso-PrNHC(O)C(CH3)2 |
| 2-533 | C—CF3 | N | C—H | C—H | H | CF3 | C—CF3 | H | cyclo-PrNHC(O)C(CH3)2 |
| 2-534 | C—CF3 | N | C—H | C—H | H | CF3 | C—CF3 | H | CF3CH2NHC(O)C(CH3)2 |
| 2-535 | C—CF3 | N | C—CF3 | C—H | H | CF3 | C—CF3 | H | CF3CH2 |
| 2-536 | C—CF3 | N | C—CF3 | C—H | H | CF3 | C—CF3 | H | CH3OCH2 |

TABLE 2-continued

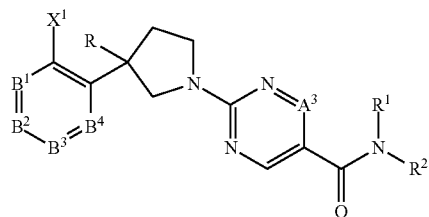

| Table 2-Ex.-No. | B¹ | B² | B³ | B⁴ | X¹ | R | A³ | R¹ | R² |
|---|---|---|---|---|---|---|---|---|---|
| 2-537 | C—CF3 | N | C—CF3 | C—H | H | CF3 | C—CF3 | CH3CO | CH3OCH2 |
| 2-538 | C—CF3 | N | C—CF3 | C—H | H | CF3 | C—CF3 | H | CH3CH2OCH2 |
| 2-539 | C—CF3 | N | C—CF3 | C—H | H | CF3 | C—CF3 | H | CH3OCH2CH2 |
| 2-540 | C—CF3 | N | C—CF3 | C—H | H | CF3 | C—CF3 | H | CH3CH2OCH2CH2 |
| 2-541 | C—CF3 | N | C—CF3 | C—H | H | CF3 | C—CF3 | H | tetrahydrofuran-2-yl |
| 2-542 | C—CF3 | N | C—CF3 | C—H | H | CF3 | C—CF3 | H | CH3SCH2CH2 |
| 2-543 | C—CF3 | N | C—CF3 | C—H | H | CF3 | C—CF3 | H | CH3S(O)CH2CH2 |
| 2-544 | C—CF3 | N | C—CF3 | C—H | H | CF3 | C—CF3 | H | CH3SO2CH2CH2 |
| 2-545 | C—CF3 | N | C—CF3 | C—H | H | CF3 | C—CF3 | H | CH3SCH2CH(CH3) |
| 2-546 | C—CF3 | N | C—CF3 | C—H | H | CF3 | C—CF3 | H | CH3S(O)CH2CH(CH3) |
| 2-547 | C—CF3 | N | C—CF3 | C—H | H | CF3 | C—CF3 | H | CH3SO2CH2CH(CH3) |
| 2-548 | C—CF3 | N | C—CF3 | C—H | H | CF3 | C—CF3 | H | CH3SCH2C(CH3)2 |
| 2-549 | C—CF3 | N | C—CF3 | C—H | H | CF3 | C—CF3 | H | CH3S(O)CH2C(CH3)2 |
| 2-550 | C—CF3 | N | C—CF3 | C—H | H | CF3 | C—CF3 | H | CH3SO2CH2C(CH3)2 |
| 2-551 | C—CF3 | N | C—CF3 | C—H | H | CF3 | C—CF3 | H | (Methoxyimino)methyl |
| 2-552 | C—CF3 | N | C—CF3 | C—H | H | CF3 | C—CF3 | H | (Ethoxyimino)methyl |
| 2-553 | C—CF3 | N | C—CF3 | C—H | H | CF3 | C—CF3 | H | 2-PyridylCH2 |
| 2-554 | C—CF3 | N | C—CF3 | C—H | H | CF3 | C—CF3 | H | [1-(1,3-thiazol-4-yl)]CH2 |
| 2-555 | C—CF3 | N | C—CF3 | C—H | H | CF3 | C—CF3 | H | [1-(1-methyl-1H-pyrazol-5-yl]CH2 |
| 2-556 | C—CF3 | N | C—CF3 | C—H | H | CF3 | C—CF3 | H | 5-chloropyrimidin-2-yl |
| 2-557 | C—CF3 | N | C—CF3 | C—H | H | CF3 | C—CF3 | H | 5-bromopyrimidin-2-yl |
| 2-558 | C—CF3 | N | C—CF3 | C—H | H | CF3 | C—CF3 | H | 5-cyanopyrimidin-2-yl |
| 2-559 | C—CF3 | N | C—CF3 | C—H | H | CF3 | C—CF3 | H | CH3NHC(O)CH2 |
| 2-560 | C—CF3 | N | C—CF3 | C—H | H | CF3 | C—CF3 | H | CH3CH2NHC(O)CH2 |
| 2-561 | C—CF3 | N | C—CF3 | C—H | H | CF3 | C—CF3 | H | iso-PrNHC(O)CH2 |
| 2-562 | C—CF3 | N | C—CF3 | C—H | H | CF3 | C—CF3 | H | cyclo-PrNHC(O)CH2 |
| 2-563 | C—CF3 | N | C—CF3 | C—H | H | CF3 | C—CF3 | H | CF3CH2NHC(O)CH2 |
| 2-564 | C—CF3 | N | C—CF3 | C—H | H | CF3 | C—CF3 | H | CH3NHC(O)CH(CH3) |
| 2-565 | C—CF3 | N | C—CF3 | C—H | H | CF3 | C—CF3 | H | CH3CH2NHC(O)CH(CH3) |
| 2-566 | C—CF3 | N | C—CF3 | C—H | H | CF3 | C—CF3 | H | iso-PrNHC(O)CH(CH3) |
| 2-567 | C—CF3 | N | C—CF3 | C—H | H | CF3 | C—CF3 | H | cyclo-PrNHC(O)CH(CH3) |
| 2-568 | C—CF3 | N | C—CF3 | C—H | H | CF3 | C—CF3 | H | CF3CH2NHC(O)CH(CH3) |
| 2-569 | C—CF3 | N | C—CF3 | C—H | H | CF3 | C—CF3 | H | CH3NHC(O)C(CH3)2 |
| 2-570 | C—CF3 | N | C—CF3 | C—H | H | CF3 | C—CF3 | H | CH3CH2NHC(O)C(CH3)2 |
| 2-571 | C—CF3 | N | C—CF3 | C—H | H | CF3 | C—CF3 | H | iso-PrNHC(O)C(CH3)2 |
| 2-572 | C—CF3 | N | C—CF3 | C—H | H | CF3 | C—CF3 | H | cyclo-PrNHC(O)C(CH3)2 |
| 2-573 | C—CF3 | N | C—CF3 | C—H | H | CF3 | C—CF3 | H | CF3CH2NHC(O)C(CH3)2 |
| 2-574 | C—CF3 | C—H | C—CF3 | N | H | CF3 | C—CF3 | H | CF3CH2 |
| 2-575 | C—CF3 | C—H | C—CF3 | N | H | CF3 | C—CF3 | H | CH3OCH2 |
| 2-576 | C—CF3 | C—H | C—CF3 | N | H | CF3 | C—CF3 | CH3CO | CH3OCH2 |
| 2-577 | C—CF3 | C—H | C—CF3 | N | H | CF3 | C—CF3 | H | CH3CH2OCH2 |
| 2-578 | C—CF3 | C—H | C—CF3 | N | H | CF3 | C—CF3 | H | CH3OCH2CH2 |
| 2-579 | C—CF3 | C—H | C—CF3 | N | H | CF3 | C—CF3 | H | CH3CH2OCH2CH2 |
| 2-580 | C—CF3 | C—H | C—CF3 | N | H | CF3 | C—CF3 | H | tetrahydrofuran-2-yl |
| 2-581 | C—CF3 | C—H | C—CF3 | N | H | CF3 | C—CF3 | H | CH3SCH2CH2 |
| 2-582 | C—CF3 | C—H | C—CF3 | N | H | CF3 | C—CF3 | H | CH3S(O)CH2CH2 |
| 2-583 | C—CF3 | C—H | C—CF3 | N | H | CF3 | C—CF3 | H | CH3SO2CH2CH2 |
| 2-584 | C—CF3 | C—H | C—CF3 | N | H | CF3 | C—CF3 | H | CH3SCH2CH(CH3) |
| 2-585 | C—CF3 | C—H | C—CF3 | N | H | CF3 | C—CF3 | H | CH3S(O)CH2CH(CH3) |
| 2-586 | C—CF3 | C—H | C—CF3 | N | H | CF3 | C—CF3 | H | CH3SO2CH2CH(CH3) |
| 2-587 | C—CF3 | C—H | C—CF3 | N | H | CF3 | C—CF3 | H | CH3SCH2C(CH3)2 |
| 2-588 | C—CF3 | C—H | C—CF3 | N | H | CF3 | C—CF3 | H | CH3S(O)CH2C(CH3)2 |
| 2-589 | C—CF3 | C—H | C—CF3 | N | H | CF3 | C—CF3 | H | CH3SO2CH2C(CH3)2 |
| 2-590 | C—CF3 | C—H | C—CF3 | N | H | CF3 | C—CF3 | H | (Methoxyimino)methyl |
| 2-591 | C—CF3 | C—H | C—CF3 | N | H | CF3 | C—CF3 | H | (Ethoxyimino)methyl |
| 2-592 | C—CF3 | C—H | C—CF3 | N | H | CF3 | C—CF3 | H | 2-PyridylCH2 |
| 2-593 | C—CF3 | C—H | C—CF3 | N | H | CF3 | C—CF3 | H | [1-(1,3-thiazol-4-yl)]CH2 |
| 2-594 | C—CF3 | C—H | C—CF3 | N | H | CF3 | C—CF3 | H | [1-(1-methyl-1H-pyrazol-5-yl]CH2 |
| 2-595 | C—CF3 | C—H | C—CF3 | N | H | CF3 | C—CF3 | H | 5-chloropyrimidin-2-yl |
| 2-596 | C—CF3 | C—H | C—CF3 | N | H | CF3 | C—CF3 | H | 5-bromopyrimidin-2-yl |
| 2-597 | C—CF3 | C—H | C—CF3 | N | H | CF3 | C—CF3 | H | 5-cyanopyrimidin-2-yl |
| 2-598 | C—CF3 | C—H | C—CF3 | N | H | CF3 | C—CF3 | H | CH3NHC(O)CH2 |
| 2-599 | C—CF3 | C—H | C—CF3 | N | H | CF3 | C—CF3 | H | CH3CH2NHC(O)CH2 |
| 2-600 | C—CF3 | C—H | C—CF3 | N | H | CF3 | C—CF3 | H | iso-PrNHC(O)CH2 |
| 2-601 | C—CF3 | C—H | C—CF3 | N | H | CF3 | C—CF3 | H | cyclo-PrNHC(O)CH2 |
| 2-602 | C—CF3 | C—H | C—CF3 | N | H | CF3 | C—CF3 | H | CF3CH2NHC(O)CH2 |
| 2-603 | C—CF3 | C—H | C—CF3 | N | H | CF3 | C—CF3 | H | CH3NHC(O)CH(CH3) |

TABLE 2-continued

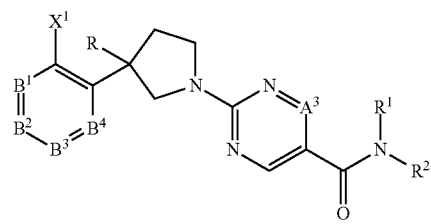

| Table 2-Ex.-No. | B¹ | B² | B³ | B⁴ | X¹ | R | A³ | R¹ | R² |
|---|---|---|---|---|---|---|---|---|---|
| 2-604 | C—CF3 | C—H | C—CF3 | N | H | CF3 | C—CF3 | H | CH3CH2NHC(O)CH(CH3) |
| 2-605 | C—CF3 | C—H | C—CF3 | N | H | CF3 | C—CF3 | H | iso-PrNHC(O)CH(CH3) |
| 2-606 | C—CF3 | C—H | C—CF3 | N | H | CF3 | C—CF3 | H | cyclo-PrNHC(O)CH(CH3) |
| 2-607 | C—CF3 | C—H | C—CF3 | N | H | CF3 | C—CF3 | H | CF3CH2NHC(O)CH(CH3) |
| 2-608 | C—CF3 | C—H | C—CF3 | N | H | CF3 | C—CF3 | H | CH3NHC(O)C(CH3)2 |
| 2-609 | C—CF3 | C—H | C—CF3 | N | H | CF3 | C—CF3 | H | CH3CH2NHC(O)C(CH3)2 |
| 2-610 | C—CF3 | C—H | C—CF3 | N | H | CF3 | C—CF3 | H | iso-PrNHC(O)C(CH3)2 |
| 2-611 | C—CF3 | C—H | C—CF3 | N | H | CF3 | C—CF3 | H | cyclo-PrNHC(O)C(CH3)2 |
| 2-612 | C—CF3 | C—H | C—CF3 | N | H | CF3 | C—CF3 | H | CF3CH2NHC(O)C(CH3)2 |
| 2-613 | C—CF3 | C—H | C—CF3 | C—H | H | CF3 | C—CF3 | H | tert-BuOC(O)CH2 |

TABLE 3

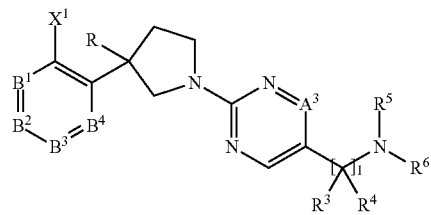

| Ex.-No. | B¹ | B² | B³ | B⁴ | X¹ | R | A³ | R³ | R⁴ | R⁵ | R⁶ | l |
|---|---|---|---|---|---|---|---|---|---|---|---|---|
| 3-1 | C—Cl | C—H | C—Cl | C—H | H | CF3 | C—CF3 | H | H | H | H | 1 |
| 3-2 | C—Cl | C—H | C—Cl | C—H | H | CF3 | C—CF3 | H | H | H | HCO | 1 |
| 3-3 | C—Cl | C—H | C—Cl | C—H | H | CF3 | C—CF3 | H | H | H | CH3CO | 1 |
| 3-4 | C—Cl | C—H | C—Cl | C—H | H | CF3 | C—CF3 | H | H | H | CH3CH2CO | 1 |
| 3-5 | C—Cl | C—H | C—Cl | C—H | H | CF3 | C—CF3 | H | H | H | n-PrCO | 1 |
| 3-6 | C—Cl | C—H | C—Cl | C—H | H | CF3 | C—CF3 | H | H | H | iso-PrCO | 1 |
| 3-7 | C—Cl | C—H | C—Cl | C—H | H | CF3 | C—CF3 | H | H | H | cyclo-PrCO | 1 |
| 3-8 | C—Cl | C—H | C—Cl | C—H | H | CF3 | C—CF3 | H | H | H | n-BuCO | 1 |
| 3-9 | C—Cl | C—H | C—Cl | C—H | H | CF3 | C—CF3 | H | H | H | tert-BuCO | 1 |
| 3-10 | C—Cl | C—H | C—Cl | C—H | H | CF3 | C—CF3 | H | H | H | iso-BuCO | 1 |
| 3-11 | C—Cl | C—H | C—Cl | C—H | H | CF3 | C—CF3 | H | H | H | cyclo-BuCO | 1 |
| 3-12 | C—Cl | C—H | C—Cl | C—H | H | CF3 | C—CF3 | H | H | H | (CH3)3CCH2CO | 1 |
| 3-13 | C—Cl | C—H | C—Cl | C—H | H | CF3 | C—CF3 | H | H | H | cyclo-PenCO | 1 |
| 3-14 | C—Cl | C—H | C—Cl | C—H | H | CF3 | C—CF3 | H | H | H | cyclo-HexCO | 1 |
| 3-15 | C—Cl | C—H | C—Cl | C—H | H | CF3 | C—CF3 | H | H | H | cyclo-PrCH2CO | 1 |
| 3-16 | C—Cl | C—H | C—Cl | C—H | H | CF3 | C—CF3 | H | H | H | CF3CO | 1 |
| 3-17 | C—Cl | C—H | C—Cl | C—H | H | CF3 | C—CF3 | H | H | H | CCl3CO | 1 |
| 3-18 | C—Cl | C—H | C—Cl | C—H | H | CF3 | C—CF3 | H | H | H | ClCH2CO | 1 |
| 3-19 | C—Cl | C—H | C—Cl | C—H | H | CF3 | C—CF3 | H | H | H | CF2ClCO | 1 |
| 3-20 | C—Cl | C—H | C—Cl | C—H | H | CF3 | C—CF3 | H | H | H | ClCH2CH2CO | 1 |
| 3-21 | C—Cl | C—H | C—Cl | C—H | H | CF3 | C—CF3 | H | H | H | HCF2CF2CO | 1 |
| 3-22 | C—Cl | C—H | C—Cl | C—H | H | CF3 | C—CF3 | H | H | H | CF3CH2CO | 1 |
| 3-23 | C—Cl | C—H | C—Cl | C—H | H | CF3 | C—CF3 | H | H | H | (CF3)2CHCO | 1 |
| 3-24 | C—Cl | C—H | C—Cl | C—H | H | CF3 | C—CF3 | H | H | H | HCF2CO | 1 |
| 3-25 | C—Cl | C—H | C—Cl | C—H | H | CF3 | C—CF3 | H | H | H | ClCH2CO | 1 |
| 3-26 | C—Cl | C—H | C—Cl | C—H | H | CF3 | C—CF3 | H | H | H | H3C-cyclopropyl-CO | 1 |
| 3-27 | C—Cl | C—H | C—Cl | C—H | H | CF3 | C—CF3 | H | H | H | Cl,Cl-cyclopropyl-CO | 1 |

TABLE 3-continued

| Ex.-No. | B¹ | B² | B³ | B⁴ | X¹ | R | A³ | R³ | R⁴ | R⁵ | R⁶ | l |
|---|---|---|---|---|---|---|---|---|---|---|---|---|
| 3-28 | C—Cl | C—H | C—Cl | C—H | H | CF3 | C—CF3 | H | H | H |  | 1 |
| 3-29 | C—Cl | C—H | C—Cl | C—H | H | CF3 | C—CF3 | H | H | H |  | 1 |
| 3-30 | C—Cl | C—H | C—Cl | C—H | H | CF3 | C—CF3 | H | H | H |  | 1 |
| 3-31 | C—Cl | C—H | C—Cl | C—H | H | CF3 | C—CF3 | H | H | H | 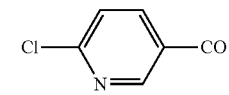 | 1 |
| 3-32 | C—Cl | C—H | C—Cl | C—H | H | CF3 | C—CF3 | H | H | H | CH2=CH—CO | 1 |
| 3-33 | C—Cl | C—H | C—Cl | C—H | H | CF3 | C—CF3 | H | H | H | CH3CH=CH—CO | 1 |
| 3-34 | C—Cl | C—H | C—Cl | C—H | H | CF3 | C—CF3 | H | H | H | CH2=C(CH3)—CO | 1 |
| 3-35 | C—Cl | C—H | C—Cl | C—H | H | CF3 | C—CF3 | H | H | H | CH3CH=C(CH3)—CO | 1 |
| 3-36 | C—Cl | C—H | C—Cl | C—H | H | CF3 | C—CF3 | H | H | H | (CH3)2C=CH—CO | 1 |
| 3-37 | C—Cl | C—H | C—Cl | C—H | H | CF3 | C—CF3 | H | H | H | CH2=C(Cl)—CO | 1 |
| 3-38 | C—Cl | C—H | C—Cl | C—H | H | CF3 | C—CF3 | H | H | H | ClCH=C(CH3)—CO | 1 |
| 3-39 | C—Cl | C—H | C—Cl | C—H | H | CF3 | C—CF3 | H | H | H | CH2=CHCH2—CO | 1 |
| 3-40 | C—Cl | C—H | C—Cl | C—H | H | CF3 | C—CF3 | H | H | H | HCC—CO | 1 |
| 3-41 | C—Cl | C—H | C—Cl | C—H | H | CF3 | C—CF3 | H | H | H | CH3CC—CO | 1 |
| 3-42 | C—Cl | C—H | C—Cl | C—H | H | CF3 | C—CF3 | H | H | H | NCCH2—CO | 1 |
| 3-43 | C—Cl | C—H | C—Cl | C—H | H | CF3 | C—CF3 | H | H | H | CH3OCH2—CO | 1 |
| 3-44 | C—Cl | C—H | C—Cl | C—H | H | CF3 | C—CF3 | H | H | H | C2H5OCH2—CO | 1 |
| 3-45 | C—Cl | C—H | C—Cl | C—H | H | CF3 | C—CF3 | H | H | H | CH3SCH2CO | 1 |
| 3-46 | C—Cl | C—H | C—Cl | C—H | H | CF3 | C—CF3 | H | H | H | CH3O(CO)CH2—CO | 1 |
| 3-47 | C—Cl | C—H | C—Cl | C—H | H | CF3 | C—CF3 | H | H | H | CH3(CO)OCH2—CO | 1 |
| 3-48 | C—Cl | C—H | C—Cl | C—H | H | CF3 | C—CF3 | H | H | H | CH3O(CO)—CO | 1 |
| 3-49 | C—Cl | C—H | C—Cl | C—H | H | CF3 | C—CF3 | H | H | H | CF3O(CO)—CO | 1 |
| 3-50 | C—Cl | C—H | C—Cl | C—H | H | CF3 | C—CF3 | H | H | H | CH3(CO)CH2—CO | 1 |
| 3-51 | C—Cl | C—H | C—Cl | C—H | H | CF3 | C—CF3 | H | H | H | (CH3)2NCH2—CO | 1 |
| 3-52 | C—Cl | C—H | C—Cl | C—H | H | CF3 | C—CF3 | H | H | H | PhCO | 1 |
| 3-53 | C—Cl | C—H | C—Cl | C—H | H | CF3 | C—CF3 | H | H | H | PhCH2CO | 1 |
| 3-54 | C—Cl | C—H | C—Cl | C—H | H | CF3 | C—CF3 | H | H | H | 2-py—CO | 1 |
| 3-55 | C—Cl | C—H | C—Cl | C—H | H | CF3 | C—CF3 | H | H | H | 3-py—CO | 1 |
| 3-56 | C—Cl | C—H | C—Cl | C—H | H | CF3 | C—CF3 | H | H | H | 4-py—CO | 1 |
| 3-57 | C—Cl | C—H | C—Cl | C—H | H | CF3 | C—CF3 | H | H | H | 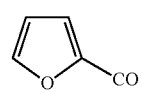 | 1 |
| 3-58 | C—Cl | C—H | C—Cl | C—H | H | CF3 | C—CF3 | H | H | H | 2-F—PhCO | 1 |
| 3-59 | C—Cl | C—H | C—Cl | C—H | H | CF3 | C—CF3 | H | H | H | 3-F—PhCO | 1 |
| 3-60 | C—Cl | C—H | C—Cl | C—H | H | CF3 | C—CF3 | H | H | H | 4-F—PhCO | 1 |
| 3-61 | C—Cl | C—H | C—Cl | C—H | H | CF3 | C—CF3 | H | H | H | 2-Cl—PhCO | 1 |
| 3-62 | C—Cl | C—H | C—Cl | C—H | H | CF3 | C—CF3 | H | H | H | 3-Cl—PhCO | 1 |
| 3-63 | C—Cl | C—H | C—Cl | C—H | H | CF3 | C—CF3 | H | H | H | 4-Cl—PhCO | 1 |
| 3-64 | C—Cl | C—H | C—Cl | C—H | H | CF3 | C—CF3 | H | H | H | 2-Br—PhCO | 1 |
| 3-65 | C—Cl | C—H | C—Cl | C—H | H | CF3 | C—CF3 | H | H | H | 2-CF3—PhCO | 1 |
| 3-66 | C—Cl | C—H | C—Cl | C—H | H | CF3 | C—CF3 | H | H | H | 2-CH3—PhCO | 1 |
| 3-67 | C—Cl | C—H | C—Cl | C—H | H | CF3 | C—CF3 | H | H | H | 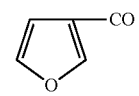 | 1 |
| 3-68 | C—Cl | C—H | C—Cl | C—H | H | CF3 | C—CF3 | H | H | H |  | 1 |

TABLE 3-continued

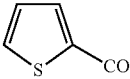

| Ex.-No. | B¹ | B² | B³ | B⁴ | X¹ | R | A³ | R³ | R⁴ | R⁵ | R⁶ | 1 |
|---|---|---|---|---|---|---|---|---|---|---|---|---|
| 3-69 | C—Cl | C—H | C—Cl | C—H | H | CF3 | C—CF3 | H | H | H | 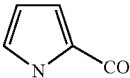 | 1 |
| 3-70 | C—Cl | C—H | C—Cl | C—H | H | CF3 | C—CF3 | H | H | H | 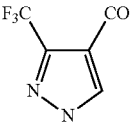 | 1 |
| 3-71 | C—Cl | C—H | C—Cl | C—H | H | CF3 | C—CF3 | H | H | H | 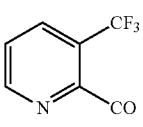 | 1 |
| 3-72 | C—Cl | C—H | C—Cl | C—H | H | CF3 | C—CF3 | H | H | H | 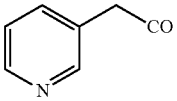 | 1 |
| 3-73 | C—Cl | C—H | C—Cl | C—H | H | CF3 | C—CF3 | H | H | H | 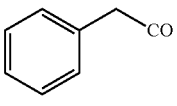 | 1 |
| 3-74 | C—Cl | C—H | C—Cl | C—H | H | CF3 | C—CF3 | H | H | H | 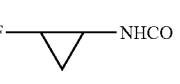 | 1 |
| 3-75 | C—Cl | C—H | C—Cl | C—H | H | CF3 | C—CF3 | H | H | CH3 | CH3CO | 1 |
| 3-76 | C—Cl | C—H | C—Cl | C—H | H | CF3 | C—CF3 | H | H | CH3 | cyclo-PrCO | 1 |
| 3-77 | C—Cl | C—H | C—Cl | C—H | H | CF3 | C—CF3 | H | H | H | CH3NHCO | 1 |
| 3-78 | C—Cl | C—H | C—Cl | C—H | H | CF3 | C—CF3 | H | H | H | CH3CH2NHCO | 1 |
| 3-79 | C—Cl | C—H | C—Cl | C—H | H | CF3 | C—CF3 | H | H | H | CF3CH2NHCO | 1 |
| 3-80 | C—Cl | C—H | C—Cl | C—H | H | CF3 | C—CF3 | H | H | H | n-PrNHCO | 1 |
| 3-81 | C—Cl | C—H | C—Cl | C—H | H | CF3 | C—CF3 | H | H | H | iso-PrNHCO | 1 |
| 3-82 | C—Cl | C—H | C—Cl | C—H | H | CF3 | C—CF3 | H | H | H | cyclo-PrNHCO | 1 |
| 3-83 | C—Cl | C—H | C—Cl | C—H | H | CF3 | C—CF3 | H | H | H | n-BuNHCO | 1 |
| 3-84 | C—Cl | C—H | C—Cl | C—H | H | CF3 | C—CF3 | H | H | H | tert-BuNHCO | 1 |
| 3-85 | C—Cl | C—H | C—Cl | C—H | H | CF3 | C—CF3 | H | H | H | cyclo-BuNHCO | 1 |
| 3-86 | C—Cl | C—H | C—Cl | C—H | H | CF3 | C—CF3 | H | H | H | cyclo-PenNHCO | 1 |
| 3-87 | C—Cl | C—H | C—Cl | C—H | H | CF3 | C—CF3 | H | H | H | cyclo-HexNHCO | 1 |
| 3-88 | C—Cl | C—H | C—Cl | C—H | H | CF3 | C—CF3 | H | H | H | CH2=CHCH2NHCO | 1 |
| 3-89 | C—Cl | C—H | C—Cl | C—H | H | CF3 | C—CF3 | H | H | H | HCCCH2NHCO | 1 |
| 3-90 | C—Cl | C—H | C—Cl | C—H | H | CF3 | C—CF3 | H | H | H | cyclo-PrCH2NHCO | 1 |
| 3-91 | C—Cl | C—H | C—Cl | C—H | H | CF3 | C—CF3 | H | H | H | NCCH2NHCO | 1 |
| 3-92 | C—Cl | C—H | C—Cl | C—H | H | CF3 | C—CF3 | H | H | H | CF3(CH3)CHNHCO | 1 |
| 3-93 | C—Cl | C—H | C—Cl | C—H | H | CF3 | C—CF3 | H | H | H | CF3(CH3)2CNCO | 1 |
| 3-95 | C—Cl | C—H | C—Cl | C—H | H | CF3 | C—CF3 | H | H | H | FCH2CH2NHCO | 1 |
| 3-96 | C—Cl | C—H | C—Cl | C—H | H | CF3 | C—CF3 | H | H | H | CF3CH2CH2NHCO | 1 |
| 3-97 | C—Cl | C—H | C—Cl | C—H | H | CF3 | C—CF3 | H | H | H | HCF2CF2CH2NHCO | 1 |
| 3-98 | C—Cl | C—H | C—Cl | C—H | H | CF3 | C—CF3 | H | H | H | 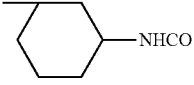 | 1 |
| 3-99 | C—Cl | C—H | C—Cl | C—H | H | CF3 | C—CF3 | H | H | H |  | 1 |
| 3-100 | C—Cl | C—H | C—Cl | C—H | H | CF3 | C—CF3 | H | H | H | EtO2CCH2NHCO | 1 |
| 3-101 | C—Cl | C—H | C—Cl | C—H | H | CF3 | C—CF3 | H | H | H | 2-CF3—PhNHCO | 1 |

TABLE 3-continued

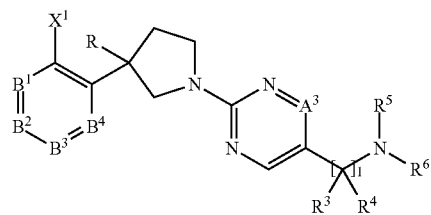

| ExNo. | B¹ | B² | B³ | B⁴ | X¹ | R | A³ | R³ | R⁴ | R⁵ | R⁶ | l |
|---|---|---|---|---|---|---|---|---|---|---|---|---|
| 3-102 | C—Cl | C—H | C—Cl | C—H | H | CF3 | C—CF3 | H | H | H | 3-CF3—PhNHCO | 1 |
| 3-103 | C—Cl | C—H | C—Cl | C—H | H | CF3 | C—CF3 | H | H | H | 4-CF3—PhNHCO | 1 |
| 3-104 | C—Cl | C—H | C—Cl | C—H | H | CF3 | C—CF3 | H | H | H | 2-py—NHCO | 1 |
| 3-105 | C—Cl | C—H | C—Cl | C—H | H | CF3 | C—CF3 | H | H | H | 3-py—NHCO | 1 |
| 3-106 | C—Cl | C—H | C—Cl | C—H | H | CF3 | C—CF3 | H | H | H | 4-py—NHCO | 1 |
| 3-107 | C—Cl | C—H | C—Cl | C—H | H | CF3 | C—CF3 | H | H | H | 5-CF3-2-pyridyl-NHCO | 1 |
| 3-108 | C—Cl | C—H | C—Cl | C—H | H | CF3 | C—CF3 | H | H | H | 6-CF3-3-pyridyl-NHCO | 1 |
| 3-109 | C—Cl | C—H | C—Cl | C—H | H | CF3 | C—CF3 | H | H | H | PhCH2HNCO | 1 |
| 3-110 | C—Cl | C—H | C—Cl | C—H | H | CF3 | C—CF3 | H | H | H | (2-pyridyl)CH2NHCO | 1 |
| 3-111 | C—Cl | C—H | C—Cl | C—H | H | CF3 | C—CF3 | H | H | H | (CH3)2NCO | 1 |
| 3-112 | C—Cl | C—H | C—Cl | C—H | H | CF3 | C—CF3 | H | H | CH3 | CH3NHCO | 1 |
| 3-113 | C—Cl | C—H | C—Cl | C—H | H | CF3 | C—CF3 | H | H | CH3 | CH3CH2NHCO | 1 |
| 3-114 | C—Cl | C—H | C—Cl | C—H | H | CF3 | C—CF3 | H | H | CH3 | cyclo-PrNHCO | 1 |
| 3-115 | C—Cl | C—H | C—Cl | C—H | H | CF3 | C—CF3 | H | H | H | pyrrolidineCO | 1 |
| 3-116 | C—Cl | C—H | C—Cl | C—H | H | CF3 | C—CF3 | H | H | H | piperidineCO | 1 |
| 3-117 | C—Cl | C—H | C—Cl | C—H | H | CF3 | C—CF3 | H | H | H | morpholineCO | 1 |
| 3-118 | C—Cl | C—H | C—Cl | C—H | H | CF3 | C—CF3 | H | H | H | CH3OCO | 1 |
| 3-119 | C—Cl | C—H | C—Cl | C—H | H | CF3 | C—CF3 | H | H | H | CH3CH2OCO | 1 |
| 3-120 | C—Cl | C—H | C—Cl | C—H | H | CF3 | C—CF3 | H | H | H | n-PrOCO | 1 |
| 3-121 | C—Cl | C—H | C—Cl | C—H | H | CF3 | C—CF3 | H | H | H | cyclo-PrOCO | 1 |
| 3-122 | C—Cl | C—H | C—Cl | C—H | H | CF3 | C—CF3 | H | H | H | CF3CH2OCO | 1 |
| 3-123 | C—Cl | C—H | C—Cl | C—H | H | CF3 | C—CF3 | H | H | H | CH2=CHCH2OCO | 1 |
| 3-124 | C—Cl | C—H | C—Cl | C—H | H | CF3 | C—CF3 | H | H | H | HCCCH2OCO | 1 |
| 3-125 | C—Cl | C—H | C—Cl | C—H | H | CF3 | C—CF3 | H | H | H | PhOCO | 1 |
| 3-126 | C—Cl | C—H | C—Cl | C—H | H | CF3 | C—CF3 | H | H | H | PhCH2OCO | 1 |
| 3-127 | C—Cl | C—H | C—Cl | C—H | H | CF3 | C—CF3 | H | H | H | tert-BuOCO | 1 |
| 3-128 | C—Cl | C—H | C—Cl | C—H | H | CF3 | C—CF3 | H | H | CH3 | tert-BuOCO | 1 |
| 3-129 | C—Cl | C—H | C—Cl | C—H | H | CF3 | C—CF3 | H | H | H | CH3SO2 | 1 |
| 3-130 | C—Cl | C—H | C—Cl | C—H | H | CF3 | C—CF3 | H | H | H | CH3CH2SO2 | 1 |
| 3-131 | C—Cl | C—H | C—Cl | C—H | H | CF3 | C—CF3 | H | H | H | CF3SO2 | 1 |
| 3-132 | C—Cl | C—H | C—Cl | C—H | H | CF3 | C—CF3 | H | H | H | CF3CH2SO2 | 1 |
| 3-133 | C—Cl | C—H | C—Cl | C—H | H | CF3 | C—CF3 | H | H | H | PhSO2 | 1 |
| 3-134 | C—Cl | C—H | C—Cl | C—H | H | CF3 | C—CF3 | H | H | H | CH3NHCONHSO2 | 1 |
| 3-135 | C—Cl | C—H | C—Cl | C—H | H | CF3 | C—CF3 | H | H | H | (CH3)2NCONHSO2 | 1 |
| 3-136 | C—Cl | C—H | C—Cl | C—H | H | CF3 | C—CF3 | H | H | H | CH3CS | 1 |
| 3-137 | C—Cl | C—H | C—Cl | C—H | H | CF3 | C—CF3 | H | H | H | CH3CH2CS | 1 |
| 3-138 | C—Cl | C—H | C—Cl | C—H | H | CF3 | C—CF3 | H | H | H | cyclo-PrCS | 1 |
| 3-139 | C—Cl | C—H | C—Cl | C—H | H | CF3 | C—CF3 | H | H | H | CF3CH2CS | 1 |
| 3-140 | C—Cl | C—Cl | C—Cl | C—H | H | CF3 | C—CF3 | H | H | H | H | 1 |
| 3-141 | C—Cl | C—Cl | C—Cl | C—H | H | CF3 | C—CF3 | H | H | H | CH3CO | 1 |
| 3-142 | C—Cl | C—Cl | C—Cl | C—H | H | CF3 | C—CF3 | H | H | H | CH3CH2CO | 1 |
| 3-143 | C—Cl | C—Cl | C—Cl | C—H | H | CF3 | C—CF3 | H | H | H | cyclo-PrCO | 1 |
| 3-144 | C—Cl | C—Cl | C—Cl | C—H | H | CF3 | C—CF3 | H | H | H | CF3CH2CO | 1 |
| 3-145 | C—Cl | C—Cl | C—Cl | C—H | H | CF3 | C—CF3 | H | H | H | CH3CH2NHCO | 1 |
| 3-146 | C—CF3 | C—H | C—CF3 | C—H | H | CF3 | C—CF3 | H | H | H | H | 1 |
| 3-147 | C—CF3 | C—H | C—CF3 | C—H | H | CF3 | C—CF3 | H | H | H | CH3CO | 1 |
| 3-148 | C—CF3 | C—H | C—CF3 | C—H | H | CF3 | C—CF3 | H | H | H | CH3CH2CO | 1 |
| 3-149 | C—CF3 | C—H | C—CF3 | C—H | H | CF3 | C—CF3 | H | H | H | cyclo-PrCO | 1 |
| 3-150 | C—CF3 | C—H | C—CF3 | C—H | H | CF3 | C—CF3 | H | H | H | CF3CH2CO | 1 |
| 3-151 | C—CF3 | C—H | C—CF3 | C—H | H | CF3 | C—CF3 | H | H | H | CH3CH2NHCO | 1 |
| 3-152 | C—Cl | C—Cl | C—CF3 | C—H | H | CF3 | C—CF3 | H | H | H | CH3CO | 1 |

TABLE 3-continued

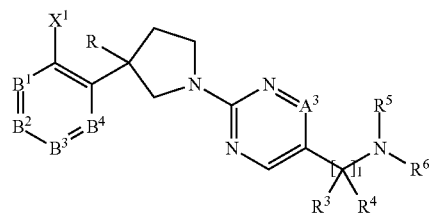

| Ex.-No. | B¹ | B² | B³ | B⁴ | X¹ | R | A³ | R³ | R⁴ | R⁵ | R⁶ | l |
|---|---|---|---|---|---|---|---|---|---|---|---|---|
| 3-153 | C—Cl | C—Cl | C—CF3 | C—H | H | CF3 | C—CF3 | H | H | H | CH3CH2CO | 1 |
| 3-154 | C—Cl | C—Cl | C—CF3 | C—H | H | CF3 | C—CF3 | H | H | H | cyclo-PrCO | 1 |
| 3-155 | C—Cl | C—Cl | C—CF3 | C—H | H | CF3 | C—CF3 | H | H | H | CF3CH2CO | 1 |
| 3-156 | C—Cl | C—Cl | C—CF3 | C—H | H | CF3 | C—CF3 | H | H | H | CH3CH2NHCO | 1 |
| 3-157 | C—Br | C—H | C—Br | C—H | H | CF3 | C—CF3 | H | H | H | CH3CO | 1 |
| 3-158 | C—Br | C—H | C—Br | C—H | H | CF3 | C—CF3 | H | H | H | CH3CH2CO | 1 |
| 3-159 | C—Br | C—H | C—Br | C—H | H | CF3 | C—CF3 | H | H | H | cyclo-PrCO | 1 |
| 3-160 | C—Br | C—H | C—Br | C—H | H | CF3 | C—CF3 | H | H | H | CF3CH2CO | 1 |
| 3-161 | C—Br | C—H | C—Br | C—H | H | CF3 | C—CF3 | H | H | H | CH3CH2NHCO | 1 |
| 3-162 | C—Cl | C—H | C—Cl | C—H | H | CF3 | C—H | H | H | H | CH3CO | 1 |
| 3-163 | C—Cl | C—H | C—Cl | C—H | H | CF3 | C—H | H | H | H | CH3CH2CO | 1 |
| 3-164 | C—Cl | C—H | C—Cl | C—H | H | CF3 | C—H | H | H | H | cyclo-PrCO | 1 |
| 3-165 | C—Cl | C—H | C—Cl | C—H | H | CF3 | C—H | H | H | H | CF3CH2CO | 1 |
| 3-166 | C—Cl | C—H | C—Cl | C—H | H | CF3 | C—H | H | H | H | CH3CH2NHCO | 1 |
| 3-167 | C—Cl | C—Cl | C—Cl | C—H | H | CF3 | C—H | H | H | H | CH3CO | 1 |
| 3-168 | C—Cl | C—Cl | C—Cl | C—H | H | CF3 | C—H | H | H | H | CH3CH2CO | 1 |
| 3-169 | C—Cl | C—Cl | C—Cl | C—H | H | CF3 | C—H | H | H | H | cyclo-PrCO | 1 |
| 3-170 | C—Cl | C—Cl | C—Cl | C—H | H | CF3 | C—H | H | H | H | CF3CH2CO | 1 |
| 3-171 | C—Cl | C—Cl | C—Cl | C—H | H | CF3 | C—H | H | H | H | CH3CH2NHCO | 1 |
| 3-172 | C—CF3 | C—H | C—CF3 | C—H | H | CF3 | C—H | H | H | H | CH3CO | 1 |
| 3-173 | C—CF3 | C—H | C—CF3 | C—H | H | CF3 | C—H | H | H | H | CH3CH2CO | 1 |
| 3-174 | C—CF3 | C—H | C—CF3 | C—H | H | CF3 | C—H | H | H | H | cyclo-PrCO | 1 |
| 3-175 | C—CF3 | C—H | C—CF3 | C—H | H | CF3 | C—H | H | H | H | CF3CH2CO | 1 |
| 3-176 | C—CF3 | C—H | C—CF3 | C—H | H | CF3 | C—H | H | H | H | CH3CH2NHCO | 1 |
| 3-177 | C—Cl | C—H | C—Cl | C—H | H | CF3 | C—CH3 | H | H | H | CH3CO | 1 |
| 3-178 | C—Cl | C—H | C—Cl | C—H | H | CF3 | C—CH3 | H | H | H | CH3CH2CO | 1 |
| 3-179 | C—Cl | C—H | C—Cl | C—H | H | CF3 | C—CH3 | H | H | H | cyclo-PrCO | 1 |
| 3-180 | C—Cl | C—H | C—Cl | C—H | H | CF3 | C—CH3 | H | H | H | CF3CH2CO | 1 |
| 3-181 | C—Cl | C—H | C—Cl | C—H | H | CF3 | C—CH3 | H | H | H | CH3CH2NHCO | 1 |
| 3-182 | C—Cl | C—Cl | C—Cl | C—H | H | CF3 | C—CH3 | H | H | H | CH3CO | 1 |
| 3-183 | C—Cl | C—Cl | C—Cl | C—H | H | CF3 | C—CH3 | H | H | H | CH3CH2CO | 1 |
| 3-184 | C—Cl | C—Cl | C—Cl | C—H | H | CF3 | C—CH3 | H | H | H | cyclo-PrCO | 1 |
| 3-185 | C—Cl | C—Cl | C—Cl | C—H | H | CF3 | C—CH3 | H | H | H | CF3CH2CO | 1 |
| 3-186 | C—Cl | C—Cl | C—Cl | C—H | H | CF3 | C—CH3 | H | H | H | CH3CH2NHCO | 1 |
| 3-187 | C—CF3 | C—H | C—CF3 | C—H | H | CF3 | C—CH3 | H | H | H | CH3CO | 1 |
| 3-188 | C—CF3 | C—H | C—CF3 | C—H | H | CF3 | C—CH3 | H | H | H | CH3CH2CO | 1 |
| 3-189 | C—CF3 | C—H | C—CF3 | C—H | H | CF3 | C—CH3 | H | H | H | cyclo-PrCO | 1 |
| 3-190 | C—CF3 | C—H | C—CF3 | C—H | H | CF3 | C—CH3 | H | H | H | CF3CH2CO | 1 |
| 3-191 | C—CF3 | C—H | C—CF3 | C—H | H | CF3 | C—CH3 | H | H | H | CH3CH2NHCO | 1 |
| 3-192 | C—Cl | C—H | C—Cl | C—H | H | CF3 | C—Cl | H | H | H | CH3CO | 1 |
| 3-193 | C—Cl | C—H | C—Cl | C—H | H | CF3 | C—Cl | H | H | H | CH3CH2CO | 1 |
| 3-194 | C—Cl | C—H | C—Cl | C—H | H | CF3 | C—Cl | H | H | H | cyclo-PrCO | 1 |
| 3-195 | C—Cl | C—H | C—Cl | C—H | H | CF3 | C—Cl | H | H | H | CF3CH2CO | 1 |
| 3-196 | C—Cl | C—H | C—Cl | C—H | H | CF3 | C—Cl | H | H | H | CH3CH2NHCO | 1 |
| 3-197 | C—Cl | C—Cl | C—Cl | C—H | H | CF3 | C—Cl | H | H | H | CH3CO | 1 |
| 3-198 | C—Cl | C—Cl | C—Cl | C—H | H | CF3 | C—Cl | H | H | H | CH3CH2CO | 1 |
| 3-199 | C—Cl | C—Cl | C—Cl | C—H | H | CF3 | C—Cl | H | H | H | cyclo-PrCO | 1 |
| 3-200 | C—Cl | C—Cl | C—Cl | C—H | H | CF3 | C—Cl | H | H | H | CF3CH2CO | 1 |
| 3-201 | C—Cl | C—Cl | C—Cl | C—H | H | CF3 | C—Cl | H | H | H | CH3CH2NHCO | 1 |
| 3-202 | C—CF3 | C—H | C—CF3 | C—H | H | CF3 | C—Cl | H | H | H | CH3CO | 1 |
| 3-203 | C—CF3 | C—H | C—CF3 | C—H | H | CF3 | C—Cl | H | H | H | CH3CH2CO | 1 |
| 3-204 | C—CF3 | C—H | C—CF3 | C—H | H | CF3 | C—Cl | H | H | H | cyclo-PrCO | 1 |
| 3-205 | C—CF3 | C—H | C—CF3 | C—H | H | CF3 | C—Cl | H | H | H | CF3CH2CO | 1 |
| 3-206 | C—CF3 | C—H | C—CF3 | C—H | H | CF3 | C—Cl | H | H | H | CH3CH2NHCO | 1 |
| 3-207 | C—Cl | C—H | C—Cl | C—H | H | CF3 | C—H | H | H | H | n-PrCO | 1 |
| 3-208 | C—Cl | C—H | C—Cl | C—H | H | CF3 | C—H | H | H | H | cyclo-PrCH2CO | 1 |
| 3-209 | C—Cl | C—H | C—Cl | C—H | H | CF3 | C—H | H | H | H | CH3SCH2CO | 1 |
| 3-210 | C—Cl | C—H | C—Cl | C—H | H | CF3 | C—H | H | H | H | CH3S(O)CH2CO | 1 |
| 3-211 | C—Cl | C—H | C—Cl | C—H | H | CF3 | C—H | H | H | H | CH3SO2CH2CO | 1 |
| 3-212 | C—Cl | C—Cl | C—Cl | C—H | H | CF3 | C—H | H | H | H | n-PrCO | 1 |
| 3-213 | C—Cl | C—Cl | C—Cl | C—H | H | CF3 | C—H | H | H | H | cyclo-PrCH2CO | 1 |
| 3-214 | C—Cl | C—Cl | C—Cl | C—H | H | CF3 | C—H | H | H | H | CH3SCH2CO | 1 |
| 3-215 | C—Cl | C—Cl | C—Cl | C—H | H | CF3 | C—H | H | H | H | CH3S(O)CH2CO | 1 |
| 3-216 | C—Cl | C—Cl | C—Cl | C—H | H | CF3 | C—H | H | H | H | CH3SO2CH2CO | 1 |
| 3-217 | C—CF3 | C—H | C—CF3 | C—H | H | CF3 | C—H | H | H | H | n-PrCO | 1 |
| 3-218 | C—CF3 | C—H | C—CF3 | C—H | H | CF3 | C—H | H | H | H | cyclo-PrCH2CO | 1 |
| 3-219 | C—CF3 | C—H | C—CF3 | C—H | H | CF3 | C—H | H | H | H | CH3SCH2CO | 1 |

TABLE 3-continued

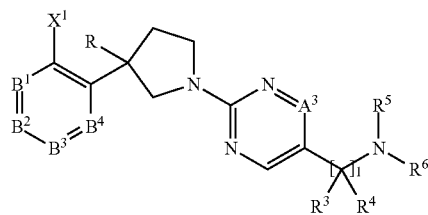

| ExNo. | B¹ | B² | B³ | B⁴ | X¹ | R | A³ | R³ | R⁴ | R⁵ | R⁶ | l |
|---|---|---|---|---|---|---|---|---|---|---|---|---|
| 3-220 | C—CF3 | C—H | C—CF3 | C—H | H | CF3 | C—H | H | H | H | CH3S(O)CH2CO | 1 |
| 3-221 | C—CF3 | C—H | C—CF3 | C—H | H | CF3 | C—H | H | H | H | CH3SO2CH2CO | 1 |
| 3-222 | C—Cl | C—Cl | C—CF3 | C—H | H | CF3 | C—H | H | H | H | n-PrCO | 1 |
| 3-223 | C—Cl | C—Cl | C—CF3 | C—H | H | CF3 | C—H | H | H | H | cyclo-PrCH2CO | 1 |
| 3-224 | C—Cl | C—Cl | C—CF3 | C—H | H | CF3 | C—H | H | H | H | CH3SCH2CO | 1 |
| 3-225 | C—Cl | C—Cl | C—CF3 | C—H | H | CF3 | C—H | H | H | H | CH3S(O)CH2CO | 1 |
| 3-226 | C—Cl | C—Cl | C—CF3 | C—H | H | CF3 | C—H | H | H | H | CH3SO2CH2CO | 1 |
| 3-227 | C—Cl | C—H | C—Cl | C—H | H | CF3 | C—CH3 | H | H | H | n-PrCO | 1 |
| 3-228 | C—Cl | C—H | C—Cl | C—H | H | CF3 | C—CH3 | H | H | H | cyclo-PrCH2CO | 1 |
| 3-229 | C—Cl | C—H | C—Cl | C—H | H | CF3 | C—CH3 | H | H | H | CH3SCH2CO | 1 |
| 3-230 | C—Cl | C—H | C—Cl | C—H | H | CF3 | C—CH3 | H | H | H | CH3S(O)CH2CO | 1 |
| 3-231 | C—Cl | C—H | C—Cl | C—H | H | CF3 | C—CH3 | H | H | H | CH3SO2CH2CO | 1 |
| 3-232 | C—Cl | C—Cl | C—Cl | C—H | H | CF3 | C—CH3 | H | H | H | n-PrCO | 1 |
| 3-233 | C—Cl | C—Cl | C—Cl | C—H | H | CF3 | C—CH3 | H | H | H | cyclo-PrCH2CO | 1 |
| 3-234 | C—Cl | C—Cl | C—Cl | C—H | H | CF3 | C—CH3 | H | H | H | CH3SCH2CO | 1 |
| 3-235 | C—Cl | C—Cl | C—Cl | C—H | H | CF3 | C—CH3 | H | H | H | CH3S(O)CH2CO | 1 |
| 3-236 | C—Cl | C—Cl | C—Cl | C—H | H | CF3 | C—CH3 | H | H | H | CH3SO2CH2CO | 1 |
| 3-237 | C—CF3 | C—H | C—CF3 | C—H | H | CF3 | C—CH3 | H | H | H | n-PrCO | 1 |
| 3-238 | C—CF3 | C—H | C—CF3 | C—H | H | CF3 | C—CH3 | H | H | H | cyclo-PrCH2CO | 1 |
| 3-239 | C—CF3 | C—H | C—CF3 | C—H | H | CF3 | C—CH3 | H | H | H | CH3SCH2CO | 1 |
| 3-240 | C—CF3 | C—H | C—CF3 | C—H | H | CF3 | C—CH3 | H | H | H | CH3S(O)CH2CO | 1 |
| 3-241 | C—CF3 | C—H | C—CF3 | C—H | H | CF3 | C—CH3 | H | H | H | CH3SO2CH2CO | 1 |
| 3-242 | C—Cl | C—Cl | C—CF3 | C—H | H | CF3 | C—CH3 | H | H | H | n-PrCO | 1 |
| 3-243 | C—Cl | C—Cl | C—CF3 | C—H | H | CF3 | C—CH3 | H | H | H | cyclo-PrCH2CO | 1 |
| 3-244 | C—Cl | C—Cl | C—CF3 | C—H | H | CF3 | C—CH3 | H | H | H | CH3SCH2CO | 1 |
| 3-245 | C—Cl | C—Cl | C—CF3 | C—H | H | CF3 | C—CH3 | H | H | H | CH3S(O)CH2CO | 1 |
| 3-246 | C—Cl | C—Cl | C—CF3 | C—H | H | CF3 | C—CH3 | H | H | H | CH3SO2CH2CO | 1 |
| 3-247 | C—Cl | C—H | C—Cl | C—H | H | CF3 | C—Cl | H | H | H | n-PrCO | 1 |
| 3-248 | C—Cl | C—H | C—Cl | C—H | H | CF3 | C—Cl | H | H | H | cyclo-PrCH2CO | 1 |
| 3-249 | C—Cl | C—H | C—Cl | C—H | H | CF3 | C—Cl | H | H | H | CH3SCH2CO | 1 |
| 3-250 | C—Cl | C—H | C—Cl | C—H | H | CF3 | C—Cl | H | H | H | CH3S(O)CH2CO | 1 |
| 3-251 | C—Cl | C—H | C—Cl | C—H | H | CF3 | C—Cl | H | H | H | CH3SO2CH2CO | 1 |
| 3-252 | C—Cl | C—Cl | C—Cl | C—H | H | CF3 | C—Cl | H | H | H | n-PrCO | 1 |
| 3-253 | C—Cl | C—Cl | C—Cl | C—H | H | CF3 | C—Cl | H | H | H | cyclo-PrCH2CO | 1 |
| 3-254 | C—Cl | C—Cl | C—Cl | C—H | H | CF3 | C—Cl | H | H | H | CH3SCH2CO | 1 |
| 3-255 | C—Cl | C—Cl | C—Cl | C—H | H | CF3 | C—Cl | H | H | H | CH3S(O)CH2CO | 1 |
| 3-256 | C—Cl | C—Cl | C—Cl | C—H | H | CF3 | C—Cl | H | H | H | CH3SO2CH2CO | 1 |
| 3-257 | C—CF3 | C—H | C—CF3 | C—H | H | CF3 | C—Cl | H | H | H | n-PrCO | 1 |
| 3-258 | C—CF3 | C—H | C—CF3 | C—H | H | CF3 | C—Cl | H | H | H | cyclo-PrCH2CO | 1 |
| 3-259 | C—CF3 | C—H | C—CF3 | C—H | H | CF3 | C—Cl | H | H | H | CH3SCH2CO | 1 |
| 3-260 | C—CF3 | C—H | C—CF3 | C—H | H | CF3 | C—Cl | H | H | H | CH3S(O)CH2CO | 1 |
| 3-261 | C—CF3 | C—H | C—CF3 | C—H | H | CF3 | C—Cl | H | H | H | CH3SO2CH2CO | 1 |
| 3-262 | C—Cl | C—Cl | C—CF3 | C—H | H | CF3 | C—Cl | H | H | H | n-PrCO | 1 |
| 3-263 | C—Cl | C—Cl | C—CF3 | C—H | H | CF3 | C—Cl | H | H | H | cyclo-PrCH2CO | 1 |
| 3-264 | C—Cl | C—Cl | C—CF3 | C—H | H | CF3 | C—Cl | H | H | H | CH3SCH2CO | 1 |
| 3-265 | C—Cl | C—Cl | C—CF3 | C—H | H | CF3 | C—Cl | H | H | H | CH3S(O)CH2CO | 1 |
| 3-266 | C—Cl | C—Cl | C—CF3 | C—H | H | CF3 | C—Cl | H | H | H | CH3SO2CH2CO | 1 |
| 3-267 | C—Cl | C—H | C—Cl | C—H | H | CF3 | C—Br | H | H | H | CH3CO | 1 |
| 3-268 | C—Cl | C—H | C—Cl | C—H | H | CF3 | C—Br | H | H | H | CH3CH2CO | 1 |
| 3-269 | C—Cl | C—H | C—Cl | C—H | H | CF3 | C—Br | H | H | H | n-PrCO | 1 |
| 3-270 | C—Cl | C—H | C—Cl | C—H | H | CF3 | C—Br | H | H | H | cyclo-PrCO | 1 |
| 3-271 | C—Cl | C—H | C—Cl | C—H | H | CF3 | C—Br | H | H | H | cyclo-PrCH2CO | 1 |
| 3-272 | C—Cl | C—H | C—Cl | C—H | H | CF3 | C—Br | H | H | H | CF3CH2CO | 1 |
| 3-273 | C—Cl | C—H | C—Cl | C—H | H | CF3 | C—Br | H | H | H | CH3SCH2CO | 1 |
| 3-274 | C—Cl | C—H | C—Cl | C—H | H | CF3 | C—Br | H | H | H | CH3S(O)CH2CO | 1 |
| 3-275 | C—Cl | C—H | C—Cl | C—H | H | CF3 | C—Br | H | H | H | CH3SO2CH2CO | 1 |
| 3-276 | C—Cl | C—H | C—Cl | C—H | H | CF3 | C—Br | H | H | H | CH3CH2NHCO | 1 |
| 3-277 | C—Cl | C—Cl | C—Cl | C—H | H | CF3 | C—Br | H | H | H | CH3CO | 1 |
| 3-278 | C—Cl | C—Cl | C—Cl | C—H | H | CF3 | C—Br | H | H | H | CH3CH2CO | 1 |
| 3-279 | C—Cl | C—Cl | C—Cl | C—H | H | CF3 | C—Br | H | H | H | n-PrCO | 1 |
| 3-280 | C—Cl | C—Cl | C—Cl | C—H | H | CF3 | C—Br | H | H | H | cyclo-PrCO | 1 |
| 3-281 | C—Cl | C—Cl | C—Cl | C—H | H | CF3 | C—Br | H | H | H | cyclo-PrCH2CO | 1 |
| 3-282 | C—Cl | C—Cl | C—Cl | C—H | H | CF3 | C—Br | H | H | H | CF3CH2CO | 1 |
| 3-283 | C—Cl | C—Cl | C—Cl | C—H | H | CF3 | C—Br | H | H | H | CH3SCH2CO | 1 |
| 3-284 | C—Cl | C—Cl | C—Cl | C—H | H | CF3 | C—Br | H | H | H | CH3S(O)CH2CO | 1 |
| 3-285 | C—Cl | C—Cl | C—Cl | C—H | H | CF3 | C—Br | H | H | H | CH3SO2CH2CO | 1 |
| 3-286 | C—Cl | C—Cl | C—Cl | C—H | H | CF3 | C—Br | H | H | H | CH3CH2NHCO | 1 |

TABLE 3-continued

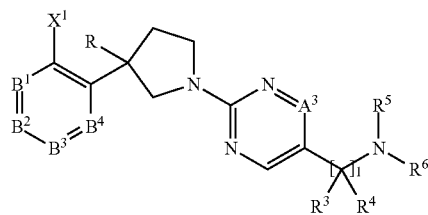

| ExNo. | B¹ | B² | B³ | B⁴ | X¹ | R | A³ | R³ | R⁴ | R⁵ | R⁶ | l |
|---|---|---|---|---|---|---|---|---|---|---|---|---|
| 3-287 | C—CF3 | C—H | C—CF3 | C—H | H | CF3 | C—Br | H | H | H | CH3CO | 1 |
| 3-288 | C—CF3 | C—H | C—CF3 | C—H | H | CF3 | C—Br | H | H | H | CH3CH2CO | 1 |
| 3-289 | C—CF3 | C—H | C—CF3 | C—H | H | CF3 | C—Br | H | H | H | n-PrCO | 1 |
| 3-290 | C—CF3 | C—H | C—CF3 | C—H | H | CF3 | C—Br | H | H | H | cyclo-PrCO | 1 |
| 3-291 | C—CF3 | C—H | C—CF3 | C—H | H | CF3 | C—Br | H | H | H | cyclo-PrCH2CO | 1 |
| 3-292 | C—CF3 | C—H | C—CF3 | C—H | H | CF3 | C—Br | H | H | H | CF3CH2CO | 1 |
| 3-293 | C—CF3 | C—H | C—CF3 | C—H | H | CF3 | C—Br | H | H | H | CH3SCH2CO | 1 |
| 3-294 | C—CF3 | C—H | C—CF3 | C—H | H | CF3 | C—Br | H | H | H | CH3S(O)CH2CO | 1 |
| 3-295 | C—CF3 | C—H | C—CF3 | C—H | H | CF3 | C—Br | H | H | H | CH3SO2CH2CO | 1 |
| 3-296 | C—CF3 | C—H | C—CF3 | C—H | H | CF3 | C—Br | H | H | H | CH3CH2NHCO | 1 |
| 3-297 | C—Cl | C—Cl | C—CF3 | C—H | H | CF3 | C—Br | H | H | H | CH3CO | 1 |
| 3-298 | C—Cl | C—Cl | C—CF3 | C—H | H | CF3 | C—Br | H | H | H | CH3CH2CO | 1 |
| 3-299 | C—Cl | C—Cl | C—CF3 | C—H | H | CF3 | C—Br | H | H | H | n-PrCO | 1 |
| 3-300 | C—Cl | C—Cl | C—CF3 | C—H | H | CF3 | C—Br | H | H | H | cyclo-PrCO | 1 |
| 3-301 | C—Cl | C—Cl | C—CF3 | C—H | H | CF3 | C—Br | H | H | H | cyclo-PrCH2CO | 1 |
| 3-302 | C—Cl | C—Cl | C—CF3 | C—H | H | CF3 | C—Br | H | H | H | CF3CH2CO | 1 |
| 3-303 | C—Cl | C—Cl | C—CF3 | C—H | H | CF3 | C—Br | H | H | H | CH3SCH2CO | 1 |
| 3-304 | C—Cl | C—Cl | C—CF3 | C—H | H | CF3 | C—Br | H | H | H | CH3S(O)CH2CO | 1 |
| 3-305 | C—Cl | C—Cl | C—CF3 | C—H | H | CF3 | C—Br | H | H | H | CH3SO2CH2CO | 1 |
| 3-306 | C—Cl | C—Cl | C—CF3 | C—H | H | CF3 | C—Br | H | H | H | CH3CH2NHCO | 1 |
| 3-307 | C—Cl | C—H | C—Cl | C—H | H | CF3 | C—CF3 | H | H | H | CH3CH2OCH2CO | 1 |
| 3-308 | C—Cl | C—H | C—Cl | C—H | H | CF3 | C—CF3 | H | H | H | CH3OCH2CH2CO | 1 |
| 3-309 | C—Cl | C—H | C—Cl | C—H | H | CF3 | C—CF3 | H | H | H | CH3CH2OCH2CH2CO | 1 |
| 3-310 | C—Cl | C—H | C—Cl | C—H | H | CF3 | C—CF3 | H | H | H | CH3S(O)CH2CO | 1 |
| 3-311 | C—Cl | C—H | C—Cl | C—H | H | CF3 | C—CF3 | H | H | H | CH3SO2CH2CO | 1 |
| 3-312 | C—Cl | C—H | C—Br | C—H | H | CF3 | C—CF3 | H | H | H | CH3CO | 1 |
| 3-313 | C—Cl | C—H | C—Br | C—H | H | CF3 | C—CF3 | H | H | H | CH3CH2CO | 1 |
| 3-314 | C—Cl | C—H | C—Br | C—H | H | CF3 | C—CF3 | H | H | H | n-PrCO | 1 |
| 3-315 | C—Cl | C—H | C—Br | C—H | H | CF3 | C—CF3 | H | H | H | cyclo-PrCO | 1 |
| 3-316 | C—Cl | C—H | C—Br | C—H | H | CF3 | C—CF3 | H | H | H | cyclo-PrCH2CO | 1 |
| 3-317 | C—Cl | C—H | C—Br | C—H | H | CF3 | C—CF3 | H | H | H | CF3CH2CO | 1 |
| 3-318 | C—Cl | C—H | C—Br | C—H | H | CF3 | C—CF3 | H | H | H | CH3SCH2CO | 1 |
| 3-319 | C—Cl | C—H | C—Br | C—H | H | CF3 | C—CF3 | H | H | H | CH3S(O)CH2CO | 1 |
| 3-320 | C—Cl | C—H | C—Br | C—H | H | CF3 | C—CF3 | H | H | H | CH3SO2CH2CO | 1 |
| 3-321 | C—Cl | C—H | C—Br | C—H | H | CF3 | C—CF3 | H | H | H | CH3CH2NHCO | 1 |
| 3-322 | C—Br | C—H | C—Br | C—H | H | CF3 | C—CF3 | H | H | H | CH3SCH2CO | 1 |
| 3-323 | C—Br | C—H | C—Br | C—H | H | CF3 | C—CF3 | H | H | H | CH3S(O)CH2CO | 1 |
| 3-324 | C—Br | C—H | C—Br | C—H | H | CF3 | C—CF3 | H | H | H | CH3SO2CH2CO | 1 |
| 3-325 | C—Cl | C—F | C—Cl | C—H | H | CF3 | C—CF3 | H | H | H | CH3CO | 1 |
| 3-326 | C—Cl | C—F | C—Cl | C—H | H | CF3 | C—CF3 | H | H | H | CH3CH2CO | 1 |
| 3-327 | C—Cl | C—F | C—Cl | C—H | H | CF3 | C—CF3 | H | H | H | n-PrCO | 1 |
| 3-328 | C—Cl | C—F | C—Cl | C—H | H | CF3 | C—CF3 | H | H | H | cyclo-PrCO | 1 |
| 3-329 | C—Cl | C—F | C—Cl | C—H | H | CF3 | C—CF3 | H | H | H | cyclo-PrCH2CO | 1 |
| 3-330 | C—Cl | C—F | C—Cl | C—H | H | CF3 | C—CF3 | H | H | H | CF3CH2CO | 1 |
| 3-331 | C—Cl | C—F | C—Cl | C—H | H | CF3 | C—CF3 | H | H | H | CH3SCH2CO | 1 |
| 3-332 | C—Cl | C—F | C—Cl | C—H | H | CF3 | C—CF3 | H | H | H | CH3S(O)CH2CO | 1 |
| 3-333 | C—Cl | C—F | C—Cl | C—H | H | CF3 | C—CF3 | H | H | H | CH3SO2CH2CO | 1 |
| 3-334 | C—Cl | C—F | C—Cl | C—H | H | CF3 | C—CF3 | H | H | H | CH3CH2NHCO | 1 |
| 3-335 | C—Cl | C—Cl | C—Cl | C—H | H | CF3 | C—CF3 | H | H | H | cyclo-PrCH2CO | 1 |
| 3-336 | C—Cl | C—Cl | C—Cl | C—H | H | CF3 | C—CF3 | H | H | H | tert-BuCH2CO | 1 |
| 3-337 | C—Cl | C—Cl | C—Cl | C—H | H | CF3 | C—CF3 | H | H | H | CH3OCH2CH2CO | 1 |
| 3-338 | C—Cl | C—Cl | C—Cl | C—H | H | CF3 | C—CF3 | H | H | H | CH3CH2OCH2CH2CO | 1 |
| 3-339 | C—Cl | C—Cl | C—Cl | C—H | H | CF3 | C—CF3 | H | H | H | CH3SCH2CO | 1 |
| 3-340 | C—Cl | C—Cl | C—Cl | C—H | H | CF3 | C—CF3 | H | H | H | CH3S(O)CH2CO | 1 |
| 3-341 | C—Cl | C—Cl | C—Cl | C—H | H | CF3 | C—CF3 | H | H | H | CH3SO2CH2CO | 1 |
| 3-342 | C—Cl | C—Cl | C—Cl | C—H | H | CF3 | C—CF3 | H | H | H | CH3CONHCH(CH3)CO | 1 |
| 3-343 | C—Cl | C—Br | C—Cl | C—H | H | CF3 | C—CF3 | H | H | H | CH3CO | 1 |
| 3-344 | C—Cl | C—Br | C—Cl | C—H | H | CF3 | C—CF3 | H | H | H | CH3CH2CO | 1 |
| 3-345 | C—Cl | C—Br | C—Cl | C—H | H | CF3 | C—CF3 | H | H | H | n-PrCO | 1 |
| 3-346 | C—Cl | C—Br | C—Cl | C—H | H | CF3 | C—CF3 | H | H | H | cyclo-PrCO | 1 |
| 3-347 | C—Cl | C—Br | C—Cl | C—H | H | CF3 | C—CF3 | H | H | H | cyclo-PrCH2CO | 1 |
| 3-348 | C—Cl | C—Br | C—Cl | C—H | H | CF3 | C—CF3 | H | H | H | CF3CH2CO | 1 |
| 3-349 | C—Cl | C—Br | C—Cl | C—H | H | CF3 | C—CF3 | H | H | H | CH3SCH2CO | 1 |
| 3-350 | C—Cl | C—Br | C—Cl | C—H | H | CF3 | C—CF3 | H | H | H | CH3S(O)CH2CO | 1 |
| 3-351 | C—Cl | C—Br | C—Cl | C—H | H | CF3 | C—CF3 | H | H | H | CH3SO2CH2CO | 1 |
| 3-352 | C—Cl | C—Br | C—Cl | C—H | H | CF3 | C—CF3 | H | H | H | CH3CH2NHCO | 1 |
| 3-353 | C—Cl | C—Cl | C—Br | C—H | H | CF3 | C—CF3 | H | H | H | CH3CO | 1 |

TABLE 3-continued

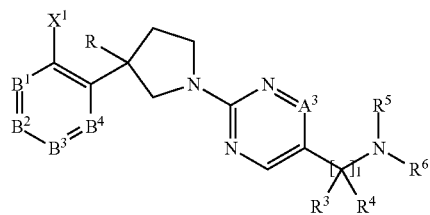

| ExNo. | $B^1$ | $B^2$ | $B^3$ | $B^4$ | $X^1$ | R | $A^3$ | $R^3$ | $R^4$ | $R^5$ | $R^6$ | l |
|---|---|---|---|---|---|---|---|---|---|---|---|---|
| 3-354 | C—Cl | C—Cl | C—Br | C—H | H | CF3 | C—CF3 | H | H | H | CH3CH2CO | 1 |
| 3-355 | C—Cl | C—Cl | C—Br | C—H | H | CF3 | C—CF3 | H | H | H | n-PrCO | 1 |
| 3-356 | C—Cl | C—Cl | C—Br | C—H | H | CF3 | C—CF3 | H | H | H | cyclo-PrCO | 1 |
| 3-357 | C—Cl | C—Cl | C—Br | C—H | H | CF3 | C—CF3 | H | H | H | cyclo-PrCH2CO | 1 |
| 3-358 | C—Cl | C—Cl | C—Br | C—H | H | CF3 | C—CF3 | H | H | H | CF3CH2CO | 1 |
| 3-359 | C—Cl | C—Cl | C—Br | C—H | H | CF3 | C—CF3 | H | H | H | CH3SCH2CO | 1 |
| 3-360 | C—Cl | C—Cl | C—Br | C—H | H | CF3 | C—CF3 | H | H | H | CH3S(O)CH2CO | 1 |
| 3-361 | C—Cl | C—Cl | C—Br | C—H | H | CF3 | C—CF3 | H | H | H | CH3SO2CH2CO | 1 |
| 3-362 | C—Cl | C—Cl | C—Br | C—H | H | CF3 | C—CF3 | H | H | H | CH3CH2NHCO | 1 |
| 3-363 | C—Cl | C—F | C—Cl | C—H | F | CF3 | C—CF3 | H | H | H | CH3CO | 1 |
| 3-364 | C—Cl | C—F | C—Cl | C—H | F | CF3 | C—CF3 | H | H | H | CH3CH2CO | 1 |
| 3-365 | C—Cl | C—F | C—Cl | C—H | F | CF3 | C—CF3 | H | H | H | n-PrCO | 1 |
| 3-366 | C—Cl | C—F | C—Cl | C—H | F | CF3 | C—CF3 | H | H | H | cyclo-PrCO | 1 |
| 3-367 | C—Cl | C—F | C—Cl | C—H | F | CF3 | C—CF3 | H | H | H | cyclo-PrCH2CO | 1 |
| 3-368 | C—Cl | C—F | C—Cl | C—H | F | CF3 | C—CF3 | H | H | H | CF3CH2CO | 1 |
| 3-369 | C—Cl | C—F | C—Cl | C—H | F | CF3 | C—CF3 | H | H | H | CH3SCH2CO | 1 |
| 3-370 | C—Cl | C—F | C—Cl | C—H | F | CF3 | C—CF3 | H | H | H | CH3S(O)CH2CO | 1 |
| 3-371 | C—Cl | C—F | C—Cl | C—H | F | CF3 | C—CF3 | H | H | H | CH3SO2CH2CO | 1 |
| 3-372 | C—Cl | C—F | C—Cl | C—H | F | CF3 | C—CF3 | H | H | H | CH3CH2NHCO | 1 |
| 3-373 | C—Cl | C—H | C—CF3 | C—H | H | CF3 | C—CF3 | H | H | H | CH3CO | 1 |
| 3-374 | C—Cl | C—H | C—CF3 | C—H | H | CF3 | C—CF3 | H | H | H | CH3CH2CO | 1 |
| 3-375 | C—Cl | C—H | C—CF3 | C—H | H | CF3 | C—CF3 | H | H | H | n-PrCO | 1 |
| 3-376 | C—Cl | C—H | C—CF3 | C—H | H | CF3 | C—CF3 | H | H | H | cyclo-PrCO | 1 |
| 3-377 | C—Cl | C—H | C—CF3 | C—H | H | CF3 | C—CF3 | H | H | H | cyclo-PrCH2CO | 1 |
| 3-378 | C—Cl | C—H | C—CF3 | C—H | H | CF3 | C—CF3 | H | H | H | CF3CH2CO | 1 |
| 3-379 | C—Cl | C—H | C—CF3 | C—H | H | CF3 | C—CF3 | H | H | H | CH3OCH2CH2CO | 1 |
| 3-380 | C—Cl | C—H | C—CF3 | C—H | H | CF3 | C—CF3 | H | H | H | CH3CH2OCH2CH2CO | 1 |
| 3-381 | C—Cl | C—H | C—CF3 | C—H | H | CF3 | C—CF3 | H | H | H | CH3SCH2CO | 1 |
| 3-382 | C—Cl | C—H | C—CF3 | C—H | H | CF3 | C—CF3 | H | H | H | CH3S(O)CH2CO | 1 |
| 3-383 | C—Cl | C—H | C—CF3 | C—H | H | CF3 | C—CF3 | H | H | H | CH3SO2CH2CO | 1 |
| 3-384 | C—Cl | C—H | C—CF3 | C—H | H | CF3 | C—CF3 | H | H | H | CH3CH2NHCO | 1 |
| 3-385 | C—CF3 | C—H | C—CF3 | C—H | H | CF3 | C—CF3 | H | H | H | CH3OCH2CH2CO | 1 |
| 3-386 | C—CF3 | C—H | C—CF3 | C—H | H | CF3 | C—CF3 | H | H | H | CH3CH2OCH2CH2CO | 1 |
| 3-387 | C—CF3 | C—H | C—CF3 | C—H | H | CF3 | C—CF3 | H | H | H | CH3SCH2CO | 1 |
| 3-388 | C—CF3 | C—H | C—CF3 | C—H | H | CF3 | C—CF3 | H | H | H | CH3S(O)CH2CO | 1 |
| 3-389 | C—CF3 | C—H | C—CF3 | C—H | H | CF3 | C—CF3 | H | H | H | CH3SO2CH2CO | 1 |
| 3-390 | C—Cl | C—Cl | C—CF3 | C—H | H | CF3 | C—CF3 | H | H | H | CH3SCH2CO | 1 |
| 3-391 | C—Cl | C—Cl | C—CF3 | C—H | H | CF3 | C—CF3 | H | H | H | CH3S(O)CH2CO | 1 |
| 3-392 | C—Cl | C—Cl | C—CF3 | C—H | H | CF3 | C—CF3 | H | H | H | CH3SO2CH2CO | 1 |
| 3-393 | C—Cl | N | C—Cl | C—H | H | CF3 | C—CF3 | H | H | H | CH3CO | 1 |
| 3-394 | C—Cl | N | C—Cl | C—H | H | CF3 | C—CF3 | H | H | H | CH3CH2CO | 1 |
| 3-395 | C—Cl | N | C—Cl | C—H | H | CF3 | C—CF3 | H | H | H | n-PrCO | 1 |
| 3-396 | C—Cl | N | C—Cl | C—H | H | CF3 | C—CF3 | H | H | H | cyclo-PrCO | 1 |
| 3-397 | C—Cl | N | C—Cl | C—H | H | CF3 | C—CF3 | H | H | H | cyclo-PrCH2CO | 1 |
| 3-398 | C—Cl | N | C—Cl | C—H | H | CF3 | C—CF3 | H | H | H | CF3CH2CO | 1 |
| 3-399 | C—Cl | N | C—Cl | C—H | H | CF3 | C—CF3 | H | H | H | CH3SCH2CO | 1 |
| 3-400 | C—Cl | N | C—Cl | C—H | H | CF3 | C—CF3 | H | H | H | CH3S(O)CH2CO | 1 |
| 3-401 | C—Cl | N | C—Cl | C—H | H | CF3 | C—CF3 | H | H | H | CH3SO2CH2CO | 1 |
| 3-402 | C—Cl | N | C—Cl | C—H | H | CF3 | C—CF3 | H | H | H | CH3CH2NHCO | 1 |
| 3-403 | C—CF3 | N | C—H | C—H | H | CF3 | C—CF3 | H | H | H | CH3CO | 1 |
| 3-404 | C—CF3 | N | C—H | C—H | H | CF3 | C—CF3 | H | H | H | CH3CH2CO | 1 |
| 3-405 | C—CF3 | N | C—H | C—H | H | CF3 | C—CF3 | H | H | H | n-PrCO | 1 |
| 3-406 | C—CF3 | N | C—H | C—H | H | CF3 | C—CF3 | H | H | H | cyclo-PrCO | 1 |
| 3-407 | C—CF3 | N | C—H | C—H | H | CF3 | C—CF3 | H | H | H | cyclo-PrCH2CO | 1 |
| 3-408 | C—CF3 | N | C—H | C—H | H | CF3 | C—CF3 | H | H | H | CF3CH2CO | 1 |
| 3-409 | C—CF3 | N | C—H | C—H | H | CF3 | C—CF3 | H | H | H | CH3SCH2CO | 1 |
| 3-410 | C—CF3 | N | C—H | C—H | H | CF3 | C—CF3 | H | H | H | CH3S(O)CH2CO | 1 |
| 3-411 | C—CF3 | N | C—H | C—H | H | CF3 | C—CF3 | H | H | H | CH3SO2CH2CO | 1 |
| 3-412 | C—CF3 | N | C—H | C—H | H | CF3 | C—CF3 | H | H | H | CH3CH2NHCO | 1 |
| 3-413 | C—CF3 | N | C—CF3 | C—H | H | CF3 | C—CF3 | H | H | H | CH3CO | 1 |
| 3-414 | C—CF3 | N | C—CF3 | C—H | H | CF3 | C—CF3 | H | H | H | CH3CH2CO | 1 |
| 3-415 | C—CF3 | N | C—CF3 | C—H | H | CF3 | C—CF3 | H | H | H | n-PrCO | 1 |
| 3-416 | C—CF3 | N | C—CF3 | C—H | H | CF3 | C—CF3 | H | H | H | cyclo-PrCO | 1 |
| 3-417 | C—CF3 | N | C—CF3 | C—H | H | CF3 | C—CF3 | H | H | H | cyclo-PrCH2CO | 1 |
| 3-418 | C—CF3 | N | C—CF3 | C—H | H | CF3 | C—CF3 | H | H | H | CF3CH2CO | 1 |
| 3-419 | C—CF3 | N | C—CF3 | C—H | H | CF3 | C—CF3 | H | H | H | CH3SCH2CO | 1 |
| 3-420 | C—CF3 | N | C—CF3 | C—H | H | CF3 | C—CF3 | H | H | H | CH3S(O)CH2CO | 1 |

TABLE 3-continued

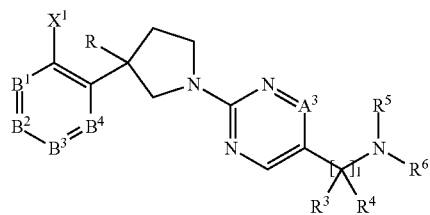

| Ex.-No. | B¹ | B² | B³ | B⁴ | X¹ | R | A³ | R³ | R⁴ | R⁵ | R⁶ | 1 |
|---|---|---|---|---|---|---|---|---|---|---|---|---|
| 3-421 | C—CF3 | N | C—CF3 | C—H | H | CF3 | C—CF3 | H | H | H | CH3SO2CH2CO | 1 |
| 3-422 | C—CF3 | N | C—CF3 | C—H | H | CF3 | C—CF3 | H | H | H | CH3CH2NHCO | 1 |
| 3-423 | C—CF3 | C—H | C—CF3 | N | H | CF3 | C—CF3 | H | H | H | CH3CO | 1 |
| 3-424 | C—CF3 | C—H | C—CF3 | N | H | CF3 | C—CF3 | H | H | H | CH3CH2CO | 1 |
| 3-425 | C—CF3 | C—H | C—CF3 | N | H | CF3 | C—CF3 | H | H | H | n-PrCO | 1 |
| 3-426 | C—CF3 | C—H | C—CF3 | N | H | CF3 | C—CF3 | H | H | H | cyclo-PrCO | 1 |
| 3-427 | C—CF3 | C—H | C—CF3 | N | H | CF3 | C—CF3 | H | H | H | cyclo-PrCH2CO | 1 |
| 3-428 | C—CF3 | C—H | C—CF3 | N | H | CF3 | C—CF3 | H | H | H | CF3CH2CO | 1 |
| 3-429 | C—CF3 | C—H | C—CF3 | N | H | CF3 | C—CF3 | H | H | H | CH3SCH2CO | 1 |
| 3-430 | C—CF3 | C—H | C—CF3 | N | H | CF3 | C—CF3 | H | H | H | CH3S(O)CH2CO | 1 |
| 3-431 | C—CF3 | C—H | C—CF3 | N | H | CF3 | C—CF3 | H | H | H | CH3SO2CH2CO | 1 |
| 3-432 | C—CF3 | C—H | C—CF3 | N | H | CF3 | C—CF3 | H | H | H | CH3CH2NHCO | 1 |
| 3-433 | C—CF3 | C—H | C—CF3 | C—H | H | CF3 | C—CF3 | H | H | H | cyclo-PrCH2CO | 1 |
| 3-434 | C—CF3 | C—H | C—CF3 | C—H | H | CF3 | C—CF3 | H | H | H | tert-BuCH2CO | 1 |
| 3-435 | C—Cl | C—Cl | C—Cl | C—H | H | CF3 | C—CF3 | H | H | H | CH3SO2 | 1 |
| 3-436 | C—CF3 | C—H | C—CF3 | C—H | H | CF3 | C—CF3 | H | H | H | CH3SO2 | 1 |
| 3-437 | C—CF3 | C—H | C—CF3 | C—H | H | CF3 | C—CF3 | H | H | H | CF3CF2CO | 1 |
| 3-438 | C—CF3 | C—H | C—CF3 | C—H | H | CF3 | C—CF3 | H | H | H | PhSCH2CH2CO | 1 |
| 3-439 | C—CF3 | C—H | C—H | C—H | H | CF3 | C—CF3 | H | H | H | CH3CH2CO | 1 |
| 3-440 | C—CF3 | C—H | C—H | C—H | H | CF3 | C—CF3 | H | H | H | cyclo-PrCO | 1 |
| 3-441 | C—CF3 | C—H | C—H | C—H | H | CF3 | C—CF3 | H | H | H | CH3SCH2CO | 1 |
| 3-442 | C—CF3 | C—H | C—H | C—H | H | CF3 | C—CF3 | H | H | H | CH3S(O)CH2CO | 1 |
| 3-443 | C—CF3 | C—H | C—H | C—H | H | CF3 | C—CF3 | H | H | H | CH3SO2CH2CO | 1 |
| 3-444 | C—Br | C—H | C—Br | C—H | H | CF3 | C—CF3 | H | H | H | cyclo-PrCH2CO | 1 |

TABLE 4

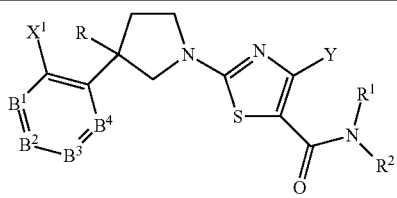

| Ex.-No. | B¹ | B² | B³ | B⁴ | X¹ | R | Y | R¹ | R² |
|---|---|---|---|---|---|---|---|---|---|
| 4-1 | C—Cl | C—H | C—Cl | C—H | H | CF3 | CF3 | H | H |
| 4-2 | C—Cl | C—H | C—Cl | C—H | H | CF3 | CF3 | H | CH3 |
| 4-3 | C—Cl | C—H | C—Cl | C—H | H | CF3 | CF3 | H | CH3CH2 |
| 4-4 | C—Cl | C—H | C—Cl | C—H | H | CF3 | CF3 | H | n-Pr |
| 4-5 | C—Cl | C—H | C—Cl | C—H | H | CF3 | CF3 | H | cyclo-Pr |
| 4-6 | C—Cl | C—H | C—Cl | C—H | H | CF3 | CF3 | H | n-Bu |
| 4-7 | C—Cl | C—H | C—Cl | C—H | H | CF3 | CF3 | H | tert-Bu |
| 4-8 | C—Cl | C—H | C—Cl | C—H | H | CF3 | CF3 | H | CF3CH2 |
| 4-9 | C—Cl | C—H | C—Cl | C—H | H | CF3 | CF3 | H | 2-PyridylCH2 |
| 4-10 | C—Cl | C—H | C—Cl | C—H | H | CF3 | CF3 | H | Ph |
| 4-11 | C—Cl | C—H | C—Cl | C—H | H | CF3 | CF3 | H | PhCH2 |
| 4-12 | C—Cl | C—H | C—Cl | C—H | H | CF3 | CF3 | H | MeO2CCH2 |
| 4-13 | C—Cl | C—H | C—Cl | C—H | H | CF3 | CF3 | H | cyclo-PrCH2 |
| 4-14 | C—Cl | C—Cl | C—Cl | C—H | H | CF3 | CF3 | H | H |
| 4-15 | C—Cl | C—Cl | C—Cl | C—H | H | CF3 | CF3 | H | CH3 |
| 4-16 | C—Cl | C—Cl | C—Cl | C—H | H | CF3 | CF3 | H | CH3CH2 |
| 4-17 | C—Cl | C—Cl | C—Cl | C—H | H | CF3 | CF3 | H | n-Pr |
| 4-18 | C—Cl | C—Cl | C—Cl | C—H | H | CF3 | CF3 | H | cyclo-Pr |
| 4-19 | C—Cl | C—Cl | C—Cl | C—H | H | CF3 | CF3 | H | n-Bu |
| 4-20 | C—Cl | C—Cl | C—Cl | C—H | H | CF3 | CF3 | H | tert-Bu |
| 4-21 | C—Cl | C—Cl | C—Cl | C—H | H | CF3 | CF3 | H | CF3CH2 |
| 4-22 | C—Cl | C—Cl | C—Cl | C—H | H | CF3 | CF3 | H | 2-PyridylCH2 |
| 4-23 | C—Cl | C—Cl | C—Cl | C—H | H | CF3 | CF3 | H | Ph |
| 4-24 | C—Cl | C—Cl | C—Cl | C—H | H | CF3 | CF3 | H | PhCH2 |
| 4-25 | C—Cl | C—Cl | C—Cl | C—H | H | CF3 | CF3 | H | MeO2CCH2 |
| 4-26 | C—Cl | C—Cl | C—Cl | C—H | H | CF3 | CF3 | H | cyclo-PrCH2 |

TABLE 4-continued

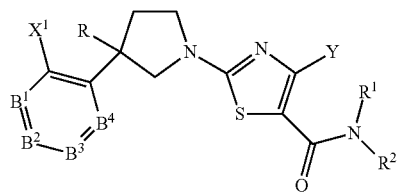

| Ex.-No. | B¹ | B² | B³ | B⁴ | X¹ | R | Y | R¹ | R² |
|---|---|---|---|---|---|---|---|---|---|
| 4-27 | C—CF3 | C—H | C—CF3 | C—H | H | CF3 | CF3 | H | H |
| 4-28 | C—CF3 | C—H | C—CF3 | C—H | H | CF3 | CF3 | H | CH3 |
| 4-29 | C—CF3 | C—H | C—CF3 | C—H | H | CF3 | CF3 | H | CH3CH2 |
| 4-30 | C—CF3 | C—H | C—CF3 | C—H | H | CF3 | CF3 | H | n-Pr |
| 4-31 | C—CF3 | C—H | C—CF3 | C—H | H | CF3 | CF3 | H | cyclo-Pr |
| 4-32 | C—CF3 | C—H | C—CF3 | C—H | H | CF3 | CF3 | H | n-Bu |
| 4-33 | C—CF3 | C—H | C—CF3 | C—H | H | CF3 | CF3 | H | tert-Bu |
| 4-34 | C—CF3 | C—H | C—CF3 | C—H | H | CF3 | CF3 | H | CF3CH2 |
| 4-35 | C—CF3 | C—H | C—CF3 | C—H | H | CF3 | CF3 | H | 2-PyridylCH2 |
| 4-36 | C—CF3 | C—H | C—CF3 | C—H | H | CF3 | CF3 | H | Ph |
| 4-37 | C—CF3 | C—H | C—CF3 | C—H | H | CF3 | CF3 | H | PhCH2 |
| 4-38 | C—CF3 | C—H | C—CF3 | C—H | H | CF3 | CF3 | H | MeO2CCH2 |
| 4-39 | C—CF3 | C—H | C—CF3 | C—H | H | CF3 | CF3 | H | cyclo-PrCH2 |
| 4-40 | C—Cl | C—Cl | C—CF3 | C—H | H | CF3 | CF3 | H | H |
| 4-41 | C—Cl | C—Cl | C—CF3 | C—H | H | CF3 | CF3 | H | CH3 |
| 4-42 | C—Cl | C—Cl | C—CF3 | C—H | H | CF3 | CF3 | H | CH3CH2 |
| 4-43 | C—Cl | C—Cl | C—CF3 | C—H | H | CF3 | CF3 | H | n-Pr |
| 4-44 | C—Cl | C—Cl | C—CF3 | C—H | H | CF3 | CF3 | H | cyclo-Pr |
| 4-45 | C—Cl | C—Cl | C—CF3 | C—H | H | CF3 | CF3 | H | n-Bu |
| 4-46 | C—Cl | C—Cl | C—CF3 | C—H | H | CF3 | CF3 | H | tert-Bu |
| 4-47 | C—Cl | C—Cl | C—CF3 | C—H | H | CF3 | CF3 | H | CF3CH2 |
| 4-48 | C—Cl | C—Cl | C—CF3 | C—H | H | CF3 | CF3 | H | 2-PyridylCH2 |
| 4-49 | C—Cl | C—Cl | C—CF3 | C—H | H | CF3 | CF3 | H | Ph |
| 4-50 | C—Cl | C—Cl | C—CF3 | C—H | H | CF3 | CF3 | H | PhCH2 |
| 4-51 | C—Cl | C—Cl | C—CF3 | C—H | H | CF3 | CF3 | H | MeO2CCH2 |
| 4-52 | C—Cl | C—Cl | C—CF3 | C—H | H | CF3 | CF3 | H | cyclo-PrCH2 |
| 4-53 | C—Cl | C—H | C—Cl | C—H | H | CF3 | H | H | CH3 |
| 4-54 | C—Cl | C—H | C—Cl | C—H | H | CF3 | H | H | CF3CH2 |
| 4-55 | C—Cl | C—H | C—Cl | C—H | H | CF3 | H | H | 2-PyridylCH2 |
| 4-56 | C—Cl | C—H | C—Cl | C—H | H | CF3 | H | H | PhCH2 |
| 4-57 | C—Cl | C—H | C—Cl | C—H | H | CF3 | H | H | MeO2CCH2 |
| 4-58 | C—Cl | C—Cl | C—Cl | C—H | H | CF3 | H | H | CH3 |
| 4-59 | C—Cl | C—Cl | C—Cl | C—H | H | CF3 | H | H | CF3CH2 |
| 4-60 | C—Cl | C—Cl | C—Cl | C—H | H | CF3 | H | H | 2-PyridylCH2 |
| 4-61 | C—Cl | C—Cl | C—Cl | C—H | H | CF3 | H | H | PhCH2 |
| 4-62 | C—Cl | C—Cl | C—Cl | C—H | H | CF3 | H | H | MeO2CCH2 |
| 4-63 | C—CF3 | C—Cl | C—CF3 | C—H | H | CF3 | H | H | CH3 |
| 4-64 | C—CF3 | C—Cl | C—CF3 | C—H | H | CF3 | H | H | CF3CH2 |
| 4-65 | C—CF3 | C—Cl | C—CF3 | C—H | H | CF3 | H | H | 2-PyridylCH2 |
| 4-66 | C—CF3 | C—Cl | C—CF3 | C—H | H | CF3 | H | H | PhCH2 |
| 4-67 | C—CF3 | C—Cl | C—CF3 | C—H | H | CF3 | H | H | MeO2CCH2 |
| 4-68 | C—Cl | C—H | C—Cl | C—H | H | CF3 | CH3 | H | CH3 |
| 4-69 | C—Cl | C—H | C—Cl | C—H | H | CF3 | CH3 | H | CF3CH2 |
| 4-70 | C—Cl | C—H | C—Cl | C—H | H | CF3 | CH3 | H | 2-PyridylCH2 |
| 4-71 | C—Cl | C—H | C—Cl | C—H | H | CF3 | CH3 | H | PhCH2 |
| 4-72 | C—Cl | C—H | C—Cl | C—H | H | CF3 | CH3 | H | MeO2CCH2 |
| 4-73 | C—Cl | C—Cl | C—Cl | C—H | H | CF3 | CH3 | H | CH3 |
| 4-74 | C—Cl | C—Cl | C—Cl | C—H | H | CF3 | CH3 | H | CF3CH2 |
| 4-75 | C—Cl | C—Cl | C—Cl | C—H | H | CF3 | CH3 | H | 2-PyridylCH2 |
| 4-76 | C—Cl | C—Cl | C—Cl | C—H | H | CF3 | CH3 | H | PhCH2 |
| 4-77 | C—Cl | C—Cl | C—Cl | C—H | H | CF3 | CH3 | H | MeO2CCH2 |
| 4-78 | C—CF3 | C—Cl | C—CF3 | C—H | H | CF3 | CH3 | H | CH3 |
| 4-79 | C—CF3 | C—Cl | C—CF3 | C—H | H | CF3 | CH3 | H | CF3CH2 |
| 4-80 | C—CF3 | C—Cl | C—CF3 | C—H | H | CF3 | CH3 | H | 2-PyridylCH2 |
| 4-81 | C—CF3 | C—Cl | C—CF3 | C—H | H | CF3 | CH3 | H | PhCH2 |
| 4-82 | C—CF3 | C—Cl | C—CF3 | C—H | H | CF3 | CH3 | H | MeO2CCH2 |
| 4-83 | C—Cl | C—H | C—Cl | C—H | H | CF3 | Cl | H | CH3 |
| 4-84 | C—Cl | C—H | C—Cl | C—H | H | CF3 | Cl | H | CF3CH2 |
| 4-85 | C—Cl | C—H | C—Cl | C—H | H | CF3 | Cl | H | 2-PyridylCH2 |
| 4-86 | C—Cl | C—H | C—Cl | C—H | H | CF3 | Cl | H | PhCH2 |
| 4-87 | C—Cl | C—H | C—Cl | C—H | H | CF3 | Cl | H | MeO2CCH2 |
| 4-88 | C—Cl | C—Cl | C—Cl | C—H | H | CF3 | Cl | H | CH3 |
| 4-89 | C—Cl | C—Cl | C—Cl | C—H | H | CF3 | Cl | H | CF3CH2 |
| 4-90 | C—Cl | C—Cl | C—Cl | C—H | H | CF3 | Cl | H | 2-PyridylCH2 |
| 4-91 | C—Cl | C—Cl | C—Cl | C—H | H | CF3 | Cl | H | PhCH2 |
| 4-92 | C—Cl | C—Cl | C—Cl | C—H | H | CF3 | Cl | H | MeO2CCH2 |
| 4-93 | C—CF3 | C—Cl | C—CF3 | C—H | H | CF3 | Cl | H | CH3 |
| 4-94 | C—CF3 | C—Cl | C—CF3 | C—H | H | CF3 | Cl | H | CF3CH2 |

TABLE 4-continued

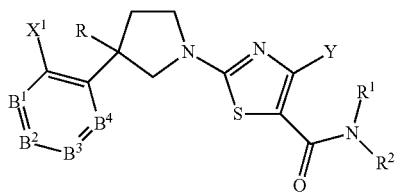

| Ex.-No. | B¹ | B² | B³ | B⁴ | X¹ | R | Y | R¹ | R² |
|---|---|---|---|---|---|---|---|---|---|
| 4-95 | C—CF3 | C—Cl | C—CF3 | C—H | H | CF3 | Cl | H | 2-PyridylCH2 |
| 4-96 | C—CF3 | C—Cl | C—CF3 | C—H | H | CF3 | Cl | H | PhCH2 |
| 4-97 | C—CF3 | C—Cl | C—CF3 | C—H | H | CF3 | Cl | H | MeO2CCH2 |
| 4-98 | C—CF3 | C—H | C—CF3 | C—H | H | CF3 | H | H | CF3CH2 |
| 4-99 | C—CF3 | C—H | C—CF3 | C—H | H | CF3 | H | H | 2-PyridylCH2 |
| 4-100 | C—CF3 | C—H | C—CF3 | C—H | H | CF3 | CH3 | H | CF3CH2 |
| 4-101 | C—CF3 | C—H | C—CF3 | C—H | H | CF3 | CH3 | H | 2-PyridylCH2 |
| 4-102 | C—Cl | C—H | C—Cl | C—H | H | CF3 | Cl | H | CH3OCH2 |
| 4-103 | C—Cl | C—H | C—Cl | C—H | H | CF3 | Cl | CH3CO | CH3OCH2 |
| 4-104 | C—Cl | C—H | C—Cl | C—H | H | CF3 | Cl | H | CH3CH2OCH2 |
| 4-105 | C—Cl | C—H | C—Cl | C—H | H | CF3 | Cl | H | CH3OCH2CH2 |
| 4-106 | C—Cl | C—H | C—Cl | C—H | H | CF3 | Cl | H | CH3CH2OCH2CH2 |
| 4-107 | C—Cl | C—H | C—Cl | C—H | H | CF3 | Cl | H | tetrahydrofuran-2-yl |
| 4-108 | C—Cl | C—H | C—Cl | C—H | H | CF3 | Cl | H | CH3SCH2CH2 |
| 4-109 | C—Cl | C—H | C—Cl | C—H | H | CF3 | Cl | H | CH3S(O)CH2CH2 |
| 4-110 | C—Cl | C—H | C—Cl | C—H | H | CF3 | Cl | H | CH3SO2CH2CH2 |
| 4-111 | C—Cl | C—H | C—Cl | C—H | H | CF3 | Cl | H | CH3SCH2CH(CH3) |
| 4-112 | C—Cl | C—H | C—Cl | C—H | H | CF3 | Cl | H | CH3S(O)CH2CH(CH3) |
| 4-113 | C—Cl | C—H | C—Cl | C—H | H | CF3 | Cl | H | CH3SO2CH2CH(CH3) |
| 4-114 | C—Cl | C—H | C—Cl | C—H | H | CF3 | Cl | H | CH3SCH2C(CH3)2 |
| 4-115 | C—Cl | C—H | C—Cl | C—H | H | CF3 | Cl | H | CH3S(O)CH2C(CH3)2 |
| 4-116 | C—Cl | C—H | C—Cl | C—H | H | CF3 | Cl | H | CH3SO2CH2C(CH3)2 |
| 4-117 | C—Cl | C—H | C—Cl | C—H | H | CF3 | Cl | H | (Methoxyimino)methyl |
| 4-118 | C—Cl | C—H | C—Cl | C—H | H | CF3 | Cl | H | (Ethoxyimino)methyl |
| 4-119 | C—Cl | C—H | C—Cl | C—H | H | CF3 | Cl | H | [1-(1,3-thiazol-4-yl)]CH2 |
| 4-120 | C—Cl | C—H | C—Cl | C—H | H | CF3 | Cl | H | [1-(1-methyl-1H-pyrazol-5-yl]CH2 |
| 4-121 | C—Cl | C—H | C—Cl | C—H | H | CF3 | Cl | H | 5-chloropyrimidin-2-yl |
| 4-122 | C—Cl | C—H | C—Cl | C—H | H | CF3 | Cl | H | 5-bromopyrimidin-2-yl |
| 4-123 | C—Cl | C—H | C—Cl | C—H | H | CF3 | Cl | H | 5-cyanopyrimidin-2-yl |
| 4-124 | C—Cl | C—H | C—Cl | C—H | H | CF3 | Cl | H | CH3NHC(O)CH2 |
| 4-125 | C—Cl | C—H | C—Cl | C—H | H | CF3 | Cl | H | CH3CH2NHC(O)CH2 |
| 4-126 | C—Cl | C—H | C—Cl | C—H | H | CF3 | Cl | H | iso-PrNHC(O)CH2 |
| 4-127 | C—Cl | C—H | C—Cl | C—H | H | CF3 | Cl | H | cyclo-PrNHC(O)CH2 |
| 4-128 | C—Cl | C—H | C—Cl | C—H | H | CF3 | Cl | H | CF3CH2NHC(O)CH2 |
| 4-129 | C—Cl | C—H | C—Cl | C—H | H | CF3 | Cl | H | CH3NHC(O)CH(CH3) |
| 4-130 | C—Cl | C—H | C—Cl | C—H | H | CF3 | Cl | H | CH3CH2NHC(O)CH(CH3) |
| 4-131 | C—Cl | C—H | C—Cl | C—H | H | CF3 | Cl | H | iso-PrNHC(O)CH(CH3) |
| 4-132 | C—Cl | C—H | C—Cl | C—H | H | CF3 | Cl | H | cyclo-PrNHC(O)CH(CH3) |
| 4-133 | C—Cl | C—H | C—Cl | C—H | H | CF3 | Cl | H | CF3CH2NHC(O)CH(CH3) |
| 4-134 | C—Cl | C—H | C—Cl | C—H | H | CF3 | Cl | H | CH3NHC(O)C(CH3)2 |
| 4-135 | C—Cl | C—H | C—Cl | C—H | H | CF3 | Cl | H | CH3CH2NHC(O)C(CH3)2 |
| 4-136 | C—Cl | C—H | C—Cl | C—H | H | CF3 | Cl | H | iso-PrNHC(O)C(CH3)2 |
| 4-137 | C—Cl | C—H | C—Cl | C—H | H | CF3 | Cl | H | cyclo-PrNHC(O)C(CH3)2 |
| 4-138 | C—Cl | C—H | C—Cl | C—H | H | CF3 | Cl | H | CF3CH2NHC(O)C(CH3)2 |
| 4-139 | C—Cl | C—Cl | C—Cl | C—H | H | CF3 | Cl | H | CH3OCH2 |
| 4-140 | C—Cl | C—Cl | C—Cl | C—H | H | CF3 | Cl | CH3CO | CH3OCH2 |
| 4-141 | C—Cl | C—Cl | C—Cl | C—H | H | CF3 | Cl | H | CH3CH2OCH2 |
| 4-142 | C—Cl | C—Cl | C—Cl | C—H | H | CF3 | Cl | H | CH3OCH2CH2 |
| 4-143 | C—Cl | C—Cl | C—Cl | C—H | H | CF3 | Cl | H | CH3CH2OCH2CH2 |
| 4-144 | C—Cl | C—Cl | C—Cl | C—H | H | CF3 | Cl | H | tetrahydrofuran-2-yl |
| 4-145 | C—Cl | C—Cl | C—Cl | C—H | H | CF3 | Cl | H | CH3SCH2CH2 |
| 4-146 | C—Cl | C—Cl | C—Cl | C—H | H | CF3 | Cl | H | CH3S(O)CH2CH2 |
| 4-147 | C—Cl | C—Cl | C—Cl | C—H | H | CF3 | Cl | H | CH3SO2CH2CH2 |
| 4-148 | C—Cl | C—Cl | C—Cl | C—H | H | CF3 | Cl | H | CH3SCH2CH(CH3) |
| 4-149 | C—Cl | C—Cl | C—Cl | C—H | H | CF3 | Cl | H | CH3S(O)CH2CH(CH3) |
| 4-150 | C—Cl | C—Cl | C—Cl | C—H | H | CF3 | Cl | H | CH3SO2CH2CH(CH3) |
| 4-151 | C—Cl | C—Cl | C—Cl | C—H | H | CF3 | Cl | H | CH3SCH2C(CH3)2 |
| 4-152 | C—Cl | C—Cl | C—Cl | C—H | H | CF3 | Cl | H | CH3S(O)CH2C(CH3)2 |
| 4-153 | C—Cl | C—Cl | C—Cl | C—H | H | CF3 | Cl | H | CH3SO2CH2C(CH3)2 |
| 4-154 | C—Cl | C—Cl | C—Cl | C—H | H | CF3 | Cl | H | (Methoxyimino)methyl |
| 4-155 | C—Cl | C—Cl | C—Cl | C—H | H | CF3 | Cl | H | (Ethoxyimino)methyl |
| 4-156 | C—Cl | C—Cl | C—Cl | C—H | H | CF3 | Cl | H | [1-(1,3-thiazol-4-yl)]CH2 |
| 4-157 | C—Cl | C—Cl | C—Cl | C—H | H | CF3 | Cl | H | [1-(1-methyl-1H-pyrazol-5-yl]CH2 |
| 4-158 | C—Cl | C—Cl | C—Cl | C—H | H | CF3 | Cl | H | 5-chloropyrimidin-2-yl |
| 4-159 | C—Cl | C—Cl | C—Cl | C—H | H | CF3 | Cl | H | 5-bromopyrimidin-2-yl |
| 4-160 | C—Cl | C—Cl | C—Cl | C—H | H | CF3 | Cl | H | 5-cyanopyrimidin-2-yl |
| 4-161 | C—Cl | C—Cl | C—Cl | C—H | H | CF3 | Cl | H | CH3NHC(O)CH2 |
| 4-162 | C—Cl | C—Cl | C—Cl | C—H | H | CF3 | Cl | H | CH3CH2NHC(O)CH2 |

TABLE 4-continued

| Ex.-No. | B¹ | B² | B³ | B⁴ | X¹ | R | Y | R¹ | R² |
|---|---|---|---|---|---|---|---|---|---|
| 4-163 | C—Cl | C—Cl | C—Cl | C—H | H | CF3 | Cl | H | iso-PrNHC(O)CH2 |
| 4-164 | C—Cl | C—Cl | C—Cl | C—H | H | CF3 | Cl | H | cyclo-PrNHC(O)CH2 |
| 4-165 | C—Cl | C—Cl | C—Cl | C—H | H | CF3 | Cl | H | CF3CH2NHC(O)CH2 |
| 4-166 | C—Cl | C—Cl | C—Cl | C—H | H | CF3 | Cl | H | CH3NHC(O)CH(CH3) |
| 4-167 | C—Cl | C—Cl | C—Cl | C—H | H | CF3 | Cl | H | CH3CH2NHC(O)CH(CH3) |
| 4-168 | C—Cl | C—Cl | C—Cl | C—H | H | CF3 | Cl | H | iso-PrNHC(O)CH(CH3) |
| 4-169 | C—Cl | C—Cl | C—Cl | C—H | H | CF3 | Cl | H | cyclo-PrNHC(O)CH(CH3) |
| 4-170 | C—Cl | C—Cl | C—Cl | C—H | H | CF3 | Cl | H | CF3CH2NHC(O)CH(CH3) |
| 4-171 | C—Cl | C—Cl | C—Cl | C—H | H | CF3 | Cl | H | CH3NHC(O)C(CH3)2 |
| 4-172 | C—Cl | C—Cl | C—Cl | C—H | H | CF3 | Cl | H | CH3CH2NHC(O)C(CH3)2 |
| 4-173 | C—Cl | C—Cl | C—Cl | C—H | H | CF3 | Cl | H | iso-PrNHC(O)C(CH3)2 |
| 4-174 | C—Cl | C—Cl | C—Cl | C—H | H | CF3 | Cl | H | cyclo-PrNHC(O)C(CH3)2 |
| 4-175 | C—Cl | C—Cl | C—Cl | C—H | H | CF3 | Cl | H | CF3CH2NHC(O)C(CH3)2 |
| 4-176 | C—Cl | C—H | C—CF3 | C—H | H | CF3 | Cl | H | CF3CH2 |
| 4-177 | C—Cl | C—H | C—CF3 | C—H | H | CF3 | Cl | H | CH3OCH2 |
| 4-178 | C—Cl | C—H | C—CF3 | C—H | H | CF3 | Cl | CH3CO | CH3OCH2 |
| 4-179 | C—Cl | C—H | C—CF3 | C—H | H | CF3 | Cl | H | CH3CH2OCH2 |
| 4-180 | C—Cl | C—H | C—CF3 | C—H | H | CF3 | Cl | H | CH3OCH2CH2 |
| 4-181 | C—Cl | C—H | C—CF3 | C—H | H | CF3 | Cl | H | CH3CH2OCH2CH2 |
| 4-182 | C—Cl | C—H | C—CF3 | C—H | H | CF3 | Cl | H | tetrahydrofuran-2-yl |
| 4-183 | C—Cl | C—H | C—CF3 | C—H | H | CF3 | Cl | H | CH3SCH2 |
| 4-184 | C—Cl | C—H | C—CF3 | C—H | H | CF3 | Cl | H | CH3S(O)CH2CH2 |
| 4-185 | C—Cl | C—H | C—CF3 | C—H | H | CF3 | Cl | H | CH3SO2CH2CH2 |
| 4-186 | C—Cl | C—H | C—CF3 | C—H | H | CF3 | Cl | H | CH3SCH2CH(CH3) |
| 4-187 | C—Cl | C—H | C—CF3 | C—H | H | CF3 | Cl | H | CH3S(O)CH2CH(CH3) |
| 4-188 | C—Cl | C—H | C—CF3 | C—H | H | CF3 | Cl | H | CH3SO2CH2CH(CH3) |
| 4-189 | C—Cl | C—H | C—CF3 | C—H | H | CF3 | Cl | H | CH3SCH2C(CH3)2 |
| 4-190 | C—Cl | C—H | C—CF3 | C—H | H | CF3 | Cl | H | CH3S(O)CH2C(CH3)2 |
| 4-191 | C—Cl | C—H | C—CF3 | C—H | H | CF3 | Cl | H | CH3SO2CH2C(CH3)2 |
| 4-192 | C—Cl | C—H | C—CF3 | C—H | H | CF3 | Cl | H | (Methoxyimino)methyl |
| 4-193 | C—Cl | C—H | C—CF3 | C—H | H | CF3 | Cl | H | (Ethoxyimino)methyl |
| 4-194 | C—Cl | C—H | C—CF3 | C—H | H | CF3 | Cl | H | 2-PyridylCH2 |
| 4-195 | C—Cl | C—H | C—CF3 | C—H | H | CF3 | Cl | H | [1-(1,3-thiazol-4-yl)]CH2 |
| 4-196 | C—Cl | C—H | C—CF3 | C—H | H | CF3 | Cl | H | [1-(1-methyl-1H-pyrazol-5-yl)]CH2 |
| 4-197 | C—Cl | C—H | C—CF3 | C—H | H | CF3 | Cl | H | 5-chloropyrimidin-2-yl |
| 4-198 | C—Cl | C—H | C—CF3 | C—H | H | CF3 | Cl | H | 5-bromopyrimidin-2-yl |
| 4-199 | C—Cl | C—H | C—CF3 | C—H | H | CF3 | Cl | H | 5-cyanopyrimidin-2-yl |
| 4-200 | C—Cl | C—H | C—CF3 | C—H | H | CF3 | Cl | H | CH3NHC(O)CH2 |
| 4-201 | C—Cl | C—H | C—CF3 | C—H | H | CF3 | Cl | H | CH3CH2NHC(O)CH2 |
| 4-202 | C—Cl | C—H | C—CF3 | C—H | H | CF3 | Cl | H | iso-PrNHC(O)CH2 |
| 4-203 | C—Cl | C—H | C—CF3 | C—H | H | CF3 | Cl | H | cyclo-PrNHC(O)CH2 |
| 4-204 | C—Cl | C—H | C—CF3 | C—H | H | CF3 | Cl | H | CF3CH2NHC(O)CH2 |
| 4-205 | C—Cl | C—H | C—CF3 | C—H | H | CF3 | Cl | H | CH3NHC(O)CH(CH3) |
| 4-206 | C—Cl | C—H | C—CF3 | C—H | H | CF3 | Cl | H | CH3CH2NHC(O)CH(CH3) |
| 4-207 | C—Cl | C—H | C—CF3 | C—H | H | CF3 | Cl | H | iso-PrNHC(O)CH(CH3) |
| 4-208 | C—Cl | C—H | C—CF3 | C—H | H | CF3 | Cl | H | cyclo-PrNHC(O)CH(CH3) |
| 4-209 | C—Cl | C—H | C—CF3 | C—H | H | CF3 | Cl | H | CF3CH2NHC(O)CH(CH3) |
| 4-210 | C—Cl | C—H | C—CF3 | C—H | H | CF3 | Cl | H | CH3NHC(O)C(CH3)2 |
| 4-211 | C—Cl | C—H | C—CF3 | C—H | H | CF3 | Cl | H | CH3CH2NHC(O)C(CH3)2 |
| 4-212 | C—Cl | C—H | C—CF3 | C—H | H | CF3 | Cl | H | iso-PrNHC(O)C(CH3)2 |
| 4-213 | C—Cl | C—H | C—CF3 | C—H | H | CF3 | Cl | H | cyclo-PrNHC(O)C(CH3)2 |
| 4-214 | C—Cl | C—H | C—CF3 | C—H | H | CF3 | Cl | H | CF3CH2NHC(O)C(CH3)2 |
| 4-215 | C—CF3 | C—H | C—CF3 | C—H | H | CF3 | Cl | H | CF3CH2 |
| 4-216 | C—CF3 | C—H | C—CF3 | C—H | H | CF3 | Cl | H | CH3OCH2 |
| 4-217 | C—CF3 | C—H | C—CF3 | C—H | H | CF3 | Cl | CH3CO | CH3OCH2 |
| 4-218 | C—CF3 | C—H | C—CF3 | C—H | H | CF3 | Cl | H | CH3CH2OCH2 |
| 4-219 | C—CF3 | C—H | C—CF3 | C—H | H | CF3 | Cl | H | CH3OCH2CH2 |
| 4-220 | C—CF3 | C—H | C—CF3 | C—H | H | CF3 | Cl | H | CH3CH2OCH2CH2 |
| 4-221 | C—CF3 | C—H | C—CF3 | C—H | H | CF3 | Cl | H | tetrahydrofuran-2-yl |
| 4-222 | C—CF3 | C—H | C—CF3 | C—H | H | CF3 | Cl | H | CH3SCH2 |
| 4-223 | C—CF3 | C—H | C—CF3 | C—H | H | CF3 | Cl | H | CH3S(O)CH2CH2 |
| 4-224 | C—CF3 | C—H | C—CF3 | C—H | H | CF3 | Cl | H | CH3SO2CH2CH2 |
| 4-225 | C—CF3 | C—H | C—CF3 | C—H | H | CF3 | Cl | H | CH3SCH2CH(CH3) |
| 4-226 | C—CF3 | C—H | C—CF3 | C—H | H | CF3 | Cl | H | CH3S(O)CH2CH(CH3) |
| 4-227 | C—CF3 | C—H | C—CF3 | C—H | H | CF3 | Cl | H | CH3SO2CH2CH(CH3) |
| 4-228 | C—CF3 | C—H | C—CF3 | C—H | H | CF3 | Cl | H | CH3SCH2C(CH3)2 |
| 4-229 | C—CF3 | C—H | C—CF3 | C—H | H | CF3 | Cl | H | CH3S(O)CH2C(CH3)2 |
| 4-230 | C—CF3 | C—H | C—CF3 | C—H | H | CF3 | Cl | H | CH3SO2CH2C(CH3)2 |

TABLE 4-continued

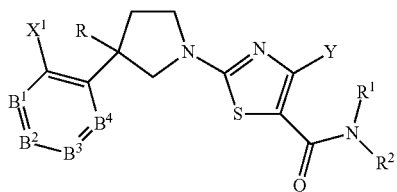

| Ex.-No. | B¹ | B² | B³ | B⁴ | X¹ | R | Y | R¹ | R² |
|---|---|---|---|---|---|---|---|---|---|
| 4-231 | C—CF3 | C—H | C—CF3 | C—H | H | CF3 | Cl | H | (Methoxyimino)methyl |
| 4-232 | C—CF3 | C—H | C—CF3 | C—H | H | CF3 | Cl | H | (Ethoxyimino)methyl |
| 4-233 | C—CF3 | C—H | C—CF3 | C—H | H | CF3 | Cl | H | 2-PyridylCH2 |
| 4-234 | C—CF3 | C—H | C—CF3 | C—H | H | CF3 | Cl | H | [1-(1,3-thiazol-4-yl)]CH2 |
| 4-235 | C—CF3 | C—H | C—CF3 | C—H | H | CF3 | Cl | H | [1-(1-methyl-1H-pyrazol-5-yl]CH2 |
| 4-236 | C—CF3 | C—H | C—CF3 | C—H | H | CF3 | Cl | H | 5-chloropyrimidin-2-yl |
| 4-237 | C—CF3 | C—H | C—CF3 | C—H | H | CF3 | Cl | H | 5-bromopyrimidin-2-yl |
| 4-238 | C—CF3 | C—H | C—CF3 | C—H | H | CF3 | Cl | H | 5-cyanopyrimidin-2-yl |
| 4-239 | C—CF3 | C—H | C—CF3 | C—H | H | CF3 | Cl | H | CH3NHC(O)CH2 |
| 4-240 | C—CF3 | C—H | C—CF3 | C—H | H | CF3 | Cl | H | CH3CH2NHC(O)CH2 |
| 4-241 | C—CF3 | C—H | C—CF3 | C—H | H | CF3 | Cl | H | iso-PrNHC(O)CH2 |
| 4-242 | C—CF3 | C—H | C—CF3 | C—H | H | CF3 | Cl | H | cyclo-PrNHC(O)CH2 |
| 4-243 | C—CF3 | C—H | C—CF3 | C—H | H | CF3 | Cl | H | CF3CH2NHC(O)CH2 |
| 4-244 | C—CF3 | C—H | C—CF3 | C—H | H | CF3 | Cl | H | CH3NHC(O)CH(CH3) |
| 4-245 | C—CF3 | C—H | C—CF3 | C—H | H | CF3 | Cl | H | CH3CH2NHC(O)CH(CH3) |
| 4-246 | C—CF3 | C—H | C—CF3 | C—H | H | CF3 | Cl | H | iso-PrNHC(O)CH(CH3) |
| 4-247 | C—CF3 | C—H | C—CF3 | C—H | H | CF3 | Cl | H | cyclo-PrNHC(O)CH(CH3) |
| 4-248 | C—CF3 | C—H | C—CF3 | C—H | H | CF3 | Cl | H | CF3CH2NHC(O)CH(CH3) |
| 4-249 | C—CF3 | C—H | C—CF3 | C—H | H | CF3 | Cl | H | CH3NHC(O)C(CH3)2 |
| 4-250 | C—CF3 | C—H | C—CF3 | C—H | H | CF3 | Cl | H | CH3CH2NHC(O)C(CH3)2 |
| 4-251 | C—CF3 | C—H | C—CF3 | C—H | H | CF3 | Cl | H | iso-PrNHC(O)C(CH3)2 |
| 4-252 | C—CF3 | C—H | C—CF3 | C—H | H | CF3 | Cl | H | cyclo-PrNHC(O)C(CH3)2 |
| 4-253 | C—CF3 | C—H | C—CF3 | C—H | H | CF3 | Cl | H | CF3CH2NHC(O)C(CH3)2 |
| 4-254 | C—Cl | C—H | C—Cl | C—H | H | CF3 | Br | H | CF3CH2 |
| 4-255 | C—Cl | C—H | C—Cl | C—H | H | CF3 | Br | H | 2-PyridylCH2 |
| 4-256 | C—Cl | C—Cl | C—Cl | C—H | H | CF3 | Br | H | CF3CH2 |
| 4-257 | C—Cl | C—Cl | C—Cl | C—H | H | CF3 | Br | H | 2-PyridylCH2 |
| 4-258 | C—Cl | C—H | C—CF3 | C—H | H | CF3 | Br | H | CF3CH2 |
| 4-259 | C—Cl | C—H | C—CF3 | C—H | H | CF3 | Br | H | 2-PyridylCH2 |
| 4-260 | C—CF3 | C—H | C—CF3 | C—H | H | CF3 | Br | H | CF3CH2 |
| 4-261 | C—CF3 | C—H | C—CF3 | C—H | H | CF3 | Br | H | 2-PyridylCH2 |
| 4-262 | C—Cl | C—H | C—Cl | C—H | H | CF3 | I | H | CF3CH2 |
| 4-263 | C—Cl | C—H | C—Cl | C—H | H | CF3 | I | H | 2-PyridylCH2 |
| 4-264 | C—Cl | C—Cl | C—Cl | C—H | H | CF3 | I | H | CF3CH2 |
| 4-265 | C—Cl | C—Cl | C—Cl | C—H | H | CF3 | I | H | 2-PyridylCH2 |
| 4-266 | C—Cl | C—H | C—CF3 | C—H | H | CF3 | I | H | CF3CH2 |
| 4-267 | C—Cl | C—H | C—CF3 | C—H | H | CF3 | I | H | 2-PyridylCH2 |
| 4-268 | C—CF3 | C—H | C—CF3 | C—H | H | CF3 | I | H | CF3CH2 |
| 4-269 | C—CF3 | C—H | C—CF3 | C—H | H | CF3 | I | H | 2-PyridylCH2 |
| 4-270 | C—Cl | C—H | C—Cl | C—H | H | CF3 | CF3 | H | CH3OCH2 |
| 4-271 | C—Cl | C—H | C—Cl | C—H | H | CF3 | CF3 | CH3CO | CH3OCH2 |
| 4-272 | C—Cl | C—H | C—Cl | C—H | H | CF3 | CF3 | H | CH3CH2OCH2 |
| 4-273 | C—Cl | C—H | C—Cl | C—H | H | CF3 | CF3 | H | CH3OCH2CH2 |
| 4-274 | C—Cl | C—H | C—Cl | C—H | H | CF3 | CF3 | H | CH3CH2OCH2CH2 |
| 4-275 | C—Cl | C—H | C—Cl | C—H | H | CF3 | CF3 | H | tetrahydrofuran-2-yl |
| 4-276 | C—Cl | C—H | C—Cl | C—H | H | CF3 | CF3 | H | CH3SCH2CH2 |
| 4-277 | C—Cl | C—H | C—Cl | C—H | H | CF3 | CF3 | H | CH3S(O)CH2CH2 |
| 4-278 | C—Cl | C—H | C—Cl | C—H | H | CF3 | CF3 | H | CH3SO2CH2CH2 |
| 4-279 | C—Cl | C—H | C—Cl | C—H | H | CF3 | CF3 | H | CH3SCH2CH(CH3) |
| 4-280 | C—Cl | C—H | C—Cl | C—H | H | CF3 | CF3 | H | CH3S(O)CH2CH(CH3) |
| 4-281 | C—Cl | C—H | C—Cl | C—H | H | CF3 | CF3 | H | CH3SO2CH2CH(CH3) |
| 4-282 | C—Cl | C—H | C—Cl | C—H | H | CF3 | CF3 | H | CH3SCH2C(CH3)2 |
| 4-283 | C—Cl | C—H | C—Cl | C—H | H | CF3 | CF3 | H | CH3S(O)CH2C(CH3)2 |
| 4-284 | C—Cl | C—H | C—Cl | C—H | H | CF3 | CF3 | H | CH3SO2CH2C(CH3)2 |
| 4-285 | C—Cl | C—H | C—Cl | C—H | H | CF3 | CF3 | H | (Methoxyimino)methyl |
| 4-286 | C—Cl | C—H | C—Cl | C—H | H | CF3 | CF3 | H | (Ethoxyimino)methyl |
| 4-287 | C—Cl | C—H | C—Cl | C—H | H | CF3 | CF3 | H | [1-(1,3-thiazol-4-yl)]CH2 |
| 4-288 | C—Cl | C—H | C—Cl | C—H | H | CF3 | CF3 | H | [1-(1-methyl-1H-pyrazol-5-yl]CH2 |
| 4-289 | C—Cl | C—H | C—Cl | C—H | H | CF3 | CF3 | H | 5-chloropyrimidin-2-yl |
| 4-290 | C—Cl | C—H | C—Cl | C—H | H | CF3 | CF3 | H | 5-bromopyrimidin-2-yl |
| 4-291 | C—Cl | C—H | C—Cl | C—H | H | CF3 | CF3 | H | 5-cyanopyrimidin-2-yl |
| 4-292 | C—Cl | C—H | C—Cl | C—H | H | CF3 | CF3 | H | CH3NHC(O)CH2 |
| 4-293 | C—Cl | C—H | C—Cl | C—H | H | CF3 | CF3 | H | CH3CH2NHC(O)CH2 |
| 4-294 | C—Cl | C—H | C—Cl | C—H | H | CF3 | CF3 | H | iso-PrNHC(O)CH2 |
| 4-295 | C—Cl | C—H | C—Cl | C—H | H | CF3 | CF3 | H | cyclo-PrNHC(O)CH2 |
| 4-296 | C—Cl | C—H | C—Cl | C—H | H | CF3 | CF3 | H | CF3CH2NHC(O)CH2 |
| 4-297 | C—Cl | C—H | C—Cl | C—H | H | CF3 | CF3 | H | CH3NHC(O)CH(CH3) |
| 4-298 | C—Cl | C—H | C—Cl | C—H | H | CF3 | CF3 | H | CH3CH2NHC(O)CH(CH3) |

TABLE 4-continued

| Ex.-No. | B¹ | B² | B³ | B⁴ | X¹ | R | Y | R¹ | R² |
|---|---|---|---|---|---|---|---|---|---|
| 4-299 | C—Cl | C—H | C—Cl | C—H | H | CF3 | CF3 | H | iso-PrNHC(O)CH(CH3) |
| 4-300 | C—Cl | C—H | C—Cl | C—H | H | CF3 | CF3 | H | cyclo-PrNHC(O)CH(CH3) |
| 4-301 | C—Cl | C—H | C—Cl | C—H | H | CF3 | CF3 | H | CF3CH2NHC(O)CH(CH3) |
| 4-302 | C—Cl | C—H | C—Cl | C—H | H | CF3 | CF3 | H | CH3NHC(O)C(CH3)2 |
| 4-303 | C—Cl | C—H | C—Cl | C—H | H | CF3 | CF3 | H | CH3CH2NHC(O)C(CH3)2 |
| 4-304 | C—Cl | C—H | C—Cl | C—H | H | CF3 | CF3 | H | iso-PrNHC(O)C(CH3)2 |
| 4-305 | C—Cl | C—H | C—Cl | C—H | H | CF3 | CF3 | H | cyclo-PrNHC(O)C(CH3)2 |
| 4-306 | C—Cl | C—H | C—Cl | C—H | H | CF3 | CF3 | H | CF3CH2NHC(O)C(CH3)2 |
| 4-307 | C—Cl | C—Cl | C—Cl | C—H | H | CF3 | CF3 | H | CH3OCH2 |
| 4-308 | C—Cl | C—Cl | C—Cl | C—H | H | CF3 | CF3 | CH3CO | CH3OCH2 |
| 4-309 | C—Cl | C—Cl | C—Cl | C—H | H | CF3 | CF3 | H | CH3CH2OCH2 |
| 4-310 | C—Cl | C—Cl | C—Cl | C—H | H | CF3 | CF3 | H | CH3OCH2CH2 |
| 4-311 | C—Cl | C—Cl | C—Cl | C—H | H | CF3 | CF3 | H | CH3CH2OCH2CH2 |
| 4-312 | C—Cl | C—Cl | C—Cl | C—H | H | CF3 | CF3 | H | tetrahydrofuran-2-yl |
| 4-313 | C—Cl | C—Cl | C—Cl | C—H | H | CF3 | CF3 | H | CH3SCH2CH2 |
| 4-314 | C—Cl | C—Cl | C—Cl | C—H | H | CF3 | CF3 | H | CH3S(O)CH2CH2 |
| 4-315 | C—Cl | C—Cl | C—Cl | C—H | H | CF3 | CF3 | H | CH3SO2CH2CH2 |
| 4-316 | C—Cl | C—Cl | C—Cl | C—H | H | CF3 | CF3 | H | CH3SCH2CH(CH3) |
| 4-317 | C—Cl | C—Cl | C—Cl | C—H | H | CF3 | CF3 | H | CH3S(O)CH2CH(CH3) |
| 4-318 | C—Cl | C—Cl | C—Cl | C—H | H | CF3 | CF3 | H | CH3SO2CH2CH(CH3) |
| 4-319 | C—Cl | C—Cl | C—Cl | C—H | H | CF3 | CF3 | H | CH3SCH2C(CH3)2 |
| 4-320 | C—Cl | C—Cl | C—Cl | C—H | H | CF3 | CF3 | H | CH3S(O)CH2C(CH3)2 |
| 4-321 | C—Cl | C—Cl | C—Cl | C—H | H | CF3 | CF3 | H | CH3SO2CH2C(CH3)2 |
| 4-322 | C—Cl | C—Cl | C—Cl | C—H | H | CF3 | CF3 | H | (Methoxyimino)methyl |
| 4-323 | C—Cl | C—Cl | C—Cl | C—H | H | CF3 | CF3 | H | (Ethoxyimino)methyl |
| 4-324 | C—Cl | C—Cl | C—Cl | C—H | H | CF3 | CF3 | H | [1-(1,3-thiazol-4-yl)]CH2 |
| 4-325 | C—Cl | C—Cl | C—Cl | C—H | H | CF3 | CF3 | H | [1-(1-methyl-1H-pyrazol-5-yl]CH2 |
| 4-326 | C—Cl | C—Cl | C—Cl | C—H | H | CF3 | CF3 | H | 5-chloropyrimidin-2-yl |
| 4-327 | C—Cl | C—Cl | C—Cl | C—H | H | CF3 | CF3 | H | 5-bromopyrimidin-2-yl |
| 4-328 | C—Cl | C—Cl | C—Cl | C—H | H | CF3 | CF3 | H | 5-cyanopyrimidin-2-yl |
| 4-329 | C—Cl | C—Cl | C—Cl | C—H | H | CF3 | CF3 | H | CH3NHC(O)CH2 |
| 4-330 | C—Cl | C—Cl | C—Cl | C—H | H | CF3 | CF3 | H | CH3CH2NHC(O)CH2 |
| 4-331 | C—Cl | C—Cl | C—Cl | C—H | H | CF3 | CF3 | H | iso-PrNHC(O)CH2 |
| 4-332 | C—Cl | C—Cl | C—Cl | C—H | H | CF3 | CF3 | H | cyclo-PrNHC(O)CH2 |
| 4-333 | C—Cl | C—Cl | C—Cl | C—H | H | CF3 | CF3 | H | CF3CH2NHC(O)CH2 |
| 4-334 | C—Cl | C—Cl | C—Cl | C—H | H | CF3 | CF3 | H | CH3NHC(O)CH(CH3) |
| 4-335 | C—Cl | C—Cl | C—Cl | C—H | H | CF3 | CF3 | H | CH3CH2NHC(O)CH(CH3) |
| 4-336 | C—Cl | C—Cl | C—Cl | C—H | H | CF3 | CF3 | H | iso-PrNHC(O)CH(CH3) |
| 4-337 | C—Cl | C—Cl | C—Cl | C—H | H | CF3 | CF3 | H | cyclo-PrNHC(O)CH(CH3) |
| 4-338 | C—Cl | C—Cl | C—Cl | C—H | H | CF3 | CF3 | H | CF3CH2NHC(O)CH(CH3) |
| 4-339 | C—Cl | C—Cl | C—Cl | C—H | H | CF3 | CF3 | H | CH3NHC(O)C(CH3)2 |
| 4-340 | C—Cl | C—Cl | C—Cl | C—H | H | CF3 | CF3 | H | CH3CH2NHC(O)C(CH3)2 |
| 4-341 | C—Cl | C—Cl | C—Cl | C—H | H | CF3 | CF3 | H | iso-PrNHC(O)C(CH3)2 |
| 4-342 | C—Cl | C—Cl | C—Cl | C—H | H | CF3 | CF3 | H | cyclo-PrNHC(O)C(CH3)2 |
| 4-343 | C—Cl | C—Cl | C—Cl | C—H | H | CF3 | CF3 | H | CF3CH2NHC(O)C(CH3)2 |
| 4-344 | C—Cl | C—H | C—CF3 | C—H | H | CF3 | CF3 | H | CF3CH2 |
| 4-345 | C—Cl | C—H | C—CF3 | C—H | H | CF3 | CF3 | H | CH3OCH2 |
| 4-346 | C—Cl | C—H | C—CF3 | C—H | H | CF3 | CF3 | CH3CO | CH3OCH2 |
| 4-347 | C—Cl | C—H | C—CF3 | C—H | H | CF3 | CF3 | H | CH3CH2OCH2 |
| 4-348 | C—Cl | C—H | C—CF3 | C—H | H | CF3 | CF3 | H | CH3OCH2CH2 |
| 4-349 | C—Cl | C—H | C—CF3 | C—H | H | CF3 | CF3 | H | CH3CH2OCH2CH2 |
| 4-350 | C—Cl | C—H | C—CF3 | C—H | H | CF3 | CF3 | H | tetrahydrofuran-2-yl |
| 4-351 | C—Cl | C—H | C—CF3 | C—H | H | CF3 | CF3 | H | CH3SCH2CH2 |
| 4-352 | C—Cl | C—H | C—CF3 | C—H | H | CF3 | CF3 | H | CH3S(O)CH2CH2 |
| 4-353 | C—Cl | C—H | C—CF3 | C—H | H | CF3 | CF3 | H | CH3SO2CH2CH2 |
| 4-354 | C—Cl | C—H | C—CF3 | C—H | H | CF3 | CF3 | H | CH3SCH2CH(CH3) |
| 4-355 | C—Cl | C—H | C—CF3 | C—H | H | CF3 | CF3 | H | CH3S(O)CH2CH(CH3) |
| 4-356 | C—Cl | C—H | C—CF3 | C—H | H | CF3 | CF3 | H | CH3SO2CH2CH(CH3) |
| 4-357 | C—Cl | C—H | C—CF3 | C—H | H | CF3 | CF3 | H | CH3SCH2C(CH3)2 |
| 4-358 | C—Cl | C—H | C—CF3 | C—H | H | CF3 | CF3 | H | CH3S(O)CH2C(CH3)2 |
| 4-359 | C—Cl | C—H | C—CF3 | C—H | H | CF3 | CF3 | H | CH3SO2CH2C(CH3)2 |
| 4-360 | C—Cl | C—H | C—CF3 | C—H | H | CF3 | CF3 | H | (Methoxyimino)methyl |
| 4-361 | C—Cl | C—H | C—CF3 | C—H | H | CF3 | CF3 | H | (Ethoxyimino)methyl |
| 4-362 | C—Cl | C—H | C—CF3 | C—H | H | CF3 | CF3 | H | 2-PyridylCH2 |
| 4-363 | C—Cl | C—H | C—CF3 | C—H | H | CF3 | CF3 | H | [1-(1,3-thiazol-4-yl)]CH2 |
| 4-364 | C—Cl | C—H | C—CF3 | C—H | H | CF3 | CF3 | H | [1-(1-methyl-1H-pyrazol-5-yl]CH2 |
| 4-365 | C—Cl | C—H | C—CF3 | C—H | H | CF3 | CF3 | H | 5-chloropyrimidin-2-yl |
| 4-366 | C—Cl | C—H | C—CF3 | C—H | H | CF3 | CF3 | H | 5-bromopyrimidin-2-yl |

TABLE 4-continued

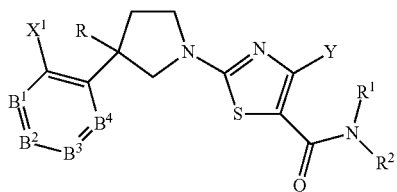

| Ex.-No. | B¹ | B² | B³ | B⁴ | X¹ | R | Y | R¹ | R² |
|---|---|---|---|---|---|---|---|---|---|
| 4-367 | C—Cl | C—H | C—CF3 | C—H | H | CF3 | CF3 | H | 5-cyanopyrimidin-2-yl |
| 4-368 | C—Cl | C—H | C—CF3 | C—H | H | CF3 | CF3 | H | CH3NHC(O)CH2 |
| 4-369 | C—Cl | C—H | C—CF3 | C—H | H | CF3 | CF3 | H | CH3CH2NHC(O)CH2 |
| 4-370 | C—Cl | C—H | C—CF3 | C—H | H | CF3 | CF3 | H | iso-PrNHC(O)CH2 |
| 4-371 | C—Cl | C—H | C—CF3 | C—H | H | CF3 | CF3 | H | cyclo-PrNHC(O)CH2 |
| 4-372 | C—Cl | C—H | C—CF3 | C—H | H | CF3 | CF3 | H | CF3CH2NHC(O)CH2 |
| 4-373 | C—Cl | C—H | C—CF3 | C—H | H | CF3 | CF3 | H | CH3NHC(O)CH(CH3) |
| 4-374 | C—Cl | C—H | C—CF3 | C—H | H | CF3 | CF3 | H | CH3CH2NHC(O)CH(CH3) |
| 4-375 | C—Cl | C—H | C—CF3 | C—H | H | CF3 | CF3 | H | iso-PrNHC(O)CH(CH3) |
| 4-376 | C—Cl | C—H | C—CF3 | C—H | H | CF3 | CF3 | H | cyclo-PrNHC(O)CH(CH3) |
| 4-377 | C—Cl | C—H | C—CF3 | C—H | H | CF3 | CF3 | H | CF3CH2NHC(O)CH(CH3) |
| 4-378 | C—Cl | C—H | C—CF3 | C—H | H | CF3 | CF3 | H | CH3NHC(O)C(CH3)2 |
| 4-379 | C—Cl | C—H | C—CF3 | C—H | H | CF3 | CF3 | H | CH3CH2NHC(O)C(CH3)2 |
| 4-380 | C—Cl | C—H | C—CF3 | C—H | H | CF3 | CF3 | H | iso-PrNHC(O)C(CH3)2 |
| 4-381 | C—Cl | C—H | C—CF3 | C—H | H | CF3 | CF3 | H | cyclo-PrNHC(O)C(CH3)2 |
| 4-382 | C—Cl | C—H | C—CF3 | C—H | H | CF3 | CF3 | H | CF3CH2NHC(O)C(CH3)2 |
| 4-383 | C—CF3 | C—H | C—CF3 | C—H | H | CF3 | CF3 | H | CH3OCH2 |
| 4-384 | C—CF3 | C—H | C—CF3 | C—H | H | CF3 | CF3 | CH3CO | CH3OCH2 |
| 4-385 | C—CF3 | C—H | C—CF3 | C—H | H | CF3 | CF3 | H | CH3CH2OCH2 |
| 4-386 | C—CF3 | C—H | C—CF3 | C—H | H | CF3 | CF3 | H | CH3OCH2CH2 |
| 4-387 | C—CF3 | C—H | C—CF3 | C—H | H | CF3 | CF3 | H | CH3CH2OCH2CH2 |
| 4-388 | C—CF3 | C—H | C—CF3 | C—H | H | CF3 | CF3 | H | tetrahydrofuran-2-yl |
| 4-389 | C—CF3 | C—H | C—CF3 | C—H | H | CF3 | CF3 | H | CH3SCH2CH2 |
| 4-390 | C—CF3 | C—H | C—CF3 | C—H | H | CF3 | CF3 | H | CH3S(O)CH2CH2 |
| 4-391 | C—CF3 | C—H | C—CF3 | C—H | H | CF3 | CF3 | H | CH3SO2CH2CH2 |
| 4-392 | C—CF3 | C—H | C—CF3 | C—H | H | CF3 | CF3 | H | CH3SCH2CH(CH3) |
| 4-393 | C—CF3 | C—H | C—CF3 | C—H | H | CF3 | CF3 | H | CH3S(O)CH2CH(CH3) |
| 4-394 | C—CF3 | C—H | C—CF3 | C—H | H | CF3 | CF3 | H | CH3SO2CH2CH(CH3) |
| 4-395 | C—CF3 | C—H | C—CF3 | C—H | H | CF3 | CF3 | H | CH3SCH2C(CH3)2 |
| 4-396 | C—CF3 | C—H | C—CF3 | C—H | H | CF3 | CF3 | H | CH3S(O)CH2C(CH3)2 |
| 4-397 | C—CF3 | C—H | C—CF3 | C—H | H | CF3 | CF3 | H | CH3SO2CH2C(CH3)2 |
| 4-398 | C—CF3 | C—H | C—CF3 | C—H | H | CF3 | CF3 | H | (Methoxyimino)methyl |
| 4-399 | C—CF3 | C—H | C—CF3 | C—H | H | CF3 | CF3 | H | (Ethoxyimino)methyl |
| 4-400 | C—CF3 | C—H | C—CF3 | C—H | H | CF3 | CF3 | H | [1-(1,3-thiazol-4-yl)]CH2 |
| 4-401 | C—CF3 | C—H | C—CF3 | C—H | H | CF3 | CF3 | H | [1-(1-methyl-1H-pyrazol-5-yl]CH2 |
| 4-402 | C—CF3 | C—H | C—CF3 | C—H | H | CF3 | CF3 | H | 5-chloropyrimidin-2-yl |
| 4-403 | C—CF3 | C—H | C—CF3 | C—H | H | CF3 | CF3 | H | 5-bromopyrimidin-2-yl |
| 4-404 | C—CF3 | C—H | C—CF3 | C—H | H | CF3 | CF3 | H | 5-cyanopyrimidin-2-yl |
| 4-405 | C—CF3 | C—H | C—CF3 | C—H | H | CF3 | CF3 | H | CH3NHC(O)CH2 |
| 4-406 | C—CF3 | C—H | C—CF3 | C—H | H | CF3 | CF3 | H | CH3CH2NHC(O)CH2 |
| 4-407 | C—CF3 | C—H | C—CF3 | C—H | H | CF3 | CF3 | H | iso-PrNHC(O)CH2 |
| 4-408 | C—CF3 | C—H | C—CF3 | C—H | H | CF3 | CF3 | H | cyclo-PrNHC(O)CH2 |
| 4-409 | C—CF3 | C—H | C—CF3 | C—H | H | CF3 | CF3 | H | CF3CH2NHC(O)CH2 |
| 4-410 | C—CF3 | C—H | C—CF3 | C—H | H | CF3 | CF3 | H | CH3NHC(O)CH(CH3) |
| 4-411 | C—CF3 | C—H | C—CF3 | C—H | H | CF3 | CF3 | H | CH3CH2NHC(O)CH(CH3) |
| 4-412 | C—CF3 | C—H | C—CF3 | C—H | H | CF3 | CF3 | H | iso-PrNHC(O)CH(CH3) |
| 4-413 | C—CF3 | C—H | C—CF3 | C—H | H | CF3 | CF3 | H | cyclo-PrNHC(O)CH(CH3) |
| 4-414 | C—CF3 | C—H | C—CF3 | C—H | H | CF3 | CF3 | H | CF3CH2NHC(O)CH(CH3) |
| 4-415 | C—CF3 | C—H | C—CF3 | C—H | H | CF3 | CF3 | H | CH3NHC(O)C(CH3)2 |
| 4-416 | C—CF3 | C—H | C—CF3 | C—H | H | CF3 | CF3 | H | CH3CH2NHC(O)C(CH3)2 |
| 4-417 | C—CF3 | C—H | C—CF3 | C—H | H | CF3 | CF3 | H | iso-PrNHC(O)C(CH3)2 |
| 4-418 | C—CF3 | C—H | C—CF3 | C—H | H | CF3 | CF3 | H | cyclo-PrNHC(O)C(CH3)2 |
| 4-419 | C—CF3 | C—H | C—CF3 | C—H | H | CF3 | CF3 | H | CF3CH2NHC(O)C(CH3)2 |
| 4-420 | C—Cl | C—Cl | C—CF3 | C—H | H | CF3 | CF3 | H | CH3OCH2 |
| 4-421 | C—Cl | C—Cl | C—CF3 | C—H | H | CF3 | CF3 | CH3CO | CH3OCH2 |
| 4-422 | C—Cl | C—Cl | C—CF3 | C—H | H | CF3 | CF3 | H | CH3CH2OCH2 |
| 4-423 | C—Cl | C—Cl | C—CF3 | C—H | H | CF3 | CF3 | H | CH3OCH2CH2 |
| 4-424 | C—Cl | C—Cl | C—CF3 | C—H | H | CF3 | CF3 | H | CH3CH2OCH2CH2 |
| 4-425 | C—Cl | C—Cl | C—CF3 | C—H | H | CF3 | CF3 | H | tetrahydrofuran-2-yl |
| 4-426 | C—Cl | C—Cl | C—CF3 | C—H | H | CF3 | CF3 | H | CH3SCH2CH2 |
| 4-427 | C—Cl | C—Cl | C—CF3 | C—H | H | CF3 | CF3 | H | CH3S(O)CH2CH2 |
| 4-428 | C—Cl | C—Cl | C—CF3 | C—H | H | CF3 | CF3 | H | CH3SO2CH2CH2 |
| 4-429 | C—Cl | C—Cl | C—CF3 | C—H | H | CF3 | CF3 | H | CH3SCH2CH(CH3) |
| 4-430 | C—Cl | C—Cl | C—CF3 | C—H | H | CF3 | CF3 | H | CH3S(O)CH2CH(CH3) |
| 4-431 | C—Cl | C—Cl | C—CF3 | C—H | H | CF3 | CF3 | H | CH3SO2CH2CH(CH3) |
| 4-432 | C—Cl | C—Cl | C—CF3 | C—H | H | CF3 | CF3 | H | CH3SCH2C(CH3)2 |
| 4-433 | C—Cl | C—Cl | C—CF3 | C—H | H | CF3 | CF3 | H | CH3S(O)CH2C(CH3)2 |
| 4-434 | C—Cl | C—Cl | C—CF3 | C—H | H | CF3 | CF3 | H | CH3SO2CH2C(CH3)2 |

TABLE 4-continued

| Ex.-No. | B¹ | B² | B³ | B⁴ | X¹ | R | Y | R¹ | R² |
|---|---|---|---|---|---|---|---|---|---|
| 4-435 | C—Cl | C—Cl | C—CF3 | C—H | H | CF3 | CF3 | H | (Methoxyimino)methyl |
| 4-436 | C—Cl | C—Cl | C—CF3 | C—H | H | CF3 | CF3 | H | (Ethoxyimino)methyl |
| 4-437 | C—Cl | C—Cl | C—CF3 | C—H | H | CF3 | CF3 | H | [1-(1,3-thiazol-4-yl)]CH2 |
| 4-438 | C—Cl | C—Cl | C—CF3 | C—H | H | CF3 | CF3 | H | [1-(1-methyl-1H-pyrazol-5-yl]CH2 |
| 4-439 | C—Cl | C—Cl | C—CF3 | C—H | H | CF3 | CF3 | H | 5-chloropyrimidin-2-yl |
| 4-440 | C—Cl | C—Cl | C—CF3 | C—H | H | CF3 | CF3 | H | 5-bromopyrimidin-2-yl |
| 4-441 | C—Cl | C—Cl | C—CF3 | C—H | H | CF3 | CF3 | H | 5-cyanopyrimidin-2-yl |
| 4-442 | C—Cl | C—Cl | C—CF3 | C—H | H | CF3 | CF3 | H | CH3NHC(O)CH2 |
| 4-443 | C—Cl | C—Cl | C—CF3 | C—H | H | CF3 | CF3 | H | CH3CH2NHC(O)CH2 |
| 4-444 | C—Cl | C—Cl | C—CF3 | C—H | H | CF3 | CF3 | H | iso-PrNHC(O)CH2 |
| 4-445 | C—Cl | C—Cl | C—CF3 | C—H | H | CF3 | CF3 | H | cyclo-PrNHC(O)CH2 |
| 4-446 | C—Cl | C—Cl | C—CF3 | C—H | H | CF3 | CF3 | H | CF3CH2NHC(O)CH2 |
| 4-447 | C—Cl | C—Cl | C—CF3 | C—H | H | CF3 | CF3 | H | CH3NHC(O)CH(CH3) |
| 4-448 | C—Cl | C—Cl | C—CF3 | C—H | H | CF3 | CF3 | H | CH3CH2NHC(O)CH(CH3) |
| 4-449 | C—Cl | C—Cl | C—CF3 | C—H | H | CF3 | CF3 | H | iso-PrNHC(O)CH(CH3) |
| 4-450 | C—Cl | C—Cl | C—CF3 | C—H | H | CF3 | CF3 | H | cyclo-PrNHC(O)CH(CH3) |
| 4-451 | C—Cl | C—Cl | C—CF3 | C—H | H | CF3 | CF3 | H | CF3CH2NHC(O)CH(CH3) |
| 4-452 | C—Cl | C—Cl | C—CF3 | C—H | H | CF3 | CF3 | H | CH3NHC(O)C(CH3)2 |
| 4-453 | C—Cl | C—Cl | C—CF3 | C—H | H | CF3 | CF3 | H | CH3CH2NHC(O)C(CH3)2 |
| 4-454 | C—Cl | C—Cl | C—CF3 | C—H | H | CF3 | CF3 | H | iso-PrNHC(O)C(CH3)2 |
| 4-455 | C—Cl | C—Cl | C—CF3 | C—H | H | CF3 | CF3 | H | cyclo-PrNHC(O)C(CH3)2 |
| 4-456 | C—Cl | C—Cl | C—CF3 | C—H | H | CF3 | CF3 | H | CF3CH2NHC(O)C(CH3)2 |
| 4-457 | C—Cl | N | C—Cl | C—H | H | CF3 | CF3 | H | CF3CH2 |
| 4-458 | C—Cl | N | C—Cl | C—H | H | CF3 | CF3 | H | CH3OCH2 |
| 4-459 | C—Cl | N | C—Cl | C—H | H | CF3 | CF3 | CH3CO | CH3OCH2 |
| 4-460 | C—Cl | N | C—Cl | C—H | H | CF3 | CF3 | H | CH3CH2OCH2 |
| 4-461 | C—Cl | N | C—Cl | C—H | H | CF3 | CF3 | H | CH3OCH2CH2 |
| 4-462 | C—Cl | N | C—Cl | C—H | H | CF3 | CF3 | H | CH3CH2OCH2CH2 |
| 4-463 | C—Cl | N | C—Cl | C—H | H | CF3 | CF3 | H | tetrahydrofuran-2-yl |
| 4-464 | C—Cl | N | C—Cl | C—H | H | CF3 | CF3 | H | CH3SCH2CH2 |
| 4-465 | C—Cl | N | C—Cl | C—H | H | CF3 | CF3 | H | CH3S(O)CH2CH2 |
| 4-466 | C—Cl | N | C—Cl | C—H | H | CF3 | CF3 | H | CH3SO2CH2CH2 |
| 4-467 | C—Cl | N | C—Cl | C—H | H | CF3 | CF3 | H | CH3SCH2CH(CH3) |
| 4-468 | C—Cl | N | C—Cl | C—H | H | CF3 | CF3 | H | CH3S(O)CH2CH(CH3) |
| 4-469 | C—Cl | N | C—Cl | C—H | H | CF3 | CF3 | H | CH3SO2CH2CH(CH3) |
| 4-470 | C—Cl | N | C—Cl | C—H | H | CF3 | CF3 | H | CH3SCH2C(CH3)2 |
| 4-471 | C—Cl | N | C—Cl | C—H | H | CF3 | CF3 | H | CH3S(O)CH2C(CH3)2 |
| 4-472 | C—Cl | N | C—Cl | C—H | H | CF3 | CF3 | H | CH3SO2CH2C(CH3)2 |
| 4-473 | C—Cl | N | C—Cl | C—H | H | CF3 | CF3 | H | (Methoxyimino)methyl |
| 4-474 | C—Cl | N | C—Cl | C—H | H | CF3 | CF3 | H | (Ethoxyimino)methyl |
| 4-475 | C—Cl | N | C—Cl | C—H | H | CF3 | CF3 | H | 2-PyridylCH2 |
| 4-476 | C—Cl | N | C—Cl | C—H | H | CF3 | CF3 | H | [1-(1,3-thiazol-4-yl)]CH2 |
| 4-477 | C—Cl | N | C—Cl | C—H | H | CF3 | CF3 | H | [1-(1-methyl-1H-pyrazol-5-yl]CH2 |
| 4-478 | C—Cl | N | C—Cl | C—H | H | CF3 | CF3 | H | 5-chloropyrimidin-2-yl |
| 4-479 | C—Cl | N | C—Cl | C—H | H | CF3 | CF3 | H | 5-bromopyrimidin-2-yl |
| 4-480 | C—Cl | N | C—Cl | C—H | H | CF3 | CF3 | H | 5-cyanopyrimidin-2-yl |
| 4-481 | C—Cl | N | C—Cl | C—H | H | CF3 | CF3 | H | CH3NHC(O)CH2 |
| 4-482 | C—Cl | N | C—Cl | C—H | H | CF3 | CF3 | H | CH3CH2NHC(O)CH2 |
| 4-483 | C—Cl | N | C—Cl | C—H | H | CF3 | CF3 | H | iso-PrNHC(O)CH2 |
| 4-484 | C—Cl | N | C—Cl | C—H | H | CF3 | CF3 | H | cyclo-PrNHC(O)CH2 |
| 4-485 | C—Cl | N | C—Cl | C—H | H | CF3 | CF3 | H | CF3CH2NHC(O)CH2 |
| 4-486 | C—Cl | N | C—Cl | C—H | H | CF3 | CF3 | H | CH3NHC(O)CH(CH3) |
| 4-487 | C—Cl | N | C—Cl | C—H | H | CF3 | CF3 | H | CH3CH2NHC(O)CH(CH3) |
| 4-488 | C—Cl | N | C—Cl | C—H | H | CF3 | CF3 | H | iso-PrNHC(O)CH(CH3) |
| 4-489 | C—Cl | N | C—Cl | C—H | H | CF3 | CF3 | H | cyclo-PrNHC(O)CH(CH3) |
| 4-490 | C—Cl | N | C—Cl | C—H | H | CF3 | CF3 | H | CF3CH2NHC(O)CH(CH3) |
| 4-491 | C—Cl | N | C—Cl | C—H | H | CF3 | CF3 | H | CH3NHC(O)C(CH3)2 |
| 4-492 | C—Cl | N | C—Cl | C—H | H | CF3 | CF3 | H | CH3CH2NHC(O)C(CH3)2 |
| 4-493 | C—Cl | N | C—Cl | C—H | H | CF3 | CF3 | H | iso-PrNHC(O)C(CH3)2 |
| 4-494 | C—Cl | N | C—Cl | C—H | H | CF3 | CF3 | H | cyclo-PrNHC(O)C(CH3)2 |
| 4-495 | C—Cl | N | C—Cl | C—H | H | CF3 | CF3 | H | CF3CH2NHC(O)C(CH3)2 |
| 4-496 | C—CF3 | N | C—H | C—H | H | CF3 | CF3 | H | CF3CH2 |
| 4-497 | C—CF3 | N | C—H | C—H | H | CF3 | CF3 | H | CH3OCH2 |
| 4-498 | C—CF3 | N | C—H | C—H | H | CF3 | CF3 | CH3CO | CH3OCH2 |
| 4-499 | C—CF3 | N | C—H | C—H | H | CF3 | CF3 | H | CH3CH2OCH2 |
| 4-500 | C—CF3 | N | C—H | C—H | H | CF3 | CF3 | H | CH3OCH2CH2 |
| 4-501 | C—CF3 | N | C—H | C—H | H | CF3 | CF3 | H | CH3CH2OCH2CH2 |
| 4-502 | C—CF3 | N | C—H | C—H | H | CF3 | CF3 | H | tetrahydrofuran-2-yl |

TABLE 4-continued

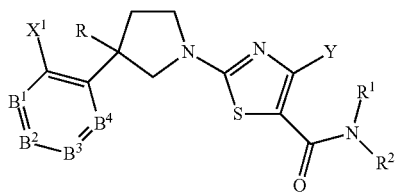

| Ex.-No. | B¹ | B² | B³ | B⁴ | X¹ | R | Y | R¹ | R² |
|---|---|---|---|---|---|---|---|---|---|
| 4-503 | C—CF3 | N | C—H | C—H | H | CF3 | CF3 | H | CH3SCH2CH2 |
| 4-504 | C—CF3 | N | C—H | C—H | H | CF3 | CF3 | H | CH3S(O)CH2CH2 |
| 4-505 | C—CF3 | N | C—H | C—H | H | CF3 | CF3 | H | CH3SO2CH2CH2 |
| 4-506 | C—CF3 | N | C—H | C—H | H | CF3 | CF3 | H | CH3SCH2CH(CH3) |
| 4-507 | C—CF3 | N | C—H | C—H | H | CF3 | CF3 | H | CH3S(O)CH2CH(CH3) |
| 4-508 | C—CF3 | N | C—H | C—H | H | CF3 | CF3 | H | CH3SO2CH2CH(CH3) |
| 4-509 | C—CF3 | N | C—H | C—H | H | CF3 | CF3 | H | CH3SCH2C(CH3)2 |
| 4-510 | C—CF3 | N | C—H | C—H | H | CF3 | CF3 | H | CH3S(O)CH2C(CH3)2 |
| 4-511 | C—CF3 | N | C—H | C—H | H | CF3 | CF3 | H | CH3SO2CH2C(CH3)2 |
| 4-512 | C—CF3 | N | C—H | C—H | H | CF3 | CF3 | H | (Methoxyimino)methyl |
| 4-513 | C—CF3 | N | C—H | C—H | H | CF3 | CF3 | H | (Ethoxyimino)methyl |
| 4-514 | C—CF3 | N | C—H | C—H | H | CF3 | CF3 | H | 2-PyridylCH2 |
| 4-515 | C—CF3 | N | C—H | C—H | H | CF3 | CF3 | H | [1-(1,3-thiazol-4-yl)]CH2 |
| 4-516 | C—CF3 | N | C—H | C—H | H | CF3 | CF3 | H | [1-(1-methyl-1H-pyrazol-5-yl]CH2 |
| 4-517 | C—CF3 | N | C—H | C—H | H | CF3 | CF3 | H | 5-chloropyrimidin-2-yl |
| 4-518 | C—CF3 | N | C—H | C—H | H | CF3 | CF3 | H | 5-bromopyrimidin-2-yl |
| 4-519 | C—CF3 | N | C—H | C—H | H | CF3 | CF3 | H | 5-cyanopyrimidin-2-yl |
| 4-520 | C—CF3 | N | C—H | C—H | H | CF3 | CF3 | H | CH3NHC(O)CH2 |
| 4-521 | C—CF3 | N | C—H | C—H | H | CF3 | CF3 | H | CH3CH2NHC(O)CH2 |
| 4-522 | C—CF3 | N | C—H | C—H | H | CF3 | CF3 | H | iso-PrNHC(O)CH2 |
| 4-523 | C—CF3 | N | C—H | C—H | H | CF3 | CF3 | H | cyclo-PrNHC(O)CH2 |
| 4-524 | C—CF3 | N | C—H | C—H | H | CF3 | CF3 | H | CF3CH2NHC(O)CH2 |
| 4-525 | C—CF3 | N | C—H | C—H | H | CF3 | CF3 | H | CH3NHC(O)CH(CH3) |
| 4-526 | C—CF3 | N | C—H | C—H | H | CF3 | CF3 | H | CH3CH2NHC(O)CH(CH3) |
| 4-527 | C—CF3 | N | C—H | C—H | H | CF3 | CF3 | H | iso-PrNHC(O)CH(CH3) |
| 4-528 | C—CF3 | N | C—H | C—H | H | CF3 | CF3 | H | cyclo-PrNHC(O)CH(CH3) |
| 4-529 | C—CF3 | N | C—H | C—H | H | CF3 | CF3 | H | CF3CH2NHC(O)CH(CH3) |
| 4-530 | C—CF3 | N | C—H | C—H | H | CF3 | CF3 | H | CH3NHC(O)C(CH3)2 |
| 4-531 | C—CF3 | N | C—H | C—H | H | CF3 | CF3 | H | CH3CH2NHC(O)C(CH3)2 |
| 4-532 | C—CF3 | N | C—H | C—H | H | CF3 | CF3 | H | iso-PrNHC(O)C(CH3)2 |
| 4-533 | C—CF3 | N | C—H | C—H | H | CF3 | CF3 | H | cyclo-PrNHC(O)C(CH3)2 |
| 4-534 | C—CF3 | N | C—H | C—H | H | CF3 | CF3 | H | CF3CH2NHC(O)C(CH3)2 |
| 4-535 | C—CF3 | N | C—CF3 | C—H | H | CF3 | CF3 | H | CF3CH2 |
| 4-536 | C—CF3 | N | C—CF3 | C—H | H | CF3 | CF3 | H | CH3OCH2 |
| 4-537 | C—CF3 | N | C—CF3 | C—H | H | CF3 | CF3 | CH3CO | CH3OCH2 |
| 4-538 | C—CF3 | N | C—CF3 | C—H | H | CF3 | CF3 | H | CH3CH2OCH2 |
| 4-539 | C—CF3 | N | C—CF3 | C—H | H | CF3 | CF3 | H | CH3OCH2CH2 |
| 4-540 | C—CF3 | N | C—CF3 | C—H | H | CF3 | CF3 | H | CH3CH2OCH2CH2 |
| 4-541 | C—CF3 | N | C—CF3 | C—H | H | CF3 | CF3 | H | tetrahydrofuran-2-yl |
| 4-542 | C—CF3 | N | C—CF3 | C—H | H | CF3 | CF3 | H | CH3SCH2CH2 |
| 4-543 | C—CF3 | N | C—CF3 | C—H | H | CF3 | CF3 | H | CH3S(O)CH2CH2 |
| 4-544 | C—CF3 | N | C—CF3 | C—H | H | CF3 | CF3 | H | CH3SO2CH2CH2 |
| 4-545 | C—CF3 | N | C—CF3 | C—H | H | CF3 | CF3 | H | CH3SCH2CH(CH3) |
| 4-546 | C—CF3 | N | C—CF3 | C—H | H | CF3 | CF3 | H | CH3S(O)CH2CH(CH3) |
| 4-547 | C—CF3 | N | C—CF3 | C—H | H | CF3 | CF3 | H | CH3SO2CH2CH(CH3) |
| 4-548 | C—CF3 | N | C—CF3 | C—H | H | CF3 | CF3 | H | CH3SCH2C(CH3)2 |
| 4-549 | C—CF3 | N | C—CF3 | C—H | H | CF3 | CF3 | H | CH3S(O)CH2C(CH3)2 |
| 4-550 | C—CF3 | N | C—CF3 | C—H | H | CF3 | CF3 | H | CH3SO2CH2C(CH3)2 |
| 4-551 | C—CF3 | N | C—CF3 | C—H | H | CF3 | CF3 | H | (Methoxyimino)methyl |
| 4-552 | C—CF3 | N | C—CF3 | C—H | H | CF3 | CF3 | H | (Ethoxyimino)methyl |
| 4-553 | C—CF3 | N | C—CF3 | C—H | H | CF3 | CF3 | H | 2-PyridylCH2 |
| 4-554 | C—CF3 | N | C—CF3 | C—H | H | CF3 | CF3 | H | [1-(1,3-thiazol-4-yl)]CH2 |
| 4-555 | C—CF3 | N | C—CF3 | C—H | H | CF3 | CF3 | H | [1-(1-methyl-1H-pyrazol-5-yl]CH2 |
| 4-556 | C—CF3 | N | C—CF3 | C—H | H | CF3 | CF3 | H | 5-chloropyrimidin-2-yl |
| 4-557 | C—CF3 | N | C—CF3 | C—H | H | CF3 | CF3 | H | 5-bromopyrimidin-2-yl |
| 4-558 | C—CF3 | N | C—CF3 | C—H | H | CF3 | CF3 | H | 5-cyanopyrimidin-2-yl |
| 4-559 | C—CF3 | N | C—CF3 | C—H | H | CF3 | CF3 | H | CH3NHC(O)CH2 |
| 4-560 | C—CF3 | N | C—CF3 | C—H | H | CF3 | CF3 | H | CH3CH2NHC(O)CH2 |
| 4-561 | C—CF3 | N | C—CF3 | C—H | H | CF3 | CF3 | H | iso-PrNHC(O)CH2 |
| 4-562 | C—CF3 | N | C—CF3 | C—H | H | CF3 | CF3 | H | cyclo-PrNHC(O)CH2 |
| 4-563 | C—CF3 | N | C—CF3 | C—H | H | CF3 | CF3 | H | CF3CH2NHC(O)CH2 |
| 4-564 | C—CF3 | N | C—CF3 | C—H | H | CF3 | CF3 | H | CH3NHC(O)CH(CH3) |
| 4-565 | C—CF3 | N | C—CF3 | C—H | H | CF3 | CF3 | H | CH3CH2NHC(O)CH(CH3) |
| 4-566 | C—CF3 | N | C—CF3 | C—H | H | CF3 | CF3 | H | iso-PrNHC(O)CH(CH3) |
| 4-567 | C—CF3 | N | C—CF3 | C—H | H | CF3 | CF3 | H | cyclo-PrNHC(O)CH(CH3) |
| 4-568 | C—CF3 | N | C—CF3 | C—H | H | CF3 | CF3 | H | CF3CH2NHC(O)CH(CH3) |
| 4-569 | C—CF3 | N | C—CF3 | C—H | H | CF3 | CF3 | H | CH3NHC(O)C(CH3)2 |
| 4-570 | C—CF3 | N | C—CF3 | C—H | H | CF3 | CF3 | H | CH3CH2NHC(O)C(CH3)2 |

TABLE 4-continued

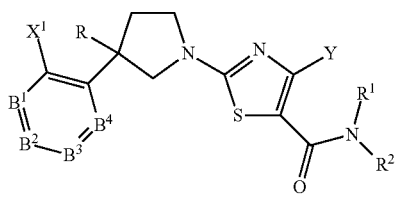

| Ex.-No. | B¹ | B² | B³ | B⁴ | X¹ | R | Y | R¹ | R² |
|---|---|---|---|---|---|---|---|---|---|
| 4-571 | C—CF3 | N | C—CF3 | C—H | H | CF3 | CF3 | H | iso-PrNHC(O)C(CH3)2 |
| 4-572 | C—CF3 | N | C—CF3 | C—H | H | CF3 | CF3 | H | cyclo-PrNHC(O)C(CH3)2 |
| 4-573 | C—CF3 | N | C—CF3 | C—H | H | CF3 | CF3 | H | CF3CH2NHC(O)C(CH3)2 |
| 4-574 | C—CF3 | C—H | C—CF3 | N | H | CF3 | CF3 | H | CF3CH2 |
| 4-575 | C—CF3 | C—H | C—CF3 | N | H | CF3 | CF3 | H | CH3OCH2 |
| 4-576 | C—CF3 | C—H | C—CF3 | N | H | CF3 | CF3 | CH3CO | CH3OCH2 |
| 4-577 | C—CF3 | C—H | C—CF3 | N | H | CF3 | CF3 | H | CH3CH2OCH2 |
| 4-578 | C—CF3 | C—H | C—CF3 | N | H | CF3 | CF3 | H | CH3OCH2CH2 |
| 4-579 | C—CF3 | C—H | C—CF3 | N | H | CF3 | CF3 | H | CH3CH2OCH2CH2 |
| 4-580 | C—CF3 | C—H | C—CF3 | N | H | CF3 | CF3 | H | tetrahydrofuran-2-yl |
| 4-581 | C—CF3 | C—H | C—CF3 | N | H | CF3 | CF3 | H | CH3SCH2CH2 |
| 4-582 | C—CF3 | C—H | C—CF3 | N | H | CF3 | CF3 | H | CH3S(O)CH2CH2 |
| 4-583 | C—CF3 | C—H | C—CF3 | N | H | CF3 | CF3 | H | CH3SO2CH2CH2 |
| 4-584 | C—CF3 | C—H | C—CF3 | N | H | CF3 | CF3 | H | CH3SCH2CH(CH3) |
| 4-585 | C—CF3 | C—H | C—CF3 | N | H | CF3 | CF3 | H | CH3S(O)CH2CH(CH3) |
| 4-586 | C—CF3 | C—H | C—CF3 | N | H | CF3 | CF3 | H | CH3SO2CH2CH(CH3) |
| 4-587 | C—CF3 | C—H | C—CF3 | N | H | CF3 | CF3 | H | CH3SCH2C(CH3)2 |
| 4-588 | C—CF3 | C—H | C—CF3 | N | H | CF3 | CF3 | H | CH3S(O)CH2C(CH3)2 |
| 4-589 | C—CF3 | C—H | C—CF3 | N | H | CF3 | CF3 | H | CH3SO2CH2C(CH3)2 |
| 4-590 | C—CF3 | C—H | C—CF3 | N | H | CF3 | CF3 | H | (Methoxyimino)methyl |
| 4-591 | C—CF3 | C—H | C—CF3 | N | H | CF3 | CF3 | H | (Ethoxyimino)methyl |
| 4-592 | C—CF3 | C—H | C—CF3 | N | H | CF3 | CF3 | H | 2-PyridylCH2 |
| 4-593 | C—CF3 | C—H | C—CF3 | N | H | CF3 | CF3 | H | [1-(1,3-thiazol-4-yl)]CH2 |
| 4-594 | C—CF3 | C—H | C—CF3 | N | H | CF3 | CF3 | H | [1-(1-methyl-1H-pyrazol-5-yl]CH2 |
| 4-595 | C—CF3 | C—H | C—CF3 | N | H | CF3 | CF3 | H | 5-chloropyrimidin-2-yl |
| 4-596 | C—CF3 | C—H | C—CF3 | N | H | CF3 | CF3 | H | 5-bromopyrimidin-2-yl |
| 4-597 | C—CF3 | C—H | C—CF3 | N | H | CF3 | CF3 | H | 5-cyanopyrimidin-2-yl |
| 4-598 | C—CF3 | C—H | C—CF3 | N | H | CF3 | CF3 | H | CH3NHC(O)CH2 |
| 4-599 | C—CF3 | C—H | C—CF3 | N | H | CF3 | CF3 | H | CH3CH2NHC(O)CH2 |
| 4-600 | C—CF3 | C—H | C—CF3 | N | H | CF3 | CF3 | H | iso-PrNHC(O)CH2 |
| 4-601 | C—CF3 | C—H | C—CF3 | N | H | CF3 | CF3 | H | cyclo-PrNHC(O)CH2 |
| 4-602 | C—CF3 | C—H | C—CF3 | N | H | CF3 | CF3 | H | CF3CH2NHC(O)CH2 |
| 4-603 | C—CF3 | C—H | C—CF3 | N | H | CF3 | CF3 | H | CH3NHC(O)CH(CH3) |
| 4-604 | C—CF3 | C—H | C—CF3 | N | H | CF3 | CF3 | H | CH3CH2NHC(O)CH(CH3) |
| 4-605 | C—CF3 | C—H | C—CF3 | N | H | CF3 | CF3 | H | iso-PrNHC(O)CH(CH3) |
| 4-606 | C—CF3 | C—H | C—CF3 | N | H | CF3 | CF3 | H | cyclo-PrNHC(O)CH(CH3) |
| 4-607 | C—CF3 | C—H | C—CF3 | N | H | CF3 | CF3 | H | CF3CH2NHC(O)CH(CH3) |
| 4-608 | C—CF3 | C—H | C—CF3 | N | H | CF3 | CF3 | H | CH3NHC(O)C(CH3)2 |
| 4-609 | C—CF3 | C—H | C—CF3 | N | H | CF3 | CF3 | H | CH3CH2NHC(O)C(CH3)2 |
| 4-610 | C—CF3 | C—H | C—CF3 | N | H | CF3 | CF3 | H | iso-PrNHC(O)C(CH3)2 |
| 4-611 | C—CF3 | C—H | C—CF3 | N | H | CF3 | CF3 | H | cyclo-PrNHC(O)C(CH3)2 |
| 4-612 | C—CF3 | C—H | C—CF3 | N | H | CF3 | CF3 | H | CF3CH2NHC(O)C(CH3)2 |
| 4-613 | C—Cl | C—H | C—Cl | C—H | H | CF3 | CF3 | H | (pyrimidin-2-yl)CH2 |
| 4-614 | C—Cl | C—H | C—Cl | C—H | H | CF3 | CF3 | H | (pyridin-2-yl)CH2NHC(O)CH2 |
| 4-615 | C—Cl | C—H | C—Cl | C—H | H | CF3 | CF3 | H | ClCH2CH2NHC(O)CH2 |
| 4-616 | C—Cl | C—H | C—Cl | C—H | H | CF3 | CF3 | H | CH3OCO |
| 4-617 | C—Cl | C—H | C—Cl | C—H | H | CF3 | CF3 | (dimethylamino)methylene | prop-2-yn-1-yl |
| 4-618 | C—Cl | C—H | C—Cl | C—H | H | CF3 | CF3 | H | |

TABLE 5

| Ex.-No. | B¹ | B² | B³ | B⁴ | X¹ | R | Y | R³ | R⁴ | R⁵ | R⁶ | l |
|---|---|---|---|---|---|---|---|---|---|---|---|---|
| 5-1 | C—Cl | C—H | C—Cl | C—H | H | CF3 | CF3 | H | H | H | H | 1 |
| 5-2 | C—Cl | C—H | C—Cl | C—H | H | CF3 | CF3 | H | H | H | HCO | 1 |
| 5-3 | C—Cl | C—H | C—Cl | C—H | H | CF3 | CF3 | H | H | H | CH3CO | 1 |
| 5-4 | C—Cl | C—H | C—Cl | C—H | H | CF3 | CF3 | H | H | H | CH3CH2CO | 1 |
| 5-5 | C—Cl | C—H | C—Cl | C—H | H | CF3 | CF3 | H | H | H | n-PrCO | 1 |
| 5-6 | C—Cl | C—H | C—Cl | C—H | H | CF3 | CF3 | H | H | H | iso-PrCO | 1 |
| 5-7 | C—Cl | C—H | C—Cl | C—H | H | CF3 | CF3 | H | H | H | cyclo-PrCO | 1 |
| 5-8 | C—Cl | C—H | C—Cl | C—H | H | CF3 | CF3 | H | H | H | n-BuCO | 1 |
| 5-9 | C—Cl | C—H | C—Cl | C—H | H | CF3 | CF3 | H | H | H | tert-BuCO | 1 |
| 5-10 | C—Cl | C—H | C—Cl | C—H | H | CF3 | CF3 | H | H | H | iso-BuCO | 1 |
| 5-11 | C—Cl | C—H | C—Cl | C—H | H | CF3 | CF3 | H | H | H | cyclo-BuCO | 1 |
| 5-12 | C—Cl | C—H | C—Cl | C—H | H | CF3 | CF3 | H | H | H | (CH3)3CCH2CO | 1 |
| 5-13 | C—Cl | C—H | C—Cl | C—H | H | CF3 | CF3 | H | H | H | cyclo-PenCO | 1 |
| 5-14 | C—Cl | C—H | C—Cl | C—H | H | CF3 | CF3 | H | H | H | cyclo-HexCO | 1 |
| 5-15 | C—Cl | C—H | C—Cl | C—H | H | CF3 | CF3 | H | H | H | cyclo-PrCH2CO | 1 |
| 5-16 | C—Cl | C—H | C—Cl | C—H | H | CF3 | CF3 | H | H | H | CF3CO | 1 |
| 5-17 | C—Cl | C—H | C—Cl | C—H | H | CF3 | CF3 | H | H | H | CCl3CO | 1 |
| 5-18 | C—Cl | C—H | C—Cl | C—H | H | CF3 | CF3 | H | H | H | ClCH2CO | 1 |
| 5-19 | C—Cl | C—H | C—Cl | C—H | H | CF3 | CF3 | H | H | H | CF2ClCO | 1 |
| 5-20 | C—Cl | C—H | C—Cl | C—H | H | CF3 | CF3 | H | H | H | ClCH2CH2CO | 1 |
| 5-21 | C—Cl | C—H | C—Cl | C—H | H | CF3 | CF3 | H | H | H | HCF2CF2CO | 1 |
| 5-22 | C—Cl | C—H | C—Cl | C—H | H | CF3 | CF3 | H | H | H | CF3CH2CO | 1 |
| 5-23 | C—Cl | C—H | C—Cl | C—H | H | CF3 | CF3 | H | H | H | (CF3)2CHCO | 1 |
| 5-24 | C—Cl | C—H | C—Cl | C—H | H | CF3 | CF3 | H | H | H | HCF2CO | 1 |
| 5-25 | C—Cl | C—H | C—Cl | C—H | H | CF3 | CF3 | H | H | H | ClCH2CO | 1 |
| 5-26 | C—Cl | C—H | C—Cl | C—H | H | CF3 | CF3 | H | H | H | 1-methylcyclopropyl-CO | 1 |
| 5-27 | C—Cl | C—H | C—Cl | C—H | H | CF3 | CF3 | H | H | H | 2,2-dichlorocyclopropyl-CO | 1 |
| 5-28 | C—Cl | C—H | C—Cl | C—H | H | CF3 | CF3 | H | H | H | 2,2-difluorocyclopropyl-CO | 1 |
| 5-29 | C—Cl | C—H | C—Cl | C—H | H | CF3 | CF3 | H | H | H | 2-fluorocyclopropyl-CO | 1 |
| 5-30 | C—Cl | C—H | C—Cl | C—H | H | CF3 | CF3 | H | H | H | 2-methylcyclopropyl-CO | 1 |
| 5-31 | C—Cl | C—H | C—Cl | C—H | H | CF3 | CF3 | H | H | H | 2-cyanocyclopropyl-CO | 1 |
| 5-32 | C—Cl | C—H | C—Cl | C—H | H | CF3 | CF3 | H | H | H | CH2=CH—CO | 1 |
| 5-33 | C—Cl | C—H | C—Cl | C—H | H | CF3 | CF3 | H | H | H | CH3CH=CH—CO | 1 |
| 5-34 | C—Cl | C—H | C—Cl | C—H | H | CF3 | CF3 | H | H | H | CH2=C(CH3)—CO | 1 |
| 5-35 | C—Cl | C—H | C—Cl | C—H | H | CF3 | CF3 | H | H | H | CH3CH=C(CH3)—CO | 1 |
| 5-36 | C—Cl | C—H | C—Cl | C—H | H | CF3 | CF3 | H | H | H | (CH3)2C=CH—CO | 1 |
| 5-37 | C—Cl | C—H | C—Cl | C—H | H | CF3 | CF3 | H | H | H | CH2=C(Cl)—CO | 1 |
| 5-38 | C—Cl | C—H | C—Cl | C—H | H | CF3 | CF3 | H | H | H | ClCH=C(CH3)—CO | 1 |
| 5-39 | C—Cl | C—H | C—Cl | C—H | H | CF3 | CF3 | H | H | H | CH2=CHCH2—CO | 1 |
| 5-40 | C—Cl | C—H | C—Cl | C—H | H | CF3 | CF3 | H | H | H | HCC—CO | 1 |
| 5-41 | C—Cl | C—H | C—Cl | C—H | H | CF3 | CF3 | H | H | H | CH3CC—CO | 1 |
| 5-42 | C—Cl | C—H | C—Cl | C—H | H | CF3 | CF3 | H | H | H | NCCH2—CO | 1 |
| 5-43 | C—Cl | C—H | C—Cl | C—H | H | CF3 | CF3 | H | H | H | CH3OCH2CO | 1 |
| 5-44 | C—Cl | C—H | C—Cl | C—H | H | CF3 | CF3 | H | H | H | C2H5OCH2—CO | 1 |
| 5-45 | C—Cl | C—H | C—Cl | C—H | H | CF3 | CF3 | H | H | H | CH3SCH2CO | 1 |
| 5-46 | C—Cl | C—H | C—Cl | C—H | H | CF3 | CF3 | H | H | H | CH3O(CO)CH2—CO | 1 |
| 5-47 | C—Cl | C—H | C—Cl | C—H | H | CF3 | CF3 | H | H | H | CH3(CO)OCH2—CO | 1 |

TABLE 5-continued

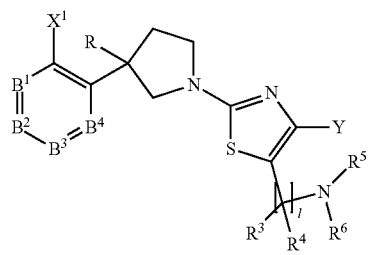

| Ex.-No. | B¹ | B² | B³ | B⁴ | X¹ | R | Y | R³ | R⁴ | R⁵ | R⁶ | 1 |
|---|---|---|---|---|---|---|---|---|---|---|---|---|
| 5-48 | C—Cl | C—H | C—Cl | C—H | H | CF3 | CF3 | H | H | H | CH3O(CO)—CO | 1 |
| 5-49 | C—Cl | C—H | C—Cl | C—H | H | CF3 | CF3 | H | H | H | CF3O(CO)—CO | 1 |
| 5-50 | C—Cl | C—H | C—Cl | C—H | H | CF3 | CF3 | H | H | H | CH3(CO)CH2—CO | 1 |
| 5-51 | C—Cl | C—H | C—Cl | C—H | H | CF3 | CF3 | H | H | H | (CH3)2NCH2—CO | 1 |
| 5-52 | C—Cl | C—H | C—Cl | C—H | H | CF3 | CF3 | H | H | H | PhCO | 1 |
| 5-53 | C—Cl | C—H | C—Cl | C—H | H | CF3 | CF3 | H | H | H | PhCH2CO | 1 |
| 5-54 | C—Cl | C—H | C—Cl | C—H | H | CF3 | CF3 | H | H | H | 2-py-CO | 1 |
| 5-55 | C—Cl | C—H | C—Cl | C—H | H | CF3 | CF3 | H | H | H | 3-py-CO | 1 |
| 5-56 | C—Cl | C—H | C—Cl | C—H | H | CF3 | CF3 | H | H | H | 4-py-CO | 1 |
| 5-57 | C—Cl | C—H | C—Cl | C—H | H | CF3 | CF3 | H | H | H | 6-Cl-pyridin-3-yl-CO | 1 |
| 5-58 | C—Cl | C—H | C—Cl | C—H | H | CF3 | CF3 | H | H | H | 2-F—PhCO | 1 |
| 5-59 | C—Cl | C—H | C—Cl | C—H | H | CF3 | CF3 | H | H | H | 3-F—PhCO | 1 |
| 5-60 | C—Cl | C—H | C—Cl | C—H | H | CF3 | CF3 | H | H | H | 4-F—PhCO | 1 |
| 5-61 | C—Cl | C—H | C—Cl | C—H | H | CF3 | CF3 | H | H | H | 2-Cl—PhCO | 1 |
| 5-62 | C—Cl | C—H | C—Cl | C—H | H | CF3 | CF3 | H | H | H | 3-Cl—PhCO | 1 |
| 5-63 | C—Cl | C—H | C—Cl | C—H | H | CF3 | CF3 | H | H | H | 4-Cl—PhCO | 1 |
| 5-64 | C—Cl | C—H | C—Cl | C—H | H | CF3 | CF3 | H | H | H | 2-Br—PhCO | 1 |
| 5-65 | C—Cl | C—H | C—Cl | C—H | H | CF3 | CF3 | H | H | H | 2-CF3—PhCO | 1 |
| 5-66 | C—Cl | C—H | C—Cl | C—H | H | CF3 | CF3 | H | H | H | 2-CH3—PhCO | 1 |
| 5-67 | C—Cl | C—H | C—Cl | C—H | H | CF3 | CF3 | H | H | H | furan-2-yl-CO | 1 |
| 5-68 | C—Cl | C—H | C—Cl | C—H | H | CF3 | CF3 | H | H | H | furan-3-yl-CO | 1 |
| 5-69 | C—Cl | C—H | C—Cl | C—H | H | CF3 | CF3 | H | H | H | thiophen-2-yl-CO | 1 |
| 5-70 | C—Cl | C—H | C—Cl | C—H | H | CF3 | CF3 | H | H | H | pyrrol-2-yl-CO | 1 |
| 5-71 | C—Cl | C—H | C—Cl | C—H | H | CF3 | CF3 | H | H | H | 3-CF3-pyrazol-4-yl-CO | 1 |
| 5-72 | C—Cl | C—H | C—Cl | C—H | H | CF3 | CF3 | H | H | H | 3-CF3-pyridin-2-yl-CO | 1 |
| 5-73 | C—Cl | C—H | C—Cl | C—H | H | CF3 | CF3 | H | H | H | pyridin-3-yl-CH2-CO | 1 |

TABLE 5-continued

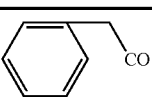

| Ex.-No. | B¹ | B² | B³ | B⁴ | X¹ | R | Y | R³ | R⁴ | R⁵ | R⁶ | 1 |
|---|---|---|---|---|---|---|---|---|---|---|---|---|
| 5-74 | C—Cl | C—H | C—Cl | C—H | H | CF3 | CF3 | H | H | H | CO | 1 |
| 5-75 | C—Cl | C—H | C—Cl | C—H | H | CF3 | CF3 | H | H | CH3 | CH3CO | 1 |
| 5-76 | C—Cl | C—H | C—Cl | C—H | H | CF3 | CF3 | H | H | CH3 | cyclo-PrCO | 1 |
| 5-77 | C—Cl | C—H | C—Cl | C—H | H | CF3 | CF3 | H | H | H | CH3NHCO | 1 |
| 5-78 | C—Cl | C—H | C—Cl | C—H | H | CF3 | CF3 | H | H | H | CH3CH2NHCO | 1 |
| 5-79 | C—Cl | C—H | C—Cl | C—H | H | CF3 | CF3 | H | H | H | CF3CH2NHCO | 1 |
| 5-80 | C—Cl | C—H | C—Cl | C—H | H | CF3 | CF3 | H | H | H | n-PrNHCO | 1 |
| 5-81 | C—Cl | C—H | C—Cl | C—H | H | CF3 | CF3 | H | H | H | iso-PrNHCO | 1 |
| 5-82 | C—Cl | C—H | C—Cl | C—H | H | CF3 | CF3 | H | H | H | cyclo-PrNHCO | 1 |
| 5-83 | C—Cl | C—H | C—Cl | C—H | H | CF3 | CF3 | H | H | H | n-BuNHCO | 1 |
| 5-84 | C—Cl | C—H | C—Cl | C—H | H | CF3 | CF3 | H | H | H | tert-BuNHCO | 1 |
| 5-85 | C—Cl | C—H | C—Cl | C—H | H | CF3 | CF3 | H | H | H | cyclo-BuNHCO | 1 |
| 5-86 | C—Cl | C—H | C—Cl | C—H | H | CF3 | CF3 | H | H | H | cyclo-PenNHCO | 1 |
| 5-87 | C—Cl | C—H | C—Cl | C—H | H | CF3 | CF3 | H | H | H | cyclo-HexNHCO | 1 |
| 5-88 | C—Cl | C—H | C—Cl | C—H | H | CF3 | CF3 | H | H | H | CH2=CHCH2NHCO | 1 |
| 5-89 | C—Cl | C—H | C—Cl | C—H | H | CF3 | CF3 | H | H | H | HCCCH2NHCO | 1 |
| 5-90 | C—Cl | C—H | C—Cl | C—H | H | CF3 | CF3 | H | H | H | cyclo-PrCH2NHCO | 1 |
| 5-91 | C—Cl | C—H | C—Cl | C—H | H | CF3 | CF3 | H | H | H | NCCH2NHCO | 1 |
| 5-92 | C—Cl | C—H | C—Cl | C—H | H | CF3 | CF3 | H | H | H | CF3(CH3)CHNHCO | 1 |
| 5-93 | C—Cl | C—H | C—Cl | C—H | H | CF3 | CF3 | H | H | H | CF3(CH3)2CNCO | 1 |
| 5-95 | C—Cl | C—H | C—Cl | C—H | H | CF3 | CF3 | H | H | H | FCH2CH2NHCO | 1 |
| 5-96 | C—Cl | C—H | C—Cl | C—H | H | CF3 | CF3 | H | H | H | CF3CH2CH2NHCO | 1 |
| 5-97 | C—Cl | C—H | C—Cl | C—H | H | CF3 | CF3 | H | H | H | HCF2CF2CH2NHCO | 1 |
| 5-98 | C—Cl | C—H | C—Cl | C—H | H | CF3 | CF3 | H | H | H | F—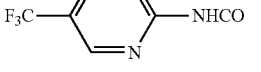—NHCO | 1 |
| 5-99 | C—Cl | C—H | C—Cl | C—H | H | CF3 | CF3 | H | H | H | 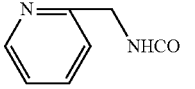 | 1 |
| 5-100 | C—Cl | C—H | C—Cl | C—H | H | CF3 | CF3 | H | H | H | EtO2CCH2NHCO | 1 |
| 5-101 | C—Cl | C—H | C—Cl | C—H | H | CF3 | CF3 | H | H | H | 2-CF3—PhNHCO | 1 |
| 5-102 | C—Cl | C—H | C—Cl | C—H | H | CF3 | CF3 | H | H | H | 3-CF3—PhNHCO | 1 |
| 5-103 | C—Cl | C—H | C—Cl | C—H | H | CF3 | CF3 | H | H | H | 4-CF3—PhNHCO | 1 |
| 5-104 | C—Cl | C—H | C—Cl | C—H | H | CF3 | CF3 | H | H | H | 2-py-NHCO | 1 |
| 5-105 | C—Cl | C—H | C—Cl | C—H | H | CF3 | CF3 | H | H | H | 3-py-NHCO | 1 |
| 5-106 | C—Cl | C—H | C—Cl | C—H | H | CF3 | CF3 | H | H | H | 4-py-NHCO | 1 |
| 5-107 | C—Cl | C—H | C—Cl | C—H | H | CF3 | CF3 | H | H | H | F3C-pyridyl-NHCO | 1 |
| 5-108 | C—Cl | C—H | C—Cl | C—H | H | CF3 | CF3 | H | H | H | F3C-pyridyl-NHCO | 1 |
| 5-109 | C—Cl | C—H | C—Cl | C—H | H | CF3 | CF3 | H | H | H | PhCH2HNCO | 1 |
| 5-110 | C—Cl | C—H | C—Cl | C—H | H | CF3 | CF3 | H | H | H | pyridyl-CH2-NHCO | 1 |
| 5-111 | C—Cl | C—H | C—Cl | C—H | H | CF3 | CF3 | H | H | H | (CH3)2NCO | 1 |

TABLE 5-continued

| Ex.-No. | B¹ | B² | B³ | B⁴ | X¹ | R | Y | R³ | R⁴ | R⁵ | R⁶ | l |
|---|---|---|---|---|---|---|---|---|---|---|---|---|
| 5-112 | C—Cl | C—H | C—Cl | C—H | H | CF3 | CF3 | H | H | CH3 | CH3NHCO | 1 |
| 5-113 | C—Cl | C—H | C—Cl | C—H | H | CF3 | CF3 | H | H | CH3 | CH3CH2NHCO | 1 |
| 5-114 | C—Cl | C—H | C—Cl | C—H | H | CF3 | CF3 | H | H | CH3 | cyclo-PrNHCO | 1 |
| 5-115 | C—Cl | C—H | C—Cl | C—H | H | CF3 | CF3 | H | H | H | pyrrolidineCO | 1 |
| 5-116 | C—Cl | C—H | C—Cl | C—H | H | CF3 | CF3 | H | H | H | piperidineCO | 1 |
| 5-117 | C—Cl | C—H | C—Cl | C—H | H | CF3 | CF3 | H | H | H | morpholineCO | 1 |
| 5-118 | C—Cl | C—H | C—Cl | C—H | H | CF3 | CF3 | H | H | H | CH3OCO | 1 |
| 5-119 | C—Cl | C—H | C—Cl | C—H | H | CF3 | CF3 | H | H | H | CH3CH2OCO | 1 |
| 5-120 | C—Cl | C—H | C—Cl | C—H | H | CF3 | CF3 | H | H | H | n-PrOCO | 1 |
| 5-121 | C—Cl | C—H | C—Cl | C—H | H | CF3 | CF3 | H | H | H | cyclo-PrOCO | 1 |
| 5-122 | C—Cl | C—H | C—Cl | C—H | H | CF3 | CF3 | H | H | H | CF3CH2OCO | 1 |
| 5-123 | C—Cl | C—H | C—Cl | C—H | H | CF3 | CF3 | H | H | H | CH2=CHCH2OCO | 1 |
| 5-124 | C—Cl | C—H | C—Cl | C—H | H | CF3 | CF3 | H | H | H | HCCCH2OCO | 1 |
| 5-125 | C—Cl | C—H | C—Cl | C—H | H | CF3 | CF3 | H | H | H | PhOCO | 1 |
| 5-126 | C—Cl | C—H | C—Cl | C—H | H | CF3 | CF3 | H | H | H | PhCH2OCO | 1 |
| 5-127 | C—Cl | C—H | C—Cl | C—H | H | CF3 | CF3 | H | H | H | tert-BuOCO | 1 |
| 5-128 | C—Cl | C—H | C—Cl | C—H | H | CF3 | CF3 | H | H | CH3 | tert-BuOCO | 1 |
| 5-129 | C—Cl | C—H | C—Cl | C—H | H | CF3 | CF3 | H | H | H | CH3SO2 | 1 |
| 5-130 | C—Cl | C—H | C—Cl | C—H | H | CF3 | CF3 | H | H | H | CH3CH2SO2 | 1 |
| 5-131 | C—Cl | C—H | C—Cl | C—H | H | CF3 | CF3 | H | H | H | CF3SO2 | 1 |
| 5-132 | C—Cl | C—H | C—Cl | C—H | H | CF3 | CF3 | H | H | H | CF3CH2SO2 | 1 |
| 5-133 | C—Cl | C—H | C—Cl | C—H | H | CF3 | CF3 | H | H | H | PhSO2 | 1 |
| 5-134 | C—Cl | C—H | C—Cl | C—H | H | CF3 | CF3 | H | H | H | CH3NHCONHSO2 | 1 |
| 5-135 | C—Cl | C—H | C—Cl | C—H | H | CF3 | CF3 | H | H | H | (CH3)2NCONHSO2 | 1 |
| 5-136 | C—Cl | C—H | C—Cl | C—H | H | CF3 | CF3 | H | H | H | CH3CS | 1 |
| 5-137 | C—Cl | C—H | C—Cl | C—H | H | CF3 | CF3 | H | H | H | CH3CH2CS | 1 |
| 5-138 | C—Cl | C—H | C—Cl | C—H | H | CF3 | CF3 | H | H | H | cyclo-PrCS | 1 |
| 5-139 | C—Cl | C—H | C—Cl | C—H | H | CF3 | CF3 | H | H | H | CF3CH2CS | 1 |
| 5-140 | C—Cl | C—Cl | C—Cl | C—H | H | CF3 | CF3 | H | H | H | H | 1 |
| 5-141 | C—Cl | C—Cl | C—Cl | C—H | H | CF3 | CF3 | H | H | H | CH3CO | 1 |
| 5-142 | C—Cl | C—Cl | C—Cl | C—H | H | CF3 | CF3 | H | H | H | CH3CH2CO | 1 |
| 5-143 | C—Cl | C—Cl | C—Cl | C—H | H | CF3 | CF3 | H | H | H | cyclo-PrCO | 1 |
| 5-144 | C—Cl | C—Cl | C—Cl | C—H | H | CF3 | CF3 | H | H | H | CF3CH2CO | 1 |
| 5-145 | C—Cl | C—Cl | C—Cl | C—H | H | CF3 | CF3 | H | H | H | CH3CH2NHCO | 1 |
| 5-146 | C—CF3 | C—H | C—CF3 | C—H | H | CF3 | CF3 | H | H | H | H | 1 |
| 5-147 | C—CF3 | C—H | C—CF3 | C—H | H | CF3 | CF3 | H | H | H | CH3CO | 1 |
| 5-148 | C—CF3 | C—H | C—CF3 | C—H | H | CF3 | CF3 | H | H | H | CH3CH2CO | 1 |
| 5-149 | C—CF3 | C—H | C—CF3 | C—H | H | CF3 | CF3 | H | H | H | cyclo-PrCO | 1 |
| 5-150 | C—CF3 | C—H | C—CF3 | C—H | H | CF3 | CF3 | H | H | H | CF3CH2CO | 1 |
| 5-151 | C—CF3 | C—H | C—CF3 | C—H | H | CF3 | CF3 | H | H | H | CH3CH2NHCO | 1 |
| 5-152 | C—Cl | C—Cl | C—CF3 | C—H | H | CF3 | CF3 | H | H | H | CH3CO | 1 |
| 5-153 | C—Cl | C—Cl | C—CF3 | C—H | H | CF3 | CF3 | H | H | H | CH3CH2CO | 1 |
| 5-154 | C—Cl | C—Cl | C—CF3 | C—H | H | CF3 | CF3 | H | H | H | cyclo-PrCO | 1 |
| 5-155 | C—Cl | C—Cl | C—CF3 | C—H | H | CF3 | CF3 | H | H | H | CF3CH2CO | 1 |
| 5-156 | C—Cl | C—Cl | C—CF3 | C—H | H | CF3 | CF3 | H | H | H | CH3CH2NHCO | 1 |
| 5-157 | C—Br | C—H | C—Br | C—H | H | CF3 | CF3 | H | H | H | CH3CO | 1 |
| 5-158 | C—Br | C—H | C—Br | C—H | H | CF3 | CF3 | H | H | H | CH3CH2CO | 1 |
| 5-159 | C—Br | C—H | C—Br | C—H | H | CF3 | CF3 | H | H | H | cyclo-PrCO | 1 |
| 5-160 | C—Br | C—H | C—Br | C—H | H | CF3 | CF3 | H | H | H | CF3CH2CO | 1 |
| 5-161 | C—Br | C—H | C—Br | C—H | H | CF3 | CF3 | H | H | H | CH3CH2NHCO | 1 |
| 5-162 | C—Cl | C—H | C—Cl | C—H | H | CF3 | H | H | H | H | CH3CO | 1 |
| 5-163 | C—Cl | C—H | C—Cl | C—H | H | CF3 | H | H | H | H | CH3CH2CO | 1 |
| 5-164 | C—Cl | C—H | C—Cl | C—H | H | CF3 | H | H | H | H | cyclo-PrCO | 1 |
| 5-165 | C—Cl | C—H | C—Cl | C—H | H | CF3 | H | H | H | H | CF3CH2CO | 1 |
| 5-166 | C—Cl | C—H | C—Cl | C—H | H | CF3 | H | H | H | H | CH3CH2NHCO | 1 |
| 5-167 | C—Cl | C—Cl | C—Cl | C—H | H | CF3 | H | H | H | H | CH3CO | 1 |
| 5-168 | C—Cl | C—Cl | C—Cl | C—H | H | CF3 | H | H | H | H | CH3CH2CO | 1 |
| 5-169 | C—Cl | C—Cl | C—Cl | C—H | H | CF3 | H | H | H | H | cyclo-PrCO | 1 |
| 5-170 | C—Cl | C—Cl | C—Cl | C—H | H | CF3 | H | H | H | H | CF3CH2CO | 1 |
| 5-171 | C—Cl | C—Cl | C—Cl | C—H | H | CF3 | H | H | H | H | CH3CH2NHCO | 1 |
| 5-172 | C—CF3 | C—H | C—CF3 | C—H | H | CF3 | H | H | H | H | CH3CO | 1 |
| 5-173 | C—CF3 | C—H | C—CF3 | C—H | H | CF3 | H | H | H | H | CH3CH2CO | 1 |
| 5-174 | C—CF3 | C—H | C—CF3 | C—H | H | CF3 | H | H | H | H | cyclo-PrCO | 1 |
| 5-175 | C—CF3 | C—H | C—CF3 | C—H | H | CF3 | H | H | H | H | CF3CH2CO | 1 |
| 5-176 | C—CF3 | C—H | C—CF3 | C—H | H | CF3 | H | H | H | H | CH3CH2NHCO | 1 |

TABLE 5-continued

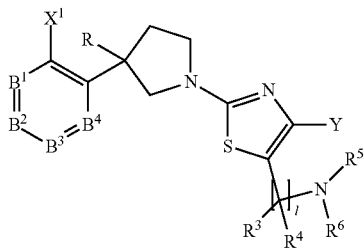

| Ex.-No. | B¹ | B² | B³ | B⁴ | X¹ | R | Y | R³ | R⁴ | R⁵ | R⁶ | l |
|---|---|---|---|---|---|---|---|---|---|---|---|---|
| 5-177 | C—Cl | C—H | C—Cl | C—H | H | CF3 | CH3 | H | H | H | CH3CO | 1 |
| 5-178 | C—Cl | C—H | C—Cl | C—H | H | CF3 | CH3 | H | H | H | CH3CH2CO | 1 |
| 5-179 | C—Cl | C—H | C—Cl | C—H | H | CF3 | CH3 | H | H | H | cyclo-PrCO | 1 |
| 5-180 | C—Cl | C—H | C—Cl | C—H | H | CF3 | CH3 | H | H | H | CF3CH2CO | 1 |
| 5-181 | C—Cl | C—H | C—Cl | C—H | H | CF3 | CH3 | H | H | H | CH3CH2NHCO | 1 |
| 5-182 | C—Cl | C—Cl | C—Cl | C—H | H | CF3 | CH3 | H | H | H | CH3CO | 1 |
| 5-183 | C—Cl | C—Cl | C—Cl | C—H | H | CF3 | CH3 | H | H | H | CH3CH2CO | 1 |
| 5-184 | C—Cl | C—Cl | C—Cl | C—H | H | CF3 | CH3 | H | H | H | cyclo-PrCO | 1 |
| 5-185 | C—Cl | C—Cl | C—Cl | C—H | H | CF3 | CH3 | H | H | H | CF3CH2CO | 1 |
| 5-186 | C—Cl | C—Cl | C—Cl | C—H | H | CF3 | CH3 | H | H | H | CH3CH2NHCO | 1 |
| 5-187 | C—CF3 | C—H | C—CF3 | C—H | H | CF3 | CH3 | H | H | H | CH3CO | 1 |
| 5-188 | C—CF3 | C—H | C—CF3 | C—H | H | CF3 | CH3 | H | H | H | CH3CH2CO | 1 |
| 5-189 | C—CF3 | C—H | C—CF3 | C—H | H | CF3 | CH3 | H | H | H | cyclo-PrCO | 1 |
| 5-190 | C—CF3 | C—H | C—CF3 | C—H | H | CF3 | CH3 | H | H | H | CF3CH2CO | 1 |
| 5-191 | C—CF3 | C—H | C—CF3 | C—H | H | CF3 | CH3 | H | H | H | CH3CH2NHCO | 1 |
| 5-192 | C—Cl | C—H | C—Cl | C—H | H | CF3 | Cl | H | H | H | CH3CO | 1 |
| 5-193 | C—Cl | C—H | C—Cl | C—H | H | CF3 | Cl | H | H | H | CH3CH2CO | 1 |
| 5-194 | C—Cl | C—H | C—Cl | C—H | H | CF3 | Cl | H | H | H | cyclo-PrCO | 1 |
| 5-195 | C—Cl | C—H | C—Cl | C—H | H | CF3 | Cl | H | H | H | CF3CH2CO | 1 |
| 5-196 | C—Cl | C—H | C—Cl | C—H | H | CF3 | Cl | H | H | H | CH3CH2NHCO | 1 |
| 5-197 | C—Cl | C—Cl | C—Cl | C—H | H | CF3 | Cl | H | H | H | CH3CO | 1 |
| 5-198 | C—Cl | C—Cl | C—Cl | C—H | H | CF3 | Cl | H | H | H | CH3CH2CO | 1 |
| 5-199 | C—Cl | C—Cl | C—Cl | C—H | H | CF3 | Cl | H | H | H | cyclo-PrCO | 1 |
| 5-200 | C—Cl | C—Cl | C—Cl | C—H | H | CF3 | Cl | H | H | H | CF3CH2CO | 1 |
| 5-201 | C—Cl | C—Cl | C—Cl | C—H | H | CF3 | Cl | H | H | H | CH3CH2NHCO | 1 |
| 5-202 | C—CF3 | C—H | C—CF3 | C—H | H | CF3 | Cl | H | H | H | CH3CO | 1 |
| 5-203 | C—CF3 | C—H | C—CF3 | C—H | H | CF3 | Cl | H | H | H | CH3CH2CO | 1 |
| 5-204 | C—CF3 | C—H | C—CF3 | C—H | H | CF3 | Cl | H | H | H | cyclo-PrCO | 1 |
| 5-205 | C—CF3 | C—H | C—CF3 | C—H | H | CF3 | Cl | H | H | H | CF3CH2CO | 1 |
| 5-206 | C—CF3 | C—H | C—CF3 | C—H | H | CF3 | Cl | H | H | H | CH3CH2NHCO | 1 |
| 5-207 | C—Cl | C—H | C—Cl | C—H | H | CF3 | H | H | H | H | n-PrCO | 1 |
| 5-208 | C—Cl | C—H | C—Cl | C—H | H | CF3 | H | H | H | H | cyclo-PrCH2CO | 1 |
| 5-209 | C—Cl | C—H | C—Cl | C—H | H | CF3 | H | H | H | H | CH3SCH2CO | 1 |
| 5-210 | C—Cl | C—H | C—Cl | C—H | H | CF3 | H | H | H | H | CH3S(O)CH2CO | 1 |
| 5-211 | C—Cl | C—H | C—Cl | C—H | H | CF3 | H | H | H | H | CH3SO2CH2CO | 1 |
| 5-212 | C—Cl | C—Cl | C—Cl | C—H | H | CF3 | H | H | H | H | n-PrCO | 1 |
| 5-213 | C—Cl | C—Cl | C—Cl | C—H | H | CF3 | H | H | H | H | cyclo-PrCH2CO | 1 |
| 5-214 | C—Cl | C—Cl | C—Cl | C—H | H | CF3 | H | H | H | H | CH3SCH2CO | 1 |
| 5-215 | C—Cl | C—Cl | C—Cl | C—H | H | CF3 | H | H | H | H | CH3S(O)CH2CO | 1 |
| 5-216 | C—Cl | C—Cl | C—Cl | C—H | H | CF3 | H | H | H | H | CH3SO2CH2CO | 1 |
| 5-217 | C—CF3 | C—H | C—CF3 | C—H | H | CF3 | H | H | H | H | n-PrCO | 1 |
| 5-218 | C—CF3 | C—H | C—CF3 | C—H | H | CF3 | H | H | H | H | cyclo-PrCH2CO | 1 |
| 5-219 | C—CF3 | C—H | C—CF3 | C—H | H | CF3 | H | H | H | H | CH3SCH2CO | 1 |
| 5-220 | C—CF3 | C—H | C—CF3 | C—H | H | CF3 | H | H | H | H | CH3S(O)CH2CO | 1 |
| 5-221 | C—CF3 | C—H | C—CF3 | C—H | H | CF3 | H | H | H | H | CH3SO2CH2CO | 1 |
| 5-222 | C—Cl | C—Cl | C—CF3 | C—H | H | CF3 | H | H | H | H | n-PrCO | 1 |
| 5-223 | C—Cl | C—Cl | C—CF3 | C—H | H | CF3 | H | H | H | H | cyclo-PrCH2CO | 1 |
| 5-224 | C—Cl | C—Cl | C—CF3 | C—H | H | CF3 | H | H | H | H | CH3SCH2CO | 1 |
| 5-225 | C—Cl | C—Cl | C—CF3 | C—H | H | CF3 | H | H | H | H | CH3S(O)CH2CO | 1 |
| 5-226 | C—Cl | C—Cl | C—CF3 | C—H | H | CF3 | H | H | H | H | CH3SO2CH2CO | 1 |
| 5-227 | C—Cl | C—H | C—Cl | C—H | H | CF3 | CH3 | H | H | H | n-PrCO | 1 |
| 5-228 | C—Cl | C—H | C—Cl | C—H | H | CF3 | CH3 | H | H | H | cyclo-PrCH2CO | 1 |
| 5-229 | C—Cl | C—H | C—Cl | C—H | H | CF3 | CH3 | H | H | H | CH3SCH2CO | 1 |
| 5-230 | C—Cl | C—H | C—Cl | C—H | H | CF3 | CH3 | H | H | H | CH3S(O)CH2CO | 1 |
| 5-231 | C—Cl | C—H | C—Cl | C—H | H | CF3 | CH3 | H | H | H | CH3SO2CH2CO | 1 |
| 5-232 | C—Cl | C—Cl | C—Cl | C—H | H | CF3 | CH3 | H | H | H | n-PrCO | 1 |
| 5-233 | C—Cl | C—Cl | C—Cl | C—H | H | CF3 | CH3 | H | H | H | cyclo-PrCH2CO | 1 |
| 5-234 | C—Cl | C—Cl | C—Cl | C—H | H | CF3 | CH3 | H | H | H | CH3SCH2CO | 1 |
| 5-235 | C—Cl | C—Cl | C—Cl | C—H | H | CF3 | CH3 | H | H | H | CH3S(O)CH2CO | 1 |
| 5-236 | C—Cl | C—Cl | C—Cl | C—H | H | CF3 | CH3 | H | H | H | CH3SO2CH2CO | 1 |
| 5-237 | C—CF3 | C—H | C—CF3 | C—H | H | CF3 | CH3 | H | H | H | n-PrCO | 1 |
| 5-238 | C—CF3 | C—H | C—CF3 | C—H | H | CF3 | CH3 | H | H | H | cyclo-PrCH2CO | 1 |
| 5-239 | C—CF3 | C—H | C—CF3 | C—H | H | CF3 | CH3 | H | H | H | CH3SCH2CO | 1 |
| 5-240 | C—CF3 | C—H | C—CF3 | C—H | H | CF3 | CH3 | H | H | H | CH3S(O)CH2CO | 1 |
| 5-241 | C—CF3 | C—H | C—CF3 | C—H | H | CF3 | CH3 | H | H | H | CH3SO2CH2CO | 1 |

TABLE 5-continued

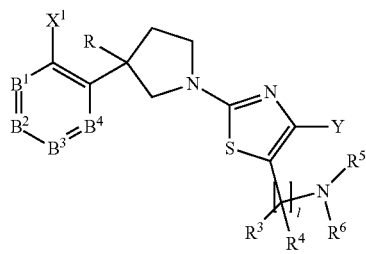

| Ex.-No. | B¹ | B² | B³ | B⁴ | X¹ | R | Y | R³ | R⁴ | R⁵ | R⁶ | l |
|---|---|---|---|---|---|---|---|---|---|---|---|---|
| 5-242 | C—Cl | C—Cl | C—CF3 | C—H | H | CF3 | CH3 | H | H | H | n-PrCO | 1 |
| 5-243 | C—Cl | C—Cl | C—CF3 | C—H | H | CF3 | CH3 | H | H | H | cyclo-PrCH2CO | 1 |
| 5-244 | C—Cl | C—Cl | C—CF3 | C—H | H | CF3 | CH3 | H | H | H | CH3SCH2CO | 1 |
| 5-245 | C—Cl | C—Cl | C—CF3 | C—H | H | CF3 | CH3 | H | H | H | CH3S(O)CH2CO | 1 |
| 5-246 | C—Cl | C—Cl | C—CF3 | C—H | H | CF3 | CH3 | H | H | H | CH3SO2CH2CO | 1 |
| 5-247 | C—Cl | C—H | C—Cl | C—H | H | CF3 | Cl | H | H | H | n-PrCO | 1 |
| 5-248 | C—Cl | C—H | C—Cl | C—H | H | CF3 | Cl | H | H | H | cyclo-PrCH2CO | 1 |
| 5-249 | C—Cl | C—H | C—Cl | C—H | H | CF3 | Cl | H | H | H | CH3SCH2CO | 1 |
| 5-250 | C—Cl | C—H | C—Cl | C—H | H | CF3 | Cl | H | H | H | CH3S(O)CH2CO | 1 |
| 5-251 | C—Cl | C—H | C—Cl | C—H | H | CF3 | Cl | H | H | H | CH3SO2CH2CO | 1 |
| 5-252 | C—Cl | C—Cl | C—Cl | C—H | H | CF3 | Cl | H | H | H | n-PrCO | 1 |
| 5-253 | C—Cl | C—Cl | C—Cl | C—H | H | CF3 | Cl | H | H | H | cyclo-PrCH2CO | 1 |
| 5-254 | C—Cl | C—Cl | C—Cl | C—H | H | CF3 | Cl | H | H | H | CH3SCH2CO | 1 |
| 5-255 | C—Cl | C—Cl | C—Cl | C—H | H | CF3 | Cl | H | H | H | CH3S(O)CH2CO | 1 |
| 5-256 | C—Cl | C—Cl | C—Cl | C—H | H | CF3 | Cl | H | H | H | CH3SO2CH2CO | 1 |
| 5-257 | C—CF3 | C—H | C—CF3 | C—H | H | CF3 | Cl | H | H | H | n-PrCO | 1 |
| 5-258 | C—CF3 | C—H | C—CF3 | C—H | H | CF3 | Cl | H | H | H | cyclo-PrCH2CO | 1 |
| 5-259 | C—CF3 | C—H | C—CF3 | C—H | H | CF3 | Cl | H | H | H | CH3SCH2CO | 1 |
| 5-260 | C—CF3 | C—H | C—CF3 | C—H | H | CF3 | Cl | H | H | H | CH3S(O)CH2CO | 1 |
| 5-261 | C—CF3 | C—H | C—CF3 | C—H | H | CF3 | Cl | H | H | H | CH3SO2CH2CO | 1 |
| 5-262 | C—Cl | C—Cl | C—CF3 | C—H | H | CF3 | Cl | H | H | H | n-PrCO | 1 |
| 5-263 | C—Cl | C—Cl | C—CF3 | C—H | H | CF3 | Cl | H | H | H | cyclo-PrCH2CO | 1 |
| 5-264 | C—Cl | C—Cl | C—CF3 | C—H | H | CF3 | Cl | H | H | H | CH3SCH2CO | 1 |
| 5-265 | C—Cl | C—Cl | C—CF3 | C—H | H | CF3 | Cl | H | H | H | CH3S(O)CH2CO | 1 |
| 5-266 | C—Cl | C—Cl | C—CF3 | C—H | H | CF3 | Cl | H | H | H | CH3SO2CH2CO | 1 |
| 5-267 | C—Cl | C—H | C—Cl | C—H | H | CF3 | Br | H | H | H | CH3CO | 1 |
| 5-268 | C—Cl | C—H | C—Cl | C—H | H | CF3 | Br | H | H | H | CH3CH2CO | 1 |
| 5-269 | C—Cl | C—H | C—Cl | C—H | H | CF3 | Br | H | H | H | n-PrCO | 1 |
| 5-270 | C—Cl | C—H | C—Cl | C—H | H | CF3 | Br | H | H | H | cyclo-PrCO | 1 |
| 5-271 | C—Cl | C—H | C—Cl | C—H | H | CF3 | Br | H | H | H | cyclo-PrCH2CO | 1 |
| 5-272 | C—Cl | C—H | C—Cl | C—H | H | CF3 | Br | H | H | H | CF3CH2CO | 1 |
| 5-273 | C—Cl | C—H | C—Cl | C—H | H | CF3 | Br | H | H | H | CH3SCH2CO | 1 |
| 5-274 | C—Cl | C—H | C—Cl | C—H | H | CF3 | Br | H | H | H | CH3S(O)CH2CO | 1 |
| 5-275 | C—Cl | C—H | C—Cl | C—H | H | CF3 | Br | H | H | H | CH3SO2CH2CO | 1 |
| 5-276 | C—Cl | C—H | C—Cl | C—H | H | CF3 | Br | H | H | H | CH3CH2NHCO | 1 |
| 5-277 | C—Cl | C—Cl | C—Cl | C—H | H | CF3 | Br | H | H | H | CH3CO | 1 |
| 5-278 | C—Cl | C—Cl | C—Cl | C—H | H | CF3 | Br | H | H | H | CH3CH2CO | 1 |
| 5-279 | C—Cl | C—Cl | C—Cl | C—H | H | CF3 | Br | H | H | H | n-PrCO | 1 |
| 5-280 | C—Cl | C—Cl | C—Cl | C—H | H | CF3 | Br | H | H | H | cyclo-PrCO | 1 |
| 5-281 | C—Cl | C—Cl | C—Cl | C—H | H | CF3 | Br | H | H | H | cyclo-PrCH2CO | 1 |
| 5-282 | C—Cl | C—Cl | C—Cl | C—H | H | CF3 | Br | H | H | H | CF3CH2CO | 1 |
| 5-283 | C—Cl | C—Cl | C—Cl | C—H | H | CF3 | Br | H | H | H | CH3SCH2CO | 1 |
| 5-284 | C—Cl | C—Cl | C—Cl | C—H | H | CF3 | Br | H | H | H | CH3S(O)CH2CO | 1 |
| 5-285 | C—Cl | C—Cl | C—Cl | C—H | H | CF3 | Br | H | H | H | CH3SO2CH2CO | 1 |
| 5-286 | C—Cl | C—Cl | C—Cl | C—H | H | CF3 | Br | H | H | H | CH3CH2NHCO | 1 |
| 5-287 | C—CF3 | C—H | C—CF3 | C—H | H | CF3 | Br | H | H | H | CH3CO | 1 |
| 5-288 | C—CF3 | C—H | C—CF3 | C—H | H | CF3 | Br | H | H | H | CH3CH2CO | 1 |
| 5-289 | C—CF3 | C—H | C—CF3 | C—H | H | CF3 | Br | H | H | H | n-PrCO | 1 |
| 5-290 | C—CF3 | C—H | C—CF3 | C—H | H | CF3 | Br | H | H | H | cyclo-PrCO | 1 |
| 5-291 | C—CF3 | C—H | C—CF3 | C—H | H | CF3 | Br | H | H | H | cyclo-PrCH2CO | 1 |
| 5-292 | C—CF3 | C—H | C—CF3 | C—H | H | CF3 | Br | H | H | H | CF3CH2CO | 1 |
| 5-293 | C—CF3 | C—H | C—CF3 | C—H | H | CF3 | Br | H | H | H | CH3SCH2CO | 1 |
| 5-294 | C—CF3 | C—H | C—CF3 | C—H | H | CF3 | Br | H | H | H | CH3S(O)CH2CO | 1 |
| 5-295 | C—CF3 | C—H | C—CF3 | C—H | H | CF3 | Br | H | H | H | CH3SO2CH2CO | 1 |
| 5-296 | C—CF3 | C—H | C—CF3 | C—H | H | CF3 | Br | H | H | H | CH3CH2NHCO | 1 |
| 5-297 | C—Cl | C—Cl | C—CF3 | C—H | H | CF3 | Br | H | H | H | CH3CO | 1 |
| 5-298 | C—Cl | C—Cl | C—CF3 | C—H | H | CF3 | Br | H | H | H | CH3CH2CO | 1 |
| 5-299 | C—Cl | C—Cl | C—CF3 | C—H | H | CF3 | Br | H | H | H | n-PrCO | 1 |
| 5-300 | C—Cl | C—Cl | C—CF3 | C—H | H | CF3 | Br | H | H | H | cyclo-PrCO | 1 |
| 5-301 | C—Cl | C—Cl | C—CF3 | C—H | H | CF3 | Br | H | H | H | cyclo-PrCH2CO | 1 |
| 5-302 | C—Cl | C—Cl | C—CF3 | C—H | H | CF3 | Br | H | H | H | CF3CH2CO | 1 |
| 5-303 | C—Cl | C—Cl | C—CF3 | C—H | H | CF3 | Br | H | H | H | CH3SCH2CO | 1 |
| 5-304 | C—Cl | C—Cl | C—CF3 | C—H | H | CF3 | Br | H | H | H | CH3S(O)CH2CO | 1 |
| 5-305 | C—Cl | C—Cl | C—CF3 | C—H | H | CF3 | Br | H | H | H | CH3SO2CH2CO | 1 |
| 5-306 | C—Cl | C—Cl | C—CF3 | C—H | H | CF3 | Br | H | H | H | CH3CH2NHCO | 1 |

TABLE 5-continued

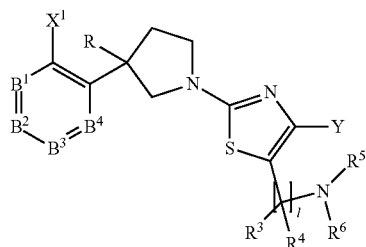

| Ex.-No. | B¹ | B² | B³ | B⁴ | X¹ | R | Y | R³ | R⁴ | R⁵ | R⁶ | l |
|---|---|---|---|---|---|---|---|---|---|---|---|---|
| 5-307 | C—Cl | C—H | C—Cl | C—H | H | CF3 | CF3 | H | H | H | CH3CH2OCH2CO | 1 |
| 5-308 | C—Cl | C—H | C—Cl | C—H | H | CF3 | CF3 | H | H | H | CH3OCH2CH2CO | 1 |
| 5-309 | C—Cl | C—H | C—Cl | C—H | H | CF3 | CF3 | H | H | H | CH3CH2OCH2CH2CO | 1 |
| 5-310 | C—Cl | C—H | C—Cl | C—H | H | CF3 | CF3 | H | H | H | CH3S(O)CH2CO | 1 |
| 5-311 | C—Cl | C—H | C—Cl | C—H | H | CF3 | CF3 | H | H | H | CH3SO2CH2CO | 1 |
| 5-312 | C—Cl | C—H | C—Br | C—H | H | CF3 | CF3 | H | H | H | CH3CO | 1 |
| 5-313 | C—Cl | C—H | C—Br | C—H | H | CF3 | CF3 | H | H | H | CH3CH2CO | 1 |
| 5-314 | C—Cl | C—H | C—Br | C—H | H | CF3 | CF3 | H | H | H | n-PrCO | 1 |
| 5-315 | C—Cl | C—H | C—Br | C—H | H | CF3 | CF3 | H | H | H | cyclo-PrCO | 1 |
| 5-316 | C—Cl | C—H | C—Br | C—H | H | CF3 | CF3 | H | H | H | cyclo-PrCH2CO | 1 |
| 5-317 | C—Cl | C—H | C—Br | C—H | H | CF3 | CF3 | H | H | H | CF3CH2CO | 1 |
| 5-318 | C—Cl | C—H | C—Br | C—H | H | CF3 | CF3 | H | H | H | CH3SCH2CO | 1 |
| 5-319 | C—Cl | C—H | C—Br | C—H | H | CF3 | CF3 | H | H | H | CH3S(O)CH2CO | 1 |
| 5-320 | C—Cl | C—H | C—Br | C—H | H | CF3 | CF3 | H | H | H | CH3SO2CH2CO | 1 |
| 5-321 | C—Cl | C—H | C—Br | C—H | H | CF3 | CF3 | H | H | H | CH3CH2NHCO | 1 |
| 5-322 | C—Br | C—H | C—Br | C—H | H | CF3 | CF3 | H | H | H | CH3SCH2CO | 1 |
| 5-323 | C—Br | C—H | C—Br | C—H | H | CF3 | CF3 | H | H | H | CH3S(O)CH2CO | 1 |
| 5-324 | C—Br | C—H | C—Br | C—H | H | CF3 | CF3 | H | H | H | CH3SO2CH2CO | 1 |
| 5-325 | C—Cl | C—F | C—Cl | C—H | H | CF3 | CF3 | H | H | H | CH3CO | 1 |
| 5-326 | C—Cl | C—F | C—Cl | C—H | H | CF3 | CF3 | H | H | H | CH3CH2CO | 1 |
| 5-327 | C—Cl | C—F | C—Cl | C—H | H | CF3 | CF3 | H | H | H | n-PrCO | 1 |
| 5-328 | C—Cl | C—F | C—Cl | C—H | H | CF3 | CF3 | H | H | H | cyclo-PrCO | 1 |
| 5-329 | C—Cl | C—F | C—Cl | C—H | H | CF3 | CF3 | H | H | H | cyclo-PrCH2CO | 1 |
| 5-330 | C—Cl | C—F | C—Cl | C—H | H | CF3 | CF3 | H | H | H | CF3CH2CO | 1 |
| 5-331 | C—Cl | C—F | C—Cl | C—H | H | CF3 | CF3 | H | H | H | CH3SCH2CO | 1 |
| 5-332 | C—Cl | C—F | C—Cl | C—H | H | CF3 | CF3 | H | H | H | CH3S(O)CH2CO | 1 |
| 5-333 | C—Cl | C—F | C—Cl | C—H | H | CF3 | CF3 | H | H | H | CH3SO2CH2CO | 1 |
| 5-334 | C—Cl | C—F | C—Cl | C—H | H | CF3 | CF3 | H | H | H | CH3CH2NHCO | 1 |
| 5-335 | C—Cl | C—Cl | C—Cl | C—H | H | CF3 | CF3 | H | H | H | n-PrCH2CO | 1 |
| 5-336 | C—Cl | C—Cl | C—Cl | C—H | H | CF3 | CF3 | H | H | H | cyclo-PrCH2CO | 1 |
| 5-337 | C—Cl | C—Cl | C—Cl | C—H | H | CF3 | CF3 | H | H | H | tert-BuCH2CO | 1 |
| 5-338 | C—Cl | C—Cl | C—Cl | C—H | H | CF3 | CF3 | H | H | H | CH3OCH2CH2CO | 1 |
| 5-339 | C—Cl | C—Cl | C—Cl | C—H | H | CF3 | CF3 | H | H | H | CH3CH2OCH2CH2CO | 1 |
| 5-340 | C—Cl | C—Cl | C—Cl | C—H | H | CF3 | CF3 | H | H | H | CH3SCH2CO | 1 |
| 5-341 | C—Cl | C—Cl | C—Cl | C—H | H | CF3 | CF3 | H | H | H | CH3S(O)CH2CO | 1 |
| 5-342 | C—Cl | C—Cl | C—Cl | C—H | H | CF3 | CF3 | H | H | H | CH3SO2CH2CO | 1 |
| 5-343 | C—Cl | C—Br | C—Cl | C—H | H | CF3 | CF3 | H | H | H | CH3CO | 1 |
| 5-344 | C—Cl | C—Br | C—Cl | C—H | H | CF3 | CF3 | H | H | H | CH3CH2CO | 1 |
| 5-345 | C—Cl | C—Br | C—Cl | C—H | H | CF3 | CF3 | H | H | H | n-PrCO | 1 |
| 5-346 | C—Cl | C—Br | C—Cl | C—H | H | CF3 | CF3 | H | H | H | cyclo-PrCO | 1 |
| 5-347 | C—Cl | C—Br | C—Cl | C—H | H | CF3 | CF3 | H | H | H | cyclo-PrCH2CO | 1 |
| 5-348 | C—Cl | C—Br | C—Cl | C—H | H | CF3 | CF3 | H | H | H | CF3CH2CO | 1 |
| 5-349 | C—Cl | C—Br | C—Cl | C—H | H | CF3 | CF3 | H | H | H | CH3SCH2CO | 1 |
| 5-350 | C—Cl | C—Br | C—Cl | C—H | H | CF3 | CF3 | H | H | H | CH3S(O)CH2CO | 1 |
| 5-351 | C—Cl | C—Br | C—Cl | C—H | H | CF3 | CF3 | H | H | H | CH3SO2CH2CO | 1 |
| 5-352 | C—Cl | C—Br | C—Cl | C—H | H | CF3 | CF3 | H | H | H | CH3CH2NHCO | 1 |
| 5-353 | C—Cl | C—Cl | C—Br | C—H | H | CF3 | CF3 | H | H | H | CH3CO | 1 |
| 5-354 | C—Cl | C—Cl | C—Br | C—H | H | CF3 | CF3 | H | H | H | CH3CH2CO | 1 |
| 5-355 | C—Cl | C—Cl | C—Br | C—H | H | CF3 | CF3 | H | H | H | n-PrCO | 1 |
| 5-356 | C—Cl | C—Cl | C—Br | C—H | H | CF3 | CF3 | H | H | H | cyclo-PrCO | 1 |
| 5-357 | C—Cl | C—Cl | C—Br | C—H | H | CF3 | CF3 | H | H | H | cyclo-PrCH2CO | 1 |
| 5-358 | C—Cl | C—Cl | C—Br | C—H | H | CF3 | CF3 | H | H | H | CF3CH2CO | 1 |
| 5-359 | C—Cl | C—Cl | C—Br | C—H | H | CF3 | CF3 | H | H | H | CH3SCH2CO | 1 |
| 5-360 | C—Cl | C—Cl | C—Br | C—H | H | CF3 | CF3 | H | H | H | CH3S(O)CH2CO | 1 |
| 5-361 | C—Cl | C—Cl | C—Br | C—H | H | CF3 | CF3 | H | H | H | CH3SO2CH2CO | 1 |
| 5-362 | C—Cl | C—Cl | C—Br | C—H | H | CF3 | CF3 | H | H | H | CH3CH2NHCO | 1 |
| 5-363 | C—Cl | C—F | C—Cl | C—H | F | CF3 | CF3 | H | H | H | CH3CO | 1 |
| 5-364 | C—Cl | C—F | C—Cl | C—H | F | CF3 | CF3 | H | H | H | CH3CH2CO | 1 |
| 5-365 | C—Cl | C—F | C—Cl | C—H | F | CF3 | CF3 | H | H | H | n-PrCO | 1 |
| 5-366 | C—Cl | C—F | C—Cl | C—H | F | CF3 | CF3 | H | H | H | cyclo-PrCO | 1 |
| 5-367 | C—Cl | C—F | C—Cl | C—H | F | CF3 | CF3 | H | H | H | cyclo-PrCH2CO | 1 |
| 5-368 | C—Cl | C—F | C—Cl | C—H | F | CF3 | CF3 | H | H | H | CF3CH2CO | 1 |
| 5-369 | C—Cl | C—F | C—Cl | C—H | F | CF3 | CF3 | H | H | H | CH3SCH2CO | 1 |
| 5-370 | C—Cl | C—F | C—Cl | C—H | F | CF3 | CF3 | H | H | H | CH3S(O)CH2CO | 1 |
| 5-371 | C—Cl | C—F | C—Cl | C—H | F | CF3 | CF3 | H | H | H | CH3SO2CH2CO | 1 |

TABLE 5-continued

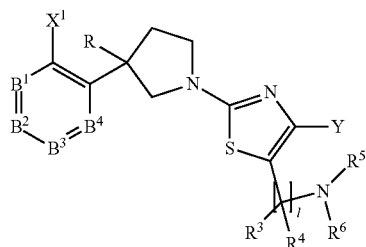

| Ex.-No. | B¹ | B² | B³ | B⁴ | X¹ | R | Y | R³ | R⁴ | R⁵ | R⁶ | l |
|---|---|---|---|---|---|---|---|---|---|---|---|---|
| 5-372 | C—Cl | C—F | C—Cl | C—H | F | CF3 | CF3 | H | H | H | CH3CH2NHCO | 1 |
| 5-373 | C—Cl | C—H | C—CF3 | C—H | H | CF3 | CF3 | H | H | H | CH3CO | 1 |
| 5-374 | C—Cl | C—H | C—CF3 | C—H | H | CF3 | CF3 | H | H | H | CH3CH2CO | 1 |
| 5-375 | C—Cl | C—H | C—CF3 | C—H | H | CF3 | CF3 | H | H | H | n-PrCO | 1 |
| 5-376 | C—Cl | C—H | C—CF3 | C—H | H | CF3 | CF3 | H | H | H | cyclo-PrCO | 1 |
| 5-377 | C—Cl | C—H | C—CF3 | C—H | H | CF3 | CF3 | H | H | H | cyclo-PrCH2CO | 1 |
| 5-378 | C—Cl | C—H | C—CF3 | C—H | H | CF3 | CF3 | H | H | H | CF3CH2CO | 1 |
| 5-379 | C—Cl | C—H | C—CF3 | C—H | H | CF3 | CF3 | H | H | H | CH3OCH2CH2CO | 1 |
| 5-380 | C—Cl | C—H | C—CF3 | C—H | H | CF3 | CF3 | H | H | H | CH3CH2OCH2CH2CO | 1 |
| 5-381 | C—Cl | C—H | C—CF3 | C—H | H | CF3 | CF3 | H | H | H | CH3SCH2CO | 1 |
| 5-382 | C—Cl | C—H | C—CF3 | C—H | H | CF3 | CF3 | H | H | H | CH3S(O)CH2CO | 1 |
| 5-383 | C—Cl | C—H | C—CF3 | C—H | H | CF3 | CF3 | H | H | H | CH3SO2CH2CO | 1 |
| 5-384 | C—Cl | C—H | C—CF3 | C—H | H | CF3 | CF3 | H | H | H | CH3CH2NHCO | 1 |
| 5-385 | C—Cl | C—H | C—CF3 | C—H | H | CF3 | CF3 | H | H | H | CH3OCH2CO | 1 |
| 5-386 | C—Cl | C—H | C—CF3 | C—H | H | CF3 | CF3 | H | H | H | CH3CH2OCH2CH2CO | 1 |
| 5-387 | C—CF3 | C—H | C—CF3 | C—H | H | CF3 | CF3 | H | H | H | CH3SCH2CO | 1 |
| 5-388 | C—CF3 | C—H | C—CF3 | C—H | H | CF3 | CF3 | H | H | H | CH3S(O)CH2CO | 1 |
| 5-389 | C—CF3 | C—H | C—CF3 | C—H | H | CF3 | CF3 | H | H | H | CH3SO2CH2CO | 1 |
| 5-390 | C—Cl | C—Cl | C—CF3 | C—H | H | CF3 | CF3 | H | H | H | CH3SCH2CO | 1 |
| 5-391 | C—Cl | C—Cl | C—CF3 | C—H | H | CF3 | CF3 | H | H | H | CH3S(O)CH2CO | 1 |
| 5-392 | C—Cl | C—Cl | C—CF3 | C—H | H | CF3 | CF3 | H | H | H | CH3SO2CH2CO | 1 |
| 5-393 | C—Cl | N | C—Cl | C—H | H | CF3 | CF3 | H | H | H | CH3CO | 1 |
| 5-394 | C—Cl | N | C—Cl | C—H | H | CF3 | CF3 | H | H | H | CH3CH2CO | 1 |
| 5-395 | C—Cl | N | C—Cl | C—H | H | CF3 | CF3 | H | H | H | n-PrCO | 1 |
| 5-396 | C—Cl | N | C—Cl | C—H | H | CF3 | CF3 | H | H | H | cyclo-PrCO | 1 |
| 5-397 | C—Cl | N | C—Cl | C—H | H | CF3 | CF3 | H | H | H | cyclo-PrCH2CO | 1 |
| 5-398 | C—Cl | N | C—Cl | C—H | H | CF3 | CF3 | H | H | H | CF3CH2CO | 1 |
| 5-399 | C—Cl | N | C—Cl | C—H | H | CF3 | CF3 | H | H | H | CH3SCH2CO | 1 |
| 5-400 | C—Cl | N | C—Cl | C—H | H | CF3 | CF3 | H | H | H | CH3S(O)CH2CO | 1 |
| 5-401 | C—Cl | N | C—Cl | C—H | H | CF3 | CF3 | H | H | H | CH3SO2CH2CO | 1 |
| 5-402 | C—Cl | N | C—Cl | C—H | H | CF3 | CF3 | H | H | H | CH3CH2NHCO | 1 |
| 5-403 | C—CF3 | N | C—H | C—H | H | CF3 | CF3 | H | H | H | CH3CO | 1 |
| 5-404 | C—CF3 | N | C—H | C—H | H | CF3 | CF3 | H | H | H | CH3CH2CO | 1 |
| 5-405 | C—CF3 | N | C—H | C—H | H | CF3 | CF3 | H | H | H | n-PrCO | 1 |
| 5-406 | C—CF3 | N | C—H | C—H | H | CF3 | CF3 | H | H | H | cyclo-PrCO | 1 |
| 5-407 | C—CF3 | N | C—H | C—H | H | CF3 | CF3 | H | H | H | cyclo-PrCH2CO | 1 |
| 5-408 | C—CF3 | N | C—H | C—H | H | CF3 | CF3 | H | H | H | CF3CH2CO | 1 |
| 5-409 | C—CF3 | N | C—H | C—H | H | CF3 | CF3 | H | H | H | CH3SCH2CO | 1 |
| 5-410 | C—CF3 | N | C—H | C—H | H | CF3 | CF3 | H | H | H | CH3S(O)CH2CO | 1 |
| 5-411 | C—CF3 | N | C—H | C—H | H | CF3 | CF3 | H | H | H | CH3SO2CH2CO | 1 |
| 5-412 | C—CF3 | N | C—H | C—H | H | CF3 | CF3 | H | H | H | CH3CH2NHCO | 1 |
| 5-413 | C—CF3 | N | C—CF3 | C—H | H | CF3 | CF3 | H | H | H | CH3CO | 1 |
| 5-414 | C—CF3 | N | C—CF3 | C—H | H | CF3 | CF3 | H | H | H | CH3CH2CO | 1 |
| 5-415 | C—CF3 | N | C—CF3 | C—H | H | CF3 | CF3 | H | H | H | n-PrCO | 1 |
| 5-416 | C—CF3 | N | C—CF3 | C—H | H | CF3 | CF3 | H | H | H | cyclo-PrCO | 1 |
| 5-417 | C—CF3 | N | C—CF3 | C—H | H | CF3 | CF3 | H | H | H | cyclo-PrCH2CO | 1 |
| 5-418 | C—CF3 | N | C—CF3 | C—H | H | CF3 | CF3 | H | H | H | CF3CH2CO | 1 |
| 5-419 | C—CF3 | N | C—CF3 | C—H | H | CF3 | CF3 | H | H | H | CH3SCH2CO | 1 |
| 5-420 | C—CF3 | N | C—CF3 | C—H | H | CF3 | CF3 | H | H | H | CH3S(O)CH2CO | 1 |
| 5-421 | C—CF3 | N | C—CF3 | C—H | H | CF3 | CF3 | H | H | H | CH3SO2CH2CO | 1 |
| 5-422 | C—CF3 | N | C—CF3 | C—H | H | CF3 | CF3 | H | H | H | CH3CH2NHCO | 1 |
| 5-423 | C—CF3 | C—H | C—CF3 | N | H | CF3 | CF3 | H | H | H | CH3CO | 1 |
| 5-424 | C—CF3 | C—H | C—CF3 | N | H | CF3 | CF3 | H | H | H | CH3CH2CO | 1 |
| 5-425 | C—CF3 | C—H | C—CF3 | N | H | CF3 | CF3 | H | H | H | n-PrCO | 1 |
| 5-426 | C—CF3 | C—H | C—CF3 | N | H | CF3 | CF3 | H | H | H | cyclo-PrCO | 1 |
| 5-427 | C—CF3 | C—H | C—CF3 | N | H | CF3 | CF3 | H | H | H | cyclo-PrCH2CO | 1 |
| 5-428 | C—CF3 | C—H | C—CF3 | N | H | CF3 | CF3 | H | H | H | CF3CH2CO | 1 |
| 5-429 | C—CF3 | C—H | C—CF3 | N | H | CF3 | CF3 | H | H | H | CH3SCH2CO | 1 |
| 5-430 | C—CF3 | C—H | C—CF3 | N | H | CF3 | CF3 | H | H | H | CH3S(O)CH2CO | 1 |
| 5-431 | C—CF3 | C—H | C—CF3 | N | H | CF3 | CF3 | H | H | H | CH3SO2CH2CO | 1 |
| 5-432 | C—CF3 | C—H | C—CF3 | N | H | CF3 | CF3 | H | H | H | CH3CH2NHCO | 1 |
| 5-433 | C—CF3 | C—H | C—CF3 | C—H | H | CF3 | CF3 | H | H | H | cyclo-PrCH2CO | 1 |
| 5-434 | C—CF3 | C—H | C—CF3 | C—H | H | CF3 | CF3 | H | H | H | tert-BuCH2CO | 1 |

TABLE 5-continued

| Ex.-No. | B¹ | B² | B³ | B⁴ | X¹ | R | Y | R³ | R⁴ | R⁵ | R⁶ | l |
|---|---|---|---|---|---|---|---|---|---|---|---|---|
| 5-435 | C—Cl | C—H | C—Cl | C—H | H | CF3 | Cl | H | H | H | CH3SCO | 1 |
| 5-436 | C—Cl | C—H | C—Cl | C—H | H | CF3 | CH3 | H | H | H | CH3SCO | 1 |
| 5-437 | C—Cl | C—H | C—Cl | C—H | H | CF3 | CF3 | H | H | H | CH3SCO | 1 |

TABLE 6

| Ex.-No. | B¹ | B² | B³ | B⁴ | X¹ | R | W¹ | R⁵ | R⁶ |
|---|---|---|---|---|---|---|---|---|---|
| 6-1 | C—Cl | C—H | C—Cl | C—H | H | CF3 | — | H | H |
| 6-2 | C—Cl | C—H | C—Cl | C—H | H | CF3 | — | H | HCO |
| 6-3 | C—Cl | C—H | C—Cl | C—H | H | CF3 | — | H | CH3CO |
| 6-4 | C—Cl | C—H | C—Cl | C—H | H | CF3 | — | H | CH3CH2CO |
| 6-5 | C—Cl | C—H | C—Cl | C—H | H | CF3 | — | H | n-PrCO |
| 6-6 | C—Cl | C—H | C—Cl | C—H | H | CF3 | — | H | iso-PrCO |
| 6-7 | C—Cl | C—H | C—Cl | C—H | H | CF3 | — | H | cyclo-PrCO |
| 6-8 | C—Cl | C—H | C—Cl | C—H | H | CF3 | — | H | n-BuCO |
| 6-9 | C—Cl | C—H | C—Cl | C—H | H | CF3 | — | H | tert-BuCO |
| 6-10 | C—Cl | C—H | C—Cl | C—H | H | CF3 | — | H | iso-BuCO |
| 6-11 | C—Cl | C—H | C—Cl | C—H | H | CF3 | — | H | cyclo-BuCO |
| 6-12 | C—Cl | C—H | C—Cl | C—H | H | CF3 | — | H | (CH3)3CCH2CO |
| 6-13 | C—Cl | C—H | C—Cl | C—H | H | CF3 | — | H | cyclo-PenCO |
| 6-14 | C—Cl | C—H | C—Cl | C—H | H | CF3 | — | H | cyclo-HexCO |
| 6-15 | C—Cl | C—H | C—Cl | C—H | H | CF3 | — | H | cyclo-PrCH2CO |
| 6-16 | C—Cl | C—H | C—Cl | C—H | H | CF3 | — | H | CF3CO |
| 6-17 | C—Cl | C—H | C—Cl | C—H | H | CF3 | — | H | CCl3CO |
| 6-18 | C—Cl | C—H | C—Cl | C—H | H | CF3 | — | H | ClCH2CO |
| 6-19 | C—Cl | C—H | C—Cl | C—H | H | CF3 | — | H | CF2ClCO |
| 6-20 | C—Cl | C—H | C—Cl | C—H | H | CF3 | — | H | ClCH2CH2CO |
| 6-21 | C—Cl | C—H | C—Cl | C—H | H | CF3 | — | H | HCF2CF2CO |
| 6-22 | C—Cl | C—H | C—Cl | C—H | H | CF3 | — | H | CF3CH2CO |
| 6-23 | C—Cl | C—H | C—Cl | C—H | H | CF3 | — | H | (CF3)2CHCO |
| 6-24 | C—Cl | C—H | C—Cl | C—H | H | CF3 | — | H | HCF2CO |
| 6-25 | C—Cl | C—H | C—Cl | C—H | H | CF3 | — | H | ClCH2CO |
| 6-26 | C—Cl | C—H | C—Cl | C—H | H | CF3 | — | H | 1-methylcyclopropyl-CO |
| 6-27 | C—Cl | C—H | C—Cl | C—H | H | CF3 | — | H | 2,2-dichlorocyclopropyl-CO |
| 6-28 | C—Cl | C—H | C—Cl | C—H | H | CF3 | — | H | 2,2-difluorocyclopropyl-CO |
| 6-29 | C—Cl | C—H | C—Cl | C—H | H | CF3 | — | H | 2-fluorocyclopropyl-CO |

TABLE 6-continued

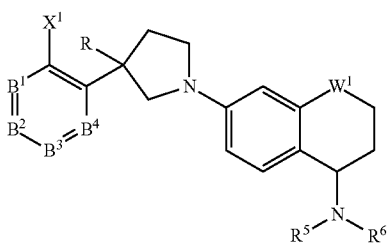

| ExNo. | B¹ | B² | B³ | B⁴ | X¹ | R | W¹ | R⁵ | R⁶ |
|---|---|---|---|---|---|---|---|---|---|
| 6-30 | C—Cl | C—H | C—Cl | C—H | H | CF3 | — | H | H₃C—[cyclopropyl]—CO |
| 6-31 | C—Cl | C—H | C—Cl | C—H | H | CF3 | — | H | CN—[cyclopropyl]—CO |
| 6-32 | C—Cl | C—H | C—Cl | C—H | H | CF3 | — | H | CH2=CH—CO |
| 6-33 | C—Cl | C—H | C—Cl | C—H | H | CF3 | — | H | CH3CH=CH—CO |
| 6-34 | C—Cl | C—H | C—Cl | C—H | H | CF3 | — | H | CH2=C(CH3)—CO |
| 6-35 | C—Cl | C—H | C—Cl | C—H | H | CF3 | — | H | CH3CH=C(CH3)—CO |
| 6-36 | C—Cl | C—H | C—Cl | C—H | H | CF3 | — | H | (CH3)2C=CH—CO |
| 6-37 | C—Cl | C—H | C—Cl | C—H | H | CF3 | — | H | CH2=C(Cl)—CO |
| 6-38 | C—Cl | C—H | C—Cl | C—H | H | CF3 | — | H | ClCH=C(CH3)—CO |
| 6-39 | C—Cl | C—H | C—Cl | C—H | H | CF3 | — | H | CH2=CHCH2—CO |
| 6-40 | C—Cl | C—H | C—Cl | C—H | H | CF3 | — | H | HCC—CO |
| 6-41 | C—Cl | C—H | C—Cl | C—H | H | CF3 | — | H | CH3CC—CONH |
| 6-42 | C—Cl | C—H | C—Cl | C—H | H | CF3 | — | H | NCCH2—CO |
| 6-43 | C—Cl | C—H | C—Cl | C—H | H | CF3 | — | H | CH3OCH2—CO |
| 6-44 | C—Cl | C—H | C—Cl | C—H | H | CF3 | — | H | C2H5OCH2—CO |
| 6-45 | C—Cl | C—H | C—Cl | C—H | H | CF3 | — | H | CH3SCH2CO |
| 6-46 | C—Cl | C—H | C—Cl | C—H | H | CF3 | — | H | CH3O(CO)CH2—CO |
| 6-47 | C—Cl | C—H | C—Cl | C—H | H | CF3 | — | H | CH3(CO)OCH2—CO |
| 6-48 | C—Cl | C—H | C—Cl | C—H | H | CF3 | — | H | CH3O(CO)—CO |
| 6-49 | C—Cl | C—H | C—Cl | C—H | H | CF3 | — | H | CF3O(CO)—CO |
| 6-50 | C—Cl | C—H | C—Cl | C—H | H | CF3 | — | H | CH3(CO)CH2—CO |
| 6-51 | C—Cl | C—H | C—Cl | C—H | H | CF3 | — | H | (CH3)2NCH2—CO |
| 6-52 | C—Cl | C—H | C—Cl | C—H | H | CF3 | — | H | PhCO |
| 6-53 | C—Cl | C—H | C—Cl | C—H | H | CF3 | — | H | PhCH2CO |
| 6-54 | C—Cl | C—H | C—Cl | C—H | H | CF3 | — | H | 2-py-CO |
| 6-55 | C—Cl | C—H | C—Cl | C—H | H | CF3 | — | H | 3-py-CO |
| 6-56 | C—Cl | C—H | C—Cl | C—H | H | CF3 | — | H | 4-py-CO |
| 6-57 | C—Cl | C—H | C—Cl | C—H | H | CF3 | — | H | Cl—[pyridyl]—CO |
| 6-58 | C—Cl | C—H | C—Cl | C—H | H | CF3 | — | H | 2-F—PhCO |
| 6-59 | C—Cl | C—H | C—Cl | C—H | H | CF3 | — | H | 3-F—PhCO |
| 6-60 | C—Cl | C—H | C—Cl | C—H | H | CF3 | — | H | 4-F—PhCO |
| 6-61 | C—Cl | C—H | C—Cl | C—H | H | CF3 | — | H | 2-Cl—PhCO |
| 6-62 | C—Cl | C—H | C—Cl | C—H | H | CF3 | — | H | 3-Cl—PhCO |
| 6-63 | C—Cl | C—H | C—Cl | C—H | H | CF3 | — | H | 4-Cl—PhCO |
| 6-64 | C—Cl | C—H | C—Cl | C—H | H | CF3 | — | H | 2-Br—PhCO |
| 6-65 | C—Cl | C—H | C—Cl | C—H | H | CF3 | — | H | 2-CF3—PhCO |
| 6-66 | C—Cl | C—H | C—Cl | C—H | H | CF3 | — | H | 2-CH3—PhCO |
| 6-67 | C—Cl | C—H | C—Cl | C—H | H | CF3 | — | H | [2-furyl]—CO |
| 6-68 | C—Cl | C—H | C—Cl | C—H | H | CF3 | — | H | [3-furyl]—CO |
| 6-69 | C—Cl | C—H | C—Cl | C—H | H | CF3 | — | H | [2-thienyl]—CO |

TABLE 6-continued

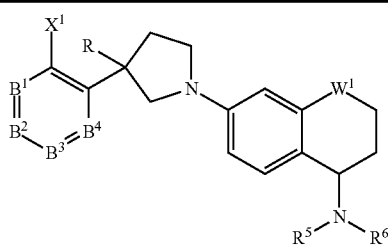

| Ex.-No. | B¹ | B² | B³ | B⁴ | X¹ | R | W¹ | R⁵ | R⁶ |
|---|---|---|---|---|---|---|---|---|---|
| 6-70 | C—Cl | C—H | C—Cl | C—H | H | CF3 | — | H | pyrrole-2-CO |
| 6-71 | C—Cl | C—H | C—Cl | C—H | H | CF3 | — | H | 3-CF3-pyrazol-4-CO |
| 6-72 | C—Cl | C—H | C—Cl | C—H | H | CF3 | — | H | 3-CF3-pyridin-2-CO |
| 6-73 | C—Cl | C—H | C—Cl | C—H | H | CF3 | — | H | pyridin-3-CH2CO |
| 6-74 | C—Cl | C—H | C—Cl | C—H | H | CF3 | — | H | Ph(CH3)CHCO |
| 6-75 | C—Cl | C—H | C—Cl | C—H | H | CF3 | — | H | CH3NHCO |
| 6-76 | C—Cl | C—H | C—Cl | C—H | H | CF3 | — | H | CH3CH2NHCO |
| 6-77 | C—Cl | C—H | C—Cl | C—H | H | CF3 | — | H | CF3CH2NHCO |
| 6-78 | C—Cl | C—H | C—Cl | C—H | H | CF3 | — | H | n-PrNHCO |
| 6-79 | C—Cl | C—H | C—Cl | C—H | H | CF3 | — | H | iso-PrNHCO |
| 6-80 | C—Cl | C—H | C—Cl | C—H | H | CF3 | — | H | cyclo-PrNHCO |
| 6-81 | C—Cl | C—H | C—Cl | C—H | H | CF3 | — | H | n-BuNHCO |
| 6-82 | C—Cl | C—H | C—Cl | C—H | H | CF3 | — | H | tert-BuNHCO |
| 6-83 | C—Cl | C—H | C—Cl | C—H | H | CF3 | — | H | cyclo-BuNHCO |
| 6-84 | C—Cl | C—H | C—Cl | C—H | H | CF3 | — | H | cyclo-PenNHCO |
| 6-85 | C—Cl | C—H | C—Cl | C—H | H | CF3 | — | H | cyclo-HexNHCO |
| 6-86 | C—Cl | C—H | C—Cl | C—H | H | CF3 | — | H | CH2=CHCH2NHCO |
| 6-87 | C—Cl | C—H | C—Cl | C—H | H | CF3 | — | H | HCCCH2NHCO |
| 6-88 | C—Cl | C—H | C—Cl | C—H | H | CF3 | — | H | cyclo-PrCH2NHCO |
| 6-89 | C—Cl | C—H | C—Cl | C—H | H | CF3 | — | H | NCCH2NHCO |
| 6-90 | C—Cl | C—H | C—Cl | C—H | H | CF3 | — | H | CF3(CH3)CHNHCO |
| 6-91 | C—Cl | C—H | C—Cl | C—H | H | CF3 | — | H | CF3(CH3)2CNCO |
| 6-93 | C—Cl | C—H | C—Cl | C—H | H | CF3 | — | H | FCH2CH2NHCO |
| 6-94 | C—Cl | C—H | C—Cl | C—H | H | CF3 | — | H | CF3CH2CH2NHCO |
| 6-95 | C—Cl | C—H | C—Cl | C—H | H | CF3 | — | H | HCF2CF2CH2NHCO |
| 6-96 | C—Cl | C—H | C—Cl | C—H | H | CF3 | — | H | 2-F-cyclopropyl-NHCO |
| 6-97 | C—Cl | C—H | C—Cl | C—H | H | CF3 | — | H | 3-CF3-cyclohexyl-NHCO |
| 6-98 | C—Cl | C—H | C—Cl | C—H | H | CF3 | — | H | EtO2CCH2NHCO |
| 6-99 | C—Cl | C—H | C—Cl | C—H | H | CF3 | — | H | 2-CF3—PhNHCO |
| 6-100 | C—Cl | C—H | C—Cl | C—H | H | CF3 | — | H | 3-CF3—PhNHCO |
| 6-101 | C—Cl | C—H | C—Cl | C—H | H | CF3 | — | H | 4-CF3—PhNHCO |
| 6-102 | C—Cl | C—H | C—Cl | C—H | H | CH3 | — | H | 2-py-NHCO |
| 6-103 | C—Cl | C—H | C—Cl | C—H | H | CH3 | — | H | 3-py-NHCO |
| 6-104 | C—Cl | C—H | C—Cl | C—H | H | CH3 | — | H | 4-py-NHCO |

TABLE 6-continued

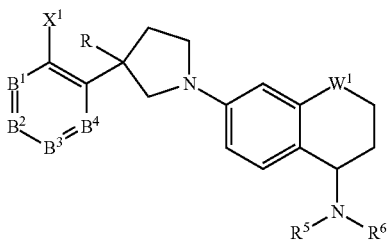

| Ex.-No. | B¹ | B² | B³ | B⁴ | X¹ | R | W¹ | R⁵ | R⁶ |
|---|---|---|---|---|---|---|---|---|---|
| 6-105 | C—Cl | C—H | C—Cl | C—H | H | CH3 | — | H | $F_3C$-pyridine-NHCO (5-CF3-2-pyridyl) |
| 6-106 | C—Cl | C—H | C—Cl | C—H | H | CH3 | — | H | $F_3C$-pyridine-NHCO (6-CF3-3-pyridyl) |
| 6-107 | C—Cl | C—H | C—Cl | C—H | H | CH3 | — | H | PhCH2HNCO |
| 6-108 | C—Cl | C—H | C—Cl | C—H | H | CH3 | — | H | 2-pyridyl-CH2-NHCO |
| 6-109 | C—Cl | C—H | C—Cl | C—H | H | CH3 | — | H | (CH3)2NCO |
| 6-110 | C—Cl | C—H | C—Cl | C—H | H | CH3 | — | H | pyrrolidineCO |
| 6-111 | C—Cl | C—H | C—Cl | C—H | H | CH3 | — | H | piperidineCO |
| 6-112 | C—Cl | C—H | C—Cl | C—H | H | CH3 | — | H | morpholineCO |
| 6-113 | C—Cl | C—H | C—Cl | C—H | H | CF3 | — | H | CH3OCO |
| 6-114 | C—Cl | C—H | C—Cl | C—H | H | CF3 | — | H | CH3CH2OCO |
| 6-115 | C—Cl | C—H | C—Cl | C—H | H | CF3 | — | H | n-PrOCO |
| 6-116 | C—Cl | C—H | C—Cl | C—H | H | CF3 | — | H | cyclo-PrOCO |
| 6-117 | C—Cl | C—H | C—Cl | C—H | H | CF3 | — | H | CF3CH2OCO |
| 6-118 | C—Cl | C—H | C—Cl | C—H | H | CF3 | — | H | CH2=CHCH2OCO |
| 6-119 | C—Cl | C—H | C—Cl | C—H | H | CF3 | — | H | HCCCH2OCO |
| 6-120 | C—Cl | C—H | C—Cl | C—H | H | CF3 | — | H | PhOCO |
| 6-121 | C—Cl | C—H | C—Cl | C—H | H | CF3 | — | H | PhCH2OCO |
| 6-122 | C—Cl | C—H | C—Cl | C—H | H | CF3 | — | H | tert-BuOCO |
| 6-123 | C—Cl | C—H | C—Cl | C—H | H | CF3 | — | H | CH3SO2 |
| 6-124 | C—Cl | C—H | C—Cl | C—H | H | CF3 | — | H | CH3CH2SO2 |
| 6-125 | C—Cl | C—H | C—Cl | C—H | H | CF3 | — | H | CF3SO2NH |
| 6-126 | C—Cl | C—H | C—Cl | C—H | H | CF3 | — | H | CF3CH2SO2 |
| 6-127 | C—Cl | C—H | C—Cl | C—H | H | CF3 | — | H | PhSO2 |
| 6-128 | C—Cl | C—H | C—Cl | C—H | H | CF3 | — | H | CH3NHCONHSO2 |
| 6-129 | C—Cl | C—H | C—Cl | C—H | H | CF3 | — | H | (CH3)2NCONHSO2 |
| 6-130 | C—Cl | C—H | C—Cl | C—H | H | CF3 | — | H | CH3CS |
| 6-131 | C—Cl | C—H | C—Cl | C—H | H | CF3 | — | H | CH3CH2CS |
| 6-132 | C—Cl | C—H | C—Cl | C—H | H | CF3 | — | H | cyclo-PrCS |
| 6-133 | C—Cl | C—H | C—Cl | C—H | H | CF3 | — | H | CF3CH2CS |
| 6-134 | C—Cl | C—H | C—Cl | C—H | H | CF3 | CH2 | H | H |
| 6-135 | C—Cl | C—H | C—Cl | C—H | H | CF3 | CH2 | H | HCO |
| 6-136 | C—Cl | C—H | C—Cl | C—H | H | CF3 | CH2 | H | CH3CO |
| 6-137 | C—Cl | C—H | C—Cl | C—H | H | CF3 | CH2 | H | CH3CH2CO |
| 6-138 | C—Cl | C—H | C—Cl | C—H | H | CF3 | CH2 | H | n-PrCO |
| 6-139 | C—Cl | C—H | C—Cl | C—H | H | CF3 | CH2 | H | iso-PrCO |
| 6-140 | C—Cl | C—H | C—Cl | C—H | H | CF3 | CH2 | H | cyclo-PrCO |
| 6-141 | C—Cl | C—H | C—Cl | C—H | H | CF3 | CH2 | H | n-BuCO |
| 6-142 | C—Cl | C—H | C—Cl | C—H | H | CF3 | CH2 | H | tert-BuCO |
| 6-143 | C—Cl | C—H | C—Cl | C—H | H | CF3 | CH2 | H | iso-BuCO |
| 6-144 | C—Cl | C—H | C—Cl | C—H | H | CF3 | CH2 | H | cyclo-BuCO |
| 6-145 | C—Cl | C—H | C—Cl | C—H | H | CF3 | CH2 | H | (CH3)3CCH2CO |
| 6-146 | C—Cl | C—H | C—Cl | C—H | H | CF3 | CH2 | H | cyclo-PenCO |
| 6-147 | C—Cl | C—H | C—Cl | C—H | H | CF3 | CH2 | H | cyclo-HexCO |
| 6-148 | C—Cl | C—H | C—Cl | C—H | H | CF3 | CH2 | H | cyclo-PrCH2CO |
| 6-149 | C—Cl | C—H | C—Cl | C—H | H | CF3 | CH2 | H | CF3CO |
| 6-150 | C—Cl | C—H | C—Cl | C—H | H | CF3 | CH2 | H | CCl3CO |
| 6-151 | C—Cl | C—H | C—Cl | C—H | H | CF3 | CH2 | H | ClCH2CO |
| 6-152 | C—Cl | C—H | C—Cl | C—H | H | CF3 | CH2 | H | CF2ClCO |
| 6-153 | C—Cl | C—H | C—Cl | C—H | H | CF3 | CH2 | H | ClCH2CH2CO |
| 6-154 | C—Cl | C—H | C—Cl | C—H | H | CF3 | CH2 | H | HCF2CF2CO |
| 6-155 | C—Cl | C—H | C—Cl | C—H | H | CF3 | CH2 | H | CF3CH2CO |

TABLE 6-continued

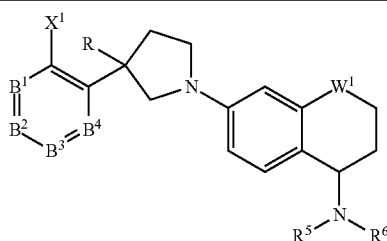

| ExNo. | B¹ | B² | B³ | B⁴ | X¹ | R | W¹ | R⁵ | R⁶ |
|---|---|---|---|---|---|---|---|---|---|
| 6-156 | C—Cl | C—H | C—Cl | C—H | H | CF3 | CH2 | H | (CF3)2CHCO |
| 6-157 | C—Cl | C—H | C—Cl | C—H | H | CF3 | CH2 | H | HCF2CO |
| 6-158 | C—Cl | C—H | C—Cl | C—H | H | CF3 | CH2 | H | ClCH2CO |
| 6-159 | C—Cl | C—H | C—Cl | C—H | H | CF3 | CH2 | H | H3C−⟨△⟩−CO |
| 6-160 | C—Cl | C—H | C—Cl | C—H | H | CF3 | CH2 | H | Cl,Cl−⟨△⟩−CO |
| 6-161 | C—Cl | C—H | C—Cl | C—H | H | CF3 | CH2 | H | F,F−⟨△⟩−CO |
| 6-162 | C—Cl | C—H | C—Cl | C—H | H | CF3 | CH2 | H | F−⟨△⟩−CO |
| 6-163 | C—Cl | C—H | C—Cl | C—H | H | CF3 | CH2 | H | H3C−⟨△⟩−CO |
| 6-164 | C—Cl | C—H | C—Cl | C—H | H | CF3 | CH2 | H | CN−⟨△⟩−CO |
| 6-165 | C—Cl | C—H | C—Cl | C—H | H | CF3 | CH2 | H | CH2=CH—CO |
| 6-166 | C—Cl | C—H | C—Cl | C—H | H | CF3 | CH2 | H | CH3CH=CH—CO |
| 6-167 | C—Cl | C—H | C—Cl | C—H | H | CF3 | CH2 | H | CH2=C(CH3)—CO |
| 6-168 | C—Cl | C—H | C—Cl | C—H | H | CF3 | CH2 | H | CH3CH=C(CH3)—CO |
| 6-169 | C—Cl | C—H | C—Cl | C—H | H | CF3 | CH2 | H | (CH3)2C=CH—CO |
| 6-170 | C—Cl | C—H | C—Cl | C—H | H | CF3 | CH2 | H | CH2=C(Cl)—CO |
| 6-171 | C—Cl | C—H | C—Cl | C—H | H | CF3 | CH2 | H | ClCH=C(CH3)—CO |
| 6-172 | C—Cl | C—H | C—Cl | C—H | H | CF3 | CH2 | H | CH2=CHCH2—CO |
| 6-173 | C—Cl | C—H | C—Cl | C—H | H | CF3 | CH2 | H | HCC—CO |
| 6-174 | C—Cl | C—H | C—Cl | C—H | H | CF3 | CH2 | H | CH3CC—CONH |
| 6-175 | C—Cl | C—H | C—Cl | C—H | H | CF3 | CH2 | H | NCCH2—CO |
| 6-176 | C—Cl | C—H | C—Cl | C—H | H | CF3 | CH2 | H | CH3OCH2—CO |
| 6-177 | C—Cl | C—H | C—Cl | C—H | H | CF3 | CH2 | H | C2H5OCH2—CO |
| 6-178 | C—Cl | C—H | C—Cl | C—H | H | CF3 | CH2 | H | CH3SCH2CO |
| 6-179 | C—Cl | C—H | C—Cl | C—H | H | CF3 | CH2 | H | CH3O(CO)CH2—CO |
| 6-180 | C—Cl | C—H | C—Cl | C—H | H | CF3 | CH2 | H | CH3(CO)OCH2—CO |
| 6-181 | C—Cl | C—H | C—Cl | C—H | H | CF3 | CH2 | H | CH3O(CO)—CO |
| 6-182 | C—Cl | C—H | C—Cl | C—H | H | CF3 | CH2 | H | CF3O(CO)—CO |
| 6-183 | C—Cl | C—H | C—Cl | C—H | H | CF3 | CH2 | H | CH3(CO)CH2—CO |
| 6-184 | C—Cl | C—H | C—Cl | C—H | H | CF3 | CH2 | H | (CH3)2NCH2—CO |
| 6-185 | C—Cl | C—H | C—Cl | C—H | H | CF3 | CH2 | H | PhCO |
| 6-186 | C—Cl | C—H | C—Cl | C—H | H | CF3 | CH2 | H | PhCH2CO |
| 6-187 | C—Cl | C—H | C—Cl | C—H | H | CF3 | CH2 | H | 2-py-CO |
| 6-188 | C—Cl | C—H | C—Cl | C—H | H | CF3 | CH2 | H | 3-py-CO |
| 6-189 | C—Cl | C—H | C—Cl | C—H | H | CF3 | CH2 | H | 4-py-CO |
| 6-190 | C—Cl | C—H | C—Cl | C—H | H | CF3 | CH2 | H | Cl-pyridyl-CO |
| 6-191 | C—Cl | C—H | C—Cl | C—H | H | CF3 | CH2 | H | 2-F—PhCO |
| 6-192 | C—Cl | C—H | C—Cl | C—H | H | CF3 | CH2 | H | 3-F—PhCO |
| 6-193 | C—Cl | C—H | C—Cl | C—H | H | CF3 | CH2 | H | 4-F—PhCO |
| 6-194 | C—Cl | C—H | C—Cl | C—H | H | CF3 | CH2 | H | 2-Cl—PhCO |
| 6-195 | C—Cl | C—H | C—Cl | C—H | H | CF3 | CH2 | H | 3-Cl—PhCO |
| 6-196 | C—Cl | C—H | C—Cl | C—H | H | CF3 | CH2 | H | 4-Cl—PhCO |
| 6-197 | C—Cl | C—H | C—Cl | C—H | H | CF3 | CH2 | H | 2-Br—PhCO |
| 6-198 | C—Cl | C—H | C—Cl | C—H | H | CF3 | CH2 | H | 2-CF3—PhCO |

TABLE 6-continued

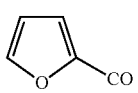

| Ex.-No. | B¹ | B² | B³ | B⁴ | X¹ | R | W¹ | R⁵ | R⁶ |
|---|---|---|---|---|---|---|---|---|---|
| 6-199 | C—Cl | C—H | C—Cl | C—H | H | CF3 | CH2 | H | 2-CH3—PhCO |
| 6-200 | C—Cl | C—H | C—Cl | C—H | H | CF3 | CH2 | H | 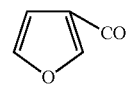 |
| 6-201 | C—Cl | C—H | C—Cl | C—H | H | CF3 | CH2 | H | 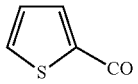 |
| 6-202 | C—Cl | C—H | C—Cl | C—H | H | CF3 | CH2 | H | 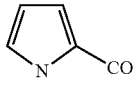 |
| 6-203 | C—Cl | C—H | C—Cl | C—H | H | CF3 | CH2 | H | 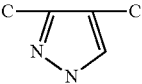 |
| 6-204 | C—Cl | C—H | C—Cl | C—H | H | CF3 | CH2 | H | 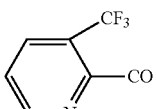 |
| 6-205 | C—Cl | C—H | C—Cl | C—H | H | CF3 | CH2 | H | 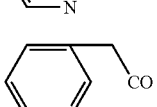 |
| 6-206 | C—Cl | C—H | C—Cl | C—H | H | CF3 | CH2 | H | 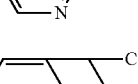 |
| 6-207 | C—Cl | C—H | C—Cl | C—H | H | CF3 | CH2 | H | |
| 6-208 | C—Cl | C—H | C—Cl | C—H | H | CF3 | CH2 | H | CH3NHCO |
| 6-209 | C—Cl | C—H | C—Cl | C—H | H | CF3 | CH2 | H | CH3CH2NHCO |
| 6-210 | C—Cl | C—H | C—Cl | C—H | H | CF3 | CH2 | H | CF3CH2NHCO |
| 6-211 | C—Cl | C—H | C—Cl | C—H | H | CF3 | CH2 | H | n-PrNHCO |
| 6-212 | C—Cl | C—H | C—Cl | C—H | H | CF3 | CH2 | H | iso-PrNHCO |
| 6-213 | C—Cl | C—H | C—Cl | C—H | H | CF3 | CH2 | H | cyclo-PrNHCO |
| 6-214 | C—Cl | C—H | C—Cl | C—H | H | CF3 | CH2 | H | n-BuNHCO |
| 6-215 | C—Cl | C—H | C—Cl | C—H | H | CF3 | CH2 | H | tert-BuNHCO |
| 6-216 | C—Cl | C—H | C—Cl | C—H | H | CF3 | CH2 | H | cyclo-BuNHCO |
| 6-217 | C—Cl | C—H | C—Cl | C—H | H | CF3 | CH2 | H | cyclo-PenNHCO |
| 6-218 | C—Cl | C—H | C—Cl | C—H | H | CF3 | CH2 | H | cyclo-HexNHCO |
| 6-219 | C—Cl | C—H | C—Cl | C—H | H | CF3 | CH2 | H | CH2=CHCH2NHCO |
| 6-220 | C—Cl | C—H | C—Cl | C—H | H | CF3 | CH2 | H | HCCCH2NHCO |
| 6-221 | C—Cl | C—H | C—Cl | C—H | H | CF3 | CH2 | H | cyclo-PrCH2NHCO |
| 6-222 | C—Cl | C—H | C—Cl | C—H | H | CF3 | CH2 | H | NCCH2NHCO |
| 6-223 | C—Cl | C—H | C—Cl | C—H | H | CF3 | CH2 | H | CF3(CH3)CHNHCO |
| 6-224 | C—Cl | C—H | C—Cl | C—H | H | CF3 | CH2 | H | CF3(CH3)2CNCO |
| 6-226 | C—Cl | C—H | C—Cl | C—H | H | CF3 | CH2 | H | FCH2CH2NHCO |
| 6-227 | C—Cl | C—H | C—Cl | C—H | H | CF3 | CH2 | H | CF3CH2CH2NHCO |
| 6-228 | C—Cl | C—H | C—Cl | C—H | H | CF3 | CH2 | H | HCF2CF2CH2NHCO |

TABLE 6-continued

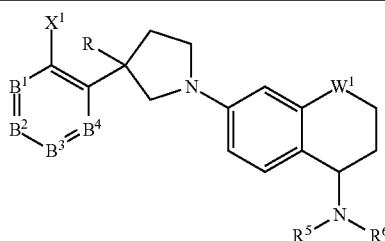

| ExNo. | B¹ | B² | B³ | B⁴ | X¹ | R | W¹ | R⁵ | R⁶ |
|---|---|---|---|---|---|---|---|---|---|
| 6-229 | C—Cl | C—H | C—Cl | C—H | H | CF3 | CH2 | H | F-cyclopropyl-NHCO |
| 6-230 | C—Cl | C—H | C—Cl | C—H | H | CF3 | CH2 | H | CF3-cyclohexyl-NHCO |
| 6-231 | C—Cl | C—H | C—Cl | C—H | H | CF3 | CH2 | H | EtO2CCH2NHCO |
| 6-232 | C—Cl | C—H | C—Cl | C—H | H | CF3 | CH2 | H | 2-CF3—PhNHCO |
| 6-233 | C—Cl | C—H | C—Cl | C—H | H | CF3 | CH2 | H | 3-CF3—PhNHCO |
| 6-234 | C—Cl | C—H | C—Cl | C—H | H | CF3 | CH2 | H | 4-CF3—PhNHCO |
| 6-235 | C—Cl | C—H | C—Cl | C—H | H | CF3 | CH2 | H | 2-py-NHCO |
| 6-236 | C—Cl | C—H | C—Cl | C—H | H | CF3 | CH2 | H | 3-py-NHCO |
| 6-237 | C—Cl | C—H | C—Cl | C—H | H | CF3 | CH2 | H | 4-py-NHCO |
| 6-238 | C—Cl | C—H | C—Cl | C—H | H | CF3 | CH2 | H | 5-CF3-pyridin-2-yl-NHCO |
| 6-239 | C—Cl | C—H | C—Cl | C—H | H | CF3 | CH2 | H | 6-CF3-pyridin-3-yl-NHCO |
| 6-240 | C—Cl | C—H | C—Cl | C—H | H | CF3 | CH2 | H | PhCH2HNCO |
| 6-241 | C—Cl | C—H | C—Cl | C—H | H | CF3 | CH2 | H | (pyridin-2-yl)CH2NHCO |
| 6-242 | C—Cl | C—H | C—Cl | C—H | H | CF3 | CH2 | H | (CH3)2NCO |
| 6-243 | C—Cl | C—H | C—Cl | C—H | H | CF3 | CH2 | H | pyrrolidineCO |
| 6-244 | C—Cl | C—H | C—Cl | C—H | H | CF3 | CH2 | H | piperidineCO |
| 6-245 | C—Cl | C—H | C—Cl | C—H | H | CF3 | CH2 | H | morpholineCO |
| 6-246 | C—Cl | C—H | C—Cl | C—H | H | CF3 | CH2 | H | CH3OCO |
| 6-247 | C—Cl | C—H | C—Cl | C—H | H | CF3 | CH2 | H | CH3CH2OCO |
| 6-248 | C—Cl | C—H | C—Cl | C—H | H | CF3 | CH2 | H | n-PrOCO |
| 6-249 | C—Cl | C—H | C—Cl | C—H | H | CF3 | CH2 | H | cyclo-PrOCO |
| 6-250 | C—Cl | C—H | C—Cl | C—H | H | CF3 | CH2 | H | CF3CH2OCO |
| 6-251 | C—Cl | C—H | C—Cl | C—H | H | CF3 | CH2 | H | CH2=CHCH2OCO |
| 6-252 | C—Cl | C—H | C—Cl | C—H | H | CF3 | CH2 | H | HCCCH2OCO |
| 6-253 | C—Cl | C—H | C—Cl | C—H | H | CF3 | CH2 | H | PhOCO |
| 6-254 | C—Cl | C—H | C—Cl | C—H | H | CF3 | CH2 | H | PhCH2OCO |
| 6-255 | C—Cl | C—H | C—Cl | C—H | H | CF3 | CH2 | H | tert-BuOCO |
| 6-256 | C—Cl | C—H | C—Cl | C—H | H | CF3 | CH2 | H | CH3SO2 |
| 6-257 | C—Cl | C—H | C—Cl | C—H | H | CF3 | CH2 | H | CH3CH2SO2 |
| 6-258 | C—Cl | C—H | C—Cl | C—H | H | CF3 | CH2 | H | CF3SO2NH |
| 6-259 | C—Cl | C—H | C—Cl | C—H | H | CF3 | CH2 | H | CF3CH2SO2 |
| 6-260 | C—Cl | C—H | C—Cl | C—H | H | CF3 | CH2 | H | PhSO2 |
| 6-261 | C—Cl | C—H | C—Cl | C—H | H | CF3 | CH2 | H | CH3NHCONHSO2 |
| 6-262 | C—Cl | C—H | C—Cl | C—H | H | CF3 | CH2 | H | (CH3)2NCONHSO2 |
| 6-263 | C—Cl | C—H | C—Cl | C—H | H | CF3 | CH2 | H | CH3CS |
| 6-264 | C—Cl | C—H | C—Cl | C—H | H | CF3 | CH2 | H | CH3CH2CS |
| 6-265 | C—Cl | C—H | C—Cl | C—H | H | CF3 | CH2 | H | cyclo-PrCS |
| 6-266 | C—Cl | C—H | C—Cl | C—H | H | CF3 | CH2 | H | CF3CH2CS |
| 6-267 | C—Cl | C—Cl | C—Cl | C—H | H | CF3 | — | H | CH3CO |
| 6-268 | C—Cl | C—Cl | C—Cl | C—H | H | CF3 | — | H | CH3CH2CO |
| 6-269 | C—Cl | C—Cl | C—Cl | C—H | H | CF3 | — | H | cyclo-PrCO |
| 6-270 | C—Cl | C—Cl | C—Cl | C—H | H | CF3 | — | H | CF3CH2CO |
| 6-271 | C—Cl | C—Cl | C—Cl | C—H | H | CF3 | — | H | CH3CH2NHCO |

TABLE 6-continued

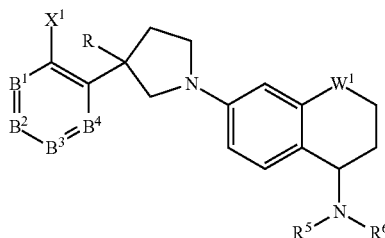

| Ex.-No. | B¹ | B² | B³ | B⁴ | X¹ | R | W¹ | R⁵ | R⁶ |
|---|---|---|---|---|---|---|---|---|---|
| 6-272 | C—CF3 | C—H | C—CF3 | C—H | H | CF3 | — | H | CH3CO |
| 6-273 | C—CF3 | C—H | C—CF3 | C—H | H | CF3 | — | H | CH3CH2CO |
| 6-274 | C—CF3 | C—H | C—CF3 | C—H | H | CF3 | — | H | cyclo-PrCO |
| 6-275 | C—CF3 | C—H | C—CF3 | C—H | H | CF3 | — | H | CF3CH2CO |
| 6-276 | C—CF3 | C—H | C—CF3 | C—H | H | CF3 | — | H | CH3CH2NHCO |
| 6-277 | C—Cl | C—Cl | C—CF3 | C—H | H | CF3 | — | H | CH3CO |
| 6-278 | C—Cl | C—Cl | C—CF3 | C—H | H | CF3 | — | H | CH3CH2CO |
| 6-279 | C—Cl | C—Cl | C—CF3 | C—H | H | CF3 | — | H | cyclo-PrCO |
| 6-280 | C—Cl | C—Cl | C—CF3 | C—H | H | CF3 | — | H | CF3CH2CO |
| 6-281 | C—Cl | C—Cl | C—CF3 | C—H | H | CF3 | — | H | CH3CH2NHCO |
| 6-282 | C—Br | C—H | C—Br | C—H | H | CF3 | — | H | CH3CO |
| 6-283 | C—Br | C—H | C—Br | C—H | H | CF3 | — | H | CH3CH2CO |
| 6-284 | C—Br | C—H | C—Br | C—H | H | CF3 | — | H | cyclo-PrCO |
| 6-285 | C—Br | C—H | C—Br | C—H | H | CF3 | — | H | CF3CH2CO |
| 6-286 | C—Br | C—H | C—Br | C—H | H | CF3 | — | H | CH3CH2NHCO |
| 6-287 | C—Cl | C—Cl | C—Cl | C—H | H | CF3 | CH2 | H | CH3CO |
| 6-288 | C—Cl | C—Cl | C—Cl | C—H | H | CF3 | CH2 | H | CH3CH2CO |
| 6-289 | C—Cl | C—Cl | C—Cl | C—H | H | CF3 | CH2 | H | cyclo-PrCO |
| 6-290 | C—Cl | C—Cl | C—Cl | C—H | H | CF3 | CH2 | H | CF3CH2CO |
| 6-291 | C—Cl | C—Cl | C—Cl | C—H | H | CF3 | CH2 | H | CH3CH2NHCO |
| 6-292 | C—CF3 | C—H | C—CF3 | C—H | H | CF3 | CH2 | H | CH3CO |
| 6-293 | C—CF3 | C—H | C—CF3 | C—H | H | CF3 | CH2 | H | CH3CH2CO |
| 6-294 | C—CF3 | C—H | C—CF3 | C—H | H | CF3 | CH2 | H | cyclo-PrCO |
| 6-295 | C—CF3 | C—H | C—CF3 | C—H | H | CF3 | CH2 | H | CF3CH2CO |
| 6-296 | C—CF3 | C—H | C—CF3 | C—H | H | CF3 | CH2 | H | CH3CH2NHCO |
| 6-297 | C—Cl | C—Cl | C—CF3 | C—H | H | CF3 | CH2 | H | CH3CO |
| 6-298 | C—Cl | C—Cl | C—CF3 | C—H | H | CF3 | CH2 | H | CH3CH2CO |
| 6-299 | C—Cl | C—Cl | C—CF3 | C—H | H | CF3 | CH2 | H | cyclo-PrCO |
| 6-300 | C—Cl | C—Cl | C—CF3 | C—H | H | CF3 | CH2 | H | CF3CH2CO |
| 6-301 | C—Cl | C—Cl | C—CF3 | C—H | H | CF3 | CH2 | H | CH3CH2NHCO |
| 6-302 | C—Cl | C—H | C—H | C—H | H | CF3 | — | H | CH3CO |
| 6-303 | C—Cl | C—H | C—H | C—H | H | CF3 | — | H | CH3CH2CO |
| 6-304 | C—Cl | C—H | C—H | C—H | H | CF3 | — | H | n-PrCO |
| 6-305 | C—Cl | C—H | C—H | C—H | H | CF3 | — | H | cyclo-PrCO |
| 6-306 | C—Cl | C—H | C—H | C—H | H | CF3 | — | H | cyclo-PrCH2CO |
| 6-307 | C—Cl | C—H | C—H | C—H | H | CF3 | — | H | CF3CH2CO |
| 6-308 | C—Cl | C—H | C—H | C—H | H | CF3 | — | H | CH3SCH2CO |
| 6-309 | C—Cl | C—H | C—H | C—H | H | CF3 | — | H | CH3S(O)CH2CO |
| 6-310 | C—Cl | C—H | C—H | C—H | H | CF3 | — | H | CH3SO2CH2CO |
| 6-311 | C—Cl | C—H | C—H | C—H | H | CF3 | — | H | CH3CH2NHCO |
| 6-312 | C—Cl | C—H | C—H | C—H | F | CF3 | — | H | CH3CO |
| 6-313 | C—Cl | C—H | C—H | C—H | F | CF3 | — | H | CH3CH2CO |
| 6-314 | C—Cl | C—H | C—H | C—H | F | CF3 | — | H | n-PrCO |
| 6-315 | C—Cl | C—H | C—H | C—H | F | CF3 | — | H | cyclo-PrCO |
| 6-316 | C—Cl | C—H | C—H | C—H | F | CF3 | — | H | cyclo-PrCH2CO |
| 6-317 | C—Cl | C—H | C—H | C—H | F | CF3 | — | H | CF3CH2CO |
| 6-318 | C—Cl | C—H | C—H | C—H | F | CF3 | — | H | CH3SCH2CO |
| 6-319 | C—Cl | C—H | C—H | C—H | F | CF3 | — | H | CH3S(O)CH2CO |
| 6-320 | C—Cl | C—H | C—H | C—H | F | CF3 | — | H | CH3SO2CH2CO |
| 6-321 | C—Cl | C—H | C—H | C—H | F | CF3 | — | H | CH3CH2NHCO |
| 6-322 | C—H | C—H | C—Cl | C—H | F | CF3 | — | H | CH3CO |
| 6-323 | C—H | C—H | C—Cl | C—H | F | CF3 | — | H | CH3CH2CO |
| 6-324 | C—H | C—H | C—Cl | C—H | F | CF3 | — | H | n-PrCO |
| 6-325 | C—H | C—H | C—Cl | C—H | F | CF3 | — | H | cyclo-PrCO |
| 6-326 | C—H | C—H | C—Cl | C—H | F | CF3 | — | H | cyclo-PrCH2CO |
| 6-327 | C—H | C—H | C—Cl | C—H | F | CF3 | — | H | CF3CH2CO |
| 6-328 | C—H | C—H | C—Cl | C—H | F | CF3 | — | H | CH3SCH2CO |
| 6-329 | C—H | C—H | C—Cl | C—H | F | CF3 | — | H | CH3S(O)CH2CO |
| 6-330 | C—H | C—H | C—Cl | C—H | F | CF3 | — | H | CH3SO2CH2CO |
| 6-331 | C—H | C—H | C—Cl | C—H | F | CF3 | — | H | CH3CH2NHCO |
| 6-332 | C—Cl | C—H | C—Cl | C—H | H | CF3 | — | H | CH3OCH2CH2CO |
| 6-333 | C—Cl | C—H | C—Cl | C—H | H | CF3 | — | H | CH3CH2OCH2CH2CO |
| 6-334 | C—Cl | C—H | C—Cl | C—H | H | CF3 | — | H | CH3S(O)CH2CO |
| 6-335 | C—Cl | C—H | C—Cl | C—H | H | CF3 | — | H | CH3SO2CH2CO |
| 6-336 | C—Cl | C—H | C—Br | C—H | H | CF3 | — | H | CH3CO |
| 6-337 | C—Cl | C—H | C—Br | C—H | H | CF3 | — | H | CH3CH2CO |

TABLE 6-continued

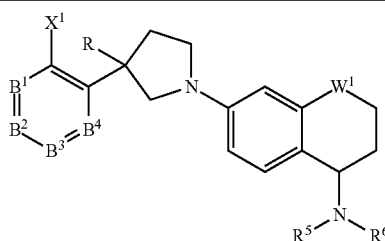

| Ex.-No. | B¹ | B² | B³ | B⁴ | X¹ | R | W¹ | R⁵ | R⁶ |
|---|---|---|---|---|---|---|---|---|---|
| 6-338 | C—Cl | C—H | C—Br | C—H | H | CF3 | — | H | n-PrCO |
| 6-339 | C—Cl | C—H | C—Br | C—H | H | CF3 | — | H | cyclo-PrCO |
| 6-340 | C—Cl | C—H | C—Br | C—H | H | CF3 | — | H | cyclo-PrCH2CO |
| 6-341 | C—Cl | C—H | C—Br | C—H | H | CF3 | — | H | CF3CH2CO |
| 6-342 | C—Cl | C—H | C—Br | C—H | H | CF3 | — | H | CH3SCH2CO |
| 6-343 | C—Cl | C—H | C—Br | C—H | H | CF3 | — | H | CH3S(O)CH2CO |
| 6-344 | C—Cl | C—H | C—Br | C—H | H | CF3 | — | H | CH3SO2CH2CO |
| 6-345 | C—Cl | C—H | C—Br | C—H | H | CF3 | — | H | CH3CH2NHCO |
| 6-346 | C—Br | C—H | C—Br | C—H | H | CF3 | — | H | n-PrCO |
| 6-347 | C—Br | C—H | C—Br | C—H | H | CF3 | — | H | cyclo-PrCH2CO |
| 6-348 | C—Br | C—H | C—Br | C—H | H | CF3 | — | H | CH3SCH2CO |
| 6-349 | C—Br | C—H | C—Br | C—H | H | CF3 | — | H | CH3S(O)CH2CO |
| 6-350 | C—Br | C—H | C—Br | C—H | H | CF3 | — | H | CH3SO2CH2CO |
| 6-351 | C—Cl | C—F | C—Cl | C—H | H | CF3 | — | H | CH3CO |
| 6-352 | C—Cl | C—F | C—Cl | C—H | H | CF3 | — | H | CH3CH2CO |
| 6-353 | C—Cl | C—F | C—Cl | C—H | H | CF3 | — | H | n-PrCO |
| 6-354 | C—Cl | C—F | C—Cl | C—H | H | CF3 | — | H | cyclo-PrCO |
| 6-355 | C—Cl | C—F | C—Cl | C—H | H | CF3 | — | H | cyclo-PrCH2CO |
| 6-356 | C—Cl | C—F | C—Cl | C—H | H | CF3 | — | H | CF3CH2CO |
| 6-357 | C—Cl | C—F | C—Cl | C—H | H | CF3 | — | H | CH3SCH2CO |
| 6-358 | C—Cl | C—F | C—Cl | C—H | H | CF3 | — | H | CH3S(O)CH2CO |
| 6-359 | C—Cl | C—F | C—Cl | C—H | H | CF3 | — | H | CH3SO2CH2CO |
| 6-360 | C—Cl | C—F | C—Cl | C—H | H | CF3 | — | H | CH3CH2NHCO |
| 6-361 | C—Cl | C—Cl | C—Cl | C—H | H | CF3 | — | H | n-PrCO |
| 6-362 | C—Cl | C—Cl | C—Cl | C—H | H | CF3 | — | H | cyclo-PrCH2CO |
| 6-363 | C—Cl | C—Cl | C—Cl | C—H | H | CF3 | — | H | CH3OCH2CH2CO |
| 6-364 | C—Cl | C—Cl | C—Cl | C—H | H | CF3 | — | H | CH3CH2OCH2CH2CO |
| 6-365 | C—Cl | C—Cl | C—Cl | C—H | H | CF3 | — | H | CH3SCH2CO |
| 6-366 | C—Cl | C—Cl | C—Cl | C—H | H | CF3 | — | H | CH3S(O)CH2CO |
| 6-367 | C—Cl | C—Cl | C—Cl | C—H | H | CF3 | — | H | CH3SO2CH2CO |
| 6-368 | C—Cl | C—Br | C—Cl | C—H | H | CF3 | — | H | CH3CO |
| 6-369 | C—Cl | C—Br | C—Cl | C—H | H | CF3 | — | H | CH3CH2CO |
| 6-370 | C—Cl | C—Br | C—Cl | C—H | H | CF3 | — | H | n-PrCO |
| 6-371 | C—Cl | C—Br | C—Cl | C—H | H | CF3 | — | H | cyclo-PrCO |
| 6-372 | C—Cl | C—Br | C—Cl | C—H | H | CF3 | — | H | cyclo-PrCH2CO |
| 6-373 | C—Cl | C—Br | C—Cl | C—H | H | CF3 | — | H | CF3CH2CO |
| 6-374 | C—Cl | C—Br | C—Cl | C—H | H | CF3 | — | H | CH3SCH2CO |
| 6-375 | C—Cl | C—Br | C—Cl | C—H | H | CF3 | — | H | CH3S(O)CH2CO |
| 6-376 | C—Cl | C—Br | C—Cl | C—H | H | CF3 | — | H | CH3SO2CH2CO |
| 6-377 | C—Cl | C—Br | C—Cl | C—H | H | CF3 | — | H | CH3CH2NHCO |
| 6-378 | C—Cl | C—Cl | C—Br | C—H | H | CF3 | — | H | CH3CO |
| 6-379 | C—Cl | C—Cl | C—Br | C—H | H | CF3 | — | H | CH3CH2CO |
| 6-380 | C—Cl | C—Cl | C—Br | C—H | H | CF3 | — | H | n-PrCO |
| 6-381 | C—Cl | C—Cl | C—Br | C—H | H | CF3 | — | H | cyclo-PrCO |
| 6-382 | C—Cl | C—Cl | C—Br | C—H | H | CF3 | — | H | cyclo-PrCH2CO |
| 6-383 | C—Cl | C—Cl | C—Br | C—H | H | CF3 | — | H | CF3CH2CO |
| 6-384 | C—Cl | C—Cl | C—Br | C—H | H | CF3 | — | H | CH3SCH2CO |
| 6-385 | C—Cl | C—Cl | C—Br | C—H | H | CF3 | — | H | CH3S(O)CH2CO |
| 6-386 | C—Cl | C—Cl | C—Br | C—H | H | CF3 | — | H | CH3SO2CH2CO |
| 6-387 | C—Cl | C—Cl | C—Br | C—H | H | CF3 | — | H | CH3CH2NHCO |
| 6-388 | C—Cl | C—F | C—Cl | C—H | F | CF3 | — | H | CH3CO |
| 6-389 | C—Cl | C—F | C—Cl | C—H | F | CF3 | — | H | CH3CH2CO |
| 6-390 | C—Cl | C—F | C—Cl | C—H | F | CF3 | — | H | n-PrCO |
| 6-391 | C—Cl | C—F | C—Cl | C—H | F | CF3 | — | H | cyclo-PrCO |
| 6-392 | C—Cl | C—F | C—Cl | C—H | F | CF3 | — | H | cyclo-PrCH2CO |
| 6-393 | C—Cl | C—F | C—Cl | C—H | F | CF3 | — | H | CF3CH2CO |
| 6-394 | C—Cl | C—F | C—Cl | C—H | F | CF3 | — | H | CH3SCH2CO |
| 6-395 | C—Cl | C—F | C—Cl | C—H | F | CF3 | — | H | CH3S(O)CH2CO |
| 6-396 | C—Cl | C—F | C—Cl | C—H | F | CF3 | — | H | CH3SO2CH2CO |
| 6-397 | C—Cl | C—F | C—Cl | C—H | F | CF3 | — | H | CH3CH2NHCO |
| 6-398 | C—CF3 | C—H | C—H | C—H | H | CF3 | — | H | CH3CO |
| 6-399 | C—CF3 | C—H | C—H | C—H | H | CF3 | — | H | CH3CH2CO |
| 6-400 | C—CF3 | C—H | C—H | C—H | H | CF3 | — | H | n-PrCO |
| 6-401 | C—CF3 | C—H | C—H | C—H | H | CF3 | — | H | cyclo-PrCO |
| 6-402 | C—CF3 | C—H | C—H | C—H | H | CF3 | — | H | cyclo-PrCH2CO |
| 6-403 | C—CF3 | C—H | C—H | C—H | H | CF3 | — | H | CF3CH2CO |

TABLE 6-continued

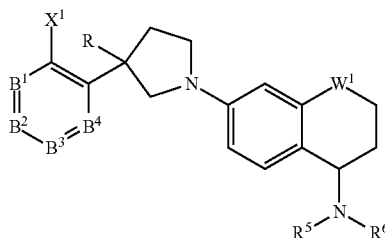

| Ex.-No. | B¹ | B² | B³ | B⁴ | X¹ | R | W¹ | R⁵ | R⁶ |
|---|---|---|---|---|---|---|---|---|---|
| 6-404 | C—CF3 | C—H | C—H | C—H | H | CF3 | — | H | CH3SCH2CO |
| 6-405 | C—CF3 | C—H | C—H | C—H | H | CF3 | — | H | CH3S(O)CH2CO |
| 6-406 | C—CF3 | C—H | C—H | C—H | H | CF3 | — | H | CH3SO2CH2CO |
| 6-407 | C—CF3 | C—H | C—H | C—H | H | CF3 | — | H | CH3CH2NHCO |
| 6-408 | C—CF3 | C—F | C—H | C—H | H | CF3 | — | H | CH3CO |
| 6-409 | C—CF3 | C—F | C—H | C—H | H | CF3 | — | H | CH3CH2CO |
| 6-410 | C—CF3 | C—F | C—H | C—H | H | CF3 | — | H | n-PrCO |
| 6-411 | C—CF3 | C—F | C—H | C—H | H | CF3 | — | H | cyclo-PrCO |
| 6-412 | C—CF3 | C—F | C—H | C—H | H | CF3 | — | H | cyclo-PrCH2CO |
| 6-413 | C—CF3 | C—F | C—H | C—H | H | CF3 | — | H | CF3CH2CO |
| 6-414 | C—CF3 | C—F | C—H | C—H | H | CF3 | — | H | CH3SCH2CO |
| 6-415 | C—CF3 | C—F | C—H | C—H | H | CF3 | — | H | CH3S(O)CH2CO |
| 6-416 | C—CF3 | C—F | C—H | C—H | H | CF3 | — | H | CH3SO2CH2CO |
| 6-417 | C—CF3 | C—F | C—H | C—H | H | CF3 | — | H | CH3CH2NHCO |
| 6-418 | C—CF3 | C—H | C—H | C—H | F | CF3 | — | H | CH3CO |
| 6-419 | C—CF3 | C—H | C—H | C—H | F | CF3 | — | H | CH3CH2CO |
| 6-420 | C—CF3 | C—H | C—H | C—H | F | CF3 | — | H | n-PrCO |
| 6-421 | C—CF3 | C—H | C—H | C—H | F | CF3 | — | H | cyclo-PrCO |
| 6-422 | C—CF3 | C—H | C—H | C—H | F | CF3 | — | H | cyclo-PrCH2CO |
| 6-423 | C—CF3 | C—H | C—H | C—H | F | CF3 | — | H | CF3CH2CO |
| 6-424 | C—CF3 | C—H | C—H | C—H | F | CF3 | — | H | CH3SCH2CO |
| 6-425 | C—CF3 | C—H | C—H | C—H | F | CF3 | — | H | CH3S(O)CH2CO |
| 6-426 | C—CF3 | C—H | C—H | C—H | F | CF3 | — | H | CH3SO2CH2CO |
| 6-427 | C—CF3 | C—H | C—H | C—H | F | CF3 | — | H | CH3CH2NHCO |
| 6-428 | C—H | C—H | C—CF3 | C—H | F | CF3 | — | H | CH3CO |
| 6-429 | C—H | C—H | C—CF3 | C—H | F | CF3 | — | H | CH3CH2CO |
| 6-430 | C—H | C—H | C—CF3 | C—H | F | CF3 | — | H | n-PrCO |
| 6-431 | C—H | C—H | C—CF3 | C—H | F | CF3 | — | H | cyclo-PrCO |
| 6-432 | C—H | C—H | C—CF3 | C—H | F | CF3 | — | H | cyclo-PrCH2CO |
| 6-433 | C—H | C—H | C—CF3 | C—H | F | CF3 | — | H | CF3CH2CO |
| 6-434 | C—H | C—H | C—CF3 | C—H | F | CF3 | — | H | CH3SCH2CO |
| 6-435 | C—H | C—H | C—CF3 | C—H | F | CF3 | — | H | CH3S(O)CH2CO |
| 6-436 | C—H | C—H | C—CF3 | C—H | F | CF3 | — | H | CH3SO2CH2CO |
| 6-437 | C—H | C—H | C—CF3 | C—H | F | CF3 | — | H | CH3CH2NHCO |
| 6-438 | C—Cl | C—H | C—CF3 | C—H | H | CF3 | — | H | CH3CO |
| 6-439 | C—Cl | C—H | C—CF3 | C—H | H | CF3 | — | H | CH3CH2CO |
| 6-440 | C—Cl | C—H | C—CF3 | C—H | H | CF3 | — | H | n-PrCO |
| 6-441 | C—Cl | C—H | C—CF3 | C—H | H | CF3 | — | H | cyclo-PrCO |
| 6-442 | C—Cl | C—H | C—CF3 | C—H | H | CF3 | — | H | cyclo-PrCH2CO |
| 6-443 | C—Cl | C—H | C—CF3 | C—H | H | CF3 | — | H | CF3CH2CO |
| 6-444 | C—Cl | C—H | C—CF3 | C—H | H | CF3 | — | H | CH3OCH2CH2CO |
| 6-445 | C—Cl | C—H | C—CF3 | C—H | H | CF3 | — | H | CH3CH2OCH2CH2CO |
| 6-446 | C—Cl | C—H | C—CF3 | C—H | H | CF3 | — | H | CH3SCH2CO |
| 6-447 | C—Cl | C—H | C—CF3 | C—H | H | CF3 | — | H | CH3S(O)CH2CO |
| 6-448 | C—Cl | C—H | C—CF3 | C—H | H | CF3 | — | H | CH3SO2CH2CO |
| 6-449 | C—Cl | C—H | C—CF3 | C—H | H | CF3 | — | H | CH3CH2NHCO |
| 6-450 | C—CF3 | C—H | C—CF3 | C—H | H | CF3 | — | H | n-PrCO |
| 6-451 | C—CF3 | C—H | C—CF3 | C—H | H | CF3 | — | H | cyclo-PrCH2CO |
| 6-452 | C—CF3 | C—H | C—CF3 | C—H | H | CF3 | — | H | CH3OCH2CO |
| 6-453 | C—CF3 | C—H | C—CF3 | C—H | H | CF3 | — | H | CH3CH2OCH2CH2CO |
| 6-454 | C—CF3 | C—H | C—CF3 | C—H | H | CF3 | — | H | CH3SCH2CO |
| 6-455 | C—CF3 | C—H | C—CF3 | C—H | H | CF3 | — | H | CH3S(O)CH2CO |
| 6-456 | C—CF3 | C—H | C—CF3 | C—H | H | CF3 | — | H | CH3SO2CH2CO |
| 6-457 | C—Cl | C—Cl | C—CF3 | C—H | H | CF3 | — | H | n-PrCO |
| 6-458 | C—Cl | C—Cl | C—CF3 | C—H | H | CF3 | — | H | cyclo-PrCH2CO |
| 6-459 | C—Cl | C—Cl | C—CF3 | C—H | H | CF3 | — | H | CH3SCH2CO |
| 6-460 | C—Cl | C—Cl | C—CF3 | C—H | H | CF3 | — | H | CH3S(O)CH2CO |
| 6-461 | C—Cl | C—Cl | C—CF3 | C—H | H | CF3 | — | H | CH3SO2CH2CO |
| 6-462 | C—Cl | N | C—H | C—H | H | CF3 | — | H | CH3CO |
| 6-463 | C—Cl | N | C—H | C—H | H | CF3 | — | H | CH3CH2CO |
| 6-464 | C—Cl | N | C—H | C—H | H | CF3 | — | H | n-PrCO |
| 6-465 | C—Cl | N | C—H | C—H | H | CF3 | — | H | cyclo-PrCO |
| 6-466 | C—Cl | N | C—H | C—H | H | CF3 | — | H | cyclo-PrCH2CO |
| 6-467 | C—Cl | N | C—H | C—H | H | CF3 | — | H | CF3CH2CO |
| 6-468 | C—Cl | N | C—H | C—H | H | CF3 | — | H | CH3SCH2CO |
| 6-469 | C—Cl | N | C—H | C—H | H | CF3 | — | H | CH3S(O)CH2CO |

TABLE 6-continued

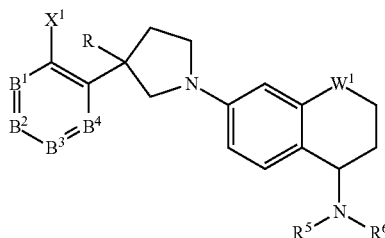

| ExNo. | $B^1$ | $B^2$ | $B^3$ | $B^4$ | $X^1$ | R | $W^1$ | $R^5$ | $R^6$ |
|---|---|---|---|---|---|---|---|---|---|
| 6-470 | C—Cl | N | C—H | C—H | H | CF3 | — | H | CH3SO2CH2CO |
| 6-471 | C—Cl | N | C—H | C—H | H | CF3 | — | H | CH3CH2NHCO |
| 6-472 | C—Cl | N | C—Cl | C—H | H | CF3 | — | H | CH3CO |
| 6-473 | C—Cl | N | C—Cl | C—H | H | CF3 | — | H | CH3CH2CO |
| 6-474 | C—Cl | N | C—Cl | C—H | H | CF3 | — | H | n-PrCO |
| 6-475 | C—Cl | N | C—Cl | C—H | H | CF3 | — | H | cyclo-PrCO |
| 6-476 | C—Cl | N | C—Cl | C—H | H | CF3 | — | H | cyclo-PrCH2CO |
| 6-477 | C—Cl | N | C—Cl | C—H | H | CF3 | — | H | CF3CH2CO |
| 6-478 | C—Cl | N | C—Cl | C—H | H | CF3 | — | H | CH3SCH2CO |
| 6-479 | C—Cl | N | C—Cl | C—H | H | CF3 | — | H | CH3S(O)CH2CO |
| 6-480 | C—Cl | N | C—Cl | C—H | H | CF3 | — | H | CH3SO2CH2CO |
| 6-481 | C—Cl | N | C—Cl | C—H | H | CF3 | — | H | CH3CH2NHCO |
| 6-482 | C—CF3 | N | C—H | C—H | H | CF3 | — | H | CH3CO |
| 6-483 | C—CF3 | N | C—H | C—H | H | CF3 | — | H | CH3CH2CO |
| 6-484 | C—CF3 | N | C—H | C—H | H | CF3 | — | H | n-PrCO |
| 6-485 | C—CF3 | N | C—H | C—H | H | CF3 | — | H | cyclo-PrCO |
| 6-486 | C—CF3 | N | C—H | C—H | H | CF3 | — | H | cyclo-PrCH2CO |
| 6-487 | C—CF3 | N | C—H | C—H | H | CF3 | — | H | CF3CH2CO |
| 6-488 | C—CF3 | N | C—H | C—H | H | CF3 | — | H | CH3SCH2CO |
| 6-489 | C—CF3 | N | C—H | C—H | H | CF3 | — | H | CH3S(O)CH2CO |
| 6-490 | C—CF3 | N | C—H | C—H | H | CF3 | — | H | CH3SO2CH2CO |
| 6-491 | C—CF3 | N | C—H | C—H | H | CF3 | — | H | CH3CH2NHCO |
| 6-492 | C—CF3 | N | C—CF3 | C—H | H | CF3 | — | H | CH3CO |
| 6-493 | C—CF3 | N | C—CF3 | C—H | H | CF3 | — | H | CH3CH2CO |
| 6-494 | C—CF3 | N | C—CF3 | C—H | H | CF3 | — | H | n-PrCO |
| 6-495 | C—CF3 | N | C—CF3 | C—H | H | CF3 | — | H | cyclo-PrCO |
| 6-496 | C—CF3 | N | C—CF3 | C—H | H | CF3 | — | H | cyclo-PrCH2CO |
| 6-497 | C—CF3 | N | C—CF3 | C—H | H | CF3 | — | H | CF3CH2CO |
| 6-498 | C—CF3 | N | C—CF3 | C—H | H | CF3 | — | H | CH3SCH2CO |
| 6-499 | C—CF3 | N | C—CF3 | C—H | H | CF3 | — | H | CH3S(O)CH2CO |
| 6-500 | C—CF3 | N | C—CF3 | C—H | H | CF3 | — | H | CH3SO2CH2CO |
| 6-501 | C—CF3 | N | C—CF3 | C—H | H | CF3 | — | H | CH3CH2NHCO |
| 6-502 | C—CF3 | C—H | C—H | N | H | CF3 | — | H | CH3CO |
| 6-503 | C—CF3 | C—H | C—H | N | H | CF3 | — | H | CH3CH2CO |
| 6-504 | C—CF3 | C—H | C—H | N | H | CF3 | — | H | n-PrCO |
| 6-505 | C—CF3 | C—H | C—H | N | H | CF3 | — | H | cyclo-PrCO |
| 6-506 | C—CF3 | C—H | C—H | N | H | CF3 | — | H | cyclo-PrCH2CO |
| 6-507 | C—CF3 | C—H | C—H | N | H | CF3 | — | H | CF3CH2CO |
| 6-508 | C—CF3 | C—H | C—H | N | H | CF3 | — | H | CH3SCH2CO |
| 6-509 | C—CF3 | C—H | C—H | N | H | CF3 | — | H | CH3S(O)CH2CO |
| 6-510 | C—CF3 | C—H | C—H | N | H | CF3 | — | H | CH3SO2CH2CO |
| 6-511 | C—CF3 | C—H | C—H | N | H | CF3 | — | H | CH3CH2NHCO |
| 6-512 | C—H | C—H | C—CF3 | N | H | CF3 | — | H | CH3CO |
| 6-513 | C—H | C—H | C—CF3 | N | H | CF3 | — | H | CH3CH2CO |
| 6-514 | C—H | C—H | C—CF3 | N | H | CF3 | — | H | n-PrCO |
| 6-515 | C—H | C—H | C—CF3 | N | H | CF3 | — | H | cyclo-PrCO |
| 6-516 | C—H | C—H | C—CF3 | N | H | CF3 | — | H | cyclo-PrCH2CO |
| 6-517 | C—H | C—H | C—CF3 | N | H | CF3 | — | H | CF3CH2CO |
| 6-518 | C—H | C—H | C—CF3 | N | H | CF3 | — | H | CH3SCH2CO |
| 6-519 | C—H | C—H | C—CF3 | N | H | CF3 | — | H | CH3S(O)CH2CO |
| 6-520 | C—H | C—H | C—CF3 | N | H | CF3 | — | H | CH3SO2CH2CO |
| 6-521 | C—H | C—H | C—CF3 | N | H | CF3 | — | H | CH3CH2NHCO |
| 6-522 | C—CF3 | C—H | C—Cl | N | H | CF3 | — | H | CH3CO |
| 6-523 | C—CF3 | C—H | C—Cl | N | H | CF3 | — | H | CH3CH2CO |
| 6-524 | C—CF3 | C—H | C—Cl | N | H | CF3 | — | H | n-PrCO |
| 6-525 | C—CF3 | C—H | C—Cl | N | H | CF3 | — | H | cyclo-PrCO |
| 6-526 | C—CF3 | C—H | C—Cl | N | H | CF3 | — | H | cyclo-PrCH2CO |
| 6-527 | C—CF3 | C—H | C—Cl | N | H | CF3 | — | H | CF3CH2CO |
| 6-528 | C—CF3 | C—H | C—Cl | N | H | CF3 | — | H | CH3SCH2CO |
| 6-529 | C—CF3 | C—H | C—Cl | N | H | CF3 | — | H | CH3S(O)CH2CO |
| 6-530 | C—CF3 | C—H | C—Cl | N | H | CF3 | — | H | CH3SO2CH2CO |
| 6-531 | C—CF3 | C—H | C—Cl | N | H | CF3 | — | H | CH3CH2NHCO |
| 6-532 | C—CF3 | C—H | C—Br | N | H | CF3 | — | H | CH3CO |
| 6-533 | C—CF3 | C—H | C—Br | N | H | CF3 | — | H | CH3CH2CO |
| 6-534 | C—CF3 | C—H | C—Br | N | H | CF3 | — | H | n-PrCO |
| 6-535 | C—CF3 | C—H | C—Br | N | H | CF3 | — | H | cyclo-PrCO |

TABLE 6-continued

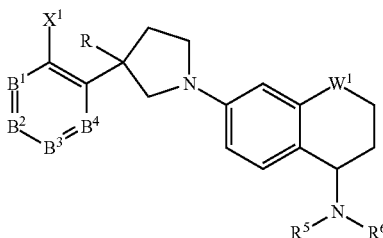

| Ex.-No. | B¹ | B² | B³ | B⁴ | X¹ | R | W¹ | R⁵ | R⁶ |
|---|---|---|---|---|---|---|---|---|---|
| 6-536 | C—CF3 | C—H | C—Br | N | H | CF3 | — | H | cyclo-PrCH2CO |
| 6-537 | C—CF3 | C—H | C—Br | N | H | CF3 | — | H | CF3CH2CO |
| 6-538 | C—CF3 | C—H | C—Br | N | H | CF3 | — | H | CH3SCH2CO |
| 6-539 | C—CF3 | C—H | C—Br | N | H | CF3 | — | H | CH3S(O)CH2CO |
| 6-540 | C—CF3 | C—H | C—Br | N | H | CF3 | — | H | CH3SO2CH2CO |
| 6-541 | C—CF3 | C—H | C—Br | N | H | CF3 | — | H | CH3CH2NHCO |
| 6-542 | C—CF3 | C—H | C—CF3 | N | H | CF3 | — | H | CH3CO |
| 6-543 | C—CF3 | C—H | C—CF3 | N | H | CF3 | — | H | CH3CH2CO |
| 6-544 | C—CF3 | C—H | C—CF3 | N | H | CF3 | — | H | n-PrCO |
| 6-545 | C—CF3 | C—H | C—CF3 | N | H | CF3 | — | H | cyclo-PrCO |
| 6-546 | C—CF3 | C—H | C—CF3 | N | H | CF3 | — | H | cyclo-PrCH2CO |
| 6-547 | C—CF3 | C—H | C—CF3 | N | H | CF3 | — | H | CF3CH2CO |
| 6-548 | C—CF3 | C—H | C—CF3 | N | H | CF3 | — | H | CH3SCH2CO |
| 6-549 | C—CF3 | C—H | C—CF3 | N | H | CF3 | — | H | CH3S(O)CH2CO |
| 6-550 | C—CF3 | C—H | C—CF3 | N | H | CF3 | — | H | CH3SO2CH2CO |
| 6-551 | C—CF3 | C—H | C—CF3 | N | H | CF3 | — | H | CH3CH2NHCO |
| 6-552 | C—Cl | C—H | C—H | C—H | H | CF3 | CH2 | H | CH3CO |
| 6-553 | C—Cl | C—H | C—H | C—H | H | CF3 | CH2 | H | CH3CH2CO |
| 6-554 | C—Cl | C—H | C—H | C—H | H | CF3 | CH2 | H | n-PrCO |
| 6-555 | C—Cl | C—H | C—H | C—H | H | CF3 | CH2 | H | cyclo-PrCO |
| 6-556 | C—Cl | C—H | C—H | C—H | H | CF3 | CH2 | H | cyclo-PrCH2CO |
| 6-557 | C—Cl | C—H | C—H | C—H | H | CF3 | CH2 | H | CF3CH2CO |
| 6-558 | C—Cl | C—H | C—H | C—H | H | CF3 | CH2 | H | CH3SCH2CO |
| 6-559 | C—Cl | C—H | C—H | C—H | H | CF3 | CH2 | H | CH3S(O)CH2CO |
| 6-560 | C—Cl | C—H | C—H | C—H | H | CF3 | CH2 | H | CH3SO2CH2CO |
| 6-561 | C—Cl | C—H | C—H | C—H | H | CF3 | CH2 | H | CH3CH2NHCO |
| 6-562 | C—Cl | C—H | C—H | C—H | F | CF3 | CH2 | H | CH3CO |
| 6-563 | C—Cl | C—H | C—H | C—H | F | CF3 | CH2 | H | CH3CH2CO |
| 6-564 | C—Cl | C—H | C—H | C—H | F | CF3 | CH2 | H | n-PrCO |
| 6-565 | C—Cl | C—H | C—H | C—H | F | CF3 | CH2 | H | cyclo-PrCO |
| 6-566 | C—Cl | C—H | C—H | C—H | F | CF3 | CH2 | H | cyclo-PrCH2CO |
| 6-567 | C—Cl | C—H | C—H | C—H | F | CF3 | CH2 | H | CF3CH2CO |
| 6-568 | C—Cl | C—H | C—H | C—H | F | CF3 | CH2 | H | CH3SCH2CO |
| 6-569 | C—Cl | C—H | C—H | C—H | F | CF3 | CH2 | H | CH3S(O)CH2CO |
| 6-570 | C—Cl | C—H | C—H | C—H | F | CF3 | CH2 | H | CH3SO2CH2CO |
| 6-571 | C—Cl | C—H | C—H | C—H | F | CF3 | CH2 | H | CH3CH2NHCO |
| 6-572 | C—H | C—H | C—Cl | C—H | F | CF3 | CH2 | H | CH3CO |
| 6-573 | C—H | C—H | C—Cl | C—H | F | CF3 | CH2 | H | CH3CH2CO |
| 6-574 | C—H | C—H | C—Cl | C—H | F | CF3 | CH2 | H | n-PrCO |
| 6-575 | C—H | C—H | C—Cl | C—H | F | CF3 | CH2 | H | cyclo-PrCO |
| 6-576 | C—H | C—H | C—Cl | C—H | F | CF3 | CH2 | H | cyclo-PrCH2CO |
| 6-577 | C—H | C—H | C—Cl | C—H | F | CF3 | CH2 | H | CF3CH2CO |
| 6-578 | C—H | C—H | C—Cl | C—H | F | CF3 | CH2 | H | CH3SCH2CO |
| 6-579 | C—H | C—H | C—Cl | C—H | F | CF3 | CH2 | H | CH3S(O)CH2CO |
| 6-580 | C—H | C—H | C—Cl | C—H | F | CF3 | CH2 | H | CH3SO2CH2CO |
| 6-581 | C—H | C—H | C—Cl | C—H | F | CF3 | CH2 | H | CH3CH2NHCO |
| 6-582 | C—Cl | C—H | C—Cl | C—H | H | CF3 | CH2 | H | CH3OCH2CH2CO |
| 6-583 | C—Cl | C—H | C—Cl | C—H | H | CF3 | CH2 | H | CH3CH2OCH2CH2CO |
| 6-584 | C—Cl | C—H | C—Cl | C—H | H | CF3 | CH2 | H | CH3S(O)CH2CO |
| 6-585 | C—Cl | C—H | C—Cl | C—H | H | CF3 | CH2 | H | CH3SO2CH2CO |
| 6-586 | C—Cl | C—H | C—Br | C—H | H | CF3 | CH2 | H | CH3CO |
| 6-587 | C—Cl | C—H | C—Br | C—H | H | CF3 | CH2 | H | CH3CH2CO |
| 6-588 | C—Cl | C—H | C—Br | C—H | H | CF3 | CH2 | H | n-PrCO |
| 6-589 | C—Cl | C—H | C—Br | C—H | H | CF3 | CH2 | H | cyclo-PrCO |
| 6-590 | C—Cl | C—H | C—Br | C—H | H | CF3 | CH2 | H | cyclo-PrCH2CO |
| 6-591 | C—Cl | C—H | C—Br | C—H | H | CF3 | CH2 | H | CF3CH2CO |
| 6-592 | C—Cl | C—H | C—Br | C—H | H | CF3 | CH2 | H | CH3SCH2CO |
| 6-593 | C—Cl | C—H | C—Br | C—H | H | CF3 | CH2 | H | CH3S(O)CH2CO |
| 6-594 | C—Cl | C—H | C—Br | C—H | H | CF3 | CH2 | H | CH3SO2CH2CO |
| 6-595 | C—Cl | C—H | C—Br | C—H | H | CF3 | CH2 | H | CH3CH2NHCO |
| 6-596 | C—Br | C—H | C—Br | C—H | H | CF3 | CH2 | H | n-PrCO |
| 6-597 | C—Br | C—H | C—Br | C—H | H | CF3 | CH2 | H | cyclo-PrCH2CO |
| 6-598 | C—Br | C—H | C—Br | C—H | H | CF3 | CH2 | H | CH3SCH2CO |
| 6-599 | C—Br | C—H | C—Br | C—H | H | CF3 | CH2 | H | CH3S(O)CH2CO |
| 6-600 | C—Br | C—H | C—Br | C—H | H | CF3 | CH2 | H | CH3SO2CH2CO |
| 6-601 | C—Cl | C—F | C—Cl | C—H | H | CF3 | CH2 | H | CH3CO |

TABLE 6-continued

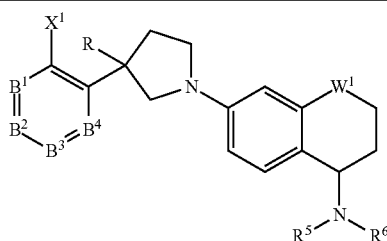

| ExNo. | B¹ | B² | B³ | B⁴ | X¹ | R | W¹ | R⁵ | R⁶ |
|---|---|---|---|---|---|---|---|---|---|
| 6-602 | C—Cl | C—F | C—Cl | C—H | H | CF3 | CH2 | H | CH3CH2CO |
| 6-603 | C—Cl | C—F | C—Cl | C—H | H | CF3 | CH2 | H | n-PrCO |
| 6-604 | C—Cl | C—F | C—Cl | C—H | H | CF3 | CH2 | H | cyclo-PrCO |
| 6-605 | C—Cl | C—F | C—Cl | C—H | H | CF3 | CH2 | H | cyclo-PrCH2CO |
| 6-606 | C—Cl | C—F | C—Cl | C—H | H | CF3 | CH2 | H | CF3CH2CO |
| 6-607 | C—Cl | C—F | C—Cl | C—H | H | CF3 | CH2 | H | CH3SCH2CO |
| 6-608 | C—Cl | C—F | C—Cl | C—H | H | CF3 | CH2 | H | CH3S(O)CH2CO |
| 6-609 | C—Cl | C—F | C—Cl | C—H | H | CF3 | CH2 | H | CH3SO2CH2CO |
| 6-610 | C—Cl | C—F | C—Cl | C—H | H | CF3 | CH2 | H | CH3CH2NHCO |
| 6-611 | C—Cl | C—Cl | C—Cl | C—H | H | CF3 | CH2 | H | n-PrCO |
| 6-612 | C—Cl | C—Cl | C—Cl | C—H | H | CF3 | CH2 | H | cyclo-PrCH2CO |
| 6-613 | C—Cl | C—Cl | C—Cl | C—H | H | CF3 | CH2 | H | CH3OCH2CH2CO |
| 6-614 | C—Cl | C—Cl | C—Cl | C—H | H | CF3 | CH2 | H | CH3CH2OCH2CH2CO |
| 6-615 | C—Cl | C—Cl | C—Cl | C—H | H | CF3 | CH2 | H | CH3SCH2CO |
| 6-616 | C—Cl | C—Cl | C—Cl | C—H | H | CF3 | CH2 | H | CH3S(O)CH2CO |
| 6-617 | C—Cl | C—Cl | C—Cl | C—H | H | CF3 | CH2 | H | CH3SO2CH2CO |
| 6-618 | C—Cl | C—Br | C—Cl | C—H | H | CF3 | CH2 | H | CH3CO |
| 6-619 | C—Cl | C—Br | C—Cl | C—H | H | CF3 | CH2 | H | CH3CH2CO |
| 6-620 | C—Cl | C—Br | C—Cl | C—H | H | CF3 | CH2 | H | n-PrCO |
| 6-621 | C—Cl | C—Br | C—Cl | C—H | H | CF3 | CH2 | H | cyclo-PrCO |
| 6-622 | C—Cl | C—Br | C—Cl | C—H | H | CF3 | CH2 | H | cyclo-PrCH2CO |
| 6-623 | C—Cl | C—Br | C—Cl | C—H | H | CF3 | CH2 | H | CF3CH2CO |
| 6-624 | C—Cl | C—Br | C—Cl | C—H | H | CF3 | CH2 | H | CH3SCH2CO |
| 6-625 | C—Cl | C—Br | C—Cl | C—H | H | CF3 | CH2 | H | CH3S(O)CH2CO |
| 6-626 | C—Cl | C—Br | C—Cl | C—H | H | CF3 | CH2 | H | CH3SO2CH2CO |
| 6-627 | C—Cl | C—Br | C—Cl | C—H | H | CF3 | CH2 | H | CH3CH2NHCO |
| 6-628 | C—Cl | C—Cl | C—Br | C—H | H | CF3 | CH2 | H | CH3CO |
| 6-629 | C—Cl | C—Cl | C—Br | C—H | H | CF3 | CH2 | H | CH3CH2CO |
| 6-630 | C—Cl | C—Cl | C—Br | C—H | H | CF3 | CH2 | H | n-PrCO |
| 6-631 | C—Cl | C—Cl | C—Br | C—H | H | CF3 | CH2 | H | cyclo-PrCO |
| 6-632 | C—Cl | C—Cl | C—Br | C—H | H | CF3 | CH2 | H | cyclo-PrCH2CO |
| 6-633 | C—Cl | C—Cl | C—Br | C—H | H | CF3 | CH2 | H | CF3CH2CO |
| 6-634 | C—Cl | C—Cl | C—Br | C—H | H | CF3 | CH2 | H | CH3SCH2CO |
| 6-635 | C—Cl | C—Cl | C—Br | C—H | H | CF3 | CH2 | H | CH3S(O)CH2CO |
| 6-636 | C—Cl | C—Cl | C—Br | C—H | H | CF3 | CH2 | H | CH3SO2CH2CO |
| 6-637 | C—Cl | C—Cl | C—Br | C—H | H | CF3 | CH2 | H | CH3CH2NHCO |
| 6-638 | C—Cl | C—F | C—Cl | C—H | F | CF3 | CH2 | H | CH3CO |
| 6-639 | C—Cl | C—F | C—Cl | C—H | F | CF3 | CH2 | H | CH3CH2CO |
| 6-640 | C—Cl | C—F | C—Cl | C—H | F | CF3 | CH2 | H | n-PrCO |
| 6-641 | C—Cl | C—F | C—Cl | C—H | F | CF3 | CH2 | H | cyclo-PrCO |
| 6-642 | C—Cl | C—F | C—Cl | C—H | F | CF3 | CH2 | H | cyclo-PrCH2CO |
| 6-643 | C—Cl | C—F | C—Cl | C—H | F | CF3 | CH2 | H | CF3CH2CO |
| 6-644 | C—Cl | C—F | C—Cl | C—H | F | CF3 | CH2 | H | CH3SCH2CO |
| 6-645 | C—Cl | C—F | C—Cl | C—H | F | CF3 | CH2 | H | CH3S(O)CH2CO |
| 6-646 | C—Cl | C—F | C—Cl | C—H | F | CF3 | CH2 | H | CH3SO2CH2CO |
| 6-647 | C—Cl | C—F | C—Cl | C—H | F | CF3 | CH2 | H | CH3CH2NHCO |
| 6-648 | C—CF3 | C—H | C—H | C—H | H | CF3 | CH2 | H | CH3CO |
| 6-649 | C—CF3 | C—H | C—H | C—H | H | CF3 | CH2 | H | CH3CH2CO |
| 6-650 | C—CF3 | C—H | C—H | C—H | H | CF3 | CH2 | H | n-PrCO |
| 6-651 | C—CF3 | C—H | C—H | C—H | H | CF3 | CH2 | H | cyclo-PrCO |
| 6-652 | C—CF3 | C—H | C—H | C—H | H | CF3 | CH2 | H | cyclo-PrCH2CO |
| 6-653 | C—CF3 | C—H | C—H | C—H | H | CF3 | CH2 | H | CF3CH2CO |
| 6-654 | C—CF3 | C—H | C—H | C—H | H | CF3 | CH2 | H | CH3SCH2CO |
| 6-655 | C—CF3 | C—H | C—H | C—H | H | CF3 | CH2 | H | CH3S(O)CH2CO |
| 6-656 | C—CF3 | C—H | C—H | C—H | H | CF3 | CH2 | H | CH3SO2CH2CO |
| 6-657 | C—CF3 | C—H | C—H | C—H | H | CF3 | CH2 | H | CH3CH2NHCO |
| 6-658 | C—CF3 | C—F | C—H | C—H | H | CF3 | CH2 | H | CH3CO |
| 6-659 | C—CF3 | C—F | C—H | C—H | H | CF3 | CH2 | H | CH3CH2CO |
| 6-660 | C—CF3 | C—F | C—H | C—H | H | CF3 | CH2 | H | n-PrCO |
| 6-661 | C—CF3 | C—F | C—H | C—H | H | CF3 | CH2 | H | cyclo-PrCO |
| 6-662 | C—CF3 | C—F | C—H | C—H | H | CF3 | CH2 | H | cyclo-PrCH2CO |
| 6-663 | C—CF3 | C—F | C—H | C—H | H | CF3 | CH2 | H | CF3CH2CO |
| 6-664 | C—CF3 | C—F | C—H | C—H | H | CF3 | CH2 | H | CH3SCH2CO |
| 6-665 | C—CF3 | C—F | C—H | C—H | H | CF3 | CH2 | H | CH3S(O)CH2CO |
| 6-666 | C—CF3 | C—F | C—H | C—H | H | CF3 | CH2 | H | CH3SO2CH2CO |
| 6-667 | C—CF3 | C—F | C—H | C—H | H | CF3 | CH2 | H | CH3CH2NHCO |

TABLE 6-continued

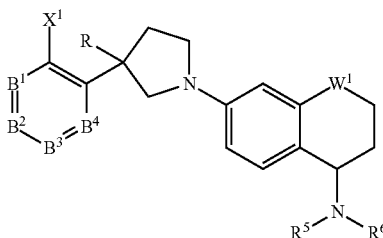

| Ex.-No. | B¹ | B² | B³ | B⁴ | X¹ | R | W¹ | R⁵ | R⁶ |
|---|---|---|---|---|---|---|---|---|---|
| 6-668 | C—CF3 | C—H | C—H | C—H | F | CF3 | CH2 | H | CH3CO |
| 6-669 | C—CF3 | C—H | C—H | C—H | F | CF3 | CH2 | H | CH3CH2CO |
| 6-670 | C—CF3 | C—H | C—H | C—H | F | CF3 | CH2 | H | n-PrCO |
| 6-671 | C—CF3 | C—H | C—H | C—H | F | CF3 | CH2 | H | cyclo-PrCO |
| 6-672 | C—CF3 | C—H | C—H | C—H | F | CF3 | CH2 | H | cyclo-PrCH2CO |
| 6-673 | C—CF3 | C—H | C—H | C—H | F | CF3 | CH2 | H | CF3CH2CO |
| 6-674 | C—CF3 | C—H | C—H | C—H | F | CF3 | CH2 | H | CH3SCH2CO |
| 6-675 | C—CF3 | C—H | C—H | C—H | F | CF3 | CH2 | H | CH3S(O)CH2CO |
| 6-676 | C—CF3 | C—H | C—H | C—H | F | CF3 | CH2 | H | CH3SO2CH2CO |
| 6-677 | C—CF3 | C—H | C—H | C—H | F | CF3 | CH2 | H | CH3CH2NHCO |
| 6-678 | C—H | C—H | C—CF3 | C—H | F | CF3 | CH2 | H | CH3CO |
| 6-679 | C—H | C—H | C—CF3 | C—H | F | CF3 | CH2 | H | CH3CH2CO |
| 6-680 | C—H | C—H | C—CF3 | C—H | F | CF3 | CH2 | H | n-PrCO |
| 6-681 | C—H | C—H | C—CF3 | C—H | F | CF3 | CH2 | H | cyclo-PrCO |
| 6-682 | C—H | C—H | C—CF3 | C—H | F | CF3 | CH2 | H | cyclo-PrCH2CO |
| 6-683 | C—H | C—H | C—CF3 | C—H | F | CF3 | CH2 | H | CF3CH2CO |
| 6-684 | C—H | C—H | C—CF3 | C—H | F | CF3 | CH2 | H | CH3SCH2CO |
| 6-685 | C—H | C—H | C—CF3 | C—H | F | CF3 | CH2 | H | CH3S(O)CH2CO |
| 6-686 | C—H | C—H | C—CF3 | C—H | F | CF3 | CH2 | H | CH3SO2CH2CO |
| 6-687 | C—H | C—H | C—CF3 | C—H | F | CF3 | CH2 | H | CH3CH2NHCO |
| 6-688 | C—Cl | C—H | C—CF3 | C—H | H | CF3 | CH2 | H | CH3CO |
| 6-689 | C—Cl | C—H | C—CF3 | C—H | H | CF3 | CH2 | H | CH3CH2CO |
| 6-690 | C—Cl | C—H | C—CF3 | C—H | H | CF3 | CH2 | H | n-PrCO |
| 6-691 | C—Cl | C—H | C—CF3 | C—H | H | CF3 | CH2 | H | cyclo-PrCO |
| 6-692 | C—Cl | C—H | C—CF3 | C—H | H | CF3 | CH2 | H | cyclo-PrCH2CO |
| 6-693 | C—Cl | C—H | C—CF3 | C—H | H | CF3 | CH2 | H | CF3CH2CO |
| 6-694 | C—Cl | C—H | C—CF3 | C—H | H | CF3 | CH2 | H | CH3OCH2CH2CO |
| 6-695 | C—Cl | C—H | C—CF3 | C—H | H | CF3 | CH2 | H | CH3CH2OCH2CH2CO |
| 6-696 | C—Cl | C—H | C—CF3 | C—H | H | CF3 | CH2 | H | CH3SCH2CO |
| 6-697 | C—Cl | C—H | C—CF3 | C—H | H | CF3 | CH2 | H | CH3S(O)CH2CO |
| 6-698 | C—Cl | C—H | C—CF3 | C—H | H | CF3 | CH2 | H | CH3SO2CH2CO |
| 6-699 | C—Cl | C—H | C—CF3 | C—H | H | CF3 | CH2 | H | CH3CH2NHCO |
| 6-700 | C—CF3 | C—H | C—CF3 | C—H | H | CF3 | CH2 | H | n-PrCO |
| 6-701 | C—CF3 | C—H | C—CF3 | C—H | H | CF3 | CH2 | H | cyclo-PrCH2CO |
| 6-702 | C—CF3 | C—H | C—CF3 | C—H | H | CF3 | CH2 | H | CH3OCH2CH2CO |
| 6-703 | C—CF3 | C—H | C—CF3 | C—H | H | CF3 | CH2 | H | CH3CH2OCH2CH2CO |
| 6-704 | C—CF3 | C—H | C—CF3 | C—H | H | CF3 | CH2 | H | CH3SCH2CO |
| 6-705 | C—CF3 | C—H | C—CF3 | C—H | H | CF3 | CH2 | H | CH3S(O)CH2CO |
| 6-706 | C—CF3 | C—H | C—CF3 | C—H | H | CF3 | CH2 | H | CH3SO2CH2CO |
| 6-707 | C—Cl | C—Cl | C—CF3 | C—H | H | CF3 | CH2 | H | n-PrCO |
| 6-708 | C—Cl | C—Cl | C—CF3 | C—H | H | CF3 | CH2 | H | cyclo-PrCH2CO |
| 6-709 | C—Cl | C—Cl | C—CF3 | C—H | H | CF3 | CH2 | H | CH3SCH2CO |
| 6-710 | C—Cl | C—Cl | C—CF3 | C—H | H | CF3 | CH2 | H | CH3S(O)CH2CO |
| 6-711 | C—Cl | C—Cl | C—CF3 | C—H | H | CF3 | CH2 | H | CH3SO2CH2CO |
| 6-712 | C—Cl | N | C—H | C—H | H | CF3 | CH2 | H | CH3CO |
| 6-713 | C—Cl | N | C—H | C—H | H | CF3 | CH2 | H | CH3CH2CO |
| 6-714 | C—Cl | N | C—H | C—H | H | CF3 | CH2 | H | n-PrCO |
| 6-715 | C—Cl | N | C—H | C—H | H | CF3 | CH2 | H | cyclo-PrCO |
| 6-716 | C—Cl | N | C—H | C—H | H | CF3 | CH2 | H | cyclo-PrCH2CO |
| 6-717 | C—Cl | N | C—H | C—H | H | CF3 | CH2 | H | CF3CH2CO |
| 6-718 | C—Cl | N | C—H | C—H | H | CF3 | CH2 | H | CH3SCH2CO |
| 6-719 | C—Cl | N | C—H | C—H | H | CF3 | CH2 | H | CH3S(O)CH2CO |
| 6-720 | C—Cl | N | C—H | C—H | H | CF3 | CH2 | H | CH3SO2CH2CO |
| 6-721 | C—Cl | N | C—H | C—H | H | CF3 | CH2 | H | CH3CH2NHCO |
| 6-722 | C—Cl | N | C—Cl | C—H | H | CF3 | CH2 | H | CH3CO |
| 6-723 | C—Cl | N | C—Cl | C—H | H | CF3 | CH2 | H | CH3CH2CO |
| 6-724 | C—Cl | N | C—Cl | C—H | H | CF3 | CH2 | H | n-PrCO |
| 6-725 | C—Cl | N | C—Cl | C—H | H | CF3 | CH2 | H | cyclo-PrCO |
| 6-726 | C—Cl | N | C—Cl | C—H | H | CF3 | CH2 | H | cyclo-PrCH2CO |
| 6-727 | C—Cl | N | C—Cl | C—H | H | CF3 | CH2 | H | CF3CH2CO |
| 6-728 | C—Cl | N | C—Cl | C—H | H | CF3 | CH2 | H | CH3SCH2CO |
| 6-729 | C—Cl | N | C—Cl | C—H | H | CF3 | CH2 | H | CH3S(O)CH2CO |
| 6-730 | C—Cl | N | C—Cl | C—H | H | CF3 | CH2 | H | CH3SO2CH2CO |
| 6-731 | C—Cl | N | C—Cl | C—H | H | CF3 | CH2 | H | CH3CH2NHCO |
| 6-732 | C—CF3 | N | C—H | C—H | H | CF3 | CH2 | H | CH3CO |
| 6-733 | C—CF3 | N | C—H | C—H | H | CF3 | CH2 | H | CH3CH2CO |

TABLE 6-continued

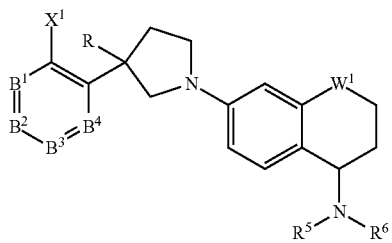

| Ex.-No. | B¹ | B² | B³ | B⁴ | X¹ | R | W¹ | R⁵ | R⁶ |
|---|---|---|---|---|---|---|---|---|---|
| 6-734 | C—CF3 | N | C—H | C—H | H | CF3 | CH2 | H | n-PrCO |
| 6-735 | C—CF3 | N | C—H | C—H | H | CF3 | CH2 | H | cyclo-PrCO |
| 6-736 | C—CF3 | N | C—H | C—H | H | CF3 | CH2 | H | cyclo-PrCH2CO |
| 6-737 | C—CF3 | N | C—H | C—H | H | CF3 | CH2 | H | CF3CH2CO |
| 6-738 | C—CF3 | N | C—H | C—H | H | CF3 | CH2 | H | CH3SCH2CO |
| 6-739 | C—CF3 | N | C—H | C—H | H | CF3 | CH2 | H | CH3S(O)CH2CO |
| 6-740 | C—CF3 | N | C—H | C—H | H | CF3 | CH2 | H | CH3SO2CH2CO |
| 6-741 | C—CF3 | N | C—H | C—H | H | CF3 | CH2 | H | CH3CH2NHCO |
| 6-742 | C—CF3 | N | C—CF3 | C—H | H | CF3 | CH2 | H | CH3CO |
| 6-743 | C—CF3 | N | C—CF3 | C—H | H | CF3 | CH2 | H | CH3CH2CO |
| 6-744 | C—CF3 | N | C—CF3 | C—H | H | CF3 | CH2 | H | n-PrCO |
| 6-745 | C—CF3 | N | C—CF3 | C—H | H | CF3 | CH2 | H | cyclo-PrCO |
| 6-746 | C—CF3 | N | C—CF3 | C—H | H | CF3 | CH2 | H | cyclo-PrCH2CO |
| 6-747 | C—CF3 | N | C—CF3 | C—H | H | CF3 | CH2 | H | CF3CH2CO |
| 6-748 | C—CF3 | N | C—CF3 | C—H | H | CF3 | CH2 | H | CH3SCH2CO |
| 6-749 | C—CF3 | N | C—CF3 | C—H | H | CF3 | CH2 | H | CH3S(O)CH2CO |
| 6-750 | C—CF3 | N | C—CF3 | C—H | H | CF3 | CH2 | H | CH3SO2CH2CO |
| 6-751 | C—CF3 | N | C—CF3 | C—H | H | CF3 | CH2 | H | CH3CH2NHCO |
| 6-752 | C—CF3 | C—H | C—H | N | H | CF3 | CH2 | H | CH3CO |
| 6-753 | C—CF3 | C—H | C—H | N | H | CF3 | CH2 | H | CH3CH2CO |
| 6-754 | C—CF3 | C—H | C—H | N | H | CF3 | CH2 | H | n-PrCO |
| 6-755 | C—CF3 | C—H | C—H | N | H | CF3 | CH2 | H | cyclo-PrCO |
| 6-756 | C—CF3 | C—H | C—H | N | H | CF3 | CH2 | H | cyclo-PrCH2CO |
| 6-757 | C—CF3 | C—H | C—H | N | H | CF3 | CH2 | H | CF3CH2CO |
| 6-758 | C—CF3 | C—H | C—H | N | H | CF3 | CH2 | H | CH3SCH2CO |
| 6-759 | C—CF3 | C—H | C—H | N | H | CF3 | CH2 | H | CH3S(O)CH2CO |
| 6-760 | C—CF3 | C—H | C—H | N | H | CF3 | CH2 | H | CH3SO2CH2CO |
| 6-761 | C—CF3 | C—H | C—H | N | H | CF3 | CH2 | H | CH3CH2NHCO |
| 6-762 | C—H | C—H | C—CF3 | N | H | CF3 | CH2 | H | CH3CO |
| 6-763 | C—H | C—H | C—CF3 | N | H | CF3 | CH2 | H | CH3CH2CO |
| 6-764 | C—H | C—H | C—CF3 | N | H | CF3 | CH2 | H | n-PrCO |
| 6-765 | C—H | C—H | C—CF3 | N | H | CF3 | CH2 | H | cyclo-PrCO |
| 6-766 | C—H | C—H | C—CF3 | N | H | CF3 | CH2 | H | cyclo-PrCH2CO |
| 6-767 | C—H | C—H | C—CF3 | N | H | CF3 | CH2 | H | CF3CH2CO |
| 6-768 | C—H | C—H | C—CF3 | N | H | CF3 | CH2 | H | CH3SCH2CO |
| 6-769 | C—H | C—H | C—CF3 | N | H | CF3 | CH2 | H | CH3S(O)CH2CO |
| 6-770 | C—H | C—H | C—CF3 | N | H | CF3 | CH2 | H | CH3SO2CH2CO |
| 6-771 | C—H | C—H | C—CF3 | N | H | CF3 | CH2 | H | CH3CH2NHCO |
| 6-772 | C—CF3 | C—H | C—Cl | N | H | CF3 | CH2 | H | CH3CO |
| 6-773 | C—CF3 | C—H | C—Cl | N | H | CF3 | CH2 | H | CH3CH2CO |
| 6-774 | C—CF3 | C—H | C—Cl | N | H | CF3 | CH2 | H | n-PrCO |
| 6-775 | C—CF3 | C—H | C—Cl | N | H | CF3 | CH2 | H | cyclo-PrCO |
| 6-776 | C—CF3 | C—H | C—Cl | N | H | CF3 | CH2 | H | cyclo-PrCH2CO |
| 6-777 | C—CF3 | C—H | C—Cl | N | H | CF3 | CH2 | H | CF3CH2CO |
| 6-778 | C—CF3 | C—H | C—Cl | N | H | CF3 | CH2 | H | CH3SCH2CO |
| 6-779 | C—CF3 | C—H | C—Cl | N | H | CF3 | CH2 | H | CH3S(O)CH2CO |
| 6-780 | C—CF3 | C—H | C—Cl | N | H | CF3 | CH2 | H | CH3SO2CH2CO |
| 6-781 | C—CF3 | C—H | C—Cl | N | H | CF3 | CH2 | H | CH3CH2NHCO |
| 6-782 | C—CF3 | C—H | C—Br | N | H | CF3 | CH2 | H | CH3CO |
| 6-783 | C—CF3 | C—H | C—Br | N | H | CF3 | CH2 | H | CH3CH2CO |
| 6-784 | C—CF3 | C—H | C—Br | N | H | CF3 | CH2 | H | n-PrCO |
| 6-785 | C—CF3 | C—H | C—Br | N | H | CF3 | CH2 | H | cyclo-PrCO |
| 6-786 | C—CF3 | C—H | C—Br | N | H | CF3 | CH2 | H | cyclo-PrCH2CO |
| 6-787 | C—CF3 | C—H | C—Br | N | H | CF3 | CH2 | H | CF3CH2CO |
| 6-788 | C—CF3 | C—H | C—Br | N | H | CF3 | CH2 | H | CH3SCH2CO |
| 6-789 | C—CF3 | C—H | C—Br | N | H | CF3 | CH2 | H | CH3S(O)CH2CO |
| 6-790 | C—CF3 | C—H | C—Br | N | H | CF3 | CH2 | H | CH3SO2CH2CO |
| 6-791 | C—CF3 | C—H | C—Br | N | H | CF3 | CH2 | H | CH3CH2NHCO |
| 6-792 | C—CF3 | C—H | C—CF3 | N | H | CF3 | CH2 | H | CH3CO |
| 6-793 | C—CF3 | C—H | C—CF3 | N | H | CF3 | CH2 | H | CH3CH2CO |
| 6-794 | C—CF3 | C—H | C—CF3 | N | H | CF3 | CH2 | H | n-PrCO |
| 6-795 | C—CF3 | C—H | C—CF3 | N | H | CF3 | CH2 | H | cyclo-PrCO |
| 6-796 | C—CF3 | C—H | C—CF3 | N | H | CF3 | CH2 | H | cyclo-PrCH2CO |
| 6-797 | C—CF3 | C—H | C—CF3 | N | H | CF3 | CH2 | H | CF3CH2CO |
| 6-798 | C—CF3 | C—H | C—CF3 | N | H | CF3 | CH2 | H | CH3SCH2CO |
| 6-799 | C—CF3 | C—H | C—CF3 | N | H | CF3 | CH2 | H | CH3S(O)CH2CO |

TABLE 6-continued

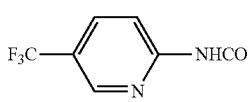

| Ex.-No. | B¹ | B² | B³ | B⁴ | X¹ | R | W¹ | R⁵ | R⁶ |
|---|---|---|---|---|---|---|---|---|---|
| 6-800 | C—CF3 | C—H | C—CF3 | N | H | CF3 | CH2 | H | CH3SO2CH2CO |
| 6-801 | C—CF3 | C—H | C—CF3 | N | H | CF3 | CH2 | H | CH3CH2NHCO |
| 6-802 | C—Cl | C—Cl | C—Cl | C—H | H | CF3 | — | H | tert-BuOCO |
| 6-803 | C—Cl | C—H | C—Cl | C—H | H | CF3 | — | H | 2-py-NHCO |
| 6-804 | C—Cl | C—H | C—Cl | C—H | H | CF3 | — | H | 3-py-NHCO |
| 6-805 | C—Cl | C—H | C—Cl | C—H | H | CF3 | — | H | 4-py-NHCO |
| 6-806 | C—Cl | C—H | C—Cl | C—H | H | CF3 | — | H | 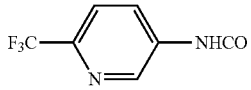 |
| 6-807 | C—Cl | C—H | C—Cl | C—H | H | CF3 | — | H | |
| 6-808 | C—Cl | C—H | C—Cl | C—H | H | CF3 | — | H | PhCH2HNCO |
| 6-809 | C—Cl | C—H | C—Cl | C—H | H | CF3 | — | H | |
| 6-810 | C—Cl | C—H | C—Cl | C—H | H | CF3 | — | H | (CH3)2NCO |
| 6-811 | C—Cl | C—H | C—Cl | C—H | H | CF3 | — | H | pyrrolidineCO |
| 6-812 | C—Cl | C—H | C—Cl | C—H | H | CF3 | — | H | piperidineCO |
| 6-813 | C—Cl | C—H | C—Cl | C—H | H | CF3 | — | H | morpholineCO |

TABLE 7

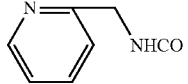

| Ex.-No. | B¹ | B² | B³ | B⁴ | X¹ | R | A¹ | A² | A³ | A⁴ | R' |
|---|---|---|---|---|---|---|---|---|---|---|---|
| 7-1 | C—Cl | C—H | C—Cl | C—H | H | CF3 | CH | CH | C—CF3 | CH | CN |
| 7-2 | C—Cl | C—H | C—Cl | C—H | H | CF3 | CH | CH | C—Cl | CH | CN |
| 7-3 | C—Cl | C—H | C—Cl | C—H | H | CF3 | CH | CH | C—Br | CH | CN |
| 7-4 | C—Cl | C—H | C—Cl | C—H | H | CF3 | CH | CH | C—F | CH | CN |
| 7-5 | C—Cl | C—H | C—Cl | C—H | H | CF3 | CH | CH | C—CH3 | CH | CN |
| 7-6 | C—Cl | C—H | C—Cl | C—H | H | CF3 | CH | CH | C—SCF3 | CH | CN |
| 7-7 | C—Cl | C—H | C—Cl | C—H | H | CF3 | CH | CH | C—S(O)CF3 | CH | CN |
| 7-8 | C—Cl | C—H | C—Cl | C—H | H | CF3 | CH | CH | C—S(O)2CF3 | CH | CN |
| 7-9 | C—Cl | C—H | C—Cl | C—H | H | CF3 | CH | CH | C—SCH2CF3 | CH | CN |
| 7-10 | C—Cl | C—H | C—Cl | C—H | H | CF3 | CH | CH | C—S(O)CH2CF3 | CH | CN |
| 7-11 | C—Cl | C—H | C—Cl | C—H | H | CF3 | CH | CH | C—S(O)2CH2CF3 | CH | CN |
| 7-12 | C—Cl | C—Cl | C—Cl | C—H | H | CF3 | CH | CH | C—CF3 | CH | CN |
| 7-13 | C—Cl | C—Cl | C—Cl | C—H | H | CF3 | CH | CH | C—Cl | CH | CN |
| 7-14 | C—Cl | C—Cl | C—Cl | C—H | H | CF3 | CH | CH | C—Br | CH | CN |
| 7-15 | C—Cl | C—Cl | C—Cl | C—H | H | CF3 | CH | CH | C—F | CH | CN |
| 7-16 | C—Cl | C—Cl | C—Cl | C—H | H | CF3 | CH | CH | C—CH3 | CH | CN |
| 7-17 | C—Cl | C—Cl | C—Cl | C—H | H | CF3 | CH | CH | C—SCF3 | CH | CN |
| 7-18 | C—Cl | C—Cl | C—Cl | C—H | H | CF3 | CH | CH | C—S(O)CF3 | CH | CN |
| 7-19 | C—Cl | C—Cl | C—Cl | C—H | H | CF3 | CH | CH | C—S(O)2CF3 | CH | CN |
| 7-20 | C—Cl | C—Cl | C—Cl | C—H | H | CF3 | CH | CH | C—SCH2CF3 | CH | CN |
| 7-21 | C—Cl | C—Cl | C—Cl | C—H | H | CF3 | CH | CH | C—S(O)CH2CF3 | CH | CN |

TABLE 7-continued

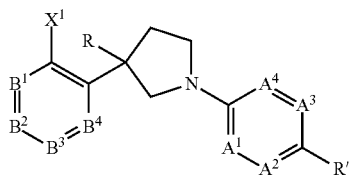

| Ex.-No. | B$^1$ | B$^2$ | B$^3$ | B$^4$ | X$^1$ | R | A$^1$ | A$^2$ | A$^3$ | A$^4$ | R' |
|---|---|---|---|---|---|---|---|---|---|---|---|
| 7-22 | C—Cl | C—Cl | C—Cl | C—H | H | CF3 | CH | CH | C—S(O)2CH2CF3 | CH | CN |
| 7-23 | C—CF3 | C—H | C—CF3 | C—H | H | CF3 | CH | CH | C—CF3 | CH | CN |
| 7-24 | C—CF3 | C—H | C—CF3 | C—H | H | CF3 | CH | CH | C—Cl | CH | CN |
| 7-25 | C—CF3 | C—H | C—CF3 | C—H | H | CF3 | CH | CH | C—Br | CH | CN |
| 7-26 | C—CF3 | C—H | C—CF3 | C—H | H | CF3 | CH | CH | C—F | CH | CN |
| 7-27 | C—CF3 | C—H | C—CF3 | C—H | H | CF3 | CH | CH | C—CH3 | CH | CN |
| 7-28 | C—CF3 | C—H | C—CF3 | C—H | H | CF3 | CH | CH | C—NO2 | CH | CN |
| 7-29 | C—CF3 | C—H | C—CF3 | C—H | H | CF3 | CH | CH | C—SCF3 | CH | CN |
| 7-30 | C—CF3 | C—H | C—CF3 | C—H | H | CF3 | CH | CH | C—S(O)CF3 | CH | CN |
| 7-31 | C—CF3 | C—H | C—CF3 | C—H | H | CF3 | CH | CH | C—S(O)2CF3 | CH | CN |
| 7-32 | C—CF3 | C—H | C—CF3 | C—H | H | CF3 | CH | CH | C—SCH2CF3 | CH | CN |
| 7-33 | C—CF3 | C—H | C—CF3 | C—H | H | CF3 | CH | CH | C—S(O)CH2CF3 | CH | CN |
| 7-34 | C—CF3 | C—H | C—CF3 | C—H | H | CF3 | CH | CH | C—S(O)2CH2CF3 | CH | CN |
| 7-35 | C—Cl | C—Cl | C—CF3 | C—H | H | CF3 | CH | CH | C—CF3 | CH | CN |
| 7-36 | C—Cl | C—Cl | C—CF3 | C—H | H | CF3 | CH | CH | C—Cl | CH | CN |
| 7-37 | C—Cl | C—Cl | C—CF3 | C—H | H | CF3 | CH | CH | C—Br | CH | CN |
| 7-38 | C—Cl | C—Cl | C—CF3 | C—H | H | CF3 | CH | CH | C—F | CH | CN |
| 7-39 | C—Cl | C—Cl | C—CF3 | C—H | H | CF3 | CH | CH | C—CH3 | CH | CN |
| 7-40 | C—Cl | C—Cl | C—CF3 | C—H | H | CF3 | CH | CH | C—SCF3 | CH | CN |
| 7-41 | C—Cl | C—Cl | C—CF3 | C—H | H | CF3 | CH | CH | C—S(O)CF3 | CH | CN |
| 7-42 | C—Cl | C—Cl | C—CF3 | C—H | H | CF3 | CH | CH | C—S(O)2CF3 | CH | CN |
| 7-43 | C—Cl | C—Cl | C—CF3 | C—H | H | CF3 | CH | CH | C—SCH2CF3 | CH | CN |
| 7-44 | C—Cl | C—Cl | C—CF3 | C—H | H | CF3 | CH | CH | C—S(O)CH2CF3 | CH | CN |
| 7-45 | C—Cl | C—Cl | C—CF3 | C—H | H | CF3 | CH | CH | C—S(O)2CH2CF3 | CH | CN |
| 7-46 | C—Cl | C—H | C—Cl | C—H | H | CF3 | CH | CH | C—SCH3 | CH | CN |
| 7-47 | C—Cl | C—H | C—Cl | C—H | H | CF3 | CH | CH | C—SCH3 | CH | CH2OH |
| 7-49 | C—Cl | C—H | C—Cl | C—H | H | CF3 | CH | CH | C—Br | N | CH2OH |
| 7-51 | C—Cl | C—H | C—CF3 | C—H | H | CF3 | CH | CH | C—Br | CH | CH2OH |
| 7-53 | C—Cl | C—H | C—Cl | C—H | H | CF3 | CH | CH | C—Br | CH | CH2OH |
| 7-55 | C—Cl | C—H | C—Cl | C—H | H | CF3 | CH | CH | C—I | CH | CH2OH |
| 7-57 | C—Cl | C—Cl | C—Cl | C—H | H | CF3 | CH | CH | C—Br | CH | CH2OH |
| 7-59 | C—Cl | C—H | C—Cl | C—H | H | CF3 | CH | CH | C—Cl | C—F | CH2OH |
| 7-61 | C—Cl | C—H | C—Cl | C—H | H | CF3 | C—F | CH | C—Cl | CH | CH2OH |
| 7-63 | C—CF3 | C—H | C—CF3 | C—H | H | CF3 | CH | CH | C—Cl | C—F | CH2OH |
| 7-65 | C—CF3 | C—H | C—CF3 | C—H | H | CF3 | CH | CH | C—Br | CH | CH2OH |
| 7-67 | C—CF3 | C—H | C—CF3 | C—H | H | CF3 | CH | CH | C—I | CH | CH2OH |
| 7-69 | C—CF3 | C—H | C—CF3 | C—H | H | CF3 | CH | CH | C—F | C—F | CH2OH |
| 7-71 | C—CF3 | C—H | C—CF3 | C—H | H | CF3 | CH | CH | C—F | C—F | CN |
| 7-72 | C—Cl | C—Cl | C—Cl | C—H | H | CF3 | CH | CH | C—Cl | C—F | CH2OH |
| 7-74 | C—CF3 | C—H | C—CF3 | C—H | H | CF3 | CH | CH | C—CH3 | C—F | CH2OH |
| 7-76 | C—Cl | C—Cl | C—Cl | C—H | H | CF3 | CH | CH | C—CH3 | C—F | CH2OH |
| 7-78 | C—Br | C—H | C—Br | C—H | H | CF3 | CH | CH | C—CF3 | CH | CH2OH |
| 7-86 | C—Cl | C—H | C—Cl | C—H | H | CF3 | CH | CH | C—Cl | N | CH2OH |
| 7-87 | C—Cl | C—Cl | C—Cl | C—H | H | CF3 | CH | CH | C—Cl | N | CO2CH3 |
| 7-88 | C—Cl | C—Cl | C—Cl | C—H | H | CF3 | CH | CH | C—Cl | N | CO2H |
| 7-89 | C—Cl | C—Cl | C—Cl | C—H | H | CF3 | CH | CH | C—Cl | N | CH2OH |
| 7-90 | C—CF3 | C—H | C—CF3 | C—H | H | CF3 | CH | CH | C—Cl | N | CO2CH3 |
| 7-91 | C—CF3 | C—H | C—CF3 | C—H | H | CF3 | CH | CH | C—Cl | N | CO2H |
| 7-92 | C—CF3 | C—H | C—CF3 | C—H | H | CF3 | CH | CH | C—Cl | N | CH2OH |
| 7-93 | C—Cl | C—Cl | C—Cl | C—H | H | CF3 | CH | CH | C—Br | N | CH2OH |
| 7-95 | C—CF3 | C—H | C—CF3 | C—H | H | CF3 | CH | CH | C—Br | N | CH2OH |
| 7-97 | C—Cl | C—H | C—Cl | C—H | H | CF3 | C—F | CH | C—Cl | N | CN |
| 7-98 | C—Cl | C—Cl | C—Cl | C—H | H | CF3 | C—F | CH | C—Cl | N | CN |
| 7-99 | C—CF3 | C—H | C—CF3 | C—H | H | CF3 | C—F | CH | C—Cl | N | CN |
| 7-100 | C—Cl | C—H | C—Cl | C—H | H | CF3 | CH | CH | C—OCH3 | CH | CH2OH |
| 7-102 | C—CF3 | C—H | C—CF3 | C—H | H | CF3 | CH | CH | C—OCF3 | CH | CN |
| 7-103 | C—Br | C—H | C—Br | C—H | H | CF3 | CH | CH | C—CF3 | CH | CN |
| 7-104 | C—Cl | C—H | C—Cl | C—H | H | CF3 | CH | CH | CH | N | CH2OH |
| 7-105 | C—Cl | C—Cl | C—Cl | C—H | H | CF3 | N | CH | C—CF3 | CH | CO2Et |
| 7-106 | C—Cl | C—Cl | C—Cl | C—H | H | CF3 | N | CH | C—CF3 | CH | CO2H |
| 7-107 | C—Cl | C—Cl | C—Cl | C—H | H | CF3 | N | CH | C—CF3 | CH | CH2OH |
| 7-108 | C—CF3 | C—H | C—CF3 | C—H | H | CF3 | N | CH | C—CF3 | CH | CO2Et |
| 7-109 | C—CF3 | C—H | C—CF3 | C—H | H | CF3 | N | CH | C—CF3 | CH | CO2H |
| 7-110 | C—CF3 | C—H | C—CF3 | C—H | H | CF3 | N | CH | C—CF3 | CH | CH2OH |
| 7-111 | C—Cl | C—H | C—Cl | C—H | H | CF3 | CH | CH | C—CF3 | N | CH2OH |
| 7-112 | C—Cl | C—Cl | C—Cl | C—H | H | CF3 | CH | CH | C—CF3 | N | CH2OH |
| 7-113 | C—Cl | C—H | C—CF3 | C—H | H | CF3 | CH | CH | C—CF3 | N | CO2Et |
| 7-114 | C—Cl | C—H | C—CF3 | C—H | H | CF3 | CH | CH | C—CF3 | N | CH2OH |

TABLE 7-continued

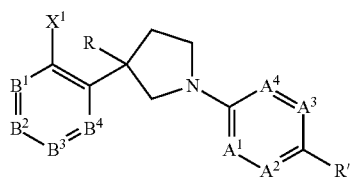

| Ex.-No. | $B^1$ | $B^2$ | $B^3$ | $B^4$ | $X^1$ | R | $A^1$ | $A^2$ | $A^3$ | $A^4$ | R' |
|---|---|---|---|---|---|---|---|---|---|---|---|
| 7-115 | C—CF3 | C—H | C—H | C—H | H | CF3 | CH | CH | C—CF3 | N | CO2Et |
| 7-116 | C—CF3 | C—H | C—H | C—H | H | CF3 | CH | CH | C—CF3 | N | CO2H |
| 7-117 | C—CF3 | C—H | C—H | C—H | H | CF3 | CH | CH | C—CF3 | N | CH2OH |
| 7-118 | C—CF3 | C—H | C—CF3 | C—H | H | CF3 | CH | CH | C—CF3 | N | CO2H |
| 7-119 | C—CF3 | C—H | C—CF3 | C—H | H | CF3 | CH | CH | C—CF3 | N | CH2OH |
| 7-120 | C—Br | C—H | C—Br | C—H | H | CF3 | CH | CH | C—CF3 | N | CO2Et |
| 7-121 | C—Br | C—H | C—Br | C—H | H | CF3 | CH | CH | C—CF3 | N | CH2OH |
| 7-122 | C—Cl | C—H | C—Cl | C—H | H | CF3 | CH | CH | C—CH3 | N | CO2Et |
| 7-123 | C—Cl | C—H | C—Cl | C—H | H | CF3 | CH | CH | C—CH3 | N | CO2H |
| 7-124 | C—Cl | C—H | C—Cl | C—H | H | CF3 | CH | CH | C—CH3 | N | CH2OH |
| 7-125 | C—Cl | C—H | C—Cl | C—H | H | CF3 | CH | CH | C—cyclo-Pr | N | CO2Et |
| 7-126 | C—Cl | C—H | C—Cl | C—H | H | CF3 | CH | CH | C—cyclo-Pr | N | CO2H |
| 7-127 | C—Cl | C—H | C—Cl | C—H | H | CF3 | CH | CH | C—cyclo-Pr | N | CH2OH |
| 7-128 | C—CF3 | C—H | C—CF3 | C—H | H | CF3 | CH | CH | C—cyclo-Pr | N | CO2Et |
| 7-129 | C—CF3 | C—H | C—CF3 | C—H | H | CF3 | CH | CH | C—cyclo-Pr | N | CH2OH |
| 7-130 | C—Cl | C—H | C—Cl | C—H | H | CF3 | N | CH | CH | N | CO2CH3 |
| 7-131 | C—Cl | C—H | C—Cl | C—H | H | CF3 | N | CH | CH | N | CO2H |
| 7-132 | C—Cl | C—H | C—Cl | C—H | H | CF3 | N | CH | C—CF3 | N | CO2Et |
| 7-133 | C—Cl | C—H | C—Cl | C—H | H | CF3 | N | CH | C—CF3 | N | CO2H |
| 7-134 | C—Cl | C—H | C—Cl | C—H | H | CF3 | N | CH | C—CF3 | N | CH2OH |
| 7-135 | C—Cl | C—Cl | C—Cl | C—H | H | CF3 | N | CH | C—CF3 | N | CO2Et |
| 7-136 | C—Cl | C—Cl | C—Cl | C—H | H | CF3 | N | CH | C—CF3 | N | CO2H |
| 7-137 | C—Cl | C—Cl | C—Cl | C—H | H | CF3 | N | CH | C—CF3 | N | CH2OH |
| 7-138 | C—Cl | C—Cl | C—Cl | C—H | H | CF3 | N | CH | C—CF3 | N | CH2OSO2CH3 |
| 7-139 | C—CF3 | C—H | C—H | C—H | H | CF3 | N | CH | C—CF3 | N | CO2Et |
| 7-140 | C—CF3 | C—H | C—H | C—H | H | CF3 | N | CH | C—CF3 | N | CO2H |
| 7-141 | C—CF3 | C—H | C—H | C—H | H | CF3 | N | CH | C—CF3 | N | CH2OH |
| 7-142 | C—CF3 | C—H | C—CF3 | C—H | H | CF3 | N | CH | C—CF3 | N | CO2Et |
| 7-143 | C—CF3 | C—H | C—CF3 | C—H | H | CF3 | N | CH | C—CF3 | N | CO2H |
| 7-144 | C—CF3 | C—H | C—CF3 | C—H | H | CF3 | N | CH | C—CF3 | N | CH2OH |
| 7-145 | C—CF3 | C—H | C—CF3 | C—H | H | CF3 | N | CH | C—CF3 | N | CH2OSO2CH3 |
| 7-146 | C—Br | C—H | C—Br | C—H | H | CF3 | N | CH | C—CF3 | N | CO2Et |
| 7-147 | C—Br | C—H | C—Br | C—H | H | CF3 | N | CH | C—CF3 | N | CH2OH |

TABLE 7a

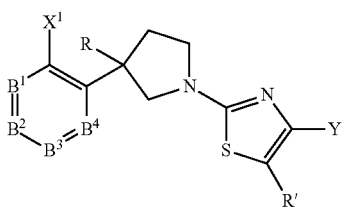

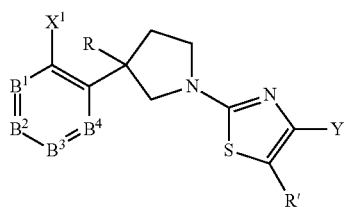

| Ex.-No. | B1 | B2 | B3 | B4 | X1 | R | Y | R' |
|---|---|---|---|---|---|---|---|---|
| 7a-1 | C—Cl | C—H | C—Cl | C—H | H | CF3 | C—Cl | CHO |
| 7a-2 | C—Cl | C—H | C—Cl | C—H | H | CF3 | C—Cl | CH2OH |
| 7a-3 | C—Cl | C—H | C—Cl | C—H | H | CF3 | C—CH3 | CO2Et |
| 7a-4 | C—Cl | C—H | C—Cl | C—H | H | CF3 | C—CH3 | CO2CH3 |
| 7a-5 | C—Cl | C—H | C—Cl | C—H | H | CF3 | C—CH3 | CH2OH |
| 7a-6 | C—Cl | C—H | C—Cl | C—H | H | CF3 | C—CF3 | CO2Et |
| 7a-7 | C—Cl | C—H | C—Cl | C—H | H | CF3 | C—CF3 | CO2H |
| 7a-8 | C—Cl | C—H | C—Cl | C—H | H | CF3 | C—CF3 | CH2OH |
| 7a-9 | C—Cl | C—Cl | C—Cl | C—H | H | CF3 | C—CF3 | CO2Et |
| 7a-10 | C—Cl | C—Cl | C—Cl | C—H | H | CF3 | C—CF3 | CO2H |
| 7a-11 | C—Cl | C—Cl | C—Cl | C—H | H | CF3 | C—CF3 | CH2OH |
| 7a-12 | C—CF3 | C—H | C—CF3 | C—H | H | CF3 | C—CF3 | CO2Et |
| 7a-13 | C—CF3 | C—H | C—CF3 | C—H | H | CF3 | C—CF3 | CO2H |
| 7a-14 | C—CF3 | C—H | C—CF3 | C—H | H | CF3 | C—CF3 | CH2OH |

TABLE 8

| Table 8 - Ex.-No. | 1H-NMR |
|---|---|
| 1-3 | 1H-NMR (CDCl3) δ: 1.14 (6H, d), 2.30-2.39 (1H, m), 2.53-2.55 (1H, m), 2.82-2.86 (1H, m), 3.45-3.52 (2H, m), 3.74 (1H, d), 4.02 (1H, d), 4.42 (2H, d), 5.79 (1H, s), 6.45 (1H, d), 6.59 (1H, d), 7.25-7.27 (3H, m), 7.39 (1H, t) |
| 1-4 | 1H-NMR (CDCl3) δ: 0.70-0.74 (2H, m), 0.88-1.00 (2H, m), 1.26-1.32 (1H, m), 2.51-2.55 (1H, m), 2.81-2.84 (1H, m), 3.45-3.52 (2H, m), 3.74 (1H, d), 4.02 (1H, d), 4.45 (2H, d), 5.98 (1H, s), 6.45 (1H, dd), 6.60 (1H, d), 7.27-7.28 (4H, m), 7.39 (1H, t) |
| 1-7 | 1H-NMR (CDCl3) δ: 0.92 (6H, d), 2.07-2.18 (3H, m), 2.51-2.54 (1H, m), 2.81-2.89 (1H, m), 3.45-3.52 (2H, m), 3.74 (1H, d), 4.02 (1H, d), 4.43 (2H, d), 5.75 (1H, s), 6.45 (1H, dd), 6.59 (1H, d), 7.26-7.29 (3H, m), 7.39 (1H, t) |
| 1-8 | 1H-NMR (CDCl3) δ: 1.83-2.36 (6H, m), 2.53-2.55 (1H, m), 2.80-2.89 (1H, m), 2.97-3.00 (1H, m), 3.47-3.51 (2H, m), 3.74 (1H, d), 4.02 (1H, d), 4.43 (2H, d), 5.67 (1H, s), 6.45 (1H, dd), 6.59 (1H, d), 7.26-7.27 (3H, m), 7.39 (1H, t) |
| 1-12 | 1H-NMR (CDCl3) δ: 0.18-0.19 (2H, m), 0.58-0.61 (3H, m), 0.90-0.97 (1H, m), 2.16 (2H, d), 2.53-2.56 (1H, m), 2.81-2.89 (1H, m), 3.45-3.54 (2H, m), 3.75 (1H, d), 4.03 (1H, d), 4.46 (2H, d), 6.31 (1H, s), 6.46 (1H, dd), 6.60 (1H, d), 7.27-7.29 (3H, m), 7.39 (1H, t) |
| 1-15 | 1H-NMR (CDCl3) δ: 2.51-2.56 (1H, m), 2.83-2.84 (1H, m), 3.44-3.55 (2H, m), 3.75 (1H, d), 4.01-4.05 (3H, m), 4.49 (2H, d), 6.46 (1H, dd), 6.61 (1H, br s), 7.28 (2H, s), 7.39 (1H, t) |
| 1-19 | 1H-NMR (CDCl3) δ: 2.48-2.58 (1H, m), 2.82-2.87 (1H, m), 3.06 (2H, q), 3.48-3.51 (1H, m), 3.75 (1H, d), 4.03 (1H, d), 4.47 (2H, d), 6.04 (1H, s), 6.46 (1H, dd), 6.60 (1H, d), 7.24-7.26 (3H, m), 7.39 (1H, t) |
| 1-20 | 1H-NMR (CDCl3) δ: 2.53-2.57 (1H, m), 2.86-2.88 (1H, m), 3.47-3.52 (2H, m), 3.73-3.85 (2H, m), 4.04 (1H, d), 4.51 (2H, d), 6.21 (1H, s), 6.46 (1H, dd), 6.61 (1H, d), 7.22-7.26 (3H, m), 7.39 (1H, t) |
| 1-21 | 1H-NMR (CDCl3) δ: 2.51-2.59 (1H, m), 2.82-2.90 (1H, m), 3.44-3.55 (2H, m), 3.75 (1H, d), 4.03 (1H, d), 4.51 (2H, d), 5.89 (1H, t), 6.46 (1H, dd), 6.61-6.62 (2H, m), 7.26-7.27 (3H, m), 7.39 (1H, s) |
| 1-23 | 1H-NMR (CDCl3) δ: 0.54-0.56 (2H, m), 1.18-1.21 (1H, m), 1.30 (3H, s), 2.51-2.58 (1H, m), 2.80-2.89 (1H, m), 3.46-3.52 (2H, m), 3.75 (1H, d), 4.02 (1H, d), 4.44 (2H, d), 6.13 (1H, s), 6.46 (1H, dd), 6.60 (1H, d), 7.26-7.28 (3H, m), 7.39 (1H, t) |
| 1-24 | 1H-NMR (CDCl3) δ: 1.77-1.81 (1H, m), 2.12-2.14 (1H, m), 2.32-2.36 (1H, m), 2.52-2.54 (1H, m), 2.82-2.87 (1H, m), 3.45-3.52 (2H, m), 3.74 (1H, d), 4.02 (1H, d), 4.50-4.51 (2H, m), 6.25 (1H, s), 6.46 (1H, dd), 6.60 (1H, d), 7.27-7.30 (3H, m), 7.39 (1H, t) |
| 1-25 | 1H-NMR (CDCl3) δ: 1.59-1.71 (1H, m), 2.07-2.28 (2H, m), 2.53-2.56 (1H, m), 2.81-2.89 (1H, m), 3.44-3.54 (3H, m), 3.75 (1H, d), 4.02 (1H, d), 4.45-4.52 (2H, m), 6.03 (1H, s), 6.46 (1H, dd), 6.60 (1H, d), 7.26-7.27 (3H, m), 7.39 (1H, t) |
| 1-28 | 1H-NMR (CDCl3) δ: 1.47-1.48 (2H, m), 1.67-1.70 (2H, m), 2.53-2.55 (1H, m), 2.82-2.90 (1H, m), 3.47-3.53 (2H, m), 3.75 (1H, d), 4.04 (1H, d), 4.48 (2H, m), 6.46 (1H, dd), 6.62 (1H, d), 6.74 (1H, s), 7.23-7.28 (3H, m), 7.39 (1H, t) |
| 1-30 | 1H-NMR (CDCl3) δ: 1.84 (3H, dd), 2.51-2.55 (1H, m), 2.83-2.84 (1H, m), 3.47-3.50 (2H, m), 3.74 (1H, d), 4.02 (1H, d), 4.49 (2H, d), 5.78 (2H, dd), 6.45 (1H, dd), 6.59 (1H, d), 6.85 (1H, dd), 7.27-7.30 (3H, m), 7.39 (1H, t) |
| 1-31 | 1H-NMR (CDCl3) δ: 1.55 (3H, s), 2.30-2.37 (1H, m), 2.52-2.54 (1H, m), 2.81-2.93 (2H, m), 3.49 (2H, m), 3.74 (1H, d), 4.02 (1H, d), 4.36-4.38 (2H, m), 6.44 (1H, dd), 6.59 (1H, d), 7.16 (1H, d), 7.27-7.28 (2H, m), 7.39 (1H, t) |
| 1-32 | 1H-NMR (CDCl3) δ: 1.74 (3H, d), 1.83 (3H, s), 2.51-2.55 (1H, m), 2.83-2.87 (1H, m), 3.46-3.52 (2H, m), 3.74 (1H, d), 4.02 (1H, d), 4.49 (2H, d), 6.06 (1H, s), 6.42-6.47 (2H, m), 6.59 (1H, d), 7.27-7.30 (3H, m), 7.39 (1H, t) |
| 1-36 | 1H-NMR (CDCl3) δ: 2.51-2.55 (1H, m), 2.82-2.84 (1H, m), 3.01 (2H, d), 3.46-3.52 (2H, m), 3.74 (1H, d), 4.02 (1H, d), 4.43 (2H, d), 5.17-5.24 (2H, m), 5.88-5.97 (2H, m), 6.45 (1H, dd), 6.59 (1H, d), 7.25-7.27 (3H, m), 7.39 (1H, t) |
| 1-39 | 1H-NMR (CDCl3) δ: 2.54-2.58 (1H, m), 2.84-2.86 (1H, m), 3.36 (2H, s), 3.48-3.51 (2H, m), 3.75 (1H, d), 4.03 (1H, d), 4.47 (2H, d), 6.45-6.47 (2H, m), 6.61 (1H, d), 7.25-7.27 (3H, m), 7.39 (1H, t) |
| 1-40 | 1H-NMR (CDCl3) δ: 2.48-2.58 (1H, m), 2.81-2.89 (1H, m), 3.42-3.54 (5H, m), 3.75 (1H, d), 3.90 (2H, s), 4.02 (1H, d), 4.48 (2H, d), 6.46 (1H, dd), 6.60 (1H, d), 6.84 (1H, s), 7.27 (3H, t), 7.39 (1H, dd) |
| 1-42 | 1H-NMR (CDCl3) δ: 2.09 (3H, s), 2.51-2.58 (1H, m), 2.81-2.89 (1H, m), 3.22 (2H, s), 3.46-3.52 (2H, m), 3.75 (1H, d), 4.03 (1H, d), 4.47 (2H, d), 6.46 (1H, dd), 6.60 (1H, d), 7.24-7.27 (4H, m), 7.39 (1H, t) |
| 1-50 | 1H-NMR (CDCl3) δ: 2.51-2.55 (1H, m), 2.81-2.86 (1H, m), 3.43-3.60 (5H, m), 3.73 (1H, m), 3.74 (1H, d), 4.00 (1H, d), 4.38 (2H, d), 5.79 (1H, s), 6.42 (1H, dd), 6.55 (1H, d), 7.17-7.40 (8H, m) |
| 1-51 | 1H-NMR (CDCl3) δ: 2.52-2.55 (1H, m), 2.80-2.88 (1H, m), 3.45-3.51 (2H, m), 3.74 (1H, d), 4.02 (1H, d), 4.67 (2H, d), 6.46 (1H, dd), 6.62 (1H, d), 7.26-7.27 (2H, m), 7.34-7.43 (3H, m), 7.83 (1H, td), 8.20 (1H, dt), 8.38 (1H, s), 8.53 (1H, dq) |
| 1-52 | 1H-NMR (CDCl3) δ: 2.51-2.56 (1H, m), 2.84-2.87 (1H, m), 3.48-3.52 (2H, m), 3.75 (1H, d), 4.03 (1H, d), 4.65 (2H, d), 6.46-6.62 (3H, m), 7.26-7.39 (4H, m), 8.10 (1H, ddd), 8.71 (1H, dd), 8.96 (1H, d) |
| 1-53 | 1H-NMR (CDCl3) δ: 2.51-2.56 (1H, m), 2.83-2.87 (1H, m), 3.46-3.53 (2H, m), 3.75 (1H, d), 4.03 (1H, d), 4.63 (2H, d), 6.47 (1H, dd), 6.61-6.62 (2H, m), 7.27 (3H, s), 7.34 (1H, d), 7.39 (1H, t), 7.59 (2H, dd), 8.71 (2H, dd) |

TABLE 8-continued

| Table 8 - Ex.-No. | 1H-NMR |
|---|---|
| 1-72 | 1H-NMR (CDCl3) δ: 2.14 (3H, d), 2.51-2.55 (1H, m), 2.82-2.88 (1H, m), 2.93 (3H, s), 3.46-3.53 (2H, m), 3.74 (1H, d), 4.03 (1H, dd), 4.58 (2H, d), 6.46-6.49 (1H, m), 6.60 (1H, dd), 7.09 (1H, dd), 7.26-7.28 (2H, m), 7.39 (1H, m). |
| 1-73 | 1H-NMR (CDCl3) δ: 1.13-1.21 (3H, m), 2.35-2.40 (2H, m), 2.50-2.56 (1H, m), 2.86-2.91 (4H, m), 3.46-3.51 (2H, m), 3.74 (1H, d), 4.01-4.04 (1H, m), 4.59 (2H, d), 6.44-6.50 (1H, m), 6.60 (1H, dd), 7.07 (1H, dd), 7.26-7.28 (3H, m), 7.39 (1H, t). |
| 1-74 | 1H-NMR (CDCl3) δ: 0.83-0.97 (4H, m), 1.57-1.80 (1H, m), 2.52-2.55 (1H, m), 2.84-2.86 (1H, m), 3.04 (3H, t), 3.46-3.55 (2H, m), 3.76 (1H, d), 4.03 (1H, dd), 4.69 (2H, d), 6.51-6.58 (2H, m), 7.16-7.27 (4H, m). |
| 1-75 | 1H-NMR (CDCl3) δ: 2.53-2.55 (1H, m), 2.84-2.86 (1H, m), 2.96 (3H, s), 3.27 (2H, q), 3.45-3.53 (2H, m), 3.75 (1H, dd), 4.03 (1H, dd), 4.51 (1H, s), 4.69 (1H, d), 6.49 (1H, d), 6.61 (1H, dd), 7.08 (1H, dd), 7.28 (2H, s), 7.39-7.40 (1H, m). |
| 1-77 | 1H-NMR (CDCl3) δ: 1.12 (3H, t), 2.50-2.55 (1H, m), 2.82-2.83 (1H, m), 3.17-3.22 (2H, m), 3.46-3.50 (2H, m), 3.74 (1H, d), 4.01 (1H, d), 4.36 (2H, d), 4.64 (1H, s), 6.46 (1H, dd), 6.58 (1H, d), 7.26-7.31 (3H, m), 7.39 (1H, t). |
| 1-78 | 1H-NMR (CDCl3) δ: 2.51-2.55 (1H, m), 2.83-2.86 (1H, m), 3.46-3.51 (2H, m), 3.74 (1H, d), 3.82-3.88 (2H, m), 4.02 (1H, d), 4.38 (2H, d), 4.87 (1H, s), 6.46 (1H, dd), 6.58 (1H, d), 7.23-7.27 (3H, m), 7.39 (1H, t). |
| 1-79 | 1H-NMR (CDCl3) δ: 0.90 (3H, t), 1.46-1.53 (2H, m), 2.50-2.55 (1H, m), 2.80-2.88 (1H, m), 3.08-3.15 (2H, m), 3.47-3.50 (2H, m), 3.74 (1H, d), 4.01 (1H, d), 4.36 (2H, d), 4.64 (1H, s), 6.46 (1H, d), 6.58 (1H, d), 7.23-7.31 (3H, m), 7.39 (1H, t). |
| 1-80 | 1H-NMR (CDCl3) δ: 1.12 (6H, d), 2.52-2.55 (1H, m), 2.80-2.88 (1H, m), 3.45-3.51 (2H, m), 3.75-3.83 (2H, m), 4.01 (1H, d), 4.34 (2H, d), 4.63 (1H, q), 6.45 (1H, d), 6.57 (1H, d), 7.27-7.29 (3H, m), 7.39 (1H, t). |
| 1-81 | 1H-NMR (CDCl3) δ: 0.53-0.58 (2H, m), 0.69-0.75 (2H, m), 2.45-2.50 (2H, m), 2.80-2.88 (1H, m), 3.48-3.51 (2H, m), 3.74 (1H, d), 4.02 (1H, d), 4.42 (2H, d), 5.44 (1H, d), 6.46 (1H, dd), 6.60 (1H, d), 7.26-7.32 (3H, m), 7.39 (1H, t). |
| 1-83 | 1H-NMR (acetone-d6) δ: 1.27 (9H, s), 2.73-2.79 (1H, m), 2.98-3.02 (1H, m), 3.50-3.53 (3H, m), 3.93 (1H, d), 4.22-4.24 (3H, m), 5.57 (1H, s), 6.61 (1H, dd), 6.69 (1H, d), 7.25 (1H, d), 7.54 (1H, t), 7.62 (3H, d). |
| 1-86 | 1H-NMR (CDCl3) δ: 1.24-1.74 (10H, m), 2.50-2.55 (1H, m), 2.82-2.83 (1H, m), 3.45-3.52 (3H, m), 3.74 (1H, d), 4.01 (1H, d), 4.35 (2H, d), 4.60 (1H, d), 6.46 (1H, dd), 6.58 (1H, d), 7.27-7.28 (3H, m), 7.39 (1H, t). |
| 1-87 | 1H-NMR (acetone-d6) δ: 2.63-2.91 (2H, m), 3.39-3.42 (2H, m), 3.62-3.64 (2H, m), 3.81 (1H, d), 4.10-4.19 (3H, m), 4.86 (1H, d), 5.01 (1H, d), 5.68-5.75 (1H, m), 6.50-6.58 (3H, m), 7.41-7.51 (4H, m). |
| 1-88 | 1H-NMR (CDCl3) δ: 2.21 (1H, t), 2.50-2.54 (1H, m), 2.82-2.85 (1H, m), 3.46-3.50 (3H, m), 3.73 (1H, d), 3.96-4.03 (3H, m), 4.36 (2H, d), 4.86 (1H, t), 6.45 (1H, dd), 6.57 (1H, d), 7.27-7.29 (3H, m), 7.39 (1H, t). |
| 1-89 | 1H-NMR (CDCl3) δ: 0.14-0.17 (2H, m), 0.45-0.49 (2H, m), 0.86-0.96 (1H, m), 2.52-2.55 (1H, m), 2.80-2.88 (1H, m), 3.02 (2H, m), 3.47-3.50 (2H, m), 3.74 (1H, d), 4.01 (1H, d), 4.36 (2H, d), 4.69 (1H, s), 6.45 (1H, dd), 6.58 (1H, d), 7.25-7.31 (3H, m), 7.39 (1H, t). |
| 1-97 | 1H-NMR (CDCl3) δ: 2.48-2.58 (1H, m), 2.81-2.89 (1H, m), 3.42-3.54 (5H, m), 3.75 (1H, d), 3.90 (2H, s), 4.02 (1H, d), 4.48 (2H, d), 6.46 (1H, dd), 6.60 (1H, d), 6.84 (1H, s), 7.27 (3H, t), 7.39 (1H, dd). |
| 1-98 | 1H-NMR (CDCl3) δ: 2.07 (3H, s), 2.52-2.60 (3H, m), 2.81-2.87 (1H, m), 3.38-3.48 (4H, m), 3.72 (1H, d), 4.01 (1H, d), 4.34 (2H, d), 4.94-4.96 (2H, m), 6.44 (1H, dd), 6.56 (1H, d), 7.26-7.29 (3H, m), 7.38 (1H, t). |
| 1-99 | 1H-NMR (CDCl3) δ: 0.92-0.96 (1H, m), 1.28-1.42 (1H, m), 2.52-2.56 (1H, m), 2.82-2.85 (2H, m), 3.48-3.51 (2H, m), 3.75 (1H, d), 4.02 (1H, d), 4.39-4.65 (4H, m), 5.29 (1H, t), 6.45 (1H, d), 6.60 (1H, d), 7.28 (3H, t), 7.39 (1H, t). |
| 1-101 | 1H-NMR (CDCl3) δ: 1.27 (3H, t), 2.52 (1H, d), 2.82-2.83 (1H, m), 3.46-3.49 (2H, m), 3.73 (1H, d), 3.99-4.01 (3H, m), 4.19 (2H, q), 4.37 (2H, d), 4.88 (1H, s), 6.45 (1H, dd), 6.57 (1H, d), 7.27-7.29 (3H, m), 7.39 (1H, t). |
| 1-110 | 1H-NMR (CDCl3) δ: 2.52-2.56 (1H, m), 2.82-2.83 (1H, m), 3.44-3.49 (2H, m), 3.72 (1H, d), 4.00 (1H, d), 4.33-4.36 (4H, m), 4.75 (2H, br s), 6.42 (1H, d), 6.55 (1H, d), 7.22-7.33 (8H, m), 7.39 (1H, t). |
| 1-113 | 1H-NMR (CDCl3) δ: 1.12 (3H, t), 2.52-2.57 (1H, m), 2.78-2.90 (4H, m), 3.24-3.35 (2H, m), 3.48-3.51 (2H, m), 3.75 (1H, d), 4.02 (1H, d), 4.34 (1H, s), 4.49 (2H, s), 6.48 (1H, dd), 6.59 (1H, d), 7.15 (1H, d), 7.27-7.28 (2H, m), 7.39 (1H, t). |
| 1-115 | 1H-NMR (CDCl3) δ: 1.85-1.90 (4H, m), 2.51-2.53 (1H, m), 2.81-2.85 (1H, m), 3.30-3.33 (4H, m), 3.45-3.51 (2H, m), 3.74 (1H, d), 4.01 (1H, d), 4.41 (2H, d), 4.64 (1H, d), 6.45 (1H, d), 6.58 (1H, d), 7.27-7.28 (3H, m), 7.35 (1H, d), 7.38 (1H, t). |
| 1-116 | 1H-NMR (CDCl3) δ: 1.52-1.55 (6H, m), 2.47-2.57 (1H, m), 2.80-2.88 (1H, m), 3.29-3.31 (4H, m), 3.45-3.51 (2H, m), 3.74 (1H, d), 4.01 (1H, d), 4.40 (2H, m), 4.85 (1H, t), 6.45 (1H, dd), 6.58 (1H, d), 7.26-7.33 (3H, m), 7.38 (1H, t). |
| 1-117 | 1H-NMR (CDCl3) δ: 2.50-2.55 (1H, m), 2.81-2.83 (1H, m), 3.33 (4H, t), 3.45-3.51 (2H, m), 3.66 (4H, t), 3.74 (1H, d), 4.02 (1H, d), 4.41 (2H, d), 4.88 (1H, t), 6.45 (1H, dd), 6.59 (1H, d), 7.26-7.32 (3H, m), 7.39 (1H, t). |
| 1-118 | 1H-NMR (CDCl3) δ: 2.51-2.53 (1H, m), 2.80-2.92 (7H, m), 3.45-3.51 (2H, m), 3.74 (1H, d), 4.01 (1H, d), 4.40 (2H, d), 4.82 (1H, t), 6.45 (1H, dd), 6.58 (1H, d), 7.27-7.28 (2H, m), 7.33 (1H, m), 7.38 (1H, t). |
| 1-123 | 1H-NMR (CDCl3) δ: 2.53-2.56 (1H, m), 2.81-2.89 (1H, m), 3.46-3.52 (2H, m), 3.75 (1H, d), 4.03 (1H, d), 4.38 (2H, d), 4.45 (2H), 5.30 (1H, s), 6.46 (1H, dd), 6.60 (1H, d), 7.24-7.28 (3H, m), 7.39 (1H, t) |

TABLE 8-continued

| Table 8 - Ex.-No. | 1H-NMR |
|---|---|
| 1-128 | 1H-NMR (CDCl3) δ: 1.44 (9H, s), 2.72-2.87 (1H, m), 3.45-3.52 (2H, m), 3.74 (1H, d), 4.02 (1H, d), 4.30 (2H, d), 4.92 (1H, br s), 6.45 (1H, dd), 6.58 (1H, d), 7.25-7.27 (3H, m), 7.38-7.39 (1H, m). |
| 1-129 | 1H-NMR (CDCl3) δ: 1.48 (9H, s), 2.53-2.55 (1H, m), 2.83-2.87 (4H, m), 3.43-3.51 (2H, m), 3.75 (1H, d), 4.02 (1H, d), 4.47 (2H, s), 6.48 (1H, dd), 6.58 (1H, d), 7.12 (1H, s), 7.26-7.28 (3H, m), 7.39 (1H, t). |
| 1-141 1-143 | 1H-NMR (CDCl3) δ: 2.50-2.60 (1H, m), 2.83-2.91 (1H, m), 3.48-3.61 (2H, m), 3.79 (1H, d), 3.91 (2H, s), 4.06 (1H, d), 6.74 (1H, d), 6.80 (1H, d), 7.30 (2H, d), 7.40 (2H, dd), 5.68 (1H, t), 6.70 (1H, dd), 6.79 (1H, d), 7.29 (2H, d), 7.40 (1H, t), 7.45 (1H, d). |
| 1-145 | 1H-NMR (CDCl3) δ: 0.92 (6H, d), 2.03-2.17 (1H, m), 2.50-2.60 (1H, m), 2.83-2.91 (1H, m), 3.48-3.60 (2H, m), 3.78 (1H, d), 4.06 (1H, d), 4.49 (2H, d), 5.65 (1H, bt), 6.67-6.80 (2H, m), 7.28-7.46 (3H, m) |
| 1-146 | 1H-NMR (CDCl3) δ: 0.72 (2H, dt), 0.97 (2H, dt), 1.28-1.36 (1H, m), 2.50-2.60 (1H, m), 2.83-2.91 (1H, m), 3.45-3.61 (2H, m), 3.78 (1H, d), 4.06 (1H, d), 4.51 (2H, d), 5.95 (1H, br s), 6.70 (1H, dd), 6.80 (1H, d), 7.29 (2H, d), 7.39 (1H, t), 7.44 (1H, d). |
| 1-150 | 1H-NMR (CDCl3) δ: 1.86-1.98 (2H, m), 2.10-2.32 (4H, m), 2.50-2.60 (1H, m), 2.83-3.00 (2H, m), 3.48-3.59 (2H, m), 3.78 (1H, d), 4.06 (1H, d), 4.49 (2H, d), 5.59 (1H, bt), 6.68-6.80 (2H, m), 7.26-7.46 (4H, m) |
| 1-151 | 1H-NMR (CDCl3) δ: 1.00 (9H, s), 2.04 (2H, s), 2.50-2.60 (1H, m), 2.83-2.91 (1H, m), 3.48-3.60 (2H, m), 3.78 (1H, d), 4.06 (1H, d), 4.49 (2H, d), 5.60 (1H, bt), 6.67-6.80 (2H, m), 7.28-7.48 (3H, m) |
| 1-154 | 1H-NMR (CDCl3) δ: 1.93-2.02 (2H, m), 2.43-2.57 (5H, m), 2.50-2.60 (1H, m), 3.45-3.59 (2H, m), 3.78 (1H, d), 4.05 (1H, d), 4.56 (2H, d), 5.92 (1H, b), 6.51-6.81 (3H, m), 7.29-7.49 (4H, m) |
| 1-155 | 1H-NMR (CDCl3) δ: 0.14-0.19 (2H, m), 0.55-0.61 (2H, m), 0.88-0.93 (1H, m), 2.16 (2H, d), 2.50-2.60 (1H, m), 2.82-2.90 (1H, m), 3.46-3.59 (2H, m), 3.78 (1H, d), 4.12 (1H, d), 4.14 (2H, d), 6.21 (1H, b), 6.67-6.81 (2H, m), 7.29-7.48 (4H, m) |
| 1-162 | 1H-NMR (acetone-d6) δ: 2.72-2.82 (1H, m), 2.99-3.09 (1H, m), 3.28 (2H, q), 3.54-3.66 (2H, m), 4.02 (1H, d), 4.34 (1H, d), 4.48 (2H, d), 6.92 (1H, dd), 6.96 (1H, d), 7.42 (1H, d), 7.55 (1H, t), 7.63 (2H, d), 7.70 (1H, br s). |
| 1-164 | 1H-NMR (CDCl3) δ: 2.50-2.61 (1H, m), 2.84-2.92 (1H, m), 3.50-3.60 (2H, m), 3.78 (1H, d), 4.08 (1H, d), 4.58 (2H, d), 5.89 (1H, t), 6.51 (1H, b), 6.69-6.83 (3H, m), 7.27-7.44 (3H, m) |
| 1-166 | 1H-NMR (CDCl3) δ: 1.45-1.70 (2H, m), 1.71-1.80 (3H, m), 1.95-2.05 (4H, m), 2.38-2.42 (1H, m), 2.50-2.60 (1H, m), 3.49-3.61 (2H, m), 3.78 (1H, d), 4.06 (1H, d), 4.56 (2H, d), 4.09 (1H, m), 4.48 (2H, d), 5.84 (1H, d), 6.68-6.80 (2H, m), 7.29-7.42 (4H, m) |
| 1-167 | 1H-NMR (CDCl3) δ: 0.53-0.58 (2H, m), 1.17-1.21 (2H, m), 1.26 (1H, s), 2.50-2.61 (1H, m), 2.82-2.89 (1H, m), 3.47-3.60 (2H, m), 3.78 (1H, d), 4.06 (1H, d), 4.51 (2H, d), 6.02 (1H, bt), 6.68-6.81 (2H, m), 7.28-7.45 (4H, m) |
| 1-173 | 1H-NMR (CDCl3) δ: 2.50-2.60 (1H, m), 2.83-2.89 (1H, m), 3.48-3.60 (2H, m), 3.78 (1H, d), 4.08 (1H, d), 4.58 (2H, d), 5.62-5.67 (1H, m), 5.82 (1H, bt), 6.01-6.27 (1H, m), 6.26-6.33 (1H, m), 6.70-6.83 (1H, m), 7.28-7.51 (3H, m) |
| 1-174 | 1H-NMR (CDCl3) δ: 1.84 (3H, dd), 2.50-2.60 (1H, m), 2.82-2.91 (1H, m), 3.47-3.60 (2H, m), 3.78 (1H, d), 4.06 (1H, d), 4.56 (2H, d), 5.65 (1H, bt), 5.73-5.79 (1H, m), 6.68-6.89 (3H, m), 7.28-7.48 (3H, m) |
| 1-176 | 1H-NMR (CDCl3) δ: 1.73 (3H, d), 1.82 (3H, s), 2.50-2.64 (1H, m), 2.83-2.91 (1H, m), 3.49-3.61 (2H, m), 3.78 (1H, d), 4.06 (1H, d), 4.56 (2H, d), 5.97 (1H, bt), 6.01 (1H, q), 6.68-6.81 (2H, m), 7.26-7.48 (4H, m) |
| 1-180 | 1H-NMR (CDCl3) δ: 2.50-2.60 (1H, m), 2.83-2.89 (1H, m), 3.00 (2H, d), 3.48-3.60 (2H, m), 3.78 (1H, d), 4.06 (1H, d), 4.49 (2H, d), 5.15-5.24 (2H, m), 5.83-5.68 (2H, m), 6.33 (1H, m), 6.67-6.80 (2H, m), 7.28-7.45 (3H, m) |
| 1-182 | 1H-NMR (CDCl3) δ: 1.92 (3H, s), 2.50-2.60 (1H, m), 2.83-2.92 (1H, m), 3.48-3.61 (2H, m), 3.78 (1H, d), 4.06 (1H, d), 4.52 (2H, d), 5.96 (1H, bt), 6.68-6.81 (2H, m), 7.29-7.46 (3H, m) |
| 1-183 | 1H-NMR (CDCl3) δ: 2.50-2.64 (1H, m), 2.83-2.91 (1H, m), 3.36 (2H, s), 3.49-3.61 (2H, m), 3.79 (1H, d), 4.08 (1H, d), 4.54 (2H, d), 6.30 (1H, bt), 6.01 (1H, q), 6.68-6.83 (2H, m), 7.28-7.43 (4H, m) |
| 1-185 | 1H-NMR (CDCl3) δ: 1.18 (3H, t), 2.50-2.61 (1H, m), 2.83-2.92 (1H, m), 3.50-3.60 (4H, m), 3.78 (1H, d), 3.94 (2H, s), 4.07 (1H, d), 4.55 (2H, d), 6.68-6.89 (3H, m), 7.28-7.45 (3H, m) |
| 1-186 | 1H-NMR (CDCl3) δ: 2.06 (3H, s), 2.50-2.61 (1H, m), 2.84-2.92 (1H, m), 2.84-2.92 (1H, m), 3.50-3.62 (2H, m), 3.78 (1H, d), 4.07 (1H, d), 4.54 (2H, d), 6.68-6.82 (2H, m), 7.13 (1H, b), 7.28-7.45 (4H, m) |
| 1-188 | 1H-NMR (CDCl3) δ: 2.12 (3H, s), 2.54-2.63 (1H, m), 2.84-2.92 (1H, m), 3.54-3.60 (2H, m), 3.78 (1H, d), 4.06 (1H, d). |
| 1-198 | 1H-NMR (CDCl3) δ: 2.50-2.64 (1H, m), 2.83-2.88 (1H, m), 3.36 (2H, s), 3.49-3.60 (2H, m), 3.79 (1H, d), 4.08 (1H, d), 4.70 (2H, d), 6.30 (1H, bt), 6.70-6.83 (2H, m), 7.26-7.51 (5H, m), 8.01-8.71 (2H, m) |
| 1-210 1-211 | 1H-NMR (CDCl3) δ: 2.53-2.60 (1H, m), 2.83-2.91 (1H, m), 3.48-3.59 (2H, m), 3.78 (1H, d), 4.06 (1H, d), 4.68 (2H, d), 6.25 (1H, bt), 6.68-7.07 (3H, m), 7.28-7.55 (6H, m), 1H-NMR (CDCl3) δ: 2.50-2.60 (1H, m), 2.82-2.90 (1H, m), 3.45-3.59 (2H, m), 3.78 (1H, m), 3.95 (3H, s), 4.06 (1H, d), 4.62 (2H, d), 6.04-6.82 (6H, m), 7.29-7.50 (4H, m) |

TABLE 8-continued

| Table 8 - Ex.-No. | 1H-NMR |
|---|---|
| 1-216 | 1H-NMR (CDCl3) δ: 2.50-2.60 (1H, m), 2.82-2.90 (1H, m), 3.45-3.59 (2H, m), 3.78 (1H, d), 4.06 (1H, d), 4.63 (2H, d), 5.88 (1H, b), 6.36 (1H, d), 6.69-6.81 (2H, m), 7.29-7.53 (9H, m), 7.64 (1H, d) |
| 1-220 | 1H-NMR (CDCl3) δ: 1.11 (3H, t), 2.50-2.60 (1H, m), 2.83-2.91 (1H, m), 3.15-3.24 (2H, m), 3.44-3.58 (3H, m), 3.78 (1H, d), 4.06 (1H, d), 4.52-4.44 (4H, m), 6.71 (1H, d), 6.79 (1H, d), 7.29 (2H, s), 7.39 (1H, t), 7.50 (1H, d) |
| 1-222 | 1H-NMR (CDCl3) δ: 0.88 (3H, t), 1.42-1.52 (2H, m), 2.50-2.60 (1H, m), 2.82-2.90 (1H, m), 3.13 (2H, q), 3.46-3.59 (2H, m), 3.78 (1H, d), 4.06 (1H, d), 4.25 (1H, b), 4.44 (2H, d), 4.57 (1H, b), 6.68-6.78 (2H, m), 7.28-7.51 (4H, m) |
| 1-224 | 1H-NMR (CDCl3) δ: 0.50-0.56 (2H, m), 0.67-0.73 (2H, m), 2.37-2.41 (1H, m), 2.50-2.60 (1H, m), 2.82-2.90 (1H, m), 3.46-3.59 (2H, m), 3.74 (1H, d), 4.50 (1H, d), 4.63 (1H, bs), 5.32 (1H, bt), 6.68-6.81 (2H, m), 7.29-7.51 (4H, m) |
| 1-227 | 1H-NMR (CDCl3) δ: 1.62-1.82 (4H, m), 2.26-2.31 (3H, m), 2.50-2.60 (1H, m), 2.82-2.90 (1H, m), 3.46-3.59 (2H, m), 3.78 (1H, d), 4.12 (1H, d), 4.35-4.44 (3H, m), 6.68-6.79 (2H, m), 7.29-7.50 (4H, m) |
| 1-228 | 1H-NMR (CDCl3) δ: 1.25-1.40 (2H, m), 1.50-1.65 (4H, m), 1.89-2.00 (2H, m), 2.50-2.60 (1H, m), 2.75-2.89 (1H, m), 3.40-3.60 (2H, m), 3.78 (1H, d), 3.91-3.96 (1H, m), 4.09 (1H, d), 4.23 (1H, b), 4.44 (2H, d), 4.56 (1H, b), 6.68-6.80 (2H, m), 7.29-7.51 (4H, m) |
| 1-230 | 1H-NMR (CDCl3) δ: 2.50-2.60 (1H, m), 2.82-2.90 (1H, m), 3.46-3.62 (2H, m), 3.76-3.81 (3H, m), 4.08 (1H, d), 4.32 (1H, b), 4.45 (2H, d), 4.63 (1H, b), 6.68-6.79 (2H, m), 7.28-7.51 (4H, m) |
| 1-231 | 1H-NMR (CDCl3) δ: 2.21 (1H, t), 2.50-2.60 (1H, m), 2.82-2.90 (1H, m), 3.46-3.58 (2H, m), 3.78 (1H, d), 3.97-4.00 (2H, m), 4.45 (3H, m), 4.71 (1H, b), 6.68-6.78 (2H, m), 7.28-7.50 (4H, m) |
| 1-232 | 1H-NMR (CDCl3) δ: 0.12-0.18 (2H, m), 0.43-0.50 (2H, m), 0.86-0.95 (1H, m), 2.50-2.60 (1H, m), 2.82-2.90 (1H, m), 3.00-3.04 (2H, m), 3.46-3.59 (2H, m), 3.78 (1H, d), 4.12 (1H, d), 4.36 (1H, t), 4.44 (2H, d), 4.58 (1H, t), 6.68-6.78 (2H, m), 7.29-7.52 (4H, m) |
| 1-238 | 1H-NMR (CDCl3) δ: 2.24-2.40 (2H, m), 2.50-2.60 (1H, m), 2.82-2.90 (1H, m), 3.46-3.57 (4H, m), 3.77 (1H, d), 4.07 (1H, d), 4.41 (2H, d), 4.65 (1H, b), 4.78 (1H, b), 6.68-6.83 (2H, m), 7.29-7.46 (4H, m) |
| 1-243 | 1H-NMR (CDCl3) δ: 2.50-2.60 (1H, m), 3.30 (3H, s), 3.30-3.60 (6H, m), 3.78 (1H, d), 4.09 (1H, d), 4.44 (2H, d), 4.60 (1H, b), 4.84 (1H, b), 6.68-6.80 (2H, m), 7.29-7.51 (4H, m) |
| 1-244 | 1H-NMR (CDCl3) δ: 2.12 (3H, s), 2.50-2.64 (2H, m), 2.82-2.91 (1H, m), 3.36-3.79 (4H, m), 3.78 (1H, d), 4.08 (1H, d), 4.44 (2H, d), 4.72 (2H, b), 6.68-6.80 (2H, m), 7.29-7.50 (4H, m) |
| 1-253 | 1H-NMR (CDCl3) δ: 2.50-2.60 (1H, m), 2.82-2.90 (1H, m), 3.46-3.60 (2H, m), 3.76 (1H, d), 4.04 (1H, d), 4.33 (2H, d), 4.43 (2H, d), 4.70 (2H, b), 6.66-6.77 (2H, m), 7.14-7.48 (9H, m) |
| 1-254 | 1H-NMR (CDCl3) δ: 2.49-2.59 (1H, m), 2.81-2.90 (1H, m), 3.46-3.57 (2H, m), 3.76 (1H, d), 4.04 (1H, d), 4.47 (4H, d), 5.14 (1H, b), 5.59 (1H, b), 6.66-6.77 (2H, m), 7.14-7.66 (7H, m), 8.45-8.48 (1H, m) |
| 1-255 | 1H-NMR (CDCl3) δ: 1.85-1.92 (4H, m), 2.50-2.60 (1H, m), 2.82-2.90 (1H, m), 3.32-3.49 (4H, m), 3.50-3.62 (2H, m), 3.78 (1H, d), 4.08 (1H, d), 4.50 (3H, s), 6.71-6.80 (2H, m), 7.29-7.56 (4H, m) |
| 1-257 | 1H-NMR (CDCl3) δ: 2.50-2.60 (1H, m), 2.82-2.90 (1H, m), 3.31 (4H, t), 3.50-3.62 (2H, m), 3.66 (4H, t), 3.78 (1H, d), 4.08 (1H, d), 4.50 (2H, d), 4.74 (1H, b), 6.68-6.80 (2H, m), 7.28-7.45 (4H, m) |
| 1-258 | 1H-NMR (CDCl3) δ: 2.50-2.60 (1H, m), 2.83-3.00 (1H, m), 2.86 (6H, s), 3.48-3.58 (2H, m), 3.78 (1H, d), 4.08 (1H, d), 4.48 (2H, d), 4.68 (1H, bt), 6.68-6.80 (2H, m), 7.26-7.46 (4H, m) |
| 1-260 | 1H-NMR (CDCl3) δ: 0.61-0.80 (4H, m), 2.36-2.42 (1H, m), 2.50-2.60 (1H, m), 2.82-3.00 (1H, m), 2.89 (3H, s), 3.47-3.58 (2H, m), 3.78 (1H, d), 4.06 (1H, d), 4.50 (2H, d), 5.62 (1H, bt), 6.67-6.80 (2H, m), 7.28-7.62 (4H, m) |
| 1-270 | 1H-NMR (CDCl3) δ: 1.45 (9H, s), 2.50-2.60 (1H, m), 2.83-2.91 (1H, m), 3.45-3.61 (2H, m), 3.78 (1H, d), 4.06 (1H, d), 4.38 (2H, d), 4.83 (1H, br s), 6.71 (1H, dd), 6.79 (1H, d), 7.29 (2H, d), 7.39 (1H, t), 7.44 (1H, d) |
| 1-274 | 1H-NMR (CDCl3) δ: 2.55-2.60 (1H, m), 2.88-2.92 (1H, m), 3.52-3.61 (2H, m), 3.80-3.87 (1H, m), 4.09-4.11 (1H, m), 4.50 (2H, d), 5.06 (1H, t), 6.73-6.76 (1H, m), 7.30-7.37 (4H, m) |
| 1-275 | 1H-NMR (CDCl3) δ: 2.55-2.60 (1H, m), 2.87-2.92 (1H, m), 3.51-3.82 (5H, m), 4.12-4.19 (1H, m), 4.42 (2H, d), 4.88 (1H, t), 6.72-6.75 (1H, m), 7.26-7.69 (5H, m) |
| 1-276 | 1H-NMR (CDCl3) δ: 2.52-2.57 (1H, m), 2.85-2.89 (1H, m), 3.47-3.55 (2H, m), 3.69-3.86 (1H, m), 3.98-4.27 (3H, m), 4.79 (1H, t), 6.61-6.76 (2H, m), 7.20-7.95 (9H, m). |
| 1-285 | 1H-NMR (CDCl3) δ: 1.16 (3H, t), 2.22 (2H, q), 2.42-2.53 (1H, m), 2.81-2.89 (1H, m), 3.44-3.56 (2H, m), 3.69-3.76 (1H, m), 4.00-4.04 (1H, m), 4.42-4.44 (2H, m), 5.81 (1H, br s), 6.49-6.51 (1H, m), 6.77-6.78 (1H, m), 7.27-7.29 (3H, m), 7.39-7.39 (1H, m). |
| 1-286 | 1H-NMR (CDCl3) δ: 0.68-0.75 (2H, m), 0.95-1.00 (2H, m), 1.30-1.35 (1H, m), 2.50-2.56 (1H, m), 3.42-3.54 (2H, m), 3.74 (1H, d), 4.02 (1H, d), 4.44 (2H, d), 5.99 (1H, b), 6.48-7.40 (6H, m) |
| 1-287 | 1H-NMR (CDCl3) δ: 2.50-2.60 (1H, m), 2.81-2.90 (1H, m), 3.03 (1H, d), 3.43-3.54 (1H, m), 3.74 (1H, d), 4.02 (1H, d), 4.47 (2H, d), 6.07 (1H, b), 6.48-6.70 (2H, m), 7.22-7.40 (4H, m) |

TABLE 8-continued

| Table 8 - Ex.-No. | 1H-NMR |
|---|---|
| 1-291 | 1H-NMR (CDCl3) δ: 1.10 (3H, t), 2.14 (2H, q), 2.25 (3H, s), 2.41-2.51 (1H, m), 2.73-2.80 (1H, m), 3.36-3.52 (2H, m), 3.70 (1H, d), 3.97 (1H, d), 4.29 (2H, d), 5.40 (1H, s), 6.33-6.37 (2H, m), 7.06 (1H, d), 7.24 (2H, d), 7.32 (1H, t). |
| 1-295 | 1H-NMR (CDCl3) δ: 2.62-2.66 (1H, m), 2.97-3.05 (1H, m), 3.57-3.62 (2H, m), 3.86-3.89 (3H, m), 4.19 (1H, d), 6.77-6.82 (2H, m), 7.42 (1H, d), 7.85-7.93 (3H, m). |
| 1-296 | 1H-NMR (CDCl3) δ: 2.58-2.68 (1H, m), 2.97-3.05 (1H, m), 3.24 (2H, q), 3.51-3.68 (2H, m), 3.85 (1H, d), 4.20 (1H, d), 4.55 (2H, d), 5.99 (1H, t), 6.79 (2H, dd), 7.44 (1H, d), 7.84 (2H, s), 7.93 (1H, s). |
| 1-297 | 1H-NMR (CDCl3) δ: 2.58-2.68 (3H, m), 2.97-3.05 (1H, m), 3.50-3.66 (2H, m), 3.78-3.87 (3H, m), 4.19 (1H, d), 4.53 (2H, d), 5.94 (1H, t), 6.74 (1H, dd), 6.83 (1H, d), 7.46 (1H, d), 7.85 (2H, s), 7.93 (1H, s). |
| 1-298 | 1H-NMR (CDCl3) δ: 2.58-2.67 (1H, m), 2.97-3.05 (1H, m), 3.53-3.68 (4H, m), 3.84 (1H, d), 4.19 (1H, d), 4.43 (2H, d), 4.98 (1H, br s), 6.74 (1H, dd), 6.83 (1H, d), 7.48 (1H, d), 7.84 (2H, s), 7.93 (1H, s). |
| 1-299 | 1H-NMR (CDCl3) δ: 1.24 (3H, t), 2.58-2.68 (1H, m), 2.97-3.05 (1H, m), 3.50-3.67 (2H, m), 3.85 (1H, d), 4.09-4.21 (3H, m), 4.43 (2H, d), 4.96 (1H, br s), 6.74 (1H, dd), 6.83 (1H, d), 7.85 (2H, d), 7.93 (1H, s). |
| 1-300 | 1H-NMR (CDCl3) δ: 1.57 (9H, s), 2.58-2.68 (1H, m), 2.96-3.05 (1H, m), 3.50-3.63 (2H, m), 3.85 (1H, d), 4.19 (1H, d), 4.38 (2H, d), 4.83 (1H, br s), 6.74 (1H, dd), 6.82 (1H, d), 7.46 (1H, d), 7.84 (2H, s), 7.93 (1H, s). |
| 1-301 | 1H-NMR (CDCl3) δ: 2.57-2.67 (1H, m), 2.74 (3H, d), 2.96-3.04 (1H, m), 3.49-3.65 (2H, m), 3.84 (1H, d), 4.18 (1H, d), 4.44-4.39 (3H, m), 4.75 (1H, t), 6.73 (1H, dd), 6.81 (1H, d), 7.50 (1H, d), 7.84 (2H, s), 7.93 (1H, s). |
| 1-302 | 1H-NMR (CDCl3) δ: 1.11 (3H, t), 2.57-2.68 (1H, m), 2.96-3.04 (1H, m), 3.14-3.23 (2H, m), 3.49-3.66 (2H, m), 3.84 (1H, d), 4.18 (1H, d), 4.27 (1H, br s), 4.44 (2H, d), 4.63 (1H, d), 6.81 (1H, dd), 6.81 (1H, d), 7.51 (1H, d), 7.84 (2H, s), 7.93 (1H, s). |
| 1-303 | 1H-NMR (CDCl3) δ: 0.86 (3H, t), 1.39-1.51 (2H, m), 2.56-2.67 (1H, m), 2.95-3.10 (3H, m), 3.48-3.64 (2H, m), 3.82 (1H, d), 4.17 (1H, d), 4.40 (2H, d), 4.75 (1H, br s), 5.01 (1H, t), 6.71 (1H, dd), 6.79 (1H, d), 7.47 (1H, d), 7.84 (2H, s), 7.93 (1H, s). |
| 1-304 | 1H-NMR (CDCl3) δ: 1.11 (6H, d), 2.57-2.67 (1H, m), 2.96-3.04 (1H, m), 3.49-3.65 (2H, m), 3.78-3.88 (2H, m), 4.15-4.20 (2H, m), 4.43 (2H, d), 4.60 (1H, t), 6.73 (1H, dd), 6.81 (1H, d), 7.50 (1H, d), 7.84 (2H, s), 7.93 (1H, s). |
| 1-305 | 1H-NMR (CDCl3) δ: 0.53 (2H, td), 0.70 (2H, td), 2.36-2.43 (1H, m), 2.58-2.68 (1H, m), 2.96-3.05 (1H, m), 3.50-3.67 (2H, m), 3.85 (1H, d), 4.19 (1H, d), 4.51 (2H, d), 4.67 (1H, s), 5.34 (1H, t), 6.74 (1H, dd), 6.83 (1H, d), 7.51 (1H, d), 7.85 (2H, s), 7.93 (1H, s). |
| 1-306 | 1H-NMR (CDCl3) δ: 2.59-2.62 (1H, m), 2.96-3.00 (1H, m), 3.46-3.62 (2H, m), 3.82-3.88 (3H, m), 4.10-4.16 (1H, m), 6.49-6.53 (1H, m), 6.64-6.65 (1H, m), 7.21-7.24 (1H, m), 7.85 (2H, s), 7.92 (1H, s). |
| 1-307 | 1H-NMR (CDCl3) δ: 1.15 (3H, t), 2.21 (2H, q), 2.55-2.65 (1H, m), 2.94-3.02 (1H, m), 3.45-3.62 (2H, m), 3.80 (1H, d), 4.15 (1H, d), 4.44 (2H, d), 5.79 (1H, br s), 6.49 (1H, dd), 6.62 (1H, d), 7.29 (1H, d), 7.83 (2H, s), 7.92 (1H, s). |
| 1-308 | 1H-NMR (CDCl3) δ: 0.72 (2H, dt), 0.97 (2H, dt), 1.29-1.38 (1H, m), 2.55-2.66 (1H, m), 2.94-3.02 (1H, m), 3.46-3.62 (2H, m), 3.81 (1H, d), 4.15 (2H, d), 4.45 (2H, d), 6.01 (1H, t), 6.49 (1H, t), 6.63 (1H, d), 7.29 (1H, d), 7.92 (2H, s), 7.88 (1H, s). |
| 1-309 | 1H-NMR (CDCl3) δ: 2.56-2.66 (1H, m), 2.95-3.11 (3H, m), 3.45-3.62 (2H, m), 3.81 (1H, d), 4.16 (1H, d), 4.46 (2H, d), 6.20 (1H, br s), 6.49 (1H, dd), 6.63 (1H, d), 7.26 (1H, d), 7.83 (2H, s), 7.93 (1H, s). |
| 1-312 | 1H-NMR (CDCl3) δ: 1.16 (3H, t), 2.21 (3H, q), 2.60-2.63 (1H, m), 2.94-3.02 (1H, m), 3.48-3.59 (2H, m), 3.80 (1H, d), 4.09-4.16 (1H, m), 4.43 (2H, d), 5.81 (1H, br s), 6.52-6.55 (1H, m), 6.81 (1H, d), 7.28-7.30 (1H, m), 7.83-7.92 (3H, m). |
| 1-313 | 1H-NMR (CDCl3) δ: 0.71-0.74 (2H, m), 0.96-0.99 (2H, m), 1.25-1.36 (1H, m), 2.59-2.61 (1H, m), 2.96-3.00 (1H, m), 3.48-3.59 (1H, m), 3.78-3.82 (2H, m), 4.13-4.16 (1H, m), 4.44-4.46 (2H, m), 5.96-5.99 (1H, m), 6.52-6.55 (1H, m), 6.83-6.89 (1H, m), 7.25-7.2 |
| 1-314 | 1H-NMR (CDCl3) δ: 2.57-2.63 (1H, m), 2.95-3.26 (3H, m), 3.52-3.58 (2H, m), 3.80 (1H, d), 4.15 (1H, d), 4.46 (2H, d), 6.24 (1H, br s), 6.52-6.55 (1H, m), 6.81 (1H, d), 7.26-7.27 (1H, m), 7.83-7.93 (3H, m). |
| 1-317 | 1H-NMR (CDCl3) δ: 1.97 (3H, s), 2.61-2.70 (1H, m), 3.00-3.08 (1H, m), 3.53-3.70 (2H, m), 3.87 (1H, d), 4.23 (1H, d), 4.53 (2H, d), 6.34 (1H, t), 6.83 (1H, dd), 7.23 (1H, d), 7.55 (1H, d), 7.84 (2H, s), 7.94 (1H, s). |
| 1-319 | 1H-NMR (CDCl3) δ: 0.72 (2H, dt), 0.95 (2H, dt), 1.30-1.39 (1H, m), 2.59-2.70 (1H, m), 3.00-3.08 (1H, m), 3.53-3.69 (2H, m), 3.86 (1H, d), 4.23 (1H, d), 4.56 (2H, d), 6.49 (1H, t), 6.82 (1H, d), 7.24 (1H, d), 7.53 (1H, d), 7.84 (2H, s), 7.94 (1H, s). |
| 1-321 | 1H-NMR (CDCl3) δ: 2.59-2.69 (1H, m), 2.88 (3H, s), 2.99-3.07 (1H, m), 3.69-3.51 (2H, m), 3.86 (1H, d), 4.21 (1H, d), 4.39 (2H, d), 4.53 (1H, t), 6.77 (1H, dd), 6.85 (1H, d), 7.49 (1H, d), 7.84 (2H, s), 7.94 (1H, s). |
| 1-322 | 1H-NMR (CDCl3) δ: 1.33 (3H, t), 2.59-2.69 (1H, m), 2.96-3.07 (3H, m), 3.52-3.69 (2H, m), 3.86 (1H, d), 4.22 (1H, d), 4.37 (2H, d), 4.49 (1H, t), 6.78 (1H, d), 6.84 (1H, d), 7.50 (1H, d), 7.85 (2H, s), 7.94 (1H, s). |
| 1-323 | 1H-NMR (CDCl3) δ: 2.60-2.73 (1H, m), 3.00-3.13 (1H, m), 3.61-3.70 (2H, m), 3.87-3.93 (1H, m), 4.19-4.32 (1H, m), 4.50-4.58 (2H, m), 5.10 (1H, br s), 6.80-6.84 (2H, m), 7.39-7.48 (1H, m), 7.78-7.94 (3H, m). |
| 1-324 | 1H-NMR (CDCl3) δ: 2.62-2.67 (1H, m), 3.01-3.05 (1H, m), 3.56-3.88 (5H, m), 4.16-4.21 (1H, m), 4.43-4.50 (2H, m), 4.85 (1H, t), 6.78-6.84 (2H, m), 7.47 (1H, d), 7.84-7.94 (3H, m). |
| 1-325 | 1H-NMR (CDCl3) δ: 2.57-2.71 (1H, m), 2.99-3.03 (1H, m), 3.56-3.63 (2H, m), 3.81-3.84 (1H, m), 4.13-4.26 (4H, m), 4.69 (1H, t), 6.68-6.75 (2H, m), 7.28-7.61 (4H, m), 7.87-7.90 (1H, m). |

TABLE 8-continued

| Table 8 - Ex.-No. | 1H-NMR |
|---|---|
| 1-327 | 1H-NMR (CDCl3) δ: 2.49-2.59 (1H, m), 2.83-2.91 (1H, m), 3.05 (2H, q), 3.46-3.62 (2H, m), 3.78 (1H, d), 4.06 (1H, d), 4.53 (2H, d), 6.04 (1H, br s), 6.70 (1H, dd), 6.80 (1H, d), 7.43-7.40 (3H, m). |
| 1-328 | 1H-NMR (CDCl3) δ: 0.92 (3H, t), 1.60-1.71 (3H, m), 2.14 (2H, t), 2.49-2.59 (1H, m), 2.82-2.90 (1H, m), 3.47-3.62 (2H, m), 3.77 (1H, d), 4.05 (1H, d), 4.50 (2H, d), 5.70 (1H, t), 6.70 (1H, dd), 6.79 (1H, d), 7.46-7.43 (3H, m). |
| 1-329 | 1H-NMR (CDCl3) δ: 1.14 (6H, d), 2.29-2.38 (1H, m), 2.49-2.59 (1H, m), 2.82-2.90 (1H, m), 3.45-3.61 (2H, m), 3.77 (1H, d), 4.05 (1H, d), 4.49 (2H, d), 5.71 (1H, t), 6.70 (1H, dd), 6.79 (1H, d), 7.44-7.42 (3H, m). |
| 1-330 | 1H-NMR (CDCl3) δ: 1.11 (3H, t), 2.49-2.58 (1H, m), 2.82-2.91 (1H, m), 3.18 (2H, q), 3.45-3.60 (2H, m), 3.77 (1H, d), 4.04 (1H, d), 4.23 (1H, br s), 4.44 (2H, d), 4.59 (1H, br s), 6.70 (1H, dd), 6.78 (1H, d), 7.43 (2H, s), 7.50 (1H, d). |
| 1-333 | 1H-NMR (CDCl3) δ: 2.54-2.61 (1H, m), 2.81-2.94 (1H, m), 3.50-3.60 (2H, m), 3.82-3.88 (1H, m), 4.02-4.10 (1H, m), 4.50 (2H, d), 5.04 (1H, t), 6.73-6.75 (1H, m), 7.30-7.42 (3H, m). |
| 1-334 | 1H-NMR (CDCl3) δ: 2.53-2.60 (1H, m), 2.85-2.91 (1H, m), 3.50-3.80 (5H, m), 4.11-4.18 (1H, m), 4.40 (2H, d), 4.86 (1H, t), 6.72-6.76 (1H, m), 7.21-7.70 (4H, m). |
| 1-335 | 1H-NMR (CDCl3) δ: 2.52-2.58 (1H, m), 2.85-2.90 (1H, m), 3.47-3.60 (2H, m), 3.70-3.87 (1H, m), 3.98-4.29 (3H, m), 4.80 (1H, t), 6.60-6.77 (2H, m), 7.11-7.80 (8H, m). |
| 1-336 | 1H-NMR (CDCl3) δ: 2.46-2.56 (1H, m), 2.79-2.87 (1H, m), 3.48-3.51 (2H, m), 3.74 (1H, d), 3.83 (1H, d), 4.01 (1H, d), 6.47 (1H, dd), 6.60 (1H, d), 7.21 (1H, d), 7.42 (2H, s). |
| 1-337 | 1H-NMR (CDCl3) δ: 1.98 (3H, s), 2.47-2.57 (1H, m), 2.80-2.88 (1H, m), 3.42-3.57 (2H, m), 3.73 (1H, d), 4.01 (1H, d), 4.41 (2H, d), 5.86 (1H, br s), 6.45 (1H, dd), 6.59 (1H, d), 7.27 (1H, d), 7.41 (2H, s). |
| 1-338 | 1H-NMR (CDCl3) δ: 1.15 (4H, t), 2.47-2.57 (1H, m), 2.80-2.88 (1H, m), 3.40-3.56 (2H, m), 3.73 (1H, d), 4.01 (1H, d), 4.43 (2H, d), 5.81 (1H, s), 6.45 (1H, dd), 6.59 (1H, d), 7.27 (1H, d), 7.42 (2H, s). |
| 1-339 | 1H-NMR (CDCl3) δ: 0.72 (2H, d), 0.97 (2H, d), 1.29-1.37 (1H, m), 2.46-2.57 (1H, m), 2.79-2.88 (1H, m), 3.41-3.56 (2H, m), 3.74 (1H, d), 4.01 (1H, d), 4.45 (2H, d), 5.99 (1H, br s), 6.45 (1H, dd), 6.59 (1H, d), 7.28 (1H, d), 7.42 (2H, s). |
| 1-340 | 1H-NMR (CDCl3) δ: 2.46-2.56 (1H, m), 2.79-2.88 (1H, m), 3.07 (2H, q), 3.40-3.56 (2H, m), 3.72 (1H, d), 4.01 (1H, d), 4.44 (2H, d), 6.32 (1H, br s), 6.44 (1H, dd), 6.58 (1H, d), 7.23 (1H, d), 7.41 (2H, s). |
| 1-341 | 1H-NMR (CDCl3) δ: 1.10 (3H, t), 2.45-2.56 (1H, m), 2.79-2.87 (1H, m), 3.13-3.22 (2H, m), 3.39-3.55 (2H, m), 3.72 (1H, d), 3.99 (1H, d), 4.33-4.38 (3H, m), 4.78 (1H, t), 6.44 (1H, dd), 6.57 (1H, d), 7.28 (2H, d), 7.41 (2H, s). |
| 1-344 | 1H-NMR (CDCl3) δ: 1.98 (3H, s), 2.45-2.56 (1H, m), 2.80-2.87 (1H, m), 3.40-3.60 (2H, m), 3.73 (1H, d), 4.01 (1H, d), 4.41 (2H, d), 5.82 (1H, b), 6.48-7.46 (5H, m). |
| 1-345 | 1H-NMR (CDCl3) δ: 1.16 (3H, t), 2.21 (2H, q), 2.44-2.52 (1H, m), 2.79-2.88 (1H, m), 3.43-3.56 (2H, m), 3.71-3.74 (1H, m), 3.99-4.02 (1H, m), 4.42-4.44 (2H, m), 5.81 (1H, br s), 6.50 (1H, dd), 6.77 (1H, d), 7.29 (1H, d), 7.40 (2H, s). |
| 1-346 | 1H-NMR (CDCl3) δ: 0.69-1.37 (5H, m), 2.46-2.56 (1H, m), 2.79-2.88 (1H, m), 3.43-3.56 (2H, m), 3.72-3.74 (1H, m), 3.99-4.02 (1H, m), 4.43-4.45 (2H, m), 6.00 (1H, br s), 6.50 (1H, dd), 6.78 (1H, d), 7.26-7.41 (3H, m). |
| 1-347 | 1H-NMR (CDCl3) δ: 2.47-2.57 (1H, m), 2.80-2.89 (1H, m), 3.07 (2H, q), 3.47-3.55 (2H, m), 3.72-3.74 (1H, m), 4.00-4.03 (1H, m), 4.46-4.48 (2H, m), 6.12 (1H, br s), 6.50 (1H, dd), 6.78 (1H, d), 7.26-7.30 (1H, m), 7.43 (2H, s). |
| 1-355 | 1H-NMR (CDCl3) δ: 1.98 (3H, s), 2.54-2.64 (1H, m), 2.90-2.98 (1H, m), 3.47-3.64 (2H, m), 3.82 (1H, d), 4.13 (1H, d), 4.49 (2H, d), 5.75 (1H, br s), 6.72 (1H, dd), 6.81 (1H, d), 7.46 (1H, d), 7.54 (1H, s), 7.59 (1H, s), 7.65 (1H, s). |
| 1-356 | 1H-NMR (CDCl3) δ: 1.15 (3H, t), 2.20 (2H, q), 2.54-2.64 (1H, m), 2.89-2.98 (1H, m), 3.48-3.64 (2H, m), 3.81 (1H, d), 4.12 (1H, d), 4.50 (2H, d), 5.71 (1H, br s), 6.72 (1H, dd), 6.81 (1H, d), 7.45 (1H, d), 7.54 (1H, s), 7.59 (1H, s), 7.65 (1H, s). |
| 1-357 | 1H-NMR (CDCl3) δ: 0.70-0.76 (2H, m), 0.96-1.01 (2H, m), 1.27-1.34 (1H, m), 2.54-2.67 (1H, m), 2.90-2.98 (1H, m), 3.48-3.64 (2H, m), 3.81 (1H, d), 4.12 (1H, dd), 5.89 (1H, br s), 6.72 (1H, dd), 6.81 (1H, d), 7.46 (1H, d), 7.54 (1H, s), 7.59 (1 H), 4.52 (1H, d), 4.12 (1H, dd), 5.89 (1H, br s), 6.72 (1H, dd), 6.81 (1H, d), 7.46 (1H, d), 7.54 (1H, s), 7.59 (1H, s). |
| 1-377 | 1H-NMR (CDCl3) δ: 2.00 (3H, s), 2.54-2.59 (1H, m), 2.87-2.96 (1H, m), 2.87-2.95 (1H, m), 3.61-3.72 (2H, m), 3.94-3.98 (1H, m), 4.43-4.46 (3H, m), 5.73 (1H, br s), 6.61 (1H, s), 7.44 (2H, s), 8.37 (1H, s). |
| 1-378 | 1H-NMR (CDCl3) δ: 1.16 (3H, t), 2.22 (2H, q), 2.54-2.59 (1H, m), 2.87-2.95 (1H, m), 3.62-3.68 (2H, m), 3.94-3.98 (1H, m), 4.41-4.66 (3H, m), 5.70 (1H, br s), 6.57 (1H, s), 7.42 (2H, s), 8.37 (1H, s). |
| 1-379 | 1H-NMR (CDCl3) δ: 0.71-1.36 (5H, m), 2.51-2.61 (1H, m), 2.87-2.95 (1H, m), 3.60-3.73 (2H, m), 3.94-3.98 (1H, m), 4.42-4.49 (3H, m), 5.88 (1H, br s), 6.57 (1H, s), 7.44 (2H, s), 8.37 (1H, s). |
| 1-380 | 1H-NMR (CDCl3) δ: 2.54-2.59 (1H, m), 2.87-2.96 (1H, m), 3.05-3.09 (2H, m), 3.61-3.73 (2H, m), 3.94-3.98 (1H, m), 4.43-4.51 (3H, m), 5.99 (1H, br s), 6.58 (1H, s), 7.45 (2H, d), 8.36 (1H, s). |
| 1-381 | 1H-NMR (CDCl3) δ: 1.14 (3H, t), 2.50-2.61 (1H, m), 2.86-2.94 (1H, m), 3.17-3.21 (2H, m), 3.60-3.71 (2H, m), 3.93-3.97 (1H, m), 4.29-4.30 (1H, m), 4.41-4.43 (3H, m), 4.58-4.60 (1H, m), 6.55 (1H, s), 7.44 (2H, s), 8.40 (1H, s). |
| 1-386 | 1H-NMR (CDCl3) δ: 2.61-2.69 (1H, m), 3.02-3.12 (3H, m), 3.69-3.72 (2H, m), 4.03-4.07 (1H, m), 4.53-4.61 (3H, m), 5.98 (1H, br s), 6.61 (1H, s), 7.85 (2H, s), 7.93 (1H, s), 8.38 (1H, s). |

TABLE 8-continued

| Table 8 - Ex.-No. | 1H-NMR |
|---|---|
| 1-390 | 1H-NMR (CDCl3) δ: 1.18 (3H, t), 2.15 (2H, q,), 2.49-2.59 (1H, m), 2.83-2.92 (1H, m), 3.57-3.70 (2H, m), 3.95 (1H, d), 4.38-4.45 (3H, m), 5.76 (1H, br s), 6.51 (1H, d), 7.30 (2H, s), 7.39 (1H, t), 7.72 (1H, d). |
| 1-391 | 1H-NMR (CDCl3) δ: 0.71-0.82 (2H, m), 0.95-1.05 (2H, m), 1.24-1.40 (1H, m), 2.52-2.57 (1H, m), 2.83-2.92 (1H, m), 3.61-3.64 (2H, m), 3.95 (1H, d), 4.38-4.47 (3H, m), 5.95 (1H, br s), 6.51 (1H, d), 7.26-7.39 (3H, m), 7.72 (1H, d). |
| 1-398 | 1H-NMR (CDCl3) δ: 2.49-2.59 (1H, m), 2.83-2.92 (1H, m), 3.01-3.12 (2H, m), 3.61-3.68 (2H, m), 3.96 (1H, d), 4.38 (1H, d), 4.49-4.51 (2H, m), 6.08 (1H, br s), 6.52 (1H, d), 7.43 (2H, s), 7.69 (1H, d). |
| 1-404 | 1H-NMR (CDCl3) δ: 2.57-2.67 (1H, m), 3.02-3.07 (3H, m), 3.63-3.70 (2H, m), 4.08-4.10 (1H, m), 4.50-4.51 (3H, m), 6.06 (1H, br s), 6.55 (1H, dz), 7.71 (1H, d), 7.85 (2H, s), 7.92 (1H, s). |
| 1-408 | 1H-NMR (CDCl3) δ: 1.14 (3H, t), 2.20 (2H, q), 2.50-2.58 (1H, m), 2.81-2.90 (1H, m), 3.42-3.60 (2H, m), 3.76 (1H, d), 4.02 (1H, d), 4.58 (2H, d), 5.73 (1H, b), 6.67-7.44 (5H, m). |
| 1-442 | 1H-NMR (CDCl3) δ: 1.27 (3H, d), 2.52-2.54 (1H, m), 2.80-2.88 (1H, m), 3.43-3.52 (2H, m), 3.73 (1H, d), 4.01 (1H, d), 4.35 (2H, dd), 4.50-4.54 (2H, m), 4.90 (1H, t), 6.44 (1H, dd), 6.57 (1H, d), 7.25-7.27 (3H, m), 7.39 (1H, t) |
| 1-443 | 1H-NMR (CDCl3) δ: 2.51-2.60 (5H, m), 2.80-2.89 (1H, m), 3.47-3.50 (2H, m), 3.66 (4H, dd), 3.74 (1H, d), 4.02 (1H, d), 4.41 (2H, d), 4.81 (1H, t), 6.46 (1H, dd), 6.59 (1H, d), 7.27-7.31 (3H, m), 7.39 (1H, t). |
| 1-444 | 1H-NMR (CDCl3) δ: 2.51-2.56 (1H, m), 2.80-2.88 (1H, m), 3.29-3.53 (10H, m), 3.74 (1H, d), 4.01 (1H, d), 4.34-4.36 (3H, m), 4.50 (1H, t), 4.89 (1H, t), 6.45 (1H, dd), 6.58 (1H, d), 7.27-7.29 (3H, m), 7.39 (1H, t). |
| 1-445 | 1H-NMR (CDCl3) δ: 1.85-1.93 (4H, m), 2.50-2.55 (1H, m), 2.80-2.88 (1H, m), 3.03-3.12 (1H, m), 3.45-3.50 (3H, m), 3.73-3.81 (4H, m), 3.91-4.03 (2H, m), 4.36 (2H, d), 4.62 (1H, s), 5.07 (1H, br s), 6.45 (1H, dd), 6.58 (1H, d), 7.28 (3H, t), 7.38-7.39 (1H, m). |
| 1-446 | 1H-NMR (CDCl3) δ: 1.55 (3H, d), 2.51-2.53 (1H, m), 2.81-2.85 (1H, m), 3.43-3.48 (2H, m), 3.71 (1H, d), 3.99 (1H, d), 4.34 (2H, d), 5.28-5.43 (3H, m), 6.41 (1H, d), 6.54 (1H, d), 7.21-7.26 (4H, m), 7.38 (1H, d), 7.64 (1H, d). |
| 1-448 | 1H-NMR (CDCl3) δ: 1.16 (3H, t), 2.20 (2H, q), 2.48-2.57 (1H, m), 2.80-2.88 (1H, m), 3.39-3.55 (2H, m), 3.74 (1H, d), 4.01 (1H, d), 4.37 (2H, d), 5.77 (1H, s), 6.30 (2H, dd), 7.21 (1H, dd), 7.28 (2H, d), 7.38 (1H, t). |
| 1-457 | 1H-NMR (CDCl3) δ: 2.43-2.55 (3H, m), 2.82-2.83 (1H, m), 3.43-3.54 (2H, m), 3.76 (3H, t), 4.02 (1H, dd), 6.60 (1H, d), 6.47 (1H, dd), 7.24-7.39 (4H, m). |
| 1-458 | 1H-NMR (CDCl3) δ: 1.74 (3H, d), 2.51-2.64 (1H, m), 2.81-2.89 (1H, m), 3.46-3.53 (2H, m), 3.75 (1H, d), 4.03 (1H, d), 4.43-4.47 (3H, m), 6.46 (1H, dd), 6.61 (1H, d), 7.25-7.27 (3H, m), 7.39 (1H, t). |
| 1-461 | 1H-NMR (CDCl3) δ: 1.23 (3H, t), 2.51-2.53 (1H, m), 2.82-2.86 (1H, m), 3.24 (2H, s), 3.44-3.54 (2H, m), 3.75 (1H, d), 4.03 (1H, d), 4.46 (2H, d), 6.45 (1H, dd), 6.60 (1H, d), 7.26-7.28 (3H, m), 7.39 (1H, t). |
| 1-464 | 1H-NMR (CDCl3) δ: 1.23 (6H, dd), 2.54-2.57 (1H, m), 2.82-2.89 (1H, m), 3.25 (2H, s), 3.46-3.51 (2H, m), 3.75 (1H, d), 4.03 (1H, d), 4.45 (2H, d), 6.45 (1H, dd), 6.60 (1H, d), 7.26-7.27 (3H, m), 7.39 (1H, t). |
| 1-467 | 1H-NMR (CDCl3) δ: 2.11 (3H, s), 2.45-2.89 (6H, m), 3.44-3.54 (2H, m), 3.74 (1H, d), 4.02 (1H, d), 4.45 (2H, d), 6.03 (1H, br s), 6.45 (1H, dd), 6.59 (1H, d), 7.26-7.30 (3H, m), 7.39 (1H, t). |
| 1-468 | 1H-NMR (CDCl3) δ: 0.66-0.68 (2H, m), 0.78-0.81 (2H, m), 2.49-2.59 (1H, m), 2.84-2.85 (1H, m), 3.47-3.53 (2H, m), 3.75 (1H, d), 4.03 (1H, d), 4.85 (2H, d), 6.25 (1H, s), 6.47 (1H, dd), 6.61 (1H, s), 6.68 (1H, s), 7.28-7.28 (2H, m), 7.39-7.42 (1H, m). |
| 1-469 | 1H-NMR (CDCl3) δ: 2.51-2.53 (1H, m), 2.81-2.85 (1H, m), 3.43-3.62 (6H, m), 3.73 (1H, d), 4.01 (1H, d), 4.35 (2H, d), 4.86-4.93 (1H, m), 6.45 (1H, dd), 6.57 (1H, d), 7.26-7.29 (3H, m), 7.39 (1H, t). |
| 1-471 | 1H-NMR (CDCl3) δ: 2.09 (3H, s), 2.48-2.58 (4H, m), 2.79-2.88 (1H, m), 3.05 (3H, s), 3.40-3.57 (2H, m), 3.74 (1H, m), 4.02 (1H, m), 4.46 (2H, d), 6.48-7.40 (7H, m). |
| 1-472 | 1H-NMR (CDCl3) δ: 2.48-2.60 (1H, m), 2.66 (3H, s), 2.80-2.88 (1H, m), 3.40-3.54 (2H, m), 3.66 (1H, d), 3.29 (1H, d), 3.40-3.54 (2H, m), 3.74 (1H, m), 4.02 (1H, s), 4.02 (1H, m), 4.49 (2H, d), 6.48-7.40 (7H, m). |
| 1-473 | 1H-NMR (CDCl3) δ: 2.48-2.60 (1H, m), 1.16 (3H, t), 2.22 (2H, q), 2.47-2.57 (1H, m), 2.80-2.88 (1H, m), 3.40-3.56 (2H, m), 3.73 (1H, d), 4.00 (1H, d), 4.40 (2H, |
| 1-474 | d), 5.76 (1H, br s), 6.54 (1H, d), 7.03 (1H, dd), 7.25 (1H, dd), 7.28 (2H, d), 7.39 (1H, t). |
| 1-490 | 1H-NMR (CDCl3) δ: 2.48 (3H, s), 2.54-2.64 (1H, m), 2.86-2.92 (1H, m), 3.50-3.58 (2H, m), 3.78 (1H, m), 4.07 (1H, d), 4.53 (2H, d), 6.68-6.85 (2H, m), 7.15-7.43 (5H, m) |
| 1-491 | 1H-NMR (CDCl3) δ: 2.48 (3H, t), 2.50-2.63 (1H, m), 2.82-2.91 (1H, m), 3.34 (3H, s), 3.48-3.59 (5H, m), 3.75 (1H, d), 4.06 (1H, d), 4.50 (2H, d), 6.55 (1H, b), 6.67-6.80 (2H, m), 7.29-7.46 (4H, m) |
| 1-493 | 1H-NMR (CDCl3) δ: 2.48-2.63 (1H, m), 2.80-2.90 (1H, m), 3.24 (2H, d), 3.47-3.60 (2H, m), 3.58 (1H, m), 4.07 (1H, d), 4.53 (2H, d), 6.69-6.95 (3H, m), 7.23-7.45 (4H, m) |
| 1-494 | 1H-NMR (CDCl3) δ: 2.50-2.63 (1H, m), 2.65 (3H, s), 2.83-2.91 (1H, m), 3.28 (1H, d), 3.51-3.61 (2H, m), 3.65 (1H, d), 3.78 (1H, d), 4.06 (1H, d), 4.58 (2H, d), 6.67-6.81 (2H, m), 7.11 (1H, b), 7.26-7.47 (4H, m) |
| 1-495 | 1H-NMR (CDCl3) δ: 2.50-2.63 (1H, m), 2.83-2.91 (1H, m), 3.05 (3H, s), 3.48-3.61 (2H, m), 3.78 (1H, d), 3.85 (2H, s), 4.06 (1H, d), 4.57 (2H, d), 6.56 (1H, b), 6.69-6.82 (2H, m), 7.26-7.47 (4H, m) |
| 1-496 | 1H-NMR (CDCl3) δ: 2.50-2.61 (1H, m), 2.83-2.91 (1H, m), 3.49-3.62 (2H, m), 3.59 (2H, s), 3.78 (1H, d), 4.06 (1H, d), 4.54 (2H, d), 6.58 (1H, b), 6.68-6.81 (2H, m), 7.26-7.42 (4H, m) |

TABLE 8-continued

| Table 8 - Ex.-No. | 1H-NMR |
|---|---|
| 1-498 | 1H-NMR (CDCl3) δ: 2.50-2.61 (1H, m), 2.86-2.91 (1H, m), 3.49-3.65 (2H, m), 3.75-3.80 (3H, m), 4.06 (1H, d), 4.57 (2H, d), 6.46 (1H, b), 6.68-6.81 (2H, m), 7.26-7.44 (4H, m) |
| 1-499 | 1H-NMR (CDCl3) δ: 1.20 (3H, t), 2.49 (2H, q), 2.48-2.61 (1H, m), 2.84-2.91 (1H, m), 3.23 (2H, s), 3.49-3.60 (2H, m), 3.79 (1H, d), 4.12 (1H, d), 4.53 (2H, d), 6.68-6.81 (2H, m), 7.15 (1H, b), 7.27-7.44 (4H, m) |
| 1-500 | 1H-NMR (CDCl3) δ: 1.24 (3H, t), 2.51-2.61 (1H, m), 2.78-2.90 (3H, m), 3.29 (1H, d), 3.49-3.60 (2H, m), 3.57 (1H, d), 3.78 (1H, d), 4.06 (1H, d), 4.57 (2H, d), 6.67-6.80 (2H, m), 7.11 (1H, b), 7.28-7.46 (4H, m) |
| 1-501 | 1H-NMR (CDCl3) δ: 1.26 (3H, t), 2.51-2.61 (1H, m), 2.83-2.92 (1H, m), 3.15 (2H, q), 3.49-3.62 (2H, m), 3.78 (1H, d), 3.83 (2H, s), 4.07 (1H, d), 4.55 (2H, d), 6.68-6.81 (3H, m), 7.28-7.44 (4H, m) |
| 1-502 | 1H-NMR (CDCl3) δ: 2.38 (3H, s), 2.50-2.60 (1H, m), 2.83-2.92 (1H, m), 3.48-3.58 (2H, m), 3.56 (2H, s), 3.78 (1H, d), 4.06 (1H, d), 4.47 (2H, d), 6.44 (1H, b), 6.67-6.80 (2H, m), 7.28-7.40 (4H, m) |
| 1-503 | 1H-NMR (CDCl3) δ: 2.50-2.61 (1H, m), 2.83-2.92 (1H, m), 3.07 (2H, d), 3.18 (2H, s), 3.49-3.60 (2H, m), 3.79 (1H, d), 4.07 (1H, d), 4.52 (2H, d), 5.02-5.09 (2H, m), 5.61-5.72 (1H, m), 6.68-6.82 (2H, m), 7.04 (1H, b), 7.28-7.45 (4H, m) |
| 1-504 | 1H-NMR (CDCl3) δ: 2.50-2.62 (1H, m), 2.83-2.92 (1H, m), 3.33 (1H, d), 3.52-3.63 (5H, m), 3.78 (1H, d), 4.07 (1H, d), 4.56 (2H, d), 5.35-5.47 (2H, m), 5.79-5.86 (1H, m), 6.67-6.80 (2H, m), 7.03 (1H, b), 7.28-7.47 (4H, m) |
| 1-505 | 1H-NMR (CDCl3) δ: 2.50-2.61 (1H, m), 2.83-2.92 (1H, m), 3.49-3.60 (2H, m), 3.80-3.87 (5H, m), 4.07 (1H, d), 4.55 (2H, d), 5.51-5.57 (2H, m), 6.63 (1H, b), 6.68-6.82 (2H, m), .28-7.45 (4H, m) |
| 1-506 | 1H-NMR (CDCl3) δ: 1.45 (3H, d), 2.01 (3H, s), 2.50-2.60 (1H, m), 2.83-2.91 (1H, m), 3.32 (1H, q), 3.49-3.59 (2H, m), 3.78 (1H, d), 4.07 (1H, d), 4.51 (2H, d), 6.68-6.82 (2H, m), 6.95 (1H, b), 7.28-7.44 (4H, m) |
| 1-507 | 1H-NMR (CDCl3) δ: 1.30, 1.60 (3H, d), 2.42-2.57 (3H, s), 2.53-2.63 (1H, m), 2.83-2.91 (1H, m), 3.18, 3.56 (1H, q), 3.48-3.80 (2H, m), 3.78 (1H, d), 4.06 (1H, d), 4.55-4.60 (2H, m), 6.68-6.80 (2H, m), 6.98-7.10 (1H, b), 7.28-7.45 (4H, m) |
| 1-508 | 1H-NMR (CDCl3) δ: 2.50-2.62 (1H, m), 2.83-2.91 (1H, m), 2.90 (3H, s), 3.48-3.80 (4H, m), 3.38 (1H, d), 4.07 (1H, d), 4.56 (2H, d), 6.57 (1H, b), 6.68-6.82 (2H, m), 7.28-7.43 (4H, m) |
| 1-509 | 1H-NMR (CDCl3) δ: 2.11 (3H, s), 2.46 (2H, t), 2.50-2.60 (1H, m), 2.80 (2H, t), 2.83-2.91 (1H, m), 3.49-3.59 (2H, m), 3.78 (1H, d), 4.06 (1H, d), 4.52 (2H, m), 5.90 (1H, b), 6.68-6.80 (2H, m), 7.28-7.47 (4H, m) |
| 1-513 | 1H-NMR (CDCl3) δ: 0.75-0.80 (2H, m), 0.92-0.97 (2H, m), 1.39-1.44 (1H, m), 2.51-2.60 (1H, m), 2.83-2.91 (1H, m), 3.48-3.60 (2H, m), 3.77 (1H, b), 3.93 (2H, d), 4.06 (1H, d), 4.51 (2H, d), 6.43 (1H, b), 6.60 (1H, b), 6.67-6.80 (2H, m), 7.28-7.41 (4H, m) |
| 1-516 | 1H-NMR (CDCl3) δ: 2.50-2.60 (1H, m), 2.83-2.91 (1H, m), 2.84-2.91 (1H, m), 3.10 (2H, q), 3.48-3.60 (2H, m), 3.77 (1H, d), 3.90 (2H, d), 4.05 (1H, d), 4.50 (2H, d), 6.66 (1H, b), 6.66-6.80 (2H, m), 6.86 (1H, b), 7.28-7.40 (4H, m) |
| 1-517 | 1H-NMR (CDCl3) δ: 2.17 (3H, s), 2.50-2.63 (1H, m), 2.83-2.92 (1H, m), 3.20 (2H, s), 3.48-3.60 (2H, m), 3.78 (1H, d), 3.95 (2H, d), 4.06 (1H, d), 4.51 (2H, d), 6.27 (1H, b), 6.67-6.80 (2H, m), 7.28-7.42 (4H, m) |
| 1-520 | 1H-NMR (CDCl3) δ: 1.45 (9H, s), 2.50-2.60 (1H, m), 2.83-2.92 (1H, m), 3.48-3.60 (2H, m), 3.76-3.79 (3H, m), 4.06 (1H, d), 4.52 (2H, d), 5.02 (1H, b), 6.29 (1H, b), 6.67-6.80 (2H, m), 7.26-7.43 (4H, m) |
| 1-521 | 1H-NMR (CDCl3) δ: 1.34 (3H, d), 1.98 (3H, s), 2.52-2.57 (1H, m), 2.83-2.91 (1H, m), 3.47-3.60 (2H, m), 3.72-3.77 (1H, m), 4.05-4.07 (1H, m), 4.44-4.51 (1H, m), 6.21-6.24 (1H, m), 6.45-6.47 (1H, m), 6.69-6.77 (2H, m), 7.27-7.28 (1H, m), 7.34-7.38 (2H, m) |
| 1-522 | 1H-NMR (CDCl3) δ: 1.11 (3H, d), 1.34 (3H, d), 2.21 (2H, q), 2.47-2.59 (1H, m), 2.84-2.89 (1H, m), 3.47-3.60 (2H, m), 3.74-3.77 (2H, m), 4.03-4.13 (1H, m), 4.46-4.53 (1H, m), 4.69-6.75 (1H, m), 7.27-7.28 (1H, m), 7.34-7.46 (2H, m) |
| 1-523 | 1H-NMR (CDCl3) δ: 0.69-0.98 (4H, m), 1.23-1.46 (3H, m), 2.49-2.57 (1H, m), 2.82-2.90 (1H, m), 3.46-3.59 (2H, m), 3.75-3.77 (2H, m), 4.04-4.11 (1H, m), 4.40-4.64 (3H, m), 6.35-6.38 (1H, m), 6.70-6.87 (3H, m), 7.16-7.45 (3H, m) |
| 1-525 | 1H-NMR (CDCl3) δ: 1.38-1.46 (3H, m), 2.50-2.60 (1H, m), 2.01-2.08 (3H, m), 2.50-2.60 (1H, m), 2.83-2.91 (1H, m), 3.14-3.20 (2H, m), 3.49-3.61 (2H, m), 3.77-3.79 (1H, m), 4.04-4.13 (1H, m), 4.41-4.65 (3H, m), 6.36-6.38 (1H, m), 6.69-6.77 (2H, m), 7.29-7.39 (3H, m) |
| 1-528 | 1H-NMR (CDCl3) δ: 1.55 (6H, s), 2.07 (3H, s), 2.49-2.60 (1H, m), 2.82-2.90 (1H, m), 3.48-3.61 (2H, m), 3.78 (1H, d), 4.06 (1H, d), 4.50 (2H, d), 6.17 (1H, b), 6.69-6.80 (3H, m), 7.26-7.43 (4H, m) |
| 1-530 | 1H-NMR (CDCl3) δ: 0.68-0.74 (2H, m), 0.88-0.93 (2H, m), 1.32-1.63 (1H, m), 1.55 (6H, s), 2.50-2.60 (1H, m), 2.82-2.90 (1H, m), 3.48-3.61 (2H, m), 3.78 (1H, d), 4.06 (1H, d), 4.50 (2H, d), 6.19 (1H, s), 6.67-6.83 (3H, m), 7.26-7.41 (4H, m) |
| 1-532 | 1H-NMR (CDCl3) δ: 1.57 (6H, s), 2.11 (3H, s), 2.50-2.61 (1H, m), 2.82-2.91 (1H, m), 3.55 (2H, s), 3.47-3.59 (2H, m), 3.78 (1H, d), 4.06 (1H, d), 4.51 (2H, d), 6.64-6.80 (3H, m), 7.26-7.44 (4H, m) |
| 1-543 | 1H-NMR (CDCl3) δ: 2.50-2.63 (1H, m), 2.83-2.91 (1H, m), 3.50-3.61 (2H, m), 3.77 (1H, d), 4.06 (1H, d), 4.47 (2H, d), 4.64 (2H, s), 5.71 (1H, b), 6.65-7.48 (9H, m) |
| 1-544 | 1H-NMR (CDCl3) δ: 2.52-2.60 (1H, m), 2.82-2.90 (1H, m), 3.47-3.60 (2H, m), 3.77 (1H, d), 4.05 (1H, d), 4.47 (2H, d), 4.83 (2H, s), 6.31-6.77 (4H, m), 7.26-7.61 (6H, m) |

TABLE 8-continued

| Table 8 - Ex.-No. | 1H-NMR |
|---|---|
| 1-547 | 1H-NMR (CDCl3) δ: 2.50-2.63 (1H, m), 2.83-2.91 (1H, m), 3.45-3.78 (2H, m), 3.77 (1H, d), 4.09 (1H, d), 4.48 (2H, d), 4.74 (2H, s), 6.45 (1H, b), 6.65-6.78 (2H, m), 7.26-7.50 (6H, m) |
| 1-553 | 1H-NMR (CDCl3) δ: 2.50-2.63 (1H, m), 2.84-2.92 (1H, m), 3.48-3.61 (2H, m), 3.77 (1H, d), 4.06 (1H, d), 4.49 (2H, d), 4.82 (2H, s), 6.40 (1H, b), 6.65-6.79 (2H, m), 7.26-7.95 (6H, m) |
| 1-555 | 1H-NMR (CDCl3) δ: 2.50-2.60 (1H, m), 2.84-2.91 (1H, m), 3.45-3.58 (2H, m), 3.77 (1H, d), 4.06 (1H, d), 4.49 (2H, d), 4.84 (2H, s), 6.41 (1H, b), 6.58-6.78 (3H, m), 7.28-7.52 (5H, m) |
| 1-558 | 1H-NMR (CDCl3) δ: 2.50-2.61 (1H, m), 2.83-2.91 (1H, m), 3.48-3.58 (2H, m), 3.77 (1H, d), 4.06 (1H, d), 4.50 (2H, d), 4.86 (2H, s), 6.54 (1H, b), 6.65-6.78 (2H, m), 7.26-8.15 (6H, m) |
| 1-574 | 1H-NMR (CDCl3) δ: 2.50-2.61 (1H, m), 2.80-2.93 (7H, m), 3.49-3.63 (2H, m), 3.79 (1H, d), 4.08 (1H, d), 4.28 (2H, s), 6.71-6.80 (2H, m), 7.29-7.47 (4H, m) |
| 1-586 | 1H-NMR (CDCl3) δ: 1.15 (3H, t), 2.19 (2H, q), 2.50-2.56 (4H, m), 2.79-2.88 (1H, m), 3.50-3.57 (1H, m), 3.77 (1H, d), 4.04 (1H, d), 4.45 (2H, d), 5.75 (1H, b), 6.37-6.46 (2H, m), 7.20-7.40 (4H, m) |
| 1-587 | 1H-NMR (CDCl3) δ: 0.68-0.75 (2H, m), 0.95-1.00 (2H, m), 1.58-1.61 (1H, m), 2.45-2.55 (4H, m), 2.78-2.90 (1H, m), 3.42-3.60 (2H, m), 3.77 (1H, d), 4.03 (1H, d), 4.46 (2H, d), 5.97 (1H, b), 6.37-6.47 (2H, m), 7.20-7.40 (4H, m) |
| 1-588 | 1H-NMR (CDCl3) δ: 2.49-2.60 (4H, m), 2.76-2.91 (1H, m), 2.99-3.10 (2H, m), 3.45-3.55 (2H, m), 3.78 (1H, d), 4.04 (1H, d), 4.48 (2H, d), 6.04 (1H, b), 6.35-6.47 (2H, m), 7.18-7.40 (4H, m) |
| 1-597 | 1H-NMR (CDCl3) δ: 2.60-2.64 (1H, m), 2.85-3.02 (3H, m), 3.14 (3H, s), 3.50-3.61 (2H, m), 3.78 (1H, d), 4.09 (1H, d), 4.61 (2H, d), 6.74-6.78 (2H, m), 7.15-7.54 (5H, m) |
| 1-598 | 1H-NMR (CDCl3) δ: 1.17 (3H, t), 2.22 (2H, q), 2.49-2.60 (1H, m), 2.83-2.91 (1H, m), 3.42-3.60 (2H, m), 3.77 (1H, d), 4.04 (1H, d), 4.58 (2H, d), 5.74 (1H, b), 6.67-7.43 (6H, m) |
| 1-645 | 1H-NMR (CDCl3) δ: 1.14 (3H, t), 2.20 (2H, q), 2.50-2.60 (1H, m), 2.83-2.91 (1H, m), 3.46-3.61 (2H, m), 3.77 (1H, d), 4.06 (1H, d), 4.50 (2H, d), 5.76 (1H, br s), 6.70 (1H, dd), 6.80 (1H, m), 7.44 (1H, d), 7.48 (2H, d), 7.70 (1H, t). |
| 1-647 | 1H-NMR (CDCl3) δ: 0.69-0.75 (2H, m), 0.96-1.00 (2H, m), 1.28-1.35 (1H, m), 2.50-2.60 (1H, m), 2.83-2.91 (1H, m), 3.46-3.61 (3H, m), 3.77 (1H, d), 4.06 (1H, d), 4.52 (2H, d), 5.88 (1H, t), 6.70 (1H, dd), 6.80 (1H, m), 7.45 (1H, d), 7.48 (2H, d), 7.70 (1H, t). |
| 1-650 | 1H-NMR (CDCl3) δ: 2.06 (3H, s), 2.50-2.60 (1H, m), 2.83-2.91 (1H, m), 3.20 (1H, s), 3.46-3.62 (2H, m), 3.77 (1H, d), 4.07 (1H, d), 4.54 (2H, d), 6.70 (1H, dd), 6.81 (1H, m), 7.14 (1H, t), 7.43 (1H, d), 7.48 (2H, d), 7.70 (1H, t). |
| 1-651 | 1H-NMR (CDCl3) δ: 2.50-2.59 (1H, m), 2.65 (3H, s), 2.83-2.91 (1H, m), 3.28 (1H, m), 3.46-3.61 (2H, m), 3.66 (1H, m), 3.75-3.78 (2H, m), 4.06 (1H, d), 4.58 (2H, d), 6.70 (1H, dd), 6.80 (1H, m), 7.11 (1H, t), 7.46 (1H, d), 7.47 (2H, d), 7.70 (1H, t) |
| 1-652 | 1H-NMR (DMSO-d6) δ: 2.60-2.68 (1H, m), 2.89-2.98 (1H, m), 3.12 (3H, s), 3.42-3.47 (2H, m), 3.80 (1H, d), 4.14 (2H, s), 4.24 (1H, d), 4.37 (2H, d), 6.90-6.92 (2H, m), 7.39 (1H, d), 7.83 (2H, s), 7.92 (1H, s), 8.72 (1H, t). |
| 1-675 | 1H-NMR (CDCl3) δ: 1.14 (3H, t), 2.20 (2H, q), 2.48-2.59 (1H, m), 2.83-2.91 (1H, m), 3.46-3.61 (2H, m), 3.77 (1H, d), 4.06 (1H, d), 4.49 (2H, d), 5.76 (1H, s), 6.70 (1H, dd), 6.79 (1H, d), 7.37 (2H, d), 7.45 (1H, d). |
| 1-694 | 1H-NMR (CDCl3) δ: 1.44 (9H, s), 2.47-2.56 (1H, m), 2.79-2.88 (1H, m), 3.41-3.56 (2H, m), 3.73 (1H, m), 4.01 (1H, d), 4.30 (2H, d), 4.90 (1H, br s), 6.45 (1H, dd), 6.58 (1H, d), 7.26 (2H, d), 7.41 (2H, s). |
| 1-698 | 1H-NMR (CDCl3) δ: 2.09 (3H, s), 2.47-2.57 (1H, m), 2.80-2.88 (1H, m), 3.20 (2H, s), 3.42-3.57 (2H, m), 3.74 (1H, m), 4.02 (1H, d), 4.47 (2H, d), 6.46 (1H, dd), 6.60 (1H, d), 7.28 (1H, d), 7.42 (2H, s). |
| 1-699 | 1H-NMR (acetone-d6) δ: 2.63 (3H, s), 2.70-2.78 (1H, m), 2.95-3.04 (1H, m), 3.49-3.58 (3H, m), 3.70 (1H, m), 3.94 (1H, d), 4.24 (1H, d), 4.40 (2H, dd), 6.59 (1H, dd), 6.71 (1H, d), 7.23 (1H, brs), 7.31 (1H, d), 7.76 (1H, br s), 7.82 (2H, s). |
| 1-700 | 1H-NMR (acetone-d6) δ: 2.69-2.80 (1H, m), 2.97-3.05 (1H, m), 3.10 (3H, s), 3.50-3.62 (1H, m), 3.47-3.59 (2H, m), 3.95 (1H, d), 4.05 (2H, s), 4.25 (1H, d), 4.41 (2H, d), 6.61 (1H, dd), 6.72 (1H, d), 7.31 (1H, d), 7.82 (2H, s), 7.84 (1H, s). |
| 1-708 | 1H-NMR (CDCl3) δ: 2.09 (3H, s), 2.46-2.56 (1H, m), 2.80-2.88 (1H, m), 3.20 (2H, s), 3.41-3.57 (2H, m), 3.73 (1H, m), 4.01 (1H, d), 4.46 (2H, d), 6.50 (1H, d), 6.78 (1H, d), 7.28 (1H, d), 7.41 (2H, s). |
| 1-709 | 1H-NMR (CDCl3) δ: 2.45-2.63 (1H, m), 2.80-2.93 (1H, m), 3.27 (1H, m), 3.40-3.54 (2H, m), 3.64-3.74 (2H, m), 4.01 (1H, d), 4.48-4.51 (2H, m), 6.47-7.41 (6H, m) |
| 1-710 | 1H-NMR (CDCl3) δ: 2.46-2.60 (1H, m), 2.80-2.93 (1H, m), 3.05 (3H, s), 3.40-3.60 (2H, m), 3.76 (1H, d), 3.86 (2H, s), 4.01 (1H, d), 4.48 (2H, d), 6.48-7.41 (6H, m) |
| 1-723 | 1H-NMR (CDCl3) δ: 2.50-2.60 (1H, m), 2.83-2.92 (1H, m), 3.49-3.60 (2H, m), 3.78 (1H, d), 4.04-4.08 (3H, m), 4.55 (2H, d), 6.68-6.82 (3H, m), 7.42-7.45 (3H, m) |
| 1-725 | 1H-NMR (CDCl3) δ: 2.44-2.59 (4H, m), 2.85-2.90 (1H, m), 3.34 (3H, s), 3.50-3.63 (4H, m), 3.77 (1H, d), 4.05 (1H, d), 4.51 (2H, d), 6.57 (1H, b), 6.67-6.80 (2H, m), 7.43-7.48 (3H, m) |
| 1-727 | 1H-NMR (CDCl3) δ: 2.49-2.60 (1H, m), 2.83-2.91 (1H, m), 3.24 (2H, d), 3.50-3.62 (1H, m), 3.78 (1H, d), 4.06 (1H, d), 4.53 (2H, d), 6.68-7.05 (4H, m), 7.26-7.45 (3H, m) |
| 1-728 | 1H-NMR (CDCl3) δ: 2.06 (3H, s), 2.49-2.59 (1H, m), 2.82-2.91 (1H, m), 3.20 (2H, s), 3.50-3.60 (2H, m), 3.78 (1H, d), 4.06 (1H, d), 4.54 (2H, d), 6.69-6.81 (2H, m), 7.13 (1H, b), 7.42-7.45 (3H, m) |
| 1-729 | 1H-NMR (CDCl3) δ: 2.49-2.60 (1H, m), 2.65 (3H, s), 2.82-2.91 (1H, m), 3.26 (2H, m), 3.49-3.61 (2H, m), 3.77 (1H, d), 4.05 (1H, d), 4.58 (2H, d), 6.67-6.81 (2H, m), 7.08 (1H, b), 7.42-7.47 (3H, m) |

TABLE 8-continued

| Table 8 - Ex.-No. | 1H-NMR |
|---|---|
| 1-730 | 1H-NMR (CDCl3) δ: 2.49-2.59 (1H, m), 2.83-2.91 (1H, m), 3.04 (3H, s), 3.50-3.60 (2H, m), 3.78 (1H, d), 3.86 (2H, s), 4.06 (1H, d), 4.56 (2H, d), 6.60 (1H, b), 6.69-6.81 (2H, m), 7.42-7.45 (3H, m) |
| 1-731 | 1H-NMR (CDCl3) δ: 2.49-2.59 (1H, m), 2.83-2.91 (1H, m), 3.50-3.59 (4H, m), 3.78 (1H, d), 4.06 (1H, d), 4.54 (2H, d), 6.55 (1H, b), 6.68-6.81 (2H, m), 7.40-7.45 (3H, m) |
| 1-732 | 1H-NMR (CDCl3) δ: 2.49-2.59 (1H, m), 2.83-2.90 (1H, m), 3.07 (2H, d), 3.18 (2H, s), 3.50-3.60 (2H, m), 3.78 (1H, d), 4.06 (1H, d), 4.53 (2H, d), 5.02-5.09 (2H, m), 5.63-5.72 (1H, m), 6.68-6.81 (2H, m), 7.04 (1H, b), 7.42-7.45 (3H, m) |
| 1-733 | 1H-NMR (CDCl3) δ: 2.50-2.59 (1H, m), 2.82-2.90 (1H, m), 3.32-3.62 (6H, m), 3.77 (1H, d), 4.05 (1H, d), 4.57 (2H, d), 5.37-5.5.47 (2H, m), 5.77-5.89-5.72 (1H, m), 6.67-6.81 (2H, m), 7.07 (1H, b), 7.42-7.47 (3H, m) |
| 1-734 | 1H-NMR (CDCl3) δ: 2.50-2.59 (1H, m), 2.83-2.91 (1H, m), 3.50-3.62 (2H, m), 3.76-3.87 (5H, m), 4.06 (1H, d), 4.55 (2H, d), 5.51-5.57 (2H, m), 5.83-5.97 (1H, m), 6.64-6.81 (3H, m), 7.42-7.45 (3H, m) |
| 1-735 | 1H-NMR (CDCl3) δ: 2.38 (3H, s), 2.50-2.59 (1H, m), 2.83-2.91 (1H, m), 3.50-3.62 (2H, m), 3.77 (1H, d), 4.05 (1H, d), 4.57 (2H, d), 6.43 (1H, b), 6.68-6.79 (3H, m), 7.38-7.43 (3H, m) |
| 1-856 | 1H-NMR (CDCl3) δ: 1.14 (3H, t), 2.20 (2H, q), 2.51-2.61 (1H, m), 2.99-3.07 (1H, m), 3.49-3.61 (2H, m), 3.76 (1H, d), 4.25 (1H, dd), 4.50 (2H, d), 5.72 (1H, s), 6.71 (1H, dd), 6.81 (1H, d), 7.32 (1H, dd), 7.45 (1H, d). |
| 1-866 | 1H-NMR (CDCl3) δ: 1.15 (3H, t), 2.20 (2H, q), 2.57-2.66 (1H, m), 2.91-2.99 (1H, m), 3.46-3.64 (2H, m), 3.85 (1H, d), 4.14 (1H, d), 4.50 (2H, d), 5.67 (1H, s), 6.71 (1H, dd), 6.81 (1H, d), 7.45 (1H, d), 7.52-7.64 (4H, m). |
| 1-907 | 1H-NMR (CDCl3) δ: 2.46 (2H, t), 2.54-2.64 (1H, m), 2.89-2.98 (1H, m), 3.34 (3H, s), 3.48-3.63 (4H, m), 3.81 (1H, d), 4.12 (1H, d), 4.51 (2H, d), 6.57 (1H, b), 6.69-6.81 (2H, m), 7.44-7.65 (4H, m) |
| 1-912 | 1H-NMR (CDCl3) δ: 1.99 (3H, s), 2.51-2.62 (1H, m), 2.87-2.96 (1H, m), 3.40-3.58 (2H, m), 3.77 (1H, m), 4.08 (1H, d), 4.42 (2H, m), 5.82 (1H, b), 6.50-6.79 (2H, m), 7.26-7.65 (4H, m) |
| 1-913 | 1H-NMR (CDCl3) δ: 1.15 (3H, t), 2.21 (2H, q), 2.50-2.62 (1H, m), 2.87-2.95 (1H, m), 3.77 (1H, d), 4.08 (1H, d), 4.43 (2H, d), 5.80 (1H, b), 6.50-6.79 (2H, m), 6.27-7.65 (4H, m) |
| 1-915 | 1H-NMR (CDCl3) δ: 0.69-0.75 (2H, m), 0.95-0.98 (2H, m), 1.25-1.35 (1H, m), 2.50-2.60 (1H, m), 2.87-2.94 (1H, m), 3.77 (1H, d), 4.08 (1H, d), 4.45 (2H, d), 5.98 (1H, b), 6.49-7.65 (6H, m) |
| 1-917 | 1H-NMR (CDCl3) δ: 2.50-2.62 (1H, m), 2.87-2.96 (1H, d), 3.03 (1H, d), 3.10 (1H, d), 3.40-3.57 (2H, m), 3.78 (1H, d), 4.09 (1H, d), 4.47 (2H, d), 6.09 (1H, b), 6.50-6.80 (2H, m), 7.26-7.65 (4H, m). |
| 1-918 | 1H-NMR (CDCl3) δ: 2.09 (3H, s), 2.51-2.62 (1H, m), 2.87-2.96 (1H, m), 3.21 (2H, s), 3.40-3.60 (2H, m), 3.78 (1H, d), 4.09 (1H, d), 4.46 (2H, d), 6.50-6.81 (2H, m), 7.26-7.65 (5H, m) |
| 1-924 | 1H-NMR (CDCl3) δ: 2.07 (3H, s), 2.55-2.64 (1H, m), 2.90-3.00 (1H, m), 3.20 (2H, s), 3.82 (1H, d), 4.13 (1H, d), 4.55 (2H, d), 6.70-7.66 (7H, m) |
| 1-925 | 1H-NMR (CDCl3) δ: 2.54-2.65 (4H, m), 2.90-2.98 (1H, m), 3.27 (1H, d), 3.51-3.69 (3H, m), 3.81 (1H, d), 4.13 (1H, d), 4.59 (2H, d), 6.69-7.66 (7H, m) |
| 1-926 | 1H-NMR (CDCl3) δ: 2.54-2.65 (1H, m), 2.91-3.00 (1H, m), 3.05 (3H, s), 3.50-3.63 (2H, m), 3.81 (1H, m), 3.86 (2H, s), 4.13 (1H, d), 3.86 (2H, s), 4.13 (1H, d), 4.57 (2H, d), 6.58-6.83 (3H, m), 7.42-7.66 (4H, m) |
| 1-939 | 1H-NMR (CDCl3) δ: 2.09 (3H, s), 2.56-2.66 (1H, m), 2.95-3.03 (1H, m), 3.46-3.63 (2H, m), 3.82 (1H, m), 4.17 (1H, d), 4.47 (2H, d), 6.50 (1H, dd), 6.65 (1H, d), 7.85 (2H, s), 7.93 (1H, s), 7.30-7.23 (1H, m). |
| 1-940 | 1H-NMR (acetone-d6) δ: 2.63 (3H, s), 2.79-2.91 (1H, m), 3.13-3.21 (1H, m), 3.54-3.64 (2H, m), 4.06 (1H, m), 4.39-4.45 (3H, m), 6.64 (1H, dd), 6.74 (1H, d), 7.33 (1H, d), 7.72 (1H, br s), 8.13 (1H, s), 8.26 (2H, s). |
| 1-941 | 1H-NMR (acetone-d6) δ: 2.66-2.80 (1H, m), 2.98 (3H, s), 3.02-3.10 (1H, m), 3.40-3.52 (2H, m), 3.91-3.96 (3H, m), 4.29-4.33 (3H, m), 6.52 (1H, dd), 6.62 (1H, d), 7.20 (1H, d), 7.72 (1H, br s), 8.00 (1H, s), 8.14 (2H, s). |
| 1-945 | 1H-NMR (CDCl3) δ: 2.10 (3H, s), 2.55-2.67 (1H, m), 2.94-3.03 (1H, m), 3.80 (1H, d), 4.15 (1H, d), 4.47 (2H, d), 6.51-7.92 (7H, m) |
| 1-946 | 1H-NMR (CDCl3) δ: 2.55-2.66 (4H, m), 2.94-3.02 (1H, m), 3.27 (1H, d), 3.45-3.53 (2H, m), 3.57 (1H, d), 3.63 (1H, d), 3.80 (1H, d), 4.19 (1H, d), 4.48-4.51 (2H, m), 6.51-7.92 (7H, m) |
| 1-947 | 1H-NMR (CDCl3) δ: 2.55-2.65 (1H, m), 2.94-3.05 (4H, m), 3.40-3.62 (2H, m), 3.80 (1H, s), 3.86 (2H, s), 4.15 (1H, d), 4.48 (2H, d), 6.51-7.92 (7H, m) |
| 1-963 | 1H-NMR (CDCl3) δ: 2.25 (3H, s), 2.60-2.68 (1H, m), 2.96-3.05 (1H, m), 3.42 (2H, s), 3.50-3.62 (2H, m), 3.84 (1H, d), 4.19 (1H, d), 4.54 (2H, d), 6.70-6.84 (2H, m), 7.19 (1H, b), 7.27-7.93 (4H, m) |
| 1-966 | 1H-NMR (CDCl3) δ: 2.06 (3H, s), 2.60-2.68 (1H, m), 2.96-3.05 (1H, m), 3.20 (2H, s), 3.53-3.63 (2H, m), 3.85 (1H, d), 4.19 (1H, d), 4.55 (2H, d), 6.70-6.85 (2H, m), 7.13 (1H, b), 7.27-7.93 (4H, m) |
| 1-967 | 1H-NMR (CDCl3) δ: 2.61-2.68 (4H, m), 2.97-3.05 (1H, m), 3.29 (1H, d), 3.50-3.68 (3H, m), 3.84 (1H, d), 4.19 (1H, d), 4.58 (1H, d), 6.71-6.84 (2H, m), 7.16 (1H, b), 7.46-7.93 (4H, m) |
| 1-968 | 1H-NMR (CDCl3) δ: 2.60-2.68 (1H, m), 2.97-3.05 (4H, m), 3.52-3.65 (2H, m), 3.83-3.86 (3H, m), 4.19 (1H, d), 4.57 (2H, d), 6.61 (1H, d), 6.72-6.85 (2H, m), 7.16 (1H, b), 7.43-7.93 (4H, m) |
| 1-969 | 1H-NMR (CDCl3) δ: 2.62-2.68 (1H, m), 2.97-3.18 (3H, m), 3.57 (2H, s), 3.53-3.65 (2H, m), 3.85 (1H, d), 4.20 (1H, d), 4.53 (2H, d), 5.02-5.09 (2H, m), 5.61-5.75 (1H, m), 6.72-6.83 (2H, m), 6.75 (1H, b), 7.44-7.93 (4H, m) |

TABLE 8-continued

| Table 8 - Ex.-No. | 1H-NMR |
|---|---|
| 1-970 | 1H-NMR (CDCl3) δ: 2.62-2.68 (1H, m), 2.97-3.18 (1H, m), 3.34 (1H, d), 3.50-3.65 (3H, m), 3.84 (1H, d), 4.19 (1H, d), 4.59 (2H, d), 5.37-5.47 (2H, m), 5.78-5.87 (1H, m), 6.72-6.83 (2H, m), 7.03 (1H, b), 7.46-7.93 (4H, m) |
| 1-971 | 1H-NMR (CDCl3) δ: 2.63-2.68 (1H, m), 2.97-3.05 (1H, m), 3.52-3.62 (2H, m), 3.83-3.85 (5H, m), 4.20 (1H, d), 4.56 (2H, d), 5.51-5.57 (2H, m), 5.83-5.98 (1H, m), 6.62 (1H, b), 6.72-6.85 (2H, m), 7.44-7.93 (4H, m) |
| 1-996 | 1H-NMR (CDCl3) δ: 1.15 (3H, t), 2.21 (2H, q), 2.54-2.68 (1H, m), 2.95-3.06 (1H, m), 3.45-3.60 (2H, m), 3.83 (1H, d), 4.16 (1H, d), 4.59 (2H, d), 5.72 (1H, b), 6.71-7.93 (6H, m) |
| 1-1066 | 1H-NMR (CDCl3) δ: 1.14 (3H, t), 2.20 (3H, q), 2.49-2.61 (1H, m), 2.80-2.92 (1H, m), 3.45-3.59 (2H, m), 3.79 (1H, d), 4.04 (1H, d), 5.50 (2H, d), 5.76 (1H, s), 6.71 (1H, dd), 6.80 (1H, d), 7.32 (2H, s), 7.46 (1H, d). |
| 1-1169 | 1H-NMR (CDCl3) δ: 1.58-1.68 (1H, m), 2.10-2.30 (2H, m), 2.50-2.56 (1H, m), 2.83-2.89 (1H, m), 3.50-3.63 (2H, m), 3.91 (1H, d), 4.36-4.44 (3H, m), 6.14 (1H, b), 6.27 (1H, d), 7.30-7.55 (4H, m) |
| 1-1171 | 1H-NMR (CDCl3) δ: 2.48-2.58 (1H, m), 2.83-2.91 (1H, m), 3.07 (2H, q), 3.53-3.64 (2H, m), 3.92 (1H, d), 4.37-4.43 (3H, m), 6.16 (1H, b), 6.27 (1H, d), 7.29-7.55 (4H, m) |
| 1-1172 | 1H-NMR (CDCl3) δ: 2.09 (3H, s), 2.48-2.58 (1H, m), 2.83-2.90 (1H, m), 3.20 (2H, s), 3.53-3.66 (2H, m), 3.92 (1H, d), 4.37-4.43 (3H, m), 6.27 (1H, d), 7.29-7.56 (5H, m) |
| 1-1174 | 1H-NMR (CDCl3) δ: 2.48-2.58 (1H, m), 2.83-2.92 (1H, m), 3.06 (3H, s), 3.53-3.65 (2H, m), 3.87-3.93 (3H, m), 4.37-4.45 (3H, m), 6.27 (1H, d), 6.82 (1H, b), 7.29-7.61 (4H, m) |
| 1-1179 | 1H-NMR (CDCl3) δ: 0.68-0.77 (2H, m), 0.95-1.00 (2H, m), 1.30-1.35 (1H, m), 2.47-2.58 (1H, m), 2.81-2.92 (1H, m), 3.50-3.66 (2H, m), 3.91 (1H, d), 4.37-4.40 (3H, m), 6.10 (1H, b), 6.25-7.57 (5H, m) |
| 1-1181 | 1H-NMR (CDCl3) δ: 2.48-2.59 (1H, m), 2.84-2.91 (1H, m), 3.03 (1H, d), 3.10 (1H, d), 3.52-3.66 (2H, m), 3.91 (1H, d), 4.40-4.48 (3H, m), 6.26-6.29 (2H, m), 7.29-7.54 (4H, m) |
| 1-1182 | 1H-NMR (CDCl3) δ: 2.10 (3H, s), 2.45-2.60 (1H, m), 2.80-2.90 (1H, m), 2.54 (1H, s), 2.63-2.76 (1H, m), 3.06 (2H, q), 3.45-3.50 (1H, m), 3.68-3.73 (1H, m), 4.07 (1H, d), 4.30 (1H, d), 6.27 (1H, d), 7.26-7.57 (5H, m) |
| 1-1183 | 1H-NMR (CDCl3) δ: 2.48-2.58 (1H, m), 2.67 (3H, s), 2.82-2.91 (1H, m), 3.20 (2H, s), 3.24-3.30 (1H, m), 3.52-3.70 (3H, m), 3.91 (1H, d), 4.41-4.47 (3H, m), 6.25-7.58 (6H, m) |
| 1-1184 | 1H-NMR (CDCl3) δ: 2.48-2.59 (1H, m), 2.83-2.91 (1H, m), 3.06 (3H, s), 3.50-3.66 (2H, m), 3.87-3.92 (3H, m), 4.41-4.65 (3H, m), 6.24-7.61 (6H, m) |
| 1-1192 | 1H-NMR (CDCl3) δ: 2.08 (3H, s), 2.52-2.58 (1H, m), 2.82-2.94 (1H, m), 2.87-2.94 (1H, m), 3.22 (2H, s), 3.52-3.62 (2H, m), 3.95 (1H, d), 4.39 (1H, d), 4.49-4.51 (2H, m), 6.52 (1H, d), 7.26-7.34 (4H, m), 7.70 (1H, d). |
| 1-1196 | 1H-NMR (CDCl3) δ: 1.16 (3H, t), 2.45-2.77 (7H, m), 3.48-3.51 (1H, m), 3.68-3.75 (1H, m), 4.08 (1H, d), 4.38 (2H, d), 5.59 (1H, b), 6.67 (1H, d), 7.25-7.39 (4H, m) |
| 1-1198 | 1H-NMR (CDCl3) δ: 2.46-2.55 (1H, m), 2.54 (1H, s), 2.63-2.76 (1H, m), 3.06 (2H, q), 3.45-3.50 (1H, m), 3.68-3.73 (1H, m), 4.07 (1H, d), 4.30 (1H, d), 4.48 (2H, m), 5.93 (1H, b), 6.70 (1H, d), 7.25-7.40 (4H, m) |
| 1-1279 | 1H-NMR (CDCl3) δ: 1.15 (3H, t), 2.22 (2H, q), 2.46-2.57 (1H, m), 2.82-2.90 (1H, m), 3.54-3.66 (2H, m), 3.92 (1H, d), 4.35-4.40 (3H, m), 5.92 (1H, b), 6.27 (1H, d), 7.43-7.58 (3H, m) |
| 1-1283 | 1H-NMR (CDCl3) δ: 2.47-2.57 (1H, m), 2.82-2.90 (1H, m), 3.04 (1H, d), 3.11 (1H, d), 3.50-3.67 (2H, m), 3.91 (1H, d), 4.36-4.48 (3H, m), 6.22 (1H, m), 4.47 (1H, d), 7.39-7.55 (3H, m) |
| 1-1284 | 1H-NMR (CDCl3) δ: 2.13 (3H, s), 2.47-2.57 (1H, m), 2.82-2.90 (1H, m), 3.20 (2H, s), 3.50-3.67 (2H, m), 3.92 (1H, d), 4.36-4.43 (3H, m), 6.27 (1H, d), 7.35-7.57 (4H, m) |
| 1-1289 | 1H-NMR (CDCl3) δ: 0.14-0.24 (2H, m), 0.57-0.59 (2H, m), 0.85-0.98 (1H, m), 2.12-2.18 (2H, m), 2.49-2.58 (1H, m), 2.83-2.91 (1H, m), 3.57-3.70 (4H, m), 3.96 (1H, d), 4.37 (1H, d), 4.48-4.50 (2H, m), 6.29 (1H, br s), 6.51 (1H, d), 7.45 (2H, s), 7.74 (1H, d). |
| 1-1290 | 1H-NMR (CDCl3) δ: 2.05 (3H, s), 2.49-2.59 (1H, m), 2.83-2.91 (1H, m), 3.19 (2H, s), 3.58-3.71 (2H, m), 3.97 (1H, d), 4.37 (1H, d), 4.50-4.51 (2H, m), 6.51 (1H, d), 7.44 (2H, s), 7.71 (1H, d). |
| 1-1291 | 1H-NMR (CDCl3) δ: 2.49-2.61 (1H, m), 2.65 (3H, s), 2.83-2.89 (1H, m), 3.28 (1H, d), 3.57-3.69 (3H, m), 3.96 (1H, d), 4.37 (1H, d), 4.54-4.55 (2H, m), 6.52 (1H, d), 7.23-7.28 (1H, d), 7.48 (2H, s), 7.73 (1H, d). |
| 1-1292 | 1H-NMR (CDCl3) δ: 2.51-2.56 (1H, m), 2.83-2.92 (1H, m), 3.08 (3H, s), 3.57-3.70 (2H, m), 3.89-3.96 (3H, m), 4.37 (1H, d), 4.51-4.53 (2H, m), 6.52 (1H, d), 6.84 (1H, br s), 7.43 (2H, s), 7.69 (1H, d). |
| 1-1427 | 1H-NMR (CDCl3) δ: 1.14 (3H, t), 2.10-2.27 (2H, m), 2.54-2.63 (1H, m), 2.91-3.00 (1H, m), 3.55-3.72 (2H, m), 4.05 (1H, m), 4.44-4.47 (3H, m), 5.79 (1H, br s), 6.56 (1H, d), 7.51-7.78 (5H, m). |
| 1-1431 | 1H-NMR (CDCl3) δ: 2.59-2.67 (1H, m), 2.92-3.17 (1H, m), 3.54-3.67 (2H, m), 4.04 (1H, d), 4.47-4.54 (3H, m), 6.15 (1H, d), 6.56 (1H, d), 7.52-7.77 (5H, m). |
| 1-1432 | 1H-NMR (CDCl3) δ: 2.06 (3H, s), 2.58-2.64 (1H, m), 2.92-3.00 (1H, m), 3.19 (2H, s), 3.62-3.70 (2H, m), 4.05 (1H, d), 4.44-4.52 (3H, m), 6.52 (1H, d), 7.23 (1H, br s), 7.56-7.67 (5H, m). |
| 1-1433 | 1H-NMR (CDCl3) δ: 2.59-2.66 (4H, m), 2.88-2.95 (1H, m), 3.26 (1H, d), 3.65 (3H, m), 4.03 (1H, d), 4.45 (1H, d), 4.54-4.56 (2H, m), 6.52 (1H, br s), 7.17 (1H, br s), 7.56-7.69 (5H, m). |

TABLE 8-continued

| Table 8 - Ex.-No. | 1H-NMR |
|---|---|
| 1-1434 | 1H-NMR (CDCl3) δ: 2.58-2.64 (1H, m), 2.92-3.00 (1H, m), 3.08 (3H, s), 3.63-3.68 (2H, m), 3.86 (2H, s), 4.02 (1H, d), 4.45-4.52 (3H, m), 6.53 (1H, d), 6.71 (1H, br s), 7.52-7.69 (5H, m). |
| 1-1467 | 1H-NMR (CDCl3) δ: 1.15 (3H, t), 2.22 (2H, q), 2.57-2.66 (1H, m), 2.96-3.05 (1H, m), 3.56-3.68 (2H, m), 3.98 (1H, d), 4.38 (2H, d), 4.53 (1H, d), 5.90 (1H, b), 6.29 (1H, d), 7.57-7.91 (4H, m) |
| 1-1471 | 1H-NMR (CDCl3) δ: 2.55-2.66 (1H, m), 2.98-3.13 (3H, m), 3.56-3.68 (2H, m), 3.98 (1H, d), 4.43 (2H, d), 4.54 (1H, d), 6.16 (1H, b), 6.30 (1H, d), 7.54-7.92 (4H, m) |
| 1-1472 | 1H-NMR (CDCl3) δ: 2.10 (3H, s), 2.55-2.66 (1H, m), 2.97-3.05 (1H, m), 3.18 (2H, s), 3.55-3.68 (2H, m), 3.98 (1H, d), 4.38 (2H, d), 4.53 (1H, d), 6.30 (1H, d), 7.35 (1H, b), 7.56-7.92 (4H, m) |
| 1-1476 | 1H-NMR (CDCl3) δ: 1.99 (3H, s), 2.55-2.66 (1H, m), 2.96-3.05 (1H, m), 3.56-3.68 (2H, m), 3.98 (1H, d), 4.37 (2H, d), 4.53 (1H, d), 6.05 (1H, b), 6.29 (1H, d), 6.28-7.85 (4H, m) |
| 1-1477 | 1H-NMR (CDCl3) δ: 1.15 (3H, t), 2.22 (2H, q), 2.55-2.66 (1H, m), 2.96-3.00 (1H, m), 3.56-3.68 (2H, m), 3.98 (1H, d), 4.38 (2H, d), 4.53 (1H, d), 6.31 (1H, d), 6.28-7.91 (4H, m) |
| 1-1479 | 1H-NMR (CDCl3) δ: 0.70-0.77 (2H, m), 0.94-0.99 (2H, m), 1.28-1.38 (1H, m), 2.56-2.71 (1H, m), 2.58-3.05 (1H, m), 3.55-3.68 (2H, m), 3.98 (1H, d), 4.40 (2H, d), 4.54 (1H, d), 6.09 (1H, b), 6.29 (1H, d), 7.56-7.92 (4H, m) |
| 1-1481 | 1H-NMR (CDCl3) δ: 2.56-2.66 (1H, m), 2.98-3.13 (3H, m), 3.56-3.71 (2H, m), 3.99 (1H, d), 4.43 (2H, d), 4.54 (1H, d), 6.19 (1H, b), 6.30 (1H, d), 7.54-7.92 (4H, m) |
| 1-1482 | 1H-NMR (CDCl3) δ: 2.10 (3H, s), 2.58-2.66 (1H, m), 2.97-3.05 (1H, m), 3.20 (2H, s), 3.50-3.68 (2H, m), 3.99 (1H, d), 4.43 (2H, d), 4.54 (1H, d), 6.30 (1H, b), 7.35 (1H, b), 7.40-7.92 (4H, m) |
| 1-1483 | 1H-NMR (CDCl3) δ: 2.60-2.67 (4H, m), 2.96-3.07 (1H, m), 3.27 (1H, d), 3.50-3.76 (3H, m), 3.98 (1H, d), 4.45-4.56 (3H, m), 6.30 (1H, b), 7.30 (1H, d), 7.57-7.92 (4H, m) |
| 1-1484 | 1H-NMR (CDCl3) δ: 2.55-2.66 (1H, m), 2.97-3.06 (4H, m), 3.55-3.71 (2H, m), 3.88-4.00 (3H, m), 4.44-4.56 (3H, m), 6.21 (1H, d), 6.85 (1H, b), 7.54-7.92 (4H, m) |
| 1-1487 | 1H-NMR (CDCl3) δ: 0.16-0.22 (2H, m), 0.52-0.63 (2H, m), 0.85-0.98 (1H, m), 2.15 (1H, d), 2.59-2.64 (1H, m), 2.97-3.05 (1H, m), 3.60-3.72 (2H, m), 4.07 (1H, d), 4.49-4.51 (3H, m), 6.31 (1H, br s), 6.54 (1H, d), 7.76 (1H, d), 7.85-7.91 (3H, m) |
| 1-1488 | 1H-NMR (CDCl3) δ: 2.06 (3H, s), 2.57-2.67 (1H, m), 3.01-3.07 (1H, m), 3.20 (2H, s), 3.63-3.73 (2H, m), 4.08 (1H, d), 4.49-4.51 (3H, m), 6.54 (1H, d), 7.24 (1H, br s), 7.73 (1H, d), 7.85 (2H, s), 7.92 (1H, s). |
| 1-1489 | 1H-NMR (CDCl3) δ: 2.60-2.69 (4H, m), 2.97-3.05 (1H, m), 3.30 (1H, m), 3.58-3.75 (3H, m), 4.04-4.07 (1H, m), 4.50-4.55 (3H, m), 6.55 (1H, d), 7.24 (1H, br s), 7.74 (1H, d), 7.85 (2H, s), 7.92 (1H, s). |
| 1-1490 | 1H-NMR (CDCl3) δ: 2.59-2.65 (1H, m), 3.00-3.07 (4H, m), 3.58-3.75 (2H, m), 3.88 (2H, s), 4.05-4.13 (1H, m), 4.50-4.53 (3H, m), 6.55 (1H, d), 6.80 (1H, br s), 7.70 (1H, d), 7.85 (2H, s), 7.92 (1H, s). |
| 1-1696 | 1H-NMR (CDCl3) δ: 2.04 (3H, s), 2.45-2.55 (4H, m), 2.50 (3H, s), 2.63-2.76 (1H, m), 3.15 (2H, s), 3.51-3.59 (1H, m), 3.68-3.75 (1H, m), 4.07 (1H, d), 4.30 (1H, d), 4.49 (2H, d), 6.69 (1H, d), 6.94 (1H, b), 7.25-7.39 (4H, m) |
| 1-1730 | 1H-NMR (CDCl3) δ: 1.17-1.23 (3H, m), 2.09-2.22 (2H, m), 2.34-2.59 (4H, m), 2.80-2.89 (1H, m), 3.55-3.63 (2H, m), 3.94 (1H, d), 4.34-4.38 (3H, m), 5.48 (1H, br s), 6.20 (1H, d,z), 7.29-7.35 (4H, m). |
| 1-1733 | 1H-NMR (CDCl3) δ: 0.19-0.23 (1H, m), 0.51-0.71 (3H, m), 0.88-0.99 (1H, m), 2.18 (2H, d), 2.45-2.60 (4H, m), 2.81-2.89 (1H, m), 3.57-3.62 (2H, m), 3.95 (1H, d), 4.36-4.39 (3H, m), 5.93 (1H, d), 6.21 (1H, d), 7.26-7.54 (4H, m). |
| 1-1735 | 1H-NMR (CDCl3) δ: 2.10 (3H, s), 2.42-2.57 (4H, m), 2.81-2.89 (1H, m), 3.24 (2H, s), 3.53-3.63 (2H, m), 3.95 (1H, d), 4.38-4.40 (3H, m), 6.21 (1H, d), 6.93 (1H, d), 7.29-7.32 (4H, m). |
| 1-1770 | 1H-NMR (CDCl3) δ: 0.88-0.92 (2H, m), 1.13-1.17 (5H, m), 2.00-2.05 (1H, m), 2.21 (2H, q), 2.44-2.54 (1H, m), 2.76-2.85 (1H, m), 3.49-3.63 (2H, m), 3.90 (1H, d), 4.24 (1H, m), 4.46-4.47 (2H, m), 5.53 (1H, br s), 6.11 (1H, d), 7.28-7.36 (4H, m). |
| 1-1772 | 1H-NMR (CDCl3) δ: 0.70-1.36 (9H, m), 2.00-2.09 (1H, m), 2.44-2.54 (1H, m), 2.76-2.85 (1H, m), 3.49-3.63 (2H, m), 3.90 (1H, d), 4.24 (1H, d), 4.46-4.51 (2H, m), 5.74 (1H, m), 6.11 (1H, d), 7.38-7.43 (4H, m). |
| 1-1775 | 1H-NMR (CDCl3) δ: 0.86-0.93 (2H, m), 1.13-1.18 (2H, m), 1.97-2.13 (4H, m), 2.45-2.55 (1H, m), 2.77-2.85 (1H, m), 3.24 (2H, s), 3.47-3.64 (2H, m), 3.91 (1H, d), 4.24 (1H, d), 4.50-4.52 (2H, m), 6.12 (1H, d), 7.08 (1H, br s), 7.28-7.33 (4H, m). |
| 1-1800 | 1H-NMR (CDCl3) δ: 0.88-0.97 (2H, m), 1.07-1.19 (5H, m), 2.02-2.06 (1H, m), 2.22 (2H, q), 2.52-2.61 (1H, m), 2.89-2.97 (1H, m), 3.50-3.67 (2H, m), 4.02 (1H, d), 4.33 (1H, d), 4.47 (2H, d), 5.53 (1H, br s), 6.13 (1H, d), 7.33 (1H, d), 7.84-7.90 (3H, m). |
| 1-1802 | 1H-NMR (CDCl3) δ: 0.72-0.75 (2H, m), 0.92-0.98 (4H, m), 1.19-1.27 (3H, m), 2.01-2.10 (1H, m), 2.56-2.60 (1H, m), 2.89-2.97 (1H, m), 3.55-3.62 (2H, m), 3.90 (1H, d), 4.24 (1H, d), 4.49 (2H, d), 5.69 (1H, d), 6.14 (1H, d), 7.33 (1H, d), 7.84-7.90 (3H, m). |
| 1-1803 | 1H-NMR (CDCl3) δ: 0.15-0.20 (2H, m), 0.56-0.58 (2H, m), 0.86-0.99 (3H, m), 1.10-1.19 (2H, m), 2.00-2.09 (1H, m), 2.18 (2H, d), 2.52-2.61 (1H, m), 2.89-2.97 (1H, m), 3.54-3.65 (2H, m), 4.03 (1H, d), 4.33 (1H, d), 4.50 (2H, d), 6.00 (1H, br s), 6.14 (1H, br s), 7.33 (1H, d), 7.84-7.90 (3H, m). |
| 1-1804 | 1H-NMR (CDCl3) δ: 0.87-0.92 (2H, m), 1.13-1.15 (2H, m), 1.94-2.02 (1H, m), 2.52-2.62 (1H, m), 2.89-2.98 (1H, m), 3.08 (2H, d), 3.54-3.65 (2H, m), 4.02 (1H, d), 4.33 (1H, d), 4.51 (2H, d), 5.85 (1H, d), 6.14 (1H, d), 7.31 (1H, d), 7.84-7.90 (3H, m). |

TABLE 8-continued

| Table 8 - Ex.-No. | 1H-NMR |
|---|---|
| 1-1805 | 1H-NMR (CDCl3) δ: 0.88-0.96 (2H, m), 1.10-1.20 (2H, m), 2.00-2.05 (1H, m), 2.24 (2H, s), 2.47-2.70 (1H, m), 2.92-2.98 (1H, m), 3.24 (3H, s), 3.55-3.62 (2H, m), 4.03 (1H, d), 4.33 (1H, d), 4.52 (2H, d), 6.14 (1H, d), 7.04 (1H, d), 7.34 (1H, d), 7.84 (2H, s), 7.90 (1H, s). |
| 1-1969 | 1H-NMR (CDCl3) δ: 1.16 (3H, t), 2.24 (2H, q), 2.42-2.52 (1H, m), 2.73-2.82 (1H, m), 3.50 (1H, br s), 3.61 (1H, dd), 3.93 (1H, d), 4.10 (1H, dd), 4.39 (2H, d), 5.90 (1H, s), 6.64 (1H, d), 7.06 (1H, d), 7.28 (2H, s), 7.38 (1H, t). |
| 1-1981 | 1H-NMR (CDCl3) δ: 1.15 (3H, t, J = 7.5 Hz), 2.22 (2H, q, J = 7.6 Hz), 2.43-2.53 (1H, m), 2.73-2.82 (1H, m), 3.51 (1H, br s), 3.63 (1H, dd), 3.96 (1H, d), 4.12 (1H, dd), 4.44 (2H, d), 5.80 (1H, s), 6.55 (1H, dd), 7.07 (1H, d), 7.28 (2H, s), 7.38 (1H, t). |
| 1-1984 | 1H-NMR (CDCl3) δ: 2.02 (3H, s), 2.47-2.49 (1H, m), 2.73-2.81 (1H, m), 3.54-3.61 (2H, m), 3.97-4.08 (2H, m), 4.43 (2H, d, J = 5.9 Hz), 5.94 (1H, br s), 6.55 (1H, t, J = 8.5 Hz), 7.07 (1H, dd, J = 8.5, 1.6 Hz), 7.43 (2H, s). |
| 1-1985 | 1H-NMR (CDCl3) δ: 1.15 (3H, t), 2.22 (2H, q), 2.47-2.49 (1H, m), 2.73-2.81 (1H, m), 3.54-3.60 (2H, m), 3.92-3.96 (1H, m), 4.07-4.11 (1H, m), 4.44 (2H, d), 5.91 (1H, br s), 6.55 (1H, t), 7.06 (1H, dd), 7.42 (2H, s). |
| 1-1986 | 1H-NMR (CDCl3) δ: 0.63-0.67 (2H, m), 0.88-0.90 (2H, m), 1.25-1.29 (1H, m), 2.39-2.41 (1H, m), 2.65-2.73 (1H, m), 3.47-3.51 (2H, m), 3.89-4.00 (2H, m), 4.37 (2H, d), 6.04 (1H, t), 6.47 (1H, d), 6.98 (1H, dd), 7.35 (2H, s). |
| 1-1987 | 1H-NMR (CDCl3) δ: 2.47-2.49 (1H, m), 2.73-2.82 (1H, m), 3.07 (2H, q), 3.55-3.61 (2H, m), 4.00-4.08 (2H, m), 4.46 (2H, d), 6.29 (1H, br s), 6.55 (1H, t), 7.04 (1H, dd), 7.42 (2H, s). |
| 1-1988 | 1H-NMR (CDCl3) δ: 1.99 (3H, s), 2.51-2.60 (1H, m), 2.87-2.95 (1H, m), 3.51-3.71 (2H, m), 4.03 (1H, d), 4.21 (1H, dd), 4.43 (2H, d), 6.08 (1H, s), 6.58 (1H, dd), 7.08 (1H, dd), 7.85 (2H, s), 7.92 (1H, s). |
| 1-1989 | 1H-NMR (CDCl3) δ: 1.16 (3H, t), 2.23 (2H, q), 2.51-2.60 (1H, m), 2.87-2.95 (1H, m), 3.54 (1H, br s), 3.68 (1H, d), 4.04 (1H, d), 4.22 (1H, dd), 4.45 (2H, d), 5.90 (1H, s), 6.59 (1H, dd), 7.08 (1H, dd), 7.85 (2H, s), 7.92 (1H, s). |
| 1-1990 | 1H-NMR (CDCl3) δ: 0.70-0.76 (2H, m), 0.94-0.99 (2H, m), 1.32-1.40 (1H, m), 2.51-2.60 (1H, m), 2.87-2.95 (1H, m), 3.53 (1H, br s), 3.67 (1H, dd), 4.04 (1H, d), 4.21 (1H, dd), 4.46 (2H, d), 6.12 (1H, s), 6.59 (1H, dd), 7.08 (1H, dd), 7.85 (2H, s), 7.92 (1H, s). |
| 1-1991 | 1H-NMR (CDCl3) δ: 2.51-2.61 (1H, m), 2.88-2.96 (1H, m), 3.08 (2H, q, J = 10.6 Hz), 3.55 (1H, br s), 3.69 (1H, dd, J = 8.4, 4.2 Hz), 4.04 (1H, d, J = 10.6 Hz), 4.23 (1H, dd, J = 10.8, 2.4 Hz), 4.48 (2H, d, J = 5.9 Hz), 6.27 (1H, s), 6.59 (1H, dd, J = 8.5, 4.3 Hz), 7.06 (1H, dd, J = 8.4, 1.5 Hz), 7.84 (2H, s), 7.92 (1H, s). |
| 1-1992 | 1H-NMR (CDCl3) δ: 2.09 (3H, s), 2.48-2.58 (4H, m), 2.79-2.88 (1H, m), 3.20 (3H, s), 3.45-3.55 (2H, m), 3.78 (1H, d), 4.70 (1H, d), 4.48 (2H, d), 6.37-6.48 (1H, m), 7.19-7.45 (4H, m). |
| 1-1993 | 1H-NMR (CDCl3) δ: 2.50-2.56 (4H, m), 2.79-2.88 (1H, m), 3.05 (2H, s), 3.45-3.57 (2H, m), 3.77 (1H, d), 4.04 (1H, d), 4.49 (2H, d), 6.36-6.46 (2H, m), 6.71 (1H, b), 7.18-7.40 (4H, m) |
| 1-1995 | 1H-NMR (CDCl3) δ: 2.50-2.2.63 (1H, m), 2.83-2.91 (1H, m), 3.47-3.60 (2H, m), 3.78 (1H, d), 4.08 (1H, d), 4.54 (2H, d), 4.63 (2H, s), 5.91 (1H, b), 6.67-6.80 (2H, m), 7.26-7.81 (6H, m) |
| 1-1996 | 1H-NMR (CDCl3) δ: 2.50-2.60 (1H, m), 2.82-2.90 (1H, m), 3.47-3.52 (1H, m), 3.76 (1H, d), 4.04 (1H, d), 4.47 (2H, d), 4.82 (2H, s), 6.31-7.64 (9H, m) |
| 1-1997 | 1H-NMR (CDCl3) δ: 2.50-2.60 (1H, m), 2.89-2.97 (1H, m), 3.79 (1H, d), 4.11 (1H, d), 4.47 (2H, d), 4.83 (2H, s), 6.31-6.78 (4H, m), 7.34-7.65 (6H, m) |
| 1-1998 | 1H-NMR (CDCl3) δ: 1.99 (3H, s), 2.50-2.66 (1H, m), 2.94-3.02 (1H, m), 3.45-3.60 (2H, m), 3.80 (1H, d), 4.13 (1H, d), 4.43 (2H, d), 5.81 (1H, b), 6.51-6.81 (2H, m), 7.28-7.92 (4H, m) |
| 1-1999 | 1H-NMR (CDCl3) δ: 2.54-2.64 (1H, m), 2.93-3.01 (1H, m), 3.44-3.60 (2H, m), 3.78 (1H, d), 4.12 (1H, d), 4.39 (2H, d), 4.83 (2H, s), 6.32-6.77 (4H, m), 7.17-7.92 (6H, m) |
| 1-2000 | 1H-NMR (CDCl3) δ: 2.47 (2H, t), 2.55-2.65 (1H, m), 2.94-3.02 (1H, m), 3.34 (3H, s), 3.47-3.65 (4H, m), 3.80 (1H, d), 4.14 (1H, d), 4.43 (2H, d), 6.51-7.92 (7H, m) |
| 1-2001 | 1H-NMR (CDCl3) δ: 2.45-2.60 (3H, m), 2.82-2.91 (1H, m), 3.36 (3H, s), 3.52-3.64 (4H, m), 3.91 (1H, m), 4.36-4.40 (3H, m), 6.24-7.60 (6H, m) |
| 1-2002 | 1H-NMR (CDCl3) δ: 2.44-2.60 (3H, m), 2.80-2.90 (1H, m), 3.36 (3H, s), 3.40-3.65 (4H, m), 3.74 (1H, d), 4.02 (1H, d), 4.44 (2H, d), 6.47-7.40 (6H, m) |
| 1-2003 | 1H-NMR (CDCl3) δ: 2.50-2.60 (1H, m), 2.85-2.95 (4H, m), 3.60-3.69 (2H, m), 3.97 (1H, d), 4.37-4.39 (3H, m), 6.56 (1H, d), 7.44 (1H, d), 7.74 (1H, d). |
| 1-2004 | 1H-NMR (CDCl3) δ: 2.58-2.68 (1H, m), 2.90-3.16 (4H, m), 3.66-3.74 (2H, m), 4.05-4.16 (1H, m), 4.41-4.57 (4H, m), 6.59 (1H, dz), 7.76 (1H, d), 7.85-7.92 (3H, m). |
| 1-2005 | 1H-NMR (CDCl3) δ: 2.56-2.66 (1H, m), 2.96-3.04 (1H, m), 3.64-3.70 (2H, m), 4.05 (1H, d), 4.50 (1H, d), 4.70-4.72 (2H, m), 6.54 (1H, d), 7.41-7.43 (1H, m), 7.82-7.88 (5H, m), 8.18-8.21 (1H, m), 8.39 (1H, br s), 8.53-8.54 (1H, m). |
| 1-2007 | 1H-NMR (CDCl3) δ: 1.99 (3H, s), 2.55-2.66 (1H, m), 2.94-3.02 (1H, m), 3.44-3.61 (2H, m), 3.79 (1H, d), 4.14 (1H, d), 4.40 (2H, d), 5.80 (1H, br s), 6.58 (1H, dd), 7.06 (1H, d), 7.28 (1H, d), 7.83 (2H, s), 7.92 (1H, s). |
| 1-2008 | 1H-NMR (CDCl3) δ: 1.16 (3H, t), 2.22 (2H, q), 2.55-2.65 (1H, m), 2.94-3.02 (1H, m), 3.44-3.61 (2H, m), 3.79 (1H, d), 4.14 (1H, d), 4.40 (2H, d), 5.78 (1H, br s), 6.58 (1H, dd), 7.06 (1H, d), 7.27 (1H, d), 7.83 (2H, s), 7.92 (1H, s). |

TABLE 8-continued

| Table 8 - Ex.-No. | 1H-NMR |
|---|---|
| 1-2009 | 1H-NMR (CDCl3) δ: 0.70-0.78 (2H, m), 0.95-1.01 (2H, m), 1.30-1.38 (1H, m), 2.55-2.65 (1H, m), 2.94-3.02 (1H, m), 3.44-3.61 (2H, m), 3.79 (1H, d), 4.14 (1H, d), 4.42 (2H, d), 6.00 (1H, brs), 6.58 (1H, dd), 7.07 (1H, d), 7.27 (1H, d), 7.84 (2H, s), 7.92 (1H, s). |
| 1-2010 | 1H-NMR (CDCl3) δ: 2.55-2.65 (1H, m), 2.95-3.12 (3H, m), 3.44-3.61 (2H, m), 3.79 (1H, d), 4.14 (1H, d), 4.44 (2H, d), 6.13 (1H, brs), 6.58 (1H, dd), 7.07 (1H, d), 7.25 (1H, d), 7.83 (2H, s), 7.93 (1H, s). |
| 1-2011 | 1H-NMR (CDCl3) δ: 2.11 (3H, s), 2.55-2.65 (1H, m), 2.95-3.01 (1H, m), 3.21 (1H, s), 3.45-3.62 (2H, m), 3.80 (1H, d), 4.15 (1H, d), 4.43 (2H, d), 6.58 (1H, dd), 7.08 (1H, d), 7.27 (2H, d), 7.84 (2H, s), 7.93 (1H, s). |
| 1-2012 | 1H-NMR (CDCl3) δ: 2.54-2.67 (4H, m), 2.94-3.02 (1H, m), 3.28 (1H, d, J = 14.3 Hz), 3.42-3.61 (2H, m), 3.68 (1H, d), 3.79 (1H, d), 4.14 (1H, d), 4.48 (2H, d), 6.58 (1H, dd), 7.07 (1H, d), 7.18 (1H, brs), 7.29 (1H, d), 7.83 (2H, s), 7.92 (1H, s). |
| 1-2013 | 1H-NMR (acetone-d6) δ: 2.79-2.91 (1H, m), 3.11 (3H, s), 3.13-3.21 (1H, m), 3.50-3.64 (2H, m), 4.05 (1H, d), 4.07 (1H, d), 4.37 (2H, d), 4.43 (1H, d), 6.73 (1H, dd), 7.18 (1H, d), 7.28 (1H, d), 7.84 (1H, brs), 8.12 (1H, s), 8.26 (2H, s). |
| 1-2015 | 1H-NMR (CDCl3) δ: 1.99 (3H, s), 2.50-2.63 (1H, m), 2.87-2.95 (1H, m), 3.55 (1H, brs), 3.64-3.72 (1H, m), 4.03 (1H, d), 4.22 (1H, dd), 4.39 (2H, d), 5.86 (1H, brs), 6.45-6.39 (1H, m), 7.02-6.96 (1H, m), 7.85 (2H, s), 7.92 (1H, s). |
| 1-2016 | 1H-NMR (CDCl3) δ: 1.15 (3H, t, J = 7.6 Hz), 2.22 (1H, m), 2.50-2.63 (1H, m), 2.85-2.95 (1H, m), 3.55 (1H, brs), 3.62-3.72 (1H, m), 4.02 (1H, d), 4.21 (1H, dd), 4.39 (2H, d), 5.85 (1H, brs), 6.36-6.45 (1H, m), 6.95-7.01 (1H, m), 7.85 (2H, s), 7.92 (1H, s). |
| 1-2017 | 1H-NMR (CDCl3) δ: 0.71-0.77 (2H, m), 0.95-1.00 (2H, m), 1.30-1.40 (1H, m), 2.51-2.61 (1H, m), 2.87-2.95 (1H, m), 3.56 (1H, brs), 3.64-3.72 (1H, m), 4.03 (1H, d), 4.22 (1H, dd), 4.42 (2H, d), 6.09 (1H, brs), 6.46-6.39 (1H, m), 6.96-7.02 (1H, m), 7.85 (2H, s), 7.92 (1H, s). |
| 1-2018 | 1H-NMR (CDCl3) δ: 2.51-2.60 (1H, m), 2.87-2.96 (1H, m), 3.57 (1H, m), 3.65-3.10 (2H, m), 3.57 (1H, m), 3.65-3.74 (1H, m), 4.03 (1H, d), 4.23 (1H, dd), 4.46 (2H, d), 6.03 (1H, brs), 6.46-6.40 (1H, m), 6.94-7.00 (1H, m), 7.84 (2H, s), 7.92 (1H, s). |
| 1-2019 | 1H-NMR (CDCl3) δ: 2.10 (3H, s), 2.50-2.63 (1H, m), 2.87-2.95 (1H, m), 3.21 (2H, s), 3.56 (1H, brs), 3.65-3.75 (1H, m), 4.23 (1H, dd), 4.46 (2H, d), 6.39-6.46 (1H, m), 6.96-7.02 (1H, m), 7.17 (1H, m), 7.84 (2H, s), 7.92 (1H, s). |
| 1-2020 | 1H-NMR (CDCl3) δ: 2.50-2.60 (1H, m), 2.66 (3H, s), 2.87-2.95 (1H, m), 3.26 (1H, d), 3.56 (1H, brs), 3.64-3.76 (1H, m), 3.69 (1H, d), 4.02 (1H, d), 4.22 (1H, dd), 4.49 (2H, ddd), 6.39-6.45 (1H, m), 6.98-7.04 (1H, m), 7.18 (1H, brs), 7.84 (2H, s), 7.92 (1H, s). |
| 1-2021 | 1H-NMR (CDCl3) δ: 2.50-2.60 (1H, m), 2.87-2.96 (1H, m), 3.06 (3H, s), 3.57 (1H, brs), 3.66-3.76 (1H, m), 3.88 (2H, d), 4.02 (1H, d), 4.23 (1H, dd), 4.47 (2H, d), 6.40-6.46 (1H, m), 6.73 (1H, brs), 6.95-7.01 (1H, m), 7.84 (2H, s), 7.92 (1H, s). |
| 1-2022 | 1H-NMR (CDCl3) δ: 1.44 (9H, s), 2.50-2.60 (1H, m), 2.86-2.94 (1H, m), 3.55 (1H, brs), 3.68 (1H, dd), 4.02 (1H, d), 4.21 (1H, dd), 4.28 (2H, d), 4.84 (1H), 6.39-6.45 (1H, m), 7.00-6.94 (1H, m), 7.85 (2H, s), 7.91 (1H, s). |
| 1-2023 | 1H-NMR (CDCl3) δ: 2.09 (3H, s), 2.45-2.52 (1H, m), 2.51-2.53 (1H, m), 2.74-2.82 (1H, m), 3.21 (2H, s), 3.54-3.63 (2H, m), 3.83 (2H, s), 3.94-3.97 (1H, m), 4.09-4.13 (1H, m), 4.49 (2H, d), 6.56 (1H, t), 7.08 (1H, dd), 7.43 (2H, s). |
| 1-2024 | 1H-NMR (CDCl3) δ: 2.50-2.60 (1H, m), 2.87-2.96 (1H, m), 3.06 (3H, s), 3.53-3.56 (1H, m), 3.67-3.70 (1H, m), 3.89 (2H, s), 4.01-4.05 (1H, m), 4.21-4.25 (1H, m), 4.50 (2H, d), 6.59 (1H, t), 6.89-6.91 (1H, m), 7.08 (1H, dd), 7.84 (2H, d), 7.92 (1H, s). |
| 1-2025 | 1H-NMR (CDCl3) δ: 2.52-2.57 (1H, m), 2.64 (3H, s), 2.84-2.92 (1H, m), 2.44-2.48 (1H, m), 3.37 (1H, d), 3.49-3.52 (1H, m), 3.62-3.67 (2H, m), 3.98-4.01 (1H, m), 4.17-4.21 (1H, m), 4.44-4.46 (2H, m), 6.56 (1H, t), 7.07 (1H, d), 7.57 (1H, t), 7.83 (2H, s), 7.89 (1H, s). |
| 1-2026 | 1H-NMR (CDCl3) δ: 2.09 (3H, s), 2.45-2.52 (1H, m), 2.86-2.94 (1H, m), 3.55 (1H, brs), 3.68 (1H, dd), 3.21 (2H, s), 3.54-3.63 (2H, m), 3.94-3.97 (1H, m), 4.09-4.13 (1H, m), 4.49 (2H, d), 6.56 (1H, t), 7.08 (1H, dd), 7.43 (2H, s). |
| 1-2029 | 1H-NMR (CDCl3) δ: 2.24-2.25 (3H, m), 2.51-2.53 (1H, m), 2.83-2.87 (1H, m), 3.51-3.62 (4H, m), 3.99-4.14 (2H, m), 6.57 (1H, t), 7.00 (1H, d), 7.87 (2H, s), 7.90 (1H, s). |
| 1-2030 | 1H-NMR (CDCl3) δ: 1.99 (3H, s), 2.22-2.23 (3H, m), 2.54-2.61 (1H, m), 2.86-2.91 (1H, m), 3.56-3.60 (2H, m), 4.05-4.13 (2H, m), 4.36 (2H, d), 5.50 (1H, t), 6.93 (1H, d), 7.87 (2H, s), 7.91 (1H, s). |
| 1-2031 | 1H-NMR (CDCl3) δ: 1.09 (3H, t), 2.10-2.18 (5H, m), 2.64 (3H, s), 2.44-2.48 (1H, m), 2.78-2.80 (1H, m), 3.46-3.53 (2H, m), 3.96-4.05 (2H, m), 4.29 (2H, d), 5.47 (1H, s), 6.48 (1H, t), 6.85 (1H, d), 7.80 (2H, s), 7.83 (1H, s). |
| 1-2032 | 1H-NMR (CDCl3) δ: 0.63-0.67 (2H, m), 0.90-0.92 (2H, m), 1.18-1.29 (1H, m), 2.15-2.16 (3H, m), 2.41-2.51 (1H, m), 2.76-2.84 (1H, m), 3.47-3.51 (2H, m), 3.94-4.08 (2H, m), 4.30 (2H, d), 5.67 (1H, t), 6.48 (1H, t), 6.87 (1H, d), 7.80 (2H, s), 7.83 (1H, s). |
| 1-2033 | 1H-NMR (CDCl3) δ: 2.21-2.24 (3H, m), 2.49-2.59 (1H, m), 2.84-2.93 (1H, m), 3.06 (2H, q), 3.51-3.67 (2H, m), 4.01-4.17 (2H, m), 4.39 (2H, d), 5.92 (1H, brs), 6.55 (1H, t), 6.91 (1H, d), 7.87 (2H, s), 7.91 (1H, s). |
| 1-2034 | 1H-NMR (CDCl3) δ: 2.11 (3H, s), 2.23-2.24 (3H, m), 2.52-2.57 (1H, m), 2.87-2.90 (1H, m), 3.22 (2H, s), 3.55-3.62 (2H, m), 4.05-4.15 (2H, m), 4.41 (2H, d), 6.57 (1H, t), 6.95 (1H, d), 7.88 (2H, s), 7.91 (1H, s). |
| 1-2037 | 1H-NMR (CDCl3) δ: 2.24-2.25 (3H, m), 2.44-2.46 (1H, m), 2.72-2.74 (1H, m), 3.50-3.56 (2H, m), 3.79 (2H, s), 3.93-4.01 (2H, m), 6.55 (1H, t), 6.96 (1H, d), 7.46 (2H, s). |
| 1-2038 | 1H-NMR (CDCl3) δ: 1.99 (3H, s), 2.21-2.22 (3H, m), 2.40-2.50 (1H, m), 2.70-2.79 (1H, m), 3.44-3.61 (2H, m), 3.95-4.02 (2H, m), 4.34 (2H, d), 5.62 (1H, t), 6.51 (1H, t), 6.91 (1H, d), 7.45 (2H, s). |

TABLE 8-continued

| Table 8 - Ex.-No. | 1H-NMR |
|---|---|
| 1-2039 | 1H-NMR (CDCl3) δ: 1.17 (3H, t), 2.20-2.26 (5H, m), 2.41-2.50 (1H, m), 2.70-2.79 (1H, m), 3.47-3.59 (2H, m), 3.94-4.03 (2H, m), 4.36 (2H, d), 5.52 (1H, br s), 6.51 (1H, t), 6.91 (1H, d), 7.45 (2H, s). |
| 1-2040 | 1H-NMR (CDCl3) δ: 0.69-0.76 (2H, m), 0.97-1.00 (2H, m), 1.30-1.35 (1H, m), 2.21-2.22 (3H, m), 2.40-2.50 (1H, m), 2.70-2.79 (1H, m), 3.47-3.58 (2H, m), 3.95-4.03 (2H, m), 4.36 (2H, d), 5.77 (1H, br s), 6.51 (1H, t), 6.93 (1H, d), 7.45 (2H, s). |
| 1-2041 | 1H-NMR (CDCl3) δ: 2.12-2.13 (3H, m), 2.37-2.39 (1H, m), 2.63-2.72 (1H, m), 2.98 (2H, q), 3.45-3.48 (2H, m), 3.87-3.96 (2H, m), 4.30 (2H, d), 5.82 (1H, t), 6.43 (1H, t), 6.82 (1H, d), 7.37 (2H, s). |
| 1-2042 | 1H-NMR (CDCl3) δ: 2.11 (3H, s), 2.22-2.23 (3H, m), 2.45-2.47 (1H, m), 2.71-2.79 (1H, m), 3.22 (2H, s), 3.49-3.59 (2H, m), 3.92-3.96 (1H, m), 4.03-4.07 (1H, m), 4.40 (2H, d), 6.53 (1H, t), 6.92-6.95 (2H, m), 7.45 (2H, s). |
| 1-2043 | 1H-NMR (CDCl3) δ: 2.22-2.23 (3H, m), 2.43-2.46 (1H, m), 2.64 (3H, s), 2.72-2.75 (1H, m), 3.34 (1H, d), 3.46-3.57 (1H, m), 3.62 (1H, d), 3.93-4.02 (2H, m), 4.38 (2H, d), 6.50 (1H, t), 6.95 (1H, d), 7.30 (1H, br s), 7.45 (2H, s). |
| 1-2046 | 1H-NMR (CDCl3) δ: 1.17 (3H, t), 2.18-2.23 (2H, m), 2.50-2.52 (1H, m), 2.78-2.87 (1H, m), 3.45-3.55 (2H, m), 3.76 (1H, m), 4.01 (1H, d), 4.34 (2H, d), 5.61 (1H, br s), 6.57 (2H, d), 7.20 (2H, d), 7.45 (2H, s). |
| 1-2047 | 1H-NMR (CDCl3) δ: 1.18 (3H, t), 2.17-2.26 (2H, m), 2.60-2.63 (1H, m), 2.93-3.01 (1H, m), 3.52-3.58 (2H, m), 3.83 (1H, d), 4.15 (1H, d), 4.35 (2H, d), 5.57 (1H, br s), 6.60 (2H, d), 7.21 (2H, d), 7.85 (2H, s), 7.91 (1H, s). |
| 1-2048 | 1H-NMR (CDCl3) δ: 1.10-1.15 (3H, m), 2.12-2.19 (2H, m), 2.52-2.54 (1H, m), 2.70-2.87 (3H, m), 3.46-3.52 (4H, m), 3.77 (1H, d), 4.02 (1H, d), 5.47 (1H, br s), 6.56 (2H, d), 7.09 (2H, d), 7.30-7.38 (3H, m). |
| 1-2049 | 1H-NMR (CDCl3) δ: 1.13 (3H, t), 2.14-2.17 (2H, m), 2.49-2.52 (1H, m), 2.70-2.86 (3H, m), 3.46-3.52 (4H, m), 3.76 (1H, d), 4.01 (1H, d), 5.47 (1H, br s), 6.56 (2H, d), 7.09 (2H, d), 7.44 (2H, s). |
| 1-2050 | 1H-NMR (CDCl3) δ: 1.13 (3H, t), 2.14-2.17 (2H, m), 2.57-2.62 (1H, m), 2.73-2.75 (2H, m), 2.94-2.96 (1H, m), 3.48-3.57 (4H, m), 3.83 (1H, d), 4.14 (1H, d), 5.40 (1H, br s), 6.60 (2H, d), 7.11 (2H, d), 7.85 (2H, s), 7.91 (1H, s). |
| 1-2051 | 1H-NMR (CDCl3) δ: 1.14 (3H, t), 2.18 (2H, q), 2.46-2.56 (1H, m), 2.79-2.88 (1H, m), 3.45-3.56 (2H, m), 3.77 (1H, d), 3.88 (3H, s), 4.03 (1H, d), 4.35 (2H, d), 5.82 (1H, b), 6.08-6.16 (2H, m), 7.14-7.39 (4H, m) |
| 1-2052 | 1H-NMR (CDCl3) δ: 2.07 (3H, s), 2.48-2.58 (1H, m), 2.79-2.88 (1H, m), 3.18 (2H, s), 3.45-3.60 (2H, m), 3.77 (1H, d), 3.89 (3H, s), 4.04 (1H, d), 6.09-6.16 (2H, m), 7.13-7.39 (5H, m) |
| 1-2053 | 1H-NMR (CDCl3) δ: 2.51-2.66 (4H, m), 2.88-2.95 (1H, m), 3.27 (1H, d), 3.29-3.59 (2H, m), 3.66 (1H, d), 3.77 (1H, d), 4.48-4.56 (2H, m), 6.49-6.80 (2H, m), 7.19 (1H, b), 7.29-7.65 (4H, m) |
| 1-2054 | 1H-NMR (CDCl3) δ: 2.50-2.59 (1H, m), 2.80-2.94 (1H, m), 3.05 (3H, s), 3.40-3.57 (2H, m), 3.77 (1H,d), 3.79 (2H, s), 4.09 (1H, d), 4.49 (2H, d), 6.50-6.80 (3H, m), 7.26-7.65 (4H, m) |
| 1-2058 | 1H-NMR (CDCl3) δ: 2.47 (2H, t), 2.54-2.65 (1H, m), 2.94-3.02 (1H, m), 3.36 (3H, s), 3.65-3.46 (4H, m), 3.81 (1H, d), 4.15 (1H, d), 4.44 (2H, d), 6.48 (1H, dd), 6.62 (2H, d), 7.28 (2H, d), 7.84 (2H, s), 7.92 (1H, s). |
| 1-2067 | 1H-NMR (CDCl3) δ: 2.47 (2H, t), 2.52-2.66 (1H, m), 2.96-3.05 (1H, m), 3.36 (3H, s), 3.54-3.70 (4H, m), 3.98 (1H, d), 4.37 (2H, d), 4.53 (1H, d), 6.25-7.85 (6H, m) |
| 1-2068 | 1H-NMR (CDCl3) δ: 1.15 (3H, t), 2.14 (2H, q), 2.56-2.61 (1H, m), 2.90-2.98 (1H, m), 3.56-3.72 (2H, m), 4.00 (1H, d), 4.44-4.46 (3H, m), 5.78 (1H, br s), 6.52 (1H, d), 7.56-7.62 (3H, m), 7.74 (1H, d). |
| 1-2069 | 1H-NMR (CDCl3) δ: 0.74-0.78 (2H, m), 0.82-1.00 (2H, m), 1.28-1.32 (1H, m), 2.53-2.63 (1H, m), 2.91-2.96 (1H, m), 3.61-3.70 (2H, m), 4.00 (1H, d), 4.44-4.47 (3H, m), 5.95 (1H, br s), 6.52 (1H, d), 7.52-7.62 (3H, m), 7.73 (1H, d). |
| 1-2070 | 1H-NMR (CDCl3) δ: 0.15-0.18 (2H, m), 0.56-0.60 (2H, m), 0.87-0.93 (1H, m), 2.16 (2H, d), 2.56-2.61 (1H, m), 2.90-2.98 (1H, m), 3.62-3.70 (2H, m), 4.01 (1H, d), 4.44-4.48 (3H, m), 6.31 (1H, br s), 6.53 (1H, d), 7.48-7.64 (3H, m), 7.74 (1H, d). |
| 1-2071 | 1H-NMR (CDCl3) δ: 2.05 (3H, s), 2.47-2.64 (1H, m), 2.91-2.97 (1H, m), 3.22 (2H, s), 3.63-3.71 (2H, m), 4.01 (1H, d), 4.45-4.50 (3H, m), 6.53 (1H, d), 7.26 (1H, br s), 7.49-7.73 (4H, m). |
| 1-2074 | 1H-NMR (CDCl3) δ: 1.15 (3H, t), 2.20 (2H, q), 2.48-2.59 (1H, m), 2.83-2.91 (1H, m), 2.83-2.91 (1H, m), 2.49-2.59 (1H, m), 3.58-3.70 (2H, m), 3.93 (1H, d), 4.38-4.45 (3H, m), 5.75 (1H, br s), 6.51 (1H, d), 7.48 (2H, s), 7.69-7.74 (2H, m). |
| 1-2075 | 1H-NMR (CDCl3) δ: 0.71-0.82 (2H, m), 0.92-0.97 (2H, m), 1.24-1.36 (1H, m), 2.49-2.59 (1H, m), 2.83-2.91 (1H, m), 3.59-3.65 (2H, m), 3.93 (1H, d), 4.38-4.47 (3H, m), 5.94 (1H, br s), 6.51 (1H, d), 7.45 (2H, s), 7.69-7.73 (2H, m). |
| 1-2076 | 1H-NMR (CDCl3) δ: 0.12-0.20 (2H, m), 0.51-0.67 (2H, m), 0.90-0.99 (1H, m), 2.15 (2H, d), 2.51-2.56 (1H, m), 2.83-2.91 (1H, m), 3.59-3.67 (2H, m), 3.94 (1H, d), 4.38-4.48 (3H, m), 6.31 (1H, br d), 7.45-7.52 (2H, m), 7.68-7.74 (2H, m). |
| 1-2077 | 1H-NMR (CDCl3) δ: 2.05 (3H, s), 2.52-2.57 (1H, m), 2.87-2.93 (1H, m), 3.22 (2H, s), 3.59-3.71 (2H, m), 3.94 (1H, d), 4.39 (1H, d), 4.50-4.51 (2H, m), 6.52 (1H, d), 7.24 (1H, d), 7.48-7.49 (2H, m), 7.69-7.71 (2H, m). |
| 1-2082 | 1H-NMR (CDCl3) δ: 0.74-0.79 (2H, m), 0.96-1.06 (2H, m), 1.23-1.37 (1H, m), 2.51-2.57 (1H, m), 2.85-2.90 (1H, m), 3.56-3.67 (2H, m), 3.94 (1H, d), 4.35-4.39 (3H, m), 5.88 (1H, br s), 6.38 (1H, d), 7.27-7.50 (4H, m), 8.10 (1H, d). |

TABLE 8-continued

| Table 8 - Ex.-No. | 1H-NMR |
|---|---|
| 1-2089 | 1H-NMR (CDCl3) δ: 1.53 (2H, b), 2.42-2.53 (1H, m), 2.75-2.84 (1H, m), 3.75-3.95 (4H, m), 3.79 (1H, m), 4.42 (1H, d), 7.22-7.88 (5H, m) |
| 1-2091 | 1H-NMR (CDCl3) δ: 1.17 (3H, t), 2.23 (2H, q), 2.42-2.53 (1H, m), 2.75-2.84 (1H, m), 3.75-3.93 (2H, m), 4.06 (1H, d), 3.30 (2H, d), 4.42 (1H, d), 5.67 (1H, b), 7.19-7.86 (5H, m) |
| 1-2094 | 1H-NMR (CDCl3) δ: 2.11 (3H, s), 2.43-2.53 (1H, m), 2.76-2.85 (1H, m), 3.24 (2H, s), 3.75-3.95 (2H, m), 4.07 (1H, d), 4.37 (2H, d), 4.43 (1H, d), 7.15-7.89 (6H, m) |
| 1-2107 | 1H-NMR (CDCl3) δ: 1.69 (2H, b), 2.50-2.61 (1H, m), 2.88-2.96 (1H, m), 3.75-3.98 (4H, m), 4.13 (1H, d), 7.24-7.30 (1H, m), 7.88-7.91 (4H, m) |
| 1-2109 | 1H-NMR (CDCl3) δ: 1.17 (3H, t), 2.24 (2H, q), 2.50-2.60 (1H, m), 2.89-2.97 (1H, m), 3.78-3.98 (2H, m), 4.11 (1H, d), 4.33 (2H, d), 4.55 (1H, d), 5.71 (1H, b), 7.21-7.91 (5H, m) |
| 1-2116 | 1H-NMR (CDCl3) δ: 1.53 (2H, b), 2.42-2.53 (1H, m), 2.75-2.84 (1H, m), 3.75-3.90 (4H, m), 4.05 (1H, d), 4.42 (1H, d), 7.29-7.39 (4H, m) |
| 1-2118 | 1H-NMR (CDCl3) δ: 1.16 (3H, t), 2.23 (2H, q), 2.39-2.52 (1H, m), 2.74-2.83 (1H, m), 3.75-3.92 (2H, m), 4.03 (1H, d), 4.34 (2H, d), 4.31 (1H, d), 5.96 (1H, b), 7.30-7.39 (4H, m) |
| 1-2119 | 1H-NMR (CDCl3) δ: 0.72-0.79 (2H, m), 0.95-0.99 (2H, m), 1.31-1.38 (1H, m), 2.45-2.52 (1H, m), 2.74-2.83 (1H, m), 3.75-3.95 (2H, m), 4.04 (1H, d), 4.36 (2H, d), 4.41 (1H, d), 6.13 (1H, b), 7.30-7.39 (4H, m) |
| 1-2120 | 1H-NMR (CDCl3) δ: 2.42-2.53 (1H, m), 2.75-2.84 (1H, m), 3.05 (1H, d), 3.12 (1H, d), 3.75-3.93 (2H, m), 4.04 (1H, d), 4.37-4.45 (3H, m), 6.28 (1H, b), 7.28-7.40 (4H, m) |
| 1-2121 | 1H-NMR (CDCl3) δ: 2.11 (3H, s), 2.42-2.50 (1H, m), 2.52-2.84 (1H, m), 3.21 (2H, s), 3.75-3.95 (2H, m), 4.04 (1H, d), 4.37-4.45 (3H, m), 7.30-7.39 (5H, m) |
| 1-2122 | 1H-NMR (CDCl3) δ: 2.42-2.50 (1H, m), 2.68 (3H, s), 2.75-2.84 (1H, m), 3.28 (1H, d), 3.70 (1H, d), 3.70-3.94 (2H, m), 4.04 (1H, d), 4.41-4.44 (3H, m), 7.26-7.40 (5H, m) |
| 1-2123 | 1H-NMR (CDCl3) δ: 2.42-2.52 (1H, m), 2.75-2.84 (1H, m), 3.07 (3H, s), 3.78-3.95 (4H, m), 4.04 (1H, d), 4.40-4.45 (3H, m), 6.91 (1H, b), 7.29-7.40 (4H, m) |
| 1-2125 | 1H-NMR (CDCl3) δ: 1.51 (2H, b), 2.40-2.50 (1H, m), 2.75-2.85 (1H, m), 3.75-3.93 (4H, m), 4.04 (1H, d), 4.39 (1H, d), 7.30-7.45 (3H, m) |
| 1-2127 | 1H-NMR (CDCl3) δ: 1.16 (3H, t), 2.23 (2H, q), 2.41-2.51 (1H, m), 2.75-2.84 (1H, m), 3.75-3.95 (2H, m), 4.03 (1H, d), 4.33-4.41 (3H, m), 5.93 (1H, b), 7.32-7.44 (3H, m) |
| 1-2128 | 1H-NMR (CDCl3) δ: 0.72-0.79 (2H, m), 0.95-0.99 (2H, m), 1.30-1.40 (1H, m), 2.40-2.51 (1H, m), 2.74-2.83 (1H, m), 3.75-3.90 (2H, m), 4.04 (1H, d), 4.35-4.41 (3H, m), 6.10 (1H, b), 7.31-7.44 (3H, m) |
| 1-2129 | 1H-NMR (CDCl3) δ: 2.41-2.52 (1H, m), 2.75-2.84 (1H, m), 3.05 (1H, d), 3.12 (1H, d), 3.75-3.94 (2H, m), 4.04 (1H, d), 4.37-4.43 (3H, m), 6.25 (1H, b), 7.29-7.44 (3H, m) |
| 1-2130 | 1H-NMR (CDCl3) δ: 2.11 (3H, s), 2.41-2.49 (1H, m), 2.75-2.83 (1H, m), 3.21 (2H, s), 3.75-3.90 (2H, m), 4.04 (1H, d), 4.37-4.42 (2H, m), 7.31-7.50 (4H, m) |
| 1-2131 | 1H-NMR (CDCl3) δ: 2.41-2.52 (1H, m), 2.68 (3H, s), 2.74-2.83 (1H, m), 3.07 (1H, d), 3.27 (1H, d), 3.67-3.93 (3H, m), 4.04 (1H, d), 4.37-4.43 (3H, m), 7.30-7.44 (4H, m) |
| 1-2132 | 1H-NMR (CDCl3) δ: 2.41-2.52 (1H, m), 2.74-2.84 (1H, m), 3.07 (3H, s), 3.75-3.95 (4H, m), 4.03 (1H, d), 4.38-4.42 (3H, m), 6.92 (1H, b), 7.31-7.44 (3H, m) |
| 1-2136 | 1H-NMR (CDCl3) δ: 1.16 (3H, t), 2.23 (2H, q), 2.52-2.60 (1H, m), 2.88-2.97 (1H, m), 3.75-3.96 (2H, m), 4.11 (1H, d), 4.35 (2H, d), 4.54 (1H, d), 5.91 (1H, b), 7.34-7.92 (4H, m) |
| 1-2137 | 1H-NMR (CDCl3) δ: 0.73-0.79 (2H, m), 0.95-1.01 (2H, m), 1.32-1.40 (1H, m), 2.49-2.60 (1H, m), 2.88-2.97 (1H, m), 3.76-4.00 (2H, m), 4.11 (1H, d), 4.37 (2H, d), 4.54 (1H, d), 6.12 (1H, b), 7.32-7.92 (4H, m) |
| 1-2138 | 1H-NMR (CDCl3) δ: 2.49-2.60 (1H, m), 2.88-2.98 (1H, m), 3.06 (1H, d), 3.12 (1H, d), 3.76-4.00 (2H, m), 4.12 (1H, d), 4.39 (2H, d), 4.55 (1H, d), 6.22 (1H, b), 7.31-7.92 (4H, m) |
| 1-2139 | 1H-NMR (CDCl3) δ: 2.11 (3H, s), 2.50-2.60 (1H, m), 2.89-2.97 (1H, m), 3.21 (2H, s), 3.76-4.00 (2H, m), 4.12 (1H, d), 4.39 (2H, d), 4.55 (1H, d), 7.32-7.92 (5H, m) |
| 1-2140 | 1H-NMR (CDCl3) δ: 2.11 (3H, s), 2.68 (3H, s), 2.50-2.60 (1H, m), 2.88-2.97 (1H, m), 3.21 (2H, s), 3.27 (1H, d), 3.70 (1H, d), 3.76-3.95 (2H, m), 4.11 (1H, d), 4.43 (2H, d), 4.55 (1H, d), 7.33-7.92 (4H, m) |
| 1-2141 | 1H-NMR (CDCl3) δ: 2.50-2.60 (1H, m), 2.89-2.98 (1H, m), 3.08 (3H, s), 3.80-3.97 (4H, m), 4.11 (1H, d), 4.42 (2H, d), 4.55 (1H, d), 6.96 (1H, b), 7.57-7.91 (4H, m) |
| 1-2145 | 1H-NMR (CDCl3) δ: 1.82 (1H, t), 2.53-2.65 (1H, m), 2.90-3.05 (1H, m), 2.74-2.83 (1H, m), 3.55-3.70 (2H, m), 4.00 (1H, d), 4.55 (1H, d), 4.67 (2H, d), 6.34 (1H, d), 7.21-7.39 (4H, m) |
| 1-2151 | 1H-NMR (CDCl3) δ: 1.45 (9H, s), 2.42-2.52 (1H, m), 2.74-2.83 (1H, m), 3.75-3.95 (2H, m), 4.04 (1H, m), 4.22 (2H, d), 4.42 (1H, d), 5.01 (1H, b), 7.28-7.44 (4H, m) |
| 1-2152 | 1H-NMR (CDCl3) δ: 1.45 (9H, s), 2.40-2.52 (1H, m), 2.74-2.83 (1H, m), 3.70-3.95 (2H, m), 4.04 (1H, m), 4.22 (2H, d), 4.39 (1H, d), 4.99 (1H, b), 7.18-7.86 (5H, m) |
| 1-2153 | 1H-NMR (CDCl3) δ: 1.45 (9H, s), 2.49-2.60 (1H, m), 2.88-3.00 (1H, m), 3.77-4.00 (2H, m), 4.13 (1H, d), 4.23 (2H, d), 4.54 (1H, d), 7.30-7.92 (4H, m) |
| 1-2154 | 1H-NMR (CDCl3) δ: 1.46 (9H, s), 2.43-2.53 (1H, m), 2.75-2.83 (1H, m), 3.75-3.95 (2H, m), 4.06 (1H, m), 4.17 (2H, d), 4.42 (1H, d), 4.75 (1H, b), 7.18-7.86 (5H, m) |
| 1-2156 | 1H-NMR (CDCl3) δ: 1.46 (9H, s), 2.50-2.60 (1H, m), 2.85-2.97 (1H, m), 3.77-4.00 (2H, m), 4.13 (1H, d), 4.18 (1H, d), 4.54 (1H, d), 7.21-7.90 (6H, m) |
| 1-2168 | 1H-NMR (CDCl3) δ: 2.38-2.51 (4H, m), 2.74-2.79 (1H, m), 3.51-3.66 (2H, m), 3.90-3.94 (3H, m), 4.08-4.13 (1H, m), 6.57 (1H, t), 7.04 (1H, dd), 7.40 (2H, s). |

TABLE 8-continued

| Table 8 - Ex.-No. | 1H-NMR |
|---|---|
| 1-2170 | 1H-NMR (CDCl3) δ: 1.18 (3H, t), 2.22 (2H, q), 2.48-2.58 (1H, m), 2.83-2.91 (1H, m), 3.57-3.61 (2H, m), 3.95 (1H, d), 4.34-4.43 (3H, m), 5.62 (1H, br s), 6.38 (1H, d), 7.44-7.49 (3H, m), 8.09 (1H, d). |
| 1-2171 | 1H-NMR (CDCl3) δ: 1.15 (3H, t), 2.23 (2H, q), 2.62-2.67 (1H, m), 3.02-3.06 (1H, m), 3.59-3.68 (2H, m), 4.01 (1H, d), 4.35 (2H, d), 4.56 (1H, d), 5.67 (1H, br s), 6.41 (1H, d), 7.50 (1H, dd), 7.87-7.91 (3H, m), 8.11 (1H, d). |
| 2-8 | 1H-NMR (CDCl3) δ: 2.46-2.52 (1H, m), 2.80-2.88 (1H, m), 3.78-3.79 (2H, m), 3.93-4.08 (3H, m), 4.46-4.50 (1H, m), 6.02 (1H, br s), 7.22 (2H, s), 7.34 (1H, s), 8.58 (1H, s). |
| 2-34 | 1H-NMR (CDCl3) δ: 2.45-2.55 (1H, m), 2.84-2.86 (1H, m), 3.75-3.80 (2H, m), 3.91-4.05 (3H, m), 4.46-4.55 (1H, m), 5.98 (1H, br s), 7.89 (3H, m), 8.56 (1H, s). |
| 2-35 | 1H-NMR (CDCl3) δ: 2.54-2.58 (1H, m), 2.89-2.92 (1H, m), 3.84-3.87 (1H, m), 4.02-4.06 (1H, m), 4.53-4.57 (1H, m), 4.74 (2H, d), 7.25-7.36 (5H, m), 7.69-7.72 (1H, m), 8.52-8.53 (1H, m), 8.70 (1H, s). |
| 2-55 | 1H-NMR (CDCl3) δ: 2.52-2.57 (1H, m), 2.85-2.93 (1H, m), 3.82-3.85 (2H, m), 4.03-4.08 (1H, m), 4.53-4.57 (1H, m), 4.74 (2H, d), 7.21-7.73 (7H, m), 8.56 (1H, d), 8.85 (2H, s). |
| 2-69 | 1H-NMR (CDCl3) δ: 2.47-2.57 (1H, m), 2.85-2.90 (1H, m), 3.80-3.83 (2H, m), 4.04-4.11 (3H, m), 4.50-4.54 (1H, m), 5.98 (1H, br s), 7.26-7.39 (3H, m), 8.42 (1H, s). |
| 2-613 | 1H-NMR (CDCl3) δ: 1.49 (9H, s), 2.59-2.66 (1H, m), 3.00-3.08 (1H, m), 3.87-3.91 (2H, m), 4.08-4.10 (3H, m), 4.66-4.70 (1H, m), 6.35 (1H, br s), 7.85 (2H, s), 7.93 (1H, s). |
| 3-15 | 1H-NMR (CDCl3) δ: 0.16-0.20 (2H, m), 0.58-0.64 (2H, m), 0.88-0.93 (1H, m), 2.16 (2H, d), 2.47-2.58 (1H, m), 2.83-2.91 (1H, m), 3.81-3.86 (2H, m), 4.00 (1H, d), 4.46-4.50 (1H, m), 6.32 (1H, br s), 7.27-7.39 (3H, m), 8.64 (1H, s). |
| 3-45 | 1H-NMR (CDCl3) δ: 2.08 (3H, s), 2.47-2.58 (1H, m), 2.85-2.89 (1H, m), 3.19 (2H, s), 3.80-3.83 (2H, m), 4.00 (1H, d), 4.47-4.50 (3H, m), 7.26 (2H, d), 7.41 (1H, t), 8.62 (1H, s). |
| 3-140 | 1H-NMR (CDCl3) δ: 1.65 (2H, br s), 2.49-2.54 (1H, m), 2.82-2.91 (1H, m), 3.68-4.16 (6H, m), 4.46-4.50 (1H, m), 7.44 (2H, s), 8.58 (1H, s). |
| 3-141 | 1H-NMR (CDCl3) δ: 1.98 (1H, s), 2.48-2.54 (1H, m), 2.86-2.93 (1H, m), 3.80-3.86 (2H, m), 3.98-4.02 (1H, m), 4.41-4.48 (3H, m), 5.82 (1H, br s), 7.43 (2H, s), 8.63 (1H, s). |
| 3-142 | 1H-NMR (CDCl3) δ: 1.16 (3H, t), 2.21 (2H, q), 2.46-2.56 (1H, m), 2.82-2.90 (1H, m), 3.80-3.83 (2H, m), 3.98-4.02 (1H, m), 4.42-4.47 (3H, m), 5.75-5.78 (1H, m), 7.43 (2H, s), 8.63 (1H, s). |
| 3-143 | 1H-NMR (CDCl3) δ: 0.72-1.43 (5H, m), 2.46-2.56 (1H, m), 2.95-3.08 (1H, m), 3.81-3.86 (2H, m), 3.98-4.02 (1H, m), 4.45-4.48 (1H, m), 6.00 (1H, br s), 7.46 (2H, s), 8.62 (1H, s). |
| 3-144 | 1H-NMR (CDCl3) δ: 2.46-2.57 (1H, m), 2.84-2.89 (1H, m), 3.07 (2H, q), 3.79-4.02 (3H, m), 4.46-4.49 (3H, m), 6.07 (1H, br s), 7.43 (2H, s), 8.61 (1H, s). |
| 3-145 | 1H-NMR (CDCl3) δ: 1.15 (3H, t), 2.45-2.55 (1H, m), 2.81-2.90 (1H, m), 3.18 (2H, q), 3.75-3.82 (2H, m), 3.98-4.64 (6H, m), 7.43 (2H, s), 8.67 (1H, s). |
| 3-146 | 1H-NMR (CDCl3) δ: 2.55-2.65 (1H, m), 2.97-3.05 (1H, m), 3.73-3.85 (3H, m), 4.07-4.16 (2H, m), 4.61-4.65 (1H, m), 7.86-7.92 (3H, m), 8.61 (1H, s). |
| 3-148 | 1H-NMR (CDCl3) δ: 0.72-1.37 (5H, m), 2.56-2.62 (1H, m), 2.96-3.04 (1H, m), 3.84-3.90 (2H, m), 4.06-4.16 (1H, m), 4.44-4.46 (2H, m), 4.60-4.64 (1H, m), 5.63 (1H, t), 7.85 (2H, s), 7.92 (1H, s), 8.64 (1H, s). |
| 3-149 | 1H-NMR (CDCl3) δ: 1.13 (3H, t), 2.20 (2H, q), 2.59 (1H, m), 2.96-3.04 (1H, m), 3.84-3.90 (2H, m), 4.07-4.14 (1H, m), 4.41-4.43 (2H, m), 4.60-4.64 (1H, m), 5.78 (1H, br s), 7.81 (2H, s), 7.92 (1H, s), 8.65 (1H, s). |
| 3-150 | 1H-NMR (CDCl3) δ: 2.55-2.65 (1H, m), 2.96-3.11 (1H, m), 3.04-3.11 (3H, m), 3.85-3.91 (2H, m), 4.08-4.12 (1H, m), 4.46-4.48 (2H, m), 4.61-4.64 (1H, m), 6.10 (1H, br s), 7.84 (2H, s), 7.92 (1H, s), 8.63 (1H, s). |
| 3-151 | 1H-NMR (CDCl3) δ: 1.14 (3H, t), 2.55-2.62 (1H, m), 2.95-3.04 (1H, m), 3.11-3.33 (2H, m), 3.73-4.40 (6H, m), 4.61-4.63 (2H, m), 7.85 (2H, s), 7.92 (1H, s), 8.69 (1H, s). |
| 3-157 | 1H-NMR (CDCl3) δ: 1.98 (3H, s), 2.49-2.54 (1H, m), 2.83-2.91 (1H, m), 2.95-3.04 (1H, m), 3.79-3.85 (2H, m), 3.98 (1H, d), 4.41-4.50 (3H, m), 5.86 (1H, br s), 7.54 (2H, d), 7.67 (1H, t), 8.63 (1H, s). |
| 3-158 | 1H-NMR (CDCl3) δ: 1.15 (3H, t), 2.20 (2H, q), 2.44-2.57 (1H, m), 2.84-2.89 (1H, m), 3.79-3.85 (2H, m), 3.98 (1H, d), 4.42-4.50 (3H, m), 5.81 (1H, br s), 7.48 (2H, s), 7.69 (1H, t), 8.63 (1H, s). |
| 3-159 | 1H-NMR (CDCl3) δ: 0.72-0.80 (2H, m), 0.83-0.99 (2H, m), 1.23-1.38 (1H, m), 2.49-2.54 (1H, m), 2.84-2.89 (1H, m), 3.79-3.85 (2H, m), 3.98 (1H, d), 4.44-4.50 (3H, m), 6.02 (1H, br s), 7.45 (2H, s), 7.66 (1H, t), 8.59 (1H, s). |
| 3-160 | 1H-NMR (CDCl3) δ: 2.47-2.57 (1H, m), 2.83-2.91 (1H, m), 3.10 (2H, q), 3.81-3.85 (2H, m), 3.98 (1H, d), 4.47-4.51 (3H, m), 6.15 (1H, br s), 7.48 (2H, s), 7.70 (1H, t), 8.60 (1H, s). |
| 3-310 | 1H-NMR (CDCl3) δ: 2.43-2.58 (1H, m), 2.66 (3H, s), 2.83-2.91 (1H, m), 3.28 (1H, d), 3.67 (1H, dz), 3.80-3.86 (2H, m), 4.00 (1H, d), 4.48-4.50 (3H, m), 7.28 (2H, d), 7.39 (2H, s), 8.63 (1H, s). |

TABLE 8-continued

| Table 8 - Ex.-No. | 1H-NMR |
|---|---|
| 3-311 | 1H-NMR (CDCl3) δ: 2.50-2.55 (1H, m), 2.85-2.90 (1H, m), 3.05 (3H, s), 3.79-3.82 (2H, m), 3.89 (2H, s), 3.99 (1H, d), 4.48-4.51 (3H, m), 7.03 (1H, br s), 7.28 (2H, d), 7.39 (1H, t), 8.60 (1H, s). |
| 3-322 | 1H-NMR (CDCl3) δ: 2.12 (3H, s), 2.47-2.57 (1H, m), 2.85-2.90 (1H, m), 3.22 (2H, s), 3.79-3.81 (2H, m), 3.98 (1H, d), 4.47-4.50 (3H, m), 7.48 (2H, s), 7.69 (1H, t), 8.62 (1H, s). |
| 3-335 | 1H-NMR (CDCl3) δ: 0.15-0.28 (2H, m), 0.61-0.65 (2H, m), 0.88-1.01 (1H, m), 2.21 (2H, s), 2.52-2.57 (1H, m), 2.85-2.94 (1H, m), 3.84-3.90 (2H, m), 4.01-4.06 (1H, m), 4.48-4.51 (3H, m), 6.36 (1H, t), 7.46 (2H, s), 8.67 (1H, s). |
| 3-336 | 1H-NMR (CDCl3) δ: 1.00 (9H, s), 2.04 (2H, s), 2.48-2.54 (1H, m), 2.82-2.90 (1H, m), 3.80-3.86 (2H, m), 3.98-4.03 (1H, m), 4.41-4.48 (3H, m), 5.68 (1H, br s), 7.42 (2H, s), 8.65 (1H, s). |
| 3-339 | 1H-NMR (CDCl3) δ: 2.08 (3H, s), 2.49-2.54 (1H, m), 2.82-2.91 (1H, m), 3.19 (2H, s), 3.81-3.83 (2H, m), 3.98-4.02 (1H, m), 4.46-4.49 (3H, m), 7.43 (2H, s), 8.62 (1H, s). |
| 3-389 | 1H-NMR (CDCl3) δ: 2.55-2.65 (1H, m), 2.97-3.05 (1H, m), 3.84-3.88 (4H, m), 4.05-4.16 (1H, m), 4.50-4.62 (3H, m), 6.81 (1H, br s), 7.84 (2H, s), 7.92 (1H, s), 8.63 (1H, s). |
| 3-340 | 1H-NMR (CDCl3) δ: 2.49-2.54 (1H, m), 2.66 (3H, s), 2.82-2.91 (1H, m), 3.26 (1H, d), 3.67 (1H, d), 3.81-3.87 (2H, m), 3.98-4.02 (1H, m), 4.47-4.50 (3H, m), 7.30-7.34 (1H, m), 7.45 (2H, s), 8.64 (1H, s). |
| 3-341 | 1H-NMR (CDCl3) δ: 2.47-2.57 (1H, m), 2.83-2.91 (1H, m), 3.06 (3H, s), 3.83-3.98 (5H, m), 4.47-4.49 (3H, m), 6.87-6.89 (1H, m), 7.40 (2H, s), 8.61 (1H, s). |
| 3-342 | 1H-NMR (CDCl3) δ: 1.30-1.35 (3H, m), 1.92 (3H, s), 2.04-2.10 (1H, m), 2.48-2.53 (1H, m), 2.82-2.90 (1H, m), 3.80-3.85 (2H, m), 3.97-4.01 (1H, m), 4.34-4.56 (3H, m), 6.29-6.31 (1H, m), 7.14-7.15 (1H, m), 7.42 (2H, s), 8.56 (1H, s). |
| 3-387 | 1H-NMR (CDCl3) δ: 2.08 (3H, s), 2.56-2.64 (1H, m), 2.98-3.03 (1H, m), 3.20 (2H, s), 3.85-3.87 (2H, m), 4.06-4.16 (1H, m), 4.54 (3H, s), 7.85 (2H, s), 7.92 (1H, s), 8.64 (1H, s). |
| 3-388 | 1H-NMR (CDCl3) δ: 2.55-2.66 (4H, m), 2.97-3.05 (1H, m), 3.24 (1H, d), 3.67 (1H, d), 3.85-3.87 (2H, m), 4.05-4.16 (1H, m), 4.52-4.63 (3H, m), 7.31 (1H, m), 7.84 (2H, s), 7.92 (1H, s), 8.65 (1H, s). |
| 3-433 | 1H-NMR (CDCl3) δ: 0.20-0.02 (2H, m), 0.60-0.68 (2H, m), 0.91-0.97 (1H, m), 2.19 (2H, d), 2.60-2.66 (1H, m), 3.00-3.08 (1H, m), 3.88-3.94 (2H, m), 4.09-4.19 (1H, m), 4.52-4.60 (3H, m), 6.36-6.38 (1H, m), 7.88 (2H, s), 7.95 (1H, s), 8.69 (1H, s). |
| 3-434 | 1H-NMR (CDCl3) δ: 1.00 (9H, s), 2.05 (2H, s), 2.57-2.62 (1H, m), 2.96-3.05 (1H, m), 3.85-3.91 (2H, m), 4.06-4.16 (1H, m), 4.41-4.43 (2H, m), 4.59-4.63 (1H, m), 5.72 (1H, br s), 7.85 (2H, s), 7.92 (1H, s), 8.67 (1H, s). |
| 3-435 | 1H-NMR (CDCl3) δ: 2.48-2.58 (1H, m), 2.72-3.01 (4H, m), 3.82-3.85 (2H, m), 3.99-4.03 (1H, m), 4.33-4.35 (2H, m), 4.47-4.58 (2H, m), 7.40 (2H, s), 8.61 (1H, s). |
| 3-436 | 1H-NMR (CDCl3) δ: 2.56-2.66 (1H, m), 2.91-3.18 (4H, m), 3.86-3.92 (2H, m), 4.09-4.11 (1H, m), 4.33-4.35 (2H, m), 4.60-4.72 (2H, m), 7.85 (2H, s), 7.93 (1H, s), 8.63 (1H, s). |
| 3-437 | 1H-NMR (CDCl3) δ: 1.57 (3H, s), 2.57-2.65 (1H, m), 2.98-3.06 (1H, m), 3.85-3.87 (2H, m), 4.10 (1H, d), 4.54-4.68 (3H, m), 6.69 (1H, br s), 7.84 (2H, d), 7.93 (1H, t), 8.60 (1H, s). |
| 3-438 | 1H-NMR (CDCl3) δ: 2.44-2.64 (3H, m), 2.96-3.22 (3H, m), 3.84-3.87 (2H, m), 4.05-4.09 (1H, m), 4.40-4.42 (1H, m), 4.60-4.63 (1H, m), 5.90 (1H, br s), 7.17-7.34 (5H, m), 7.84 (2H, s), 7.92 (1H, s), 8.65 (1H, s). |
| 3-439 | 1H-NMR (CDCl3) δ: 1.04-1.17 (3H, m), 2.15-2.24 (2H, m), 2.56-2.61 (1H, m), 2.91-2.99 (1H, m), 3.82-3.88 (2H, m), 4.05-4.16 (1H, m), 4.41-4.43 (2H, m), 4.55-4.59 (1H, m), 5.78 (1H, br s), 7.54-7.63 (4H, m), 8.59 (1H, s). |
| 3-440 | 1H-NMR (CDCl3) δ: 0.10-0.23 (2H, m), 0.53-0.64 (2H, m), 0.85-0.98 (1H, m), 2.15 (2H, d), 2.56-2.61 (1H, m), 2.91-2.99 (1H, m), 3.82-3.88 (2H, m), 4.08 (1H, d), 4.44-4.46 (2H, m), 4.60 (1H, d), 6.32 (1H, br s), 7.54-7.63 (4H, m), 8.63 (1H, s). |
| 3-441 | 1H-NMR (CDCl3) δ: 2.08 (3H, s), 2.55-2.62 (1H, m), 2.91-3.00 (1H, m), 3.20 (2H, s), 3.82-3.85 (2H, m), 4.10 (1H, d), 4.47-4.58 (3H, m), 7.25 (1H, br s), 7.52-7.64 (4H, m), 8.62 (1H, s). |
| 3-442 | 1H-NMR (CDCl3) δ: 2.54-2.77 (4H, m), 2.92-2.97 (1H, m), 3.29 (1H, d), 3.67 (1H, d), 3.82-3.88 (2H, m), 4.09 (1H, d), 4.50-4.58 (3H, m), 7.47 (1H, br s), 7.52-7.76 (4H, m), 8.64 (1H, s). |
| 3-443 | 1H-NMR (CDCl3) δ: 2.56-2.62 (1H, m), 2.92-3.00 (1H, m), 3.07 (3H, s), 3.82-3.87 (4H, m), 4.09 (1H, d), 4.49-4.58 (3H, m), 6.92 (1H, br s), 7.55-7.64 (4H, m), 8.62 (1H, s). |
| 3-444 | 1H-NMR (CDCl3) δ: 0.15-0.23 (2H, m), 0.58-0.61 (2H, m), 0.85-0.98 (1H, m), 2.18 (2H, d), 2.49-2.54 (1H, m), 2.83-2.91 (1H, m), 3.80-3.82 (2H, m), 3.98 (1H, d), 4.48-4.61 (3H, m), 6.33 (1H, m), 7.48 (2H, s), 7.69 (1H, t), 8.64 (1H, s). |
| 4-1 | 1H-NMR (CDCl3) δ: 2.53-2.70 (1H, m), 2.88-3.01 (m, 1H), 3.51-3.75 (m, 2H), 3.97 (d, 1H), 4.43 (d, 1H), 5.93 (bs, 1H), 7.25 (d, 2H), 7.41 (t, 1H) |
| 4-2 | 1H-NMR (CDCl3) δ: 2.52-2.70 (m, 1H), 2.86-3.07 (m, 4H), 3.95 (d, 1H), 4.41 (d, 1H), 6.12 (bs, 1H), 7.18-7.25 (m, 2H), 7.39-7.42 (m, 1H) |
| 4-3 | 1H-NMR (CDCl3) δ: 1.22 (t, 3H), 2.52-2.68 (m, 1H), 2.83-3.00 (m, 1H), 3.35-3.50 (m, 2H), 3.51-3.72 (m, 2H), 3.95 (d, 1H), 4.40 (d, 1H), 6.09 (bs, 1H), 7.21-7.28 (m, 2H), 7.37-7.43 (m, 1H) |

TABLE 8-continued

| Table 8 - Ex.-No. | 1H-NMR |
|---|---|
| 4-5 | 1H-NMR (CDCl3) δ: 0.55-0.64 (m, 2H), 0.80-0.91 (m, 2H), 2.53-2.68 (m, 1H), 2.77-3.00 (m, 2H), 3.51-3.72 (m, 2H), 3.95 (d, 1H), 4.40 (d, 1H), 6.22 (bs, 1H), 7.20-7.29 (m, 2H), 7.38-7.43 (m, 1H) |
| 4-8 | 1H-NMR (CDCl3) δ: 2.60-2.65 (1H, m), 2.93-2.98 (1H, m), 3.59-3.72 (2H, m), 3.86-4.23 (3H, m), 4.41-4.45 (1H, m), 6.36 (1H, br s), 7.25-7.53 (3H, m). |
| 4-9 | 1H-NMR (CDCl3) δ: 2.59-2.64 (1H, m), 2.92-2.96 (1H, m), 3.59-3.68 (2H, m), 3.92-3.97 (1H, m), 4.38-4.42 (1H, m), 4.67-4.75 (2H, m), 6.98-7.74 (7H, m), 8.52-8.55 (1H, m). |
| 4-21 | 1H-NMR (CDCl3) δ: 2.59-2.64 (1H, m), 2.97-3.00 (1H, m), 3.60-3.72 (2H, m), 3.95-4.16 (3H, m), 4.41-4.45 (1H, m), 6.37 (1H, br s), 7.40 (2H, s). |
| 4-22 | 1H-NMR (CDCl3) δ: 2.58-2.63 (1H, m), 2.91-2.96 (1H, m), 3.59-3.72 (2H, m), 3.99-4.12 (1H, m), 4.40-4.44 (1H, m), 4.70-4.72 (2H, m), 7.20-7.72 (6H, m), 8.56-8.57 (1H, m). |
| 4-34 | 1H-NMR (CDCl3) δ: 2.67-2.73 (1H, m), 3.08-3.12 (1H, m), 3.66-3.74 (2H, m), 4.01-4.16 (3H, m), 4.56-4.60 (1H, m), 6.38 (1H, br s), 7.80 (2H, s), 7.95 (1H, s). |
| 4-35 | 1H-NMR (CDCl3) δ: 2.67-2.73 (1H, m), 3.07-3.11 (1H, m), 3.61-3.77 (1H, m), 3.65-3.77 (m, 2H), 3.93-4.15 (m, 1H), 4.06-4.13 (1H, m), 4.66-4.84 (3H, m), 7.35-7.80 (7H, m), 8.56-8.57 (1H, m). |
| 4-38 | 1H-NMR (CDCl3) δ: 2.64-2.75 (1H, m), 3.07-3.11 (1H, m), 3.62-3.77 (5H, m), 4.04-4.07 (1H, m), 4.17-4.22 (2H, m), 4.56-4.60 (1H, m), 6.69-6.72 (1H, m), 7.80 (2H, s), 7.94 (1H, s). |
| 4-128 | 1H-NMR (acetone-d6) δ: 2.72-2.96 (m, 1H), 3.07-3.20 (m, 1H), 3.65-3.77 (m, 2H), 3.93-4.15 (m, 5H), 4.50 (d, 1H), 7.54-7.68 (m, 4H), 7.86 (bs, 1H) |
| 4-286 | 1H-NMR (CDCl3) δ: 1.29 (t, 3H), 2.57-2.70 (m, 1H), 2.91-3.02 (m, 1H), 3.55-3.77 (m, 2H), 3.98 (d, 1H), 4.16 (q, 2H), 4.45 (d, 1H), 7.21-7.28 (m, 2H), 4.40-4.48 (m, 1H), 7.68 (d, 1H), 8.99-9.11 (m, 1H) |
| 4-613 | 1H-NMR (CDCl3) δ: 2.55-2.70 (m, 1H), 2.88-3.01 (m, 1H), 3.53-3.75 (m, 2H), 3.98 (d, 1H), 4.43 (d, 1H), 4.85 (d, 1H), 7.20-7.30 (m, 3H), 7.37-7.42 (m, 1H), 7.65 (bs, 1H), 8.74 (d, 2H) |
| 4-614 | 1H-NMR (acetone-d6) δ: 2.75-2.96 (m, 1H), 3.07-3.20 (m, 1H), 3.64-3.78 (m, 2H), 4.05-4.15 (m, 3H), 4.44-4.59 (m, 3H), 7.18-7.25 (m, 1H), 7.36 (d, 1H), 7.52-7.78 (m, 5H), 7.88 (bs, 1H), 8.49 (d, 1H) |
| 4-615 | 1H-NMR (acetone-d6) δ: 2.78-2.96 (m, 1H), 3.07-3.20 (m, 1H), 3.48-3.78 (m, 6H), 3.97-4.14 (m, 3H), 4.50 (d, 1H), 7.51-7.67 (m, 3H) |
| 4-616 | 1H-NMR (CDCl3) δ: 2.55-2.70 (m, 1H), 2.88-3.02 (m, 1H), 3.52-3.75 (m, 2H), 3.84 (s, 3H), 3.97 (d, 1H), 4.43 (d, 1H), 4.85 (d, 1H), 7.21-7.28 (m, 2H), 7.38-7.44 (m, 1H), 8.02 (bs, 1H) |
| 4-617 | 1H-NMR (CDCl3) δ: 2.55-2.70 (m, 1H), 2.88-3.02 (m, 1H), 3.15 (s, 3H), 3.17 (s, 3H), 3.52-3.75 (m, 2H), 3.97 (d, 1H), 4.43 (d, 1H), 4.85 (d, 1H), 5.12 (s, 1H), 7.21-7.28 (m, 2H), 7.38-7.44 (m, 1H) |
| 4-618 | 1H-NMR (CDCl3) δ: 2.30 (t, 1H), 2.54-2.69 (m, 1H), 2.87-3.01 (m, 1H), 3.52-3.74 (m, 2H), 3.96 (d, 1H), 4.15-4.24 (m, 2H), 4.42 (d, 1H), 6.29 (bs, 1H), 7.21-7.28 (m, 2H), 7.38-7.43 (m, 1H) |
| 5-4 | 1H-NMR (CDCl3) δ: 1.18 (3H, t), 2.21 (1H, q), 2.54-2.59 (1H, m), 2.85-2.93 (1H, m), 3.57-3.63 (2H, m), 3.90-3.94 (1H, m), 4.33-4.37 (1H, m), 4.55-4.57 (2H, m), 5.91 (1H, br s), 7.27 (2H, s), 7.40 (1H, s). |
| 5-7 | 1H-NMR (CDCl3) δ: 0.75-0.84 (2H, m), 0.99-1.09 (2H, m), 1.31-1.40 (1H, m), 2.53-2.59 (1H, m), 2.87-2.91 (1H, m), 3.57-3.63 (2H, m), 3.91 (1H, d), 4.35 (1H, d), 4.56-4.58 (2H, m), 6.10 (1H, br s), 7.26 (2H, d), 7.39 (1H, t). |
| 5-15 | 1H-NMR (CDCl3) δ: 0.11-0.18 (1H, m), 0.58-0.62 (2H, m), 0.86-1.06 (1H, m), 2.18 (2H, d), 2.54-2.59 (1H, m), 2.87-2.92 (1H, m), 3.55-3.64 (2H, m), 3.92 (1H, d), 4.35 (1H, d), 4.58-4.60 (2H, m), 6.38 (1H, br s), 7.26 (2H, d), 7.40 (1H, t). |
| 5-22 | 1H-NMR (CDCl3) δ: 2.54-2.60 (1H, m), 2.88-2.93 (1H, m), 3.10 (2H, q), 3.50-3.67 (2H, m), 3.90-3.94 (1H, m), 4.34-4.38 (1H, m), 4.59-4.70 (2H, m), 6.32 (1H, t), 7.27 (2H, s), 7.41 (1H, s) |
| 5-45 | 1H-NMR (CDCl3) δ: 2.08 (3H, s), 2.47-2.62 (1H, m), 2.91-2.95 (1H, m), 3.25 (2H, s), 3.52-3.63 (2H, m), 3.92 (1H, d), 4.36 (1H, d), 4.61-4.63 (2H, m), 7.26 (2H, d), 7.36-7.39 (2H, m). |
| 5-140 | 1H-NMR (CDCl3) δ: 1.64 (2H, br s), 2.51-2.61 (1H, m), 2.88-2.92 (1H, m), 3.56-3.65 (2H, m), 3.92-3.96 (1H, m), 4.02-4.16 (2H, m), 4.16-4.38 (1H, m), 7.41 (2H, s). |
| 5-142 | 1H-NMR (CDCl3) δ: 1.14 (3H, t), 2.25 (2H, q), 2.52-2.58 (1H, m), 2.87-2.91 (1H, m), 3.55-3.64 (2H, m), 3.91 (1H, m), 4.34 (1H, m), 4.55-4.57 (2H, m), 5.91-5.93 (1H, m), 7.39 (1H, s). |
| 5-143 | 1H-NMR (CDCl3) δ: 0.72-1.39 (5H, m), 2.52-2.57 (1H, m), 2.84-2.93 (1H, m), 3.48-3.67 (2H, m), 3.89-3.93 (1H, m), 4.32-4.36 (1H, m), 4.56-4.58 (2H, m), 6.09 (1H, t), 7.39 (2H, s). |
| 5-144 | 1H-NMR (CDCl3) δ: 2.53-2.59 (1H, m), 2.88-2.92 (1H, m), 3.12 (2H, q), 3.55-3.67 (2H, m), 3.90-3.94 (1H, m), 4.34-4.37 (1H, m), 4.60-4.62 (2H, m), 6.22 (1H, br s), 7.39 (2H, s). |
| 5-148 | 1H-NMR (CDCl3) δ: 1.16 (3H, t), 2.21 (2H, q), 2.61-2.66 (1H, m), 3.02-3.06 (1H, m), 3.55-3.72 (2H, m), 3.97-4.01 (1H, m), 4.50-4.56 (3H, m), 5.94 (1H, t), 7.80 (2H, m), 7.93 (1H, s). |
| 5-150 | 1H-NMR (CDCl3) δ: 2.62-2.67 (1H, m), 3.04-3.12 (3H, m), 3.58-3.68 (2H, m), 3.98-4.02 (1H, m), 4.52-4.60 (3H, m), 6.33 (1H, t), 7.80 (2H, s), 7.93 (1H, s). |

TABLE 8-continued

| Table 8 - Ex.-No. | 1H-NMR |
|---|---|
| 5-151 | 1H-NMR (CDCl3) δ: 1.16 (3H, t), 2.59-2.67 (1H, m), 3.01-3.05 (1H, m), 3.18-3.33 (2H, m), 3.60-3.71 (2H, m), 3.97-4.01 (1H, m), 4.35-4.37 (1H, m), 4.47-4.57 (3H, m), 4.78-4.81 (1H, m), 7.80 (2H, s), 7.93 (1H, s). |
| 5-178 | 1H-NMR (CDCl3) δ: 1.13 (3H, t), 2.19-2.28 (5H, m), 2.49-2.68 (1H, m), 2.84-2.87 (1H, m), 3.52-3.62 (2H, m), 3.90 (1H, d), 4.35-4.49 (3H, m), 5.78 (1H, br s), 7.22 (2H, d), 7.38 (1H, t). |
| 5-179 | 1H-NMR (CDCl3) δ: 0.77-0.85 (2H, m), 0.95-0.99 (2H, m), 1.28-1.33 (2H, m), 2.22 (3H, s), 2.52-2.57 (1H, m), 2.85-2.89 (1H, m), 3.53-3.62 (2H, m), 3.91 (1H, d), 4.33 (1H, d), 4.41-4.42 (2H, m), 5.87 (1H, br s), 7.26 (2H, d), 7.38 (1H, t). |
| 5-193 | 1H-NMR (CDCl3) δ: 1.14 (3H, t), 2.23 (2H, q), 2.53-2.59 (1H, m), 2.87-2.92 (1H, m), 3.54-3.60 (2H, m), 3.90 (1H, d), 4.32-4.49 (3H, m), 5.92 (1H, br s), 7.25 (2H, d), 7.39 (1H, t). |
| 5-194 | 1H-NMR (CDCl3) δ: 0.72-0.85 (2H, m), 0.88-1.11 (2H, m), 1.31-1.39 (1H, m), 2.53-2.58 (1H, m), 2.87-2.91 (1H, m), 3.50-3.58 (2H, m), 3.89 (1H, d), 4.34 (1H, d), 4.42-4.44 (2H, m), 6.11 (1H, br s), 7.28 (2H, d), 7.39 (1H, t). |
| 5-228 | 1H-NMR (CDCl3) δ: 0.17-0.27 (2H, m), 0.59-0.65 (2H, m), 0.92-0.99 (1H, m), 2.16 (2H, d), 2.31 (3H, s), 2.52-2.61 (1H, m), 2.85-2.90 (1H, m), 3.54-3.63 (2H, m), 3.91 (1H, d), 4.35 (1H, d), 4.45-4.49 (2H, m), 6.11 (1H, br s), 7.26 (2H, d), 7.38 (1H, t). |
| 5-248 | 1H-NMR (CDCl3) δ: 0.18-0.21 (2H, m), 0.60-0.64 (2H, m), 0.89-1.00 (1H, m), 2.18 (2H, d), 2.53-2.59 (1H, m), 2.87-2.92 (1H, m), 3.55-3.61 (2H, m), 3.90 (1H, d), 4.34 (1H, d), 4.44-4.46 (2H, m), 6.29 (1H, br s), 7.28 (2H, d), 7.39 (1H, t). |
| 5-336 | 1H-NMR (CDCl3) δ: 0.18-0.21 (2H, m), 0.55-0.65 (2H, m), 0.88-1.01 (1H, m), 2.18 (2H, d), 2.52-2.58 (1H, m), 2.85-2.93 (1H, m), 3.55-3.68 (2H, m), 3.90-3.94 (1H, m), 4.33-4.36 (1H, m), 4.59 (2H, d), 6.35 (1H, t), 7.37 (2H, s). |
| 5-337 | 1H-NMR (CDCl3) δ: 1.00 (9H, s), 2.07 (2H, s), 2.52-2.58 (1H, m), 2.86-2.91 (1H, m), 3.51-3.67 (2H, m), 3.90-3.94 (1H, m), 4.36-4.42 (1H, m), 4.53 (2H, d), 5.85 (1H, t), 7.38 (2H, s). |
| 5-340 | 1H-NMR (CDCl3) δ: 2.11 (3H, s), 2.53-2.58 (1H, m), 2.85-2.93 (1H, m), 3.23 (2H, s), 3.55-3.64 (2H, m), 3.90-3.94 (1H, m), 4.33-4.37 (1H, m), 4.61 (2H, d), 7.34-7.37 (3H, m). |
| 5-387 | 1H-NMR (CDCl3) δ: 2.13 (3H, s), 2.62-2.67 (1H, m), 3.02-3.06 (1H, m), 3.23 (2H, s), 3.53-3.65 (2H, m), 3.98-4.02 (1H, m), 4.47-4.51 (1H, m), 4.61-4.63 (2H, m), 7.35 (1H, br s), 7.81 (2H, s), 7.93 (1H, s). |
| 5-389 | 1H-NMR (CDCl3) δ: 2.55-2.65 (1H, m), 2.97-3.05 (4H, m), 3.84-3.88 (4H, m), 4.05-4.16 (1H, m), 4.50-4.62 (3H, m), 6.81 (1H, br s), 7.84 (2H, s), 7.92 (1H, s), 8.63 (1H, s). |
| 5-433 | 1H-NMR (CDCl3) δ: 0.15-0.28 (2H, m), 0.55-0.69 (2H, m), 0.89-1.05 (1H, m), 2.20 (2H, d), 2.62-2.68 (1H, m), 3.03-3.07 (1H, m), 3.56-3.73 (2H, m), 3.99-4.03 (1H, m), 4.52-4.59 (3H, m), 6.41 (1H, t), 7.81 (2H, s), 7.94 (1H, s). |
| 5-434 | 1H-NMR (CDCl3) δ: 0.99 (9H, s), 2.07 (2H, s), 2.61-2.66 (1H, m), 3.01-3.06 (1H, m), 3.55-3.71 (2H, m), 3.98-4.02 (1H, m), 4.50-4.54 (3H, m), 5.86 (1H, t z), 7.80 (2H, s), 7.93 (1H, s). |
| 5-435 | 1H-NMR (CDCl3) δ: 2.32 (3H, s), 2.47-2.52 (1H, m), 2.81-2.85 (1H, m), 3.48-3.54 (2H, m), 3.83 (1H, d), 4.28 (1H, d), 4.39-4.41 (2H, m), 5.68 (1H, br s), 7.18 (2H, d), 7.32 (1H, t). |
| 5-436 | 1H-NMR (CDCl3) δ: 2.24 (3H, s), 2.41 (3H, s), 2.49-2.60 (1H, m), 2.83-2.91 (1H, m), 3.53-3.62 (2H, m), 3.91 (1H, d), 4.33 (1H, d), 4.43-4.45 (2H, m), 5.62 (1H, br s), 7.26 (2H, d), 7.38 (1H, t). |
| 5-437 | 1H-NMR (CDCl3) δ: 2.40 (3H, m), 2.54-2.59 (1H, m), 2.87-2.92 (1H, m), 3.56-3.65 (2H, m), 3.92 (1H, d), 4.35 (1H, d), 4.59-4.61 (2H, m), 5.84 (1H, br s), 7.23 (2H, d), 7.40 (1H, t). |
| 6-4 | 1H-NMR (CDCl3) δ: 1.18 (3H, t), 1.77-1.86 (1H, m), 2.22 (2H, m), 2.50-2.64 (2H, m), 2.78-3.01 (3H, m), 3.45-3.58 (2H, m), 3.77 (1H, d), 4.03 (1H, d), 5.41 (1H, dd), 5.56 (1H, d), 6.48 (1H, d), 6.49 (1H, s), 7.18 (1H, d), 7.30 (1H, s), 7.38 (1H, t). |
| 6-122 | 1H-NMR (CDCl3) δ: 1.48 (9H, s), 1.74-1.86 (1H, m), 2.48-2.60 (2H, m), 2.74-2.99 (3H, m), 3.41-3.57 (2H, m), 3.77 (1H, d), 4.02 (1H, d), 4.68 (1H, d), 5.10 (1H, d), 6.47-6.45 (2H, m), 7.22 (1H, d), 7.29 (2H, s), 7.37 (1H, t). |
| 6-267 | 1H-NMR (acetone-d6) δ: 1.73-1.82 (1H, m), 1.89 (3H, s), 2.34-2.49 (2H, m), 2.69-3.02 (3H, m), 3.44-3.57 (2H, m), 3.94 (1H, d), 4.19 (1H, d), 5.26 (1H, dd), 6.55-6.52 (2H, m), 7.08 (1H, d), 7.82 (2H, s). |
| 6-268 | 1H-NMR (CDCl3) δ: 1.19 (3H, t), 1.74-1.86 (1H, m), 2.23 (2H, q), 2.46-2.65 (2H, m), 2.78-3.01 (3H, m), 3.45-3.58 (2H, m), 3.77 (1H, d), 4.02 (1H, d), 5.38-5.61 (2H, m), 6.46-6.49 (2H, m), 7.18 (1H, d), 7.43 (2H, s). |
| 6-273 | 1H-NMR (CDCl3) δ: 1.18 (3H, t), 1.75-1.86 (1H, m), 2.23 (2H, q), 2.54-2.64 (2H, m), 2.79-3.02 (3H, m), 3.47-3.64 (2H, m), 3.84 (1H, d), 4.15 (1H, d), 5.38-5.57 (2H, m), 6.52-6.49 (2H, m), 7.20 (1H, d), 7.85 (2H, s), 7.91 (1H, s). |
| 6-293 | 1H-NMR (CDCl3) δ: 1.18 (3H, t), 1.76-1.87 (3H, m), 1.95-2.04 (1H, m), 2.22 (2H, q), 2.54-2.86 (3H, m), 2.91-3.00 (1H, m), 3.45-3.62 (2H, m), 3.82 (1H, d), 4.14 (1H, d), 5.16-5.09 (1H, m), 5.58 (1H, d), 6.33 (1H, d), 6.50 (1H, dd), 7.18 (1H, d), 7.85 (2H, s), 7.91 (1H, s). |
| 6-802 | 1H-NMR (CDCl3) δ: 1.48 (9H, s), 1.74-1.86 (1H, m), 2.45-2.60 (2H, m), 2.75-2.99 (3H, m), 3.45-3.57 (2H, m), 3.76 (1H, d), 4.01 (1H, d), 4.67 (1H, d), 5.11 (1H, d), 6.48-6.46 (2H, m), 7.22 (1H, d), 7.43 (2H, s). |
| 7-1 | 1H-NMR (CDCl3) δ: 2.56-2.66 (1H, m), 2.91-2.99 (1H, m), 3.55-3.71 (2H, m), 3.84 (1H, d), 4.16 (1H, d), 6.72 (1H, dd), 6.86 (1H, d), 7.27 (2H, d), 7.42 (1H, t), 7.65 (1H, d). |

TABLE 8-continued

| Table 8 - Ex.-No. | 1H-NMR |
|---|---|
| 7-2 | 1H-NMR (CDCl3) δ: 2.57-2.64 (1H, m), 2.90-2.95 (1H, m), 3.53-3.61 (2H, m), 3.81 (1H, d), 4.13 (1H, d), 6.50 (1H, dd), 6.64 (1H, d), 7.27 (2H, br s), 7.43 (1H, t), 7.50 (1H, d). |
| 7-3 | 1H-NMR (CDCl3) δ: 2.55-2.60 (1H, m), 2.89-2.93 (1H, m), 3.49-3.65 (2H, m), 3.74-3.79 (1H, d), 4.10-4.12 (1H, m), 6.52-6.54 (1H, m), 6.81-6.83 (1H, m), 7.24 (2H, s), 7.40-7.46 (2H, m). |
| 7-4 | 1H-NMR (CDCl3) δ: 2.53-2.63 (1H, m), 3.48-3.65 (1H, m), 3.52-3.62 (2H, m), 3.79 (1H, d), 4.11 (1H, d), 6.29-6.40 (2H, m), 7.26 (2H, s), 7.40-7.43 (2H, m). |
| 7-5 | 1H-NMR (CDCl3) δ: 2.49 (1H, s), 2.53-2.60 (4H, m), 2.84-2.92 (1H, t), 3.48-3.64 (2H, m), 3.79 (1H, d), 4.10 (1H, d), 6.40-6.43 (2H, m), 7.27 (2H, d), 7.40 (1H, t), 7.45 (1H, d). |
| 7-12 | 1H-NMR (CDCl3) δ: 2.55-2.65 (1H, m), 2.90-2.98 (1H, m), 3.55-3.73 (2H, m), 3.83 (1H, d), 4.16 (1H, d), 6.72 (1H, dd), 6.86 (1H, d), 7.42 (2H, s), 7.65 (1H, d). |
| 7-13 | 1H-NMR (CDCl3) δ: 2.52-2.62 (1H, m), 2.87-2.95 (1H, m), 3.49-3.66 (2H, m), 3.79 (1H, d), 4.11 (1H, d), 6.49 (1H, dd), 6.63 (1H, d), 7.40 (2H, s), 7.47 (1H, d). |
| 7-14 | 1H-NMR (CDCl3) δ: 2.51-2.61 (1H, m), 2.91-2.99 (1H, m), 3.54-3.63 (2H, m), 3.76-3.80 (1H, m), 4.09-4.12 (1H, m), 6.53 (1H, dd), 6.81 (1H, d), 7.40 (2H, s), 7.47 (1H, d). |
| 7-23 | 1H-NMR (CDCl3) δ: 2.63-2.74 (1H, m), 3.14-3.05 (1H, m), 3.77-3.61 (2H, m), 3.90 (1H, d), 4.31 (1H, d), 6.76 (1H, dd), 6.89 (1H, d), 7.66 (1H, s), 7.83 (2H, s), 7.96 (1H, s). |
| 7-24 | 1H-NMR (CDCl3) δ: 2.60-2.71 (1H, m), 3.02-3.10 (1H, m), 3.71-3.54 (2H, m), 3.85 (1H, d), 4.25 (1H, d), 6.53 (1H, dd), 6.67 (1H, d), 7.50 (1H, d), 7.82 (2H, s), 7.95 (1H, s). |
| 7-25 | 1H-NMR (CDCl3) δ: 2.60-2.70 (1H, m), 3.10-3.01 (1H, m), 3.54-3.71 (2H, m), 3.85 (1H, d), 4.25 (1H, d), 6.57 (1H, dd), 6.84 (1H, d), 7.48 (1H, d), 7.82 (2H, s), 7.95 (1H, s). |
| 7-28 | 1H-NMR (CDCl3) δ: 2.66-2.77 (1H, m), 3.08-3.17 (1H, m), 3.65-3.81 (2H, m), 3.93 (1H, d), 4.35 (1H, d), 6.88 (1H, d), 7.44 (1H, d), 7.71 (1H, d), 7.83 (2H, s), 7.94 (1H, d). |
| 7-35 | 1H-NMR (acetone-d6) δ: 2.84-2.95 (1H, m), 3.17-3.28 (1H, m), 3.74-3.80 (2H, m), 4.21 (1H, d), 4.62 (1H, d), 7.04 (1H, dd), 7.14 (1H, d), 7.77 (1H, d), 7.85 (1H, s), 7.91 (1H, s), 7.98 (1H, s). |
| 7-46 | 1H-NMR (CDCl3) δ: 2.50-2.63 (1H, m), 2.58 (3H, s), 2.85-2.94 (1H, m), 3.53-3.67 (2H, m), 3.80 (1H, d), 4.11 (1H, d), 6.29-6.41 (2H, m), 7.11-7.46 (4H, m) |
| 7-47 | 1H-NMR (CDCl3) δ: 1.76 (1H, t), 2.43-2.77 (5H, m), 3.65-4.00 (2H, m), 4.21 (1H, d), 4.40 (1H, d), 4.59-4.62 (2H, m), 6.62 (1H, m), 7.29-7.38 (4H, m) |
| 7-49 | 1H-NMR (CDCl3) δ: 1.83 (1H, b), 2.48-2.59 (1H, m), 2.83-2.91 (1H, m), 3.53-3.67 (2H, m), 3.93 (1H, d), 4.40 (1H, d), 4.65 (2H, s), 6.30 (1H, d), 7.26-7.58 (4H, m) |
| 7-51 | 1H-NMR (CDCl3) δ: 1.84 (1H, b), 2.52-2.62 (1H, m), 2.88-2.96 (1H, m), 3.45-3.58 (2H, m), 3.79 (1H, d), 4.00 (1H, d), 4.67 (2H, s), 6.53-7.65 (6H, m) |
| 7-53 | 1H-NMR (CDCl3) δ: 1.84 (1H, t), 2.48-2.58 (1H, m), 2.81-2.89 (1H, m), 3.42-3.58 (2H, m), 3.76 (1H, d), 4.03 (1H, d), 4.66 (2H, d), 6.53 (1H, dd), 6.79 (1H, d), 7.28 (2H, s), 7.29 (1H, d), 7.39 (1H, t). |
| 7-55 | 1H-NMR (CDCl3) δ: 1.82 (1H, t), 2.48-2.58 (1H, m), 2.80-2.89 (1H, m), 3.41-3.57 (2H, m), 3.74 (1H, d), 4.02 (1H, d), 4.62 (1H, d), 6.58 (1H, dd), 7.05 (1H, d), 7.28-7.26 (3H, m), 7.39 (1H, t). |
| 7-57 | 1H-NMR (CDCl3) δ: 1.84 (1H, t, J = 6.3 Hz), 2.47-2.57 (1H, m), 2.80-2.88 (1H, m), 3.58-3.42 (2H, m), 3.75 (1H, d), 4.02 (1H, d), 4.66 (2H, d), 6.53 (1H, dd), 6.79 (1H, d), 7.30 (1H, d), 7.42 (2H, s). |
| 7-63 | 1H-NMR (CDCl3) δ: 1.85 (1H, t), 2.88-2.96 (1H, m), 3.53-3.74 (1H, m), 3.56-3.74 (2H, m), 4.05 (1H, d), 4.23 (1H, dd), 4.71 (2H, d), 6.63 (1H, dd), 7.13 (1H, dd), 7.85 (2H, s), 7.92 (1H, s). |
| 7-67 | 1H-NMR (CDCl3) δ: 2.55-2.66 (1H, m), 2.95-3.03 (1H, m), 3.46-3.63 (2H, m), 3.81 (1H, d), 4.15 (1H, d), 4.62 (2H, d), 6.62 (1H, dd), 7.09 (1H, d), 7.29 (1H, d), 7.84 (2H, s), 7.93 (1H, s). |
| 7-69 | 1H-NMR (CDCl3) δ: 2.50-2.63 (1H, m), 2.88-2.96 (1H, m), 3.57 (1H, br s), 3.64-3.76 (1H, m), 4.04 (1H, d), 4.23 (1H, dd), 4.68 (2H, s), 6.49-6.43 (1H, m), 6.99-7.05 (1H, m), 7.85 (2H, s), 7.92 (1H, s). |
| 7-71 | 1H-NMR (CDCl3) δ: 2.52-2.62 (1H, m), 2.90-2.99 (1H, m), 3.81-3.90 (1H, m), 4.13-4.22 (1H, m), 4.33 (1H, dd), 4.51 (1H, dd), 6.53 (1H, dd), 6.79 (1H, d), 7.42 (2H, s), 7.94 (1H, s). |
| 7-72 | 1H-NMR (CDCl3) δ: 2.10-2.16 (1H, m), 2.33-2.43 (1H, m), 2.67-2.74 (1H, m), 3.44-3.59 (2H, m), 3.85-3.88 (1H, m), 3.99-4.04 (1H, m), 6.70-6.78 (1H, m), 7.31-7.25 (1H, m), 7.84 (2H, s), 7.94 (1H, s). |
| 7-76 | 1H-NMR (CDCl3) δ: 2.10-2.16 (1H, m), 2.33-2.43 (1H, m), 2.67-2.74 (1H, m), 3.44-3.59 (2H, m), 3.85-3.88 (1H, m), 3.99-4.04 (1H, m), 4.59 (2H, s), 6.49 (1H, t), 6.92-7.11 (1H, m), 7.37 (2H, s), 7.70 (1H, t). |
| 7-78 | 1H-NMR (CDCl3) δ: 2.09-2.17 (3H, m), 2.33-2.36 (1H, m), 2.61-2.66 (1H, m), 3.41-3.46 (2H, m), 3.82-3.97 (2H, m), 4.49 (2H, d), 6.42 (1H, t), 6.87 (1H, d), 7.35 (2H, s). |
| 7-86 | 1H-NMR (CDCl3) δ: 1.56 (1H, b), 2.49-2.59 (1H, m), 2.83-2.92 (1H, m), 3.55-3.70 (2H, m), 3.93 (1H, d), 4.40 (2H, d), 4.65 (2H, s), 6.31 (1H, d), 7.30-7.61 (4H, m) |

TABLE 8-continued

| Table 8 - Ex.-No. | 1H-NMR |
|---|---|
| 7-92 | 1H-NMR (CDCl3) δ: 1.83 (2H, b), 2.53-2.66 (1H, m), 2.97-3.04 (1H, m), 3.55-3.68 (2H, m), 3.85 (2H, s), 3.99 (1H, d), 4.54 (1H, d), 6.30-7.91 (5H, m) |
| 7-93 | 1H-NMR (CDCl3) δ: 1.86 (1H, t), 2.47-2.58 (1H, m), 2.82-2.91 (1H, m), 3.55-3.68 (2H, m), 3.93 (1H, d), 4.40 (1H, d), 4.66 (2H, d), 6.31 (1H, d), 7.44-7.59 (3H, m) |
| 7-95 | 1H-NMR (CDCl3) δ: 2.56-2.67 (1H, m), 2.97-3.06 (1H, m), 3.55-3.70 (2H, m), 4.00 (1H, d), 4.55 (1H, d), 4.67 (2H, d), 6.34 (1H, d), 7.57-7.91 (4H, m) |
| 7-97 | 1H-NMR (CDCl3) δ: 2.47-2.58 (1H, m), 2.82-2.91 (1H, m), 3.90-4.11 (4H, m), 4.54 (1H, d), 7.27-7.42 (4H, m) |
| 7-98 | 1H-NMR (CDCl3) δ: 2.46-2.57 (1H, m), 2.82-2.90 (1H, m), 3.90-4.11 (3H, m), 4.53 (1H, d), 7.36-7.41 (3H, m) |
| 7-99 | 1H-NMR (CDCl3) δ: 2.54-2.65 (1H, m), 2.97-3.05 (1H, m), 3.90-4.70 (3H, m), 4.68 (1H, d), 7.40 (1H, d), 7.83-7.95 (3H, m) |
| 7-100 | 1H-NMR (CDCl3) δ: 2.48-2.58 (1H, m), 2.79-2.88 (1H, m), 3.40-3.55 (2H, m), 3.78 (1H, d), 3.93 (3H, s), 4.04 (1H, d), 4.59 (2H, b), 6.10-6.17 (2H, m), 7.12-7.39 (4H, m) |
| 7-102 | 1H-NMR (CDCl3) δ: 2.61-2.72 (1H, m), 3.03-3.11 (1H, m), 3.54-3.73 (2H, m), 3.86 (1H, d), 4.25 (1H, d), 6.49-6.58 (2H, m), 7.26-7.96 (4H, m) |
| 7-103 | 1H-NMR (CDCl3) δ: 2.55-2.65 (1H, m), 2.90-2.98 (1H, m), 3.55-3.71 (2H, m), 3.82 (1H, d), 4.16 (1H, d), 6.72 (1H, dd), 6.86 (1H, d), 7.46 (2H, d), 7.65 (1H, d), 7.73 (1H, t). |
| 7-105 | 1H-NMR (CDCl3) δ: 1.37 (3H, t), 2.54-2.64 (1H, m), 2.90-2.99 (1H, m), 3.71-3.74 (2H, m), 4.02 (1H, d), 4.36 (2H, q), 4.51 (1H, d), 6.65 (1H, s), 7.43 (2H, s), 8.84 (1H, s). |
| 7-107 | 1H-NMR (CDCl3) δ: 2.55-2.64 (1H, m), 2.88-2.97 (1H, m), 3.71-3.75 (2H, m), 4.01 (1H, d), 4.49 (1H, d), 4.70 (2H, d), 6.61 (1H, s), 7.44 (2H, s), 8.42 (1H, s). |
| 7-108 | 1H-NMR (CDCl3) δ: 1.38 (3H, t), 2.62-2.73 (1H, m), 3.06-3.14 (1H, m), 3.76-3.79 (2H, m), 4.08 (1H, d), 4.37 (2H, q), 4.68 (1H, d), 6.68 (1H, s), 7.85 (2H, s), 7.94 (1H, s), 8.86 (1H, s). |
| 7-110 | 1H-NMR (CDCl3) δ: 2.63-2.69 (1H, m), 3.05-3.09 (1H, m), 3.66-3.75 (2H, m), 4.04 (1H, d), 4.62 (1H, d), 4.73 (2H, d), 6.62 (1H, s), 7.86 (2H, s), 7.93 (1H, s), 8.41 (1H, s). |
| 7-111 | 1H-NMR (CDCl3) δ: 2.49-2.59 (1H, m), 2.83-2.92 (1H, m), 3.57-3.70 (2H, m), 3.95 (1H, d), 4.42 (1H, d), 4.76 (1H, s), 6.59 (1H, d), 7.30 (2H, s), 7.38 (1H, s), 7.76 (1H, d). |
| 7-112 | 1H-NMR (CDCl3) δ: 2.53-2.64 (1H, m), 2.90-3.00 (1H, m), 3.69-3.74 (2H, m), 4.01 (1H, d), 4.50 (1H, d), 4.75 (2H, s), 6.59 (1H, d), 7.44 (2H, s), 7.75 (1H, d). |
| 7-113 | 1H-NMR (CDCl3) δ: 1.37 (3H, t), 2.54-2.60 (1H, m), 2.90-2.99 (1H, m), 3.57-3.75 (2H, m), 4.01 (1H, d), 4.35 (2H, q), 4.45 (1H, d), 6.55 (1H, d), 7.56-7.61 (3H, m), 8.02 (1H, d). |
| 7-114 | 1H-NMR (CDCl3) δ: 2.54-2.59 (1H, m), 2.91-2.98 (1H, m), 3.55-3.79 (2H, m), 4.00 (1H, d), 4.44 (1H, d), 4.78 (2H, d), 6.56 (1H, d), 7.53-7.65 (3H, m), 7.78 (1H, d). |
| 7-115 | 1H-NMR (CDCl3) δ: 1.36 (3H, t), 2.53-2.63 (1H, m), 2.89-3.01 (1H, m), 3.55-3.74 (2H, m), 4.03 (1H, d), 4.30-4.52 (3H, m), 6.56 (1H, d), 7.51-7.80 (4H, m), 8.03 (1H, d). |
| 7-117 | 1H-NMR (CDCl3) δ: 2.53-2.61 (1H, m), 2.88-3.01 (1H, m), 3.53-3.71 (2H, m), 4.00 (1H, d), 4.42 (1H, d), 4.75 (2H, s), 6.57 (1H, d), 7.42-7.79 (4H, m), 7.78 (1H, d). |
| 7-119 | 1H-NMR (CDCl3) δ: 2.64-2.74 (1H, m), 3.05-3.14 (1H, m), 3.75-3.81 (2H, m), 4.06 (1H, d), 4.65-4.80 (3H, m), 6.59 (1H, s), 7.69-7.96 (4H, m) |
| 7-120 | 1H-NMR (CDCl3) δ: 1.36 (3H, t), 2.46-2.60 (1H, m), 2.82-2.91 (1H, m), 3.56-3.70 (2H, m), 3.94 (1H, d), 4.34-4.45 (3H, m), 6.54 (1H, d), 7.48 (2H, s), 7.69 (1H, t), 8.01 (1H, d). |
| 7-121 | 1H-NMR (CDCl3) δ: 2.46-2.59 (1H, m), 2.83-2.94 (1H, m), 3.52-3.72 (2H, m), 3.93 (1H, d), 4.39 (1H, d), 4.75 (2H, s), 6.59 (1H, d), 7.47 (2H, s), 7.68-7.80 (2H, m). |
| 7-122 | 1H-NMR (CDCl3) δ: 1.38 (3H, t), 2.53-2.55 (1H, m), 2.75 (3H, s), 2.85-2.90 (1H, m), 3.64-3.67 (2H, m), 4.00 (1H, d), 4.31 (2H, q), 4.47 (1H, d), 6.22 (1H, dz), 7.31 (2H, s), 7.39 (1H, t), 8.06 (1H, d). |
| 7-124 | 1H-NMR (CDCl3) δ: 2.49-2.52 (4H, m), 2.80-2.89 (1H, m), 3.57-3.62 (2H, m), 3.96 (1H, d), 4.39 (1H, d), 4.60 (2H, d), 6.21 (1H, d), 7.35-7.40 (4H, m). |
| 7-125 | 1H-NMR (CDCl3) δ: 0.95-0.97 (2H, m), 1.13-1.18 (2H, m), 1.39 (3H, t), 2.46-2.56 (1H, m), 2.79-2.87 (1H, m), 3.25-3.28 (1H, m), 3.57-3.69 (2H, m), 3.94 (1H, d), 4.31-4.39 (3H, m), 6.14 (1H, d), 7.27-7.38 (3H, m), 8.01 (1H, d). |
| 7-127 | 1H-NMR (CDCl3) δ: 0.90-0.95 (2H, m), 1.13-1.17 (2H, m), 2.12-2.26 (1H, m), 2.45-2.58 (1H, m), 2.79-2.90 (1H, m), 3.51-3.70 (2H, m), 3.94 (1H, d), 4.30 (1H, d), 4.75 (2H, d), 6.15 (1H, d), 7.27-7.40 (4H, m). |
| 7-128 | 1H-NMR (CDCl3) δ: 0.94-0.99 (2H, m), 1.14-1.19 (2H, m), 1.41 (3H, t), 2.50-2.65 (1H, m), 2.91-2.97 (1H, m), 3.25-3.30 (1H, m), 3.45-3.65 (2H, m), 4.02 (1H, m), 4.29-4.40 (3H, m), 6.14 (1H, m), 7.84-8.05 (4H, m). |
| 7-129 | 1H-NMR (CDCl3) δ: 0.92-0.95 (2H, m), 1.13-1.19 (2H, m), 2.15-2.25 (1H, m), 2.50-2.64 (1H, m), 2.90-2.99 (1H, m), 3.45-3.66 (2H, m), 4.03 (1H, d), 4.34 (1H, d), 4.73 (2H, d), 6.14 (1H, d), 7.38 (1H, d), 7.84-7.90 (3H, m). |
| 7-130 | 1H-NMR (CDCl3) δ: 2.49-2.60 (1H, m), 2.86-2.94 (1H, m), 3.85-3.88 (5H, m), 4.05 (1H, d), 4.57 (1H, d.), 7.30 (2H, d.), 7.39 (1H, d), 8.90 (2H, s). |

TABLE 8-continued

| Table 8 - Ex.-No. | 1H-NMR |
|---|---|
| 7-132 | 1H-NMR (CDCl3) δ: 1.38 (3H, t), 2.52-2.59 (1H, m), 2.89-2.93 (1H, m), 3.87-3.90 (2H, m), 4.09 (1H, m), 4.41 (2H, q), 4.57 (1H, d), 7.29 (2H, s), 7.40 (1H, s), 8.95 (1H, s). |
| 7-134 | 1H-NMR (CDCl3) δ: 2.51-2.60 (1H, m), 2.86-2.93 (1H, m), 3.82-3.91 (2H, m), 4.07 (1H, d), 4.75 (2H, d), 7.29 (2H, s), 7.41 (1H, s), 8.65 (1H, s). |
| 7-135 | 1H-NMR (CDCl3) δ: 1.40 (3H, t), 2.50-2.60 (1H, m), 2.89-2.93 (1H, m), 3.87-3.89 (2H, m), 4.06 (1H, d), 4.37 (2H, q), 4.54 (1H, d), 7.45 (2H, s), 8.95 (1H, s). |
| 7-137 | 1H-NMR (CDCl3) δ: 2.50-2.55 (1H, m), 2.83-2.92 (1H, m), 3.82-3.88 (2H, m), 4.02 (1H, d), 4.49 (1H, d), 4.73 (2H, d), 7.44 (2H, s), 8.63 (1H, s). |
| 7-139 | 1H-NMR (CDCl3) δ: 1.41 (3H, t), 2.55-2.61 (1H, m), 2.91-2.97 (1H, m), 3.82-3.90 (2H, m), 4.03-4.15 (1H, m), 4.35 (2H, q), 4.60 (1H, d), 7.50-7.67 (4H, m), 8.96 (1H, s). |
| 7-141 | 1H-NMR (CDCl3) δ: 2.54-2.61 (1H, m), 2.92-3.01 (1H, m), 3.80-3.88 (2H, m), 4.01-4.16 (1H, d), 4.57 (1H, d), 4.74 (2H, d), 7.54-7.64 (4H, m), 8.64 (1H, s). |
| 7-142 | 1H-NMR (CDCl3) δ: 1.38 (3H, t), 2.63-2.66 (1H, m), 3.01-3.09 (1H, m), 3.91-3.93 (2H, m), 4.11 (1H, d), 4.38 (2H, q), 4.71 (1H, d), 7.84 (2H, s), 7.94 (1H, s), 8.96 (1H, d). |
| 7-144 | 1H-NMR (CDCl3) δ: 2.56-2.66 (1H, m), 2.98-3.06 (1H, m), 3.86-3.92 (2H, m), 4.09 (1H, d), 4.64-4.73 (3H, m), 7.85 (2H, s), 7.92 (1H, s), 8.65 (1H, s). |
| 7-147 | 1H-NMR (CDCl3) δ: 2.48-2.58 (1H, m), 2.84-2.92 (1H, m), 3.80-3.83 (2H, m), 4.00 (1H, d), 4.52 (1H, d), 4.73 (2H, d), 7.49 (2H, s), 7.69 (1H, s), 8.63 (1H, s). |
| 7a-1 | 1H-NMR (CDCl3) δ: 2.50-2.65 (1H, m), 2.92-2.99 (1H, m), 3.65-3.85 (2H, m), 4.10 (1H, d), 4.52 (1H, d), 7.25 (3H, m), 9.80 (1H, s). |
| 7a-3 | 1H-NMR (CDCl3) δ: 1.39 (3H, t), 2.52-2.67 (4H, m), 2.88-2.96 (1H, m), 3.59-3.68 (2H, m), 4.03 (1H, d), 4.23-4.30 (2H, q), 4.38-4.43 (1H, d), 7.26 (2H, d), 7.40 (1H, t). |
| 7a-5 | 1H-NMR (CDCl3) δ: 2.24 (3H, s), 2.47-2.61 (1H, m), 2.86-2.90 (1H, m), 3.51-3.67 (2H, m), 3.93 (1H, d), 4.35 (1H, d), 4.65 (2H, br s), 7.26 (2H, d), 7.39 (1H, t). |
| 7a-6 | 1H-NMR (CDCl3) δ: 1.35 (3H, t), 2.57-2.68 (1H, m), 2.92-3.00 (1H, m), 3.64-3.67 (2H, m), 3.98 (1H, d), 4.32 (2H, q), 4.44 (1H, d), 7.30 (2H, s), 7.42 (1H, t). |
| 7a-8 | 1H-NMR (CDCl3) δ: 2.55-2.68 (1H, m), 2.91-2.99 (1H, m), 3.60-3.67 (2H, m), 3.97 (1H, d), 4.44 (1H, d), 4.84-4.87 (2H, m), 7.26 (2H, s), 7.42 (1H, t). |
| 7a-9 | 1H-NMR (CDCl3) δ: 1.30 (3H, t), 2.59-2.64 (1H, m), 2.93-2.97 (1H, m), 3.61-3.73 (2H, m), 3.98 (1H, d), 4.32 (2H, q), 4.44 (1H, d), 7.41 (2H, s). |
| 7a-11 | 1H-NMR (CDCl3) δ: 2.57-2.61 (1H, m), 2.87-2.95 (1H, m), 3.56-3.70 (2H, m), 3.95 (1H, d), 4.38 (1H, d), 4.86 (2H, d), 7.40 (2H, s). |
| 7a-12 | 1H-NMR (CDCl3) δ: 1.35 (3H, t), 2.65-2.75 (1H, m), 3.09-3.13 (1H, m), 3.65-3.75 (2H, m), 4.05 (1H, d), 4.33 (2H, q), 4.59 (1H, d), 7.80 (2H, s), 7.95 (1H, s). |
| 7a-14 | 1H-NMR (CDCl3) δ: 2.63-2.69 (1H, m), 3.03-3.07 (1H, m), 3.57-3.74 (2H, m), 4.03 (1H, d), 4.53 (1H, d), 4.85-4.87 (2H, m), 7.81 (2H, s), 7.93 (1H, s). |

If not mentioned otherwise, all sample solutions were prepared as described in Biological Test Example 1 and diluted to the appropriate (predetermined) concentrations.

BIOLOGICAL TEST EXAMPLE 1

Test for Larvae of *Spodoptera litura*

Sample Solution Preparation:
Solvent: 3 parts by weight of dimethylformamide
Emulsifier: 1 part by weight of polyoxyethylene alkyl phenyl ether To prepare a suitable composition comprising the active compound, 1 part by weight of the active compound was mixed with the above amount of the solvent containing the above amount of the emulsifier, and the resulting mixture was diluted with water to predetermined concentrations.

Leaves of a sweet potato were immersed in the sample solution diluted with water to predetermined concentrations, and after the solution was air-dried, the resultant leaves were put in a petri dish of 9 cm in diameter, into which 10 of the 3rd-instar larvae of *Spodoptera litura* were then released. The dish was put in a temperature controlled room at 25° C., followed by addition of leaves of a sweet potato to the dish on the second day and fourth day and the number of dead insects after 7 days was determined to calculate the insecticidal rate. The results were the averages of two petri dishes per group in this test.

In the above biological test example 1 the following compounds, as representative examples, showed a pest-controlling effect with 100% insecticidal rate at 100 ppm of the active ingredient concentration after 7 days:

Compound Nos. 1-3, 1-4, 1-7, 1-12, 1-19, 1-21, 1-25, 1-30, 1-39, 1-42, 1-72, 1-74, 1-75, 1-77, 1-78, 1-79, 1-80, 1-81, 1-87, 1-88, 1-97, 1-99, 1-113, 1-118, 1-141, 1-143, 1-145, 1-146, 1-150, 1-155, 1-162, 1-164, 1-173, 1-174, 1-180, 1-182, 1-183, 1-185, 1-186, 1-188, 1-220, 1-222, 1-224, 1-227, 1-230, 1-231, 1-232, 1-238, 1-243, 1-254, 1-255, 1-258, 1-260, 1-270, 1-274, 1-275, 1-285, 1-295, 1-296, 1-297, 1-298, 1-299, 1-301, 1-302, 1-303, 1-304, 1-305, 1-306, 1-307, 1-308, 1-309, 1-312, 1-313, 1-314, 1-317, 1-319, 1-321, 1-322, 1-324, 1-327, 1-328, 1-329, 1-330, 1-334, 1-336, 1-338, 1-339, 1-340, 1-341, 1-345, 1-346, 1-347, 1-355, 1-356, 1-357, 1-380, 1-381, -386, 1-404, 1-444, 1-446, 1-461, 1-467, 1-468, 1-469, 1-494, 1-495, 1-496, 1-498, 1-499, 1-500, 1-501, 1-504, 1-505, 1-506, 1-507, 1-508, 1-509, 1-513, 1-516, 1-520, 1-521, 1-522, 1-523, 1-525, 1-558, 1-574, 1-728, 1-729, 1-730, 1-731, 1-732, 1-733, 1-734, 1-963, 1-966, 1-967, 1-968, 1-969, 1-970, 1-971, 1-1169, 1-1171, 1-1174, 1-1467, 1-1471, 1-1472, 2-8, 2-34, 2-35, 3-140, 3-141, 3-142, 3-143, 3-144, 3-145, 3-146, 3-148, 3-149, 3-150, 3-151, 3-335, 3-339, 3-342, 4-8, 4-21, 4-22, 4-34, 5-4, 5-22, 5-142, 5-143, 5-144, 5-148, 5-150, 5-336, 5-340, 6-4, 6-267, 6-268, 6-273, 6-802, 7-12, 7-13 and 7-14.

BIOLOGICAL TEST EXAMPLE 2

Test for *Tetranychus urticae* (Spray Test)

Test method: 50 to 100 of adult *Tetranychus urticae* were inoculated to leaves at 2-leaf stage of kidney bean planted in pots of 6 cm in diameter, to which, 1 day later, the sample solution which was diluted with water to the desired concentration was sufficiently sprayed with a spray gun. After the compounds were sprayed, the pots were left in a greenhouse and the acaricidal rate was calculated seven days later.

Test result: As representative examples, the following compounds showed a pest-controlling efficacy with 100% acaricidal rate at a concentration of 100 ppm after 7 days:

Compound Nos. 1-3, 1-4, 1-7, 1-8, 1-12, 1-15, 1-19, 1-21, 1-24, 1-25, 1-30, 1-32, 1-36, 1-39, 1-40, 1-42, 1-52, 1-72, 1-75, 1-77, 1-78, 1-79, 1-80, 1-81, 1-87, 1-88, 1-97, 1-99, 1-115, 1-117, 1-118, 1-123, 1-143, 1-145, 1-146, 1-150, 1-151, 1-155, 1-162, 1-164, 1-173, 1-174, 1-180, 1-185, 1-186, 1-198, 1-210, 1-220, 1-222, 1-224, 1-227, 1-230, 1-231, 1-232, 1-243, 1-244, 1-254, 1-257, 1-258, 1-285, 1-296, 1-297, 1-299, 1-302, 1-303, 1-304, 1-305, 1-307, 1-308, 1-309, 1-312, 1-313, 1-314, 1-319, 1-321, 1-322, 1-327, 1-328, 1-329, 1-330, 1-334, 1-338, 1-339, 1-340, 1-341, 1-345, 1-346, 1-347, 1-355, 1-356, 1-357, 1-380, 1-381, 1-404, 1-442, 1-443, 1-444, 1-458, 1-461, 1-464, 1-467, 1-468, 1-469, 1-494, 1-495, 1-496, 1-498, 1-499, 1-500, 1-501, 1-503, 1-504, 1-505, 1-506, 1-507, 1-508, 1-509, 1-513, 1-517, 1-521, 1-523, 1-558, 1-694, 1-723, 1-728, 1-729, 1-730, 1-731, 1-732, 1-733, 1-734, 1-735, 1-963, 1-966, 1-967, 1-968, 1-969, 1-970, 1-971, 1-1169, 1-1171, 1-1172, 1-1174, 1-1467, 1-1471, 1-1472, 3-141, 3-142, 3-143, 3-144, 3-145, 3-148, 3-149, 3-150, 3-151, 3-335, 3-336, 3-339, 3-342, 5-22, 5-340, 6-4, 6-267, 6-268 and 6-273.

BIOLOGICAL TEST EXAMPLE 3

Test for *Aulacophora femoralis* (Spray Test)

Leaves of cucumbers were immersed in the water-diluted solution containing the active compound at the predetermined concentration which was prepared above and, after the solution was air-dried, the leaves were put onto sterilized black soil in a plastic cup, into which five of the 2nd-instar larvae of *Aulacophora femoralis* were then released. Seven days later, the number of dead insects was counted to calculate the insecticidal rate.

Te following compounds showed a pest-controlling efficay of 100% insecticidal rate at 100 ppm of the active ingredient concentration after 7 days:

Compound Nos. 1-3, 1-4, 1-8, 1-12, 1-19, 1-21, 1-24, 1-25, 1-30, 1-36, 1-40, 1-42, 1-73, 1-74, 1-75, 1-77, 1-78, 1-79, 1-80, 1-81, 1-88, 1-97, 1-98, 1-99, 1-113, 1-115, 1-117, 1-118, 1-123, 1-143, 1-145, 1-146, 1-150, 1-154, 1-155, 1-162, 1-164, 1-166, 1-173, 1-174, 1-180, 1-183, 1-186, 1-198, 1-220, 1-224, 1-227, 1-228, 1-231, 1-238, 1-243, 1-244, 1-254, 1-257, 1-258, 1-260, 1-270, 1-285, 1-295, 1-296, 1-297, 1-298, 1-299, 1-300, 1-301, 1-302, 1-303, 1-304, 1-305, 1-307, 1-308, 1-309, 1-312, 1-313, 1-314, 1-317, 1-319, 1-321, 1-322, 1-327, 1-328, 1-329, 1-330, 1-338, 1-339, 1-340, 1-341, 1-345, 1-346, 1-347, 1-355, 1-356, 1-357, 1-380, 1-381, 1-386, 1-404, 1-442, 1-443, 1-446, 1-458, 1-461, 1-464, 1-467, 1-493, 1-494, 1-495, 1-496, 1-498, 1-499, 1-500, 1-501, 1-502, 1-503, 1-504, 1-505, 1-506, 1-507, 1-508, 1-509, 1-513, 1-521, 1-522, 1-523, 1-525, 1-558, 1-727, 1-728, 1-729, 1-730, 1-731, 1-732, 1-733, 1-734, 1-735, 1-963, 1-966, 1-967, 1-968, 1-969, 1-970, 1-971, 1-1169, 1-1171, 1-1172, 1-1174, 1-1467, 1-1471, 1-1472, 2-8, 2-34, 3-141, 3-142, 3-143, 3-144, 3-145, 3-148, 3-149, 3-150, 3-151, 3-335, 3-339, 3-342, 4-8, 4-34, 4-35, 5-4, 5-22, 5-143, 5-144, 5-150, 5-151, 5-340, 6-4, 6-267, 6-268, 6-273, 6-802.

BIOLOGICAL TEST EXAMPLE 4

Test for Organic Phosphorus Agent- and Carbamate Agent-Resistant *Myzus persicae*

About 30 to 50 of grown organic phosphorus agent- and carbamate agent-resistant *Myzus persicae* per seedling were inoculated to leaves at 2-leaf stage of eggplants grown in a pot of 6 cm in diameter, to which, after 1 day from the inoculation, the above prepared water-diluted solution of above active compound of the predetermined concentration was sufficiently sprayed with a spray gun. After the spraying, the pot was left in a greenhouse at room temperature for 7 days, followed by the pest-controlling rate calculated. The test was repeated twice.

Compound Nos. 1-143, 1-309, 1-314, 1-328, 1-356 and 3-142 showed a pest-controlling efficacy with 100% insecticidal rate at 100 ppm of an active ingredient concentratio.

BIOLOGICAL TEST EXAMPLE 5

Amblyomma hebraeum—Test (AMBYHE)

Solvent: Dimethyl Sulfoxide

To produce a suitable preparation of active compound, 10 mg of active compound are dissolved in 0.5 ml solvent, and the concentrate is diluted with water to the desired concentration. Nymphs of the tick Amblyomma hebraeum are placed in perforated plastic beakers and immersed in aqueous compound solution for one minute. Ticks are transferred to a filter paper in a Petri dish and incubated in a climate chamber for 42 days.

After 42 days mortality in % is determined. 100% means that all the ticks have been killed; 0% means that none of the ticks have been killed.

In this test for example, the following compounds from the preparation examples showed good activity of 80% at application rate of 100 ppm: Compound Nos. 1-230, 1-307 and 1-340.

In this test for example, the following compounds from the preparation examples showed good activity of 85% at application rate of 100 ppm: Compound Nos. 1-238 and 1-404.

In this test for example, the following compounds from the preparation examples showed good activity of 90% at application rate of 100 ppm: Compound Nos. 1-118, 1-297, 1-305, 1-347, 1-467, 1-509 and 1-734.

In this test for example, the following compound from the preparation examples showed good activity of 95% at application rate of 100 ppm: Compound No. 1-313.

In this test for example, the following compounds from the preparation examples showed good activity of 100% at application rate of 100 ppm: Compound Nos. 1-3, 1-4, 1-8, 1-12, 1-19, 1-30, 1-36, 1-42, 1-81, 1-88, 1-143, 1-146, 1-150, 1-155, 1-162, 1-164, 1-186, 1-224, 1-231, 1-25, 1-258, 1-260, 1-285, 1-296, 1-297, 1-305, 1-307, 1-309, 1-312, 1-314, 1-319, 1-327, 1-329, 1-330, 1-338, 1-339, 1-340, 1-341, 1-345, 1-346, 1-347, 1-357, 1-380, 1-404, 1-499, 1-501, 1-729, 1-732, 1-733, 5-144 and 6-267.

BIOLOGICAL TEST EXAMPLE 6

Lucillia cuprina—Test

Solvent: Dimethyl Sulfoxide

To produce a suitable preparation of active compound, 10 mg of active compound are dissolved in 0.5 ml solvent, and the concentrate is diluted with water to the desired concentration. Approximately 20-30 (Lucilia cuprina larvae) are transferred into a test tube containing 1cm$^3$ of minced horse meat and 0.5 ml aqueous dilution of test compound. After 2 days mortality in % is determined. 100% means that all the larvae have been killed; 0% means that none of the larvae have been killed.

In this test for example, the following compounds from the preparation examples showed good activity of 80% at application rate of 100 ppm: Compound Nos. 1-87, 1-244, 1-694 and 4-9.

In this test for example, the following compounds from the preparation examples showed good activity of 90% at application rate of 100 ppm: Compound Nos. 1-74, 1-79, 1-97, 1-306, 1-334, 1-336 and 2-69.

In this test for example, the following compounds from the preparation examples showed good activity of 95% at application rate of 100 ppm: Compound Nos. 1-243 and 1-257.

In this test for example, the following compounds from the preparation examples showed good activity of 100% at application rate of 100 ppm: Compound Nos. 1-3, 1-4, 1-8, 1-12, 1-19, 1-21, 1-24, 1-25, 1-30, 1-39, 1-40, 1-75, 1-77, 1-78, 1-81, 1-88, 1-99, 1-113, 1-118, 1-143, 1-145, 1-146, 1-150, 1-155, 1-162, 1-164, 1-173, 1-174, 1-180, 1-183, 1-186, 1-188, 1-198, 1-220, 1-222, 1-224, 1-227, 1-230, 1-231, 1-232, 1-238, 1-258, 1-260, 1-285, 1-295, 1-296, 1-297, 1-298, 1-299, 1-300, 1-301, 1-302, 1-303, 1-304, 1-305, 1-307, 1-308, 1-309, 1-312, 1-313, 1-314, 1-317, 1-319, 1-327, 1-329, 1-330, 1-338, 1-339, 1-340, 1-341, 1-345, 1-346, 1-347, 1-357, 1-36, 1-380, 1-381, 1-386, 1-404, 1-42, 1-458, 1-467, 1-468, 1-494, 1-495, 1-499, 1-500, 1-501, 1-503, 1-504, 1-505, 1-509, 1-558, 1-728, 1-729, 1-730, 1-732, 1-733, 1-734, 1-963, 1-966, 1-967, 1-968, 1-969, 1-970, 1-971, 2-34, 2-35, 3-141, 3-142, 3-143, 3-144, 3-145, 3-148, 3-149, 3-150, 3-151, 4-8, 4-21, 4-22, 4-34, 4-35, 5-142, 5-143, -5-144, 5-150, 5-22, 5-4, 6-267, 6-4 and 6-802.

BIOLOGICAL TEST EXAMPLE 7

Ctenocephalides felis—Test (CTECFE)

Solvent: Dimethyl Sulfoxide

To produce a suitable preparation of active compound, 10 mg of active compound are dissolved in 0.5 ml solvent, and the concentrate is diluted with cattle blood to the desired concentration. Approximately 10 to 15 adult unfed (Ctenocepahlides felis) are placed in flea chambers. The blood chamber, are sealed with parafilm on the bottom are filled with cattle blood supplied with compound solution and placed on top of the flea chamber, so that the fleas are able to suck the blood. The blood chamber is heated to 37° C. whereas the flea chamber is kept at room temperature. After 2 days mortality in % is determined. 100% means that all the fleas have been killed; 0% means that none of the fleas have been killed.

In this test for example, the following compounds from the preparation examples showed good activity of 80% at application rate of 100 ppm: Compound Nos. 1-12, 1-19, 1-74, 1-118, 1-141, 1-145, 1-146, 1-150, 1-186, 1-503, 1-558, 1-734, 3-148, 4-22, 5-22 and 5-4.

In this test for example, the following compounds from the preparation examples showed good activity of 90% at application rate of 100 ppm: Compound Nos. 1-21, 1-79, 1-87, 1-113, 1-143, 1-155, 1-174, 1-198, 1-230, 1-232, 1-260, 1-458, 1-505, 1-509, 1-732 and 4-35.

In this test for example, the following compounds from the preparation examples showed good activity of 95% at application rate of 100 ppm: Compound Nos. 1-78, 1-99, 1-164, 1-173, 1-180, 1-188, 1-222, 1-224, 1-254, 1-298, 1-380, 1-499, 1-504, 1-969, 1-971, 3-145, 3-149, 3-151, 4-34, 4-8 and 5-143.

In this test for example, the following compounds from the preparation examples showed good activity of 100% at application rate of 100 ppm: Compound Nos. 1-3, 1-4, 1-7, 1-8, 1-30, 1-36, 1-40, 1-42, 1-81, 1-88, 1-77, 1-162, 1-183, 1-220, 1-227, 1-231, 1-238, 1-243, 1-244, 1-25, 1-257, 1-258, 1-285, 1-296, 1-297, 1-299, 1-301, 1-302, 1-303, 1-304, 1-305, 1-307, 1-308, 1-309, 1-312, 1-313, 1-314, 1-317, 1-319, 1-327, 1-329, 1-330, 1-338, 1-339, 1-340, 1-341, 1-345, 1-346, 1-347, 1-357, 1-381, 1-386, 1-393, 1-404, 1-467, 1-494, 1-495, 1-500, 1-501, 1-728, 1-729, 1-730, 1-733, 1-963, 1-966, 1-967, 1-968, 1-970, 2-34, 2-35, 3-141, 3-142, 3-143, 3-144, 4-21, 5-142, 5-144, 6-4 and 6-267.

BIOLOGICAL TEST EXAMPLE 8

*Musca domestica*—Test

Solvent: Dimethyl Sulfoxide

To produce a suitable preparation of active compound, 10 mg of active compound are dissolved in 0.5 ml solvent, and the concentrate is diluted with water to the desired concentration. Prior to the assay, a piece or kitchen sponge is soaked with a mixture of sugar and compound solution and placed into a container. 10 adults (*Musca domestica*) are placed into the container and closed with a perforated lid. After 2 days mortality in % is determined. 100% means that all the flies have been killed; 0% means that none of the flies have been killed.

In this test for example, the following compounds from the preparation examples showed good activity of 80% at application rate of 100 ppm: Compound Nos. 1-8, 1-78, 1-304, 1-340, 1-504, 1-970, 2-69, 3-151 and 6-4.

In this test for example, the following compound from the preparation examples showed good activity of 85% at application rate of 100 ppm: Compound No. 5-4.

In this test for example, the following compounds from the preparation examples showed good activity of 90% at application rate of 100 ppm: Compound Nos. 1-39, 1-220, 1-238, 1-499 and 4-21.

In this test for example, the following compounds from the preparation examples showed good activity of 95% at application rate of 100 ppm: Compound Nos. 1-231, 5-150 and 5-22.

In this test for example, the following compounds from the preparation examples showed good activity of 100% at application rate of 100 ppm: Compound Nos. 1-4, 1-42, 1-81, 1-88, 1-99, 1-118, 1-143, 1-146, 1-150, 1-155, 1-162, 1-183, 1-186, 1-224, 1-258, 1-285, 1-296, 1-297, 1-301, 1-302, 1-305, 1-307, 1-308, 1-309, 1-312, 1-313, 1-314, 1-319, 1-327, 1-329, 1-330, 1-338, 1-339, 1-341, 1-345, 1-346, 1-347, 1-357, 1-380, 1-381, 1-386, 1-404, 1-467, 1-494, 1-495, 1-500, 1-501, 1-509, 1-728, 1-729, 1-730, 1-963, 1-966, 1-967, 1-968, 2-34, 3-141, 3-142, 3-143, 3-144, 3-148, 3-149, 3-150, 4-8, 5-142, 5-143, 5-144 and 6-267.

BIOLOGICAL TEST EXAMPLE 9

*Boophilus microplus* (Dip)

Solvent: Dimethyl Sulfoxide

To produce a suitable preparation of active compound, 10 mg of active compound are dissolved in 0.5 ml solvent, and the concentrate is diluted with water to the desired concentration. Eight to ten adult engorged female *Boophilus microplus* ticks are placed in perforated plastic beakers and immersed in aqueous compound solution for one minute. Ticks are transferred to a filter paper in a plastic tray. Egg deposition of fertile eggs is monitored after. After 7 days mortality in % is determined. 100% means that all the ticks have been killed; 0% means that none of the ticks have been killed.

In this test for example, the following compounds from the preparation examples showed good activity of 80% at application rate of 100 ppm: Compound Nos. 1-7, 1-77, 1-78, 1-174, 1-301, 1-305 and 1-558.

In this test for example, the following compounds from the preparation examples showed good activity of 90% at application rate of 100 ppm: Compound Nos. 1-302 and 1-467.

In this test for example, the following compounds from the preparation examples showed good activity of 95% at application rate of 100 ppm: Compound Nos. 1-162 and 1-164.

In this test for example, the following compounds from the preparation examples showed good activity of 100% at application rate of 100 ppm: Compound Nos. 1-3, 1-4, 1-12, 1-19, 1-25, 1-30, 1-36, 1-42, 1-74, 1-75, 1-81, 1-88, 1-118, 1-143, 1-145, 1-146, 1-150, 1-155, 1-173, 1-180, 1-186, 1-220, 1-224, 1-231, 1-258, 1-260, 1-285, 1-296, 1-297, 1-307, 1-309, 1-312, 1-314, 1-319, 1-327, 1-329, 1-330, 1-338, 1-339, 1-340, 1-341, 1-345, 1-346, 1-347, 1-357, 1-380, 1-461, 1-499, 1-500, 1-501, 1-728, 1-729, 1-730, 1-732, 1-963, 3-142, 3-143, 3-144, 3-149, 5-143 and 6-267.

BIOLOGICAL TEST EXAMPLE 10

*Boophilus microplus*—Test (Injection)

Solvent: Dimethyl Sulfoxide

To produce a suitable preparation of active compound, 10 mg of active compound are dissolved in 0.5 ml solvent, and the concentrate is diluted with solvent to the desired concentration. Five adult engorged female ticks (*Boophilus microplus*) are injected with compound solution into the abdomen. Ticks are transferred into replica plates and incubated in a climate chamber for a period of time. Egg deposition of fertile eggs is monitored. After 7 days mortality in % is determined. 100% means that all eggs are infertile; 0% means that all eggs are fertile.

In this test for example, the following compounds from the preparation examples showed good activity of 100% at application rate of 20 µg/animal: Compound Nos. 1-3, 1-4, 1-7, 1-8, 1-12, 1-19, 1-24, 1-25, 1-30, 1-39, 1-40, 1-42, 1-74, 1-75, 1-77, 1-78, 1-79, 1-81, 1-87, 1-88, 1-97, 1-99, 1-113, 1-118, 1-141, 1-143, 1-145, 1-146, 1-150, 1-155, 1-162, 1-164, 1-173, 1-174, 1-180, 1-183, 1-186, 1-188, 1-198, 1-21, 1-220, 1-222, 1-224, 1-227, 1-230, 1-231, 1-232, 1-238, 1-243, 1-244, 1-254, 1-257, 1-258, 1-260, 1-270, 1-285, 1-295, 1-296, 1-297, 1-298, 1-299, 1-300, 1-301, 1-302, 1-303, 1-304, 1-305, 1-307, 1-308, 1-309, 1-312, 1-313, 1-314, 1-317, 1-319, 1-327, 1-329, 1-330, 1-334, 1-336, 1-338, 1-339, 1-340, 1-341, 1-345, 1-346, 1-347, 1-357, 1-36, 1-380, 1-381, 1-386, 1-404, 1-442, 1-446, 1-458, 1-467, 1-468, 1-494, 1-495, 1-499, 1-500, 1-501, 1-503, 1-504, 1-505, 1-509, 1-558, 1-694, 1-728, 1-729, 1-730, 1-732, 1-733, 1-734, 1-963, 1-966, 1-967, 1-968, 1-969, 1-970, 1-971, 2-34, 2-35, 2-69, 3-141, 3-142, 3-143, 3-144, 3-145, 3-146, 3-148, 3-149, 3-150, 3-151, 4-21, 4-22, 4-34, 4-35, 4-8, 5-142, 5-143, 5-144, 5-150, 5-22, 5-4, 6-267, 6-4, 6-802, 7-12 and 7-13.

Comparison of the biological activity of compounds according to the invention and compounds described in WO2008/128711

Compound No. 1-143 and the following compound which in WO2008/128711 is listed as compound No. 3-5 are tested in the *Amblyomma hebraeum*—test (AMBYHE) under the conditions described above.

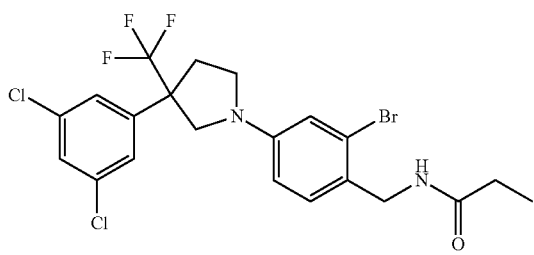

Compound Nor. 3-5 according to WO2008/12871'

The results are as follows

| Compound No. | Activity at 4 ppm | Activity at 0.8 ppm |
|---|---|---|
| No. 1-143 (accord. to the invention | 100% | 100% |
| No. 3-5 according to WO2008/128711 | 70% | 10% |

PREPARATION EXAMPLE 1

Granules

To a mixture containing 10 parts of the compound of the present invention (No. 1-3), 30 parts of bentonite (montmorillonite), 58 parts of talc and 2 parts of lignin sulfonate was added 25 parts of water, and the mixture was well kneaded and granulated with 10 to 40 meshes by an extruding granulator and dried at 40 to 50° C. to obtain granules.

PREPARATION EXAMPLE 2

Granules 95 parts of clay mineral granules having particle diameter distribution within the range of 0.2 to 2 mm were put into a rotary mixer, and then wetted evenly by spraying of 5 parts of the compound of the present invention (No. 1-3) together with a liquid diluent under rotating condition and dried at 40 to 50° C. to obtain granules.

PREPARATION EXAMPLE 3

Emulsion 30 parts of the compound of the present invention (No. 1-3), 55 parts of xylene, 8 parts of polyoxyethylene alkyl phenyl ether and 7 parts of calcium alkylbenzenesulfonate were mixed together to obtain the emulsion.

PREPARATION EXAMPLE 4

Wettable Agent 15 parts of the compound of the present invention (No. 1-3), 80 parts of a mixture of white carbon (hydrated amorphous silicon oxide fine powder) and powdered clay (1:5), formalin condensate of 2 parts of sodium alkylbenzenesulfonate and 3 parts of sodium alkylnaphthalenesulfonate were mixed together and the mixture was crushed to obtain a wettable agent.

PREPARATION EXAMPLE 5

Wettable Granules 20 parts of the active compound of the present invention (No. 1-3), 30 parts of lignin sodium sulfonate, 15 parts of bentonite and 35 parts of calcined diatomaceous earth powder were well mixed, and after addition of water, the mixture was then extruded with a screen of 0.3 mm and dried to obtain wettable granules.

The invention claimed is:
1. An arylpyrrolidine compound having the formula (H-I),

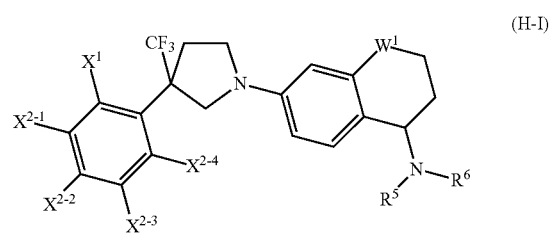

(H-I)

or a salt thereof,
Wherein
$W^1$ represents a bond or —$CH_2$;
$X^1$, $X^{2-1}$, $X^{2-2}$, $X^{2-3}$ and $X^{2-4}$ each independently represents hydrogen, halogen or $C_{1-4}$ haloalkyl;
$R^5$ represents hydrogen or methyl; and
$R^6$ represents $C_{2-5}$ alkylcarbonyl, (total carbon atom number) $C_{2-3}$ haloalkylcarbonyl, (total carbon atom number) $C_{2-3}$ alkylaminocarbonyl, (total carbon atom number) $C_{4-5}$ cycloalkylcarbonyl, $C_{3-6}$cycloalkyl($C_{1-4}$)alkylcarbonyl, (total carbon atom number) $C_{4-7}$ cycloalkylaminocarbonyl, cyclobutylcarbamoyl, $C_{1-4}$alkoxy($C_{1-4}$)alkylcarbonyl, 3-methoxypropanoyl, $C_{1-2}$alkyl-S($C_{1-2}$)alkylcarbonyl, $C_{1-2}$alkyl-SO($C_{1-2}$)alkylcarbonyl, or $C_{1-2}$alkyl-SO$_2$($C_{1-2}$)alkylcarbonyl.

2. An arylpyrrolidine compound having the formula (H-I),

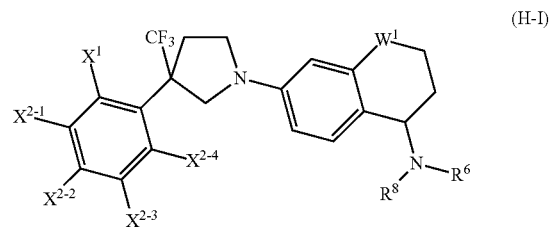

(H-I)

or a salt thereof,
wherein
$W^1$ represents a bond or —$CH_2$;
$X^1$, $X^{2-1}$, $X^{2-2}$, $X^{2-3}$ and $X^{2-4}$ each independently represent hydrogen, halogen or $C_{1-4}$haloalkyl, and at least one of them represents hydrogen, halogen, $CF_3$, $CF_2H$, $CFH_2$, $CH_2CF_3$, or $CF_2CF_3$;
$R^5$ represents hydrogen or methyl; and
$R^6$ represents acetyl, propionyl, n-propylcarbonyl, iso-propylcarbonyl, n-butylcarbonyl, difluoroacetyl, 3,3,3 -trifluoropropanoyl, ethylcarbamoyl, propylcarbamoyl, cyclopropylcarbonyl, cyclobutylcarbonyl, cyclopropylacetyl , cyclopropylcarbamoyl,

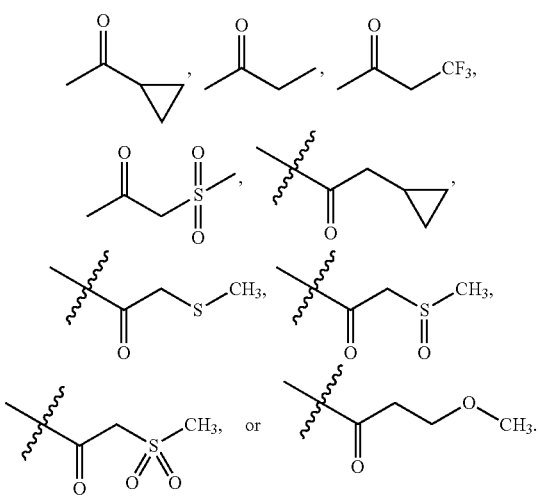

3. A composition comprising one or more compounds of claim 2 and one or more diluents, emulsifiers, or a combination thereof.

4. A method for controlling plant damaging animal pests, comprising applying the composition of claim 3 to said pests, their habitat, or a combination thereof.

5. A method for controlling parasites in or on an animal comprising administering the composition of claim 3 to said animal.

6. A method for treating seeds of a conventional or a transgenic plant comprising coating said seeds with the composition of claim 3.

7. The arylpyrrolidine compound of claim 2, wherein $R^6$ represents acetyl,

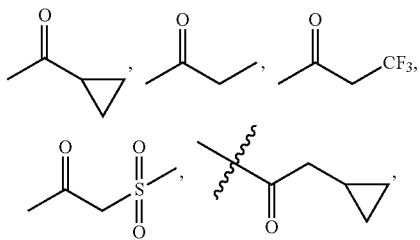

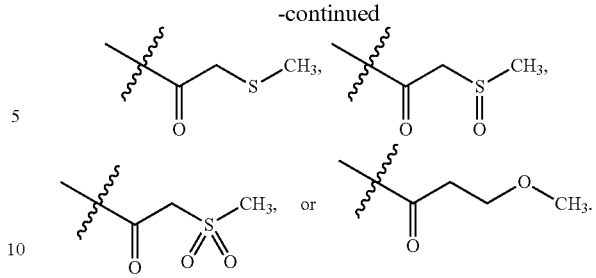

8. An arylpyrrolidine compound selected from the group consisting of Compound Nos. 6-2, 6-4, 6-88, 6-100, 6-267, 6-268, and 6-301.

9. The arylpyrrolidine compound of claim 1, wherein $W^1$ is a bond.

10. The arylpyrrolidine compound of claim 1, wherein $W^1$ is —$CH_2$—.

11. The arylpyrrolidine compound of claim 2, wherein $W^1$ is a bond.

12. The arylpyrrolidine compound of claim 2, wherein $W^1$ is —$CH_2$—.

13. A composition comprising one or more compounds selected from the compounds of claim 1 and one or more diluents, emulsifiers, or a combination thereof.

14. A composition comprising one or more compounds selected from the compounds according to claim 8 and one or more diluents, emulsifiers, or a combination thereof.

15. A method for controlling plant damaging animal pests comprising applying the composition of claim 13 to said pests, their habitat, or a combination thereof.

16. A method for controlling plant damaging animal pests comprising applying the composition of claim 14 to said pests, their habitat, or a combination thereof.

17. A method for controlling parasites in or on an animal comprising administering the composition of claim 13 to said animal.

18. A method for controlling parasites in or on an animal comprising administering the composition of claim 14 to said animal.

19. A method for treating seeds of conventional or transgenic plants comprising coating said seeds with the composition of claim 13.

20. A method for treating seeds of conventional or transgenic plants comprising coating said seeds with the composition of claim 14.

* * * * *